(12) United States Patent
Ozaki et al.

(10) Patent No.: US 7,265,108 B2
(45) Date of Patent: Sep. 4, 2007

(54) NITROGEN CONTAINING HETEROCYCLIC COMPOUNDS AND MEDICINES CONTAINING THE SAME

(75) Inventors: Fumihiro Ozaki, Ushiku (JP); Mutsuko Ono, Ushiku (JP); Koki Kawano, Tsukuba (JP); Yoshihiko Norimine, Tsukuba (JP); Tatsuhiro Onogi, Tsukuba (JP); Takashi Yoshinaga, Tsukuba (JP); Kiyoaki Kobayashi, Moriya (JP); Hiroyuki Suzuki, Tsukuba (JP); Hiroe Minami, Tsukuba (JP); Kohei Sawada, Mariya (JP)

(73) Assignee: Eisai Co., Ltd., Bunkyo-ku, Tokyo (JP)

( * ) Notice: Subject to any disclaimer, the term of this patent is extended or adjusted under 35 U.S.C. 154(b) by 232 days.

(21) Appl. No.: 11/173,099

(22) Filed: Jul. 1, 2005

(65) Prior Publication Data

US 2005/0245527 A1 Nov. 3, 2005

Related U.S. Application Data

(63) Continuation of application No. 10/388,185, filed on Mar. 12, 2003, now Pat. No. 6,995,144.

(30) Foreign Application Priority Data

Mar. 14, 2002 (JP) ............................. 2002-069529

(51) Int. Cl.
*A62K 31/535* (2006.01)
*A62K 31/4965* (2006.01)
*C07D 498/00* (2006.01)
*C07D 413/00* (2006.01)
*C07D 241/02* (2006.01)

(52) U.S. Cl. ............................. 514/230.5; 514/235.8; 514/255.02; 544/91; 544/120; 544/408

(58) Field of Classification Search ............... None
See application file for complete search history.

(56) References Cited

FOREIGN PATENT DOCUMENTS

| EP | 0 378 255 | 7/1990 |
|---|---|---|
| JP | 04-054181 | 2/1992 |
| WO | WO 01/53288 A1 | 7/2001 |

OTHER PUBLICATIONS

Charles P. Taylor, et al., Na+ channels as targets for neuroprotective drugs, Trends in Pharmacological Sciences 16 (1995) pp. 309-316.
Wade S. Kingery[a,b,*], A critical review of controlled clinical trials for peripheral neuropathic pain and complex regional pain syndromes, International Association for the Study of Pain 73(1997) 123-139.
E. Kalso[a], et al., Systemic local-anaesthetic-type drugs in chronic pain: a systematic review, European Journal of Pain (1998) 2: 3-14.
Masaki Sakurai*, et al. Positive symptoms in multiple sclerosis: their treatment with sodium channel blockers, lidocaine and mexiletine, Journal of the Neurological Sciences 162 (1999) 162-168.
S ren H. Sindrup[a*] et al., Efficacy of pharmacological treatments of neuropathic pain: an update and effect related to mechanism of drug action, International Association for the Study of Pain 83 (1999) 389-400.
Patrick Kwan, et al., The mechanisms of action of commonly used antiepileptic drugs, Pharmacology & Therapeutics 90 (2001) 21-34.
M. Nieto-Barrera[a], et al., A comparison of monotherapy with lamotrigine or carbamazepine in patients with newly diagnosed partial epilepsy, Epilepsy Research 46 (2001) 145-155.
Keri Wellington, et al., Oxcarbazepine An Update of its Efficacy in the Management of Epilepsy, CNS Drugs 2001: 15(2): 137-163.
J.M. Stutzmann, et al., 31st Annual Meeting of Society of Neuroscience 27 (2001) Abstract 199.16.
Gabriela V. Obrocea, et al., Clinical Predictors of Response to Lamotrigine and Gabapentin Monotherapy in Refractory Affective Disorders, Biological Psychiatry 51 (2002) 21-34.
M.K. Atikeler, et al., Optimum usage of prilocaine-lidocaine cream in premature ejaculation, Andrologia 34 (2002) 356-359.

*Primary Examiner*—Zachary C Tucker
(74) *Attorney, Agent, or Firm*—Robin A. Weatherhead; Choate Hall & Stewart LLP

(57) ABSTRACT

Compounds represented by the following general formula:

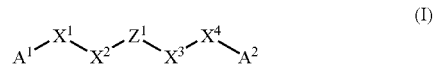

(I)

[wherein $X^1$, $X^2$, $X^3$ and $X^4$ each independently represent a single bond, $C_{1-6}$ alkylene, etc.; $A^2$ represents optionally substituted phenyl, etc.; $A^1$ represents an optionally substituted 5- to 7-membered heterocyclic group containing —C(=$Q^1$)— (wherein $Q^1$ represents oxygen, sulfur or =N—$R^{11}$ (wherein $R^{11}$ represents hydrogen or $C_{1-6}$ alkyl)) and nitrogen, etc.; and $Z^1$ represents piperidin-diyl, etc.], salts thereof and hydrates of the foregoing.

15 Claims, No Drawings

NITROGEN CONTAINING HETEROCYCLIC COMPOUNDS AND MEDICINES CONTAINING THE SAME

CROSS REFERENCE TO RELATED APPLICATIONS

This application is a continuation of U.S. patent application Ser. No. 10/388,185, filed Mar. 12, 2003, now U.S. Pat. No. 6,995,144, which claims priority to JP 2002-069529 filed Mar. 14, 2002, the entirety of each of which is incorporated herein by reference.

BACKGROUND OF THE INVENTION

1. Field of the Invention

The present invention relates to nitrogen containing heterocyclic compounds having sodium channel-inhibiting effects, salts thereof and hydrates of the foregoing, to process for producing the same and to the use of the same as medicine.

2. Related Background Art

Compounds with sodium channel-inhibiting effect are known to be useful for treatment of various types of neuralgia (for example, postherpetic neuralgia, diabetic neuralgia, HIV neuralgia, etc.).

As compounds with sodium channel-inhibiting effect there may be mentioned Lidocaine, Carbamazepine, Mexiletine, Amitriptyline and the like, which are already used as neuralgia treatment agents. For example, Lidocaine is used for treatment of postherpetic neuralgia, and Carbamazepine is used for treatment of trigeminal neuralgia.

It has also been reported that Mexiletine and Lidocaine are effective as analgesics (Pain. 83(1999) 389-400; European Journal of Pain. 2(1998) 3-14; Pain. 73(1997) 123-139).

Compounds with sodium channel-inhibiting activity have been reported to also exhibit the following pharmacological activities and therapeutic effects for diseases other than types of neuralgia.

(i) Compounds with sodium channel-inhibiting activity are used for treatment of epilepsy (Pharmacology & Therapeutics 90(2001) 21-34).

(ii) It has been reported that Carbamazepine, used as an anticonvulsant, is effective for treatment of manic-depressive psychosis (Biological Psychiatry 51(2002) 253-260).

(iii) It has been reported that Lidocaine and Mexiletine are effective for various symptoms of multiple sclerosis (Journal of Neurological Sciences 162(1999) 162-168).

(iv) It has been reported that Lidocaine is effective for treatment of premature ejaculation (Andrologia 34(2002) 356-359).

(v) Somnolence-inducing effects have been reported for Carbamazepine and Oxocarbazepine which are used as anticonvulsants (Epilepsy 46(2002) 145-155; CNS Drugs 15(2001) 137-163), suggesting the possibility of the use of sodium channel inhibitors for treatment of insomnia.

(vi) Activity by sodium channel inhibitors in various neuropathic animal models has been reported, suggesting a protective effect against neuropathy in cerebrovascular disease, cranial injuries and spinal injuries (Trends in Pharmacological Sciences 16(1995) 309-316).

(vii) The efficacy of sodium channel inhibitors in Parkinson's disease model animals has been published at a scientific conference (31st Annual Meeting of Society of Neuroscience 27(2001) Abstract 199.16).

Low-molecular weight compounds with sodium channel-inhibiting effects have also been reported, such as the following.

Sodium Channel-Inhibiting Compounds Represented by the Following General Formula ($I^1$):

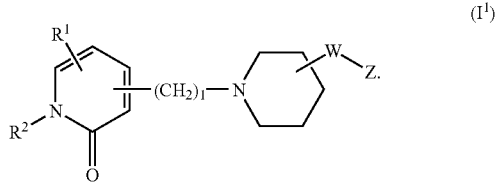

(WO01/53288)

These sodium channel inhibitors, however, exhibit effects on the cardiovascular system and inhibition effect on hepatic drug metabolizing enzymes, and have therefore been less than satisfactory.

SUMMARY OF THE INVENTION

As explained above, it has been desirable to develop drugs that exhibit excellent sodium channel-inhibiting effect, which satisfy the drug requirements for pharmacological activity and safety (in terms of effects on the cardiovascular system, inhibiting effect on hepatic drug metabolizing enzymes, enzyme induction, etc.), and which perform effectively in the clinic. It is therefore an object of the present invention to search for and discover such excellent sodium channel-inhibiting compounds.

As a result of much vigorous and dedicated research conducted in light of the circumstances described above, the present inventors have discovered novel nitrogen containing heterocyclic compounds which have excellent sodium channel-inhibiting effect and excellent safety.

The present invention provides:

<1> A compound represented by the following general formula:

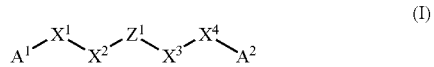

[wherein $X^1$ and $X^2$ each independently represent a single bond, optionally substituted $C_{1-6}$ alkylene, optionally substituted $C_{3-8}$ cycloalkylene, an optionally substituted monocyclic 4- to 8-membered non-aromatic heterocyclic group, optionally substituted $C_{2-6}$ alkenylene, optionally substituted $C_{2-6}$ alkynylene, oxygen, —CO—, —S—, —S(O)—, —S(O)$_2$—, —CONR$^{72}$—, —NR$^{72}$CO—, —S(O)$_2$NR$^{72}$—, —NR$^{72}$S(O)$_2$— or —NR$^{72}$—;

$R^{72}$ represents hydrogen, optionally substituted $C_{1-6}$ alkyl, optionally substituted $C_{2-6}$ alkenyl, optionally substituted $C_{2-6}$ alkynyl, optionally substituted $C_{2-7}$ acyl or optionally substituted $C_{3-8}$ cycloalkyl;

$X^3$ and $X^4$ each independently represent a single bond, optionally substituted $C_{1-6}$ alkylene, optionally substituted $C_{2-6}$ alkenylene, optionally substituted $C_{2-6}$ alkynylene, optionally substituted $C_{3-8}$ cycloalkylene, an optionally substituted monocyclic 4- to 8-membered non-aromatic heterocyclic group, an optionally substituted 5- to 10-membered aromatic heterocyclic group, oxygen, —CO—, —CS—, —S—, —S(O)—, —S(O)$_2$—, —COCH$_2$—, —CH$_2$CO—, —O—CH$_2$—, —CH$_2$O—, —CONR$^{71}$—, —NR$^{71}$CO—, —S(O)$_2$NR$^{71}$—, —NR$^{71}$S $(O)_2$—, —$NR^{71}$— or —$C(=N-OR^{70})$— (wherein $R^{70}$ represents hydrogen or optionally substituted $C_{1-6}$ alkyl);

$R^{71}$ represents hydrogen, optionally substituted $C_{1-6}$ alkyl, optionally substituted $C_{2-6}$ alkenyl, optionally substituted $C_{2-6}$ alkynyl, optionally substituted $C_{2-7}$ acyl, optionally substituted $C_{3-8}$ cycloalkyl or optionally substituted benzoyl;

$Z^1$ represents an optionally substituted monocyclic or bicyclic 4- to 12-membered non-aromatic heterocyclic group (wherein at least one nitrogen atom is included among the atoms forming the ring);

$A^2$ represents optionally substituted phenyl, optionally substituted 1-naphthyl, optionally substituted 2-naphthyl, an optionally substituted 5- to 10-membered aromatic heterocyclic group, an optionally substituted 9- to 11-membered benzene fused ring group or an optionally substituted 9- to 11-membered aromatic heterocycle fused ring group; and $A^1$ represents (1) an optionally substituted 5- to 7-membered heterocyclic group containing —$C(=Q^1)$- and nitrogen (wherein $Q^1$ represents oxygen, sulfur or =$N-R^{11}$ (wherein $R^{11}$ represents hydrogen or $C_{1-6}$ alkyl)), (2) an optionally substituted group of the formula:

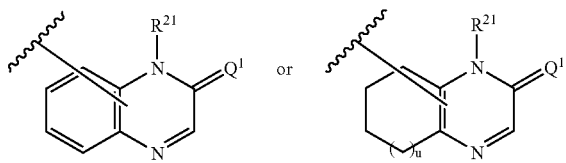

(wherein $Q^1$ has the same definition as above, $R^{21}$ represents hydrogen or $C_{1-6}$ alkyl, and u represents 0 or 1), or (3) a 5- to 10-membered aromatic heterocyclic group having at least one group selected from the group consisting of optionally substituted $C_{1-6}$ alkoxy, $C_{1-6}$ alkylthio, hydroxyl, mercapto and —$NR^{13}R^{14}$ (wherein $R^{13}$ and $R^{14}$ each independently represent hydrogen or $C_{1-6}$ alkyl), and also having other optional substituents], a salt thereof or a hydrate of the foregoing;

<2> a compound according to <1>, a salt of the compound or a hydrate of the foregoing, wherein $Z^1$ is a monocyclic or bicyclic 4- to 12-membered non-aromatic heterocyclic group optionally having 1 to 3 groups selected from the group consisting of (1) $C_{1-6}$ alkyl optionally having 1 to 3 substituents selected from the group consisting of hydroxyl, $C_{1-6}$ alkoxy, $C_{1-6}$ alkyl, amino, halogen and cyano, (2) phenyl-$C_{1-6}$ alkyl optionally having 1 to 3 substituents selected from the group consisting of hydroxyl, $C_{1-6}$ alkoxy, $C_{1-6}$ alkyl, amino, halogen and cyano, (3) phenyloxy-$C_{1-6}$ alkyl optionally having 1 to 3 substituents selected from the group consisting of hydroxyl, $C_{1-6}$ alkoxy, $C_{1-6}$ alkyl, amino, halogen and cyano, (4) hydroxyl, (5) $C_{1-6}$ alkoxy, (6) halogen, (7) cyano, (8) $C_{2-7}$ alkoxycarbonyl, and the formulas:

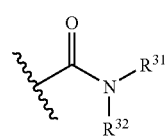
(9)

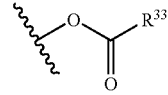
(10)

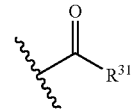
(11)

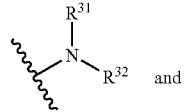
(12)
and

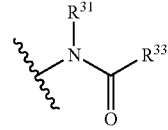
(13)

(wherein $R^{31}$, $R^{32}$ and $R^{33}$ each independently represent hydrogen or $C_{1-6}$ alkyl) and at least one nitrogen atom is included among the atoms forming the ring;

<2-2> a compound according to <1>, a salt of the compound or a hydrates of the foregoing, wherein $Z^1$ is a monocyclic or bicyclic 4- to 12-membered non-aromatic heterocyclic group optionally having 1 group selected from the group consisting of (1) $C_{1-6}$ alkyl optionally having 1-3 substituents selected from the group consisting of hydroxyl, $C_{1-6}$ alkoxy, $C_{1-6}$ alkyl, amino, halogen and cyano, (2) phenyl-$C_{1-6}$ alkyl optionally having 1-3 substituents selected from the group consisting of hydroxyl, $C_{1-6}$ alkoxy, $C_{1-6}$ alkyl, amino, halogen and cyano, (3) phenyloxy-$C_{1-6}$ alkyl optionally having 1-3 substituents selected from the group consisting of hydroxyl, $C_{1-6}$ alkoxy, $C_{1-6}$ alkyl, amino, halogen and cyano, (4) hydroxyl, (5) $C_{1-6}$ alkoxy, (6) halogen, (7) cyano, (8) $C_{2-7}$ alkoxycarbonyl, and the formulas:

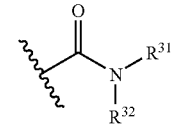
(9)

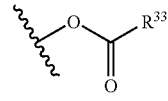
(10)

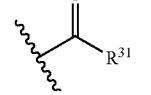
(11)

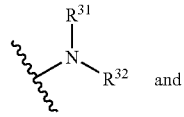
(12)
and

-continued

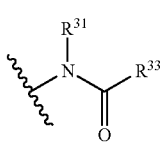

(wherein $R^{31}$, $R^{32}$ and $R^{33}$ each independently represent hydrogen or $C_{1-6}$ alkyl) (with the proviso that $Z^1$ contains at least one nitrogen atom among the atoms of the ring);

<3> a compound according to <1> or <2>, a salt of the compound or a hydrate of the foregoing, wherein the monocyclic or bicyclic 4- to 12-membered non-aromatic heterocyclic group is azetidine-diyl, pyrrolidine-diyl, piperidine-diyl, azepane-diyl, piperazine-diyl, or a group represented by the formula:

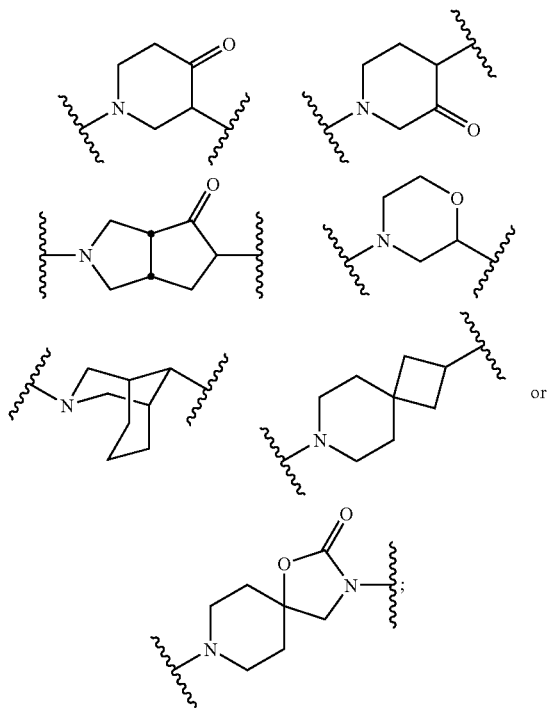

<4> a compound according to <1>, a salt of the compound or a hydrate of the foregoing, wherein $Z^1$ is a group represented by the formula:

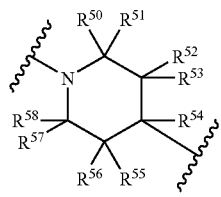
(II)

(wherein $R^{50}$, $R^{51}$, $R^{52}$, $R^{53}$, $R^{54}$, $R^{55}$, $R^{56}$, $R^{57}$ and $R^{58}$ each independently represent (1) hydrogen, (2) halogen, (3) cyano, (4) hydroxyl, (5) $C_{2-7}$ alkoxycarbonyl, (6) $C_{1-6}$ alkyl optionally substituted with 1 to 4 groups selected from the group consisting of hydroxyl, $C_{1-6}$ alkoxy and halogen, (7) $C_{1-6}$ alkoxy optionally substituted with 1 to 4 groups selected from the group consisting of hydroxyl, $C_{1-6}$ alkoxy and halogen, (8) 2-methylphenyloxymethyl or (9) 2-fluorophenyloxymethyl, wherein $R^{50}$ and $R^{51}$ may together form a carbonyl group, $R^{52}$ and $R^{53}$ may together form a carbonyl group and $R^{55}$ and $R^{56}$ may together form a carbonyl group);

<5> a compound according to <1>, a salt of the compound or a hydrate of the foregoing, wherein $Z^1$ is a group represented by the formula:

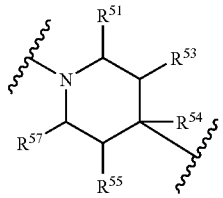

(wherein $R^{51}$, $R^{53}$, $R^{54}$, $R^{55}$ and $R^{57}$ have the same definitions as $R^{51}$, $R^{53}$, $R^{54}$, $R^{55}$ and $R^{57}$ in <4>);

<6> a compound according to <5>, a salt of the compound or a hydrate of the foregoing, wherein $R^{51}$, $R^{53}$, $R^{54}$, $R^{55}$ and $R^{57}$ each independently represent (1) hydrogen, (2) hydroxyl, (3) halogen, (4) alkyl, (5) cyano or (6) hydroxymethyl;

<7> a compound according to <5> or <6>, a salt of the compound or a hydrate of the foregoing, wherein at least one of $R^{51}$, $R^{53}$, $R^{54}$, $R^{55}$ and $R^{57}$ is not hydrogen;

<7-2> a compound according to <5> or <6>, a salt of the compound or a hydrate of the foregoing, wherein at least three of $R^{51}$, $R^{53}$, $R^{54}$, $R^{55}$ and $R^{57}$ are hydrogen atoms;

<8> a compound according to <5> or <6>, a salt of the compound or a hydrate of the foregoing, wherein at least four of $R^{51}$, $R^{53}$, $R^{54}$, $R^{55}$ and $R^{57}$ are hydrogen;

<9> a compound according to <5>, a salt of the compound or a hydrate of the foregoing, wherein all of $R^{51}$, $R^{53}$, $R^{54}$, $R^{55}$ and $R^{57}$ are hydrogen;

<10> a compound according to any one of <1> to <9>, a salt of the compound or a hydrate of the foregoing, wherein $X^1$ is a single bond, and $X^2$ is optionally substituted $C_{1-6}$ alkylene;

<11> a compound according to any one of <1> to <9>, a salt of the compound or a hydrate of the foregoing, wherein $X^1$ is a single bond, and $X^2$ is methylene, 1,2-ethylene or 1,1-ethylene;

<12> a compound according to any one of <1> to <11>, a salt of the compound or a hydrate of the foregoing, wherein —$X^3$—$X^4$— is methylene, oxygen, a single bond or a group represented by the formula:

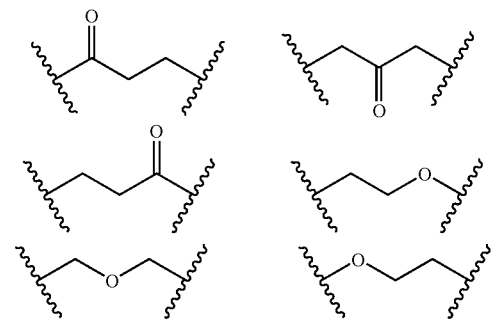

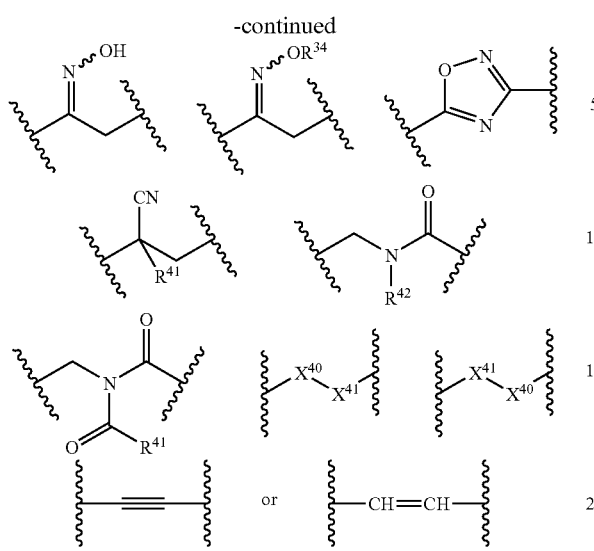

(wherein $X^{40}$ represents (1) methylene optionally having 1 or 2 groups selected from the group consisting of halogen, hydroxyl, $C_{1-6}$ alkyl, $C_{1-6}$ alkoxy and cyano, (2) oxygen, (3) —CO—, (4) —S—, (5) —S(O)— or (6) —S(O)$_2$—;

$X^{41}$ represents methylene optionally having 1 or 2 groups selected from the group consisting of halogen, hydroxyl, $C_{1-6}$ alkyl, $C_{1-6}$ alkoxy and cyano;

$R^{34}$ represents $C_{1-6}$ alkyl;

$R^{41}$ represents (1) phenyl optionally having 1 to 3 groups selected from the group consisting of halogen, hydroxyl, $C_{1-6}$ alkyl, $C_{1-6}$ alkoxy and cyano, (2) phenyl-$C_{1-6}$ alkyl optionally having 1 to 3 groups selected from the group consisting of halogen, hydroxyl, $C_{1-6}$ alkyl, $C_{1-6}$ alkoxy and cyano or (3) $C_{1-6}$ alkyl optionally having 1 to 3 groups selected from the group consisting of halogen, hydroxyl, $C_{1-6}$ alkoxy and cyano; and $R^{42}$ represents (1) $C_{1-6}$ alkyl optionally having 1 to 3 groups selected from the group consisting of halogen, hydroxyl, $C_{1-6}$ alkoxy and cyano or (2) hydrogen);

<13> a compound according to any one of <1> to <11>, a salt of the compound or a hydrate of the foregoing, wherein —$X^3$—$X^4$— is a group represented by the formula:

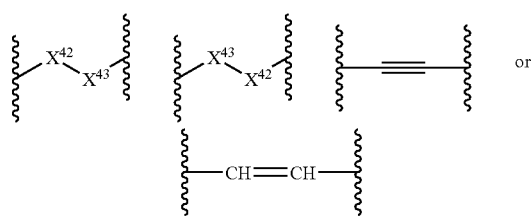

(wherein $X^{42}$ represents (1) methylene optionally having one group selected from the group consisting of halogen, hydroxyl, $C_{1-6}$ alkyl, $C_{1-6}$ alkoxy and cyano, (2) oxygen, (3) —CO—, (4) —S—, (5) —S(O)—, (6) —S(O)$_2$— or (7) —CF$_2$—, and $X^{43}$ represents either methylene optionally having one group selected from the group consisting of halogen, hydroxyl, $C_{1-6}$ alkyl, $C_{1-6}$ alkoxy and cyano, or —CF$_2$—);

<14> a compounds according to any one of <1> to <11>, a salt of the compound or a hydrate of the foregoing, wherein —$X^3$—$X^4$— is a group represented by the formula:

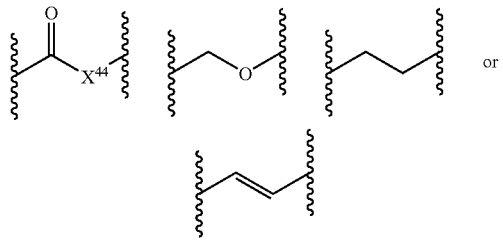

(wherein $X^{44}$ represents either methylene optionally having 1 group selected from the group consisting of fluorine, hydroxyl, $C_{1-6}$ alkyl, $C_{1-6}$ alkoxy and cyano);

<14-2> a compound according to any one of <1> to <11>, a salt of the compound or a hydrate of the foregoing, wherein —$X^3$—$X^4$— is a group represented by the formula:

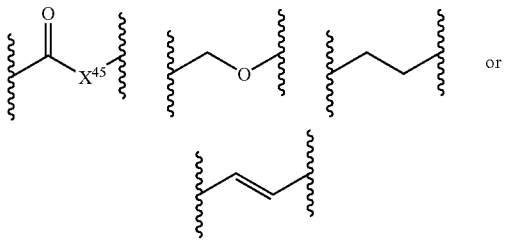

(wherein $X^{45}$ represents either methylene optionally having one group selected from the group consisting of fluorine, hydroxyl, $C_{1-6}$ alkyl, $C_{1-6}$ alkoxy and cyano, or —CF$_2$—);

<15> a compound according to any one of <1> to <11>, a salt of the compound or a hydrate of the foregoing, wherein —$X^3$—$X^4$— is a group represented by the formula:

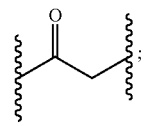

<16> a compound according to any one of <1> to <15>, a salt of the compound or a hydrate of the foregoing, wherein $A^2$ is phenyl optionally having 1 to 3 substituents selected from Substituent Group A below, 1-naphthyl optionally having 1 to 3 substituents selected from Substituent Group A below, 2-naphthyl optionally having 1 to 3 substituents selected from Substituent Group A below, a 5- to 10-membered aromatic heterocyclic group optionally having 1 to 3 substituents selected from Substituent Group A below, a 9- to 11-membered benzene fused ring group optionally having 1 to 3 substituents selected from Substituent Group A below or a 9- to 11-membered aromatic heterocycle fused ring group optionally having 1 to 3 substituents selected from Substituent Group A below;

<Substituent Group A>

The group consisting of $C_{1-6}$ alkyl optionally having 1 to 3 substituents selected from Substituent Group B below, $C_{1-6}$ alkoxy optionally having 1 to 3 substituents selected from Substituent Group B below, halogen, $C_{3-8}$ cycloalkyl, $C_{2-7}$ alkoxycarbonyl, $C_{2-7}$ acyl, $C_{1-6}$ alkylthio, $C_{1-6}$ alkylsulfinyl, $C_{1-6}$ alkylsulfonyl, cyano, nitro, phenyl, pyridyl, ethylenedioxy, methylenedioxy, a group represented by the formula:

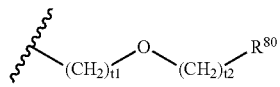

(wherein t1 and t2 each independently represent an integer of 0 to 3, and $R^{80}$ represents hydrogen, $C_{1-6}$ alkyl or $C_{3-8}$ cycloalkyl), and a group represented by the formula:

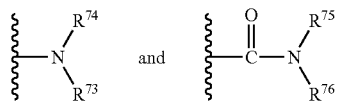

(wherein $R^{73}$ and $R^{74}$ each independently represent hydrogen, $C_{1-6}$ alkyl, $C_{2-7}$ acyl, $C_{1-6}$ alkylsulfonyl, —CO—NR$^{75}$R$^{76}$ or —CS—NR$^{75}$R$^{76}$, and $R^{75}$ and $R^{76}$ each independently represent hydrogen or $C_{1-6}$ alkyl);

<Substituent Group B>

The group consisting of halogen, $C_{1-6}$ alkoxy, cyano, hydroxyl and $C_{3-8}$ cycloalkyl;

<17> a compound according to any one of <1> to <15>, a salt of the compound or a hydrate of the foregoing, wherein $A^2$ is a monovalent group derived by removing a hydrogen atom from a compound represented by the formula:

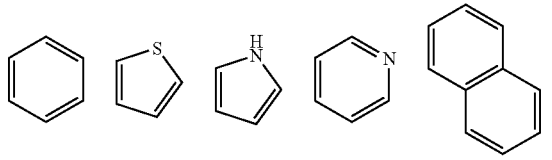
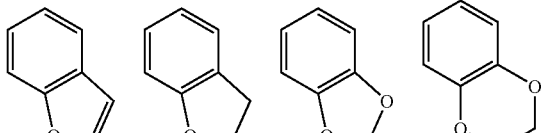
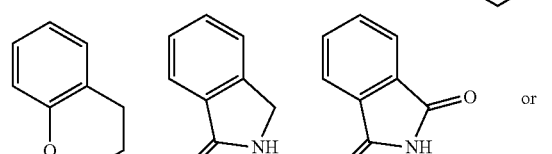
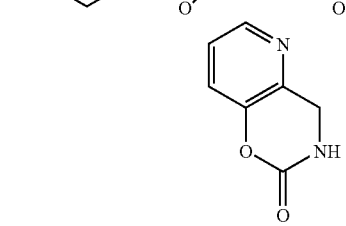

and $A^2$ optionally has 1 to 3 substituents selected from Substituent Group A in <16>;

<18> a compound according to any one of <1> to <15>, a salt of the compound or a hydrate of the foregoing, wherein $A^2$ is a monovalent group derived by removing a hydrogen atom from a compound represented by the formula:

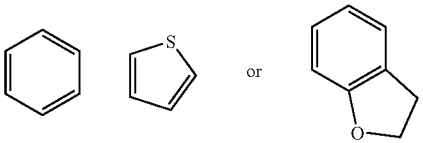

and $A^2$ optionally has 1 to 3 substituents selected from Substituent Group A in <16>;

<19> a compound according to any one of <16> to <18>, a salt of the compound or a hydrate of the foregoing, wherein Substituent Group A in <16> is the group consisting of halogen, $C_{1-6}$ alkyl optionally having 1 to 3 substituents selected from Substituent Group B in <16>, $C_{1-6}$ alkoxy optionally having 1 to 3 substituents selected from Substituent Group B in <16>, $C_{3-8}$ cycloalkyl, $C_{1-6}$ alkylthio and a group represented by the formula:

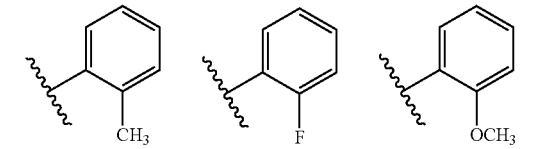

(wherein t1 and t2 each independently represent an integer of 0 to 3, and $R^{80}$ represents hydrogen, $C_{1-6}$ alkyl or $C_{3-8}$ cycloalkyl);

<20> a compound according to any one of <1> to <15>, a salt of the compound or a hydrate of the foregoing, wherein $A^2$ is a group represented by the formula:

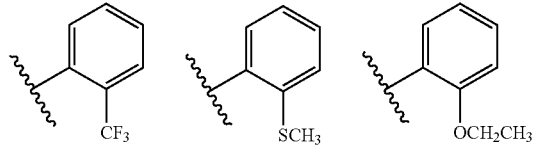

(wherein $R^{81}$ represents (1) $C_{1-6}$ alkyl optionally having 1 to 3 substituents selected from the group consisting of halogen, $C_{3-8}$ cycloalkyl and $C_{1-6}$ alkoxy, (2) $C_{1-6}$ alkoxy optionally having 1 to 3 substituents selected from the group consisting of halogen, $C_{3-8}$ cycloalkyl and $C_{1-6}$ alkoxy, (3) hydrogen, (4) $C_{1-6}$ alkylthio optionally having 1 to 3 substituents selected from the group consisting of halogen, $C_{3-8}$ cycloalkyl and $C_{1-6}$ alkoxy or (5) halogen);

<21> a compound according to any one of <1> to <15>, a salt of the compound or a hydrate of the foregoing, wherein $A^2$ is a group represented by the formula:

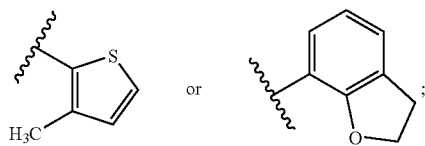

<22> a compound according to any one of <1> to <21>, a salt of the compound or a hydrate of the foregoing, wherein $A^1$ is a group represented by the formula:

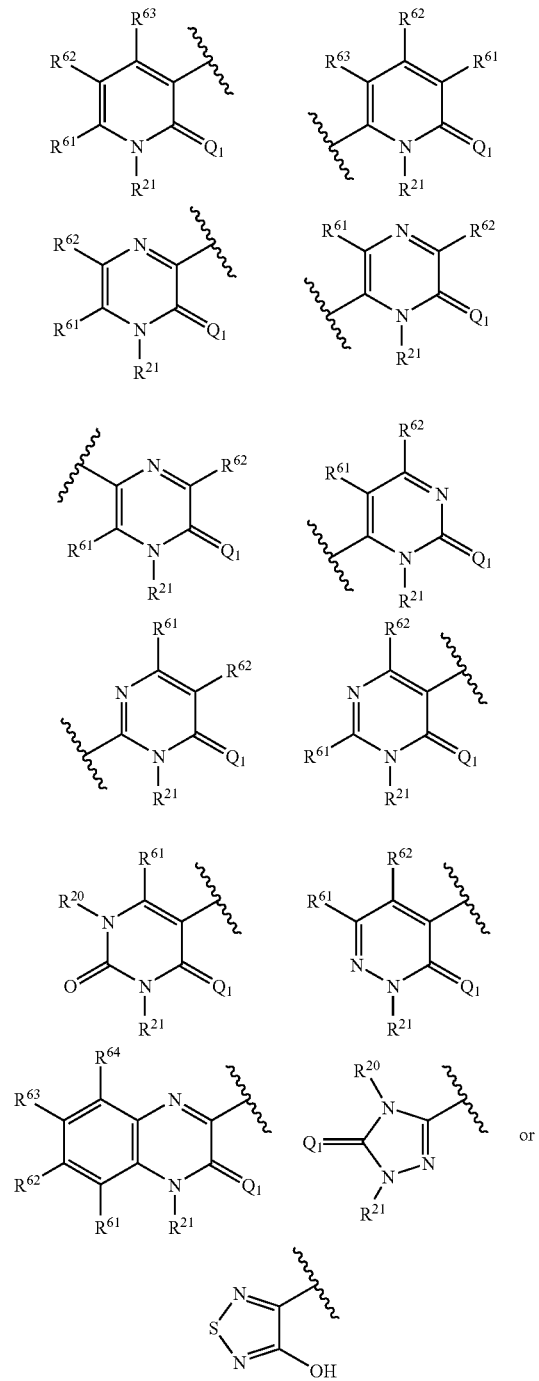

(wherein $R^{20}$ and $R^{21}$ each independently represent hydrogen or $C_{1-6}$ alkyl, $R^{61}$, $R^{62}$, $R^{63}$ and $R^{64}$ each independently represent hydrogen, halogen, optionally substituted $C_{1-6}$ alkoxy, optionally substituted $C_{1-6}$ alkyl or cyano, and $Q^1$ has the same definition as $Q^1$ in <1>);

<23> a compound according to any one of <1> to <21>, a salt of the compound or a hydrate of the foregoing, wherein $A^1$ is a group represented by the formula:

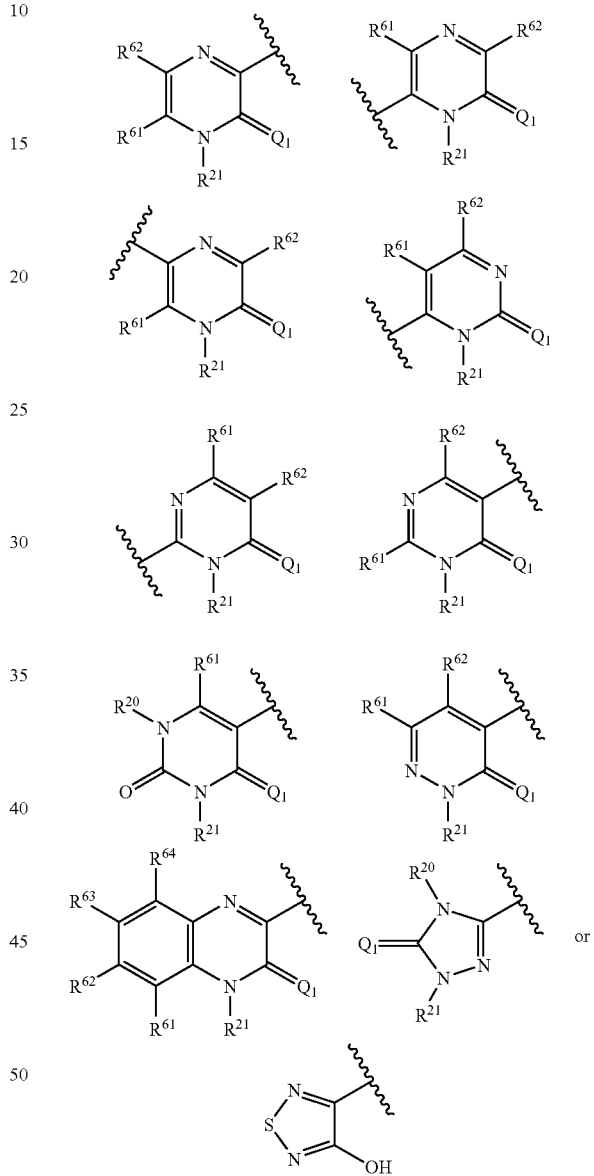

(wherein $R^{20}$ and $R^{21}$ each independently represent hydrogen or $C_{1-6}$ alkyl, $R^{61}$, $R^{62}$, $R^{63}$ and $R^{64}$ independently represent hydrogen, halogen, optionally substituted $C_{1-6}$ alkoxy, optionally substituted $C_{1-6}$ alkyl or cyano, and $Q^1$ has the same definition as $Q^1$ in <1>);

<24> a compound according to <22> or <23>, a salt of the compound or a hydrate of the foregoing, wherein $Q^1$ is oxygen;

<25> a compound according to any one of <1> to <21>, a salt of the compound or a hydrate of the foregoing, wherein $A^1$ is a group represented by the formula:

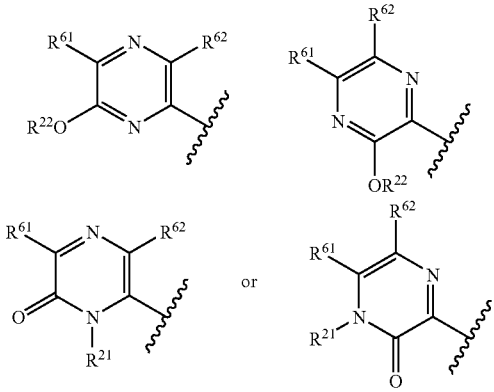

(wherein $R^{21}$, $R^{61}$ and $R^{62}$ have the same definitions as $R^{21}$, $R^{61}$ and $R^{62}$ in <22>, and $R^{22}$ represents hydrogen, $C_{1-6}$ alkyl, benzyl, p-methoxybenzyl or dimethoxybenzyl);

<26> a compound according to any one of <1> to <21>, a salt of the compound or a hydrate of the foregoing, wherein $A^1$ is a group represented by the formula:

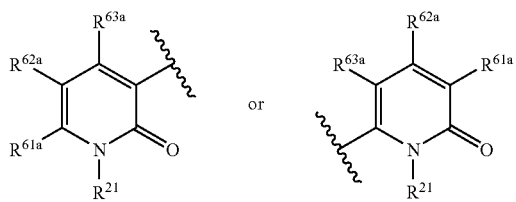

wherein $R^{21}$ represents hydrogen or $C_{1-6}$ alkyl, and $R^{61a}$, $R^{62a}$ and $R^{63a}$ each independently represent hydrogen, halogen, $C_{1-6}$ alkoxy, $C_{1-6}$ alkyl or cyano);

<27> a compound according to any one of <1> to <21>, a salt of the compound or a hydrate of the foregoing, wherein $A^1$ is a group represented by the formula:

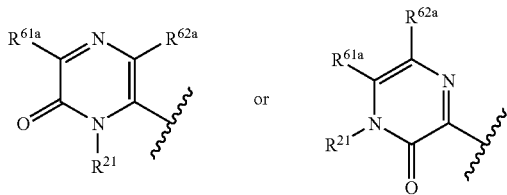

wherein $R^{21}$, $R^{61a}$ and $R^{62a}$ have the same definitions as $R^{21}$, $R^{61a}$ and $R^{62a}$ in <26>);

<28> a compound according to any one of <1> to <21>, a salt of the compound or a hydrate of the foregoing, wherein $A^1$ is a group represented by the formula:

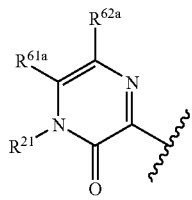

wherein $R^{21}$, $R^{61a}$ and $R^{62a}$ have the same definitions as $R^{21}$, $R^{61a}$ and $R^{62a}$ in <26>);

<29> a compound according to any one of <22> to <28>, a salt of the compound or a hydrate of the foregoing, wherein $R^{21}$ is hydrogen;

<30> a compound according to any one of <22> to <25>, a salt of the compound or a hydrate of the foregoing, wherein $R^{61a}$ and $R^{62}$ are hydrogen;

<31> a compound according to any one of <26> to <29>, a salt of the compound or a hydrate of the foregoing, wherein $R^{61a}$ and $R^{62a}$ are hydrogen;

<32> a compound according to <1>, a salt of the compound or a hydrate of the foregoing, wherein the compound is a compound selected from the group consisting of 6-[2-[4-(2-fluorophenoxymethyl)piperidino]ethyl]-1H-pyrazin-2-one, (E)-3-[4-[2-(3-methyl-2-thienyl)vinyl]piperidino]methyl-1H-pyrazin-2-one, 3-[4-[2-(2,3-dihydrobenzofuran-7-yl)ethyl]piperidino]methyl-1H-pyrazin-2-one, 3-[4-[2-(2-fluorophenyl)acetyl]piperidino]methyl-1H-pyrazin-2-one, 3-[4-[2-(2-methylphenyl)acetyl]piperidino]methyl-1H-pyrazin-2-one, 3-[4-[2-(2-methoxyphenyl)acetyl]piperidino]methyl-1H-pyrazin-2-one, 3-[4-[2-[2-(trifluoromethyl)phenyl]acetyl]piperidino]methyl-1H-pyrazin-2-one, 3-[4-[2-[2-fluoro-6-(trifluoromethyl)phenyl]acetyl]piperidino]methyl-1H-pyrazin-2-one, cis-3-[4-[2-(2-fluorophenyl)acetyl]-2-methylpiperidino]methyl-1H-pyrazin-2-one, 3-[4-[2-(2-fluorophenyl)acetyl]-4-methylpiperidino]methyl-1H-pyrazin-2-one, 3-[4-methyl-4-[2-[2-(trifluoromethyl)phenyl]acetyl]piperidino]methyl-1H-pyrazin-2-one, 3-[1-[4-[2-(2-fluorophenyl)acetyl]piperidino]ethyl]-1H-pyrazin-2-one, 3-[1-[4-[2-[2-(trifluoromethyl)phenyl]acetyl]piperidino]ethyl]-1H-pyrazin-2-one, 3-[4-(2-fluorophenoxymethyl)piperidino]methyl-1H-pyrazin-2-one, 3-[4-(2-methoxyphenoxymethyl)piperidino]methyl-1H-pyrazin-2-one, 3-[4-(2-methylphenoxymethyl)piperidino]methyl-1H-pyrazin-2-one, 3-[4-[2-(2-ethoxyphenyl)acetyl]piperidino]methyl-1H-pyrazin-2-one and 3-[4-[2-[2-(methylthio)phenyl]acetyl]piperidino]methyl-1H-pyrazin-2-one;

<33> a sodium channel inhibitor comprising a compound according to any one of <1> to <32>, a salt thereof or a hydrate of the foregoing;

<34> an analgesic agent comprising a compound according to any one of <1> to <32>, a salt thereof or a hydrate of the foregoing;

<35> a therapeutic or prophylactic agent for neuralgia comprising a compound according to any one of <1> to <32>, a salt thereof or a hydrate of the foregoing;

<36> a therapeutic or prophylactic agent for diabetic neuralgia, HIV neuralgia, postherpetic neuralgia, trigeminal neuralgia, stump pain, post spinal injury pain, thalamic pain or post-stroke pain, comprising a compound according to any one of <1> to <32>, a salt thereof or a hydrate of the foregoing;

<37> a therapeutic or prophylactic agent for pain or neuropathy, comprising a compound according to any one of <1> to <32>, a salt thereof or a hydrate of the foregoing;

<38> a therapeutic or prophylactic agent for low back pain, radiculopathy, inflammatory pain, arthralgia, postoperative pain, cancer pain, acute cerebrovascular disorder-induced neuropathy, cranial injury-induced neuropathy, spinal injury-induced neuropathy, Parkinson's disease, multiple sclerosis, epilepsy, insomnia, premature ejaculation or manic-depressive psychosis, comprising a compound according to any one of <1> to <32>, a salt thereof or a hydrate of the foregoing;

<39> a therapeutic or prophylactic method for a disease or neuralgia for which sodium channel inhibition is effective, comprising administering to a patient, a pharmacologically effective dose of a compound according to any one of <1> to <32>, a salt thereof or a hydrate of the foregoing;

<40> the use of a compound according to any one of <1> to <32>, a salt thereof or a hydrate of the foregoing for the manufacture of a therapeutic or prophylactic agent for a disease or neuralgia for which sodium channel inhibition is effective.

DETAILED DESCRIPTION OF THE INVENTION

The invention will now be explained in detail.

Many of the structural formulas for the compounds throughout the present specification represent only one isomeric form for convenience, but the invention encompasses any and all of the geometric isomers as well as optical isomers based on asymmetric carbons, stereoisomers and tautomers, and mixtures of those isomers, which are implied by the structures of the compounds, without being limited to any of the formulas shown for convenience. The compounds of the invention therefore include all those having asymmetric carbons therein and existing in optically active or racemic form, with no particular restrictions on the invention. There are also no restrictions when polymorphic crystalline forms thereof exist, and the compounds may be in one crystalline form or a mixture of different crystalline forms, while anhydrides and hydrates of the compounds of the invention are also included. Also encompassed within the scope of the invention are metabolic products of the compounds of the invention, produced by decomposition of the compounds in the body.

The definitions of the terms and symbols used throughout the present specification will now be explained for more detailed description of the invention.

The term "$C_{1-6}$ alkyl" as used throughout the present specification refers to a $C_{1-6}$ linear or branched alkyl group which is a monovalent group derived by removing a hydrogen atom from a $C_{1-6}$ aliphatic hydrocarbon, and as specific examples there may be mentioned methyl, ethyl, 1-propyl, 2-propyl, 2-methyl-1-propyl, 2-methyl-2-propyl, 1-butyl, 2-butyl, 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,3-dimethyl-1-butyl, 3,3-dimethyl-1-butyl, 2,2-dimethyl-1-butyl, 2-ethyl-1-butyl, 3,3-dimethyl-2-butyl, 2,3-dimethyl-2-butyl, and the like.

The term "$C_{2-6}$ alkenyl" as used throughout the present specification refers to a $C_{2-6}$ linear or branched alkenyl group, and as specific examples there may be mentioned vinyl, allyl, 1-propenyl, 2-propenyl, 1-butenyl, 2-butenyl, 3-butenyl, pentenyl, hexenyl, and the like.

The term "$C_{2-6}$ alkynyl" as used throughout the present specification refers to a $C_{2-6}$ linear or branched alkynyl group, and as specific examples there may be mentioned ethynyl, 1-propynyl, 2-propynyl, butynyl, pentynyl, hexynyl, and the like.

The term "$C_{3-8}$ cycloalkyl" as used throughout the present specification refers to a $C_{3-8}$ cyclic aliphatic hydrocarbon group, and as specific examples there may be mentioned cyclopropyl, cyclobutyl, cyclopentyl, cyclohexyl, cycloheptyl, cyclooctyl, and the like.

The term "$C_{1-6}$ alkylene" as used throughout the present specification refers to a divalent group derived by further removing a hydrogen atom from the aforementioned "$C_{1-6}$ alkyl" group, and as specific examples there may be mentioned methylene, 1,2-ethylene, 1,1-ethylene, 1,3-propylene, tetramethylene, pentamethylene, hexamethylene, and the like.

The term "$C_{2-6}$ alkenylene" as used throughout the present specification refers to a divalent group derived by further removing a hydrogen atom from the aforementioned "$C_{2-6}$ alkenyl" group, and as specific examples there may be mentioned vinylene, propenylene, butenylene, pentenylene, hexenylene, and the like.

The term "$C_{2-6}$ alkynylene" as used throughout the present specification refers to a divalent group derived by further removing a hydrogen atom from the aforementioned "$C_{2-6}$ alkynyl" group, and as specific examples there may be mentioned ethynylene, propynylene, butynylene, pentynylene, hexynylene, and the like.

The term "$C_{3-8}$ cycloalkylene" as used throughout the present specification refers to a divalent group derived by further removing a hydrogen atom from the aforementioned "$C_{3-8}$ cycloalkyl" group.

The term "$C_{1-6}$ alkoxy" as used throughout the present specification refers to a group having an oxy group bonded to the aforementioned "$C_{1-6}$ alkyl" group, and as specific examples there may be mentioned methoxy, ethoxy, 1-propyloxy, 2-propyloxy, 2-methyl-1-propyloxy, 2-methyl-2-propyloxy, 1-butyloxy, 2-butyloxy, 1-pentyloxy, 2-pentyloxy, 3-pentyloxy, 2-methyl-1-butyloxy, 3-methyl-1-butyloxy, 2-methyl-2-butyloxy, 3-methyl-2-butyloxy, 2,2-dimethyl-1-propyloxy, 1-hexyloxy, 2-hexyloxy, 3-hexyloxy, 2-methyl-1-pentyloxy, 3-methyl-1-pentyloxy, 4-methyl-1-pentyloxy, 2-methyl-2-pentyloxy, 3-methyl-2-pentyloxy, 4-methyl-2-pentyloxy, 2-methyl-3-pentyloxy, 3-methyl-3-pentyloxy, 2,3-dimethyl-1-butyloxy, 3,3-dimethyl-1-butyloxy, 2,2-dimethyl-1-butyloxy, 2-ethyl-1-butyloxy, 3,3-dimethyl-2-butyloxy, 2,3-dimethyl-2-butyloxy, and the like.

The term "$C_{1-6}$ alkylthio" as used throughout the present specification refers to a group having a thio group bonded to the aforementioned "$C_{1-6}$ alkyl" group, and as specific examples there may be mentioned methylthio, ethylthio, 1-propylthio, 2-propylthio, butylthio, pentylthio, and the like.

The term "$C_{1-6}$ alkylsulfinyl" as used throughout the present specification refers to a group having a sulfinyl group bonded to the aforementioned "$C_{1-6}$ alkyl" group, and as specific examples there may be mentioned methylsulfinyl, ethylsulfinyl, 1-propylsulfinyl, 2-propylsulfinyl, butylsulfinyl, pentylsulfinyl, and the like.

The term "$C_{1-6}$ alkylsulfonyl" as used throughout the present specification refers to a group having a sulfonyl group bonded to the aforementioned "$C_{1-6}$ alkyl" group, and as specific examples there may be mentioned methylsulfonyl, ethylsulfonyl, 1-propylsulfonyl, 2-propylsulfonyl, butylsulfonyl, pentylsulfonyl, and the like.

The term "$C_{2-7}$ acyl" as used throughout the present specification refers to a group having a carbonyl group bonded to the aforementioned "$C_{1-6}$ alkyl" group, and as specific examples there may be mentioned acetyl, propionyl, isopropionyl, butyryl, isobutyryl, valeryl, isovaleryl, pivaloyl, and the like.

The term "$C_{2-7}$ alkoxycarbonyl" as used throughout the present specification refers to a group having a carbonyl group bonded to the aforementioned "$C_{1-6}$ alkoxy" group, and as specific examples there may be mentioned methoxycarbonyl, ethoxycarbonyl, 1-propyloxycarbonyl, 2-propyloxycarbonyl, and the like.

The term "halogen atom" as used throughout the present specification refers to fluorine, chlorine, bromine or iodine.

The term "hetero atom" as used throughout the present specification refers to sulfur, oxygen or nitrogen.

The term "5- to 10-membered aromatic heterocycle" as used throughout the present specification refers to an aromatic ring having 5 to 10 atoms in the ring and containing one or more hetero atoms among the atoms of the ring, and as specific examples there may be mentioned pyridine, thiophene, furan, pyrrole, oxazole, isoxazole, thiazole, isothiazole, imidazole, triazole, pyrazole, furazan, thiadiazole, oxadiazole, pyridazine, pyrimidine, pyrazine, triazine, indole, isoindole, indazole, chromene, quinoline, isoquinoline, cinnoline, quinazoline, quinoxaline, naphthylidine, phthalazine, purine, pteridine, thienofuran, imidazothiazole, benzofuran, benzothiophene, benzoxazole, benzothiazole, benzothiadiazole, benzimidazole, imidazopyridine, pyrrolopyridine, pyrrolopyrimidine, pyridopyrimidine, and the like.

The term "5- to 10-membered aromatic heterocyclic group" as used throughout the present specification refers to a monovalent or divalent group derived by removing 1 or 2 hydrogen atoms from any desired position of the aforementioned "5- to 10-membered aromatic heterocycle".

The term "monocyclic 4- to 8-membered non-aromatic heterocycle" as used throughout the present specification refers to (1) a monocyclic non-aromatic ring, (2) having 4 to 8 atoms in the ring, (3) containing 1 or 2 hetero atoms among the atoms of the ring, (4) optionally including 1 or 2 double bonds in the ring, and (5) optionally including 1 to 3 carbonyl groups in the ring.

As specific examples of monocyclic 4- to 8-membered non-aromatic heterocycles there may be mentioned azetidine, pyrrolidine, piperidine, azepane, azocane, tetrahydrofuran, tetrahydropyran, morpholine, thiomorpholine, piperazine, thiazolidine, dioxane, imidazoline, thiazoline, and the like.

The term "monocyclic 4- to 8-membered non-aromatic heterocyclic group" as used throughout the present specification refers to a monovalent or divalent group derived by removing 1 or 2 hydrogen atoms from any desired position of the aforementioned "monocyclic 4- to 8-membered non-aromatic heterocycle".

The term "bicyclic 6- to 12-membered hydrocarbon ring" as used throughout the present specification refers to a bicyclic hydrocarbon ring having 6 to 12 carbons composing the ring, and specific examples thereof include (1) hydrocarbon rings represented by the formula:

wherein $M^{1a}$, $M^{2a}$, $M^{3a}$ each independently represent —(CH$_2$)$_{m1}$— (wherein m1 is an integer of 0 to 2), with the proviso that $M^{1a}$, $M^{2a}$ and $M^{3a}$ are not all —(CH$_2$)$_0$—), (2) hydrocarbon rings represented by the formula:

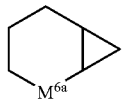

wherein $M^{6a}$ represents —(CH$_2$)$_{m3}$— (wherein m3 is an integer of 0 to 3)), and (3) hydrocarbon rings represented by the formula:

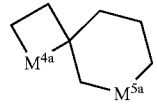

wherein $M^{4a}$, $M^{5a}$ each independently represent —(CH$_2$)$_{m2}$— (wherein m2 is an integer of 0 to 3)).

As specific examples of such a "bicyclic 6- to 12-membered hydrocarbon ring" there may be mentioned bicyclo[3.1.0]hexane, bicyclo[4.1.0]heptane, spiro[2.4]heptane, spiro[2.5]octane, bicyclo[4.4.0]decane, bicyclo[4.3.0]nonane, bicyclo[3.3.1]nonane, bicyclo[3.2.1]octane, spiro[4.5]decane, spiro[3.5]nonane, norbornane, bicyclo[2.1.0]pentane, bicyclo[3.3.0]octane, bicyclo[2.2.2]octane, bicyclo[3.3.3]undecane, and the like.

As preferred examples of the "bicyclic 6- to 12-membered hydrocarbon ring" there may be mentioned bicyclo[4.4.0]decane, bicyclo[4.3.0]nonane, bicyclo[3.3.1]nonane, bicyclo[3.2.1]octane, spiro[4.5]decane, spiro[3.5]nonane, bicyclo[3.3.0]octane, and the like.

The term "bicyclic 6- to 12-membered non-aromatic heterocycle" as used throughout the present specification refers to (1) a bicyclic non-aromatic ring, (2) having 6 to 12 atoms in the ring, (3) containing 1 to 3 hetero atoms among the atoms of the ring, (4) optionally including 1 double bond in the ring, and (5) optionally including 1 to 3 carbonyl groups in the ring.

That is, a "bicyclic 6- to 12-membered non-aromatic heterocycle" is a ring formed by replacing any 1 to 3 methine or methylene groups in the ring of the aforementioned "bicyclic 6- to 12-membered hydrocarbon ring" with oxygen, sulfur, nitrogen or —NH—.

The term "bicyclic 6- to 12-membered non-aromatic heterocyclic group" as used throughout the present specification refers to a divalent group derived by removing any 2 hydrogen atoms from the aforementioned "bicyclic 6- to 12-membered non-aromatic heterocycle".

The term "monocyclic or bicyclic 4- to 12-membered non-aromatic heterocyclic group" as used throughout the present specification refers to the aforementioned "monocyclic 4- to 8-membered non-aromatic heterocyclic group" or the aforementioned "bicyclic 6- to 12-membered non-aromatic heterocyclic group".

The term "monocyclic 5- to 7-membered carbon ring" as used throughout the present specification refers to (1) a monocyclic ring, (2) having 5 to 7 atoms in the ring, (3) wherein all of the atoms of the ring are carbon atoms, (4) optionally including 1 or 2 double bonds in the ring, and (5) optionally including 1 to 3 carbonyl groups in the ring.

As specific examples of monocyclic 5- to 7-membered carbon rings there may be mentioned cyclopentane, cyclohexane, cycloheptane, cyclopentene, cyclohexene, cyclopentanone or cyclohexanone, and the like.

The term "9- to 11-membered benzene fused ring" as used throughout the present specification refers to a ring composed of 9 to 11 atoms, formed by fusing a 5- to 7-membered non-aromatic heterocycle or monocyclic 5- to 7-membered carbon ring with benzene. Here, a "5- to 7-membered non-aromatic heterocycle" refers to the "monocyclic 4- to 8-membered non-aromatic heterocycle" mentioned above which has 5 to 7 atoms composing the ring.

Specific examples of 9- to 11-membered benzene fused rings include rings represented by the formula:

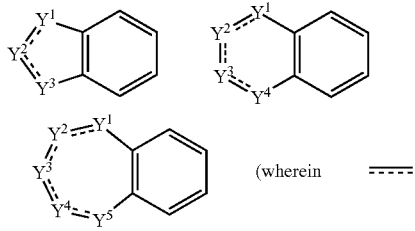

(wherein ----- represents a single bond or a double bond, and $Y^1$, $Y^2$, $Y^3$, $Y^4$ and $Y^5$ each independently represent carbonyl, oxygen, sulfur, nitrogen, methylene, methine or —$NR^{34}$— (wherein $R^{34}$ represents hydrogen or $C_{1-6}$ alkyl)), preferably rings represented by the formula:

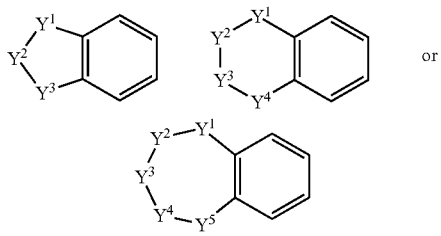

(wherein $Y^1$, $Y^2$, $Y^3$, $Y^4$ and $Y^5$ each represent carbonyl, oxygen, sulfur, methylene or —$NR^{34}$— (wherein $R^{34}$ represents hydrogen or $C_{1-6}$ alkyl)), and more preferably rings represented by the formula:

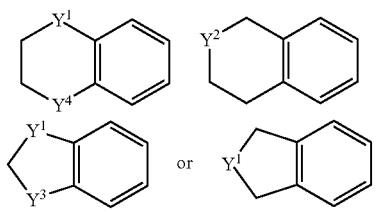

(wherein $Y^1$, $Y^2$, $Y^3$ and $Y^4$ have the same respective definitions as above).

The term "9- to 11-membered benzene fused ring group" as used throughout the present specification refers to a monovalent group derived by removing 1 hydrogen atom from any desired position of the aforementioned "9- to 11-membered benzene-fused ring".

The term "9- to 11-membered aromatic heterocycle-fused ring" as used throughout the present specification refers to a bicyclic ring composed of 9 to 11 atoms, formed by fusing the aforementioned "5- to 7-membered non-aromatic heterocycle" or "monocyclic 5- to 7-membered carbon ring" with a "5- to 6-membered aromatic heterocycle" such as pyridine, thiophene, furan or the like.

The term "9- to 11-membered aromatic heterocycle fused ring group" as used throughout the present specification refers to a monovalent group derived by removing 1 hydrogen atom from any desired position of the aforementioned "9- to 11-membered aromatic heterocycle fused ring".

The term "5-membered heterocycle containing —C(=$Q^1$)- and a nitrogen atom" as used throughout the present specification refers to a ring represented by the formula:

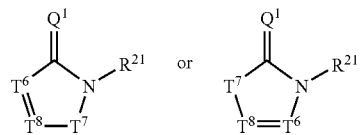

(wherein $Q^1$ has the same definition as above, $T^6$ and $T^8$ each independently represent methine or nitrogen, $T^7$ represents methylene, oxygen, sulfur or —$NR^{20}$—, and $R^{20}$ and $R^{21}$ each independently represent hydrogen or $C_{1-6}$ alkyl), and preferably a ring represented by the formula:

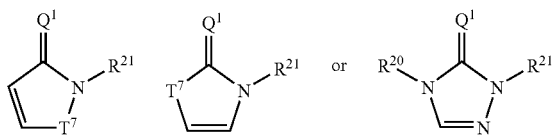

(wherein $Q^1$, $T^7$, $R^{20}$ and $R^{21}$ have the same respective definitions as above).

The term "6-membered heterocycle containing —C(=$Q^1$)- and a nitrogen atom" as used throughout the present specification refers to a ring represented by the formula:

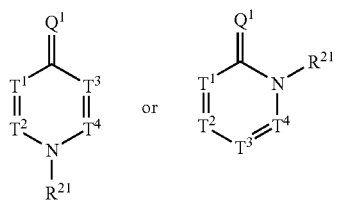

(wherein $Q^1$ has the same definition as above, $T^1$, $T^2$, $T^3$ and $T^4$ each independently represent methine or nitrogen, and $R^{21}$ represents hydrogen or $C_{1-6}$ alkyl), preferably a ring represented by the formula:

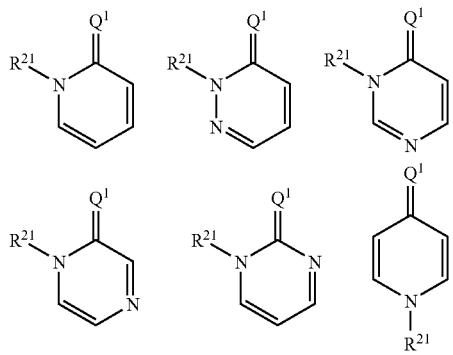

-continued

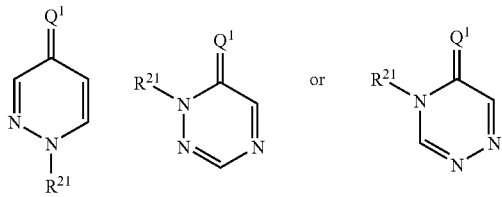

(wherein $Q^1$ and $R^{21}$ have the same respective definitions as above), more preferably a ring represented by the formula:

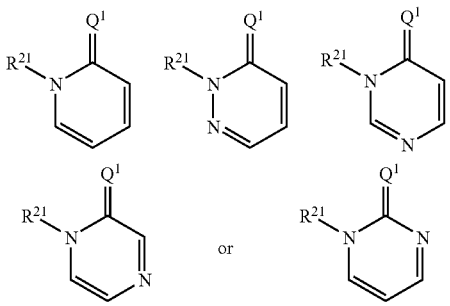

(wherein $Q^1$ and $R^{21}$ have the same respective definitions as above), and even more preferably a ring represented by the formula:

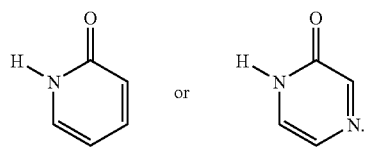

The term "7-membered heterocycle containing —C(=$Q^1$)- and a nitrogen atom" as used throughout the present specification refers to a ring represented by the formula:

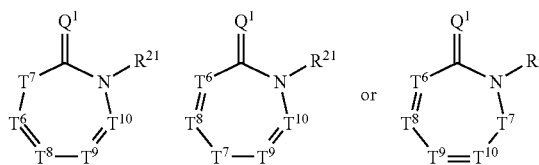

(wherein $Q^1$, $R^{20}$ and $R^{21}$ have the same definitions as above, $T^6$, $T^8$, $T^9$ and $T^{10}$ each independently represent methine or nitrogen, and $T^7$ represents methylene, oxygen, sulfur or —$NR^{20}$—)

The term "5-membered heterocyclic group containing —C(=$Q^1$)- and a nitrogen atom" as used throughout the present specification refers to a monovalent group derived by removing 1 hydrogen atom from any desired position of the aforementioned "5-membered heterocycle containing —C(=$Q^1$)- and a nitrogen atom".

The term "6-membered heterocyclic group containing —C(=$Q^1$)- and a nitrogen atom" as used throughout the present specification refers to a monovalent group derived by removing 1 hydrogen atom from any desired position of the aforementioned "6-membered heterocycle containing —C(=$Q^1$)- and a nitrogen atom".

The term "7-membered heterocyclic group containing —C(=$Q^1$)- and a nitrogen atom" as used throughout the present specification refers to a monovalent group derived by removing 1 hydrogen atom from any desired position of the aforementioned "7-membered heterocycle containing —C(=$Q^1$)- and a nitrogen atom".

The term "5- to 7-membered heterocyclic group containing —C(=$Q^1$)- and a nitrogen atom" as used throughout the present specification refers to a cyclic group having 5 to 7 atoms composing the ring of the cyclic group, containing —(C=$Q^1$)- in the ring, and including 1 to 5 hetero atoms among the atoms composing the ring of the cyclic group, and such a group is the aforementioned "5-membered heterocyclic group containing —C(=$Q^1$)- and a nitrogen atom", "6-membered heterocyclic group containing —C(=$Q^1$)- and a nitrogen atom" or "7-membered heterocyclic group containing —C(=$Q^1$)- and a nitrogen atom".

The formula:

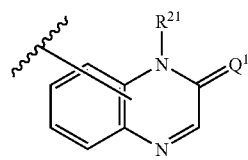

as used throughout the present specification refers to a group represented by the formula:

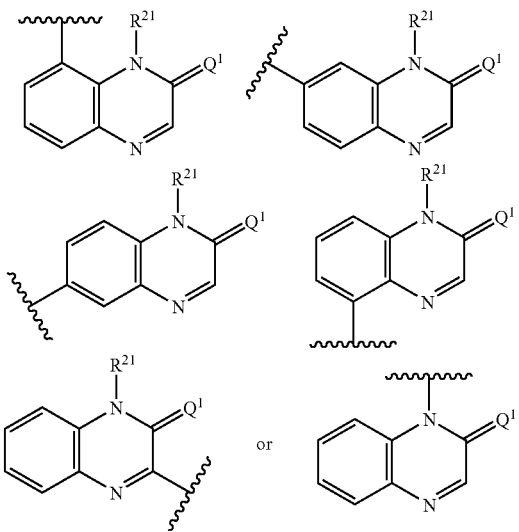

(wherein $Q^1$ and $R^{21}$ have the same definitions as above), and preferably a group represented by the formula:

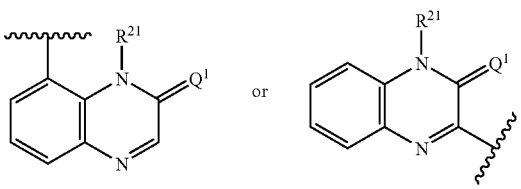

(wherein $Q^1$ and $R^{21}$ have the same definitions as above).

The formula:

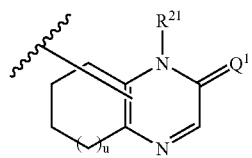

as used throughout the present specification refers to a group represented by the formula:

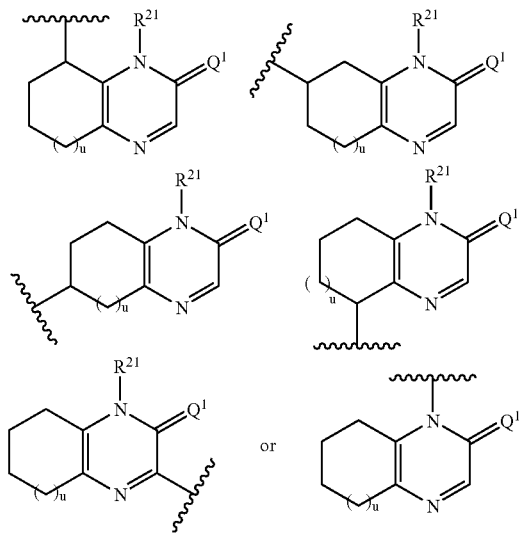

(wherein $Q^1$, $R^{21}$ and u have the same respective definitions as above), and preferably a group represented by the formula:

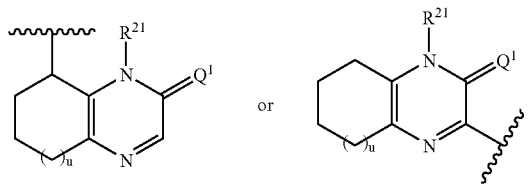

(wherein $Q^1$, $R^{21}$ and u have the same respective definitions as above).

The phrase "5- to 10-membered aromatic heterocyclic group having at least one group selected from the group consisting of optionally substituted $C_{1-6}$ alkoxy groups, $C_{1-6}$ alkylthio groups, hydroxyl, mercapto and —$NR^{13}R^{14}$ (wherein $R^{13}$ and $R^{14}$ each independently represent hydrogen or $C_{1-6}$ alkyl), and also having other optional substituents" as used throughout the present specification refers to the aforementioned "5- to 10-membered aromatic heterocyclic group" having at least one group selected from the group consisting of optionally substituted $C_{1-6}$ alkoxy groups, $C_{1-6}$ alkylthio groups, hydroxyl, mercapto and —$NR^{13}R^{14}$ (wherein $R^{13}$ and $R^{14}$ each independently represent hydrogen or $C_{1-6}$ alkyl).

Specifically, this refers to a monovalent group derived by removing 1 hydrogen atom from any desired position of a ring represented by the formula:

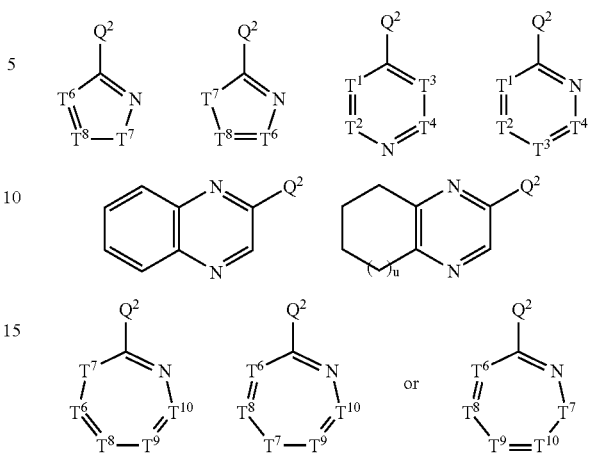

(wherein $T^1$, $T^2$, $T^3$, $T^4$, $T^6$, $T^7$, $T^8$, $T^9$ and $T^{10}$ have the same respective definitions as above, and $Q^2$ represents optionally substituted $C_{1-6}$ alkoxy, $C_{1-6}$ alkylthio, hydroxyl, mercapto or —$NR^{13}R^{14}$ (wherein $R^{13}$ and $R^{14}$ represent hydrogen or $C_{1-6}$ alkyl)), preferably a monovalent group derived by removing 1 hydrogen atom from any desired position of a ring represented by the formula:

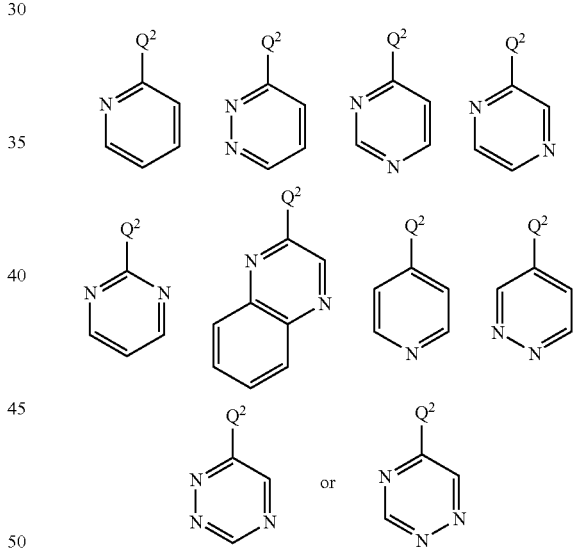

(wherein $Q^2$ has the same definition as above), more preferably a monovalent group derived by removing 1 hydrogen atom from any desired position of a ring represented by the formula:

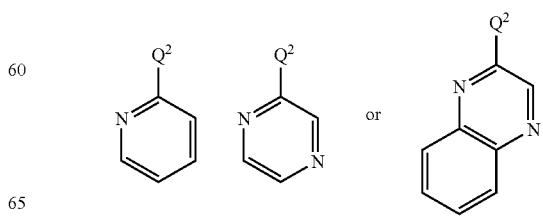

(wherein $Q^2$ has the same definition as above), and even more preferably a monovalent group derived by removing 1 hydrogen atom from any desired position of a ring represented by the formula:

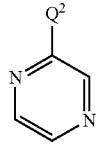

(wherein $Q^2$ has the same definition as above).

The term "piperidine-diyl" as used throughout the present specification refers to a divalent group derived by removing 2 hydrogen atoms from any desired positions of piperidine, and specific examples include groups represented by the formula:

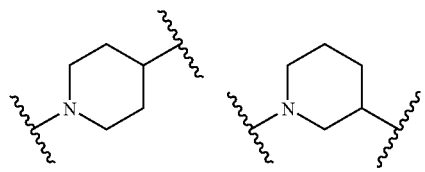

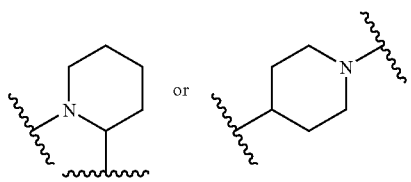

The term "azetidine-diyl" as used throughout the present specification refers to a divalent group derived by removing 2 hydrogen atoms from any desired positions of azetidine.

The term "pyrrolidine-diyl" as used throughout the present specification refers to a divalent group derived by removing 2 hydrogen atoms from any desired positions of pyrrolidine.

The term "azepane-diyl" as used throughout the present specification refers to a divalent group derived by removing 2 hydrogen atoms from any desired positions of azepane.

The term "piperazine-diyl" as used throughout the present specification refers to a divalent group derived by removing 2 hydrogen atoms from any desired positions of piperazine.

The phrase "phenyl-$C_{1-6}$ alkyl group optionally having 1 to 3 substituents selected from the group consisting of hydroxyl, $C_{1-6}$ alkoxy, $C_{1-6}$ alkyl, amino, halogen and cyano" as used throughout the present specification refers to phenyl-bonded $C_{1-6}$ alkyl groups optionally having 1 to 3 substituents selected from the group consisting of hydroxyl, $C_{1-6}$ alkoxy, $C_{1-6}$ alkyl, amino, halogen and cyano.

The phrase "phenyloxy-$C_{1-6}$ alkyl group optionally having 1 to 3 substituents selected from the group consisting of hydroxyl, $C_{1-6}$ alkoxy, $C_{1-6}$ alkyl, amino, halogen and cyano" as used throughout the present specification refers to phenyloxy-bonded $C_{1-6}$ alkyl groups optionally having 1 to 3 substituents selected from the group consisting of hydroxyl, $C_{1-6}$ alkoxy, $C_{1-6}$ alkyl, amino, halogen and cyano.

The phrase "General formula (I):

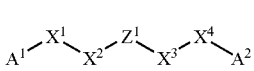

wherein $Z^1$ is a group represented by the formula:

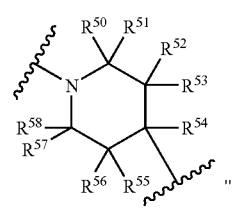

as used throughout the present specification means that general formula (I) is represented by the formula:

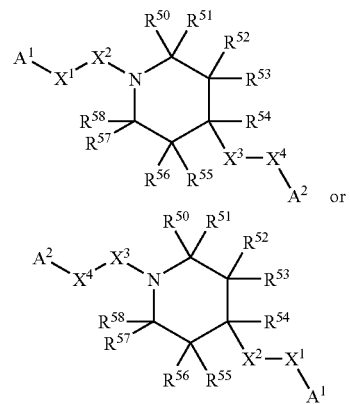

and preferably by the formula:

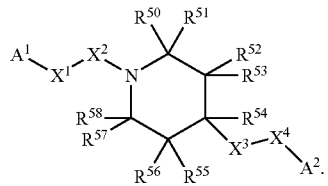

The phrase "General formula (I):

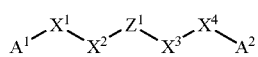

wherein $Z^1$ is a group represented by the formula:

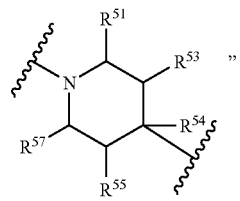

as used throughout the present specification means that formula (I) is represented by the formula:

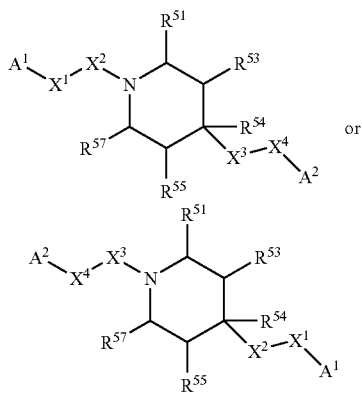

and preferably by the formula:

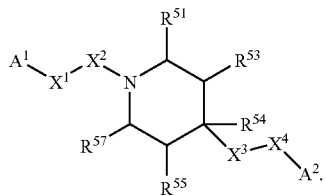

The term "optionally having . . . substituents" as used throughout the present specification means that the group may have one or more substituents in any desired combination at substitutable positions. As specific examples of such substituents there may be mentioned the following:
(1) halogen,
(2) hydroxyl,
(3) thiol,
(4) nitro,
(5) cyano,
(6) formyl,
(7) carboxyl,
(8) trifluoromethyl,
(9) trifluoromethoxy,
(10) amino, and
(11) -$T^{1x}$-$T^{2x}$ (wherein $T^{1x}$ represents a single bond, $C_{1-6}$ alkylene, oxygen, —CO—, —S—, —S(O)—, —S(O)$_2$—, —O—CO—, —CO—O—, —NR$^T$—, —CO—NR$^T$—, —NR$^T$—CO—, —SO$_2$—NR$^T$—, —NR$^T$—SO$_2$—, —NH—CO—NR$^T$— or —NH—CS—NR$^T$—,
$T^{2x}$ represents hydrogen, $C_{1-6}$ alkyl, $C_{3-8}$ cycloalkyl, $C_{2-6}$ alkenyl, $C_{2-6}$ alkynyl, phenyl, 1-naphthyl, 2-naphthyl, a 5- to 10-membered aromatic heterocyclic group or a monocyclic 4- to 8-membered non-aromatic heterocyclic group, and
$R^T$ represents hydrogen, $C_{1-6}$ alkyl, $C_{3-8}$ cycloalkyl, $C_{2-6}$ alkenyl or $C_{2-6}$ alkynyl,
with the proviso that $T^{2x}$ and $R^T$ may each independently have 1 to 3 groups selected from Substituent Group T below.

<Substituent Group T>
The group consisting of hydroxyl, cyano, halogen, $C_{1-6}$ alkyl, $C_{3-8}$ cycloalkyl, $C_{2-6}$ alkenyl, $C_{2-6}$ alkynyl, phenyl, 1-naphthyl, 2-naphthyl, a 5- to 10-membered aromatic heterocyclic group, a monocyclic 4- to 8-membered non-aromatic heterocyclic group, $C_{1-6}$ alkoxy, $C_{1-6}$ alkylthio, $C_{2-7}$ alkoxycarbonyl, etc.

The term "salt" as used throughout the present specification is not particularly restrictive so long as it is a salt of the compound of the invention and pharmacologically acceptable, and examples thereof include an inorganic acid salt, an organic acid salt, an inorganic base salt, an organic base salt, and an acidic or basic amino acid salt.

As preferred examples of an inorganic acid salt there may be mentioned hydrochloride, hydrobromide, sulfate, nitrate and phosphate, and as preferred examples of organic acid salts there may be mentioned acetate, succinate, fumarate, maleate, tartrate, citrate, lactate, stearate, benzoate, methanesulfonate and p-toluenesulfonate.

As preferred examples of an inorganic base salt there may be mentioned an alkaline metal salt such as a sodium salt and a potassium salt, an alkaline earth metal salt such as a calcium salt and a magnesium salt, an aluminum salt and an ammonium salt, and as preferred examples of an organic base salt there may be mentioned a diethylamine salt, a diethanolamine salt, a meglumine slat and a N,N'-dibenzylethylenediamine salt.

As preferred examples of an acidic amino acid salt there may be mentioned aspartate and glutamate, and as preferred examples of a basic amino acid salt there may be mentioned an arginine salt, a lysine salt and an ornithine salt.

Representative production schemes for compounds represented by general formula (I) above according to the invention will now be presented.

In the following production schemes, 1 represents an integer of 0 to 2, m represents an integer of 0 to 2, n represents an integer of 0 to 4, p represents an integer of 0 to 3, q represents an integer of 0 to 3, and r represents an integer of 0 to 2.

Met$^{x1}$ represents lithium, sodium, potassium, —Mg—Br, etc., Met$^{x2}$ represents —Zn—R, —SnR$_3$, —B(OR)$_2$ (wherein R represents $C_{1-6}$ alkyl, etc.), etc., and Met$^{x3}$ represents lithium, sodium, potassium, cesium, etc.

R$^{x1}$ represents tert-butoxycarbonyl, benzyloxycarbonyl, benzyl, etc., R represents $C_{1-6}$ alkyl, etc., R$^{x2}$, R$^{x20}$, R$^{x21}$, R$^{x22}$ each represent hydrogen or $C_{1-6}$ alkyl, R$^{x3}$ represents hydrogen, halogen, nitrile, $C_{1-6}$ alkyl, $C_{1-6}$ alkoxy, etc., R$^{x4}$ represents $C_{1-6}$ alkyl, benzyl, p-methoxybenzyl, etc., and R$^{x5}$ represents $C_{1-6}$ alkyl, $C_{2-6}$ alkenyl, $C_{2-6}$ alkynyl, etc.

Ts represents p-toluenesulfonyl.

L$^{x1}$ represents a leaving group such as halogen, methanesulfonyloxy, trifluoromethanesulfonyloxy, para-toluenesulfonyloxy, etc., L$^{x2}$ represents halogen, trifluoromethanesulfonyloxy, etc. and L$^{x3}$ represents chlorine or bromine.

V$^{1x}$ represents oxygen, sulfur, nitrogen or —NR— (wherein R has the same definition as above).

X represents halogen.

$A^1$, $A^2$, $X^1$, $X^2$, $X^3$, $X^4$, $Q^1$, $T^1$, $Z^1$ and s have the same definitions as above.

The "room temperature" referred to below is in the range of 15-30° C.

[Production Scheme A]

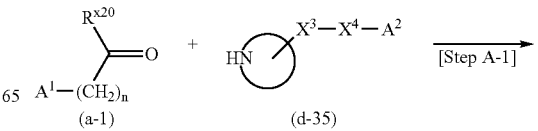

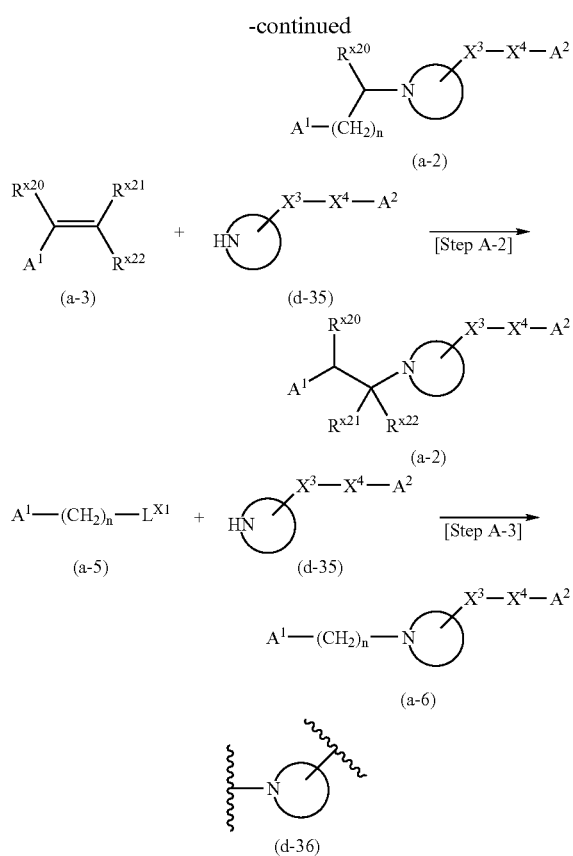

wherein (d-36) has the same definition as $Z^1$ above.

Step A-1

A step of obtaining compound (a-2) by reductive amination of compound (a-1) and compound (d-35).

The reaction may be conducted under the same conditions commonly employed for reductive amination with carbonyl compounds and amine compounds. There are no particular restrictions on the reduction reaction, and there may be mentioned reductive amination using a reducing agent such as borane, borohydride complexe, formic acid or the like, and catalytic reduction using a metal catalyst under a hydrogen atmosphere.

As examples of reductive amination using a borohydride complex there may be mentioned the processes described in W. S. Emerson, organic Reactions, 4, 174(1948), C. F. Lane, Synthesis, 135(1975), J. C. Stowell and S. J. Pedegimas, Synthesis, 127(1974), A. F. Abdel-Magid, K. G. Carson, B. D. Harris, C. A. Maryanoff and R. D. Shah, Journal of Organic Chemistry, 61, 3849(1996) and elsewhere.

Compound (d-35) may be free or in the form of a salt, and preferably a hydrochloride or a hydrobromide of compound (d-35) is used.

Sodium borohydride, sodium cyanoborohydride, sodium triacetoxyborohydride or the like may be used as the borohydride complex.

When a borohydride complex is used as the reducing agent, there are no particular restrictions on the solvent so long as it does not inhibit the reaction and dissolves the starting substances to some extent, and specifically there may be used, for example, methanol, ethanol, tetrahydrofuran, dichloromethane and 1,2-dichloroethane. The reaction may be conducted in the copresence of an acid to achieve more favorable results such as increased yield. There are no particular restrictions on such an acid, and there may be mentioned mineral acids such as hydrochloric acid, organic acids such as acetic acid, and Lewis acids such as zinc chloride, boron trifluoride diethyl ether complex and titanium (IV) tetraisopropoxide. The reaction temperature is not particularly restricted but will normally be from −78° C. to the reflux temperature of the solvent, and is preferably from freezing to room temperature.

When formic acid is used as the reducing agent, there are no particular restrictions on the solvent so long as it does not inhibit the reaction, and an excess of formic acid may be used as the solvent. The reaction temperature is not particularly restricted but will normally be from 50° C. to the reflux temperature of the solvent. High-temperature heating at 150-250° C. in a hermetic pressure-resistant vessel may provide favorable results such as shortening of the reaction time.

The solvent used for catalytic reduction under a hydrogen atmosphere is not particularly restricted so long as it does not inhibit the reaction, and there may be mentioned methanol, ethanol, tetrahydrofuran and 1,4-dioxane. The metal catalyst used for the reaction may be palladium-carbon, platinum oxide, Raney nickel or the like. The conditions for the reaction are not particularly restricted, and it may be carried out from room temperature to the reflux temperature of the solvent and from ordinary pressure to 150 atmospheres, and preferably from room temperature to 60° C. and from ordinary pressure to 5 atmospheres.

Step A-2

A step of obtaining compound (a-4) by Michael addition reaction of compound (a-3) and compound (d-35).

The reaction may be conducted under the same conditions commonly employed for Michael addition reaction with an olefin compound and an amine compound.

For example, the reaction may be conducted under the same conditions described in W. E. Doering and R. A. N. Weil, Journal of the American Chemical Society, 69, 2461 (1947), M.-C. Viaud, P. Jamoneau, L. Savelon and G. Guillaumet, Tetrahedron Letters, 37, 2409(1996).

Compound (d-35) may be free or in the form of a salt.

There are no particular restrictions on the solvent so long as it does not inhibit the reaction, and as preferred solvents there may be mentioned methanol, ethanol, 1-propanol, 2-propanol, 1-butanol, toluene, xylene and acetic acid. The reaction temperature will differ depending on the starting materials and solvent used and is not particularly restricted, but it is preferably from room temperature to the reflux temperature of the solvent. The reaction may be carried out with addition of an acid such as p-toluenesulfonic acid or camphorsulfonic acid or alumina, as this may provide favorable results such as shortening of the reaction time and increased yield.

High-temperature heating at 150-250° C. in a hermetic pressure-resistant vessel may also provide favorable results such as shortening of the reaction time.

Step A-3

A step of obtaining compound (a-6) by nucleophilic substitution reaction of compound (a-5) and compound (d-35).

The reaction may be conducted under the same conditions commonly employed for reaction between a halogenated compound and a nucleophilic reagent (for example, the conditions described in H. Arai, T. Ashizawa, K. Gomi, M. Kono, H. Saito and M. Kasai, Journal of Medicinal Chemistry, 38, 3025(1995)).

Compound (d-35) may be free or in the form of a salt.

There are no particular restrictions on the solvent used for the reaction so long as it does not inhibit the reaction and dissolves the starting substances to some extent, and as preferred solvents there may be mentioned methanol, ethanol, propanol, tetrahydrofuran, benzene, toluene, xylene, acetonitrile, dichloromethane, chloroform, N,N-dimethylformamide and dimethylsulfoxide. The reaction temperature will normally be from room temperature to the reflux temperature of the solvent, and preferably from room temperature to 100° C. Addition of a base may provide favorable results such as increased yield. The base used is not particularly restricted so long as it does not inhibit the reaction, and as preferred bases there may be mentioned sodium carbonate, potassium carbonate, sodium hydroxide, potassium hydroxide, diazabicycloundecene, sodium hydride, potassium hydride, sodium methoxide, potassium methoxide, potassium tert-butoxide and diisopropylethylamine.

[Production Scheme B]

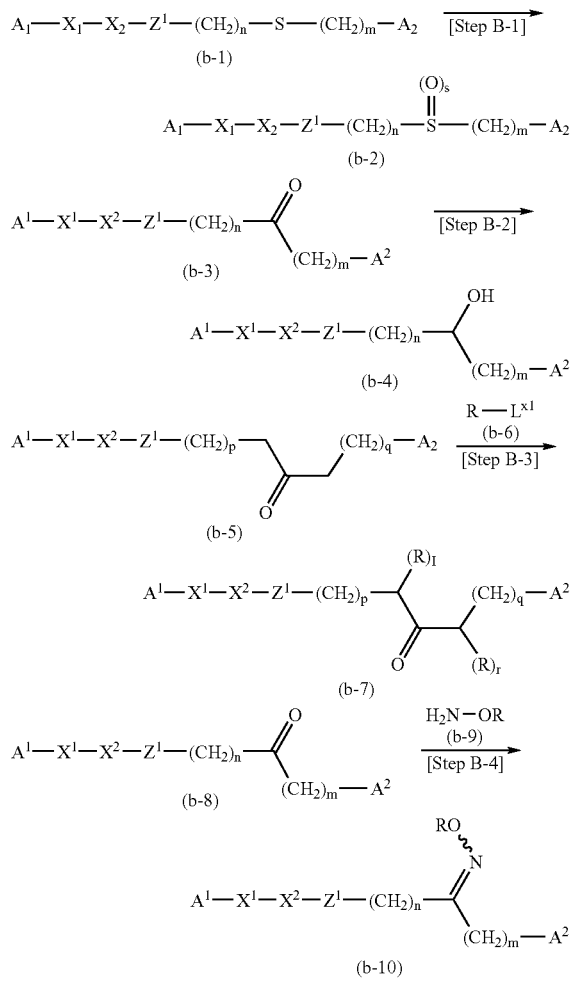

Step B-1

A step of obtaining compound (b-2) by oxidation of compound (b-1).

The reaction may be carried out under the same reaction conditions commonly employed for oxidation to obtain a sulfoxide compound or sulfone compound from a sulfide compound (for example, the conditions described in G. A. Russel and L. A. Ochrymowycz, Journal of Organic Chemistry, 35, 2106(1970)).

The oxidizing agent used may be m-chloroperbenzoic acid, hydrogen peroxide, peracetic acid or the like. There are no particular restrictions on the solvent used for the reaction so long as it does not inhibit the reaction and dissolves the starting substances to some extent, and for example, dichloromethane and chloroform are preferred. The reaction temperature is not particularly restricted but will normally be from −78° C. to room temperature. Addition of a base may provide favorable results such as increased yield. The base used is not particularly restricted so long as it does not inhibit the reaction, and as preferred bases there may be mentioned sodium carbonate, sodium bicarbonate, potassium carbonate and the like.

Step B-2

A step of obtaining compound (b-4) by reduction of compound (b-3).

Sodium borohydride, lithium borohydride, lithium aluminum hydride, zinc borohydride or the like may be used as the reducing agent.

There are no particular restrictions on the solvent used for the reaction so long as it does not inhibit the reaction and dissolves the starting substances to some extent, and specifically there may be used methanol, ethanol, tetrahydrofuran and the like.

The reaction temperature is not particularly restricted but will normally be from −78° C. to the reflux temperature of the solvent, and preferably from freezing to room temperature.

Step B-3

A step of obtaining compound (b-7) by reacting compound (b-5) with (b-6).

The reaction may be conducted under the same reaction conditions described, for example, in A. Aranda, A. Diaz, E. Diez-Barra, A. De la Hoz, A. Moreno and P. Sanchez-Verdu, Journal of the Chemical Society: Perkin Transactions I, 2427(1992).

Specifically, for example, a base is reacted with a solution of compound (b-5) to form an anion, which is then reacted with compound (b-6) to obtain compound (b-7).

There are no particular restrictions on the solvent used so long as it does not inhibit the reaction, and from 1 equivalent to a large excess of an appropriate base may be used in an organic solvent such as diethyl ether, tetrahydrofuran, 1,4-dioxane, N,N-dimethylformamide or the like. As bases to be used there may be mentioned potassium hydride, sodium hydride, sodium methoxide, sodium ethoxide, potassium tert-butoxide and lithium diisopropylamide.

Conducting the reaction in the copresence of an ammonium salt such as tetra-n-butylammonium chloride, tetra-n-butylammonium bromide or tetra-n-butylammonium iodide may provide favorable results such as increased yield and shortening of the reaction time.

The reaction temperature is not particularly restricted but will normally be from −78° C. to room temperature.

Step B-4

A step of obtaining compound (b-10) by condensation of compound (b-8) with compound (b-9).

The reaction may be conducted under the same reaction conditions described, for example, in P. R. Dave, M. Ferraro, H. L. Ammon and C. S. Choi, Journal of Organic Chemistry, 55, 4459(1990).

There are no particular restrictions on the solvent used for the reaction so long as it does not inhibit the reaction and dissolves the starting substances to some extent, and specifically there may be used methanol, ethanol, propanol, pyridine or the like. Compound (b-9) may be free or in the form of a salt, and preferably a hydrochloride or hydrobromide of compound (b-9) is used. The reaction temperature is not particularly restricted but will normally be from freezing to the reflux temperature of the solvent, and is preferably from room temperature to the reflux temperature of the solvent. Addition of a base may provide favorable results such as increased yield. The base used is not particularly restricted so long as it does not inhibit the reaction, and as preferred bases there may be mentioned sodium carbonate, potassium carbonate, sodium acetate and potassium acetate.

[Production Scheme C]

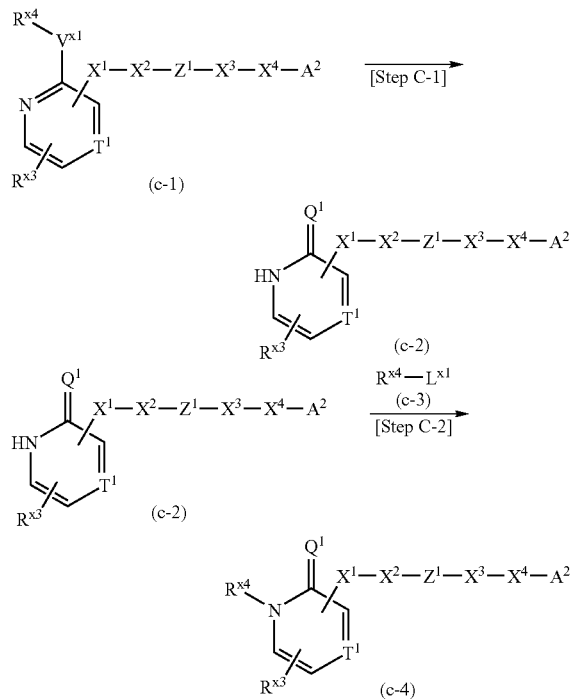

Step C-1

A step of obtaining compound (c-2) by reacting compound (c-1) with an acid.

The reaction may be conducted under the same conditions described in, for example, A. C. Rasmussen and D. A. Rawlings, Eur. Journal of Medicinal Chemistry, 28, 601-608(1993), F. G. Fang, S. Xie and M. W. Lowery, Journal of Organic Chemistry, 59, 6142(1994).

Specifically, for example, compound (c-1) may be dissolved in 5N hydrochloric acid or the like and heated to reflux to obtain compound (c-2).

The reaction may be conducted without a solvent or in water, in a mixture of water and an organic solvent such as methanol, ethanol, tetrahydrofuran or 1,4-dioxane, or in an organic solvent such as methanol, ethanol, tetrahydrofuran, 1,4-dioxane or ethyl acetate, with addition of from 1 equivalent to a large excess of an appropriate acid. The acid used is preferably, for example, hydrogen chloride, hydrochloric acid, hydrogen bromide, sulfuric acid, nitric acid, trifluoroacetic acid or the like, and thionyl chloride may also be added to an alcohol solvent to generate an acid in the reaction system.

The reaction temperature will normally be from freezing to the reflux temperature of the solvent.

The reaction may be carried out with addition of from 1 equivalent to a large excess of iodotrimethylsilane or chlorotrimethylsilane-sodium iodide instead of an acid. There are no particular restrictions on the reaction solvent so long as it does not inhibit the reaction, and there may be used dichloromethane, chloroform, acetonitrile or the like.

The reaction temperature will normally be from −78° C. to the reflux temperature of the solvent, and it is preferably from −20° C. to room temperature.

The reaction may also be carried out with addition of from 1 equivalent to a large excess of boron tribromide or boron trichloride instead of an acid. There are no particular restrictions on the reaction solvent so long as it does not inhibit the reaction, and there may be used dichloromethane, chloroform, 1,2-dichloroethane or the like.

The reaction temperature will normally be from −78° C. to the reflux temperature of the solvent, and it is preferably from −78° C. to room temperature.

Step C-2

A step of obtaining compound (c-4) by reacting compound (c-2) with compound (c-3).

The reaction may be conducted under the same conditions described in, for example, J. B. Press and J. J. Mcnally, Journal of Heterocyclic Chemistry, 25, 1571(1988).

As a specific example, a base may be reacted with a solution of compound (c-2) to form an anion, which is then reacted with compound (c-3) to obtain compound (c-4).

There are no particular restrictions on the solvent used so long as it does not inhibit the reaction, and the reaction may be conducted with from 1 equivalent to a large excess of an appropriate base in an organic solvent such as methanol, ethanol, tetrahydrofuran, 1,4-dioxane or N,N-dimethylformamide. As bases to be used there may be mentioned sodium hydride, sodium methoxide, sodium ethoxide, potassium tert-butoxide, sodium carbonate, potassium carbonate, sodium hydroxide, potassium hydroxide, triethylamine, diisopropylethylamine and the like.

The reaction temperature will normally be from freezing to the reflux temperature of the solvent.

The following is a representative synthesis scheme for a compound to be used in Step A above.

[Production Scheme D]

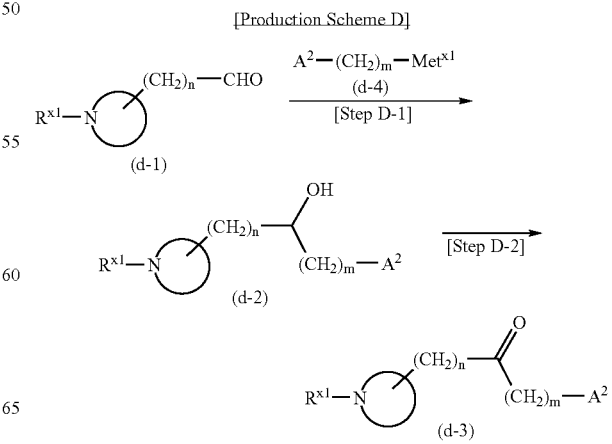

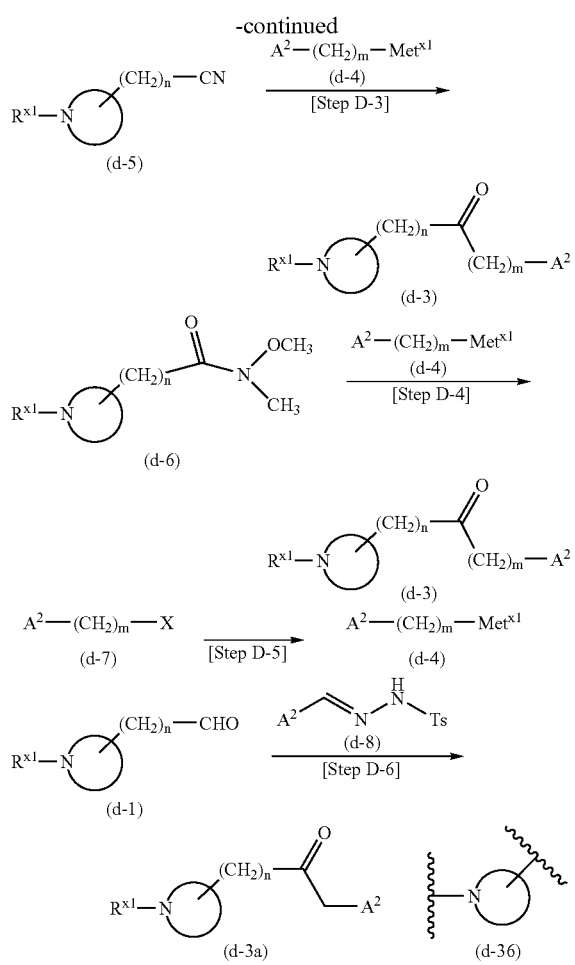

wherein (d-36) has the same definition as $Z^1$ above.

Step D-1

A step of obtaining compound (d-2) by reacting compound (d-1) with an organometallic reagent (d-4).

The reaction may be carried out under the same conditions commonly used for nucleophilic addition reaction whereby an aldehyde compound and an organometallic reagent are reacted to obtain an alcohol compound (for example, J. C. H. Hwa and H. Sims, Organic Synthesis, V, 608(1973), C. Z. DING, Synthetic Communication, 26, 4267(1996).

Specifically, the reaction may be conducted by adding a solution of compound (d-4) dropwise to a solution of compound (d-1), or conversely, by adding a solution of compound (d-1) dropwise to a solution of compound (d-4).

There are no particular restrictions on the solvent used for the reaction so long as it does not inhibit the reaction and dissolves the starting substances to some extent, and specifically there may be used diethyl ether, tetrahydrofuran, 1,4-dioxane and the like. The reaction temperature is not particularly restricted, but the reaction may usually be conducted from −78° C. to room temperature. The organometallic reagent (d-4) will generally be used in the reaction at 1-5 equivalents with respect to compound (d-1).

Step D-2

A step of obtaining compound (d-3) by oxidation of compound (d-2).

The reaction may be carried out under the same conditions commonly employed for oxidation of a secondary alcohol compound to a ketone compound (for example, the conditions described in A. J. Mancuso and D. Swern, Synthesis, 165(1981)).

The oxidation method to be used for the oxidation reaction may be Swern oxidation, Jones oxidation, Corey Kim oxidation or the like. The oxidizing agent used for the oxidation may be an alkylsulfonium ylide prepared from dimethylsulfoxide-oxalyl chloride and the like, Jones' reagent, pyridinium chlorochromate, pyridinium dichromate or sulfur trioxide-pyridine complex.

There are no particular restrictions on the solvent used for the reaction so long as it does not inhibit the reaction and dissolves the starting substances to some extent, and examples which may be used include dimethylsulfoxide, acetone, dichloromethane and chloroform. The reaction temperature is not particularly restricted, but the reaction may usually be conducted from −78° C. to room temperature.

Step D-3

A step of obtaining compound (d-3) by reacting compound (d-5) with an organometallic reagent (d-4).

The reaction may be carried out under the same conditions commonly employed for addition reaction whereby a cyano compound and an organometallic reagent are reacted to obtain a ketone compound (for example, the conditions described in R. B. Moffet and R. L. Schriner, Organic Synthesis, II, 562(1955)).

The reaction conditions including the reagent equivalents, the solvent and the temperature for the reaction are the same as in Step D-1 above.

Step D-4

A step of obtaining compound (d-3) by reacting compound (d-6) with an organometallic reagent (d-4).

The reaction may be carried out under the same conditions commonly employed for reaction of an amide compound and an organometallic reagent to obtain a ketone compound (for example, the conditions described in S. Nahm and S. M. Weinreb, Tetrahedron Letters, 22, 3825 (1981)).

The reaction conditions including the reagent equivalents, the solvent and the temperature for the reaction are the same as in Step D-1 above.

Step D-5

A step of obtaining an organometallic reagent (d-4) from compound (d-7).

The reaction may be carried out under the same conditions commonly employed for reaction of a halogenated compound with an alkyllithium reagent such as n-butyllithium or sec-butyllithium, or magnesium, to obtain an organometallic reagent (for example, J. C. H. Hwa and H. Sims, Organic Synthesis, V, 608(1973), C. Z. DING, Synthetic Communication, 26, 4267(1996)).

There are no particular restrictions on the solvent used for the reaction so long as it does not inhibit the reaction and dissolves the starting substances to some extent, and preferred examples include diethyl ether, tetrahydrofuran and 1,4-dioxane. The reaction temperature is not particularly restricted but will normally be from −78° C. to the reflux temperature of the solvent.

Step D-6

A step of obtaining compound (d-3a) by reacting compound (d-1) and compound (d-8) in the presence of a base. The reaction may be carried out under the same conditions described in, for example, S. R. Angel and M. L. Neitzel, Journal of Organic Chemistry, 65, 6485(2000).

There are no particular restrictions on the solvent used for the reaction so long as it does not inhibit the reaction and dissolves the starting substances to some extent, but methanol, ethanol, ethyleneglycol, formamide and the like are preferred. The base used is preferably, for example, sodium hydroxide, sodium methoxide, sodium ethoxide or potassium methoxide. The base is used at 1-5 equivalents with respect to the starting material. The reaction temperature is not particularly restricted but will normally be from room temperature to 100° C.

As leaving groups there may be mentioned halogen (chlorine, bromine and iodine), and sulfonyloxy groups such as methanesulfonyloxy, p-toluenesulfonyloxy and trifluoromethanesulfonyloxy.

The reaction may be carried out under the same conditions commonly employed for conversion of a hydroxyl group to a leaving group (for example, the reaction conditions described in R. K. Crossland and K. L. Servis, Journal of Organic Chemistry, 35, 3195(1970)).

When the leaving group is halogen, compound (d-12) may be produced by reacting compound (d-9) with thionyl chloride, thionyl bromide, phosphorus tribromide or tetra-

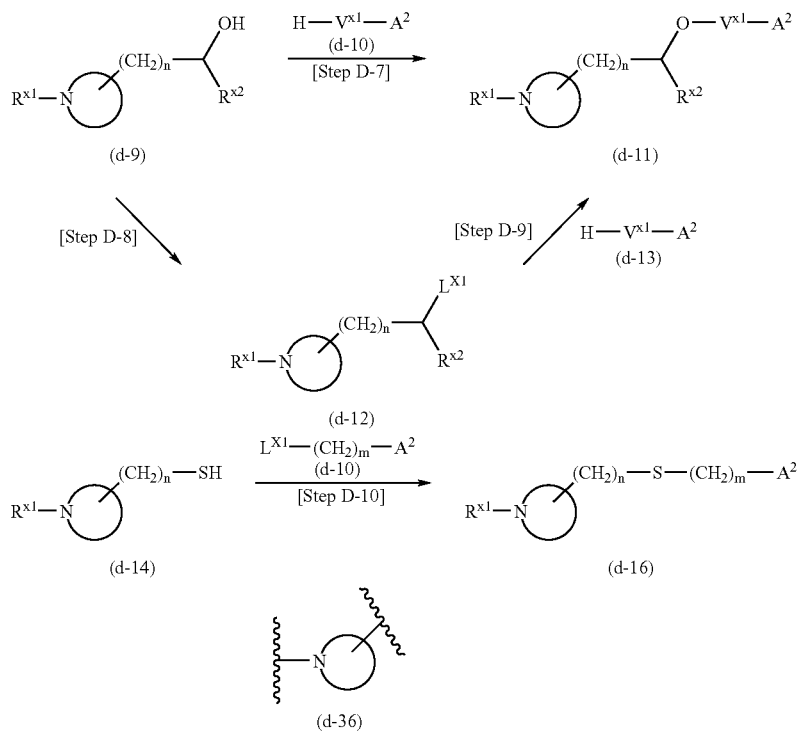

(wherein (d-36) has the same definition as $Z^1$ above).

Step D-7

A step of obtaining compound (d-11) by Mitsunobu reaction with compound (d-9) and compound (d-10).

The reaction may be carried out under the same conditions commonly employed for Mitsunobu reaction (for example, the conditions described in O. Mitsunobu, Synthesis, 1(1981), D. L. Hughes, Organic Reactions, 42, 335 (1992)).

The reaction is conducted using a phosphine derivative such as triphenylphosphine and an azodicarboxylic acid diester such as diethyl azodicarboxylate. There are no particular restrictions on the solvent used for the reaction so long as it does not inhibit the reaction and dissolves the starting substances to some extent, and for example, there may be used tetrahydrofuran, benzene, toluene or the like. The reaction temperature is not particularly restricted, but will usually be from freezing to room temperature.

Step D-8

A step of obtaining compound (d-12) by converting the hydroxyl group of compound (d-9) to a leaving group.

halogenomethane-triphenylphosphine. There are no particular restrictions on the solvent used for the reaction so long as it does not inhibit the reaction and dissolves the starting substances to some extent, and as preferred solvents there may be mentioned benzene, toluene, xylene, dichloromethane and chloroform. The reaction temperature will normally be from −78° C. to the reflux temperature of the solvent, and is preferably from freezing to the reflux temperature of the solvent.

When the leaving group is a sulfonyloxy group, compound (d-12) may be produced by reacting compound (d-9) with methanesulfonyl chloride, p-toluenesulfonyl chloride, trifluoromethanesulfonic anhydride or the like. There are no particular restrictions on the solvent used for the reaction so long as it does not inhibit the reaction and dissolves the starting substances to some extent, and as preferred solvents there may be mentioned tetrahydrofuran, toluene, xylene, dichloromethane, chloroform and N,N-dimethylformamide. The reaction temperature will normally be from −78° C. to the reflux temperature of the solvent, and is preferably from freezing to room temperature. Addition of a base may provide favorable results such as increased yield. The base used is not particularly restricted so long as it does not inhibit the reaction, and as preferred bases there may be mentioned sodium carbonate, potassium carbonate, triethylamine, pyridine and diisopropylethylamine.

Step D-9

A step of obtaining compound (d-11) by reacting compound (d-12) with compound (d-13).

The reaction may be carried out under the same conditions commonly employed for reaction between a halogenated compound and a nucleophilic reagent (for example, the conditions described in H. Arai, T. Ashizawa, K. Gomi, M. Kono, H. Saito and M. Kasai, Journal of Medicinal Chemistry, 38, 3025(1995)).

There are no particular restrictions on the solvent used for the reaction so long as it does not inhibit the reaction and dissolves the starting substances to some extent, and as preferred solvents there may be mentioned methanol, ethanol, propanol, tetrahydrofuran, benzene, toluene, xylene, acetonitrile, dichloromethane, chloroform, N,N-dimethylformamide and dimethylsulfoxide. The reaction temperature will normally be from room temperature to the reflux temperature of the solvent, and is preferably from room temperature to 150° C. Addition of a base may provide favorable results such as increased yield. The base used is not particularly restricted so long as it does not inhibit the reaction, and as preferred bases there may be mentioned sodium carbonate, potassium carbonate, sodium hydroxide, potassium hydroxide, diazabicycloundecene, sodium hydride, potassium hydride, sodium methoxide, potassium methoxide, potassium tert-butoxide and diisopropylethylamine.

Step D-10

A step of obtaining compound (d-16) by reacting compound (d-14) with compound (d-15).

The reaction may be carried out under the same conditions commonly employed for reaction between a halogenated compound and a nucleophilic reagent (for example, the conditions described in E. Montenegro, R. Echarri, C. Clayer, S. Castillon, A. Moyano, M. A. Pericas, A. Riera, Tetrahedron: Asymmetry, 7, 3553(1996)).

There are no particular restrictions on the solvent used for the reaction so long as it does not inhibit the reaction and dissolves the starting substances to some extent, and as preferred solvents there may be mentioned methanol, ethanol, propanol, tetrahydrofuran, benzene, toluene, xylene, acetonitrile, dichloromethane, chloroform, N,N-dimethylformamide and dimethylsulfoxide. The reaction temperature will normally be from room temperature to the reflux temperature of the solvent, and is preferably from room temperature to 100° C. Addition of a base may provide favorable results such as increased yield. The base used is not particularly restricted so long as it does not inhibit the reaction, and as preferred bases there may be mentioned sodium carbonate, potassium carbonate, sodium hydroxide, potassium hydroxide, diazabicycloundecene, sodium hydride, potassium hydride, sodium methoxide, potassium methoxide, potassium tert-butoxide and diisopropylethylamine.

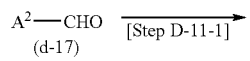

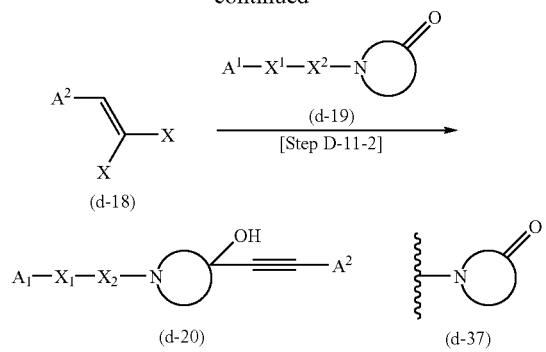

(wherein (d-37) represents a monocyclic 4- to 8-membered non-aromatic heterocycle containing a carbonyl group, such as oxoazetidin-1-yl, oxopyrrolidin-1-yl, oxopiperidin-1-yl, oxoazocan-1-yl, etc.)

Step D-11-1

A step of obtaining compound (d-18) by reacting compound (d-17) with a carbon tetrahalide such as carbon tetrabromide, and triphenylphosphine.

The reaction may be carried out under the same conditions described in, for example, E. J. Corey and P. L. Fuchs, Tetrahedron Letters, 3769(1972).

Specifically, compound (d-18) may be obtained, for example, by adding triphenylphosphine to a solution of carbon tetrabromide, stirring the mixture for several minutes to several hours, and then adding a solution of compound (d-17) dropwise and further stirring for several hours to 1 day.

There are no particular restrictions on the solvent used for the reaction so long as it does not inhibit the reaction and dissolves the starting substances to some extent, and for example, there may be used dichloromethane, chloroform, 1,2-dichloroethane and the like. The reaction temperature is not particularly restricted but will normally be from −78° C. to 100° C., and is preferably from −10° C. to room temperature.

The reaction may also be carried out in the presence of zinc.

Step D-11-2

A step of obtaining compound (d-20) by reacting compound (d-18) with a base for dehalogenation to convert it to an alkynyl metal derivative, and then reacting this with compound (d-19).

The reaction may be carried out under the same conditions described in, for example, E. J. Corey and P. L. Fuchs, Tetrahedron Letters, 3769(1972).

Specifically, compound (d-20) may be obtained, for example, by adding a solution of the base dropwise to a solution of compound (d-18), stirring the mixture for several minutes to several hours, and then adding a solution of compound (d-19) dropwise and further stirring for several minutes to several hours.

There are no particular restrictions on the solvent used for the reaction so long as it does not inhibit the reaction and dissolves the starting substances to some extent, and examples of preferred solvents include diethyl ether, tetrahydrofuran, 1,4-dioxane and the like. As examples of bases to be used there may be mentioned n-butyllithium, sec-butyllithium and tert-butyllithium. The base is usually used at 2-5 equivalents with respect to the starting material.

The reaction temperature is not particularly restricted but will normally be from −78° C. to room temperature.

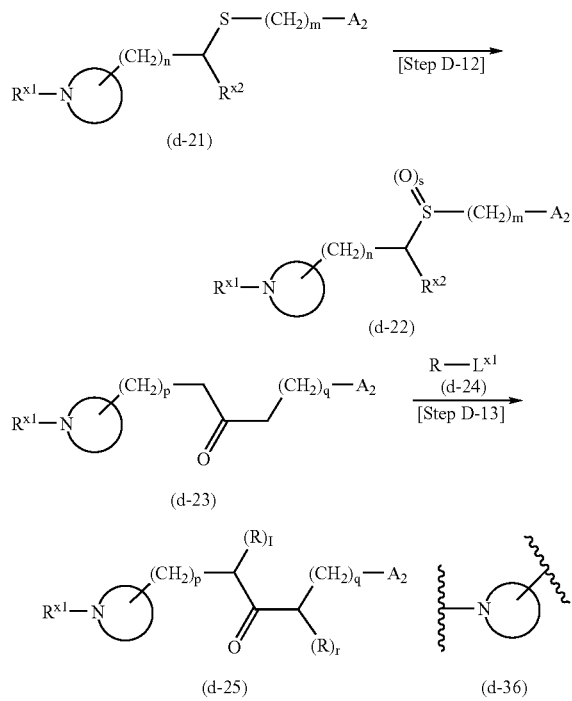

(wherein (d-36) has the same definition as $Z^1$ above).

Step D-12

A step of obtaining compound (d-22) by oxidation of compound (d-21).

The reaction may be carried out under the same conditions as for Step B-1.

Step D-13

A step of obtaining compound (d-25) by reacting compound (d-23) with compound (d-24).

The reaction may be carried out under the same conditions as for Step B-3.

When $Z^1$ is a piperidine-diyl group, the synthesis may also be carried out according to the following reaction scheme.

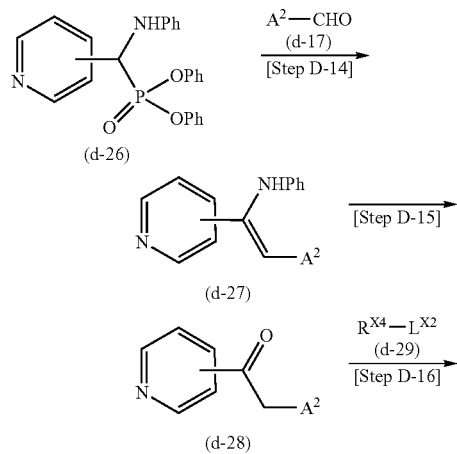

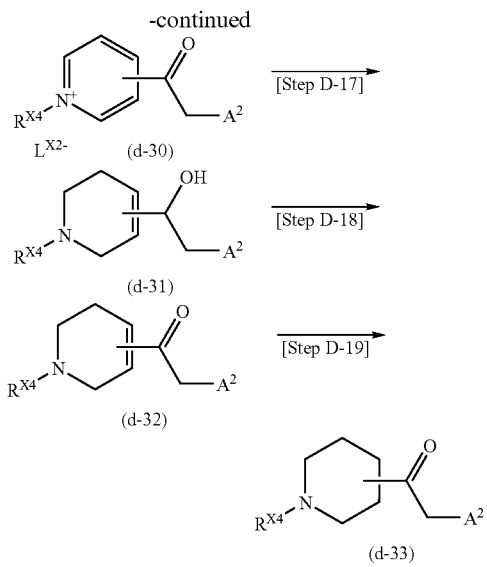

Step D-14

A step of obtaining compound (d-27) by reacting compound (d-26) with compound (d-17).

The reaction may be carried out under the same conditions described in, for example, M. Journet, D. Cai, R. D. Larsen and P. J. Reider, Tetrahedron Letters, 39, 1717(1998).

Specifically, compound (d-27) may be obtained, for example, by adding compound (d-17) and a base to a solution of compound (d-26) and stirring the mixture for several hours to 1 day.

There are no particular restrictions on the solvent used for the reaction so long as it does not inhibit the reaction and dissolves the starting substances to some extent. As examples of solvents there may be mentioned methanol, ethanol, 2-propanol and tetrahydrofuran, but a 2-propanol/tetrahydrofuran mixture is preferred. Examples of preferred bases include potassium carbonate and cesium carbonate. The base is usually used at 1-5 equivalents with respect to the starting material. The reaction temperature is not particularly restricted but will normally be from freezing to the reflux temperature of the solvent.

Step D-15

A step of obtaining compound (d-28) by hydrolysis of compound (d-27) under acidic conditions.

The reaction may be carried out under the same conditions described in, for example, M. Journet, D. Cai, R. D. Larsen and P. J. Reider, Tetrahedron Letters, 39, 1717(1998).

Specifically, compound (d-28) may be obtained, for example, by adding an acid such as hydrochloric acid to compound (d-27), stirring the mixture for several hours to 1 day, and then treating it with a base such as aqueous sodium hydroxide.

There are no particular restrictions on the solvent used for the reaction so long as it does not inhibit the reaction and dissolves the starting substances to some extent, and as examples there may be mentioned methanol, ethanol, 2-propanol, tetrahydrofuran and acetone. Examples of preferred acids include hydrochloric acid, sulfuric acid and the like. The acid is used in an amount of 1-20 equivalents with respect to the starting material. The reaction temperature is not particularly restricted but will normally be from room temperature to the reflux temperature of the solvent.

Step D-14 and Step D-15 may be carried out in the same reactor without isolation of compound (d-27).

Step D-16

A step of obtaining compound (d-30) by reacting compound (d-28) and compound (d-29).

The reaction may be carried out under the same conditions commonly employed for obtaining a pyridinium salt from a pyridine compound (for example, the conditions described in C. K. Chu, V. S. Bhadti, K. J. Doshi, J. T. Etse, J. M. Gallo, F. D. Boudinot and R. F. Schinazi, Journal of Medicinal Chemistry, 33, 2188(1990)).

There are no particular restrictions on the solvent used for the reaction so long as it does not inhibit the reaction and dissolves the starting substances to some extent, and as examples there may be mentioned benzene, toluene, xylene, acetonitrile, methanol, ethanol and 2-propanol. The reaction temperature is not particularly restricted but will normally be from room temperature to the reflux temperature of the solvent.

Step D-17

A step of obtaining compound (d-31) by reduction of compound (d-30). The reaction may be carried out under the same conditions commonly employed for reduction of a pyridinium salt to obtain a tetrahydropyridine compound (for example, the conditions described in J. W. Beach, Journal of Heterocyclic Chemistry, 34, 1861(1997)).

Sodium borohydride, potassium borohydride or the like is preferred as the reducing agent for the reaction. There are no particular restrictions on the solvent used for the reaction so long as it does not inhibit the reaction and dissolves the starting substances to some extent, and as examples there may be mentioned methanol, ethanol and 2-propanol. The reaction temperature is not particularly restricted but will normally be from freezing to the reflux temperature of the solvent.

Step D-18

A step of obtaining compound (d-32) by oxidation of compound (d-31). The reaction may be carried out under the same conditions commonly employed for oxidation of a secondary alcohol compound to a ketone compound, and specifically it may be carried out under the same conditions as in Step D-2 above.

Step D-19

A step of obtaining compound (d-33) by reduction of compound (d-32).

The reaction may be carried out under the same conditions commonly employed for catalytic reduction from an unsaturated ketone compound to a saturated ketone compound under a hydrogen atmosphere (for example, the conditions described in R. L. Augustine, Journal of Organic Chemistry, 23, 1853(1958)).

Palladium-carbon, palladium hydroxide-carbon, platinum oxide or the like is preferred as the catalyst for the reaction. There are no particular restrictions on the solvent used for the reaction so long as it does not inhibit the reaction and dissolves the starting substances to some extent, and as examples there may be mentioned methanol, ethanol and 2-propanol. The reaction temperature is not particularly restricted but will normally be from freezing to 100° C. The hydrogen pressure will usually be from ordinary pressure to 3 atmospheres.

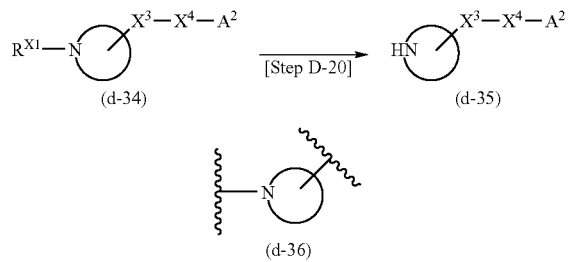

(wherein (d-36) has the same definition as $Z^1$ above).

Step D-20

A step of obtaining compound (d-35) by removing $R^{x1}$ in compound (d-34).

When $R^{x1}$ is used as an amine-protecting group, the removal of $R^{x1}$ may be accomplished under the same conditions commonly employed for the particular deprotecting reaction (for example, the conditions described in T. W. Green and P. G. M. Wuts, "Protective Groups in Organic Chemistry, Second Edition", John Wiley & Sons (1991), p. 309-405, J. H. Cooley and E. J. Evain, Synthesis, 1(1989)).

For example, when $R^{x1}$ is a tert-butoxycarbonyl group, compound (d-34) may be reacted with hydrogen chloride, hydrochloric acid, sulfuric acid, trifluoroacetic acid, p-toluenesulfonic acid or the like in an organic solvent or in a mixture of water and an organic solvent.

There are no particular restrictions on the solvent used for the reaction so long as it does not inhibit the reaction, but dichloromethane, methanol, ethanol, propanol, ethyl acetate, tetrahydrofuran, 1,4-dioxane and the like are preferred.

When $R^{x1}$ is a benzyloxycarbonyl or benzyl group, the reaction may be carried out by catalytic reduction in an organic solvent under a hydrogen atmosphere, using palladium-carbon as the catalyst.

There are no particular restrictions on the solvent used for the reaction so long as it does not inhibit the reaction, but methanol, ethanol, propanol, ethyl acetate, tetrahydrofuran, 1,4-dioxane and the like are preferred.

When $R^{x1}$ is a benzyl group, the reaction may be carried out, for example, with 1-chloroethyl chloroformate and methanol in that order, in a halogenated solvent such as 1,2-dichloroethane. The reaction temperature is not particularly restricted but will normally be from −78° C. to the reflux temperature of the solvent, and preferably from freezing to the reflux temperature of the solvent.

[Production Scheme E]

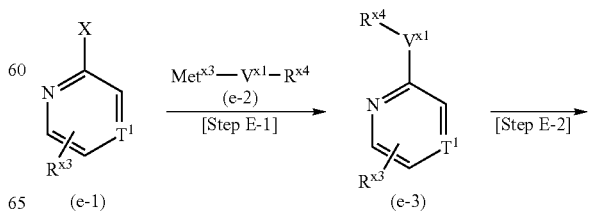

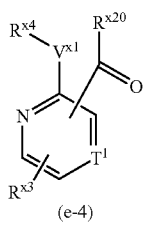

(e-4)

Step E-1

A step of obtaining compound (e-3) by nucleophilic substitution with compound (e-1) and compound (e-2).

The reaction may be carried out under the same conditions described in, for example, C. Z. Ding and A. V. Miller, Tetrahedron Letters, 37, 4447-4450(1996).

There are no particular restrictions on compound (e-2), and as preferred compounds there may be mentioned sodium alkoxides such as sodium methoxide, sodium ethoxide, sodium isopropoxide, sodium tert-butoxide and sodium 4-methoxybenzyloxide, potassium alkoxides such as potassium methoxide, potassium ethoxide, potassium isopropoxide, potassium tert-butoxide and potassium 4-methoxybenzyloxide, and sodium thioalkoxides such as sodium thiomethoxide, sodium thioethoxide, sodium thioisopropoxide and sodium tert-butylthiolate.

There are no particular restrictions on the solvent used for the reaction so long as it does not inhibit the reaction and dissolves the starting substances to some extent, and methanol, ethanol, propanol, tert-butanol, tetrahydrofuran, 1,4-dioxane, N,N-dimethylformamide and the like may be mentioned as particularly preferred. The reaction temperature is not particularly restricted but will normally be from −78° C. to the reflux temperature of the solvent, and preferably from freezing to the reflux temperature of the solvent.

Step E-2

A step of obtaining compound (e-4) by acylation of compound (e-3). It may be produced by reacting compound (e-3) with an organometallic reagent to form an anion, which is then reacted with a carboxylic acid derivative.

The reaction may be carried out under the same conditions described in, for example, R. J. Mattson and C. P. Sloan, Journal of Organic Chemistry, 55, 3410(1990), A. Turck, D. Trohay, L. Mojovic, N. Ple and G. Queguiner, Journal of Organometallic Chemistry, 412, 301(1991).

There are no particular restrictions on the organometallic reagent used for this reaction, and as preferred compounds there may be mentioned lithium reagents such as n-butyllithium, sec-butyllithium, tert-butyllithium and phenyllithium, lithium amide such as lithium diethylamide, lithium diisopropylamide, and lithium 2,2,6,6-tetramethylpiperidide, or magnesium amide such as methylmagnesium diisopropylamide, n-butylmagnesium diisopropylamide and n-butylmagnesium bis(diisopropylamide).

There are also no particular restrictions on the carboxylic acid derivative, and as preferred compounds there may be mentioned formic acid derivatives such as N,N-dimethylformamide, N-formylpiperidine, N-formylmorpholine, N-methyl-N-phenylformamide, methyl formate and ethyl formate, or acetic acid derivatives such as acetylimidazolide and N-methoxy-N-methylacetamide.

Conducting the reaction in the copresence of a base may provide favorable results such as increased yield. The base used is not particularly restricted and bases such as N,N,N',N'-tetramethylethylenediamine may be mentioned as preferable. The reaction temperature is not particularly restricted but will normally be from −78° C. to the reflux temperature of the solvent, and preferably from −78° C. to the room temperature. There are no particular restrictions on the solvent used for the reaction so long as it does not inhibit the reaction, and there may be mentioned diethyl ether and tetrahydrofuran.

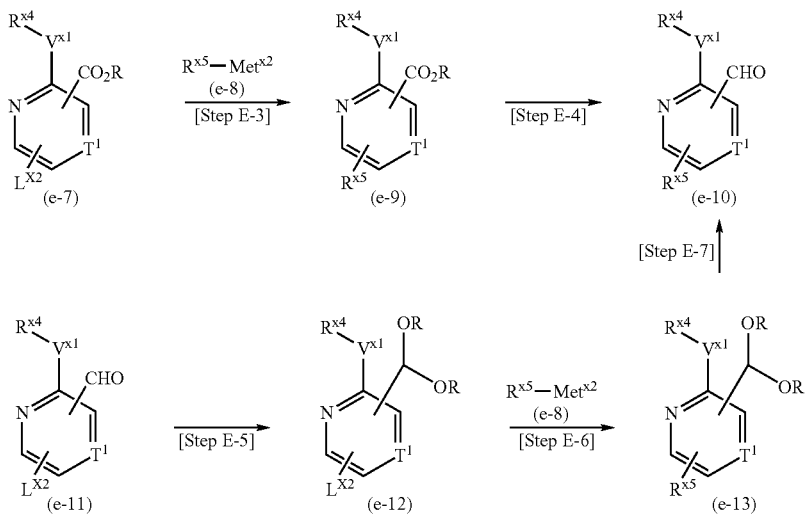

Step E-3

A step of producing compound (e-9) by reacting compound (e-7) and an organometallic compound (e-8) in the presence of an organometallic catalyst.

The reaction may be carried out under the same conditions commonly employed for coupling reaction between a halogenated heteroaryl compound or the like and an organometallic compound in the presence of an organometallic catalyst.

For example, a reaction using an organozinc reagent as the organometallic compound is described in N. Sato and T. Matsuura, Journal of the Chemical Society: Perkin Transaction 1, 2345(1996), and a reaction using an organoboron compound as the organometallic compound is described in N. Miyaura, T. Yanagi, and A. Suzuki, Synthetic Communications, 11, 513(1981).

There are no particular restrictions on the organometallic catalyst used for the reaction, and as preferred compounds there may be mentioned tetrakis(triphenylphosphine)palladium(0), dichlorobis(triphenylphosphine)palladium(II), [1,1'-bis(diphenylphosphino)ferrocene]palladium(II) dichloride, palladium(II)acetate and [1,3-bis(diphenylphosphino)propane]nickel(II). The organometallic catalyst is used at about 0.001-0.1 equivalent with respect to the starting material.

There are also no particular restrictions on the organometallic compound, and there may be mentioned as preferable organozinc reagents such as dimethylzinc and diethylzinc, or organoboric acid compounds such as methylboric acid. The organometallic compound is used at about 1-5 equivalents with respect to the starting material.

There are no particular restrictions on the solvent used for the reaction so long as it does not inhibit the reaction, and as preferred solvents there may be mentioned benzene, toluene, N,N-dimethylformamide, 1-methyl-2-pyrrolidone, tetrahydrofuran, 1,4-dioxane, acetonitrile and propionitrile. The reaction temperature is not particularly restricted but will normally be from freezing to the reflux temperature of the solvent, and preferably from room temperature to the reflux temperature of the solvent.

Conducting the reaction in the copresence of a base may provide favorable results such as increased yield. The base used is not particularly restricted and bases such as sodium carbonate, potassium carbonate, cesium carbonate, potassium phosphate and triethylamine may be mentioned as preferable.

Step E-4

A step of obtaining compound (e-10) by reduction of compound (e-9). The reaction may be carried out under the same conditions commonly employed for reduction of an ester compound to an aldehyde compound (for example, the conditions described in E. Winterfeldt, Synthesis, 617(1975)).

Preferred as reducing agents to be used for the reaction are diisobutylaluminium hydride, sodium bis(2-methoxyethoxy)aluminum hydride, bis(N-methylpiperazino)aluminum hydride, and the like.

There are no particular restrictions on the solvent used for the reaction so long as it does not inhibit the reaction and dissolves the starting substances to some extent, and tetrahydrofuran, toluene and dichloromethane may be mentioned as preferable.

The reaction temperature is not particularly restricted but will normally be from −78° C. to room temperature, and preferably from −78° C. to freezing.

Step E-5

A step of obtaining compound (e-12) by acetalization of compound (e-11). The reaction may be conducted under the same conditions commonly employed for acetalization of an aldehyde compound (for example, the conditions described in T. W. Green and P. G. M. Wuts, "Protective Groups in Organic Chemistry, Second Edition", John Wiley & Sons (1991), p. 175-223, E. C. Taylor and C. S. Chiang, Synthesis, 467(1977)).

For example, it may be carried out by reaction with hydrogen chloride in methanol solution, or by reaction with methyl orthoformate-montmorillonite K-10 in dichloromethane.

Step E-6

A step of producing compound (e-13) by reacting compound (e-12) and an organometallic compound (e-8) in the presence of an organometallic catalyst. The reaction may be carried out under the same conditions as in Step E-3.

Step E-7

A step of obtaining compound (e-10) by hydrolysis of compound (e-13).

The reaction may be conducted under the same conditions commonly employed for hydrolysis of an acetal compound (for example, the conditions described in T. W. Green and P. G. M. Wuts, "Protective Groups in Organic Chemistry, Second Edition", John Wiley & Sons (1991), p. 175-223).

The reaction may be conducted in the presence of an acid, and examples of acids which may be used include hydrochloric acid, p-toluenesulfonic acid, trifluoroacetic acid, camphorsulfonic acid and the like. There are no particular restrictions on the solvent used for the reaction so long as it does not inhibit the reaction and dissolves the starting substances to some extent, and preferred for use are solvents such as methanol, ethanol, acetone and tetrahydrofuran, or mixtures of water with methanol, ethanol, acetone, tetrahydrofuran or the like.

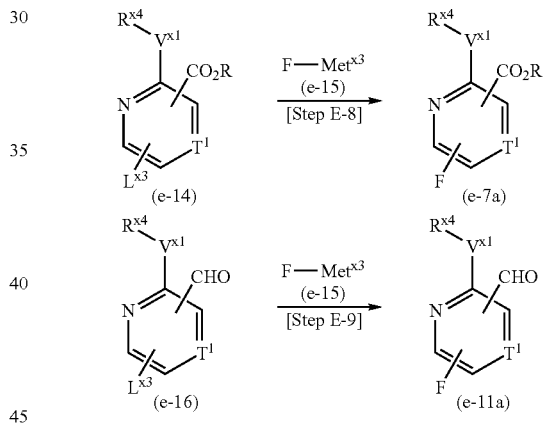

Step E-8

A step of obtaining compound (e-7a) from compound (e-14) and a fluorine compound (e-15).

The reaction may be conducted under the same conditions described in, for example, Y. Yoshida and Y. Kimura, Chemistry Letters, 1355(1988), H. Egawa, Y. Furuta, J. Sugiura, S. Uehara, S. Hamamoto and K. Yonezawa, WO 01/60834.

Specifically, compound (e-7a) may be obtained, for example, by adding the fluorine compound (e-15) to a solution of compound (e-14) and heating the mixture for several minutes to several hours.

There are no particular restrictions on the fluorine compound to be used for the reaction, and there may be mentioned lithium fluoride, sodium fluoride, potassium fluoride, cesium fluoride and the like. The fluorine compound is used at 1-10 equivalents with respect to the starting material.

There are no particular restrictions on the solvent used for the reaction so long as it does not inhibit the reaction, and as preferred solvents there may be mentioned benzene, toluene, N,N-dimethylformamide, 1-methyl-2-pyrrolidone, tetrahydrofuran, 1,4-dioxane, acetonitrile, propionitrile and dimethylsulfoxide.

The reaction temperature is not particularly restricted but will normally be from freezing to the reflux temperature of the solvent, and preferably from room temperature to the reflux temperature of the solvent.

The reaction may, if desired, be conducted in the copresence of a crown ether such as 18-crown-6 or a phosphonium salt such as tetraphenylphosphonium bromide, to achieve favorable results such as increased yield and shortening of the reaction time.

Step E-9

A step of obtaining compound (e-11a) from compound (e-16) and a fluorine compound (e-15). The reaction may be carried out under the same conditions as in Step E-8.

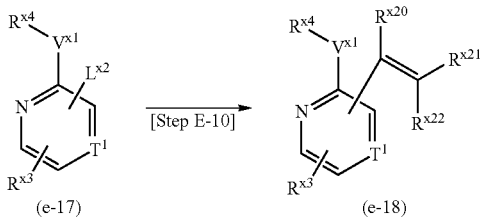

Step E-10

A step of obtaining compound (e-18) by reacting compound (e-17) and an alkenyl organometallic compound in the presence of an organometallic catalyst.

The reaction may be carried out under the same conditions commonly employed for coupling reaction between a halogenated heteroaryl compound or the like and an alkenyl organometallic compound in the presence of an organometallic catalyst.

For example, a reaction using an organotin reagent as the alkenyl organometallic compound is described in D. R. McKean, G. Parrinello, A. F. Renaldo and J. K. Stille, Journal of Organic Chemistry, 52, 422(1987), a reaction using an organoboric acid compound as the alkenyl organometallic compound is described in N. Miyaura, T. Yanagi and A. Suzuki, Synthetic Communications, 11, 513(1981), and a reaction using a Grignard reagent as the alkenyl organometallic compound is described in T. V. Lee, A. J. Leigh and C. B. Chapleo, Synthesis, 208(1989).

There are no particular restrictions on the organometallic catalyst to be used for this reaction, and as preferred compounds there may be mentioned tetrakis(triphenylphosphine)palladium(0), dichlorobis(triphenylphosphine)palladium(II), [1,1'-bis(diphenylphosphino)ferrocene]palladium(II)dichloride, palladium(II)acetate and [1,3-bis(diphenylphosphino)propane]nickel(II).

The organometallic catalyst is used at about 0.001-0.1 equivalent with respect to the starting material.

There are also no particular restrictions on the alkenyl organometallic compound, and there may be mentioned as preferable Grignard's reagents such as vinylmagnesium bromide, organotin compounds such as tributyl(vinyl)tin, and organoboric acid compounds such as vinylboric acid.

There are no particular restrictions on the solvent used for the reaction so long as it does not inhibit the reaction, and as preferred solvents there may be mentioned benzene, toluene, N,N-dimethylformamide, 1-methyl-2-pyrrolidone, tetrahydrofuran, 1,4-dioxane, acetonitrile and propionitrile.

The reaction temperature is not particularly restricted but will normally be from $-78°$ C. to the reflux temperature of the solvent, and preferably from $50°$ C. to $150°$ C. Conducting the reaction in the copresence of a base may provide favorable results such as increased yield. Such bases are not particularly restricted, and sodium carbonate, potassium carbonate, cesium carbonate, potassium phosphate and triethylamine may be mentioned as preferable.

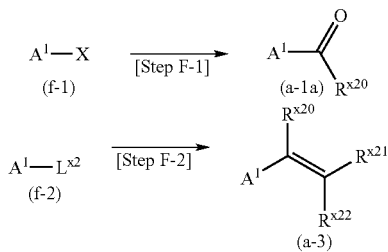

Step F-1

Compound (a-1a) may be synthesized using compound (f-1) as the starting material, according to the method of Production Scheme E above.

Step F-2

Compound (a-3) may be synthesized using compound (f-2) as the starting material, according to the method of Production Scheme E above.

Representative production schemes for compounds represented by general formula (I) according to the invention have been described above, but the starting compounds and reagents used for production of the compounds of the invention may also form salts or hydrates which will differ depending on the starting materials and solvent used, and these are not particularly restricted so long as the reaction is not inhibited. The solvents used will also differ depending on the starting materials and reagents, and they are not particularly restricted so long as they do not inhibit the reaction and dissolve the starting materials to some extent. When compound (I) of the invention is a free compound, a common method may be used to convert it to a salt which compound (I) can form. The different isomers (for example, geometric isomers, and optical isomers based on asymmetric carbons, rotational isomers and stereoisomers) obtained for compound (I) according to the invention may be purified and isolated using common separation means such as recrystallization, diastereomeric salt methods, enzymatic separation methods and chromatography (for example, thin-layer chromatography, column chromatography, gas chromatography, etc.).

The compounds represented by formula (I) and salts thereof or hydrates of the foregoing exhibit excellent sodium channel-inhibiting activity and high safety (in terms of effects on the cardiovascular system, inhibiting action on hepatic drug metabolizing enzymes, enzyme induction, etc.), and are therefore useful as drugs.

The compounds of the invention and salts thereof or hydrates of the foregoing may therefore be used to obtain pharmaceutical compositions (formulation) as therapeutic or prophylactic agents or analgesics, for diseases wherein sodium channel inhibition is effective as treatment and prevention, such as various types of neuralgia (for example, diabetic neuralgia, HIV neuralgia, postherpetic neuralgia, trigeminal neuralgia, stump pain, post spinal injury pain, thalamic pain, post-stroke pain, etc.), epilepsy, insomnia, premature ejaculation, and the like.

Furthermore, administration of compounds of the invention, salts thereof or hydrates of the foregoing at pharmacologically effective doses to patients suffering from diseases or neuralgia wherein sodium channel inhibition is effective as treatment and prevention, may serve as treatment or prevention of such diseases or neuralgia.

The compounds of the invention, salts thereof or hydrates of the foregoing may be formulated as tablets, powders, fine particles, granules, coated tablets, capsules, syrups, lozenges, inhalants, suppositories, injections, ointments, eye salves, eye drops, nasal drops, ear drops, paps, lotions and the like, by any common methods. The formulation may employ any commonly used excipients, binders, lubricants, coloring agents, corrective coatings, and if necessary, stabilizers, emulsifiers, absorbefacients, surfactants, pH adjustors, preservatives, antioxidants, or the like, in combination with various components that are ordinarily used as raw materials for pharmaceutical formulations.

As such components there may be mentioned animal and vegetable oils such as soybean oil, beef tallow and synthetic glycerides; hydrocarbons such as liquid paraffin, squalane and solid paraffin; ester oils such as octyldodecyl myristate and isopropyl myristate; higher alcohols such as cetostearyl alcohol and behenyl alcohol; silicone resins; silicone oils; surfactants such as polyoxyethylene fatty acid esters, sorbitan fatty acid esters, glycerin fatty acid esters, polyoxyethylene sorbitan fatty acid esters, polyoxyethylene hydrogenated castor oil and polyoxyethylene-polyoxypropylene block copolymer; water-soluble polymers such as hydroxyethylcellulose, polyacrylic acid, carboxyvinyl polymer, polyethylene glycol, polyvinylpyrrolidone and methylcellulose; lower alcohols such as ethanol and isopropanol; polyhydric alcohols such as glycerin, propylene glycol, dipropylene glycol and sorbitol; sugars such as glucose and sucrose; inorganic powders such as silicic acid anhydride, magnesium aluminum silicate and aluminum silicate, purified water, and the like.

Examples of excipients which may be used include lactose, corn starch, white soft sugar, glucose, mannitol, sorbit, crystalline cellulose and silicon dioxide, examples of binders which may be used include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, polypropylene glycol/polyoxyethylene block polymer and meglumine, examples of disintegrators which may be used include starch, agar, gelatin powder, crystalline cellulose, calcium carbonate, sodium bicarbonate, calcium citrate, dextrin, pectin and carboxymethylcellulose calcium, examples of lubricants which may be used include magnesium stearate, talc, polyethylene glycol, silica and hydrogenated vegetable oils, examples of coloring agents which may be used include those approved for addition to drugs, and examples of corrective coatings which may be used include cocoa powder, menthol, aromatic powders, mentha oil, borneol and powdered cinnamon.

An oral formulation may be prepared by combining a compound of the invention or pharmacologically acceptable salt thereof with an excipient, if necessary adding a binder, disintegrator, lubricant, coloring agent, corrective coating or the like, and forming a powder, fine particles, granules, tablets, coated tablets, capsules, etc. by a common method.

The tablets or granules may also be sugar coated or provided with another type of suitable coating if necessary.

For preparation of a liquid formulation such as a syrup or injection, a common method may be used to formulate a compound of the invention or a pharmacologically acceptable salt thereof with a pH adjustor, solubilizer, isotonizing agent or the like, as well as a solubilizing aid, stabilizer etc. if necessary.

There are no particular restrictions on the method of preparing an external agent, and any common method may be employed. That is, it may be prepared using as base materials any of various raw materials which are ordinarily used in drugs, quasi drugs, cosmetics and the like. As examples of specific base materials there may be mentioned raw materials such as animal and vegetable oils, mineral oils, ester oils, waxes, higher alcohols, fatty acids, silicone oils, surfactants, phospholipids, alcohols, polyhydric alcohols, water-soluble polymers, clay minerals, purified water and the like, and if necessary pH adjustors, antioxidants, chelating agents, antiseptics and fungicides, coloring agents, aromas and the like may also be added, although the base materials for external agents according to the invention are not limited to these. If necessary, there may also be included components such as circulation promoters, microbicides, antiphlogistic agents, cell activators, vitamins, amino acids, humectants, keratolytic agents and the like. The amounts of the aforementioned base materials may be the concentrations established for preparation of ordinary external agents.

There are no particular restrictions on the compound of the invention, the salt thereof or the hydrate thereof when administered, and either oral or parenteral administration may be carried out according to ordinary methods. For example, it may be prepared and administered in the form of a tablet, powder, a granule, a capsule, syrup, lozenge, inhalant, suppository, injection, ointment, eye salve, eye drop, nasal drop, ear drop, pap, lotion or the like. The dosage of a drug according to the invention may be appropriately selected depending on the age, gender, body weight and severity of symptoms of the patient, as well as the specific type of condition, form of administration, type of salt, etc.

Although the dosage of a drug according to the invention will differ depending on the patient's type of disease, severity of symptoms, age, gender and drug sensitivity, it will generally be about 0.03-1000 mg and preferably 0.1-500 mg per day for adults in the case of oral administration or about 1-3000 µg/kg and preferably about 3-1000 µg/kg in the case of injection, and any such dosages may be administered once or divided over several times a day.

The following are examples of formulations to be used for treatment or prevention in humans, which contain compounds selected from among those of Examples 140, 142, 143, 147, 157, 179, 184, 193, 233, 343, 344, 347, 350, 365, 373, 376, 394 and 415, salts thereof or hydrates of the foregoing (Compound X).

|  | Content per tablet |
|---|---|
| Tablet 1 | |
| Compound X | 100 mg |
| Titanium oxide | 11.2 mg |
| Talc | 4.0 mg |
| Mannitol | 106.7 mg |
| Microcrystalline cellulose | 60.0 mg |
| Low-substituted hydroxypropylcellulose | 20.0 mg |
| Methacrylic acid copolymer (type A) | 80.0 mg |
| Magnesium stearate | 6.0 mg |
| Hydroxypropylmethyl cellulose | 8.4 mg |
| Coloring agent | 5.6 mg |
| Purified water | quantum sufficit |
| Tablet 2 | |
| Compound X | 25.0 mg |
| Titanium oxide | 2.8 mg |

-continued

| | Content per tablet |
|---|---|
| Talc | 4.0 mg |
| Mannitol | 199.2 mg |
| Microcrystalline cellulose | 60.0 mg |
| Low-substituted hydroxypropylcellulose | 20.0 mg |
| Methacrylic acid copolymer (type A) | 80.0 mg |
| Magnesium stearate | 6.0 mg |
| Hydroxypropylmethyl cellulose | 8.4 mg |
| Coloring agent | 5.6 mg |
| Purified water | quantum sufficit |
| Tablet 3 | |
| Compound X | 2.5 mg |
| Titanium oxide | 0.28 mg |
| Talc | 1.0 mg |
| Mannitol | 54.42 mg |
| Microcrystalline cellulose | 15.0 mg |
| Low-substituted hydroxypropylcellulose | 5.0 mg |
| Methacrylic acid copolymer (type A) | 20.0 mg |
| Magnesium stearate | 1.5 mg |
| Hydroxypropylmethyl cellulose | 3.6 mg |
| Coloring agent | 2.4 mg |
| Purified water | quantum sufficit |

These formulations may be obtained by methods commonly used in the field of manufacturing pharmacy.

EXAMPLES

The following production examples, examples and test examples serve only for the purpose of illustration and are not intended to be restrictive on the compounds of the invention in any way. It will be apparent to those skilled in the art that various modifications may be added beyond these examples and within the scope of the claims of the invention in the present specification in order to maximize the effect of the invention, and such modifications are also encompassed within the claims.

Production Example 1

3-tert-Butoxypyrazine-2-carboxaldehyde

After dissolving 2.50 ml of 2,2,6,6-tetramethylpiperidine in 40 ml of tetrahydrofuran, the solution was cooled to −50° C. Next, 5.25 ml of n-butyllithium (2.6 M, n-hexane solution) was added dropwise thereto under a nitrogen atmosphere. The mixture was stirred for 25 minutes, cooled on ice, and stirred for an additional 35 minutes. It was then cooled to −78° C., and a solution of 1.89 g of 2-tert-butoxypyrazine [CAS No. 70090-30-1] in tetrahydrofuran (5 ml) was added dropwise. After stirring the mixture for 15 minutes, 1.25 ml of N,N-dimethylformamide was added dropwise. After 10 minutes, water was added to the reaction solution and extraction was performed with ethyl acetate. The organic layer was washed with water and saturated brine in that order and dried over anhydrous magnesium sulfate, and then the solvent was distilled off under reduced pressure. The residue was purified by silica gel column chromatography (solvent: n-hexane/ethyl acetate) to obtain the title compound (1.00 g, 45% yield).

1H-NMR (400 MHz, CDCl3); δ(ppm) 1.68 (9H, s), 8.28 (1H, d, J=2.4 Hz), 8.30 (1H, d, J=2.4 Hz), 10.33 (1H, s).

Production Example 2

3-(tert-Butylthio)pyrazine-2-carboxaldehyde

The title compound (1.49 g, 40% yield) was obtained in the same manner as Production Example 1 from 3.22 g of 2-(tert-butylthio)pyrazine.

1H-NMR (400 MHz, CDCl3); δ(ppm) 1.65 (9H, s), 8.40 (1H, d, J=2.4 Hz), 8.53 (1H, d, J=2.4 Hz), 10.14 (1H, s).

Production Example 3

3-tert-Butoxyquinoxaline-2-carboxaldehyde

The title compound (0.84 g, 18% yield) was obtained in the same manner as Production Example 1 from 4.00 g of 2-tert-butoxyquinoxaline.

1H-NMR (400 MHz, CDCl3); δ(ppm) 1.78 (9H, s), 7.61 (1H, ddd, J=8.4, 7.2, 1.6 Hz), 7.77 (1H, ddd, J=8.4, 7.2, 1.6 Hz), 7.84 (1H, ddd, J=8.4, 1.6, 0.8 Hz), 8.15 (1H, ddd, J=8.4, 1.6, 0.8 Hz), 10.48 (1H, s).

Production Example 4

2-tert-Butoxy-6-chloropyrazine

After dissolving 3.00 g of 2,6-dichloropyrazine in 40 ml of tetrahydrofuran, 2.26 g of potassium tert-butoxide was added and the mixture was stirred for 5.5 hours at room temperature. The reaction solution was distilled off under reduced pressure, ethyl acetate was added to the residue and filtration was performed with NH silica gel and silica gel. The solvent was distilled off under reduced pressure to obtain the title compound (3.38 g, 90% yield).

1H-NMR (400 MHz, CDCl3); δ(ppm) 1.60 (9H, s), 7.99 (1H, s), 8.06 (1H, s).

Production Example 5

2-(tert-Butylthio)pyrazine

After dissolving 2.305 g of 2-chloropyrazine in 60 ml of tetrahydrofuran, 2.76 g of sodium tert-butylthiolate was added while stirring and the mixture was heated to reflux for 3 hours. Water was added to the reaction solution and extraction was performed with ethyl acetate. The organic layer was washed with water and saturated brine in that order and dried over anhydrous magnesium sulfate, and then the solvent was distilled off under reduced pressure. Ethyl acetate was added to the residue and filtration was performed with NH silica gel and silica gel. The solvent was distilled off under reduced pressure to obtain the title compound (3.217 g, 95% yield).

1H-NMR (400 MHz, CDCl3); δ(ppm) 1.54 (9H, s), 8.28 (1H, d, J=2.8 Hz), 8.44 (1H, dd, J=2.8, 1.6 Hz), 8.50 (1H, d, J=1.6 Hz).

Production Example 6

2-tert-Butoxyquinoxaline

The title compound (5.99 g, 98% yield) was obtained in the same manner as Production Example 4 from 5.00 g of 2-chloroquinoxaline.

1H-NMR (400 MHz, CDCl3); δ(ppm) 1.71 (9H, s), 7.53 (1H, ddd, J=8.4, 7.2, 1.6 Hz), 7.64 (1H, ddd, J=8.4, 7.2, 1.6 Hz), 7.80 (1H, ddd, J=8.4, 1.6, 0.4 Hz), 7.97 (1H, ddd, J=8.4, 1.6, 0.4 Hz), 8.34 (1H, s).

Production Example 7

2-tert-Butoxy-4-chloropyrimidine and
4-tert-butoxy-2-chloropyrimidine

After dissolving 2.00 g of 2,4-dichloropyrimidine in 30 ml of tert-butanol, 1.58 g of potassium tert-butoxide was added while stirring and the mixture was stirred overnight at room temperature. The reaction mixture was poured onto ice and extraction was performed with ethyl acetate. The organic layer was washed with water and saturated brine in that order and dried over anhydrous magnesium sulfate, and then the solvent was distilled off under reduced pressure. The residue was purified by silica gel column chromatography (solvent: n-hexane/ethyl acetate), to obtain 2-tert-butoxy-4-chloropyrimidine (0.40 g, 16% yield) and 4-tert-butoxy-2-chloropyrimidine (1.28 g, 50% yield).

2-tert-Butoxy-4-chloropyrimidine

1H-NMR (400 MHz, CDCl3); δ(ppm) 1.63 (9H, s), 6.91 (1H, d, J=1.6 Hz), 8.34 (1H, d, J=1.6 Hz).

4-tert-Butoxy-2-chloropyrimidine

1H-NMR (400 MHz, CDCl3); δ(ppm) 1.62 (9H, s), 6.53 (1H, d, J=1.6 Hz), 8.22 (1H, d, J=1.6 Hz).

Production Example 8

2-tert-Butoxy-6-vinylpyrazine

After dissolving 5.25 g of 2-tert-butoxy-6-chloropyrazine in 80 ml of N,N-dimethylformamide, 9.66 g of tributyl(vinyl)tin and 0.97 g of dichlorobis(triphenylphosphine)palladium(II) were added and the mixture was stirred for 8 hours and 30 minutes at 80° C. under a nitrogen atmosphere. Saturated brine and ethyl acetate were added to the reaction solution, and the insoluble portion was filtered off. The ethyl acetate layer was washed with water and saturated brine in that order and dried over anhydrous magnesium sulfate, and then the solvent was distilled off under reduced pressure. The residue was purified by silica gel column chromatography (solvent: n-hexane/ethyl acetate) to obtain the title compound (4.24 g, 85% yield).
1H-NMR (400 MHz, CDCl3); δ(ppm) 1.63 (9H, s), 5.50 (1H, dd, J=10.8, 1.6 Hz), 6.31 (1H, dd, J=17.2, 1.6 Hz), 6.70 (1H, dd, J=17.2, 10.8 Hz), 7.95 (1H, s), 7.96 (1H, s).

Production Example 9

4-tert-Butoxy-2-vinylpyrimidine

The title compound (2.26 g, 79% yield) was obtained in the same manner as Production Example 8 from 3.00 g of 4-tert-butoxy-2-chloropyrimidine.
1H-NMR (400 MHz, CDCl3); δ(ppm) 1.64 (9H, s), 5.66 (1H, dd, J=10.4, 1.6 Hz), 6.46 (1H, d, J=6.0 Hz), 6.51 (1H, dd, J=15.2, 1.6 Hz), 6.77 (1H, dd, J=15.2, 10.4 Hz), 8.32 (1H, d, J=6.0 Hz).

Production Example 10

2-tert-Butoxy-4-vinylpyrimidine

The title compound (2.04 g, 81% yield) was obtained in the same manner as Production Example 8 from 2.64 g of 2-tert-butoxy-4-chloropyrimidine.

1H-NMR (400 MHz, CDCl3); δ(ppm) 1.65 (9H, s), 5.64 (1H, dd, J=10.4, 1.6 Hz), 6.44 (1H, dd, J=17.2, 1.6 Hz), 6.65 (1H, dd, J=17.2, 10.4 Hz), 8.12 (1H, d, J=5.2 Hz), 8.42 (1H, d, J=5.2 Hz).

Production Example 11

1-(1-Benzylpiperidin-4-yl)-2-(2-fluorophenyl)ethanol

After suspending 1.84 g of magnesium in 20 ml of diethyl ether, a catalytic amount of iodine was added, a portion of a diethyl ether solution (70 ml) containing 9.97 g of 2-fluorobenzyl chloride was added dropwise while stirring, and the mixture was heated to initiate the reaction. The remaining solution was then added dropwise at a rate to maintain reflux. After 10 minutes, the mixture was cooled on ice, a diethyl ether solution (70 ml) containing 15.4 g of 1-benzyl-4-piperidinecarboxaldehyde [CAS No. 22065-85-6] was added dropwise, and stirring was continued for 20 minutes. Saturated aqueous ammonium chloride solution was added to the reaction solution and extraction was performed with ethyl acetate. The organic layer was washed with brine and dried over anhydrous magnesium sulfate, and then the solvent was distilled off under reduced pressure. The residue was purified by NH silica gel column chromatography (solvent: n-hexane/ethyl acetate) to obtain the title compound (13.4 g, 62% yield).
1H-NMR (400 MHz, CDCl3); δ(ppm) 1.40-1.75 (4H, m), 1.82-1.90 (1H, m), 1.90-2.00 (2H, m), 2.57-2.65 (2H, m), 2.90-3.02 (3H, m), 3.50 (2H, s), 3.62-3.68 (1H, m), 7.03 (1H, ddd, J=9.6, 8.0, 1.2 Hz), 7.08 (1H, td, J=8.0, 1.6 Hz), 7.18-7.34 (7H, m).

Production Example 12

2-(1-Benzylpiperidin-4-yl)-1-(2-fluorophenyl)ethanol

After dissolving 1.64 ml of 1-bromo-2-fluorobenzene in 30 ml of tetrahydrofuran, the solution was cooled to −78° C. Next, 5.31 ml of n-butyllithium (2.6 M, n-hexane solution) was added dropwise while stirring, and after 1 hour, a solution of 2.50 g of 1-benzyl-4-piperidineacetaldehyde [CAS No. 120014-32-6] in tetrahydrofuran (10 ml) was added and stirring was continued for 1 hour. After adding water to the reaction solution, the temperature was raised to room temperature and extraction was performed with ethyl acetate. The organic layer was washed with water and saturated brine in that order and dried over anhydrous magnesium sulfate, and then the solvent was distilled off under reduced pressure. The residue was purified by NH silica gel column chromatography (solvent: n-hexane/ethyl acetate) to obtain the title compound (2.15 g, 60% yield).
1H-NMR (400 MHz, CDCl3); δ(ppm) 1.25-1.38 (2H, m), 1.41-1.52 (1H, m), 1.56-1.81 (4H, m), 1.90-1.98 (2H, m), 2.82-2.90 (2H, m), 3.47 (2H, s), 5.10 (1H, dd, J=8.4, 4.8 Hz), 7.01 (1H, ddd, J=10.4, 8.0, 1.2 Hz), 7.14 (1H, dt, J=7.2, 1.2 Hz), 7.20-7.32 (6H, m), 7.45 (1H, dt, J=7.6, 1.6 Hz).

Production Example 13

2-(1-Benzylpiperidin-4-yl)-1-(2-methoxyphenyl)ethanol

After dissolving 2.04 g of 2-bromoanisole in 22 ml of tetrahydrofuran, 3.6 ml of n-butyllithium (2.66 M, n-hexane solution) was added dropwise while stirring at below −60° C., and after 30 minutes, a solution of 1.58 g of 1-benzylpiperidine-4-acetaldehyde in tetrahydrofuran (5 ml) was added and stirring was continued for 30 minutes. Saturated aqueous ammonium chloride solution was added, the temperature was raised to room temperature, and extraction was performed with ethyl acetate. The organic layer was washed with saturated brine and dried over anhydrous magnesium sulfate, and then the solvent was distilled off under reduced pressure. The residue was purified by NH silica gel column chromatography (solvent: n-hexane/ethyl acetate) to obtain the title compound (1.63 g, 69% yield).

1H-NMR (400 MHz, CDCl3); δ(ppm) 1.22-1.38 (2H, m), 1.45-1.65 (2H, m), 1.67-1.75 (1H, m), 1.75-1.84 (2H, m), 1.91-1.99 (2H, m), 2.83-2.91 (2H, m), 3.47 (2H, s), 3.84 (3H, s), 4.94-5.01 (1H, m), 6.87 (1H, dd, J=8.4, 1.2 Hz), 6.95 (1H, td, J=7.6, 1.2 Hz), 7.21-7.33 (7H, m).

Production Example 14

2-(1-Benzylpiperidin-4-yl)-1-(3-chloro-2-thienyl)ethanol

After dissolving 1.3 ml of diisopropylamine in 20 ml of tetrahydrofuran, 3.5 ml of n-butyllithium (2.66 M, n-hexane solution) was added dropwise while stirring at below −30° C. After stirring for 30 minutes while cooling on ice, 0.86 ml of 3-chlorothiophene was added dropwise. The mixture was stirred for another 30 minutes, and then a solution of 1.68 g of 1-benzyl-4-piperidineacetaldehyde in tetrahydrofuran (5 ml) was added and stirring was continued for 1 hour. Saturated aqueous ammonium chloride solution was added to the reaction solution and extraction was performed with ethyl acetate. The organic layer was washed with saturated brine and dried over anhydrous magnesium sulfate, and then the solvent was distilled off under reduced pressure. The residue was purified by silica gel column chromatography (solvent: n-hexane/ethyl acetate) to obtain the title compound (1.53 g, 59% yield).

1H-NMR (400 MHz, CDCl3); δ(ppm) 1.26-1.54 (3H, m), 1.56-1.88 (4H, m), 1.90-1.98 (2H, m), 2.83-2.91 (2H, m), 3.49 (2H, s), 5.19 (1H, dd, J=8.4, 5.6 Hz), 6.86 (1H, d, J=5.2 Hz), 7.21-7.34 (6H, m).

Production Example 15

1-(1-Benzylpiperidin-4-yl)-2-(2-fluorophenyl)ethanone

After dissolving 7.5 ml of oxalyl chloride in 130 ml of dichloromethane, the solution was cooled to −78° C. and a solution of 6.1 ml of dimethylsulfoxide in dichloromethane (20 ml) was added dropwise while stirring. After stirring for 20 minutes, a solution of 13.4 g of 1-(1-benzylpiperidin-4-yl)-2-(2-fluorophenyl)ethanol in dichloromethane (40 ml) was added dropwise. After stirring for 30 minutes, 24 ml of triethylamine was added and the temperature was raised to room temperature. Water was added to the reaction solution, the organic layer was washed with water and saturated brine in that order and dried over anhydrous magnesium sulfate, and then the solvent was distilled off under reduced pressure. The residue was purified by NH silica gel column chromatography (solvent: n-hexane/ethyl acetate) to obtain the title compound (9.64 g, 73% yield).

1H-NMR (400 MHz, CDCl3); δ(ppm) 1.68-1.80 (2H, m), 1.81-1.88 (2H, m), 1.97-2.06 (2H, m), 2.40-2.49 (1H, m), 2.88-2.95 (2H, m), 3.50 (2H, s), 3.77 (2H, d, J=1.2 Hz), 7.04 (1H, ddd, J=9.6, 7.8, 1.2 Hz), 7.09 (1H, td, J=7.8, 1.2 Hz), 7.16 (1H, td, J=7.8, 2.0 Hz), 7.21-7.34 (6H, m).

Production Example 16

1-(1-Benzylpiperidin-4-yl)-2-(2-methoxyphenyl)ethanone

After dissolving 1.34 g of o-anisaldehyde in 10 ml of methanol, 1.83 g of p-toluenesulfonyl hydrazide was added, the mixture was stirred for 2 hours at room temperature and then 725 mg of potassium methoxide and a solution of 1.00 g of 1-benzylpiperidine-4-carboxaldehyde in methanol (3 ml) was added, and the mixture was shielded from light and stirred overnight at 55° C. Water was added to the reaction solution, and extraction was performed with ethyl acetate. The organic layer was washed with saturated brine and dried over anhydrous magnesium sulfate, and then the solvent was distilled off under reduced pressure. The residue was purified by silica gel column chromatography (solvent: toluene/ethyl acetate) to obtain the title compound (249 mg, 16% yield).

1H-NMR (400 MHz, CDCl3); δ(ppm) 1.67-1.86 (4H, m), 1.94-2.03 (2H, m), 2.39-2.48 (1H, m), 2.87-2.94 (2H, m), 3.49 (2H, s), 3.71 (2H, s), 3.77 (3H, s), 6.85 (1H, d, J=7.4 Hz), 6.91 (1H, td, J=7.4, 1.2 Hz), 7.09 (1H, dd, J=7.4, 2.0 Hz), 7.16-7.33 (6H, m).

Production Example 17

1-(1-Benzylpiperidin-4-yl)-2-(3-fluorophenyl)ethanone

The title compound (283 mg, 8% yield) was obtained in the same manner as Production Example 16 from 3.0 g of 3-fluorobenzaldehyde and 2.45 g of 1-benzylpiperidine-4-carboxaldehyde.

1H-NMR (400 MHz, CDCl3); δ(ppm) 1.65-1.84 (4H, m), 1.94-2.03 (2H, m), 2.37-2.46 (1H, m), 2.86-2.94 (2H, m), 3.49 (2H, s), 3.73 (2H, s), 6.87-6.98 (3H, m), 7.22-7.35 (6H, m).

Production Example 18

1-(1-Benzylpiperidin-4-yl)-2-(3-methylphenyl)ethanone

The title compound (241 mg, 16% yield) was obtained in the same manner as Production Example 16 from 1.18 g of m-tolualdehyde and 1.00 g of 1-benzylpiperidine-4-carboxaldehyde.

1H-NMR (400 MHz, CDCl3); δ(ppm) 1.63-1.82 (4H, m), 1.92-2.02 (2H, m), 2.33 (3H, s), 2.37-2.46 (1H, m), 2.85-2.93 (2H, m), 3.48 (2H, s), 3.69 (2H, s), 6.94-7.00 (2H, m), 7.04-7.08 (1H, m), 7.17-7.34 (6H, m).

Production Example 19

1-(1-Benzylpiperidin-4-yl)-2-(2-chlorophenyl)ethanone

The title compound (252 mg, 20% yield) was obtained in the same manner as Production Example 16 from 1.0 g of 2-chlorobenzaldehyde and 789 mg of 1-benzylpiperidine-4-carboxaldehyde.

1H-NMR (400 MHz, CDCl3); δ(ppm) 1.71-1.82 (2H, m), 1.84-1.91 (2H, m), 1.98-2.06 (2H, m), 2.42-2.52 (1H, m), 2.89-2.96 (2H, m), 3.50 (2H, s), 3.89 (2H, s), 7.08-7.20 (9H, m).

Production Example 20

1-(1-Benzylpiperidin-4-yl)-2-(2,5-difluorophenyl)ethanone

The title compound (215 mg, 13% yield) was obtained in the same manner as Production Example 16 from 1.40 g of 2,5-difluorobenzaldehyde and 1.00 g of 1-benzylpiperidine-4-carboxaldehyde.

1H-NMR (400 MHz, CDCl3); δ(ppm) 1.68-1.80 (2H, m), 1.82-1.90 (2H, m), 1.98-2.07 (2H, m), 2.40-2.49 (1H, m), 2.89-2.96 (2H, m), 3.51 (2H, s), 3.75 (2H, d, J=1.2 Hz), 6.85-7.03 (3H, m), 7.22-7.34 (5H, m).

Production Example 21

1-(1-Benzylpiperidin-4-yl)-2-(2,6-difluorophenyl)ethanone

The title compound (65 mg, 4% yield) was obtained in the same manner as Production Example 16 from 1.40 g of 2,6-difluorobenzaldehyde and 1.00 g of 1-benzylpiperidine-4-carboxaldehyde.

1H-NMR (400 MHz, CDCl3); δ(ppm) 1.72-1.84 (2H, m), 1.85-1.94 (2H, m), 1.99-2.08 (2H, m), 2.42-2.53 (1H, m), 2.89-2.97 (2H, m), 3.51 (2H, s), 3.81 (2H, s), 6.84-6.92 (2H, m), 7.16-7.34 (6H, m).

Production Example 22

1-(1-Benzylpiperidin-4-yl)-2-(2-methylphenyl)ethanone

The title compound (998 mg, 26% yield) was obtained in the same manner as Production Example 16 from 3.0 g of o-tolualdehyde and 2.54 g of 1-benzylpiperidine-4-carboxaldehyde.

1H-NMR (400 MHz, CDCl3); δ(ppm) 1.68-1.83 (4H, m), 1.94-2.02 (2H, m), 2.20 (3H, s), 2.38-2.48 (1H, m), 2.87-2.94 (2H, m), 3.49 (2H, s), 3.75 (2H, s), 7.04-7.10 (1H, m), 7.12-7.18 (3H, m), 7.22-7.34 (5H, m).

Production Example 23

2-(1-Benzylpiperidin-4-yl)-1-(2-chlorophenyl)ethanone

After dissolving 1.75 ml of 1-bromo-2-chlorobenzene in 30 ml of tetrahydrofuran, the solution was cooled to −78° C. Next, 5.31 ml of n-butyllithium (2.6 M, n-hexane solution) was added dropwise thereto while stirring and after 1 hour, a solution of 2.50 g of 1-benzylpiperidine-4-acetaldehyde in tetrahydrofuran (10 ml) was added and stirring was continued for 1 hour. After adding water to the reaction solution, the temperature was raised to room temperature and extraction was performed with ethyl acetate. The organic layer was washed with water and saturated brine in that order and dried over anhydrous magnesium sulfate, and then the solvent was distilled off under reduced pressure to obtain 2-(1-benzylpiperidin-4-yl)-1-(2-chlorophenyl)ethanol.

After dissolving 1.30 ml of oxalyl chloride in 30 ml of dichloromethane, the solution was cooled to −78° C., and a solution of 1.22 ml of dimethylsulfoxide in dichloromethane (5 ml) was added dropwise while stirring. The mixture was stirred for 3 minutes, and then a solution of 2-(1-benzylpiperidin-4-yl)-1-(2-chlorophenyl)ethanol in dichloromethane (10 ml) was added dropwise. After stirring for 30 minutes, 8.01 ml of triethylamine was added, the temperature was raised to room temperature and stirring was continued for 3 hours. Water was added to the reaction solution, and extraction was performed with ethyl acetate. The organic layer was washed with water and saturated brine in that order and dried over anhydrous magnesium sulfate, and then the solvent was distilled off under reduced pressure. The residue was purified by NH silica gel column chromatography (solvent: n-hexane/ethyl acetate) to obtain the title compound (1.78 g, 47% yield, 2 steps).

1H-NMR (400 MHz, CDCl3); δ(ppm) 1.29-1.41 (2H, m), 1.69-1.76 (2H, m), 1.92-2.04 (3H, m), 2.83-2.89 (4H, m), 3.48 (2H, s), 7.21-7.42 (9H, m).

Production Example 24

2-(1-Benzylpiperidin-4-yl)-1-(3-chloro-2-thienyl)ethanone

The title compound (682 mg, 90% yield) was obtained in the same manner as Production Example 15 from 758 mg of 2-(1-benzylpiperidin-4-yl)-1-(3-chloro-2-thienyl)ethanol.

1H-NMR (400 MHz, CDCl3); δ(ppm) 1.32-1.44 (2H, m), 1.71-1.78 (2H, m), 1.94-2.08 (3H, m), 2.84-2.90 (2H, m), 2.93 (2H, d, J=6.8 Hz), 3.49 (2H, s), 7.01 (1H, d, J=5.2 Hz), 7.21-7.33 (5H, m), 7.52 (1H, d, J=5.2 Hz).

Production Example 25

2-(1-Benzylpiperidin-4-yl)-1-(2-fluorophenyl)ethanone

The title compound (2.31 g, 84% yield) was obtained in the same manner as Production Example 15 from 2.77 g of 2-(1-benzylpiperidin-4-yl)-1-(2-fluorophenyl)ethanol.

1H-NMR (400 MHz, CDCl3); δ(ppm) 1.29-1.41 (2H, m), 1.68-1.76 (2H, m), 1.92-2.04 (3H, m), 2.83-2.92 (4H, m), 3.49 (2H, s), 7.12 (1H, ddd, J=9.6, 8.0, 1.2 Hz), 7.19-7.32 (6H, m), 7.47-7.53 (1H, m), 7.81 (1H, dt, J=7.2, 2.0 Hz).

Production Example 26

1-[1-(tert-Butoxycarbonyl)piperidin-3-yl]-2-(2-fluorophenyl)ethanone

After suspending 334 mg of magnesium in 3 ml of diethyl ether, a catalytic amount of iodine was added, a portion of 1.89 g of 2-fluorobenzyl chloride was added dropwise while stirring, and the mixture was heated to initiate the reaction. After adding 10 ml of diethyl ether, the remaining 2-fluorobenzyl chloride was added dropwise to maintain reflux. After stirring the mixture for 15 minutes, approximately 6 ml of the obtained reaction solution was added dropwise to a solution of 1.78 g of N-methoxy-N-methyl-1-(tert-butoxycarbonyl)-3-piperidinecarboxamide [CAS No. 189442-78-2] in diethyl ether (20 ml) while cooling on ice, and stirring was continued for 30 minutes. Saturated aqueous ammonium chloride solution was added to the reaction solution and extraction was performed with ethyl acetate. The organic layer was washed with saturated brine and dried over anhydrous magnesium sulfate, and then the solvent was distilled off under reduced pressure. The residue was purified by silica gel column chromatography (solvent: n-hexane/ethyl acetate) to obtain the title compound (564 mg, 27% yield).

1H-NMR (400 MHz, CDCl3); δ(ppm) 1.40-1.67 (2H, m), 1.46 (9H, s), 1.68-1.80 (1H, m), 1.96-2.07 (1H, m), 2.60-

2.87 (2H, m), 2.99 (1H, dd, J=13.4, 10.2 Hz), 3.75-4.25 (4H, m), 7.02-7.19 (3H, m), 7.22-7.32 (1H, m).

Production Example 27

1-(1-Benzylpiperidin-4-yl)-2-(2-fluoro-3-thienyl) ethanone

After dissolving 292 mg of 1-benzyl-4-[2-(2-fluoro-3-thienyl)acetyl]-1,2,3,6-tetrahydropyridine in 10 ml of ethanol, 0.1 g of 20% palladium-hydroxide-carbon (hydrous) was added and the mixture was stirred for 1 hour at room temperature under a hydrogen atmosphere (1 atm). The reaction mixture was filtered and the filtrate was distilled off under reduced pressure. The residue was purified by silica gel column chromatography (solvent: n-hexane/ethyl acetate) to obtain the title compound (239 mg, 81% yield).

1H-NMR (400 MHz, CDCl3); δ(ppm) 1.65-1.86 (4H, m), 1.96-2.05 (2H, m), 2.37-2.46 (1H, m), 2.87-2.94 (2H, m), 3.49 (2H, s), 3.64 (2H, d, J=0.8 Hz), 6.60-6.62 (2H, m), 7.22-7.34 (5H, m).

Production Example 28

1-(2-Methoxyphenyl)-2-(piperidin-4-yl)ethanone

After dissolving 1.63 g of 2-(1-benzylpiperidin-4-yl)-1-(2-methoxyphenyl)ethanol in 5 ml of dimethylsulfoxide, 4.2 ml of triethylamine was added, a solution of 2.39 g of sulfur trioxide-pyridine complex in dimethylsulfoxide (15 ml) was added dropwise and the mixture was stirred for 30 minutes at room temperature. Water was added to the reaction mixture, and extraction was performed with ethyl acetate. The organic layer was washed with saturated brine and dried over anhydrous magnesium sulfate, and then the solvent was distilled off under reduced pressure. The residue was purified by NH silica gel column chromatography (solvent: n-hexane/ethyl acetate) to obtain 1.38 g of 1-(1-benzylpiperidin-4-yl)-2-(2-methoxyphenyl)ethanone. After dissolving this in 12 ml of 1,2-dichloroethane, 0.55 ml of 1-chloroethyl chloroformate was added while stirring on ice, and the mixture was heated to reflux for 1 hour. The solvent was distilled off under reduced pressure, 10 ml of methanol was added to the residue and heating to reflux was continued for 30 minutes. The solvent was distilled off under reduced pressure. A 1N sodium hydroxide solution was added to the residue and extraction was performed with ethyl acetate. The organic layer was washed with saturated brine and dried over anhydrous magnesium sulfate, and then the solvent was distilled off under reduced pressure to obtain the title compound (750 mg, 64% yield).

1H-NMR (400 MHz, CDCl3); δ(ppm) 1.15-1.27 (2H, m), 1.68-1.80 (2H, m), 2.02-2.12 (1H, m), 2.59-2.68 (2H, m), 2.89 (2H, d, J=6.8 Hz), 3.02-3.08 (2H, m), 3.90 (3H, s), 6.96 (1H, d, J=8.6 Hz), 7.00 (1H, td, J=7.6, 1.2 Hz), 7.45 (1H, ddd, J=8.6, 7.6, 1.8 Hz), 7.62 (1H, dd, J=7.6, 1.8 Hz).

Production Example 29

2-(2-Fluorophenyl)-1-(piperidin-4-yl)ethanone hydrochloride

After dissolving 1.27 g of 1-(1-benzylpiperidin-4-yl)-2-(2-fluorophenyl)ethanone in 8 ml of 1,2-dichloroethane, 0.53 ml of 1-chloroethyl chloroformate was added while stirring on ice, and the mixture was heated to reflux for 1 hour. The solvent was distilled off under reduced pressure, 8 ml of methanol was added to the residue, and heating to reflux was continued for 40 minutes. The solvent was distilled off under reduced pressure, ethyl acetate was added to the residue, and the precipitate was filtered out to obtain the title compound (970 mg, 92% yield).

1H-NMR (400 MHz, DMSO-d6); δ(ppm) 1.63-1.76 (2H, m), 1.99-2.07 (2H, m), 2.82-2.96 (3H, m), 3.23-3.31 (2H, m), 3.95 (2H, s), 7.12-7.19 (2H, m), 7.23-7.35 (2H, m), 8.94 (2H, br s).

Production Example 30

2-(2-Methylphenyl)-1-(piperidin-4-yl)ethanone hydrochloride

The title compound (680 mg, 82% yield) was obtained in the same manner as Production Example 29 from 998 mg of 1-(1-benzylpiperidin-4-yl)-2-(2-methylphenyl)ethanone.

1H-NMR (400 MHz, DMSO-d6); δ(ppm) 1.60-1.72 (2H, m), 1.97-2.05 (2H, m), 2.11 (3H, s), 2.81-2.97 (3H, m), 3.24-3.31 (2H, m), 3.91 (2H, s), 7.08-7.17 (4H, m).

Production Example 31

1-(2-Fluorophenyl)-2-(piperidin-4-yl)ethanone hydrochloride

The title compound (2.09 g, 68% yield) was obtained in the same manner as Production Example 29 from 3.71 g of 2-(1-benzylpiperidin-4-yl)-1-(2-fluorophenyl)ethanone.

1H-NMR (400 MHz, CDCl3); δ(ppm) 1.68-1.82 (2H, m), 1.96-2.04 (2H, m), 2.24-2.38 (1H, m), 2.86-3.02 (4H, m), 3.46-3.54 (2H, m), 7.15 (1H, ddd, J=11.2, 8.4, 1.2 Hz), 7.24 (1H, dt, J=8.4, 1.2 Hz), 7.51-7.57 (1H, m), 7.84 (1H, dt, J=7.6, 2.0 Hz), 9.39 (1H, br s), 9.67 (1H, br s).

Production Example 32

1-(2-Chlorophenyl)-2-(piperidin-4-yl)ethanone hydrochloride

The title compound (1.15 g, 78% yield) was obtained in the same manner as Production Example 29 from 1.78 g of 2-(1-benzylpiperidin-4-yl)-1-(2-chlorophenyl)ethanone.

1H-NMR (400 MHz, CDCl3); δ(ppm) 1.69-1.83 (2H, m), 1.96-2.04 (2H, m), 2.30 (1H, m), 2.86-3.00 (4H, m), 3.46-3.54 (2H, m), 7.31-7.44 (4H, m), 9.38 (1H, br s), 9.63 (1H, br s).

Production Example 33

1-(3-Chloro-2-thienyl)-2-(piperidin-4-yl)ethanone hydrochloride

The title compound (520 mg, 91% yield) was obtained in the same manner as Production Example 29 from 682 mg of 2-(1-benzylpiperidin-4-yl)-1-(3-chloro-2-thienyl)ethanone.

1H-NMR (400 MHz, DMSO-d6); δ(ppm) 1.70-1.84 (2H, m), 1.98-2.06 (2H, m), 2.24-2.36 (1H, m), 2.88-2.98 (2H, m), 3.03 (2H, d, J=6.4 Hz), 3.46-3.54 (2H, m), 7.04 (1H, d, J=5.2 Hz), 7.57 (1H, d, J=5.2 Hz).

Production Example 34

2-(2-Fluoro-3-thienyl)-1-(piperidin-4-yl)ethanone hydrochloride

The title compound (173 mg, 88% yield) was obtained in the same manner as Production Example 29 from 239 mg of 1-(1-benzylpiperidin-4-yl)-2-(2-fluoro-3-thienyl)ethanone.

1H-NMR (400 MHz, DMSO-d6); δ(ppm) 1.61-1.73 (2H, m), 1.96-2.04 (2H, m), 2.79-2.96 (3H, m), 3.22-3.30 (2H, m), 3.82 (2H, s), 6.89 (1H, dd, J=6.0, 4.0 Hz), 6.93 (1H, dd, J=6.0, 4.0 Hz), 8.74 (1H, br s), 9.03 (1H, br s).

Production Example 35

1-Benzyl-4-[2-(2-fluoro-3-thienyl)acetyl]-1,2,3,6-tetrahydropyridine

The title compound (292 mg, 77% yield) was obtained in the same manner as Production Example 15 from 384 mg of 1-(1-benzyl-1,2,3,6-tetrahydropyridin-4-yl)-2-(2-fluoro-3-thienyl)ethanol.

1H-NMR (400 MHz, CDCl3); δ(ppm) 2.37-2.43 (2H, m), 2.60 (2H, t, J=5.6 Hz), 3.19-3.23 (2H, m), 3.62 (2H, s), 3.85 (2H, s), 6.60 (1H, dd, J=6.0, 4.0 Hz), 6.63 (1H, dd, J=6.0, 3.6 Hz), 6.88-6.92 (1H, m), 7.24-7.35 (5H, m).

Production Example 36

1-(tert-Butoxycarbonyl)-4-[(2-fluorophenyl)ethynyl]-4-hydroxypiperidine

After dissolving 12.6 g of carbon tetrabromide in 80 ml of dichloromethane, the solution was cooled to 0° C. A 20 g portion of triphenylphosphine was added thereto in small portions at a time, and the mixture was stirred for 1 hour. A solution of 2.4 g of 2-fluorobenzaldehyde in dichloromethane (70 ml) was added dropwise and stirring was continued at 0° C. for 4 hours. After stirring overnight at room temperature, hexane was added and the mixture was filtered. The filtrate was concentrated under reduced pressure, and the residue was purified by silica gel column chromatography (solvent: n-hexane/ethyl acetate). The obtained 3.7 g of 1,1-dibromo-2-(2-fluorophenyl)ethene was dissolved in 30 ml of tetrahydrofuran, and the solution was cooled to −78° C. Next, 18 ml of n-butyllithium (1.6 M, n-hexane solution) was added dropwise. The mixture was stirred at −78° C. for 1 hour and then at room temperature for 1 hour. The obtained reaction solution was added dropwise to a solution of 2.6 g of tert-butyl 4-oxo-1-piperidinecarboxylate in tetrahydrofuran (100 ml) which had been cooled to −78° C. After stirring the mixture for 4 hours while slowly raising the temperature to room temperature, saturated aqueous ammonium chloride solution was added and extraction was performed with ethyl acetate. The organic layer was dried over magnesium sulfate, and the solvent was distilled off under reduced pressure. The residue was purified by silica gel column chromatography (solvent: n-hexane/ethyl acetate) to obtain the title compound (1.4 g, 23% yield, 2 steps).

1H-NMR (400 MHz, CDCl3); δ(ppm) 1.47 (9H, s), 1.76-1.83 (2H, m), 1.99-2.05 (2H, m), 3.27-3.35 (2H, m), 3.81-3.90 (2H, m), 7.05-7.12 (2H, m), 7.28-7.36 (1H, m), 7.39-7.44 (1H, m).

Production Example 37

1-(tert-Butoxycarbonyl)-4-hydroxy-4-[(2-methylphenyl)ethynyl]piperidine

The title compound (3.99 g, 79% yield) was obtained in the same manner as Example 36 from 2.29 g of 2-methylbenzaldehyde.

1H-NMR (400 MHz, CDCl3); δ(ppm) 1.47 (9H, s), 1.77-1.84 (2H, m), 1.98-2.05 (2H, m), 2.42 (3H, s), 3.27-3.35 (2H, m), 3.81-3.95 (2H, m), 7.11-7.16 (1H, m), 7.19-7.26 (2H, m), 7.38-7.41 (1H, m).

Production Example 38

1-(tert-Butoxycarbonyl)-4-cyano-4-(methanesulfonyloxymethyl)piperidine

After dissolving 537 mg of 1-(tert-butoxycarbonyl)-4-cyano-4-(hydroxymethyl)piperidine in 100 ml of tetrahydrofuran, 0.4 ml of triethylamine was added and the solution was cooled to 0° C. 0.2 ml of methanesulfonyl chloride was added and the mixture was stirred overnight at room temperature. The reaction mixture was filtered and the filtrate was concentrated under reduced pressure. After adding water to the residue, extraction was performed with ethyl acetate. The organic layer was washed with water and then dried over magnesium sulfate. The solvent was distilled off under reduced pressure to obtain the title compound (799 mg, 100% yield).

1H-NMR (400 MHz, CDCl3); δ(ppm) 1.46 (9H, s), 1.95-2.05 (2H, m), 1.50-1.57 (2H, m), 3.00-3.10 (2H, m), 3.13 (3H, s), 4.13-4.30 (2H, m), 4.19 (2H, s).

Production Example 39

1-(tert-Butoxycarbonyl)-4-fluoro-4-(methanesulfonyloxymethyl)piperidine

The title compound (150 mg, 100% yield) was obtained in the same manner as Example 38 from 103 mg of 1-(tert-butoxycarbonyl)-4-fluoro-4-(hydroxymethyl)piperidine.

1H-NMR (400 MHz, CDCl3); δ(ppm) 1.46 (9H, s), 1.48-1.94 (4H, m), 3.09-3.18 (2H, m), 3.08 (3H, s), 3.95-4.05 (2H, m), 4.20 (2H, d, J=20.0 Hz).

Production Example 40

7-(tert-Butoxycarbonyl)-2-methanesulfonyloxy-7-azaspiro[3.5]nonane

After dissolving 106 mg of 7-(tert-butoxycarbonyl)-2-hydroxy-7-azaspiro[3.5]nonane in 10 ml of tetrahydrofuran, 0.04 ml of methanesulfonyl chloride and 0.07 ml of triethylamine were added and the mixture was stirred overnight at room temperature. The reaction mixture was filtered and the filtrate was concentrated under reduced pressure. After adding water to the residue, extraction was performed with ethyl acetate. The organic layer was washed with water and then dried over anhydrous magnesium sulfate. The solvent was distilled off under reduced pressure to obtain the title compound (148 mg, 100% yield).

1H-NMR (400 MHz, CDCl3); δ(ppm) 1.45 (9H, s), 1.52-1.63 (4H, m), 2.08 (1H, dd, J=10.4, 7.2 Hz), 2.09 (1H, dd, J=10.4, 7.2 Hz), 2.41 (1H, dd, J=10.4, 7.2 Hz), 2.43 (1H, dd, J=10.4, 7.2 Hz), 2.99 (3H, s), 3.29-3.30 (4H, m), 5.03 (1H, quintet, J=7.2 Hz).

Production Example 41

1-(tert-Butoxycarbonyl)-4-cyano-4-(2-methylphenoxymethyl)piperidine

After dissolving 230 mg of 2-methylphenol in 20 ml of N,N-dimethylformamide, 43 mg of sodium hydride (70% suspension in oil) was added and the mixture was stirred at 80° C. for 30 minutes. Next, 224 mg of 1-(tert-butoxycarbonyl)-4-cyano-4-(methanesulfonyloxymethyl)piperidine was added and the mixture was stirred at 100° C. for 8 hours. After cooling it to room temperature, water was added and extraction was performed with ethyl acetate. The organic layer was washed with a 1N sodium hydroxide solution and then dried over magnesium sulfate. The solvent was distilled off under reduced pressure to obtain the title compound (273 mg, 100% yield).

1H-NMR (400 MHz, CDCl3); δ(ppm) 1.48 (9H, s), 1.65 (2H, td, J=13.2, 4.4 Hz), 2.07-2.12 (2H, m), 2.27 (3H, s), 3.01-3.19 (2H, m), 3.98 (2H, s), 4.15-4.28 (2H, m), 6.74-6.77 (1H, m), 6.92 (1H, td, J=7.6, 1.2 Hz), 7.09-7.19 (2H, m).

Production Example 42

1-(tert-Butoxycarbonyl)-4-cyano-4-(2-fluorophenoxymethyl)piperidine

The title compound (239 mg, 100% yield) was obtained in the same manner as Example 41 from 83 mg of 2-fluorophenol and 212 mg of 1-(tert-butoxycarbonyl)-4-cyano-4-(methanesulfonyloxymethyl)piperidine.

1H-NMR (400 MHz, CDCl3); δ(ppm) 1.48 (9H, s), 1.67 (2H, td, J=13.4, 4.4 Hz), 2.08 (2H, d, J=12.0 Hz), 3.00-3.20 (2H, m), 4.05 (2H, s), 4.10-4.30 (2H, m), 6.96-7.03 (2H, m), 7.04-7.13 (2H, m).

Production Example 43

1-(tert-Butoxycarbonyl)-4-fluoro-4-(2-fluorophenoxymethyl)piperidine

The title compound (158 mg, 100% yield) was obtained in the same manner as Example 41 from 162 mg of 2-fluorophenol and 150 mg of 1-(tert-butoxycarbonyl)-4-fluoro-4-(methanesulfonyloxymethyl)piperidine.

1H-NMR (400 MHz, CDCl3); δ(ppm) 1.47 (9H, s), 1.50-2.02 (6H, m), 3.04-3.20 (2H, m), 4.03 (2H, d, J=17.2 Hz), 6.83-7.11 (4H, m).

Production Example 44

1-(tert-Butoxycarbonyl)-4-hydroxy-4-(2-methylphenoxymethyl)piperidine

After dissolving 120 mg of 6-(tert-butoxycarbonyl)-1-oxa-6-azaspiro[2.5]octane in 10 ml of N,N-dimethylformamide, 67 mg of 2-methylphenol and 86 mg of potassium carbonate were added and the mixture was stirred at 150° C. for 5 hours. After cooling it to room temperature, water was added and extraction was performed with ethyl acetate. The extract was dried over magnesium sulfate, and the solvent was distilled off under reduced pressure. The residue was purified by silica gel column chromatography to obtain the title compound (156 mg, 86% yield).

1H-NMR (400 MHz, CDCl3); δ(ppm) 1.47 (9H, s), 1.60-1.68 (2H, m), 1.74-1.78 (2H, m), 2.25 (3H, s), 3.23 (2H, t, J=11.6 Hz), 3.81 (2H, s), 3.92 (2H, br s), 6.78-6.81 (1H, m), 6.89 (1H, td, J=7.6, 1.2 Hz), 7.14-7.18 (2H, m).

Production Example 45

1-(tert-Butoxycarbonyl)-4-(2-fluorophenoxymethyl)-4-hydroxypiperidine

The title compound (489 mg, 100% yield) was obtained in the same manner as Production Example 44 from 302 mg of 6-(tert-butoxycarbonyl)-1-oxa-6-azaspiro[2.5]octane and 175 mg of 2-fluorophenol.

1H-NMR (400 MHz, CDCl3); δ(ppm) 1.46 (9H, s), 1.62 (2H, td, J=17.6, 4.4 Hz), 1.75-1.80 (2H, m), 3.18-3.30 (2H, m), 3.86 (2H, s), 3.86-3.99 (2H, m), 6.82-6.96 (2H, m), 6.98-7.12 (2H, m).

Production Example 46

7-(tert-Butoxycarbonyl)-2-(2-fluorophenoxy)-7-azaspiro[3.5]nonane

After dissolving 148 mg of 2-fluorophenol in 10 mg of dimethylformamide, 53 mg of sodium hydride (70% suspension in oil) was added, the mixture was stirred at 80° C. for 30 minutes, a solution of 148 mg of 7-(tert-butoxycarbonyl)-2-methanesulfonyloxy-7-azaspiro[3.5]nonane in N,N-dimethylformamide (7 ml) was added and the mixture was stirred at 80° C. for two nights. After cooling it to room temperature, water was added and extraction was performed with ethyl acetate. The organic layer was washed with a 1N sodium hydroxide solution and then dried over anhydrous magnesium sulfate. The solvent was distilled off under reduced pressure to obtain the title compound (163 mg, 100% yield).

1H-NMR (400 MHz, CDCl3); δ(ppm) 1.45 (9H, s), 1.53-1.62 (4H, m), 1.99-2.05 (1H, m), 2.02 (1H, dd, J=10.8, 6.4 Hz), 2.39-2.44 (2H, m), 3.31-3.33 (2H, m), 3.36-3.39 (2H, m), 4.72 (1H, quintet, J=6.7 Hz), 6.79 (1H, td, J=8.4, 1.6 Hz), 6.88 (1H, tdd, J=8.0, 4.8, 1.8 Hz), 6.99-7.05 (1H, m), 7.07 (1H, ddd, J=11.4, 8.0, 1.6 Hz).

Production Example 47 anti-(E)-3-Benzyl-9-[2-(2-fluorophenyl)vinyl]-3-azabicyclo[3.3.1]nonane 30 ml of tetrahydrofuran was cooled to −78° C., 4.45 ml of n-butyllithium (2.6 M, n-hexane solution) was added thereto, and 1.45 ml of 1-bromo-2-fluorobenzene was added dropwise while stirring. After 15 minutes, a solution of 2.40 g of (anti-3-benzyl-3-azabicyclo[3.3.1]non-9-yl)acetaldehyde in tetrahydrofuran (10 ml) was added dropwise. After another hour, water was added to the reaction solution and extraction was performed with ethyl acetate. The organic layer was washed with water and saturated brine in that order and dried over anhydrous magnesium sulfate, and then the solvent was distilled off under reduced pressure.

This was dissolved in 50 ml of toluene, and then 4.23 g of p-toluenesulfonic acid monohydrate was added and the mixture was heated to reflux for 2 hours. Aqueous sodium carbonate solution was added to the reaction solution and extraction was performed with ethyl acetate. The organic layer was washed with water and saturated brine in that order and dried over anhydrous magnesium sulfate, and then the solvent was distilled off under reduced pressure. The residue was purified by silica gel column chromatography (solvent: n-hexane/ethyl acetate) to obtain the title compound (2.61 g, 88% yield).

1H-NMR (400 MHz, CDCl3); δ(ppm) 1.49-1.62 (3H, m), 1.81-1.86 (2H, m), 1.87-2.00 (2H, m), 2.30-2.36 (2H, m), 2.38-2.43 (1H, m), 2.67-2.81 (1H, m), 2.98-3.03 (2H, m), 3.42 (2H, s), 6.56-6.66 (2H, m), 6.99-7.36 (8H, m), 7.48 (1H, dt, J=7.6, 2.0 Hz).

Production Example 48 anti-(E)-9-[2-(2-Fluorophenyl)vinyl]-3-azabicyclo[3.3.1]nonane hydrochloride

The title compound (1.12 g, 51% yield) was obtained in the same manner as Production Example 29 from 2.61 g of anti-(E)-3-benzyl-9-[2-(2-fluorophenyl)vinyl]-3-azabicyclo[3.3.1]nonane.

1H-NMR (400 MHz, CDCl3); δ(ppm) 1.60-1.84 (3H, m), 1.98-2.11 (2H, m), 2.14 (2H, br s), 2.23-2.38 (1H, m), 2.64 (1H, br d, J=6.0 Hz), 3.31-3.42 (2H, m), 3.53-3.61 (2H, m), 6.48 (1H, dd, J=16.0, 6.8 Hz), 6.65 (1H, d, J=16.0 Hz), 7.05 (1H, ddd, J=10.8, 8.0, 1.2 Hz), 7.11 (1H, dt, J=8.0, 1.2 Hz), 7.19-7.25 (1H, m), 7.45 (1H, dt, J=8.0, 1.2 Hz), 8.56 (1H, br s), 10.14 (1H, br s).

Production Example 49

4-[2-(3-Fluoro-2-thienyl)ethyl]piperidine

After dissolving 365 mg of 3-fluorothiophene-2-methanol in 5 ml of toluene, 0.27 ml of thionyl chloride was added while stirring on ice and the mixture was stirred for 1 hour. Saturated aqueous sodium bicarbonate solution was added to the reaction solution and extraction was performed with ethyl acetate. The organic layer was washed with saturated brine and dried over anhydrous magnesium sulfate, and then the solvent was distilled off under reduced pressure. After adding 5 ml of toluene to the residue, 647 mg of triphenylphosphine was added and the mixture was heated to reflux overnight. Ethyl acetate was added and the insoluble portion was filtered. After dissolving this in 3 ml of N,N-dimethylformamide, 154 mg of potassium tert-butoxide was added, a solution of 270 mg of 1-benzylpiperidine-4-carboxaldehyde in N,N-dimethylformamide (1 ml) was added while stirring on ice, and the mixture was stirred for 1 hour. Water was added to the reaction solution, and extraction was performed with ethyl acetate. The organic layer was washed with saturated brine and dried over anhydrous magnesium sulfate, and then the solvent was distilled off under reduced pressure. The residue was purified by NH silica gel column chromatography (solvent: n-hexane/ethyl acetate) to obtain 1-benzyl-4-[2-(3-fluoro-2-thienyl)vinyl]piperidine. After dissolving this in 5 ml of methanol, 320 mg of 10% palladium-carbon (hydrous) and 332 mg of ammonium formate were added and the mixture was heated and stirred at 50° C. for 1.5 hours. The insoluble portion was filtered off, water was added to the filtrate and extraction was performed with ethyl acetate. The organic layer was washed with saturated brine and dried over anhydrous magnesium sulfate, and then the solvent was distilled off under reduced pressure. The residue was dissolved in 3 ml of 1,2-dichloroethane, and then 0.12 ml of 1-chloroethyl chloroformate was added while stirring on ice and the mixture was heated to reflux for 1 hour. The solvent was distilled off under reduced pressure, 3 ml of methanol was added to the residue and heating to reflux was continued for 30 minutes. The solvent was distilled off under reduced pressure, a 1N sodium hydroxide solution was added and extraction was performed with ethyl acetate. The organic layer was washed with saturated brine and dried over anhydrous magnesium sulfate, and then the solvent was distilled off under reduced pressure. The residue was purified by NH silica gel column chromatography (solvent: methanol/ethyl acetate) to obtain the title compound (150 mg, 29% yield).

1H-NMR (400 MHz, CDCl3); δ(ppm) 1.07-1.18 (2H, m), 1.35-1.47 (1H, m), 1.52-1.66 (2H, m), 1.67-1.76 (2H, m), 2.53-2.62 (2H, m), 2.74 (2H, td, J=7.8, 0.8 Hz), 3.03-3.10 (2H, m), 6.73 (1H, dd, J=5.4, 1.0 Hz), 6.97 (1H, dd, J=5.4, 4.0 Hz).

Production Example 50

3-Bromothiophene-2-carboxaldehyde dimethylacetal

After dissolving 5.97 g of 3-bromothiophene-2-carboxaldehyde in 90 ml of dichloromethane, a mixture of 8.0 g of montmorillonite K-10 and 120 ml of trimethyl orthoformate was added while stirring and the mixture was stirred at room temperature for 1 hour. The reaction mixture was filtered and then the solvent was distilled off under reduced pressure to obtain the title compound (7.21 g, 97% yield).

1H-NMR (400 MHz, CDCl3); δ(ppm) 3.39 (6H, s), 5.62 (1H, s), 6.97 (1H, d, J=5.4 Hz), 7.30 (1H, d, J=5.4 Hz).

Production Example 51

3-Fluorothiophene-2-carboxaldehyde

After dissolving 5.54 g of 3-bromothiophene-2-carboxaldehyde dimethylacetal in 120 ml of diethyl ether, the solution was cooled to −78° C. Next, 9.3 ml of n-butyllithium (2.66 M, n-hexane solution) was added dropwise while stirring at below −67° C. After 30 minutes, a solution of 8.10 g of N-fluorobenzenesulfonimide in tetrahydrofuran (20 ml) was added dropwise, and the temperature was raised to room temperature. Water was added to the reaction solution, and extraction was performed with ethyl acetate. The organic layer was washed with saturated brine and dried over anhydrous magnesium sulfate, and then the solvent was distilled off under reduced pressure. The residue was dissolved in 10 ml of acetone, 10 ml of 5N hydrochloric acid was added and the mixture was stirred at room temperature for 20 minutes. A 5N sodium hydroxide solution was added to the reaction solution for neutralization and extraction was performed with ethyl acetate. The organic layer was washed with saturated brine and dried over anhydrous magnesium sulfate, and then the solvent was distilled off under reduced pressure. The residue was purified by silica gel column chromatography (solvent: n-hexane/ethyl acetate) to obtain the title compound (1.86 g, 61% yield).

1H-NMR (400 MHz, CDCl3); δ(ppm) 6.91 (1H, d, J=5.4 Hz), 7.65 (1H, ddd, J=5.4, 4.2, 1.2 Hz), 10.04 (1H, d, J=1.2 Hz).

Production Example 52

3-Fluorothiophene-2-methanol

After dissolving 1.86 g of 3-fluorothiophene-2-carboxaldehyde in 30 ml of methanol, 541 mg of sodium borohydride was added while stirring on ice and the mixture was stirred for 30 minutes. Water was added to the reaction solution, and extraction was performed with ethyl acetate. The organic layer was washed with saturated brine and dried over anhydrous magnesium sulfate, and then the solvent was distilled off under reduced pressure. The residue was purified by silica gel column chromatography (solvent: n-hexane/ethyl acetate) to obtain the title compound (1.60 g, 85% yield).

1H-NMR (400 MHz, CDCl3); δ(ppm) 1.75 (1H, t, J=5.2 Hz), 4.78 (2H, d, J=5.2 Hz), 6.78 (1H, dd, J=5.4, 0.8 Hz), 7.16 (1H, dd, J=5.4, 4.0 Hz).

Production Example 53

2-Fluorothiophene-3-carboxaldehyde

After dissolving 2.55 ml of N,N,N'-trimethylethylenediamine in 60 ml of diethyl ether, the solution was cooled to −78° C. Next, 7.58 ml of n-butyllithium (2.6 M, n-hexane solution) was added dropwise while stirring at below −60° C. After 20 minutes, a solution of 2.00 g of 3-thiophenecarboxaldehyde in diethyl ether (5 ml) was added dropwise at below −60° C. The mixture was stirred for 15 minutes, and then 7.58 ml of n-butyllithium (2.6 M, n-hexane solution) was added dropwise at below −60° C. After 10 minutes, the temperature was raised to room temperature and the mixture was stirred for 2 hours. The reaction solution was cooled to −78° C., and a solution of 6.21 g of N-fluorobenzenesulfonimide in tetrahydrofuran (20 ml) was added dropwise at below −60° C. After the dropwise addition, the reaction solution was stirred at room temperature for 1.5 hours. Water was added to the reaction solution, and extraction was performed with ethyl acetate. The organic layer was washed with water and saturated brine, and the solvent was distilled off under reduced pressure. The residue was purified by silica gel column chromatography (solvent: n-hexane/ethyl acetate) to obtain the title compound (138 mg, 6% yield).

1H-NMR (400 MHz, CDCl3); δ(ppm) 6.66-6.71 (1H, m), 7.08-7.13 (1H, m), 9.97 (1H, s).

Production Example 54

3-Hydroxy-4-hydroxymethyl-[1,2,5]thiadiazole

After dissolving 1.00 g of 4-tert-butoxymethyl-3-hydroxy-[1,2,5]thiadiazole in 6 ml of dichloromethane, 6 ml of trifluoroacetic acid was added and the mixture was stirred at room temperature for 1.5 hours. The reaction solution was concentrated, and n-hexane was added to the residue and then distilled off under reduced pressure. After further addition of n-hexane to the residue, the mixture was filtered to obtain the title compound (523 mg, 75% yield).

1H-NMR (400 MHz, DMSO-d6); δ(ppm) 4.48 (2H, s).

Production Example 55

1-(tert-Butoxycarbonyl)-4-[2-(dimethylamino)phenoxymethyl]piperidine

After dissolving 400 mg of 1-(tert-butoxycarbonyl)-4-(2-aminophenoxymethyl)piperidine in 10 ml of tetrahydrofuran, 0.33 ml of 37% formalin, 0.08 ml of acetic acid and 827 mg of sodium triacetoxyborohydride were added and the mixture was stirred at room temperature for 2.5 hours. Next, 0.33 ml of 37% formalin and 827 mg of sodium triacetoxyborohydride were added to the reaction solution and stirring was continued overnight at room temperature. After adding aqueous sodium carbonate solution to the reaction solution, extraction was performed with ethyl acetate. The organic layer was washed with water and saturated brine and dried over anhydrous magnesium sulfate, and then filtered with NH silica gel. The solvent was distilled off under reduced pressure to obtain the title compound (447 mg, 100% yield).

1H-NMR (400 MHz, CDCl3); δ(ppm) 1.24-1.36 (2H, m), 1.47 (9H, s), 1.84-1.92 (2H, m), 2.03-2.15 (1H, m), 2.50-2.84 (8H, m), 3.85 (2H, d, J=6.8 Hz), 4.08-4.26 (2H, m), 6.80-6.96 (4H, m).

Production Example 56

2-Chloro-6-methoxypyrazine

After dissolving 7.99 g of 2,6-dichloropyrazine in 100 ml of tetrahydrofuran, 11.3 ml of a 28% sodium methoxide-methanol solution was added dropwise while stirring at room temperature, and stirring was continued overnight. Water was added to the reaction solution, and extraction was performed with n-hexane. The organic layer was washed with water and saturated brine and dried over anhydrous magnesium sulfate, and then the solvent was distilled off under reduced pressure to obtain the title compound (6.96 g, 90% yield).

1H-NMR (400 MHz, CDCl3); δ(ppm) 3.98 (3H, s), 8.12 (1H, d, J=0.4 Hz), 8.13 (1H, d, J=0.4 Hz).

Production Example 57

1-(tert-Butoxycarbonyl)-4-[2-(3-methylthioureido) phenoxymethyl]piperidine

After dissolving 400 mg of 1-(tert-butoxycarbonyl)-4-(2-aminophenoxymethyl)piperidine in 10 ml of tetrahydrofuran, 124 mg of methyl isothiocyanate was added and the mixture was heated to reflux for 3.5 hours. The reaction solution was filtered with NH silica gel and the solvent was distilled off under reduced pressure. The residue was purified by silica gel column chromatography (solvent: n-hexane/ethyl acetate) to obtain the title compound (537 mg, 100% yield).

1H-NMR (400 MHz, CDCl3); δ(ppm) 1.16-1.28 (2H, m), 1.46 (9H, s), 1.79-1.87 (2H, m), 1.95-2.06 (1H, m), 2.70-2.82 (2H, m), 3.15 (3H, d, J=4.8 Hz), 3.82 (2H, d, J=5.6 Hz), 4.10-4.24 (2H, m), 6.09-6.16 (1H, m), 6.94-7.02 (2H, m), 7.20-7.34 (2H, m), 7.47 (1H, br s).

Production Example 58

1-(tert-Butoxycarbonyl)-4-[2-(3-methylureido)phenoxymethyl]piperidine

After dissolving 400 mg of 1-(tert-butoxycarbonyl)-4-(2-aminophenoxymethyl)piperidine in 10 ml of tetrahydrofuran, 458 mg of methyl isocyanate was added and the mixture was stirred overnight at room temperature. Ammonia water was added to the reaction solution and extraction was performed with ethyl acetate. The organic layer was washed with water and saturated brine and dried over anhydrous magnesium sulfate, and then filtered with NH silica gel. The solvent was distilled off under reduced pressure to obtain the title compound (469 mg, 99% yield).

1H-NMR (400 MHz, CDCl3); δ(ppm) 1.22-1.35 (2H, m), 1.47 (9H, s), 1.76-1.84 (2H, m), 1.93-2.05 (1H, m), 2.68-2.81 (2H, m), 2.86 (3H, d, J=4.8 Hz), 3.86 (2H, d, J=6.4 Hz), 4.10-4.24 (2H, m), 4.66-4.75 (1H, m), 6.62 (1H, br s), 6.84 (1H, dd, J=8.0, 1.6 Hz), 6.92-7.02 (2H, m), 7.90 (1H, dd, J=7.6, 2.0 Hz).

Production Example 59

4-Fluorothiophene-3-carboxaldehyde

After dissolving 18.38 g of 4-bromothiophene-3-carboxaldehyde dimethylacetal in 400 ml of diethyl ether, the solution was cooled to −78° C. Next, 32.81 ml of n-butyllithium (2.6 M, n-hexane solution) was added dropwise while stirring at below −65° C. After 40 minutes, a solution of 26.94 g of N-fluorobenzenesulfonimide in tetrahydrofuran (100 ml) was added dropwise, and the temperature was gradually raised to 0° C. The mixture was stirred at 0° C. for 45 minutes and then ice water was added to the reaction solution and extraction was performed with ethyl acetate. The organic layer was washed with water and brine, and the solvent was distilled off under reduced pressure. The residue was dissolved in 50 ml of acetone, and then 50 ml of 5N hydrochloric acid was added and the mixture was allowed to stand at room temperature for 1.5 hours. A 5N sodium hydroxide solution was added to the reaction solution for neutralization, and extraction was performed with ethyl acetate. The organic layer was washed with water and saturated brine and dried over anhydrous magnesium sulfate, and then the solvent was distilled off under reduced pressure. The residue was purified by silica gel column chromatography (solvent: n-hexane/ethyl acetate) to obtain the title compound (6.02 g, 63% yield).

1H-NMR (400 MHz, CDCl3); δ(ppm) 6.82 (1H, dd, J=4.0, 1.2 Hz), 8.01 (1H, t, J=4.0 Hz), 9.88 (1H, s).

Production Example 60

4-tert-Butoxymethyl-3-hydroxy-[1.2.5]thiadiazole

After dissolving 8.17 g of 2-amino-3-(tert-butoxy)propionamide in 150 ml of dichloromethane, 16.37 ml of triethylamine was added and the solution was cooled to −78° C., and then 4.10 ml of thionyl chloride was added dropwise while stirring at below −50° C. After stirring for 30 minutes, the temperature was raised to room temperature and stirring was continued overnight. Water was added to the reaction solution, and extraction was performed with dichloromethane. The organic layer was washed with saturated brine, dried over anhydrous magnesium sulfate, and filtered with silica gel. The solvent was distilled off under reduced pressure, and the residue was purified by silica gel column chromatography (solvent: n-hexane/ethyl acetate) to obtain the title compound (1.98 g, 21% yield).

1H-NMR (400 MHz, CDCl3); δ(ppm) 1.35 (9H, s), 4.83 (2H, s), 9.22 (1H, br s).

Production Example 61

2-(4-Fluoro-3-thienyl)-1-(4-pyridyl)ethanone

After dissolving 19.6 g of [(phenylamino)-(4-pyridylmethyl)]phosphonic acid diphenyl ester [CAS No. 3360-72-3] in 115 ml of tetrahydrofuran-2-propanol (4:1), 6.02 g of 4-fluorothiophene-3-carboxaldehyde and 19.61 g of anhydrous cesium carbonate were added and the mixture was stirred overnight at room temperature. Next, 90 ml of 5N hydrochloric acid was added to the reaction mixture and the mixture was stirred at room temperature for 6 hours. After adding a 5N sodium hydroxide solution to the reaction solution, extraction was performed with ethyl acetate. The organic layer was washed with water and saturated brine and dried over anhydrous magnesium sulfate, and then the solvent was distilled off under reduced pressure. The residue was purified by silica gel column chromatography (solvent: n-hexane/ethyl acetate). The obtained solid was washed with n-hexane to obtain the title compound (3.66 g, 36% yield).

1H-NMR (400 MHz, CDCl3); δ(ppm) 4.21 (2H, s), 6.76 (1H, d, J=3.6 Hz), 7.09 (1H, t, J=3.6 Hz), 7.76-7.80 (2H, m), 8.80-8.86 (2H, m).

Production Example 62

1-(tert-Butoxycarbonyl)-4-(2-fluorobenzylthio)piperidine

After dissolving 1.70 g of 1-(tert-butoxycarbonyl)-4-mercaptopiperidine in a mixture of 8 ml ethanol/8 ml 2N sodium hydroxide, 1.05 ml of 2-fluorobenzyl bromide was added and the mixture was stirred overnight at room temperature. Water was added to the reaction solution, and extraction was performed with ethyl acetate. The organic layer was washed with saturated brine and dried over anhydrous magnesium sulfate, and then the solvent was distilled off under reduced pressure. The residue was purified by silica gel column chromatography (solvent: n-hexane/ethyl acetate) to obtain the title compound (1.72 g, 68% yield).

1H-NMR (400 MHz, CDCl3); δ(ppm) 1.38-1.58 (2H, m), 1.45 (9H, s), 1.86-1.95 (2H, m), 2.68-2.77 (1H, m), 2.83-2.94 (2H, m), 3.78 (2H, s), 3.85-4.00 (2H, m), 7.02 (1H, ddd, J=9.6, 8.0, 1.2 Hz), 7.09 (1H, td, J=8.0, 1.2 Hz), 7.19-7.26 (1H, m), 7.34 (1H, td, J=8.0, 2.0 Hz).

Production Example 63

1-[1-(tert-Butoxycarbonyl)piperidin-4-yl]-2-(2-fluorophenyl)propanone

After suspending 207 mg of sodium hydride (70% suspension in oil) in 4 ml of N,N-dimethylformamide, a solution of 1.51 g of 1-[1-(tert-butoxycarbonyl)piperidin-4-yl]-2-(2-fluorophenyl)ethanone in N,N-dimethylformamide (6 ml) was added, the mixture was stirred at room temperature for 30 minutes, and then 0.32 ml of methyl iodide was added and stirring was continued for 30 minutes. Water was added to the reaction solution, and extraction was performed with ethyl acetate. The organic layer was washed with brine and dried over anhydrous magnesium sulfate, and then the solvent was distilled off under reduced pressure. The residue was purified by silica gel column chromatography (solvent: n-hexane/ethyl acetate) to obtain the title compound (1.16 g, 74% yield).

1H-NMR (400 MHz, CDCl3); δ(ppm) 1.37 (3H, d, J=7.0 Hz), 1.40-1.60 (3H, m), 1.43 (9H, s), 1.77-1.86 (1H, m), 2.48-2.76 (3H, m), 3.95-4.15 (2H, m), 4.26 (1H, q, J=7.0 Hz), 7.06 (1H, ddd, J=9.6, 7.6, 1.2 Hz), 7.11 (1H, dd, J=7.6, 1.2 Hz), 7.16 (1H, td, J=7.6, 2.0 Hz), 7.21-7.27 (1H, m).

Production Example 64 cis-1-Benzyl-3-(2-fluorophenoxymethyl)-4-hydroxypiperidine

After dissolving 1.49 g of cis-1-benzyl-4-hydroxy-3-(p-toluenesulfonyloxymethyl)piperidine in 8 ml of N,N-dimethylformamide, 0.71 ml of 2-fluorophenol and 1.22 g of anhydrous potassium carbonate were added and the mixture was stirred at 100° C. for 50 minutes. Water was added to the reaction mixture, and extraction was performed with ethyl acetate. The organic layer was washed with a 5N sodium hydroxide solution, water and saturated brine in that order and dried over anhydrous magnesium sulfate, and then the solvent was distilled off under reduced pressure. The residue was purified by NH silica gel column chromatography (solvent: n-hexane/ethyl acetate) to obtain the title compound (402 mg, 32% yield).

1H-NMR (400 MHz, CDCl3); δ(ppm) 1.74-1.89 (2H, m), 2.28-2.36 (1H, m), 2.45-2.60 (4H, m), 3.51 (1H, d, J=13.2 Hz), 3.55 (1H, d, J=13.2 Hz), 4.06-4.25 (3H, m), 6.85-6.92 (1H, m), 6.96 (1H, dt, J=8.4, 1.6 Hz), 7.00-7.08 (2H, m), 7.20-7.33 (5H, m).

Production Example 65 trans-1-Benzyl-3-(2-fluorophenoxymethyl)-4-hydroxypiperidine

The title compound (326 mg, 61% yield) was obtained in the same manner as Production Example 64 from 0.65 g of trans-1-benzyl-4-hydroxy-3-(p-toluenesulfonyloxymethyl) piperidine and 0.31 ml of 2-fluorophenol.

1H-NMR (400 MHz, CDCl3); δ(ppm) 1.62-1.74 (1H, m), 1.92-2.21 (4H, m), 2.84-2.91 (1H, m), 2.93-2.99 (1H, m), 3.50 (1H, d, J=13.2 Hz), 3.54 (1H, d, J=13.2 Hz), 3.64 (1H, dt, J=10.0, 4.8 Hz), 4.05 (1H, dd, J=6.0, 9.6 Hz), 4.11 (1H, dd, J=5.6, 9.6 Hz), 6.85-6.98 (2H, m), 7.00-7.08 (2H, m), 7.21-7.34 (5H, m).

Production Example 66

1-(tert-Butoxycarbonyl)-4-methyl-4-(2-methylphenoxymethyl)piperidine

After dissolving 541 mg of 2-methylphenol in 10 ml of N,N-dimethylformamide, 171 mg of sodium hydride (70% suspension in oil), 1.00 g of 1-(tert-butoxycarbonyl)-4-methyl-4-(methanesulfonyloxymethyl)piperidine and tetra n-butylammonium iodide (catalytic amount) were added and the mixture was stirred at 120° C. overnight. Water was added to the reaction solution, and extraction was performed with ethyl acetate. The organic layer was washed with water and saturated brine and dried over anhydrous magnesium sulfate, and then the solvent was distilled off under reduced pressure. The residue was purified by silica gel column chromatography (solvent: n-hexane/ethyl acetate) to obtain the title compound (816 mg, 78% yield).

1H-NMR (400 MHz, CDCl3); δ(ppm) 1.14 (3H, s), 1.40-1.48 (2H, m), 1.46 (9H, s), 1.60-1.69 (2H, m), 2.23 (3H, s), 3.21 (2H, ddd, J=13.6, 10.0, 3.6 Hz), 3.61-3.74 (2H, m), 3.67 (2H, s), 6.77 (1H, d, J=8.0 Hz), 6.84 (1H, dt, J=7.6, 0.8 Hz), 7.10-7.17 (2H, m).

Production Example 67

1-(tert-Butoxycarbonyl)-4-(2-chlorophenoxymethyl)-4-methylpiperidine

The title compound (810 mg, 72% yield) was obtained in the same manner as Production Example 66 from 0.40 ml of 2-chlorophenol and 1.00 g of 1-(tert-butoxycarbonyl)-4-methyl-4-(methanesulfonyloxymethyl)piperidine.

1H-NMR (400 MHz, CDCl3); δ(ppm) 1.16 (3H, s), 1.43-1.51 (2H, m), 1.46 (9H, s), 1.61-1.69 (2H, m), 3.22 (2H, ddd, J=13.6, 9.6, 3.6 Hz), 3.66-3.76 (2H, m), 3.72 (2H, s), 6.85-6.90 (1H, m), 7.16-7.21 (2H, m), 7.32-7.36 (1H, m).

Production Example 68

1-(tert-Butoxycarbonyl)-4-(2-methoxyphenoxymethyl)-4-methylpiperidine

The title compound (293 mg, 27% yield) was obtained in the same manner as Production Example 66 from 0.55 ml of 2-methoxyphenol and 1.00 g of 1-(tert-butoxycarbonyl)-4-methyl-4-(methanesulfonyloxymethyl)piperidine.

1H-NMR (400 MHz, CDCl3); δ(ppm) 1.14 (3H, s), 1.40-1.48 (2H, m), 1.46 (9H, s), 1.61-1.69 (2H, m), 3.21 (2H, ddd, J=13.6, 10.0, 3.6 Hz), 3.62-3.72 (2H, m), 3.71 (2H, s), 3.83 (3H, s), 6.86-6.91 (4H, m).

Production Example 69

2-[1-(tert-Butoxycarbonyl)piperidin-4-yl]-3-(2-fluorophenyl)propionitrile and 2-[1-(tert-butoxycarbonyl)piperidin-4-yl]-2-(2-fluorobenzyl)-3-(2-fluorophenyl)propionitrile After dissolving 1.3 ml of diisopropylamine in 20 ml of tetrahydrofuran, the solution was cooled to −78° C. Next, 5.8 ml of n-butyllithium (1.5 M, n-hexane solution) was added dropwise while stirring at below −40° C., and stirring was continued for 40 minutes. A solution of 1.49 g of 1-(tert-butoxycarbonyl)piperidine-4-acetonitrile in tetrahydrofuran (5 ml) was added dropwise at below −60° C., the mixture was stirred for 1 hour, and then 1.2 ml of 2-fluorobenzyl bromide was added and the temperature was raised to room temperature. Saturated aqueous ammonium chloride solution was added to the reaction solution, and extraction was performed with ethyl acetate. The organic layer was washed with saturated brine and dried over anhydrous magnesium sulfate, and then the solvent was distilled off under reduced pressure. The residue was purified by silica gel column chromatography (solvent: n-hexane/ethyl acetate) to obtain 2-[1-(tert-butoxycarbonyl)piperidin-4-yl]-3-(2-fluorophenyl)propionitrile (1.21 g, 55% yield) and 2-[1-(tert-butoxycarbonyl)piperidin-4-yl]-2-(2-fluorobenzyl)-3-(2-fluorophenyl)propionitrile (1.02 g, 35% yield).

2-[1-(tert-butoxycarbonyl)piperidin-4-yl]-3-(2-fluorophenyl)propionitrile

1H-NMR (400 MHz, CDCl3); δ(ppm) 1.39-1.53 (2H, m), 1.46 (9H, s), 1.65-1.78 (2H, m), 1.88-1.96 (1H, m), 2.62-2.90 (4H, m), 3.04 (1H, dd, J=13.2, 5.6 Hz), 4.10-4.30 (2H, m), 7.02-7.15 (2H, m), 7.23-7.30 (2H, m).

2-[1-(tert-butoxycarbonyl)piperidin-4-yl]-2-(2-fluorobenzyl)-3-(2-fluorophenyl)propionitrile 1H-NMR (400 MHz, CDCl3); δ(ppm) 1.40-1.69 (3H, m), 1.46 (9H, s), 1.97-2.05 (2H, m), 2.55-2.67 (2H, m), 2.81 (2H, d, J=14.0 Hz), 3.04 (2H, d, J=14.0 Hz), 4.15-4.32 (2H, m), 7.06 (2H, ddd, J=9.6, 7.6, 1.2 Hz), 7.13 (2H, td, J=7.6, 1.2 Hz), 7.24-7.31 (2H, m), 7.36 (2H, td, J=7.6, 1.6 Hz).

Production Example 70

1-(tert-Butoxycarbonyl)-4-[2-(methoxycarbonyl) phenoxymethyl]piperidine

After dissolving 300 mg of 1-(tert-butoxycarbonyl)-4-(methanesulfonyloxymethyl)piperidine in 3 ml of N,N-dimethylformamide, 0.16 ml of methyl salicylate, 180 mg of anhydrous potassium carbonate and tetra n-butylammonium iodide (catalytic amount) were added and the mixture was stirred at 100° C. for 1.5 hours. Water was added to the reaction mixture, and extraction was performed with ethyl acetate. The organic layer was washed with water and saturated brine and dried over anhydrous magnesium sulfate, and then the solvent was distilled off under reduced pressure. The residue was purified by silica gel column chromatography (solvent: n-hexane/ethyl acetate) to obtain the title compound (226 mg, 65% yield).

1H-NMR (400 MHz, CDCl3); δ(ppm) 1.25-1.37 (2H, m), 1.47 (9H, s), 1.83-1.90 (2H, m), 1.97-2.09 (1H, m), 2.68-2.84 (2H, m), 3.84-3.93 (5H, m), 4.08-4.26 (2H, m), 6.93 (1H, d, J=7.6 Hz), 6.97 (1H, t, J=7.6 Hz), 7.41-7.47 (1H, m), 7.79 (1H, dd, J=7.6, 1.6 Hz).

Production Example 71

4-(2-Acetylphenoxymethyl)-1-(tert-butoxycarbonyl)piperidine

The title compound (220 mg, 66% yield) was obtained in the same manner as Production Example 70 from 300 mg of 1-(tert-butoxycarbonyl)-4-(methanesulfonyloxymethyl)piperidine and 0.14 ml of 2-hydroxyacetophenone.

1H-NMR (400 MHz, CDCl3); δ(ppm) 1.26-1.39 (2H, m), 1.47 (9H, s), 1.80-1.88 (2H, m), 1.98-2.10 (1H, m), 2.62 (3H, s), 2.68-2.84 (2H, m), 3.92 (2H, d, J=6.4 Hz), 4.06-4.28 (2H, m), 6.93 (1H, d, J=7.6 Hz), 6.97-7.02 (1H, m), 7.41-7.47 (1H, m), 7.70-7.74 (1H, m).

Production Example 72

1-(tert-Butoxycarbonyl)-4-(2-carbamoylphenoxymethyl)piperidine

The title compound (165 mg, 73% yield) was obtained in the same manner as Production Example 70 from 200 mg of 1-(tert-butoxycarbonyl)-4-(methanesulfonyloxymethyl)piperidine and 112 mg of salicylamide.

1H-NMR (400 MHz, CDCl3); δ(ppm) 1.24-1.38 (2H, m), 1.47 (9H, s), 1.78-1.86 (2H, m), 1.99-2.12 (1H, m), 2.68-2.84 (2H, m), 4.00 (2H, d, J=6.4 Hz), 4.02-4.30 (2H, m), 5.87 (1H, br s), 6.97 (1H, d, J=8.4 Hz), 7.05-7.12 (1H, m), 7.42-7.49 (1H, m), 7.66 (1H, br s), 8.20 (1H, dd, J=8.0, 1.6 Hz).

Production Example 73

1-(tert-Butoxycarbonyl)-4-(2-nitrophenoxymethyl)piperidine

The title compound (191 mg, 84% yield) was obtained in the same manner as Production Example 70 from 200 mg of 1-(tert-butoxycarbonyl)-4-(methanesulfonyloxymethyl)piperidine and 114 mg of 2-nitrophenol.

1H-NMR (400 MHz, CDCl3); δ(ppm) 1.22-1.34 (2H, m), 1.47 (9H, s), 1.81-1.90 (2H, m), 1.97-2.10 (1H, m), 2.66-2.84 (2H, m), 3.93 (2H, d, J=5.6 Hz), 4.06-4.28 (2H, m), 7.00-7.08 (2H, m), 7.49-7.55 (1H, m), 7.83 (1H, dd, J=8.0, 1.6 Hz).

Production Example 74

1-(tert-Butoxycarbonyl)-4-[2-(acetylamino)phenoxymethyl]piperidine

After dissolving 400 mg of 1-(tert-butoxycarbonyl)-4-(2-aminophenoxymethyl)piperidine in 10 ml of tetrahydrofuran, 0.15 ml of acetic anhydride and 0.24 ml of triethylamine were added and the mixture was stirred overnight at room temperature. The reaction solution was filtered with silica gel and NH silica gel. The solvent was distilled off under reduced pressure to obtain the title compound (459 mg, 100% yield).

1H-NMR (400 MHz, CDCl3); δ(ppm) 1.24-1.36 (2H, m), 1.47 (9H, s), 1.77-1.84 (2H, m), 1.97-2.09 (1H, m), 2.20 (3H, s), 2.68-2.84 (2H, m), 3.89 (2H, d, J=6.4 Hz), 4.08-4.26 (2H, m), 6.85 (1H, dd, J=8.0, 1.2 Hz), 6.93-7.05 (2H, m), 7.67 (1H, br s), 8.34 (1H, dd, J=8.0, 1.6 Hz).

Production Example 75

2-(2,3-Dihydrobenzofuran-7-yl)-1-(piperidin-4-yl)ethanone hydrochloride

The title compound (86 mg, 64% yield) was obtained in the same manner as Production Example 29 from 159 mg of 1-(1-benzylpiperidin-4-yl)-2-(2,3-dihydrobenzofuran-7-yl)ethanone.

1H-NMR (400 MHz, DMSO-d6); δ(ppm) 1.56-1.69 (2H, m), 1.92-2.01 (2H, m), 2.75-2.93 (3H, m), 3.15 (2H, t, J=8.8 Hz), 3.20-3.35 (2H, m), 3.72 (2H, s), 4.45 (2H, t, J=8.8 Hz), 6.74 (1H, t, J=7.4 Hz), 6.87 (1H, d, J=7.4 Hz), 7.10 (1H, dd, J=7.4, 1.2 Hz).

Production Example 76

2-[2-(Methylthio)phenyl]-1-(piperidin-4-yl)ethanone hydrochloride

The title compound (660 mg, 100% yield) was obtained in the same manner as Production Example 29 from 768 mg of 1-(1-benzylpiperidin-4-yl)-2-[2-(methylthio)phenyl]ethanone.

1H-NMR (400 MHz, DMSO-d6); δ(ppm) 1.63-1.76 (2H, m), 1.98-2.06 (2H, m), 2.40 (3H, s), 2.82-2.96 (3H, m), 3.22-3.31 (2H, m), 3.95 (2H, s), 7.10-7.17 (2H, m), 7.23-7.32 (2H, m), 8.56-8.70 (1H, m), 8.86-9.02 (1H, m).

Production Example 77

1-(Piperidin-4-yl)-2-[2-(trifluoromethyl)phenyl]ethanone hydrochloride

After dissolving 1.30 g of 1-(1-benzylpiperidin-4-yl)-2-[2-(trifluoromethyl)phenyl]ethanone in 10 ml of 1,2-dichloroethane, 0.58 ml of 1-chloroethyl chloroformate was added while stirring at room temperature and the mixture was heated to reflux for 1 hour. The solvent was distilled off under reduced pressure, 10 ml of methanol was added to the residue and heating to reflux was continued for 30 minutes. The solvent was distilled off under reduced pressure, ethyl acetate/n-hexane was added to the residue and the precipitate was filtered out to obtain the title compound (916 mg, 83% yield).

1H-NMR (400 MHz, DMSO-d6); δ(ppm) 1.61-1.73 (2H, m), 1.98-2.06 (2H, m), 2.83-2.98 (3H, m), 3.24-3.36 (2H, m), 4.12 (2H, d, J=1.2 Hz), 7.37 (1H, d, J=7.6 Hz), 7.47 (1H, t, J=7.6 Hz), 7.62 (1H, t, J=7.6 Hz), 7.69 (1H, d, J=7.6 Hz), 8.50-8.68 (1H, m), 8.84-8.98 (1H, m).

Production Example 78

1-(Piperidin-4-yl)-2-[2-(trifluoromethoxy)phenyl]ethanone hydrochloride

The title compound (750 mg, 78% yield) was obtained in the same manner as Production Example 29 from 1.12 g of 1-(1-benzylpiperidin-4-yl)-2-[2-(trifluoromethoxy)phenyl]ethanone.

1H-NMR (400 MHz, DMSO-d6); δ(ppm) 1.61-1.73 (2H, m), 1.98-2.06 (2H, m), 2.82-2.98 (3H, m), 3.24-3.34 (2H, m), 3.99 (2H, s), 7.30-7.43 (4H, m).

Production Example 79

2-(2-Ethoxyphenyl)-1-(piperidin-4-yl)ethanone hydrochloride

The title compound (339 mg, 69% yield) was obtained in the same manner as Production Example 29 from 581 mg of 1-(1-benzylpiperidin-4-yl)-2-(2-ethoxyphenyl)ethanone.

1H-NMR (400 MHz, DMSO-d6); δ(ppm) 1.26 (3H, t, J=6.8 Hz), 1.62-1.74 (2H, m), 1.94-2.02 (2H, m), 2.77-2.97 (3H, m), 3.22-3.30 (2H, m), 3.75 (2H, s), 3.96 (2H, q, J=6.8 Hz), 6.86 (1H, td, J=8.0, 1.2 Hz), 6.92 (1H, dd, J=8.0, 1.2 Hz), 7.10 (1H, dd, J=8.0, 1.6 Hz), 7.20 (1H, ddd, J=9.2, 8.0, 1.6 Hz), 8.58 (1H, br s), 8.86 (1H, br s).

Production Example 80

1-(Piperidin-4-yl)-2-(2-n-propoxyphenyl)ethanone hydrochloride

The title compound (390 mg, 58% yield) was obtained in the same manner as Production Example 29 from 799 mg of 1-(1-benzylpiperidin-4-yl)-2-(2-n-propoxyphenyl)ethanone.

1H-NMR (400 MHz, DMSO-d6); δ(ppm) 0.94 (3H, t, J=7.2 Hz), 1.60-1.72 (4H, m), 1.92-2.01 (2H, m), 2.75-2.96 (3H, m), 3.32-3.30 (2H, m), 3.76 (2H, s), 3.87 (2H, t, J=6.4 Hz), 6.86 (1H, td, J=7.6, 1.2 Hz), 6.92 (1H, dd, J=7.6, 1.2 Hz), 7.10 (1H, dd, J=7.6, 1.6 Hz), 7.20 (1H, ddd, J=9.2, 7.6, 1.6 Hz), 8.56 (1H, br s), 8.85 (1H, br s).

Production Example 81

2-(1-Naphthyl)-1-(piperidin-4-yl)ethanone hydrochloride

The title compound (425 mg, 46% yield) was obtained in the same manner as Production Example 29 from 1.00 g of 1-(1-benzylpiperidin-4-yl)-2-(1-naphthyl)ethanone.

1H-NMR (400 MHz, DMSO-d6); δ(ppm) 1.65-1.77 (2H, m), 2.02-2.10 (2H, m), 2.85-3.02 (3H, m), 3.23-3.32 (2H, m), 4.37 (2H, s), 7.37 (1H, d, J=6.4 Hz), 7.42-7.53 (3H, m), 7.76-7.81 (1H, m), 7.83 (1H, d, J=8.0 Hz), 7.89-7.94 (1H, m), 8.67 (1H, br s), 8.96 (1H, br s).

Production Example 82

2-(2-Biphenyl)-1-(piperidin-4-yl)ethanone hydrochloride

The title compound (642 mg, 52% yield) was obtained in the same manner as Production Example 29 from 1.45 g of 1-(1-benzylpiperidin-4-yl)-2-(2-biphenyl)ethanone.

1H-NMR (400 MHz, DMSO-d6); δ(ppm) 1.38-1.51 (2H, m), 1.66-1.76 (2H, m), 2.53-2.62 (1H, m), 2.74-2.85 (2H, m), 3.11-3.20 (2H, m), 3.84 (2H, s), 7.14-7.24 (4H, m), 7.29-7.43 (5H, m), 8.37 (1H, br s), 8.71 (1H, br s).

Production Example 83

2-(2-Bromophenyl)-1-(piperidin-4-yl)ethanone hydrochloride

The title compound (942 mg, 68% yield) was obtained in the same manner as Production Example 29 from 1.63 g of 1-(1-benzylpiperidin-4-yl)-2-(2-bromophenyl)ethanone.

1H-NMR (400 MHz, DMSO-d6); δ(ppm) 1.65-1.77 (2H, m), 2.00-2.09 (2H, m), 2.84-2.98 (3H, m), 3.23-3.32 (2H, m), 4.04 (2H, s), 7.20 (1H, td, J=7.6, 2.0 Hz), 7.27-7.36 (2H, m), 7.58 (1H, dd, J=7.6, 1.2 Hz), 8.64 (1H, br s), 8.94 (1H, br s).

Production Example 84 trans-2-(2-Fluorophenyl)-1-(3-methylpiperidin-4-yl)ethanone hydrochloride

The title compound (496 mg, 87% yield) was obtained in the same manner as Production Example 29 from 0.69 g of trans-1-(1-benzyl-3-methylpiperidin-4-yl)-2-(2-fluorophenyl)ethanone.

1H-NMR (400 MHz, DMSO-d6); δ(ppm) 0.81 (3H, d, J=6.8 Hz), 1.51-1.64 (1H, m), 1.97-2.12 (2H, m), 2.52-2.68 (2H, m), 2.79-2.91 (1H, m), 3.15-3.22 (1H, m), 3.28-3.40 (1H, m), 3.86 (1H, d, J=18.0 Hz), 4.03 (1H, d, J=18.0 Hz), 7.10-7.20 (2H, m), 7.24-7.35 (2H, m), 8.64-8.84 (1H, m), 8.95-9.12 (1H, m).

Production Example 85

3,3-Dimethoxy-4-[2-(2-fluorophenyl)ethyl]piperidine hydrochloride

The title compound (1.01 g, 86% yield) was obtained in the same manner as Production Example 29 from 1.26 g of 1-benzyl-3-methoxy-4-[2-(2-fluorophenyl)ethyl]-1,2,5,6-tetrahydropyridine.

1H-NMR (400 MHz, DMSO-d6); δ(ppm) 1.58-1.97 (5H, m), 2.53-2.60 (1H, m), 2.66-2.76 (1H, m), 2.78-2.86 (1H, m), 2.94-3.02 (2H, m), 3.01 (3H, s), 3.13 (3H, s), 3.17-3.24 (1H, m), 7.09-7.17 (2H, m), 7.22-7.28 (1H, m), 7.34 (1H, td, J=7.6, 1.6 Hz), 8.36-8.52 (1H, m), 9.30-9.43 (1H, m).

Production Example 86

2-[2-Fluoro-6-(trifluoromethyl)phenyl]-1-(piperidin-4-yl)ethanone

After dissolving 136 mg of 1-(1-benzylpiperidin-4-yl)-2-[2-fluoro-6-(trifluoromethyl)phenyl]ethanone in 3 ml of 1,2-dichloroethane, 0.06 ml of 1-chloroethyl chloroformate was added and the mixture was stirred at room temperature for 5 minutes and then heated to reflux for 45 minutes. The solvent was distilled off under reduced pressure, 10 ml of methanol was added to the residue and heating to reflux was continued for 30 minutes. The solvent was distilled off under reduced pressure, ammonia water was added to the residue and extraction was performed with dichloromethane. After drying over anhydrous magnesium sulfate, the solvent was distilled off under reduced pressure. The residue was purified by NH silica gel column chromatography (solvent: ethyl acetate/methanol) to obtain the title compound (45 mg, 43% yield).

1H-NMR (400 MHz, CDCl3); δ(ppm) 1.56-1.67 (2H, m), 1.87-1.94 (2H, m), 2.58-2.72 (3H, m), 3.12-3.20 (2H, m), 3.99 (2H, s), 7.25 (1H, t, J=8.8 Hz), 7.33-7.40 (1H, m), 7.45 (1H, d, J=8.0 Hz).

Production Example 87

2-(3-Methyl-2-thienyl)-1-(piperidin-4-yl)ethanone hydrochloride

The title compound (624 mg, 89% yield) was obtained in the same manner as Production Example 29 from 858 mg of 1-(1-benzylpiperidin-4-yl)-2-(3-methyl-2-thienyl)ethanone.

1H-NMR (400 MHz, DMSO-d6); δ(ppm) 1.59-1.71 (2H, m), 1.95-2.02 (2H, m), 2.06 (3H, s), 2.79-2.95 (3H, m), 3.19-3.30 (2H, m), 4.02 (2H, s), 6.84 (1H, d, J=5.2 Hz), 7.27 (1H, d, J=5.2 Hz), 8.61 (1H, br s), 8.90 (1H, br s).

Production Example 88

2-(4-Fluoro-3-thienyl)-1-(piperidin-4-yl)ethanone hydrochloride

The title compound (977 mg, 93% yield) was obtained in the same manner as Production Example 29 from 1.26 g of 1-(1-benzylpiperidin-4-yl)-2-(4-fluoro-3-thienyl)ethanone.

1H-NMR (400 MHz, DMSO-d6); δ(ppm) 1.61-1.73 (2H, m), 1.97-2.05 (2H, m), 2.79-2.96 (3H, m), 3.22-3.30 (2H, m), 3.85 (2H, s), 7.15 (1H, d, J=3.6 Hz), 7.31 (1H, t J=3.6 Hz), 8.73 (1H, br s), 9.01 (1H, br s).

Production Example 89

5-Chloro-3-methoxypyrazine-2-carboxaldehyde dimethylacetal

The title compound (3.34 g, 88% yield) was obtained in the same manner as Production Example 50 from 3.01 g of 5-chloro-3-methoxypyrazine-2-carboxaldehyde.

1H-NMR (400 MHz, CDCl3); δ(ppm) 3.44 (6H, s), 4.03 (3H, s), 5.63 (1H, s), 8.17 (1H, s).

Production Example 90

4-Bromothiophene-3-carboxaldehyde dimethylacetal

The title compound (18.38 g, 100% yield) was obtained in the same manner as Production Example 50 from 14.78 g of 4-bromothiophene-3-carboxaldehyde.

1H-NMR (400 MHz, CDCl3); δ(ppm) 3.34 (6H, s), 5.41 (1H, d, J=0.8 Hz), 7.26 (1H, d, J=3.6 Hz), 7.43 (1H, dd, J=3.6, 0.8 Hz).

Production Example 91

1-[1-(tert-Butoxycarbonyl)piperidin-4-yl]-2-[2-(3-pyridyl)phenyl]ethanone

After dissolving 575 mg of 1-[1-(tert-butoxycarbonyl)piperidin-4-yl]-2-(2-bromophenyl)ethanone in 10 ml of N,N-dimethylformamide, there were added 489 mg of 2-(3-pyridyl)-1,3,2-dioxaborinane, 173 mg of tetrakis(triphenylphosphine)palladium(0) and 1.47 g of anhydrous cesium carbonate, and the mixture was stirred at 100° C. for 2 hours under a nitrogen atmosphere. Water was added to the reaction mixture, and extraction was performed with ethyl acetate. The organic layer was washed with water and saturated brine in that order and dried over anhydrous magnesium sulfate, and then the solvent was distilled off under reduced pressure. The residue was purified by silica gel column chromatography (solvent: n-hexane/ethyl acetate) to obtain the title compound (379 mg, 66% yield).

1H-NMR (400 MHz, CDCl3); δ(ppm) 1.32-1.47 (2H, m), 1.44 (9H, s), 1.55-1.66 (2H, m), 2.33 (1H, dt, J=11.2, 3.6 Hz), 2.60-2.74 (2H, m), 3.73 (2H, s), 3.92-4.12 (2H, m), 7.16-7.41 (5H, m), 7.53-7.58 (1H, m), 8.49 (1H, d, J=1.2 Hz), 8.59 (1H, dd, J=4.8, 1.6 Hz).

Production Example 92

2-(3-Methyl-2-thienyl)-1-(4-pyridyl)ethanone

The title compound (1.69 g, 78% yield) was obtained in the same manner as Production Example 61 from 4.16 g of [(phenylamino)-(4-pyridylmethyl)]phosphonic acid diphenyl ester and 1.19 ml of 3-methyl-2-thiophenecarboxaldehyde.

1H-NMR (400 MHz, CDCl3); δ(ppm) 2.18 (3H, s), 4.37 (2H, s), 6.84 (1H, d, J=5.2 Hz), 7.14 (1H, d, J=5.2 Hz), 7.74-7.78 (2H, m), 8.78-8.84 (2H, m).

Production Example 93

Methyl 3-methoxy-6-methylpyrazine-2-carboxylate

After dissolving 300 mg of methyl 6-bromo-3-methoxypyrazine-2-carboxylate in 10 ml of tetrahydrofuran, 32 mg of [1,3-bis(diphenylphosphino)propane]dichloronickel(II) was added, a solution of 0.73 ml of dimethyl zinc in toluene (2.0 M) was added dropwise under a nitrogen atmosphere and the mixture was stirred at room temperature for 3 hours. Saturated aqueous ammonium chloride solution and aqueous sodium carbonate solution were added to the reaction solution in that order, and extraction was performed with ethyl acetate. The organic layer was washed with water and saturated brine in that order and dried over anhydrous magnesium sulfate, and then the solvent was distilled off under reduced pressure. The residue was purified by silica gel column chromatography (solvent: n-hexane/ethyl acetate) to obtain the title compound (161 mg, 73% yield).

1H-NMR (400 MHz, CDCl3); δ(ppm) 2.54 (3H, d, J=0.4 Hz), 3.98 (3H, s), 4.03 (3H, s), 8.13 (1H, d, J=0.4 Hz).

Production Example 94

N-methoxy-N-methyl-1-(tert-butoxycarbonyl)-4-fluoropiperidine-4-carboxamide

After dissolving 2.19 g of 1-(tert-butoxycarbonyl)-4-fluoropiperidine-4-carboxylic acid in 30 ml of dichloromethane, 2.16 g of 1,1'-carbonyldiimidazole was added and the mixture was stirred at room temperature for 1.5 hours. Next, 1.30 g of N-methyl-O-methylhydroxylamine hydrochloride was added and the mixture was stirred overnight at room temperature. Water was added to the reaction solution, and extraction was performed with ethyl acetate. The organic layer was washed with aqueous sodium carbonate solution, water and saturated brine in that order and dried over anhydrous magnesium sulfate, and then the solvent was distilled off under reduced pressure. The residue was purified by silica gel column chromatography (solvent: n-hexane/ethyl acetate) to obtain the title compound (2.33 g, 90% yield).

1H-NMR (400 MHz, CDCl3); δ(ppm) 1.46 (9H, s), 1.93-2.14 (4H, m), 3.04-3.18 (2H, m), 3.23 (3H, s), 3.72 (3H, s), 3.86-4.08 (2H, m).

Production Example 95

1-(tert-Butoxycarbonyl)-4-[2-(methanesulfonylamino)phenoxymethyl]piperidine

After dissolving 400 mg of 1-(tert-butoxycarbonyl)-4-(2-aminophenoxymethyl)piperidine in 10 ml of tetrahydrofuran, 0.24 ml of triethylamine and 0.12 ml of methanesulfonyl chloride were added and the mixture was stirred overnight at room temperature. Next, 0.24 ml of triethylamine and 0.12 ml of methanesulfonyl chloride were added to the reaction solution and stirring was continued at room temperature for 2 hours. The reaction solution was filtered with silica gel and NH silica gel, and the filtrate was concentrated under reduced pressure. The residue was purified by silica gel column chromatography (solvent: n-hexane/ethyl acetate) to obtain the title compound (447 mg, 90% yield).

1H-NMR (400 MHz, CDCl3); δ(ppm) 1.24-1.32 (2H, m), 1.47 (9H, s), 1.78-1.85 (2H, m), 1.95-2.06 (1H, m), 2.70-2.83 (2H, m), 2.96 (3H, s), 3.87 (2H, d, J=6.8 Hz), 4.10-4.26 (2H, m), 6.74 (1H, br s), 6.90 (1H, dd, J=8.4, 1.2 Hz), 6.95-7.03 (1H, m), 7.10-7.15 (1H, m), 7.53 (1H, dd, J=8.0, 1.6 Hz).

Production Example 96

1-[1-(tert-Butoxycarbonyl)piperidin-4-yl]-2-(2-bromophenyl)ethanone

After dissolving 525 mg of 2-(2-bromophenyl)-1-(piperidin-4-yl)ethanone hydrochloride in 8 ml of a 1N sodium hydroxide solution, a solution of 431 mg of di-tert-butyldicarbonate in tetrahydrofuran (8 ml) was added and the mixture was stirred at room temperature for 3 hours. Water was added to the reaction solution, and extraction was performed with ethyl acetate. The organic layer was washed with water and saturated brine and dried over anhydrous magnesium sulfate, and then the solvent was distilled off under reduced pressure. The residue was purified by silica gel column chromatography (solvent: n-hexane/ethyl acetate) to obtain the title compound (675 mg, 94% yield).

1H-NMR (400 MHz, CDCl3); δ(ppm) 1.45 (9H, s), 1.56-1.67 (2H, m), 1.82-1.92 (2H, m), 2.60-2.68 (1H, m), 2.73-2.85 (2H, m), 3.92 (2H, s), 4.03-4.18 (2H, m), 7.13 (1H, dt, J=8.0, 1.6 Hz), 7.18 (1H, dd, J=8.0, 1.6 Hz), 7.27 (1H, dt, J=8.0, 1.2 Hz), 7.55 (1H, dd, J=8.0, 1.2 Hz).

Production Example 97

1-[1-(tert-Butoxycarbonyl)piperidin-4-yl]-2-[2-(methylthio)phenyl]ethanone

The title compound (244 mg, 80% yield) was obtained in the same manner as Production Example 96 from 250 mg of 1-(piperidin-4-yl)-2-[2-(methylthio)phenyl]ethanone hydrochloride.

1H-NMR (400 MHz, CDCl3); δ(ppm) 1.45 (9H, s), 1.55-1.66 (2H, m), 1.82-1.91 (2H, m), 2.43 (3H, s), 2.59-2.68 (1H, m), 2.72-2.82 (2H, m), 3.89 (2H, s), 4.02-4.16 (2H, m), 7.08-7.16 (2H, m), 7.24-7.29 (2H, m).

Production Example 98

5-tert-Butoxy-3-chloropyrazine-2-carboxaldehyde

The title compound (146 mg, 10% yield) was obtained in the same manner as Production Example 1 from 1.20 g of 2-tert-butoxy-6-chloropyrazine.

1H-NMR (400 MHz, CDCl3); δ(ppm) 1.66 (9H, s), 8.14 (1H, s), 10.22 (1H, s).

Production Example 99

6-tert-Butoxypyrazine-2-carboxaldehyde

After adding 7.20 g of AD-mix-β to 60 ml of 50% aqueous tert-butanol, a solution of 1.00 g of 2-tert-butoxy-6-vinylpyrazine in tert-butanol (5 ml) was added and the mixture was stirred overnight at room temperature. Next, 8.40 g of sodium sulfite was added to the reaction solution, the mixture was stirred at room temperature for 1 hour, and then water was added and extraction was performed with ethyl acetate. The organic layer was washed with water and saturated brine and dried over anhydrous magnesium sulfate, and then the solvent was distilled off under reduced pressure. The residue was dissolved in 40 ml of methanol, an aqueous solution of 2.35 g of sodium periodate (20 ml) was added while stirring on ice, and stirring was continued at room temperature for 40 minutes. Water was added to the reaction solution, and extraction was performed with ethyl acetate. The extract was washed with water and saturated brine and dried over anhydrous magnesium sulfate, and then the solvent was distilled off under reduced pressure. The residue was purified by silica gel column chromatography (solvent: n-hexane/ethyl acetate) to obtain the title compound (954 mg, 96% yield).

1H-NMR (400 MHz, CDCl3); δ(ppm) 1.66 (9H, s), 8.27 (1H, s), 8.63 (1H, s), 9.99 (1H, s).

Production Example 100

3-Methoxy-5-methylpyrazine-2-carboxaldehyde

After dissolving 3.34 g of 5-chloro-3-methoxypyrazine-2-carboxaldehyde dimethylacetal in 50 ml of tetrahydrofuran, 400 mg of [1,3-bis(diphenylphosphino)propane]dichloronickel(II) was added, 9.17 ml of dimethyl zinc (2.0 M, toluene solution) was added dropwise under a nitrogen atmosphere, and the mixture was stirred at room temperature for 2 hours and then at 50° C. for 1.5 hours. The reaction solution was cooled on ice, water was added and extraction was performed with ethyl acetate. The organic layer was washed with water and saturated brine in that order and dried over anhydrous magnesium sulfate, and then the solvent was distilled off under reduced pressure. The residue was dissolved in 16 ml of acetone, 4 ml of 5N hydrochloric acid was added and the mixture was allowed to stand at room temperature for 15 minutes. A sodium bicarbonate solution was added to the reaction solution and extraction was performed with ethyl acetate. The organic layer was washed with saturated brine and dried over anhydrous magnesium sulfate, and then the solvent was distilled off under reduced pressure. The residue was purified by silica gel column chromatography (solvent: n-hexane/ethyl acetate) to obtain the title compound (1.43 g, 61% yield).

1H-NMR (400 MHz, CDCl3); δ(ppm) 2.57 (3H, s), 4.10 (3H, s), 8.21 (1H, s), 10.22 (1H, s).

Production Example 101

5-Chloro-3-methoxypyrazine-2-carboxaldehyde

After dissolving 11.4 ml of 2,2,6,6-tetramethylpiperidine in 100 ml of tetrahydrofuran, the solution was cooled to −30° C. Next, 24.1 ml of n-butyllithium (2.6 M, n-hexane solution) was added dropwise under a nitrogen atmosphere. After stirring for 15 minutes and cooling on ice, the mixture was stirred for 10 minutes. It was then cooled to −78° C., and a solution of 6.96 g of 2-chloro-6-methoxypyrazine in tetrahydrofuran (10 ml) was added dropwise at below −70° C. The mixture was stirred for 30 minutes, and then 6 ml of N,N-dimethylformamide was added dropwise at below −65° C. After 10 minutes, 50 ml of toluene was added to the reaction solution at below −60° C., and then after 2 minutes, a tetrahydrofuran solution (5 ml) containing 2 ml of water was added at below −65° C. After an additional 5 minutes, 60 ml of 50% aqueous acetic acid was added at once, and then after 15 minutes, 100 ml of water was added and the temperature was raised to room temperature. The reaction solution was extracted with ethyl acetate, and the organic layer was washed with water, a 1N sodium hydroxide solution and saturated brine in that order and dried over anhydrous magnesium sulfate. The solvent was distilled off under reduced pressure and the residue was purified by silica gel column chromatography (solvent: n-hexane/ethyl acetate) to obtain the title compound (6.38 g, 77% yield).

1H-NMR (400 MHz, CDCl3); δ(ppm) 4.14 (3H, s), 8.33 (1H, s), 10.20 (1H, s).

Production Example 102

4-Bromothiophene-3-carboxaldehyde

After dissolving 25.2 g of 3,4-dibromothiophene in 300 ml of diethyl ether, the solution was cooled to −78° C. Next, 44.1 ml of n-butyllithium (2.6 M, n-hexane solution) was added dropwise while stirring at below −60° C. After 1 hour, 9.66 ml of N,N-dimethylformamide was added dropwise at below −60° C. After an additional 45 minutes, water was added to the reaction solution, the temperature was returned to room temperature, and extraction was performed with ethyl acetate. The organic layer was washed with water and saturated brine in that order and dried over anhydrous magnesium sulfate, and then the solvent was distilled off under reduced pressure. The residue was purified by silica gel column chromatography (solvent: n-hexane/ethyl acetate) to obtain the title compound (14.78 g, 74% yield).

1H-NMR (400 MHz, CDCl3); δ(ppm) 7.36 (1H, d, J=3.6 Hz), 8.15 (1H, d J=3.6 Hz), 9.34 (1H, s).

Production Example 103

3-Methoxy-6-methylpyrazine-2-carboxaldehyde

After dissolving 300 mg of methyl 3-methoxy-6-methylpyrazine-2-carboxylate in a mixture of 5 ml toluene/5 ml dichloromethane, the solution was cooled to −78° C. Next, 1.21 ml of diisobutylaluminium hydride (1.5 M, toluene solution) was added dropwise and the mixture was stirred for 1 hour. After adding 10 ml of 1N hydrochloric acid dropwise to the reaction solution, extraction was performed with ethyl acetate. The organic layer was washed with 1N hydrochloric acid, a saturated sodium bicarbonate solution and saturated brine in that order and dried over anhydrous magnesium sulfate, and then the solvent was distilled off under reduced pressure. The residue was purified by silica gel column chromatography (solvent: n-hexane/ethyl acetate) to obtain the title compound (118 mg, 47% yield).

1H-NMR (400 MHz, CDCl3); δ(ppm) 2.58 (3H, s), 4.09 (3H, s), 8.20 (1H, s), 10.24 (1H, s).

Production Example 104

6-Fluoro-3-methoxypyrazine-2-carboxaldehyde

After dissolving 447 mg of methyl 6-fluoro-3-methoxypyrazine-2-carboxylate in 8 ml of dichloromethane, the solution was cooled to −78° C. Next, 1.76 ml of diisobutylaluminium hydride (1.5 M, toluene solution) was added dropwise and the mixture was stirred for 30 minutes. After adding 10 ml of 1N hydrochloric acid dropwise to the reaction solution, water was added and extraction was performed with dichloromethane. After then drying over anhydrous magnesium sulfate, the solvent was distilled off under reduced pressure. The residue was purified by silica gel column chromatography (solvent: n-hexane/ethyl acetate) to obtain the title compound (245 mg, 65% yield).

1H-NMR (400 MHz, CDCl3); δ(ppm) 4.13 (3H, s), 8.23 (1H, d, J=8.0 Hz), 10.16 (1H, s).

Production Example 105

3-tert-Butoxy-5-fluoropyrazine-2-carboxaldehyde

After dissolving 11.4 ml of 2,2,6,6-tetramethylpiperidine in 100 ml of tetrahydrofuran, the solution was cooled to −30° C. Next, 24.1 ml of n-butyllithium (2.6 M, n-hexane solution) was added dropwise under a nitrogen atmosphere. After stirring for 5 minutes, the mixture was cooled on ice and stirred for an additional 20 minutes. It was then cooled to −78° C., and a solution of 9.00 g of 2-tert-butoxy-6-chloropyrazine in tetrahydrofuran (10 ml) was added dropwise at below −70° C. The mixture was then stirred for 30 minutes, and 6 ml of N,N-dimethylformamide was added dropwise at below −65° C. After 10 minutes, 50 ml of toluene was added to the reaction solution at below −60° C., and after 2 minutes, a tetrahydrofuran solution (5 ml) containing 2 ml of water was added at below −65° C. After an additional 5 minutes, 60 ml of 50% aqueous acetic acid was added at once, and after 5 minutes, 100 ml of water was added and the temperature was raised to room temperature. The reaction solution was extracted with ethyl acetate, washed with water, a 1N sodium hydroxide solution, water and saturated brine in that order, and dried over anhydrous magnesium sulfate. The solvent was distilled off under reduced pressure to obtain 9.39 g of crude 3-tert-butoxy-5-chloropyrazine-2-carboxaldehyde.

After dissolving 5.86 g of the crude 3-tert-butoxy-5-chloropyrazine-2-carboxaldehyde in 55 ml of acetonitrile, 4.77 g of potassium fluoride, 1.13 g of tetraphenylphosphonium bromide and 0.71 g of 18-crown-6 were added and the mixture was heated to reflux for 4 hours. Diethyl ether was added to the reaction mixture, the insoluble portion was filtered out, and the filtrate was distilled off under reduced pressure. Ethyl acetate was added to the residue, the insoluble portion was filtered out, and the filtrate was distilled off under reduced pressure. The residue was purified by silica gel column chromatography (solvent: toluene/ethyl acetate) to obtain the title compound (183 mg, 3% yield).

1H-NMR (400 MHz, CDCl3); δ(ppm) 1.64 (9H, s), 8.08 (1H, d, J=8.4 Hz), 10.22 (1H, s).

Production Example 106

1-(1-Benzyl-1,2,3,6-tetrahydropyridin-4-yl)-2-(2-fluoro-3-thienyl)ethanol

After dissolving 304 mg of 2-(2-fluoro-3-thienyl)-1-(4-pyridyl)ethanone in 2 ml of toluene, 0.20 ml of benzyl bromide was added, the mixture was stirred at 100° C. for 8 hours and the precipitate was filtered out. The filtered substance was dissolved in 10 ml of methanol, 157 mg of sodium borohydride was added thereto in small portions at a time while cooling on ice, and the mixture was stirred for 1 hour. The reaction solution was distilled off under reduced pressure, water was added and extraction was performed with ethyl acetate. The organic layer was washed with water and saturated brine and dried over anhydrous magnesium sulfate, and then the solvent was distilled off under reduced pressure. The residue was purified by NH silica gel column chromatography (solvent: n-hexane/ethyl acetate) to obtain the title compound (384 mg, 88% yield).

1H-NMR (400 MHz, CDCl3); δ(ppm) 2.13-2.29 (2H, m), 2.54-2.64 (2H, m), 2.73 (1H, dd, J=14.4, 8.0 Hz), 2.80 (1H, dd, J=14.4, 4.4 Hz), 2.96-3.02 (2H, m), 3.58 (2H, s), 4.18-4.24 (1H, m), 5.58-5.62 (1H, m), 6.68 (1H, dd, J=6.0, 3.6 Hz), 6.67 (1H, dd, J=6.0, 4.0 Hz), 7.22-7.38 (5H, m).

Production Example 107

1-[1-(tert-Butoxycarbonyl)-4-methylpiperidin-4-yl]-2-(2-fluorophenyl)ethanone

The title compound (165 mg, 7% yield) was obtained in the same manner as Production Example 26 from 1.96 g of N-methoxy-N-methyl-1-(tert-butoxycarbonyl)-4-methylpiperidine-4-carboxamide [CAS No. 189442-91-9] and 3.20 g of 2-fluorobenzyl chloride.

1H-NMR (400 MHz, CDCl3); δ(ppm) 1.27 (3H, s), 1.42-1.54 (2H, m), 1.45 (9H, s), 2.04-2.12 (2H, m), 3.13-3.22 (2H, m), 3.54-3.67 (2H, m), 3.80 (2H, s), 7.03 (1H, ddd, J=10.0, 8.4, 1.2 Hz), 7.09 (1H, dt, J=7.2, 1.2 Hz), 7.15 (1H, dt, J=7.2, 1.2 Hz), 7.21-7.27 (1H, m).

Production Example 108

1-[1-(tert-Butoxycarbonyl)-4-fluoropiperidin-4-yl]-2-(2-fluorophenyl)ethanone

The title compound (955 mg, 35% yield) was obtained in the same manner as Production Example 26 from 2.33 g of N-methoxy-N-methyl-1-(tert-butoxycarbonyl)-4-fluoropiperidine-4-carboxamide and 4.51 g of 2-fluorobenzyl chloride.

1H-NMR (400 MHz, CDCl3); δ(ppm) 1.46 (9H, s), 1.77-2.04 (4H, m), 3.02-3.18 (2H, m), 3.90-4.18 (2H, m), 4.01 (2H, d, J=2.8 Hz), 7.01-7.17 (3H, m), 7.23-7.29 (1H, m).

Production Example 109

1-(tert-Butoxycarbonyl)-4-[3-(2-fluorophenyl)-2-oxopropyl]piperidine

The title compound (1.86 g, 78% yield) was obtained in the same manner as Production Example 26 from 2.04 g of N-methoxy-N-methyl-1-(tert-butoxycarbonyl)-piperidine-4-acetamide and 2.06 g of 2-fluorobenzyl chloride.

1H-NMR (400 MHz, CDCl3); δ(ppm) 1.00-1.13 (2H, m), 1.44 (9H, s), 1.57-1.66 (2H, m), 1.94-2.06 (1H, m), 2.40 (2H, d, J=6.4 Hz), 2.62-2.78 (2H, m), 3.70 (2H, s), 3.92-4.14 (2H, m), 7.02-7.18 (3H, m), 7.22-7.29 (1H, m).

Production Example 110

1-[1-(tert-Butoxycarbonyl)piperidin-4-yl]-3-(2-fluorophenyl)propanone

The title compound (0.79 g, 43% yield) was obtained in the same manner as Production Example 26 from 1.50 g of N-methoxy-N-methyl-1-(tert-butoxycarbonyl)-piperidine-4-carboxamide and 1.46 g of 2-(2-fluorophenyl)ethyl bromide.

1H-NMR (400 MHz, CDCl3); δ(ppm) 1.44 (9H, s), 1.45-1.55 (2H, m), 1.72-1.82 (2H, m), 2.43 (1H, dt, J=7.6, 3.6 Hz), 2.68-2.81 (4H, m), 2.91 (2H, t, J=7.6 Hz), 3.98-4.18 (2H, m), 6.96-7.06 (2H, m), 7.13-7.20 (2H, m).

Production Example 111 trans-1-(1-Benzyl-3-methylpiperidin-4-yl)-2-(2-fluorophenyl)ethanone trans-1-(1-Benzyl-3-methylpiperidin-4-yl)-2-(2-fluorophenyl)ethanol was obtained in the same manner as Production Example 11 from 1.20 g of trans-1-benzyl-3-methylpiperidine-4-carboxaldehyde and 2.64 g of 2-fluorobenzyl chloride, and was subjected to the same process as in Production Example 15 to obtain the title compound (0.69 g, 39% yield).

1H-NMR (400 MHz, CDCl3); δ(ppm) 0.77 (3H, d, J=6.4 Hz), 1.59-1.82 (3H, m), 1.92 (1H, dt, J=10.2, 3.2 Hz), 2.00-2.12 (1H, m), 2.16-2.22 (1H, m), 2.84 (1H, ddd, J=11.2, 3.6, 1.6 Hz), 2.91-2.96 (1H, m), 3.48 (2H, s), 3.73 (1H, dd, J=16.4, 1.2 Hz), 3.78 (1H, dd, J=16.4, 1.2 Hz), 7.01-7.10 (2H, m), 7.14 (1H, dt, J=7.6, 1.6 Hz), 7.20-7.33 (6H, m).

Production Example 112

1-(tert-Butoxycarbonyl)-4-[(2-fluorophenylthio)methyl]piperidine

After dissolving 1.97 g of 2-fluorothiophenol in 50 ml of tetrahydrofuran, 3.0 g of 1-(tert-butoxycarbonyl)piperidine-4-methanol and 4.03 g of triphenylphosphine were added, and then 3.3 ml of diethyl azodicarboxylate was added dropwise while cooling on ice and the mixture was stirred overnight at room temperature. The reaction solution was concentrated under reduced pressure. The residue was purified by silica gel column chromatography (solvent: n-hexane/ethyl acetate) to obtain the title compound (216 mg, 5% yield).

1H-NMR (400 MHz, CDCl3); δ(ppm) 1.11-1.23 (2H, m), 1.45 (9H, s), 1.55-1.70 (1H, m), 1.81-1.89 (2H, m), 2.60-2.74 (2H, m), 2.82 (2H, d, J=6.4 Hz), 4.03-4.16 (2H, m), 7.04 (1H, ddd, J=9.6, 7.6, 1.2 Hz), 7.08 (1H, td, J=7.6, 1.6 Hz), 7.17-7.24 (1H, m), 7.35 (1H, td, J=7.6, 1.6 Hz).

Production Example 113

4-(2-Fluorobenzylsulfonyl)piperidine hydrochloride

After dissolving 690 mg of 1-(tert-butoxycarbonyl)-4-(2-fluorobenzylsulfonyl)piperidine in 3 ml of ethyl acetate, 3 ml of 4N hydrogen chloride/ethyl acetate was added and the mixture was stirred at room temperature for 30 minutes. The precipitate was filtered out to obtain the title compound (517 mg, 91% yield).

1H-NMR (400 MHz, DMSO-d6); δ(ppm) 1.82-1.95 (2H, m), 2.20-2.29 (2H, m), 2.90-3.00 (2H, m), 3.37-3.53 (3H, m), 4.57 (2H, s), 7.22-7.31 (2H, m), 7.42-7.49 (2H, m).

Production Example 114

4-[(2-Fluorophenylthio)methyl]piperidine hydrochloride

The title compound (52 mg, 85% yield) was obtained in the same manner as Production Example 113 from 76 mg of 1-(tert-butoxycarbonyl)-4-[(2-fluorophenylthio)methyl]piperidine.

1H-NMR (400 MHz, DMSO-d6); δ(ppm) 1.33-1.45 (2H, m), 1.69-1.81 (1H, m), 1.91-1.98 (2H, m), 2.78-2.87 (2H, m), 2.95 (2H, d, J=6.4 Hz), 3.20-3.27 (2H, m), 7.17-7.31 (3H, m), 7.47 (1H, td, J=7.6, 1.6 Hz), 8.50 (2H, br s).

Production Example 115

4-[(2-Fluorophenylsulfonyl)methyl]piperidine hydrochloride

The title compound (36 mg, 85% yield) was obtained in the same manner as Production Example 113 from 52 mg of 1-(tert-butoxycarbonyl)-4-[(2-fluorophenylsulfonyl)methyl]piperidine.

1H-NMR (400 MHz, DMSO-d6); δ(ppm) 1.42-1.55 (2H, m), 1.90-1.98 (2H, m), 2.14-2.26 (1H, m), 2.84-2.93 (2H, m), 3.17-3.24 (2H, m), 3.46 (2H, d, J=6.4 Hz), 7.49 (1H, td, J=7.6, 1.2 Hz), 7.54 (1H, ddd, J=10.6, 8.4, 1.2 Hz), 7.80-7.90 (2H, m).

Production Example 116

2-(2-Fluorophenyl)-1-(piperidin-4-yl)propanone

After dissolving 1.16 g of 1-[1-(tert-butoxycarbonyl)piperidin-4-yl]-2-(2-fluorophenyl)propanone in 10 ml of ethyl acetate, 10 ml of 4N hydrogen chloride/ethyl acetate was added and the mixture was stirred at room temperature for 1 hour. A 5N sodium hydroxide solution was added to the reaction solution, and extraction was performed with ethyl acetate. The organic layer was washed with water and saturated brine and then dried over anhydrous magnesium sulfate. The solvent was distilled off under reduced pressure to obtain the title compound (763 mg, 94% yield).

1H-NMR (400 MHz, CDCl3); δ(ppm) 1.37 (3H, d, J=6.8 Hz), 1.40-1.60 (3H, m), 1.79-1.86 (1H, m), 2.44-2.62 (3H, m), 2.99-3.12 (2H, m), 4.27 (1H, q, J=6.8 Hz), 7.05 (1H, ddd, J=9.6, 7.6, 1.2 Hz), 7.11 (1H, dd, J=7.6, 1.2 Hz), 7.16 (1H, td, J=7.6, 2.0 Hz), 7.20-7.26 (1H, m).

Production Example 117

4-(2-Chlorophenoxymethyl)-4-methylpiperidine

After dissolving 810 mg of 1-(tert-butoxycarbonyl)-4-(2-chlorophenoxymethyl)-4-methylpiperidine in 3 ml of ethyl acetate, 3 ml of 4N hydrogen chloride/ethyl acetate was added and the mixture was allowed to stand at room temperature for 2.5 hours. A sodium carbonate solution was added to the reaction solution, and extraction was performed with dichloromethane. After drying over anhydrous magnesium sulfate, the solvent was distilled off under reduced pressure to obtain the title compound (521 mg, 91% yield).

1H-NMR (400 MHz, CDCl3); δ(ppm) 1.16 (3H, s), 1.44-1.51 (2H, m), 1.61-1.69 (2H, m), 2.82-2.94 (4H, m), 3.72 (2H, s), 6.83-6.91 (2H, m), 7.18 (1H, ddd, J=8.0, 7.6, 1.6 Hz), 7.34 (1H, dd, J=8.0, 1.6 Hz).

Production Example 118

4-Methyl-4-(2-methylphenoxymethyl)piperidine

The title compound (536 mg, 96% yield) was obtained in the same manner as Production Example 117 from 816 mg of 1-(tert-butoxycarbonyl)-4-methyl-4-(2-methylphenoxymethyl)piperidine.

1H-NMR (400 MHz, CDCl3); δ(ppm) 1.13 (3H, s), 1.42-1.50 (2H, m), 1.59-1.69 (2H, m), 2.24 (3H, s), 2.82-2.94 (4H, m), 3.67 (2H, s), 6.76-6.86 (2H, m), 7.10-7.17 (2H, m).

Production Example 119

4-(2-Methoxyphenoxymethyl)-4-methylpiperidine

The title compound (190 mg, 93% yield) was obtained in the same manner as Production Example 117 from 293 mg of 1-(tert-butoxycarbonyl)-4-(2-methoxyphenoxymethyl)-4-methylpiperidine.

1H-NMR (400 MHz, CDCl3); δ(ppm) 1.14 (3H, s), 1.43-1.51 (2H, m), 1.63-1.72 (2H, m), 2.83-2.98 (4H, m), 3.71 (2H, s), 3.84 (3H, s), 6.85-6.93 (4H, m).

Production Example 120

2-[2-(Methylsulfonyl)phenyl]-1-(piperidin-4-yl)ethanone hydrochloride

The title compound (169 mg, 94% yield) was obtained in the same manner as Production Example 113 from 217 mg of 1-[1-(tert-butoxycarbonyl)piperidin-4-yl]-2-[2-(methylsulfonyl)phenyl]ethanone.

1H-NMR (400 MHz, DMSO-d6); δ(ppm) 1.64-1.75 (2H, m), 2.02-2.09 (2H, m), 2.82-2.98 (3H, m), 3.14 (3H, s), 3.25-3.34 (2H, m), 4.33 (2H, s), 7.37 (1H, dd, J=7.8, 1.4 Hz), 7.54 (1H, td, J=7.8, 1.4 Hz), 7.66 (1H, td, J=7.8, 1.4 Hz), 7.92 (1H, dd, J=7.8, 1.4 Hz), 8.55 (2H, br s).

Production Example 121

2-(2-Fluoro-3-thienyl)-1-(4-pyridyl)ethanone

The title compound (304 mg, 63% yield) was obtained in the same manner as Production Example 61 from 912 mg of [(phenylamino)-(4-pyridylmethyl)]phosphonic acid diphenyl ester and 285 mg of 2-fluorothiophene-3-carboxaldehyde.

1H-NMR (400 MHz, CDCl3); δ(ppm) 4.19 (2H, d, J=0.8 Hz), 6.64-6.69 (2H, m), 7.75-7.80 (2H, m), 8.81-8.86 (2H, m).

Production Example 122

2-(Piperidin-4-yl)-3-(2-fluorophenyl)propionitrile hydrochloride

The title compound (746 mg, 76% yield) was obtained in the same manner as Production Example 113 from 1.21 g of 2-[1-(tert-butoxycarbonyl)piperidin-4-yl]-3-(2-fluorophenyl)propionitrile.

1H-NMR (400 MHz, DMSO-d6); δ(ppm) 1.50-1.64 (2H, m), 1.86-1.98 (2H, m), 1.98-2.06 (1H, m), 2.80-2.97 (4H, m), 3.13-3.20 (1H, m), 3.24-3.38 (2H, m), 7.16-7.24 (2H, m), 7.30-7.37 (1H, m), 7.42 (1H, td, J=7.6, 1.6 Hz), 8.47-8.62 (1H, m), 8.97-9.08 (1H, m).

Production Example 123

2-(Piperidin-4-yl)-2-(2-fluorobenzyl)-3-(2-fluorophenyl)propionitrile hydrochloride The title compound (669 mg, 77% yield) was obtained in the same manner as Production Example 113 from 1.02 g of 2-[1-(tert-butoxycarbonyl)piperidin-4-yl]-2-(2-fluorobenzyl)-3-(2-fluorophenyl)propionitrile.

1H-NMR (400 MHz, DMSO-d6); δ(ppm) 1.74-1.88 (3H, m), 1.99-2.07 (2H, m), 2.80-2.93 (4H, m), 3.10 (2H, d, J=14.0 Hz), 3.31-3.42 (2H, m), 7.16-7.25 (4H, m), 7.32-7.40 (4H, m), 8.62-8.78 (1H, m), 8.82-8.96 (1H, m).

Production Example 124

2-(2-Fluorophenyl)-1-(4-methylpiperidin-4-yl)ethanone hydrochloride

The title compound (126 mg, 95% yield) was obtained in the same manner as Production Example 113 from 165 mg of 1-[1-(tert-butoxycarbonyl)-4-methylpiperidin-4-yl]-2-(2-fluorophenyl)ethanone.

1H-NMR (400 MHz, CDCl3); δ(ppm) 1.35 (3H, s), 1.92-2.02 (2H, m), 2.31-2.39 (2H, m), 2.90-3.02 (2H, m), 3.28-3.37 (2H, m), 3.79 (2H, s), 7.01-7.07 (1H, m), 7.09-7.19 (2H, m), 7.24-7.30 (1H, m), 9.40-9.66 (2H, m).

Production Example 125

2-(2-Fluorophenyl)-1-(4-fluoropiperidin-4-yl)ethanone hydrochloride

The title compound (724 mg, 94% yield) was obtained in the same manner as Production Example 113 from 955 mg of 1-[1-(tert-butoxycarbonyl)-4-fluoropiperidin-4-yl]-2-(2-fluorophenyl)ethanone.

1H-NMR (400 MHz, DMSO-d6); δ(ppm) 2.02-2.26 (4H, m), 2.98-3.10 (2H, m), 3.28-3.36 (2H, m), 4.15 (2H, d, J=2.0 Hz), 7.13-7.20 (2H, m), 7.26-7.36 (2H, m), 8.98-9.30 (2H, m).

Production Example 126

1-(4-Fluoropiperidin-4-yl)-2-[2-(trifluoromethyl)phenyl]ethanone hydrochloride

The title compound (667 mg, 98% yield) was obtained in the same manner as Production Example 113 from 0.82 g of 1-[1-(tert-butoxycarbonyl)-4-fluoropiperidin-4-yl]-2-[2-(trifluoromethyl)phenyl]ethanone.

1H-NMR (400 MHz, DMSO-d6); δ(ppm) 2.02-2.22 (4H, m), 3.06 (2H, dt, J=12.4, 4.4 Hz), 3.28-3.37 (2H, m), 4.33 (2H, s), 7.44 (1H, d, J=7.6 Hz), 7.50 (1H, t, J=7.6 Hz), 7.65 (1H, t, J=7.6 Hz), 7.71 (1H, d, J=7.6 Hz), 9.00 (2H, br s).

Production Example 127

1-(4-Methylpiperidin-4-yl)-2-[2-(trifluoromethyl)phenyl]ethanone hydrochloride

The title compound (45 mg, 100% yield) was obtained in the same manner as Production Example 113 from 54 mg of 1-[1-(tert-butoxycarbonyl)-4-methylpiperidin-4-yl]-2-[2-(trifluoromethyl)phenyl]ethanone.

1H-NMR (400 MHz, DMSO-d6); δ(ppm) 1.28 (3H, s), 1.66-1.75 (2H, m), 2.09-2.17 (2H, m), 2.86-2.96 (2H, m), 3.10-3.20 (2H, m), 4.18 (2H, s), 7.38 (1H, d, J=7.6 Hz), 7.47 (1H, t, J=7.6 Hz), 7.62 (1H, t, J=7.6 Hz), 7.69 (1H, d, J=7.6 Hz), 8.64-8.90 (2H, m).

Production Example 128

4-[3-(2-Fluorophenyl)-2-oxopropyl]piperidine hydrochloride

The title compound (1.27 g, 84% yield) was obtained in the same manner as Production Example 113 from 1.86 g of 1-(tert-butoxycarbonyl)-4-[3-(2-fluorophenyl)-2-oxopropyl]piperidine.

1H-NMR (400 MHz, CDCl3); δ(ppm) 1.54-1.66 (2H, m), 1.83-1.91 (2H, m), 2.04-2.17 (1H, m), 2.49 (2H, d, J=6.8 Hz), 2.78-2.91 (2H, m), 3.38-3.46 (2H, m), 3.69 (2H, s), 7.12-7.18 (3H, m), 7.24-7.30 (1H, m), 9.20-9.38 (1H, m), 9.52-9.67 (1H, m).

Production Example 129

1-(Piperidin-4-yl)-3-(2-fluorophenyl)propanone hydrochloride

The title compound (0.52 g, 80% yield) was obtained in the same manner as Production Example 113 from 0.79 g of 1-[1-(tert-butoxycarbonyl)piperidin-4-yl]-3-(2-fluorophenyl)propanone.

1H-NMR (400 MHz, CDCl3); δ(ppm) 1.94-2.04 (2H, m), 2.06-2.15 (2H, m), 2.51-2.59 (1H, m), 2.78 (2H, t, J=7.2 Hz), 2.89-3.02 (4H, m), 3.34-3.43 (2H, m), 6.96-7.06 (2H, m), 7.13-7.21 (2H, m), 9.42 (1H, br s), 9.62 (1H, br s).

Production Example 130

1-(Piperidin-4-yl)-2-[2-(3-pyridyl)phenyl]ethanone

The title compound (239 mg, 85% yield) was obtained in the same manner as Production Example 117 from 379 mg of 1-[1-(tert-butoxycarbonyl)piperidin-4-yl]-2-[2-(3-pyridyl)phenyl]ethanone.

1H-NMR (400 MHz, CDCl3); δ(ppm) 1.36-1.48 (2H, m), 1.58-1.66 (2H, m), 2.29-2.38 (1H, m), 2.48-2.60 (2H, m), 3.03-3.10 (2H, m), 3.72 (2H, s), 7.16-7.42 (5H, m), 7.54-7.58 (1H, m), 8.49 (1H, d, J=1.2 Hz), 8.56-8.62 (1H, m).

Production Example 131

4-[2-(Methoxycarbonyl)phenoxymethyl]piperidine hydrochloride

The title compound (190 mg, 100% yield) was obtained in the same manner as Production Example 113 from 226 mg of 1-(tert-butoxycarbonyl)-4-[2-(methoxycarbonyl)phenoxymethyl]piperidine.

1H-NMR (400 MHz, DMSO-d6); δ(ppm) 1.44-1.57 (2H, m), 1.90-1.98 (2H, m), 2.01-2.22 (1H, m), 2.84-2.97 (2H, m), 3.27-3.35 (2H, m), 3.80 (3H, s), 3.93 (2H, d, J=6.0 Hz), 7.02 (1H, t, J=7.6 Hz), 7.15 (1H, d, J=8.0 Hz), 7.50-7.56 (1H, m), 7.66 (1H, dd, J=7.6, 1.6 Hz), 8.52-8.66 (1H, m), 8.86-9.02 (1H, m).

Production Example 132

4-(2-Acetylphenoxymethyl)piperidine hydrochloride

The title compound (177 mg, 100% yield) was obtained in the same manner as Production Example 113 from 220 mg of 1-(tert-butoxycarbonyl)-4-(2-acetylphenoxymethyl)piperidine.

1H-NMR (400 MHz, DMSO-d6); δ(ppm) 1.51-1.63 (2H, m), 1.89-1.97 (2H, m), 2.07-2.19 (1H, m), 2.56 (3H, s), 2.85-2.97 (2H, m), 3.26-3.34 (2H, m), 4.00 (2H, d, J=6.0 Hz), 7.02 (1H, dt, J=7.6, 0.8 Hz), 7.17 (1H, d, J=8.0 Hz), 7.50-7.55 (1H, m), 7.57 (1H, dd, J=7.6, 2.0 Hz), 8.50-8.85 (1H, m), 8.94-9.08 (1H, m).

Production Example 133

4-(2-Carbamoylphenoxymethyl)piperidine

The title compound (105 mg, 91% yield) was obtained in the same manner as Production Example 117 from 165 mg of 1-(tert-butoxycarbonyl)-4-(2-carbamoylphenoxymethyl)piperidine.

1H-NMR (400 MHz, CDCl3); δ(ppm) 1.28-1.40 (2H, m), 1.76-1.86 (2H, m), 1.95-2.07 (1H, m), 2.62-2.73 (2H, m), 3.11-3.19 (2H, m), 3.98 (2H, d, J=6.4 Hz), 5.97 (1H, br s), 6.98 (1H, d, J=8.8 Hz), 7.03-7.12 (1H, m), 7.42-7.49 (1H, m), 7.76 (1H, br s), 8.20 (1H, dd, J=8.0, 1.6 Hz).

Production Example 134

4-(2-Nitrophenoxymethyl)piperidine hydrochloride

The title compound (132 mg, 85% yield) was obtained in the same manner as Production Example 113 from 191 mg of 1-(tert-butoxycarbonyl)-4-(2-nitrophenoxymethyl)piperidine.

1H-NMR (400 MHz, DMSO-d6); δ(ppm) 1.44-1.57 (2H, m), 1.86-1.94 (2H, m), 2.02-2.15 (1H, m), 2.84-2.96 (2H, m), 3.26-3.34 (2H, m), 4.06 (2H, d, J=6.4 Hz), 7.09-7.15 (1H, m), 7.37 (1H, d, J=7.6 Hz), 7.63-7.69 (1H, m), 7.87 (1H, dd, J=8.0, 1.6 Hz), 8.51-8.66 (1H, m), 8.89-9.04 (1H, m).

Production Example 135

4-[2-(Acetylamino)phenoxymethyl]piperidine hydrochloride

The title compound (379 mg, 100% yield) was obtained in the same manner as Production Example 113 from 459 mg of 1-(tert-butoxycarbonyl)-4-[2-(acetylamino)phenoxymethyl]piperidine.

1H-NMR (400 MHz, DMSO-d6); δ(ppm) 1.52-1.64 (2H, m), 1.91-1.99 (2H, m), 2.03-2.16 (4H, m), 2.82-2.94 (2H, m), 3.25-3.34 (2H, m), 3.90 (2H, d, J=6.4 Hz), 6.85-6.92 (1H, m), 6.99-7.10 (2H, m), 7.83 (1H, d, J=7.6 Hz), 8.80-9.02 (3H, m).

Production Example 136

4-[2-(Methanesulfonylamino)phenoxymethyl]piperidine

The title compound (271 mg, 80% yield) was obtained in the same manner as Production Example 117 from 447 mg of 1-(tert-butoxycarbonyl)-4-[2-(methanesulfonylamino)phenoxymethyl]piperidine.

1H-NMR (400 MHz, CDCl3); δ(ppm) 1.23-1.34 (2H, m), 1.77-1.84 (2H, m), 1.90-2.03 (1H, m), 2.63-2.71 (2H, m), 2.96 (3H, s), 3.10-3.16 (2H, m), 3.86 (2H, d, J=6.4 Hz), 6.90 (1H, dd, J=8.0, 1.2 Hz), 6.97 (1H, dt, J=8.0, 1.2 Hz), 7.09-7.15 (1H, m), 7.65 (1H, dd, J=7.6, 1.2 Hz).

Production Example 137

4-[2-(Dimethylamino)phenoxymethyl]piperidine

The title compound (277 mg, 91% yield) was obtained in the same manner as Production Example 117 from 447 mg of 1-(tert-butoxycarbonyl)-4-[2-(dimethylamino)phenoxymethyl]piperidine.

1H-NMR (400 MHz, CDCl3); δ(ppm) 1.33-1.46 (2H, m), 1.85-2.15 (3H, m), 2.67-2.75 (2H, m), 2.80 (6H, s), 3.18-3.24 (2H, m), 3.85 (2H, d, J=6.8 Hz), 6.82-6.96 (4H, m).

Production Example 138

4-[2-(3-Methylthioureido)phenoxymethyl]piperidine hydrochloride

The title compound (430 mg, 100% yield) was obtained in the same manner as Production Example 113 from 537 mg of 1-(tert-butoxycarbonyl)-4-[2-(3-methylthioureido)phenoxymethyl]piperidine.

1H-NMR (400 MHz, DMSO-d6); δ(ppm) 1.55-1.68 (2H, m), 1.88-1.96 (2H, m), 2.01-2.13 (1H, m), 2.83-2.95 (5H, m), 3.26-3.34 (2H, m), 3.88 (2H, d, J=6.0 Hz), 6.88-6.94 (1H, m), 7.02-7.06 (1H, m), 7.09-7.16 (1H, m), 7.68-7.78 (1H, m), 8.21 (1H, br s), 8.68-8.95 (3H, m).

Production Example 139

4-[2-(3-Methylureido)phenoxymethyl]piperidine

The title compound (320 mg, 94% yield) was obtained in the same manner as Production Example 117 from 469 mg of 1-(tert-butoxycarbonyl)-4-[2-(3-methylureido)phenoxymethyl]piperidine.

1H-NMR (400 MHz, CDCl3); δ(ppm) 1.44-1.57 (2H, m), 1.72-1.79 (2H, m), 1.87-1.99 (1H, m), 2.61-2.70 (2H, m), 2.84 (3H, d, J=4.4 Hz), 3.11-3.20 (2H, m), 3.86 (2H, d, J=5.6 Hz), 5.33 (1H, br s), 6.68-6.99 (4H, m), 8.01 (1H, dd, J=7.2, 2.0 Hz).

Production Example 140 cis-3-(2-Fluorophenoxymethyl)-4-hydroxypiperidine

After dissolving 402 mg of cis-1-benzyl-3-(2-fluorophenoxymethyl)-4-hydroxypiperidine in 20 ml of ethanol, 0.2 g of 20% palladium hydroxide-carbon (hydrous) was added and the mixture was stirred at room temperature under a hydrogen atmosphere (1 atm). The mixture was further stirred for 5.5 hours, and then ethyl acetate was added thereto and the insoluble portion was filtered off. The filtrate was distilled off under reduced pressure to obtain the title compound (276 mg, 94% yield).

1H-NMR (400 MHz, CDCl3); δ(ppm) 1.70-1.79 (2H, m), 2.15-2.24 (1H, m), 2.80 (1H, dt, J=8.8, 4.4 Hz), 2.87 (1H, dd, J=12.0, 4.4 Hz), 2.94-3.10 (2H, m), 4.07 (1H, dd, J=9.6, 6.4 Hz), 4.16 (1H, dd, J=9.2, 6.4 Hz), 4.20-4.25 (1H, m), 6.85-6.92 (1H, m), 6.95-7.09 (3H, m).

Production Example 141 trans-3-(2-Fluorophenoxymethyl)-4-hydroxypiperidine

The title compound (203 mg, 90% yield) was obtained in the same manner as Production Example 140 from 326 mg of trans-1-benzyl-3-(2-fluorophenoxymethyl)-4-hydroxypiperidine.

1H-NMR (400 MHz, CDCl3); δ(ppm) 1.43-1.54 (1H, m), 1.89-2.10 (2H, m), 2.49 (1H, dd, J=12.8, 11.2 Hz), 2.64 (1H, dd, J=12.8, 2.8 Hz), 2.99-3.16 (1H, m), 3.22 (1H, ddd, J=12.8, 4.4, 1.6 Hz), 3.69 (1H, dt, J=10.4, 4.4 Hz), 4.12 (2H, d, J=6.0 Hz), 6.86-6.93 (1H, m), 6.98 (1H, dt, J=8.4, 1.6 Hz), 7.01-7.09 (2H, m).

Production Example 142

1-(1-Benzylpiperidin-4-yl)-2-(3-methyl-2-thienyl)ethanone

The title compound (858 mg, 76% yield) was obtained in the same manner as Production Example 140 from 1.12 g of 1-(1-benzyl-1,2,3,6-tetrahydropyridin-4-yl)-2-(3-methyl-2-thienyl)ethanone.

1H-NMR (400 MHz, CDCl3); δ(ppm) 1.67-1.83 (4H, m), 1.95-2.03 (2H, m), 2.12 (3H, s), 2.41-2.49 (1H, m), 2.87-2.93 (2H, m), 3.48 (2H, s), 3.81 (2H, s), 6.80 (1H, d, J=5.2 Hz), 7.09 (1H, d, J=5.2 Hz), 7.20-7.33 (5H, m).

Production Example 143

1-(tert-Butoxycarbonyl)-4-(2-aminophenoxymethyl)piperidine

The title compound (4.28 g, 88% yield) was obtained in the same manner as Production Example 140 from 5.34 g of 1-(tert-butoxycarbonyl)-4-(2-nitrophenoxymethyl)piperidine.

1H-NMR (400 MHz, CDCl3); δ(ppm) 1.24-1.36 (2H, m), 1.47 (9H, s), 1.79-1.86 (2H, m), 1.94-2.06 (1H, m), 2.68-2.84 (2H, m), 3.77 (2H, br s), 3.85 (2H, d, J=6.0 Hz), 4.06-4.26 (2H, m), 6.68-6.82 (4H, m).

Production Example 144

1-(1-Benzylpiperidin-4-yl)-2-(4-fluoro-3-thienyl)ethanone

The title compound (1.26 g, 78% yield) was obtained in the same manner as Production Example 140 from 1.61 g of 1-(1-benzyl-1,2,3,6-tetrahydropyridin-4-yl)-2-(4-fluoro-3-thienyl)ethanone.

1H-NMR (400 MHz, CDCl3); δ(ppm) 1.67-1.78 (2H, m), 1.80-1.87 (2H, m), 1.97-2.05 (2H, m), 2.38-2.47 (1H, m), 2.88-2.95 (2H, m), 3.50 (2H, s), 3.76 (2H, s), 6.70 (1H, d, J=3.6 Hz), 7.01-7.05 (1H, m), 7.22-7.35 (5H, m).

Production Example 145

1-(1-Benzylpiperidin-4-yl)-2-(2,3-dihydrobenzofuran-7-yl)ethanone

The title compound (159 mg, 15% yield) was obtained in the same manner as Production Example 16 from 935 mg of 2,3-dihydrobenzofuran-7-carboxaldehyde and 641 mg of 1-benzylpiperidine-4-carboxaldehyde.

1H-NMR (400 MHz, CDCl3); δ(ppm) 1.66-1.78 (2H, m), 1.78-1.87 (2H, m), 1.95-2.03 (2H, m), 2.40-2.48 (1H, m), 2.87-2.93 (2H, m), 3.21 (2H, t, J=8.8 Hz), 3.49 (2H, s), 3.68 (2H, s), 4.53 (2H, t, J=8.8 Hz), 6.79 (1H, t, J=7.4 Hz), 6.91 (1H, d, J=7.4 Hz), 7.09 (1H, dd, J=7.4, 1.2 Hz), 7.21-7.36 (5H, m).

Production Example 146

1-(1-Benzylpiperidin-4-yl)-2-[2-(methylthio)phenyl]ethanone

The title compound (768 mg, 29% yield) was obtained in the same manner as Production Example 16 from 2.40 g of 2-(methylthio)benzaldehyde and 1.60 g of 1-benzylpiperidine-4-carboxaldehyde.

1H-NMR (400 MHz, CDCl3); δ(ppm) 1.71-1.82 (2H, m), 1.82-1.91 (2H, m), 1.97-2.05 (2H, m), 2.42 (3H, s), 2.42-2.53 (1H, m), 2.88-2.96 (2H, m), 3.50 (2H, s), 3.89 (2H, s), 7.08-7.17 (2H, m), 7.22-7.36 (7H, m).

Production Example 147

1-(1-Benzylpiperidin-4-yl)-2-[2-(trifluoromethyl)phenyl]ethanone

After dissolving 2.57 g of 2-(trifluoromethyl)benzaldehyde in 15 ml of methanol, 2.75 g of p-toluenesulfonyl hydrazide was added, the mixture was stirred at room temperature for 2 hours, and then 1.09 g of potassium methoxide and a methanol solution (4 ml) of 1.50 g of 1-benzylpiperidine-4-carboxaldehyde was added, and the mixture was shielded from light and stirred overnight at 55° C. The reaction solution was concentrated under reduced pressure, water was added, and extraction was performed with ethyl acetate. The organic layer was washed with saturated brine and dried over anhydrous magnesium sulfate, and then the solvent was distilled off under reduced pressure. The residue was purified by silica gel column chromatography (solvent: toluene/ethyl acetate) to obtain the title compound (1.30 g, 49% yield).

1H-NMR (400 MHz, CDCl3); δ(ppm) 1.69-1.81 (2H, m), 1.82-1.90 (2H, m), 1.98-2.06 (2H, m), 2.41-2.49 (1H, m), 2.89-2.96 (2H, m), 3.50 (2H, s), 3.95 (2H, d, J=0.8 Hz), 7.14-7.38 (7H, m), 7.49 (1H, t, J=7.6 Hz), 7.63 (1H, d, J=7.6 Hz).

Production Example 148

1-(1-Benzylpiperidin-4-yl)-2-[2-(trifluoromethoxy)phenyl]ethanone

The title compound (1.12 g, 40% yield) was obtained in the same manner as Production Example 16 from 2.81 g of 2-(trifluoromethoxy)benzaldehyde and 1.50 g of 1-benzylpiperidine-4-carboxaldehyde.

1H-NMR (400 MHz, CDCl3); δ(ppm) 1.69-1.81 (2H, m), 1.81-1.90 (2H, m), 1.97-2.06 (2H, m), 2.39-2.48 (1H, m), 2.89-2.96 (2H, m), 3.50 (2H, s), 3.80 (2H, s), 7.15-7.33 (9H, m).

Production Example 149

1-(1-Benzylpiperidin-4-yl)-2-(2-ethoxyphenyl)ethanone

The title compound (581 mg, 23% yield) was obtained in the same manner as Production Example 16 from 3.33 g of 2-ethoxybenzaldehyde and 1.50 g of 1-benzylpiperidine-4-carboxaldehyde.
1H-NMR (400 MHz, CDCl3); δ(ppm) 1.35 (3H, t, J=7.0 Hz), 1.67-1.86 (4H, m), 1.94-2.02 (2H, m), 2.40-2.48 (1H, m), 2.86-2.92 (2H, m), 3.48 (2H, s), 3.70 (2H, s), 3.99 (2H, q, J=7.0 Hz), 6.82 (1H, d, J=7.6 Hz), 6.88 (1H, td, J=7.6, 1.2 Hz), 7.08 (1H, dd, J=7.6, 2.0 Hz), 7.17-7.34 (6H, m).

Production Example 150

1-(1-Benzylpiperidin-4-yl)-2-(2-n-propoxyphenyl)ethanone

The title compound (799 mg, 31% yield) was obtained in the same manner as Production Example 16 from 3.64 g of 2-n-propoxybenzaldehyde and 1.50 g of 1-benzylpiperidine-4-carboxaldehyde.
1H-NMR (400 MHz, CDCl3); δ(ppm) 1.00 (3H, t, J=7.4 Hz), 1.67-1.85 (6H, m), 1.93-2.02 (2H, m), 2.48-2.57 (1H, m), 2.86-2.93 (2H, m), 3.48 (2H, s), 3.71 (2H, s), 3.88 (2H, t, J=6.6 Hz), 6.82 (1H, d, J=7.6 Hz), 6.87 (1H, td, J=7.6, 0.8 Hz), 7.06-7.32 (7H, m).

Production Example 151

1-(1-Benzylpiperidin-4-yl)-2-(1-naphthyl)ethanone

The title compound (1.09 g, 43% yield) was obtained in the same manner as Production Example 16 from 2.31 g of 1-naphthylcarboxaldehyde and 1.50 g of 1-benzylpiperidine-4-carboxaldehyde.
1H-NMR (400 MHz, CDCl3); δ(ppm) 1.72-1.80 (4H, m), 1.88-1.96 (2H, m), 2.42-2.51 (1H, m), 2.84-2.90 (2H, m), 3.46 (2H, s), 4.16 (2H, s), 7.14-7.34 (5H, m), 7.38-7.50 (4H, m), 7.75-7.86 (3H, m).

Production Example 152

1-(1-Benzylpiperidin-4-yl)-2-(2-biphenyl)ethanone

The title compound (1.45 g, 48% yield) was obtained in the same manner as Production Example 16 from 3.00 g of 2-biphenylcarboxaldehyde and 1.67 g of 1-benzylpiperidine-4-carboxaldehyde.
1H-NMR (400 MHz, CDCl3); δ(ppm) 1.51-1.62 (4H, m), 1.84-1.92 (2H, m), 2.10-2.19 (1H, m), 2.77-2.84 (2H, m), 3.44 (2H, s), 3.71 (2H, s), 7.14-7.40 (14H, m).

Production Example 153

1-(1-Benzylpiperidin-4-yl)-2-(2-bromophenyl)ethanone

The title compound (1.63 g, 44% yield) was obtained in the same manner as Production Example 16 from 3.65 g of 2-bromobenzaldehyde and 2.0 g of 1-benzylpiperidine-4-carboxaldehyde.
1H-NMR (400 MHz, CDCl3); δ(ppm) 1.72-1.83 (2H, m), 1.84-1.92 (2H, m), 1.98-2.06 (2H, m), 2.43-2.52 (1H, m), 2.89-2.96 (2H, m), 3.50 (2H, s), 3.90 (2H, s), 7.09-7.32 (8H, m), 7.54 (1H, dd, J=8.0, 1.2 Hz).

Production Example 154

1-(1-Benzylpiperidin-4-yl)-2-(3-pyridyl)ethanone

The title compound (925 mg, 43% yield) was obtained in the same manner as Production Example 16 from 1.59 g of 3-pyridinecarboxaldehyde and 1.50 g of 1-benzylpiperidine-4-carboxaldehyde.
1H-NMR (400 MHz, CDCl3); δ(ppm) 1.62-1.79 (2H, m), 1.80-1.88 (2H, m), 1.96-2.06 (2H, m), 2.39-2.48 (1H, m), 2.88-2.95 (2H, m), 3.50 (2H, s), 3.74 (2H, s), 7.21-7.33 (6H, m), 7.51 (1H, ddd, J=7.8, 2.4, 1.8 Hz), 8.40 (1H, dd, J=2.4, 0.8 Hz), 8.49 (1H, dd, J=5.0, 1.8 Hz).

Production Example 155

1-[1-(tert-Butoxycarbonyl)-4-fluoropiperidin-4-yl]-2-[2-(trifluoromethyl)phenyl]ethanone The title compound (0.82 g, 27% yield) was obtained in the same manner as Production Example 16 from 2.68 g of 2-(trifluoromethyl)benzaldehyde and 1.73 g of 1-(tert-butoxycarbonyl)-4-fluoropiperidine-4-carboxaldehyde.
1H-NMR (400 MHz, CDCl3); δ(ppm) 1.46 (9H, s), 1.79-2.03 (4H, m), 3.04-3.18 (2H, m), 3.96-4.15 (2H, m), 4.20 (2H, s), 7.20 (1H, d, J=7.6 Hz), 7.36-7.42 (1H, m), 7.51 (1H, dt, J=7.6, 0.8 Hz), 7.64 (1H, d, J=7.6 Hz).

Production Example 156

1-[1-(tert-Butoxycarbonyl)-4-methylpiperidin-4-yl]-2-[2-(trifluoromethyl)phenyl]ethanone The title compound (54 mg, 2% yield) was obtained in the same manner as Production Example 16 from 2.68 g of 2-(trifluoromethyl)benzaldehyde and 1.74 g of 1-(tert-butoxycarbonyl)-4-methylpiperidine-4-carboxaldehyde [CAS No. 189442-92-0].
1H-NMR (400 MHz, CDCl3); δ(ppm) 1.28 (3H, s), 1.41-1.56 (2H, m), 1.46 (9H, s), 2.01-2.09 (2H, m), 3.21-3.30 (2H, m), 3.51-3.63 (2H, m), 4.01 (2H, s), 7.16 (1H, d, J=7.6 Hz), 7.37 (1H, t, J=7.6 Hz), 7.50 (1H, t, J=7.6 Hz), 7.65 (1H, d, J=7.6 Hz).

Production Example 157

1-(1-Benzylpiperidin-4-yl)-2-[2-fluoro-6-(trifluoromethyl)phenyl]ethanone

The title compound (136 mg, 3% yield) was obtained in the same manner as Production Example 16 from 4.72 g of 2-fluoro-6-(trifluoromethyl)benzaldehyde and 2.50 g of 1-benzylpiperidine-4-carboxaldehyde.
1H-NMR (400 MHz, CDCl3); δ(ppm) 1.72-1.84 (2H, m), 1.85-1.94 (2H, m), 2.00-2.09 (2H, m), 2.44-2.52 (1H, m), 2.91-2.97 (2H, m), 3.51 (2H, s), 3.98 (2H, s), 7.21-7.44 (8H, m).

Production Example 158

1-(tert-Butoxycarbonyl)-4-(2-fluorobenzylsulfonyl) piperidine

After dissolving 695 mg of 1-(tert-butoxycarbonyl)-4-(2-fluorobenzylthio)piperidine in 7 ml of chloroform, 1.13 g of 3-chloroperbenzoic acid was added while cooling on ice, and the mixture was stirred for 30 minutes. Aqueous sodium thiosulfate solution was added to the reaction solution, and extraction was performed with chloroform. The organic layer was washed with saturated brine and dried over anhydrous magnesium sulfate, and then the solvent was distilled off under reduced pressure. The residue was purified by NH silica gel column chromatography (solvent: n-hexane/ethyl acetate) to obtain the title compound (690 mg, 90% yield).

1H-NMR (400 MHz, CDCl3); δ(ppm) 1.45 (9H, s), 1.71-1.84 (2H, m), 2.03-2.11 (2H, m), 2.63-2.78 (2H, m), 2.86-2.95 (1H, m), 4.18-4.33 (2H, m), 4.29 (2H, s), 7.12 (1H, ddd, J=9.6, 8.0, 1.2 Hz), 7.21 (1H, td, J=8.0, 1.2 Hz), 7.36-7.42 (1H, m), 7.52 (1H, td, J=8.0, 2.0 Hz).

Production Example 159

1-(tert-Butoxycarbonyl)-4-[(2-fluorophenylsulfinyl) methyl]piperidine

After dissolving 79 mg of 1-(tert-butoxycarbonyl)-4-[(2-fluorophenylthio)methyl]piperidine in 3 ml of chloroform, 42 mg of 3-chloroperbenzoic acid was added while cooling on ice, and the mixture was stirred for 30 minutes. Aqueous sodium thiosulfate solution was added to the reaction solution, and extraction was performed with ethyl acetate. The organic layer was washed with saturated brine and dried over anhydrous magnesium sulfate, and then the solvent was distilled off under reduced pressure. The residue was purified by NH silica gel column chromatography (solvent: n-hexane/ethyl acetate) to obtain the title compound (68 mg, 82% yield).

1H-NMR (400 MHz, CDCl3); δ(ppm) 1.23-1.40 (2H, m), 1.45 (9H, s), 1.65-1.73 (1H, m), 2.07-2.27 (2H, m), 2.70-2.88 (4H, m), 4.04-4.22 (2H, m), 7.11 (1H, ddd, J=9.6, 7.6, 1.0 Hz), 7.38 (1H, td, J=7.6, 1.0 Hz), 7.45-7.52 (1H, m), 7.84 (1H, td, J=7.6, 2.0 Hz).

Production Example 160

1-(tert-Butoxycarbonyl)-4-[(2-fluorophenylsulfonyl) methyl]piperidine

The title compound (52 mg, 78% yield) was obtained in the same manner as Production Example 158 from 61 mg of 1-(tert-butoxycarbonyl)-4-[(2-fluorophenylthio)methyl]piperidine.

1H-NMR (400 MHz, CDCl3); δ(ppm) 1.22-1.35 (2H, m), 1.44 (9H, s), 1.82-1.92 (2H, m), 2.17-2.28 (1H, m), 2.67-2.80 (2H, m), 3.23 (2H, d, J=6.4 Hz), 3.98-4.13 (2H, m), 7.21-7.28 (1H, m), 7.34 (1H, td, J=8.0, 1.2 Hz), 7.62-7.69 (1H, m), 7.94 (1H, ddd, J=8.4, 8.0, 1.8 Hz).

Production Example 161

1-[1-(tert-Butoxycarbonyl)piperidin-4-yl]-2-[2-(methylsulfonyl)phenyl]ethanone

The title compound (217 mg, 82% yield) was obtained in the same manner as Production Example 158 from 244 mg of 1-[1-(tert-butoxycarbonyl)piperidin-4-yl]-2-[2-(methylthio)phenyl]ethanone.

1H-NMR (400 MHz, CDCl3); δ(ppm) 1.46 (9H, s), 1.55-1.67 (2H, m), 1.89-1.98 (2H, m), 2.67-2.75 (1H, m), 2.75-2.87 (2H, m), 3.01 (3H, s), 4.08-4.21 (2H, m), 4.34 (2H, br s), 7.18 (1H, dd, J=7.6, 1.2 Hz), 7.48 (1H, td, J=7.6, 1.2 Hz), 7.57 (1H, td, J=7.6, 1.6 Hz), 8.01 (1H, dd, J=7.6, 1.6 Hz).

Production Example 162

4-(2-Fluorobenzylthio)piperidine hydrochloride

The title compound (227 mg, 69% yield) was obtained in the same manner as Production Example 113 from 406 mg of 1-(tert-butoxycarbonyl)-4-(2-fluorobenzylthio)piperidine.

1H-NMR (400 MHz, DMSO-d6); δ(ppm) 1.59-1.71 (2H, m), 2.02-2.10 (2H, m), 2.85-2.96 (3H, m), 3.18-3.25 (2H, m), 3.83 (2H, s), 7.14-7.22 (2H, m), 7.29-7.35 (1H, m), 7.43 (1H, td, J=7.8, 2.0 Hz).

Production Example 163

1-Benzyl-4-[2-(2-fluorophenyl)ethyl]-3-methoxy-1, 2,5,6-tetrahydropyridine

After dissolving 1.12 g of 4-[2-(2-fluorophenyl)ethyl]-3-methoxypyridine in 10 ml of acetonitrile, 0.63 ml of benzyl bromide was added, the mixture was stirred for 2 hours at 50° C., and the solvent was distilled off under reduced pressure. The residue was dissolved in 20 ml of methanol, and then 552 mg of sodium borohydride was added while cooling on ice and the mixture was stirred for 1 hour. Water was added to the reaction solution, and extraction was performed with ethyl acetate. The organic layer was washed with saturated brine, dried over anhydrous magnesium sulfate, and filtered with NH silica gel. The solvent was distilled off under reduced pressure to obtain the title compound (1.26 g, 80% yield).

1H-NMR (400 MHz, CDCl3); δ(ppm) 2.10-2.16 (2H, m), 2.37 (2H, t, J=8.0 Hz), 2.52 (2H, t, J=5.6 Hz), 2.71 (2H, t, J=8.0 Hz), 2.99 (2H, br s), 3.36 (3H, s), 3.60 (2H, s), 6.98 (1H, ddd, J=9.6, 7.6, 1.2 Hz), 7.03 (1H, td, J=7.6, 1.2 Hz), 7.10-7.17 (1H, m), 7.19 (1H, td, J=7.6, 2.0 Hz), 7.23-7.36 (5H, m).

Production Example 164

1-(1-Benzyl-1,2,3,6-tetrahydropyridin-4-yl)-2-(3-methyl-2-thienyl)ethanol

After dissolving 2.72 g of 2-(3-methyl-2-thienyl)-1-(4-pyridyl)ethanone in 15 ml of toluene, 1.79 ml of benzyl bromide was added, the mixture was stirred for 7 hours at 110° C. and the precipitate was filtered out. The filtered substance was dissolved in 60 ml of methanol, 1.42 g of sodium borohydride was added in small portions at a time while cooling on ice, and the mixture was stirred for 1 hour. The reaction solution was distilled off under reduced pressure, water was added, and extraction was performed with ethyl acetate. The organic layer was washed with water and saturated brine and dried over anhydrous magnesium sulfate, and then the solvent was distilled off under reduced pressure. The residue was purified by silica gel column chromatography (solvent: n-hexane/ethyl acetate) to obtain the title compound (2.85 g, 73% yield).

1H-NMR (400 MHz, CDCl3); δ(ppm) 2.14-2.30 (2H, m), 2.18 (3H, s), 2.54-2.65 (2H, m), 2.89-3.06 (4H, m), 3.58 (2H, s), 4.19 (1H, dd, J=8.4, 4.4 Hz), 5.66 (1H, d, J=0.8 Hz), 6.79 (1H, d, J=5.2 Hz), 7.06 (1H, d, J=5.2 Hz), 7.22-7.36 (5H, m).

Production Example 165

1-(1-Benzyl-1,2,3,6-tetrahydropyridin-4-yl)-2-(4-fluoro-3-thienyl)ethanol

The title compound (4.17 g, 79% yield) was obtained in the same manner as Production Example 164 from 3.66 g of 2-(4-fluoro-3-thienyl)-1-(4-pyridyl)ethanone and 2.36 ml of benzyl bromide.

1H-NMR (400 MHz, CDCl3); δ(ppm) 2.12-2.30 (2H, m), 2.56-2.64 (2H, m), 2.73 (1H, dd, J=14.4, 8.4 Hz), 2.82 (1H, dd, J=14.4, 4.4 Hz), 2.96-3.02 (2H, m), 3.58 (2H, s), 4.24 (1H, dd, J=8.0, 4.4 Hz), 5.60-5.66 (1H, m), 6.67 (1H, d, J=4.0 Hz), 6.98 (1H, t, J=4.0 Hz), 7.22-7.36 (5H, m).

Production Example 166

1-(1-Benzyl-1,2,3,6-tetrahydropyridin-4-yl)-2-(3-methyl-2-thienyl)ethanone

The title compound (1.12 g, 40% yield) was obtained in the same manner as Production Example 15 from 2.85 g of 1-(1-benzyl-1,2,3,6-tetrahydropyridin-4-yl)-2-(3-methyl-2-thienyl)ethanol.

1H-NMR (400 MHz, CDCl3); δ(ppm) 2.13 (3H, s), 2.39-2.45 (2H, m), 2.61 (2H, t, J=6.0 Hz), 3.19-3.23 (2H, m), 3.62 (2H, s), 4.04 (2H, s), 6.79 (1H, d, J=5.2 Hz), 6.88-6.91 (1H, m), 7.08 (1H, d, J=5.2 Hz), 7.23-7.34 (5H, m).

Production Example 167

1-(1-Benzyl-1,2,3,6-tetrahydropyridin-4-yl)-2-(4-fluoro-3-thienyl)ethanone

The title compound (1.61 g, 39% yield) was obtained in the same manner as Production Example 15 from 4.17 g of 1-(1-benzyl-1,2,3,6-tetrahydropyridin-4-yl)-2-(4-fluoro-3-thienyl)ethanol.

1H-NMR (400 MHz, CDCl3); δ(ppm) 2.39-2.45 (2H, m), 2.61 (2H, t, J=5.6 Hz), 3.19-3.23 (2H, m), 3.63 (2H, s), 3.87 (2H, s), 6.69 (1H, d, J=3.6 Hz), 6.87-6.91 (1H, m), 6.99-7.03 (1H, m), 7.25-7.36 (5H, m).

Production Example 168

(1-Benzylpiperidin-4-yl)-(1,3-dihydroisobenzofuran-1-yl)methanone

After dissolving 591 mg of 1,3-dihydroisobenzofuran in 10 ml of tetrahydrofuran, 3.9 ml of n-butyllithium (1.5 M, n-hexane solution) was added thereto at −70° C. under a nitrogen atmosphere, the mixture was stirred for 1 hour, and then a solution of 1 g of 1-benzylpiperidine-4-carboxaldehyde in tetrahydrofuran (5 ml) was added dropwise and the mixture was stirred for 1 hour. Water was added to the reaction solution, extraction was performed with ethyl acetate, the extract was dried over anhydrous magnesium sulfate, and then the solvent was distilled off under reduced pressure. Purification was performed by silica gel column chromatography (solvent: n-hexane/ethyl acetate) to obtain 597 mg of (1-benzylpiperidin-4-yl)-(1,3-dihydroisobenzofuran-1-yl)methanol.

After adding 0.511 ml of dimethylsulfoxide dropwise to a dichloromethane solution (15 ml) containing 0.315 ml of oxalyl chloride at −70° C., the mixture was stirred for 10 minutes, a solution of 597 mg of (1-benzylpiperidin-4-yl)-(1,3-dihydroisobenzofuran-1-yl)methanol in dichloromethane (5 ml) was added dropwise, and stirring was continued for 1 hour. Next, 2.5 ml of triethylamine was added dropwise to the reaction solution, the cooling bath was removed, and the mixture was stirred at room temperature. Water was added to the reaction solution, and extraction was performed with ethyl acetate. After drying over anhydrous magnesium sulfate, the solvent was distilled off under reduced pressure to obtain the title compound (517 mg, 33% yield).

1H-NMR (400 MHz, CDCl3); δ (ppm) 1.34-2.07 (6H, m), 2.76-2.94 (3H, m), 3.43-3.51 (2H, m), 5.23-5.34 (2H, m), 5.53-5.56 (1H, m), 7.22-7.35 (9H, m).

Production Example 169

1-(tert-Butoxycarbonyl)-4-methyl-4-(methanesulfonyloxymethyl)piperidine

The title compound (3.61 g, 98% yield) was obtained in the same manner as Example 38 from 2.74 g of 1-(tert-butoxycarbonyl)-4-fluoro-4-(hydroxymethyl)piperidine.

1H-NMR (400 MHz, CDCl3); δ (ppm) 1.07 (3H, s), 1.33-1.40 (2H, m), 1.43-1.54 (11H, m), 3.02 (3H, s), 3.11-3.19 (2H, m), 3.64-3.73 (2H, m), 3.95 (2H, s).

Production Example 170

1-(tert-Butoxycarbonyl)-4-(2-fluorophenoxymethyl)-4-methylpiperidine

The title compound (243 mg, 59% yield) was obtained in the same manner as Production Example 41 from 100 mg of 2-fluorophenol and 394 mg of 1-(tert-butoxycarbonyl)-4-(methanesulfonyloxymethyl)-4-methylpiperidine.

1H-NMR (400 MHz, CDCl3); δ (ppm) 1.14 (3H, s), 1.17-1.30 (2H, m), 1.46 (9H, s), 1.53-1.67 (2H, m), 3.15-3.25 (2H, m), 3.64-3.75 (2H, m), 3.73 (2H, s), 6.85-6.97 (2H, m), 7.01-7.09 (2H, m).

Production Example 171 trans-1-[1-(Benzyloxycarbonyl)-2-methylpiperidin-4-yl]-(2-fluorophenyl)ethanone

The title compound (0.79 g, 27% yield) was obtained in the same manner as Production Example 26 from 2.00 g of trans-1-(benzyloxycarbonyl)-2-methylpiperidine-4-carbonitrile and 2.48 g of 2-fluorobenzyl chloride.

1H-NMR (400 MHz, CDCl3); δ(ppm) 1.17 (3H, d, J=6.8 Hz), 1.48-1.60 (1H, m), 1.67-1.88 (3H, m), 2.77-2.88 (1H, m), 2.88-3.00 (1H, m), 3.78 (2H, s), 4.05-4.24 (1H, m), 4.52-4.68 (1H, m), 5.12 (2H, s), 7.02-7.18 (3H, m), 7.24-7.40 (6H, m).

Production Example 172 cis-1-(1-Benzyl-2-methylpiperidin-4-yl)-2-(2-fluorophenyl)ethanone

The title compound (373 mg, 44% yield) was obtained in the same manner as Production Example 26 from 563 mg of cis-1-benzyl-2-methylpiperidine-4-carbonitrile and 1.90 g of 2-fluorobenzyl chloride.

1H-NMR (400 MHz, CDCl3); δ(ppm) 1.25 (3H, d, J=6.8 Hz), 1.46-1.67 (2H, m), 1.72-2.00 (3H, m), 2.22-2.32 (1H, m), 2.45-2.57 (1H, m), 2.84-2.93 (1H, m), 3.11 (1H, d, J=14.1 Hz), 3.74 (2H, s), 4.11 (1H, d, J=14.1 Hz), 6.99-7.39 (9H, m).

Production Example 173 trans-1-(2-Methylpiperidin-4-yl)-2-(2-fluorophenyl)ethanone

The title compound (547 mg, 100% yield) was obtained in the same manner as Production Example 140 from 0.79 g of trans-1-[1-(benzyloxycarbonyl)-2-methylpiperidin-4-yl]-(2-fluorophenyl)ethanone.

1H-NMR (400 MHz, CDCl3); δ(ppm) 1.07 (3H, d, J=6.8 Hz), 1.39-1.48 (1H, m), 1.67-1.91 (2H, m), 1.94-2.07 (2H, m), 2.79-2.96 (4H, m), 3.79 (2H, s), 7.01-7.12 (2H, m), 7.14-7.20 (1H, m), 7.22-7.28 (1H, m).

Production Example 174 cis-1-(2-Methylpiperidin-4-yl)-2-(2-fluorophenyl)ethanone hydrochloride

The title compound (208 mg, 69% yield) was obtained in the same manner as Production Example 29 from 373 mg of cis-1-(1-benzyl-2-methylpiperidin-4-yl)-2-(2-fluorophenyl)ethanone.

1H-NMR (400 MHz, DMSO-d6); δ(ppm) 1.26 (3H, d, J=6.4 Hz), 1.37-1.48 (1H, m), 1.55-1.67 (1H, m), 2.00-2.12 (2H, m), 2.85-2.97 (2H, m), 3.10-3.22 (1H, m), 3.28-3.35 (1H, m), 3.94 (2H, s), 7.11-7.17 (2H, m), 7.21-7.33 (2H, m), 8.56-8.80 (1H, m), 9.10-9.30 (1H, m).

Example 1

2-Methoxy-3-[4-(2-methylphenoxymethyl)piperidino]methyl-pyrazine

After suspending 200 mg of 4-(2-methylphenoxymethyl)piperidine hydrochloride in 5 ml of dichloromethane, 137 mg of 3-methoxypyrazine-2-carboxaldehyde [CAS No. 63874-90-8] and 264 mg of sodium triacetoxyborohydride were added while stirring, and the stirring was continued overnight at room temperature. Aqueous sodium carbonate solution was added to the reaction mixture and extraction was performed with ethyl acetate. The organic layer was washed with saturated brine and dried over anhydrous magnesium sulfate, and then the solvent was distilled off under reduced pressure. The residue was purified by silica gel column chromatography (solvent: n-hexane/ethyl acetate) to obtain the title compound (236 mg, 87% yield).

1H-NMR (400 MHz, CDCl3); δ (ppm) 1.45-1.57 (2H, m), 1.80-1.91 (3H, m), 2.13-2.23 (5H, m), 3.04-3.10 (2H, m), 3.71 (2H, s), 3.79 (2H, d, J=6.0 Hz), 3.98 (3H, s), 6.78 (1H, d, J=8.0 Hz), 6.84 (1H, dt, J=7.6, 1.2 Hz), 7.10-7.16 (2H, m), 7.99 (1H, d, J=2.8 Hz), 8.13 (1H, d, J=2.8 Hz)

Example 2

Ethyl 1-(2-methoxy-3-pyridinylmethyl)-4-(2-phenylethyl)piperidine-4-carboxylate The title compound (275 mg, 48% yield) was obtained in the same manner as Example 1 from 300 mg of 2-methoxypyridine-3-carboxaldehyde and 445 mg of 4-(ethoxycarbonyl)-4-(2-phenylethyl)piperidine hydrochloride.

1H-NMR (400 MHz, CDCl3); δ (ppm) 1.29 (3H, t, J=7.2 Hz), 1.53-1.61 (2H, m), 1.79-1.88 (2H, m), 2.06-2.24 (4H, m), 2.49-2.53 (2H, m), 2.70-2.77 (2H, m), 3.46 (2H, s), 3.94 (3H, s), 4.18 (2H, q, J=7.2 Hz), 6.86 (1H, dd, J=7.2, 4.8 Hz), 7.12-7.20 (3H, m), 7.27 (2H, t, J=7.6 Hz), 7.62-7.66 (1H, m), 8.05 (1H, dd, J=4.8, 2.0 Hz).

Example 3

1-(2-Methoxy-3-pyridinylmethyl)-4-(2-phenylethyl)piperidine-4-methanol

After dissolving 247 mg of ethyl 1-(2-methoxy-3-pyridinylmethyl)-4-(2-phenylethyl)piperidine-4-carboxylate in 10 ml of diethyl ether, the solution was cooled to −20° C. and 1 ml of diisobutylaluminium hydride (1.5 M, toluene solution) was added dropwise. The mixture was stirred for 4 hours while slowly raising the temperature to room temperature, and then approximately 10 ml of a saturated aqueous solution of potassium sodium (+)-tartrate tetrahydrate and approximately 10 ml of ethyl acetate were added and the mixture was stirred for 10 minutes at room temperature. The organic layer was separated off and the aqueous layer was extracted with ethyl acetate. The organic layers were combined and dried over anhydrous magnesium sulfate, and then the solvent was distilled off under reduced pressure. The residue was purified by NH silica gel column chromatography (solvent: n-hexane/ethyl acetate) to obtain the title compound (173 mg, 79% yield).

1H-NMR (400 MHz, CDCl3); δ (ppm) 1.53-1.63 (4H, m), 1.65-1.77 (2H, m), 2.43-2.59 (6H, m), 3.51 (2H, s), 3.55 (2H, s), 3.94 (3H, s), 6.85-6.89 (1H, m), 7.12-7.21 (3H, m), 7.24-7.31 (2H, m), 7.60-7.67 (1H, m), 8.06 (1H, dd, J=4.8, 2.0 Hz).

Example 4

3-[4-(2-Fluorophenoxymethyl)-4-(2-phenylethyl)piperidino]methyl-2-methoxypyridine After dissolving 55 mg of 1-(2-methoxy-3-pyridinylmethyl)-4-(2-phenylethyl)piperidine-4-methanol, 51 mg of triphenylphosphine and 20 mg of 2-fluorophenol in 10 ml of tetrahydrofuran, the solution was cooled to 0° C. 0.13 ml of diethyl azodicarboxylate (40% toluene solution) was then added dropwise and the mixture was stirred overnight at room temperature. After stirring for 5 hours at 70° C. and cooling to room temperature, the solvent was distilled off under reduced pressure. The residue was purified by NH silica gel column chromatography (solvent: n-hexane/ethyl acetate) to obtain the title compound (5 mg, 7% yield).

1H-NMR (400 MHz, CDCl3); δ (ppm) 1.57-1.64 (2H, m), 1.67-1.72 (2H, m), 2.31-2.40 (2H, m), 2.59-2.64 (2H, m), 3.08-3.15 (2H, m), 3.33 (2H, td, J=12.8, 2.8 Hz), 3.63 (2H, s), 3.98 (3H, s), 4.44 (2H, s), 6.98 (1H, dd, J=7.4, 5.0 Hz), 7.16-7.20 (3H, m), 7.25-7.31 (6H, m), 8.09 (1H, dd, J=7.4, 1.6 Hz), 8.21 (1H, dd, J=5.2, 1.6 Hz).

Example 5 anti-(E)-3-(5-Chloro-2-methoxy-3-pyridinylmethyl)-9-[2-(2-fluorophenyl)vinyl]-3-azabicyclo[3.3.1]nonane After adding 150 mg of 2-methoxy-5-chloro-3-(chloromethyl)pyridine, 200 mg of anti-(E)-9-[2-(2-fluorophenyl)vinyl]-3-azabicyclo[3.3.1]nonane hydrochloride and 118 mg of anhydrous potassium carbonate to 5 ml of acetonitrile, the mixture was stirred overnight at room temperature. The stirring was continued for 2 hours at 60° C., and then ethyl acetate was added to the reaction solution, the insoluble portion was filtered off and the solvent was distilled off under reduced pressure. The residue was purified by silica gel column chromatography (solvent: n-hexane/ethyl acetate) to obtain the title compound (164 mg, 58% yield).

1H-NMR (400 MHz, CDCl3); δ(ppm) 1.54-1.65 (3H, m), 1.84-1.89 (2H, m), 1.91-2.02 (2H, m), 2.40-2.46 (3H, m), 2.59-2.73 (1H, m), 2.99-3.04 (2H, m), 3.38 (2H, s), 3.94 (3H, s), 6.55-6.66 (2H, m), 7.02 (1H, ddd, J=10.8, 8.0, 1.2 Hz), 7.09 (1H, dt, J=8.0, 1.2 Hz), 7.15-7.21 (1H, m), 7.49 (1H, dt, J=8.0, 1.2 Hz), 7.64 (1H, dt, J=2.8, 0.8 Hz), 7.98 (1H, d, J=2.8 Hz).

Example 6

3-[3-(2-Fluorophenoxymethyl)pyrrolidino]methyl-2-methoxypyrazine

After dissolving 148 mg of 3-methoxypyrazine-2-carboxaldehyde and 200 mg of 3-(2-fluorophenoxymethyl)pyrrolidine in 5 ml of dichloromethane, 0.07 ml of acetic acid and 297 mg of sodium triacetoxyborohydride were added and the mixture was stirred overnight at room temperature. Aqueous sodium carbonate solution was added to the reaction mixture and extraction was performed with ethyl acetate. The organic layer was washed with water and saturated brine in that order and dried over anhydrous magnesium sulfate, and then the solvent was distilled off under reduced pressure. The residue was purified by silica gel column chromatography (solvent: n-hexane/ethyl acetate) to obtain the title compound (245 mg, 77% yield).

1H-NMR (400 MHz, CDCl3); δ(ppm) 1.60-1.71 (1H, m), 2.05-2.15 (1H, m), 2.56 (1H, dd, J=9.6, 6.0 Hz), 2.67-2.82 (3H, m), 2.98 (1H, dd, J=9.6, 8.0 Hz), 3.82 (2H, s), 3.96 (2H, d, J=7.6 Hz), 3.98 (3H, s), 6.85-6.91 (1H, m), 6.95 (1H, dt, J=8.0, 2.0 Hz), 7.00-7.09 (2H, m), 7.99 (1H, d, J=2.8 Hz), 8.11 (1H, d, J=2.8 Hz).

Example 7

2-Methoxy-3-[3-(2-methoxyphenoxymethyl)pyrrolidino]methyl-pyrazine

The title compound (352 mg, 92% yield) was obtained in the same manner as Example 6 from 160 mg of 3-methoxypyrazine-2-carboxaldehyde and 313 mg of 3-(2-methoxyphenoxymethyl)pyrrolidine.

1H-NMR (400 MHz, CDCl3); δ(ppm) 1.59-1.69 (1H, m), 2.04-2.15 (1H, m), 2.55 (1H, dd, J=9.6, 5.6 Hz), 2.66-2.84 (3H, m), 2.98 (1H, dd, J=9.6, 7.6 Hz), 3.82 (2H, s), 3.84 (3H, s), 3.94 (2H, d, J=7.2 Hz), 3.97 (3H, s), 6.84-6.94 (4H, m), 7.98 (1H, d, J=2.8 Hz), 8.10 (1H, d, J=2.8 Hz).

Example 8

3-[3-[2-(2-Fluorophenyl)ethyl]pyrrolidino]methyl-2-methoxypyrazine

The title compound (332 mg, 88% yield) was obtained in the same manner as Example 6 from 160 mg of 3-methoxypyrazine-2-carboxaldehyde and 288 mg of 3-[2-(2-fluorophenyl)ethyl]pyrrolidine.

1H-NMR (400 MHz, CDCl3); δ(ppm) 1.42-1.51 (1H, m), 1.63-1.74 (2H, m), 2.01-2.11 (1H, m), 2.16-2.28 (2H, m), 2.51-2.68 (3H, m), 2.85-2.92 (1H, m), 3.00-3.08 (1H, m), 3.79 (2H, s), 3.97 (3H, s), 6.95-7.06 (2H, m), 7.11-7.18 (2H, m), 7.98 (1H, d, J=2.8 Hz), 8.10 (1H, d, J=2.8 Hz).

Example 9

2-Methoxy-3-[3-[2-(2-methoxyphenyl)ethyl]pyrrolidino]methyl-pyrazine

The title compound (314 mg, 88% yield) was obtained in the same manner as Example 6 from 150 mg of 3-methoxypyrazine-2-carboxaldehyde and 265 mg of 3-[2-(2-methoxyphenyl)ethyl]pyrrolidine.

1H-NMR (400 MHz, CDCl3); δ(ppm) 1.43-1.52 (1H, m), 1.60-1.72 (2H, m), 2.01-2.11 (1H, m), 2.17-2.29 (2H, m), 2.50-2.68 (3H, m), 2.85-2.92 (1H, m), 3.05 (1H, m), 3.79 (2H, s), 3.80 (3H, s), 3.97 (3H, s), 6.82 (1H, dd, J=7.6, 1.2 Hz), 6.86 (1H, dt, J=7.6, 1.2 Hz), 7.10 (1H, dd, J=7.6, 2.0 Hz), 7.16 (1H, dt, J=7.6, 2.0 Hz), 7.98 (1H, d, J=2.8 Hz), 8.10 (1H, d, J=2.8 Hz).

Example 10

2-Methoxy-3-[3-(2-methylphenoxymethyl)pyrrolidino]methyl-pyrazine

The title compound (262 mg, 76% yield) was obtained in the same manner as Example 6 from 150 mg of 3-methoxypyrazine-2-carboxaldehyde and 248 mg of 3-(2-methylphenoxymethyl)pyrrolidine.

1H-NMR (400 MHz, CDCl3); δ(ppm) 1.63-1.72 (1H, m), 2.05-2.15 (1H, m), 2.20 (3H, s), 2.52 (1H, dd, J=9.2, 6.8 Hz), 2.62-2.68 (1H, m), 2.70-2.80 (1H, m), 2.82-2.88 (1H, m), 3.03 (1H, dd, J=9.2, 8.0 Hz), 3.81 (1H, d, J=14.0 Hz), 3.85 (1H, d, J=14.0 Hz), 3.88-3.94 (2H, m), 3.98 (3H, s), 6.79 (1H, dd, J=7.6, 1.2 Hz), 6.84 (1H, dt, J=7.6, 1.2 Hz), 7.10-7.16 (2H, m), 7.99 (1H, d, J=2.8 Hz), 8.11 (1H, d, J=2.8 Hz).

Example 11

(E)-3-[4-[2-(2-Fluorophenyl)vinyl]piperidino]methyl-2-methoxypyrazine

After dissolving 186 mg of 3-methoxypyrazine-2-carboxaldehyde and 230 mg of (E)-4-[2-(2-fluorophenyl)vinyl]piperidine in 3 ml of 1,2-dichloroethane, 0.08 ml of acetic acid and 373 mg of sodium triacetoxyborohydride were added and the mixture was stirred overnight at room temperature. Saturated aqueous sodium bicarbonate solution was added to the reaction mixture and extraction was performed with ethyl acetate. The extract was washed with water and saturated brine in that order and dried over anhydrous magnesium sulfate, and then the solvent was distilled off under reduced pressure. The residue was purified by NH silica gel column chromatography (solvent: n-hexane/ethyl acetate) to obtain the title compound (296 mg, 82% yield).

1H-NMR (400 MHz, CDCl3); δ(ppm) 1.58-1.69 (2H, m), 1.72-1.80 (2H, m), 2.12-2.23 (3H, m), 3.02-3.09 (2H, m), 3.70 (2H, s), 3.98 (3H, s), 6.23 (1H, dd, J=16.0, 7.2 Hz), 6.54 (1H, d, J=16.0 Hz), 7.00 (1H, ddd, J=10.8, 8.0, 1.2 Hz), 7.06 (1H, dt, J=8.0, 1.2 Hz), 7.12-7.19 (1H, m), 7.43 (1H, dt, J=8.0, 1.6 Hz), 8.00 (1H, d, J=2.4 Hz), 8.13 (1H, d, J=2.4 Hz).

Example 12

2-[1-(3-Methoxy-2-pyrazinylmethyl)piperidin-4-yl]-1-(2-fluorophenyl)ethanone

After adding 150 mg of 3-methoxypyrazine-2-carboxaldehyde and 340 mg of 1-(2-fluorophenyl)-2-(piperidin-4-yl)ethanone hydrochloride to 5 ml of 1,2-dichloroethane, 350 mg of sodium triacetoxyborohydride was added and the mixture was stirred for 4 hours at room temperature. Aqueous sodium carbonate solution was added to the reaction mixture and extraction was performed with ethyl acetate. The organic layer was washed with water and saturated brine in that order and dried over anhydrous magnesium sulfate, and then the solvent was distilled off under reduced pressure. The residue was purified by silica gel column chromatography (solvent: n-hexane/ethyl acetate) to obtain the title compound (268 mg, 71% yield).

1H-NMR (400 MHz, CDCl3); δ(ppm) 1.38-1.50 (2H, m), 1.68-1.76 (2H, m), 1.93-2.06 (1H, m), 2.11-2.20 (2H, m), 2.89 (2H, dd, J=6.8, 3.2 Hz), 2.96-3.02 (2H, m), 3.68 (2H, s), 3.97 (3H, s), 7.12 (1H, ddd, J=11.2, 8.4, 1.2 Hz), 7.23 (1H, ddd, J=8.4, 8.0, 1.2 Hz), 7.47-7.54 (1H, m), 7.82 (1H, dt, J=7.6, 2.0 Hz), 7.98 (1H, d, J=2.8 Hz), 8.11 (1H, d, J=2.8 Hz).

Example 13

3-[4-[2-(Benzofuran-7-yl)ethyl]piperidino]methyl-2-methoxypyrazine

After adding 124 mg of 3-methoxypyrazine-2-carboxaldehyde and 200 mg of 4-[2-(benzofuran-7-yl)ethyl]piperidine hydrochloride to 3 ml of tetrahydrofuran, 238 mg of sodium triacetoxyborohydride was added and the mixture was stirred overnight at room temperature. Aqueous sodium carbonate solution was added to the reaction mixture and extraction was performed with ethyl acetate. The organic layer was washed with water and saturated brine in that order and dried over anhydrous magnesium sulfate, and then the solvent was distilled off under reduced pressure. The residue was purified by silica gel column chromatography (solvent: n-hexane/ethyl acetate) to obtain the title compound (218 mg, 82% yield).

1H-NMR (400 MHz, CDCl3); δ (ppm) 1.25-1.47 (3H, m), 1.65-1.80 (4H, m), 2.04-2.13 (2H, m), 2.88-2.94 (2H, m), 2.98-3.04 (2H, m), 3.67 (2H, s), 3.97 (3H, s), 6.75 (1H, d, J=2.0 Hz), 7.08 (1H, dd, J=7.2, 1.2 Hz), 7.15 (1H, t, J=7.2 Hz), 7.43 (1H, dd, J=7.2, 1.2 Hz), 7.60 (1H, d, J=2.0 Hz), 7.98 (1H, d, J=2.8 Hz), 8.12 (1H, d, J=2.8 Hz).

Example 14

3-[4-(2-Fluorophenoxymethyl)piperidino]methyl-2-methoxypyrazine

The title compound (72 mg, 74% yield) was obtained in the same manner as Example 13 from 60 mg of 3-methoxypyrazine-2-carboxaldehyde and 72 mg of 4-(2-fluorophenoxymethyl)piperidine hydrochloride.

1H-NMR (400 MHz, CDCl3); δ(ppm) 1.42-1.60 (2H, m), 1.81-1.94 (3H, m), 2.12-2.20 (2H, m), 3.02-3.10 (2H, m), 3.70 (2H, s), 3.85 (2H, d, J=6.4 Hz), 3.98 (3H, s), 6.84-6.90 (1H, m), 6.94 (1H, td, J=8.2, 1.6 Hz), 7.00-7.09 (2H, m), 7.99 (1H, d, J=2.8 Hz), 8.12 (1H, d, J=2.8 Hz).

Example 15

3-[4-(2,5-Difluorophenoxymethyl)piperidino]methyl-2-methoxypyrazine

The title compound (309 mg, 80% yield) was obtained in the same manner as Example 1 from 150 mg of 3-methoxypyrazine-2-carboxaldehyde and 343 mg of 4-(2,5-difluorophenoxymethyl)piperidine hydrochloride.

1H-NMR (400 MHz, CDCl3); δ(ppm) 1.43-1.56 (2H, m), 1.80-1.94 (3H, m), 2.12-2.20 (2H, m), 3.04-3.10 (2H, m), 3.70 (2H, s), 3.82 (2H, d, J=6.4 Hz), 3.98 (3H, s), 6.52-6.58 (1H, m), 6.66 (1H, ddd, J=9.6, 8.8, 3.2 Hz), 6.99 (1H, ddd, J=10.8, 8.8, 4.2 Hz), 7.99 (1H, d, J=2.8 Hz), 8.13 (1H, d, J=2.8 Hz).

Example 16

2-Methoxy-3-[4-(2-methylbenzyloxy)piperidino]methyl-pyrazine

The title compound (306 mg, 81% yield) was obtained in the same manner as Example 6 from 150 mg of 3-methoxypyrazine-2-carboxaldehyde and 340 mg of 4-(2-methylbenzyloxy)piperidine.

1H-NMR (400 MHz, CDCl3); δ(ppm) 1.70-1.81 (2H, m), 1.91-1.99 (2H, m), 2.28-2.37 (5H, m), 2.85-2.93 (2H, m), 3.41-3.48 (1H, m), 3.69 (2H, s), 3.97 (3H, s), 4.51 (2H, s), 7.13-7.22 (3H, m), 7.31-7.35 (1H, m), 7.99 (1H, d, J=2.8 Hz), 8.12 (1H, d, J=2.8 Hz).

Example 17

2-Methoxy-3-[4-(3-methylphenoxymethyl)piperidino]methylpyrazine

The title compound (217 mg, 60% yield) was obtained in the same manner as Example 1 from 150 mg of 3-methoxypyrazine-2-carboxaldehyde and 314 mg of 4-(3-methylphenoxymethyl)piperidine hydrochloride.

1H-NMR (400 MHz, CDCl3); δ (ppm) 1.42-1.55 (2H, m), 1.75-1.86 (3H, m), 2.11-2.19 (2H, m), 2.32 (3H, s), 3.03-3.09 (2H, m), 3.70 (2H, s), 3.78 (2H, d, J=6.0 Hz), 3.98 (3H, s), 6.66-6.76 (3H, m), 7.15 (1H, t, J=7.6 Hz), 7.99 (1H, d, J=2.8 Hz), 8.13 (1H, d, J=2.8 Hz).

Example 18

2-Methoxy-3-[4-(3-methoxyphenoxymethyl)piperidino]methyl-pyrazine

The title compound (278 mg, 74% yield) was obtained in the same manner as Example 1 from 150 mg of 3-methoxypyrazine-2-carboxaldehyde and 335 mg of 4-(3-methoxyphenoxymethyl)piperidine hydrochloride.

1H-NMR (400 MHz, CDCl3); δ(ppm) 1.43-1.55 (2H, m), 1.75-1.88 (3H, m), 2.11-2.20 (2H, m), 3.03-3.09 (2H, m), 3.70 (2H, s), 3.77 (2H, d, J=5.2 Hz), 3.78 (3H, s), 3.98 (3H, s), 6.43-6.52 (3H, m), 7.16 (1H, t, J=8.0 Hz), 7.99 (1H, d, J=2.8 Hz), 8.13 (1H, d, J=2.8 Hz).

Example 19

2-Methoxy-3-[4-[2-(trifluoromethyl)phenoxymethyl]piperidino]methyl-pyrazine

The title compound (255 mg, 63% yield) was obtained in the same manner as Example 1 from 150 mg of 3-methoxypyrazine-2-carboxaldehyde and 384 mg of 4-[2-(trifluoromethyl)phenoxymethyl]piperidine hydrochloride.

1H-NMR (400 MHz, CDCl3); δ(ppm) 1.41-1.53 (2H, m), 1.80-1.94 (3H, m), 2.13-2.20 (2H, m), 3.04-3.10 (2H, m), 3.71 (2H, s), 3.86 (2H, d, J=6.4 Hz), 3.98 (3H, s), 6.93-7.01 (2H, m), 7.46 (1H, t, J=7.6 Hz), 7.55 (1H, d, J=7.6 Hz), 7.99 (1H, d, J=2.8 Hz), 8.13 (1H, d, J=2.8 Hz).

Example 20

2-tert-Butylthio-3-[4-(2-fluorophenoxymethyl)piperidino]methyl-pyrazine

The title compound (205 mg, 57% yield) was obtained in the same manner as Example 1 from 180 mg of 3-(tert-butylthio)pyrazine-2-carboxaldehyde and 248 mg of 4-(2-fluorophenoxymethyl)piperidine hydrochloride.

1H-NMR (400 MHz, CDCl3); δ(ppm) 1.41-1.52 (2H, m), 1.59 (9H, s), 1.79-1.94 (3H, m), 2.12-2.20 (2H, m), 2.95-3.02 (2H, m), 3.64 (2H, s), 3.85 (2H, d, J=6.4 Hz), 6.84-6.90 (1H, m), 6.94 (1H, dt, J=8.8, 1.6 Hz), 7.01-7.09 (2H, m), 8.21 (1H, d, J=2.8 Hz), 8.23 (1H, d, J=2.8 Hz).

Example 21

(E)-2-Methoxy-3-[4-[2-(3-methyl-2-thienyl)vinyl]piperidino]methyl-pyrazine

After dissolving 139 mg of (E)-4-[2-(3-methyl-2-thienyl)vinyl]piperidine in 7 ml of tetrahydrofuran, 111 mg of 3-methoxypyrazine-2-carboxaldehyde and 213 mg of sodium triacetoxyborohydride were added while stirring, and the stirring was continued overnight at room temperature. A 1N sodium hydroxide solution was added to the reaction mixture to render it alkaline, and then extraction was performed with ethyl acetate. The extract was washed with saturated brine and dried over anhydrous magnesium sulfate, and then the solvent was distilled off under reduced pressure. The residue was purified by NH silica gel column chromatography (solvent: n-hexane/ethyl acetate) to obtain the title compound (120 mg, 54% yield).

1H-NMR (400 MHz, CDCl3); δ (ppm) 1.54-1.66 (2H, m), 1.69-1.78 (2H, m), 2.06-2.24 (3H, m), 2.19 (3H, s), 3.00-3.08 (2H, m), 3.69 (2H, s), 3.98 (3H, s), 5.94 (1H, dd, J=16.0, 7.0 Hz), 6.49 (1H, d, J=16.0 Hz), 6.75 (1H, d, J=5.2 Hz), 6.98 (1H, d, J=5.2 Hz), 7.99 (1H, d, J=2.8 Hz), 8.13 (1H, d, J=2.8 Hz).

Example 22

3-[3-[2-(2-Fluorophenyl)ethyl]piperidino]methyl-2-methoxypyrazine

The title compound (159 mg, 57% yield) was obtained in the same manner as Example 1 from 141 mg of 3-methoxypyrazine-2-carboxaldehyde and 208 mg of 3-[2-(2-fluorophenyl)ethyl]piperidine hydrochloride.

1H-NMR (400 MHz, CDCl3); δ (ppm) 0.85-0.96 (1H, m), 1.41-1.56 (2H, m), 1.58-1.72 (3H, m), 1.76-1.87 (2H, m), 2.00-2.08 (1H, m), 2.56-2.70 (2H, m), 2.92-3.03 (2H, m), 3.67 (2H, s), 3.97 (3H, s), 6.94-7.05 (2H, m), 7.10-7.18 (2H, m), 7.99 (1H, d, J=2.8 Hz), 8.12 (1H, d, J=2.8 Hz).

Example 23

3-[3-[2-(2-Methoxyphenyl)ethyl]piperidino]methyl-2-methoxypyrazine

The title compound (269 mg, 86% yield) was obtained in the same manner as Example 21 from 153 mg of 3-methoxypyrazine-2-carboxaldehyde and 202 mg of 3-[2-(2-methoxyphenyl)ethyl]piperidine.

1H-NMR (400 MHz, CDCl3); δ (ppm) 0.82-0.95 (1H, m), 1.37-1.52 (2H, m), 1.59-1.73 (3H, m), 1.75-1.88 (2H, m), 1.98-2.07 (1H, m), 2.52-2.67 (2H, m), 2.92-3.06 (2H, m), 3.67 (2H, d, J=1.6 Hz), 3.80 (3H, s), 3.97 (3H, s), 6.82 (1H, d, J=7.6 Hz), 6.86 (1H, td, J=7.6, 1.2 Hz), 7.09 (1H, dd, J=7.6, 1.6 Hz), 7.15 (1H, td, J=7.6, 1.6 Hz), 7.98 (1H, d, J=2.8 Hz), 8.12 (1H, d, J=2.8 Hz).

Example 24

2-Methoxy-3-[3-(2-methylphenoxymethyl)piperidino]methyl-pyrazine

The title compound (140 mg, 47% yield) was obtained in the same manner as Example 1 from 151 mg of 3-methoxypyrazine-2-carboxaldehyde and 221 mg of 3-(2-methylphenoxymethyl)piperidine hydrochloride.

1H-NMR (400 MHz, CDCl3); δ (ppm) 1.10-1.22 (1H, m), 1.67-1.76 (2H, m), 1.78-1.86 (1H, m), 1.98-2.07 (1H, m), 2.09-2.28 (2H, m), 2.17 (3H, s), 2.93-3.00 (1H, m), 3.14-3.20 (1H, m), 3.71 (2H, d, J=2.8 Hz), 3.77 (1H, dd, J=9.2, 7.2 Hz), 3.83 (1H, dd, J=9.2, 5.6 Hz), 3.96 (3H, s), 6.76 (1H, d, J=7.4 Hz), 6.83 (1H, td, J=7.4, 1.0 Hz), 7.09-7.15 (2H, m), 7.99 (1H, d, J=2.8 Hz), 8.11 (1H, d, J=2.8 Hz).

Example 25

3-[4-[2-(2-Methoxyphenoxy)ethyl]piperidino]methyl-2-methoxypyrazine

The title compound (180 mg, 59% yield) was obtained in the same manner as Example 1 from 141 mg of 3-methoxypyrazine-2-carboxaldehyde and 231 mg of 4-[2-(2-methoxyphenoxy)ethyl]piperidine hydrochloride.

1H-NMR (400 MHz, CDCl3); δ (ppm) 1.36-1.48 (2H, m), 1.50-1.62 (1H, m), 1.68-1.76 (2H, m), 1.80 (2H, q, J=6.8 Hz), 2.07-2.16 (2H, m), 2.97-3.05 (2H, m), 3.67 (2H, s), 3.86 (3H, s), 3.97 (3H, s), 4.05 (2H, t, J=6.8 Hz), 6.86-6.94 (4H, m), 7.98 (1H, d, J=2.8 Hz), 8.12 (1H, d, J=2.8 Hz).

Example 26

3-[3-(2-Fluorophenoxymethyl)piperidino]methyl-2-methoxypyrazine

The title compound (170 mg, 62% yield) was obtained in the same manner as Example 1 from 144 mg of 3-methoxypyrazine-2-carboxaldehyde and 205 mg of 3-(2-fluorophenoxymethyl)piperidine hydrochloride.

1H-NMR (400 MHz, CDCl3); δ (ppm) 1.10-1.22 (1H, m), 1.64-1.73 (2H, m), 1.78-1.86 (1H, m), 2.03-2.12 (1H, m), 2.12-2.29 (2H, m), 2.88-2.95 (1H, m), 3.07-3.14 (1H, m), 3.70 (2H, s), 3.85-3.93 (2H, m), 3.96 (3H, s), 6.84-6.96 (2H, m), 7.00-7.08 (2H, m), 7.99 (1H, d, J=2.8 Hz), 8.10 (1H, d, J=2.8 Hz).

Example 27

2-Methoxy-3-[3-(2-methoxyphenoxymethyl)piperidino]methyl-pyrazine

The title compound (309 mg, 80% yield) was obtained in the same manner as Example 21 from 181 mg of 3-methoxypyrazine-2-carboxaldehyde and 247 mg of 3-(2-methoxyphenoxymethyl)piperidine.

1H-NMR (400 MHz, CDCl3); δ (ppm) 1.07-1.18 (1H, m), 1.62-1.72 (2H, m), 1.80-1.88 (1H, m), 1.98-2.32 (3H, m), 2.87-2.95 (1H, m), 3.10-3.16 (1H, m), 3.67 (1H, d, J=13.2 Hz), 3.72 (1H, d, J=13.2 Hz), 3.83 (3H, s), 3.84-3.90 (2H, m), 3.96 (3H, s), 6.85-6.92 (4H, m), 7.98 (1H, d, J=2.8 Hz), 8.10 (1H, d, J=2.8 Hz).

Example 28

1-(2-Methoxyphenyl)-2-[1-(3-methoxypyrazin-2-yl)methylpiperidin-4-yl]ethanone

The title compound (211 mg, 67% yield) was obtained in the same manner as Example 21 from 146 mg of 3-methoxypyrazine-2-carboxaldehyde and 206 mg of 1-(2-methoxyphenyl)-2-(piperidin-4-yl)ethanone.

1H-NMR (400 MHz, CDCl3); δ (ppm) 1.35-1.47 (2H, m), 1.66-1.74 (2H, m), 1.90-2.02 (1H, m), 2.09-2.18 (2H, m), 2.89 (2H, d, J=6.8 Hz), 2.94-3.01 (2H, m), 3.67 (2H, s), 3.88 (3H, s), 3.97 (3H, s), 6.95 (1H, d, J=8.4 Hz), 6.99 (1H, td, J=7.4, 1.2 Hz), 7.44 (1H, ddd, J=8.4, 7.4, 1.8 Hz), 7.60 (1H, dd, J=7.4, 1.8 Hz), 7.98 (1H, d, J=2.8 Hz), 8.11 (1H, d, J=2.8 Hz).

Example 29

2-Methoxy-3-[4-(2-methoxyphenoxymethyl)piperidino]methyl-pyrazine

The title compound (148 mg, 52% yield) was obtained in the same manner as Example 1 from 138 mg of 3-methoxypyrazine-2-carboxaldehyde and 215 mg of 4-(2-methoxyphenoxymethyl)piperidine hydrochloride.

1H-NMR (400 MHz, CDCl3); δ (ppm) 1.42-1.54 (2H, m), 1.82-1.98 (3H, m), 2.11-2.20 (2H, m), 3.02-3.09 (2H, m), 3.69 (2H, s), 3.85 (2H, d, J=6.8 Hz), 3.85 (3H, s), 3.98 (3H, s), 6.85-6.94 (4H, m), 7.99 (1H, d, J=2.8 Hz), 8.12 (1H, d, J=2.8 Hz).

Example 30

3-(2-Fluorobenzyl)-8-(2-methoxy-3-pyridinylmethyl)-1-oxa-3,8-diazaspiro[4.5]deca-2-one The title compound (14 mg, 27% yield) was obtained in the same manner as Example 1 from 21 mg of 2-methoxypyridine-3-carboxaldehyde and 41 mg of 3-(2-fluorobenzyl)-1-oxa-3,8-diazaspiro[4.5]deca-2-one hydrochloride.

1H-NMR (400 MHz, CDCl3); δ (ppm) 1.70-1.80 (2H, m), 1.88-1.95 (2H, m), 2.52-2.65 (4H, m), 3.19 (2H, s), 3.52 (2H, s), 3.94 (3H, s), 4.50 (2H, s), 6.86 (1H, dd, J=7.2, 5.2 Hz), 7.07 (1H, ddd, J=9.8, 8.4, 1.2 Hz), 7.14 (1H, td, J=3.6, 1.2 Hz), 7.27-7.37 (2H, m), 7.59 (1H, dd, J=7.2, 2.0 Hz), 8.06 (1H, dd, J=7.2, 2.0 Hz).

Example 31

3-[4-(2-Fluorobenzyloxy)piperidino]methyl-2-methoxypyrazine

The title compound (210 mg, 73% yield) was obtained in the same manner as Example 1 from 148 mg of 3-methoxypyrazine-2-carboxaldehyde and 212 mg of 4-(2-fluorobenzyloxy)piperidine hydrochloride.

1H-NMR (400 MHz, CDCl3); δ (ppm) 1.70-1.80 (2H, m), 1.90-1.99 (2H, m), 2.28-2.37 (2H, m), 2.84-2.93 (2H, m), 3.42-3.49 (1H, m), 3.69 (2H, s), 3.97 (3H, s), 4.60 (2H, s), 7.02 (1H, ddd, J=9.6, 8.0, 1.0 Hz), 7.13 (1H, td, J=8.0, 1.0 Hz), 7.22-7.28 (1H, m), 7.45 (1H, td, J=8.0, 2.0 Hz), 7.99 (1H, d, J=2.8 Hz), 8.12 (1H, d, J=2.8 Hz).

Example 32

3-[4-[2-(2,3-Dihydrobenzofuran-7-yl)ethyl]piperidino]methyl-2-methoxypyrazine

The title compound (249 mg, 79% yield) was obtained in the same manner as Example 21 from 153 mg of 3-methoxypyrazine-2-carboxaldehyde and 207 mg of 4-[2-(2,3-dihydrobenzofuran-7-yl)ethyl]piperidine.

1H-NMR (400 MHz, CDCl3); δ (ppm) 1.22-1.43 (3H, m), 1.50-1.60 (2H, m), 1.68-1.76 (2H, m), 2.03-2.12 (2H, m), 2.53-2.60 (2H, m), 2.97-3.03 (2H, m), 3.20 (2H, t, J=8.8 Hz), 3.66 (2H, s), 3.97 (3H, s), 4.53 (2H, t, J=8.8 Hz), 6.76 (1H, t, J=7.4 Hz), 6.90-6.94 (1H, m), 7.03 (1H, dd, J=7.4, 1.2 Hz), 7.98 (1H, d, J=2.8 Hz), 8.12 (1H, d, J=2.8 Hz).

Example 33

2-tert-Butoxy-3-[3-[2-(2-fluorophenoxy)ethyl]azetidin-1-yl]methyl-pyrazine

The title compound (54 mg, 39% yield) was obtained in the same manner as Example 21 from 84 mg of 3-tert-butoxypyrazine-2-carboxaldehyde and 76 mg of 3-[2-(2-fluorophenoxy)ethyl]azetidine.

1H-NMR (400 MHz, CDCl3); δ (ppm) 1.60 (9H, s), 2.08 (2H, q, J=6.4 Hz), 2.72-2.82 (1H, m), 3.07 (2H, t, J=7.6 Hz), 3.70 (2H, t, J=7.6 Hz), 3.72 (2H, s), 3.99 (2H, t, J=6.4 Hz), 6.85-6.96 (2H, m), 7.01-7.09 (2H, m), 7.89 (1H, d, J=2.8 Hz), 8.00 (1H, d, J=2.8 Hz).

Example 34

2-tert-Butoxy-3-[4-(2-chlorophenoxymethyl)piperidino]methyl-pyrazine

The title compound (229 mg, 71% yield) was obtained in the same manner as Example 1 from 150 mg of 3-tert-butoxypyrazine-2-carboxaldehyde and 260 mg of 4-(2-chlorophenoxymethyl)piperidine hydrochloride.

1H-NMR (400 MHz, CDCl3); δ (ppm) 1.42-1.55 (2H, m), 1.60 (9H, s), 1.83-1.94 (3H, m), 2.13-2.22 (2H, m), 3.01-3.07 (2H, m), 3.67 (2H, s), 3.85 (2H, d, J=6.0 Hz), 6.84-6.91 (2H, m), 7.19 (1H, ddd, J=8.4, 7.6, 1.6 Hz), 7.34 (1H, dd, J=7.6, 1.2 Hz), 7.92 (1H, d, J=2.8 Hz), 8.05 (1H, d, J=2.8 Hz).

Example 35

2-tert-Butoxy-3-[4-(3-fluorophenoxymethyl)piperidino]methyl-pyrazine

The title compound (223 mg, 72% yield) was obtained in the same manner as Example 1 from 150 mg of 3-tert-butoxypyrazine-2-carboxaldehyde and 243 mg of 4-(3-fluorophenoxymethyl)piperidine hydrochloride.

1H-NMR (400 MHz, CDCl3); δ (ppm) 1.41-1.53 (2H, m), 1.60 (9H, s), 1.74-1.84 (3H, m), 2.11-2.19 (2H, m), 3.01-3.07 (2H, m), 3.65 (2H, s), 3.77 (2H, d, J=6.0 Hz), 6.56-6.68 (3H, m), 7.20 (1H, dt, J=8.4, 6.8 Hz), 7.92 (1H, d, J=2.8 Hz), 8.05 (1H, d, J=2.8 Hz).

Example 36

2-tert-Butoxy-3-[4-(2,4-difluorophenoxymethyl)piperidino]methyl-pyrazine

The title compound (183 mg, 56% yield) was obtained in the same manner as Example 1 from 150 mg of 3-tert-butoxypyrazine-2-carboxaldehyde and 261 mg of 4-(2,4-difluorophenoxymethyl)piperidine hydrochloride.

1H-NMR (400 MHz, CDCl3); δ (ppm) 1.39-1.52 (2H, m), 1.60 (9H, s), 1.78-1.86 (3H, m), 2.11-2.19 (2H, m), 3.00-3.07 (2H, m), 3.65 (2H, s), 3.81 (2H, d, J=6.0 Hz), 6.73-6.79 (1H, m), 6.81-6.92 (2H, m), 7.92 (1H, d, J=2.8 Hz), 8.05 (1H, d, J=2.8 Hz).

Example 37

2-tert-Butoxy-3-[4-(2-ethoxyphenoxymethyl)piperidino]methyl-pyrazine

The title compound (178 mg, 54% yield) was obtained in the same manner as Example 1 from 150 mg of 3-tert-butoxypyrazine-2-carboxaldehyde and 270 mg of 4-(2-ethoxyphenoxymethyl)piperidine hydrochloride.

1H-NMR (400 MHz, CDCl3); δ (ppm) 1.39-1.51 (2H, m), 1.41 (3H, t, J=6.8 Hz), 1.60 (9H, s), 1.82-1.94 (3H, m), 2.11-2.20 (2H, m), 3.00-3.06 (2H, m), 3.65 (2H, s), 3.83 (2H, d, J=6.8 Hz), 4.06 (2H, q, J=6.8 Hz), 6.88 (4H, s), 7.92 (1H, d, J=2.8 Hz), 8.05 (1H, d, J=2.8 Hz).

Example 38

2-[1-(3-tert-Butoxy-2-pyrazinylmethyl)piperidin-4-yl]methoxy-benzonitrile

The title compound (180 mg, 57% yield) was obtained in the same manner as Example 1 from 150 mg of 3-tert-butoxypyrazine-2-carboxaldehyde and 250 mg of 4-(2-cyanophenoxymethyl)piperidine hydrochloride.

1H-NMR (400 MHz, CDCl3); δ (ppm) 1.39-1.52 (2H, m), 1.61 (9H, s), 1.85-1.97 (3H, m), 2.13-2.22 (2H, m), 3.01-3.08 (2H, m), 3.66 (2H, s), 3.88 (2H, d, J=6.4 Hz), 6.94 (1H, d, J=8.4 Hz), 6.98 (1H, t, J=7.6 Hz), 7.51 (1H, ddd, J=8.4, 7.6, 1.2 Hz), 7.55 (1H, dd, J=7.6, 1.2 Hz), 7.93 (1H, d, J=2.8 Hz), 8.05 (1H, d, J=2.8 Hz).

Example 39

2-tert-Butoxy-3-[4-[2-(trifluoromethoxy)phenoxymethyl]piperidino]methyl-pyrazine The title compound (292 mg, 80% yield) was obtained in the same manner as Example 1 from 150 mg of 3-tert-butoxypyrazine-2-carboxaldehyde and 270 mg of 4-[2-(trifluoromethoxy)phenoxymethyl]piperidine hydrochloride.

1H-NMR (400 MHz, CDCl3); δ (ppm) 1.39-1.52 (2H, m), 1.60 (9H, s), 1.80-1.92 (3H, m), 2.13-2.22 (2H, m), 3.00-3.07 (2H, m), 3.66 (2H, s), 3.83 (2H, d, J=6.4 Hz), 6.92 (1H, dt, J 8.0, 1.2 Hz), 6.96 (1H, dd, J=8.4, 1.2 Hz), 7.19-7.25 (2H, m), 7.93 (1H, d, J=2.8 Hz), 8.05 (1H, d, J=2.8 Hz).

Example 40

2-tert-Butoxy-3-[4-[(2-fluorophenyl)ethynyl]piperidino]methyl-pyrazine

The title compound (338 mg, 84% yield) was obtained in the same manner as Example 6 from 200 mg of 3-tert-butoxypyrazine-2-carboxaldehyde and 269 mg of 4-[(2-fluorophenyl)ethynyl]piperidine.

1H-NMR (400 MHz, CDCl3); δ(ppm) 1.60 (9H, s), 1.75-1.87 (2H, m), 1.92-2.00 (2H, m), 2.34-2.44 (2H, m), 2.62-2.71 (1H, m), 2.83-2.91 (2H, m), 3.65 (2H, s), 7.01-7.08 (2H, m), 7.21-7.26 (1H, m), 7.38 (1H, dd, J=7.6, 2.0 Hz), 7.93 (1H, d, J=2.8 Hz), 8.05 (1H, d, J=2.8 Hz).

Example 41

(E)-2-tert-Butoxy-3-[4-[2-(2-methylphenyl)vinyl]piperidino]methyl-pyrazine

The title compound (289 mg, 95% yield) was obtained in the same manner as Example 6 from 150 mg of 3-tert-butoxypyrazine-2-carboxaldehyde and 200 mg of (E)-4-[2-(2-methylphenyl)vinyl]piperidine.

1H-NMR (400 MHz, CDCl3); δ (ppm) 1.56-1.68 (2H, m), 1.61 (9H, s), 1.72-1.79 (2H, m), 2.10-2.23 (3H, m), 2.31 (3H, s), 3.00-3.06 (2H, m), 3.66 (2H, s), 6.04 (1H, dd, J=16.0, 7.2 Hz), 6.56 (1H, dd, J=16.0, 0.8 Hz), 7.08-7.17 (3H, m), 7.40 (1H, d, J=6.8 Hz), 7.93 (1H, d, J=2.8 Hz), 8.06 (−1H, d, J=2.8 Hz).

Example 42

2-[1-(3-tert-Butoxy-2-pyrazinylmethyl)piperidin-4-yl]-1-(2-chlorophenyl)ethanone The title compound (224 mg, 67% yield) was obtained in the same manner as Example 1 from 150 mg of 3-tert-butoxypyrazine-2-carboxaldehyde and 271 mg of 1-(2-chlorophenyl)-2-(piperidin-4-yl)ethanone hydrochloride.

1H-NMR (400 MHz, CDCl3); δ(ppm) 1.35-1.47 (2H, m), 1.59 (9H, s), 1.69-1.77 (2H, m), 1.92-2.03 (1H, m), 2.15 (2H, dt, J=12.0, 2.4 Hz), 2.86 (2H, d, J=6.8 Hz), 2.93-2.99 (2H, m), 3.62 (2H, s), 7.28-7.42 (4H, m), 7.91 (1H, d, J=2.8 Hz), 8.04 (1H, d, J=2.8 Hz).

Example 43

(E)-2-tert-Butoxy-3-[4-[2-(3-fluorophenyl)vinyl]piperidino]methyl-pyrazine

The title compound (191 mg, 71% yield) was obtained in the same manner as Example 1 from 177 mg of 3-tert-butoxypyrazine-2-carboxaldehyde and 146 mg of (E)-4-[2-(3-fluorophenyl)vinyl]piperidine hydrochloride.

1H-NMR (400 MHz, CDCl3); δ (ppm) 1.54-1.66 (2H, m), 1.61 (9H, s), 1.70-1.78 (2H, m), 2.08-2.23 (3H, m), 3.00-

3.06 (2H, m), 3.66 (2H, s), 6.18 (1H, dd, J=16.0, 7.2 Hz), 6.33 (1H, d, J=16.0 Hz), 6.88 (1H, dt, J=8.8, 2.0 Hz), 7.04 (1H, dt, J=10.4, 2.0 Hz), 7.09 (1H, d, J=7.6 Hz), 7.21-7.27 (1H, m), 7.94 (1H, d, J=2.8 Hz), 8.06 (1H, d, J=2.8 Hz).

Example 44

2-tert-Butoxy-3-[4-[2-(2-fluorophenyl)ethyl]piperidino]methyl-pyrazine

The title compound (275 mg, 75% yield) was obtained in the same manner as Example 1 from 180 mg of 3-tert-butoxypyrazine-2-carboxaldehyde and 257 mg of 4-[2-(2-fluorophenyl)ethyl]piperidine hydrochloride.

1H-NMR (400 MHz, CDCl3); δ (ppm) 1.20-1.44 (3H, m), 1.50-1.58 (2H, m), 1.60 (9H, s), 1.68-1.76 (2H, m), 2.04-2.13 (2H, m), 2.60-2.67 (2H, m), 2.95-3.02 (2H, m), 3.63 (2H, s), 6.98 (1H, ddd, J=10.4, 8.0, 1.2 Hz), 7.04 (1H, dt, J=7.6, 2.0 Hz), 7.11-7.19 (2H, m), 7.91 (1H, d, J=2.8 Hz), 8.04 (1H, d, J=2.8 Hz).

Example 45

2-tert-Butoxy-3-[4-(phenoxymethyl)piperidino]methyl-pyrazine

The title compound (217 mg, 74% yield) was obtained in the same manner as Example 1 from 150 mg of 3-tert-butoxypyrazine-2-carboxaldehyde and 209 mg of 4-(phenoxymethyl)piperidine hydrochloride.

1H-NMR (400 MHz, CDCl3); δ (ppm) 1.41-1.54 (2H, m), 1.60 (9H, s), 1.75-1.86 (3H, m), 2.11-2.20 (2H, m), 3.01-3.07 (2H, m), 3.65 (2H, s), 3.79 (2H, d, J=6.0 Hz), 6.86-6.95 (3H, m), 7.24-7.30 (2H, m), 7.92 (1H, d, J=2.8 Hz), 8.05 (1H, d, J=2.8 Hz).

Example 46

2-tert-Butoxy-3-[4-(4-fluorophenoxymethyl)piperidino]methyl-pyrazine

The title compound (204 mg, 66% yield) was obtained in the same manner as Example 1 from 150 mg of 3-tert-butoxypyrazine-2-carboxaldehyde and 226 mg of 4-(4-fluorophenoxymethyl)piperidine hydrochloride.

1H-NMR (400 MHz, CDCl3); δ (ppm) 1.40-1.53 (2H, m), 1.60 (9H, s), 1.70-1.84 (3H, m), 2.11-2.19 (2H, m), 3.01-3.07 (2H, m), 3.65 (2H, s), 3.74 (2H, d, J=6.0 Hz), 6.77-6.84 (2H, m), 6.92-6.98 (2H, m), 7.92 (1H, d, J=2.8 Hz), 8.05 (1H, d, J=2.8 Hz).

Example 47

2-tert-Butoxy-3-[4-(2,6-difluorophenoxymethyl)piperidino]methyl-pyrazine

The title compound (214 mg, 66% yield) was obtained in the same manner as Example 1 from 150 mg of 3-tert-butoxypyrazine-2-carboxaldehyde and 242 mg of 4-(2,6-difluorophenoxymethyl)piperidine hydrochloride.

1H-NMR (400 MHz, CDCl3); δ (ppm) 1.38-1.50 (2H, m), 1.60 (9H, s), 1.74-1.88 (3H, m), 2.11-2.19 (2H, m), 2.99-3.06 (2H, m), 3.65 (2H, s), 3.95 (2H, d, J=6.4 Hz), 6.82-6.96 (3H, m), 7.92 (1H, d, J=2.8 Hz), 8.05 (1H, d, J=2.8 Hz).

Example 48

2-tert-Butoxy-3-[4-(2-fluorophenoxymethyl)piperidino]methyl-quinoxaline

The title compound (174 mg, 63% yield) was obtained in the same manner as Example 1 from 150 mg of 3-tert-butoxyquinoxaline-2-carboxaldehyde and 176 mg of 4-(2-fluorophenoxymethyl)piperidine hydrochloride.

1H-NMR (400 MHz, CDCl3); δ(ppm) 1.43-1.56 (2H, m), 1.71 (9H, s), 1.82-1.94 (3H, m), 2.19-2.28 (2H, m), 3.12-3.19 (2H, m), 3.81 (2H, s), 3.86 (2H, d, J=6.4 Hz), 6.84-6.90 (1H, m), 6.95 (1H, dt, J=8.0, 1.6 Hz), 7.01-7.09 (2H, m), 7.49 (1H, ddd, J=8.4, 7.2, 1.6 Hz), 7.58 (1H, ddd, J=8.4, 7.2, 1.6 Hz), 7.76 (1H, ddd, J=7.2, 1.6, 0.4 Hz), 8.00 (1H, ddd, J=7.2, 1.6, 0.4 Hz).

Example 49

1-[1-(3-tert-Butoxy-2-quinoxalinylmethyl)piperidin-4-yl]-2-(2-fluorophenyl)ethanone The title compound (150 mg, 53% yield) was obtained in the same manner as Example 1 from 150 mg of 3-tert-butoxyquinoxaline-2-carboxaldehyde and 185 mg of 2-(2-fluorophenyl)-1-(piperidin-4-yl)ethanone hydrochloride.

1H-NMR (400 MHz, CDCl3); δ(ppm) 1.70 (9H, s), 1.75-1.92 (4H, m), 2.21-2.30 (2H, m), 2.42-2.51 (1H, m), 3.10-3.17 (2H, m), 3.78 (4H, s), 7.01-7.11 (2H, m), 7.16 (1H, dt, J=7.6, 2.8 Hz), 7.21-7.28 (1H, m), 7.50 (1H, ddd, J=8.4, 7.2, 1.2 Hz), 7.59 (1H, ddd, J=8.4, 7.2, 1.2 Hz), 7.76 (1H, dd, J=8.4, 1.2 Hz), 7.99 (1H, dd, J=8.4, 1.2 Hz).

Example 50

2-tert-Butoxy-3-[4-[2-(2-fluorophenyl)-1-methoxyethyl]piperidino]methyl-pyrazine The title compound (138 mg, 80% yield) was obtained in the same manner as Example 21 from 93 mg of 3-tert-butoxypyrazine-2-carboxaldehyde and 102 mg of 4-[2-(2-fluorophenyl)-1-methoxyethyl]piperidine.

1H-NMR (400 MHz, CDCl3); δ (ppm) 1.38-1.68 (4H, m), 1.60 (9H, s), 1.76-1.82 (1H, m), 2.02-2.10 (2H, m), 2.67 (1H, dd, J=14.4, 8.8 Hz), 2.90 (1H, dd, J=14.4, 5.6 Hz), 3.00-3.08 (2H, m), 3.14-3.21 (1H, m), 3.18 (3H, s), 3.63 (2H, s), 7.00 (1H, ddd, J=9.2, 8.0, 1.2 Hz), 7.05 (1H, td, J=7.4, 1.2 Hz), 7.15-7.22 (1H, m), 7.22-7.27 (1H, m), 7.92 (1H, d, J=2.8 Hz), 8.04 (1H, d, J=2.8 Hz).

Example 51

1-[1-(3-tert-Butoxy-2-pyrazinylmethyl)piperidin-3-yl]-2-(2-fluorophenyl)ethanone 2-(2-Fluorophenyl)-1-(piperidin-3-yl)ethanone (398 mg, 100% yield) was obtained in the same manner as Production Example 116 from 564 mg of 1-[1-(tert-butoxycarbonyl)piperidin-3-yl]-2-(2-fluorophenyl)ethanone.

The title compound (193 mg, 69% yield) was then obtained in the same manner as Example 21 from 156 mg of 3-tert-butoxypyrazine-2-carboxaldehyde and 160 mg of 2-(2-fluorophenyl)-1-(piperidin-3-yl)ethanone.

1H-NMR (400 MHz, CDCl3); δ (ppm) 1.35-1.47 (1H, m), 1.55-1.77 (2H, m), 1.59 (9H, s), 1.88-1.96 (1H, m), 2.09-2.18 (1H, m), 2.25-2.34 (1H, m), 2.79-2.83 (2H, m), 3.04-3.10 (1H, m), 3.66 (2H, s), 3.75 (2H, s), 7.03 (1H, ddd, J=9.6, 7.8, 1.2 Hz), 7.07 (1H, td, J=7.8, 1.2 Hz), 7.12 (1H, td, J=7.8, 2.0 Hz), 7.20-7.28 (1H, m), 7.93 (1H, d, J=2.8 Hz), 8.04 (1H, d, J=2.8 Hz).

Example 52

2-tert-Butoxy-3-[4-(2-methyl-5-phenylpyrrol-1-yl)methyl-piperidino]methyl-pyrazine The title compound (110 mg, 65% yield) was obtained in the same manner as Example 6 from 160 mg of 3-tert-butoxypyrazine-2-carboxaldehyde and 103 mg of 4-(2-phenyl-5-methylpyrrol-1-yl)methyl-piperidine.

1H-NMR (400 MHz, CDCl3); δ (ppm) 1.08 (2H, ddd, J=25, 12.4, 4 Hz), 1.23-1.29 (2H, m), 1.34-1.48 (1H, m), 1.55 (9H, s), 1.85 (2H, td, J=11.8, 2.4 Hz), 2.29 (3H, s), 2.83 (2H, d, J=11.6 Hz), 3.52 (2H, s), 3.83 (2H, d, J=11.2 Hz), 5.94 (1H, d, J=3.2 Hz), 6.06 (1H, d, J=3.2 Hz), 7.23-7.28 (1H, m), 7.30-7.38 (4H, m), 7.88 (1H, d, J=2.6 Hz), 8.00 (1H, d, J=2.6 Hz).

Example 53

2-tert-Butoxy-3-[4-(3-phenyl-1,2,4-oxadiazol-5-yl)piperidino]methyl-pyrazine

The title compound (60 mg, 32% yield) was obtained in the same manner as Example 1 from 105 mg of 3-tert-butoxypyrazine-2-carboxaldehyde and 115 mg of 4-(3-phenyl-1,2,4-oxadiazol-5-yl)piperidine hydrochloride.

1H-NMR (400 MHz, CDCl3); δ (ppm) 1.61 (9H, s), 2.02-2.17 (4H, m), 2.34 (2H, td, J=11.2, 2.8 Hz), 2.96-3.04 (1H, m), 3.04-3.09 (2H, m), 3.68 (2H, s), 7.44-7.52 (3H, m), 7.95 (1H, d, J=2.8 Hz), 8.04-8.09 (3H, m).

Example 54

2-[1-(3-tert-Butoxy-2-pyrazinylmethyl)piperidin-4-yl]-4-fluoro-2,3-dihydro-isoindol-1-one The title compound (40 mg, 17% yield) was obtained in the same manner as Example 6 from 129 mg of 3-tert-butoxypyrazine-2-carboxaldehyde and 148 mg of 4-fluoro-2-(piperidin-4-yl)-2,3-dihydroisoindol-1-one.

1H-NMR (400 MHz, CDCl3); δ (ppm) 1.61 (9H, s), 1.78-1.83 (2H, m), 1.92 (2H, ddd, J=15.6, 12.0, 3.6 Hz), 2.33 (2H, td, J=11.8, 2.2 Hz), 3.08-3.15 (2H, m), 3.69 (2H, s), 4.29 (1H, tt, J=12.0, 4.4 Hz), 4.35 (2H, s), 7.08 (1H, t, J=8.8 Hz), 7.22 (1H, d, J=7.2 Hz), 7.43-7.54 (1H, m), 7.94 (1H, d, J=2.4 Hz), 8.06 (1H, d, J=2.4 Hz).

Example 55

2-[1-(3-tert-Butoxy-2-pyrazinylmethyl)piperidin-4-yl]methyl-4-fluoro-isoindole-1,3-dione The title compound (76 mg, 36% yield) was obtained in the same manner as Example 1 from 109 mg of 3-tert-butoxypyrazine-2-carboxaldehyde and 150 mg of 4-fluoro-2-(piperidin-4-ylmethyl)isoindole-1,3-dione hydrochloride.

1H-NMR (400 MHz, CDCl3); δ (ppm) 1.43 (2H, ddd, J=24.8, 12.8, 3.6 Hz), 1.58 (9H, s), 1.60-1.66 (1H, m), 1.70-1.84 (2H, m), 2.07 (2H, td, J=11.6, 2.2 Hz), 2.94-3.20 (2H, m), 3.58 (2H, d, J=6.8 Hz), 3.61 (2H, s), 7.34-7.39 (1H, m), 7.65 (1H, d, J=6.4 Hz), 7.71 (1H, ddd, J=8.4, 7.6, 4.4 Hz), 7.90 (1H, d, J=2.8 Hz), 8.02 (1H, d, J=2.8 Hz).

Example 56

2-tert-Butoxy-3-[4-[3-(2-fluorophenyl)-1,2,4-oxadiazol-5-yl]piperidino]methyl-pyrazine The title compound (61 mg, 61% yield) was obtained in the same manner as Example 1 from 57 mg of 3-tert-butoxypyrazine-2-carboxaldehyde and 69 mg of 4-[3-(2-fluorophenyl)-1,2,4-oxadiazol-5-yl]piperidine hydrochloride.

1H-NMR (400 MHz, CDCl3); δ (ppm) 1.61 (9H, s), 2.03-2.17 (4H, m), 2.34 (2H, td, J=11.4, 3.0 Hz), 2.97-3.10 (3H, m), 3.69 (2H, s), 7.22 (1H, ddd, J=10.4, 8.0, 1.0 Hz), 7.27 (1H, td, J=8.0, 1.4 Hz), 7.45-7.51 (1H, m), 7.95 (1H, d, J=2.4 Hz), 8.02-8.07 (2H, m).

Example 57

2-tert-Butoxy-3-[4-[3-(3-fluorophenyl)-1,2,4-oxadiazol-5-yl]piperidino]methyl-pyrazine The title compound (12 mg, 17% yield) was obtained in the same manner as Example 1 from 41 mg of 3-tert-butoxypyrazine-2-carboxaldehyde and 50 mg of 4-[3-(3-fluorophenyl)-1,2,4-oxadiazol-5-yl]piperidine hydrochloride.

1H-NMR (400 MHz, CDCl3); δ(ppm) 1.61 (9H, s), 2.01-2.16 (4H, m), 2.34 (2H, td, J=11.4, 3.0 Hz), 2.96-3.04 (1H, m), 3.04-3.10 (2H, m), 3.69 (2H, s), 7.19 (1H, tdd, J=8.4, 2.8, 1.2 Hz), 7.44 (1H, td, J=7.8, 5.6 Hz), 7.77 (1H, ddd, J=6.2, 2.4, 1.2 Hz), 7.86 (1H, ddd, J=8.0, 1.6, 1.2 Hz), 7.95 (1H, d, J=2.8 Hz), 8.05 (1H, d, J=2.8 Hz).

Example 58

2-tert-Butoxy-3-[4-[3-(4-fluorophenyl)-1,2,4-oxadiazol-5-yl]piperidino]methyl-pyrazine The title compound (16 mg, 50% yield) was obtained in the same manner as Example 1 from 22 mg of 3-tert-butoxypyrazine-2-carboxaldehyde and 22 mg of 4-[3-(4-fluorophenyl)-1,2,4-oxadiazol-5-yl]piperidine hydrochloride.

1H-NMR (400 MHz, CDCl3); δ (ppm) 1.61 (9H, s), 2.01-2.15 (4H, m), 2.32 (2H, td, J=11.6, 2.8 Hz), 2.95-3.03 (1H, m), 3.04-3.12 (2H, m), 3.69 (2H, s), 7.13-7.19 (2H, m), 7.95 (1H, d, J=2.8 Hz), 8.05 (1H, d, J=2.8 Hz), 8.06-8.09 (2H, m).

Example 59

2-tert-Butoxy-3-[2-[2-(2-fluorophenoxy)ethyl]piperidino]methyl-pyrazine

The title compound (15 mg, 14% yield) was obtained in the same manner as Example 6 from 63 mg of 3-tert-butoxypyrazine-2-carboxaldehyde and 60 mg of 2-[2-(2-fluorophenoxy)ethyl]piperidine.

1H-NMR (400 MHz, CDCl3); δ(ppm) 1.59 (9H, s), 1.36-1.62 (3H, m), 1.63-1.81 (3H, m), 1.99-2.08 (1H, m), 2.26-2.34 (1H, m), 2.39 (1H, quintet, J=6.2 Hz), 2.68-2.73 (1H, m), 2.95 (1H, tt, J=12.4, 4.8 Hz), 3.61 (1H, d, J=13.6 Hz), 3.97 (1H, d, J=13.6 Hz), 4.07-4.13 (2H, m), 6.82-6.88 (1H, m), 6.93-7.07 (3H, m), 7.87 (1H, d, J=2.8 Hz), 7.98 (1H, d, J=2.8 Hz).

Example 60

1-[1-(3-tert-Butoxy-2-pyrazinylmethyl)piperidin-4-yl]-2-(2-fluorophenyl)ethanone After suspending 295 mg of 2-(2-fluorophenyl)-1-(piperidin-4-yl)ethanone hydrochloride in 6 ml of dichloromethane, 247 mg of 3-tert-butoxypyrazine-2-carboxaldehyde and 364 mg of sodium triacetoxyborohydride were added while stirring on ice, and the stirring was continued for 3.5 days at room temperature. A 1N sodium hydroxide solution was added to the reaction mixture to render it alkaline, and then extraction was performed with ethyl acetate. The organic layer was washed with saturated brine and dried over anhydrous magnesium sulfate, and then the solvent was distilled off under reduced pressure. The residue was purified by silica gel column chromatography (solvent: n-hexane/ethyl acetate) to obtain the title compound (334 mg, 76% yield).

1H-NMR (400 MHz, CDCl3); δ(ppm) 1.60 (9H, s), 1.73-1.90 (4H, m), 2.14-2.22 (2H, m), 2.39-2.48 (1H, m), 2.99-3.06 (2H, m), 3.64 (2H, s), 3.77 (2H, s), 7.04 (1H, ddd, J=9.6, 7.8, 1.2 Hz), 7.09 (1H, td, J=7.8, 1.2 Hz), 7.15 (1H, td, J=7.8, 2.0 Hz), 7.21-7.28 (1H, m), 7.93 (1H, d, J=2.8 Hz), 8.04 (1H, d, J=2.8 Hz).

Example 61

1-[1-(3-tert-Butoxy-2-pyrazinylmethyl)piperidin-4-yl]-2-(2-chlorophenyl)ethanone After dissolving 252 mg of 1-(1-benzylpiperidin-4-yl)-2-(2-chlorophenyl)ethanone in 3 ml of 1,2-dichloroethane, 0.1 ml of 1-chloroethyl chloroformate was added while stirring on ice, and the mixture was heated to reflux for 1 hour. The reaction solution was concentrated under reduced pressure, 3 ml of methanol was added to the residue, and heating to reflux was continued for 30 minutes. The reaction solution was concentrated under reduced pressure, ethyl acetate was added to the residue and the precipitate was filtered out to obtain 171 mg of 4-(2-chlorophenylacetyl)piperidine hydrochloride. After then suspending 98 mg of the 4-(2-chlorophenylacetyl)piperidine hydrochloride in 3 ml of dichloromethane, 77 mg of 3-tert-butoxypyrazine-2-carboxaldehyde and 114 mg of sodium triacetoxyborohydride were added while stirring on ice, and the stirring was continued overnight at room temperature. A 1N sodium hydroxide solution was added to the reaction mixture to render it alkaline, and then extraction was performed with ethyl acetate. The organic layer was washed with saturated brine and dried over anhydrous magnesium sulfate, and then the solvent was distilled off under reduced pressure. The residue was purified by silica gel column chromatography (solvent: n-hexane/ethyl acetate) to obtain the title compound (112 mg, 78% yield).

1H-NMR (400 MHz, CDCl3); δ(ppm) 1.60 (9H, s), 1.74-1.92 (4H, m), 2.14-2.22 (2H, m), 2.42-2.50 (1H, m), 3.00-3.06 (2H, m), 3.64 (2H, s), 3.88 (2H, s), 7.16-7.23 (3H, m), 7.34-7.38 (1H, m), 7.93 (1H, d, J=2.8 Hz), 8.04 (1H, d, J=2.8 Hz).

Example 62

1-[1-(3-tert-Butoxy-2-pyrazinylmethyl)piperidin-4-yl]-2-(2,5-difluorophenyl)ethanone The title compound (162 mg, 62% yield, 2 steps) was obtained in the same manner as Example 61 from 215 mg of 1-(1-benzylpiperidin-4-yl)-2-(2,5-difluorophenyl)ethanone.

1H-NMR (400 MHz, CDCl3); δ(ppm) 1.60 (9H, s), 1.74-1.91 (4H, m), 2.15-2.24 (2H, m), 2.39-2.48 (1H, m), 3.00-3.06 (2H, m), 3.64 (2H, s), 3.75 (2H, d, J=1.2 Hz), 6.85-6.96 (2H, m), 6.96-7.03 (1H, m), 7.93 (1H, d, J=2.8 Hz), 8.04 (1H, d, J=2.8 Hz).

Example 63

1-[1-(3-tert-Butoxy-2-pyrazinylmethyl)piperidin-4-yl]-2-(3-methylphenyl)ethanone The title compound (108 mg, 36% yield, 2 steps) was obtained in the same manner as Example 61 from 241 mg of 1-(1-benzylpiperidin-4-yl)-2-(3-methylphenyl)ethanone.

1H-NMR (400 MHz, CDCl3); δ(ppm) 1.59 (9H, s), 1.69-1.84 (4H, m), 2.10-2.18 (2H, m), 2.33 (3H, s), 2.36-2.45 (1H, m), 2.96-3.04 (2H, m), 3.62 (2H, s), 3.69 (2H, s), 6.95-7.00 (2H, m), 7.06 (1H, d, J=7.6 Hz), 7.20 (1H, t, J=7.6 Hz), 7.93 (1H, d, J=2.8 Hz), 8.03 (1H, d, J=2.8 Hz).

Example 64

1-[1-(3-tert-Butoxy-2-pyrazinylmethyl)piperidin-4-yl]-2-(3-fluorophenyl)ethanone The title compound (132 mg, 38% yield, 2 steps) was obtained in the same manner as Example 61 from 283 mg of 1-(1-benzylpiperidin-4-yl)-2-(3-fluorophenyl)ethanone.

1H-NMR (400 MHz, CDCl3); δ(ppm) 1.60 (9H, s), 1.70-1.85 (4H, m), 2.11-2.20 (2H, m), 2.36-2.46 (1H, m), 2.98-3.05 (2H, m), 3.63 (2H, s), 3.73 (2H, s), 6.87-6.98 (3H, m), 7.24-7.32 (1H, m), 7.93 (1H, d, J=2.8 Hz), 8.03 (1H, d, J=2.8 Hz).

Example 65

1-[1-(3-tert-Butoxy-2-pyrazinylmethyl)piperidin-4-yl]-2-(2,6-difluorophenyl)ethanone The title compound (43 mg, 54% yield, 2 steps) was obtained in the same manner as Example 61 from 65 mg of 1-(1-benzylpiperidin-4-yl)-2-(2,6-difluorophenyl)ethanone.

1H-NMR (400 MHz, CDCl3); δ(ppm) 1.60 (9H, s), 1.78-1.94 (4H, m), 2.15-2.25 (2H, m), 2.42-2.52 (1H, m), 3.00-3.07 (2H, m), 3.65 (2H, s), 3.81 (2H, s), 6.83-6.92 (2H, m), 7.17-7.26 (1H, m), 7.93 (1H, d, J=2.8 Hz), 8.04 (1H, d, J=2.8 Hz).

Example 66

1-[1-(3-tert-Butoxy-2-pyrazinylmethyl)piperidin-4-yl]-2-(2-methylphenyl)ethanone After suspending 150 mg of 2-(2-methylphenyl)-1-(piperidin-4-yl)ethanone hydrochloride in 3 ml of dichloromethane, 128 mg of 3-tert-butoxypyrazine-2-carboxaldehyde and 188 mg of sodium triacetoxyborohydride were added while stirring on ice, and the stirring was continued overnight at room temperature. A 1N sodium hydroxide solution was added to the reaction mixture to render it alkaline, and then extraction was performed with ethyl acetate. The organic layer was washed with saturated brine and dried over anhydrous magnesium sulfate, and then the solvent was distilled off under reduced pressure. The residue was purified by NH silica gel column chromatography (solvent: n-hexane/ethyl acetate) to obtain the title compound (153 mg, 68% yield).

1H-NMR (400 MHz, CDCl3); δ(ppm) 1.59 (9H, s), 1.74-1.84 (4H, m), 2.11-2.20 (2H, m), 2.19 (3H, s), 2.37-2.46 (1H, m), 2.98-3.05 (2H, m), 3.63 (2H, s), 3.75 (2H, s), 7.04-7.10 (1H, m), 7.12-7.20 (3H, m), 7.93 (1H, d, J=2.8 Hz), 8.03 (1H, d, J=2.8 Hz).

Example 67

2-[1-(3-tert-Butoxy-2-pyrazinylmethyl)piperidin-4-yl]-1-(3-chloro-2-thienyl)ethanone The title compound (226 mg, 75% yield) was obtained in the same manner as Example 1 from 160 mg of 3-tert-butoxypyrazine-2-carboxaldehyde and 207 mg of 1-(3-chloro-2-thienyl)-2-(piperidin-4-yl)ethanone hydrochloride.

1H-NMR (400 MHz, CDCl3); δ (ppm) 1.38-1.50 (2H, m), 1.59 (9H, m), 1.70-1.78 (2H, m), 1.93-2.07 (1H, m), 2.12-2.20 (2H, m), 2.92 (2H, d, J=6.8 Hz), 2.93-3.00 (2H, m), 3.63 (2H, s), 7.02 (1H, d, J=5.4 Hz), 7.52 (1H, d, J=5.4 Hz), 7.92 (1H, d, J=2.4 Hz), 8.04 (1H, d, J=2.4 Hz).

Example 68

1-[1-(3-tert-Butoxy-2-pyrazinylmethyl)piperidin-4-yl ]-2-(2,3-difluorophenyl)ethanone The title compound (44 mg, 52% yield) was obtained in the same manner as Example 21 from 45 mg of 3-tert-butoxypyrazine-2-carboxaldehyde and 50 mg of 2-(2,3-difluorophenyl)-1-(piperidin-4-yl)ethanone.

1H-NMR (400 MHz, CDCl3); δ(ppm) 1.60 (9H, s), 1.68-1.90 (4H, m), 2.15-2.23 (2H, m), 2.41-2.49 (1H, m), 3.01-3.06 (2H, m), 3.64 (2H, s), 3.80 (2H, s), 6.88-6.92 (1H, m), 6.99-7.11 (2H, m), 7.93 (1H, d, J=2.8 Hz), 8.40 (1H, d, J=2.8 Hz).

Example 69

1-[1-(3-tert-Butoxy-2-pyrazinylmethyl)piperidin-4-yl]-2-phenylethanone

The title compound (54 mg, 50% yield) was obtained in the same manner as Example 21 from 64 mg of 3-tert-butoxypyrazine-2-carboxaldehyde and 60 mg of 2-phenyl-1-(piperidin-4-yl)ethanone.

1H-NMR (400 MHz, CDCl3); δ(ppm) 1.59 (9H, s), 1.60-1.65 (1H, m), 1.69-1.81 (4H, m), 2.16 (2H, dt, J=11.2, 4 Hz), 2.37-2.45 (1H, m), 3.00 (1H, td, J=11.6, 3 Hz), 3.62 (2H, s), 3.73 (2H, s), 7.16-7.19 (2H, m), 7.29-7.34 (3H, m), 7.92 (1H, d, J=2.6 Hz), 8.03 (1H, d, J=2.6 Hz).

Example 70

1-[1-(3-tert-Butoxy-2-pyrazinylmethyl)piperidin-4-yl]-2-(2,4-difluorophenyl)ethanone The title compound (33 mg, 57% yield) was obtained in the same manner as Example 21 from 30 mg of 3-tert-butoxypyrazine-2-carboxaldehyde and 33 mg of 2-(2,4-difluorophenyl)-1-(piperidin-4-yl)ethanone.

1H-NMR (400 MHz, CDCl3); δ (ppm) 1.60 (9H, s), 1.74-1.89 (4H, m), 2.18 (2H, dt, J=11.6, 2.8 Hz), 2.39-2.47 (1H, m), 3.03 (2H, td, J=12.0, 3.2 Hz), 3.64 (2H, s), 3.73 (2H, s), 6.78-6.86 (2H, m), 7.08-7.14 (1H, m), 7.94 (1H, d, J=2.8 Hz), 8.04 (1H, d, J=2.8 Hz).

Example 71

1-(3-tert-Butoxy-2-pyrazinylmethyl)-4-(2-methylphenoxymethyl)piperidin-4-ol

After adding 5 ml of 4N hydrogen chloride/ethyl acetate to 154 mg of 1-(tert-butoxycarbonyl)-4-hydroxy-4-(2-methylphenoxymethyl)piperidine, the mixture was stirred for 3 hours at room temperature. The solvent was distilled off under reduced pressure to obtain 4-hydroxy-4-(2-methylphenoxymethyl)piperidine hydrochloride (123 mg, 100% yield). The title compound (28 mg, 46% yield) was then obtained in the same manner as Example 1 from 29 mg of 3-tert-butoxypyrazine-2-carboxaldehyde and 41 mg of the 4-hydroxy-4-(2-methylphenoxymethyl)piperidine hydrochloride.

1H-NMR (400 MHz, CDCl3); δ(ppm) 1.59 (9H, s), 1.76-1.89 (4H, m), 2.24 (3H, s), 2.59 (2H, td, J=11.2, 3.6 Hz), 2.81 (2H, dt, J=12.0, 3.5 Hz), 3.70 (2H, s), 3.81 (2H, s), 6.80 (1H, d, J=8.4 Hz), 6.86-6.90 (1H, m), 7.13-7.17 (2H, m), 7.93 (1H, d, J=2.6 Hz), 8.05 (1H, d, J=2.6 Hz).

Example 72

1-(3-tert-Butoxy-2-pyrazinylmethyl)-4-(2-fluorophenoxymethyl)piperidin-4-ol 4-(2-Fluorophenoxymethyl)-4-hydroxypiperidine hydrochloride (98 mg, 100% yield) was obtained in the same manner as Example 71 from 103 mg of 1-(tert-butoxycarbonyl)-4-(2-fluorophenoxymethyl)-4-hydroxypiperidine.

The title compound (27 mg, 45% yield) was then obtained from 25 mg of 3-tert-butoxypyrazine-2-carboxaldehyde and 40 mg of 4-(2-fluorophenoxymethyl)-4-hydroxypiperidine hydrochloride.

1H-NMR (400 MHz, CDCl3); δ (ppm) 1.61 (9H, s), 1.76-1.87 (4H, m), 2.58 (2H, td, J=10.6, 4.8 Hz), 2.80 (2H, dt, J=11.6, 3.6 Hz), 3.69 (2H, s), 3.86 (2H, s), 6.88-6.98 (2H, m), 7.00-7.10 (2H, m), 7.93 (1H, d, J=2.6 Hz), 8.05 (1H, d, J=2.6 Hz).

Example 73

1-(3-tert-Butoxy-2-pyrazinylmethyl)-4-(2-methyl-5-phenylpyrrol-1-yl)methyl-piperidin-4-ol The title compound (43 mg, 76% yield) was obtained in the same manner as Example 6 from 23 mg of 3-tert-butoxypyrazine-2-carboxaldehyde and 35 mg of 4-hydroxy-4-(2-phenyl-5-methylpyrrol-1-yl)methyl-piperidine.

1H-NMR (400 MHz, CDCl3); δ (ppm) 1.20-1.60 (6H, m), 1.55 (9H, s), 2.20-2.29 (2H, m), 2.37 (3H, s), 2.53-2.65 (2H, m), 3.53 (2H, s), 5.90 (1H, d, J=3.6 Hz), 6.10 (1H, d, J=3.6 Hz), 7.23-7.27 (1H, m), 7.30-7.37 (4H, m), 7.88 (1H, d, J=2.6 Hz), 8.00 (1H, d, J=2.6 Hz).

Example 74

N-[1-(3-tert-Butoxy-2-pyrazinylmethyl)-4-hydroxypiperidin-4-yl]methyl-2-fluorobenzamide The title compound (18 mg, 52% yield) was obtained in the same manner as Example 6 from 23 mg of 3-tert-butoxypyrazine-2-carboxaldehyde and 21 mg of 2-fluoro-N-(4-hydroxypiperidin-4-yl)methyl-benzamide.

1H-NMR (400 MHz, CDCl3); δ (ppm) 1.59 (9H, s), 1.64-1.69 (2H, m), 1.72-1.80 (2H, m), 2.55 (2H, td, J=11.2, 3.2 Hz), 2.72-2.78 (2H, m), 3.50 (2H, d, J=6.0 Hz), 3.68 (2H, s), 6.62 (1H, t, J=6.0 Hz), 7.41-7.46 (2H, m), 7.48-7.53 (1H, m), 7.77-7.80 (2H, m), 7.92 (1H, d, J=2.6 Hz), 8.03 (1H, d, J=2.6 Hz).

Example 75

N-[1-(3-tert-Butoxy-2-pyrazinylmethyl)-4-hydroxypiperidin-4-yl]methyl-2-fluoro-N-(2-fluorobenzoyl)benzamide The title compound (7 mg, 32% yield) was obtained in the same manner as Example 6 from 9 mg of 3-tert-butoxypyrazine-2-carboxaldehyde and 15 mg of 2-fluoro-N-(2-fluorobenzoyl)-N-(4-hydroxypiperidin-4-yl)methyl-benzamide.
1H-NMR (400 MHz, CDCl3); δ (ppm) 1.58 (9H, s), 1.92-2.00 (2H, m), 2.39 (2H, d, J=10.0 Hz), 2.57 (2H, t, J=10.2 Hz), 2.80-2.86 (2H, m), 3.67 (2H, s), 4.08-4.09 (2H, m), 7.07-7.17 (2H, m), 7.20-7.27 (2H, m), 7.42-7.53 (2H, m), 7.90-7.97 (2H, m), 8.00-8.08 (2H, m).

Example 76

Ethyl 1-(3-tert-butoxy-2-pyrazinylmethyl)-4-(2-phenylethyl)piperidine-4-carboxylate The title compound (336 mg, 57% yield) was obtained in the same manner as Example 1 from 405 mg of 3-tert-butoxypyrazine-2-carboxaldehyde and 446 mg of 4-(ethoxycarbonyl)-4-(2-phenylethyl)piperidine hydrochloride.
1H-NMR (400 MHz, CDCl3); δ (ppm) 1.59 (9H, s), 1.28 (3H, t, J=7.0 Hz), 1.60-1.68 (2H, m), 1.74-1.83 (2H, m), 2.14-2.27 (4H, m), 2.48-2.53 (2H, m), 2.80-2.87 (2H, m), 3.60 (2H, s), 4.18 (2H, q, J=7.0 Hz), 7.12-7.19 (2H, m), 7.24-7.29 (3H, m), 7.91 (1H, d, J=2.8 Hz), 8.04 (1H, d, J=2.8 Hz).

Example 77

1-(3-tert-Butoxy-2-pyrazinylmethyl)-4-[(2-fluorophenyl)ethynyl]piperidin-4-ol

The title compound (102 mg, 69% yield) was obtained in the same manner as Example 1 from 90 mg of 3-tert-butoxypyrazine-2-carboxaldehyde and 98 mg of 4-hydroxy-4-[(2-fluorophenyl)ethynyl]piperidine hydrochloride.
1H-NMR (400 MHz, CDCl3); δ (ppm) 1.60 (9H, s), 1.94-2.05 (2H, m), 2.05-2.15 (2H, m), 2.59-2.67 (2H, m), 2.82-2.89 (2H, m), 3.70 (2H, s), 7.03-7.11 (2H, m), 7.27-7.32 (1H, m), 7.40 (1H, td, J=7.6, 1.6 Hz), 7.93 (1H, d, J=2.8 Hz), 8.04 (1H, d, J=2.8 Hz).

Example 78

1-(3-tert-Butoxy-2-pyrazinylmethyl)-4-[(2-methylphenyl)ethynyl]piperidin-4-ol

4-Hydroxy-4-[(2-methylphenyl)ethynyl]piperidine hydrochloride (1.1 g, 100% yield) was obtained in the same manner as Example 71 from 1.22 g of 1-(tert-butoxycarbonyl)-4-hydroxy-4-[(2-methylphenyl)ethynyl]piperidine.
The title compound (103 mg, 76% yield) was then obtained from 84 mg of 3-tert-butoxypyrazine-2-carboxaldehyde and 90 mg of the 4-hydroxy-4-[(2-methylphenyl)ethynyl]piperidine hydrochloride.
1H-NMR (400 MHz, CDCl3); δ (ppm) 1.60 (9H, s), 1.95-2.01 (2H, m), 2.04-2.10 (2H, m), 2.39 (3H, s), 2.56-2.66 (2H, m), 2.85-2.90 (2H, m), 3.70 (2H, s), 7.13 (1H, td, J=7.2, 2.0 Hz), 7.16-7.24 (2H, m), 7.38 (1H, d, J=7.2 Hz), 7.93 (1H, d, J=2.8 Hz), 8.05 (1H, d, J=2.8 Hz).

Example 79

1-(3-tert-Butoxy-2-pyrazinylmethyl)-4-(2-phenylethyl)piperidine-4-methanol

The title compound (62 mg, 23% yield) was obtained in the same manner as Example 3 from 306 mg of ethyl 1-(3-tert-butoxy-2-pyrazinylmethyl)-4-(2-phenylethyl)-4-piperidinecarboxylate.
1H-NMR (400 MHz, CDCl3); δ(ppm) 1.39-1.59 (2H, m), 1.60 (9H, s), 1.64-1.76 (4H, m), 2.49-2.63 (6H, m), 3.55 (2H, s), 3.65 (2H, s), 7.16-7.21 (3H, m), 7.26-7.30 (2H, m), 7.92 (1H, d, J=2.4 Hz), 8.04 (1H, d, J=2.4 Hz).

Example 80

1-(3-tert-Butoxy-2-pyrazinylmethyl)-4-[2-(2-fluorophenyl)ethyl]piperidin-4-ol

The title compound (19 mg, 18% yield) was obtained in the same manner as Example 1 from 54 mg of 3-tert-butoxypyrazine-2-carboxaldehyde and 54 mg of 4-[2-(2-fluorophenyl)ethyl]-4-hydroxypiperidine hydrochloride.
1H-NMR (400 MHz, CDCl3); δ (ppm) 1.60 (9H, s), 1.73-1.84 (4H, m), 2.45-2.54 (4H, m), 2.72-2.80 (4H, m), 3.68 (2H, s), 6.99 (1H, ddd, J=9.6, 8.0, 0.8 Hz), 7.05 (1H, td, J=7.4, 1.2 Hz), 7.13-7.21 (2H, m), 7.92 (1H, d, J=2.8 Hz), 8.05 (1H, d, J=2.8 Hz).

Example 81

1-(3-tert-Butoxy-2-pyrazinylmethyl)-4-(2-fluorophenoxymethyl)piperidine-4-carbonitrile The title compound (55 mg, 33% yield) was obtained in the same manner as Example 1 from 98 mg of 3-tert-butoxypyrazine-2-carboxaldehyde and 113 mg of 4-cyano-4-(2-fluorophenoxymethyl)piperidine hydrochloride.
1H-NMR (400 MHz, CDCl3); δ (ppm) 1.61 (9H, s), 1.86 (2H, td, J=13.2, 3.2 Hz), 2.10 (2H, dd, J=13.2, 2.2 Hz), 2.54 (2H, td, J=12.2, 2.2 Hz), 3.03-3.09 (2H, m), 3.72 (2H, s), 4.03 (2H, s), 6.93-7.01 (2H, m), 7.03-7.11 (2H, m), 7.94 (1H, d, J=2.8 Hz), 8.05 (1H, d, J=2.8 Hz).

Example 82

1-(3-tert-Butoxy-2-pyrazinylmethyl)-4-(2-methylphenoxymethyl)piperidine-4-carbonitrile The title compound (47 mg, 24% yield) was obtained in the same manner as Example 1 from 115 mg of 3-tert-butoxypyrazine-2-carboxaldehyde and 131 mg of 4-cyano-4-(2-methylphenoxymethyl)piperidine hydrochloride.
1H-NMR (400 MHz, CDCl3); δ (ppm) 1.63 (9H, s), 1.86 (2H, td, J=13.2, 3.5 Hz), 2.10-2.15 (2H, m), 2.29 (3H, s), 2.44-2.60 (2H, m), 3.05-3.10 (2H, m), 3.74 (2H, s), 3.97 (2H, s), 6.74-6.78 (1H, m), 6.88-6.94 (1H, m), 7.14-7.18 (2H, m), 7.96 (1H, d, J=2.6 Hz), 8.07 (1H, d, J=2.6 Hz).

Example 83

1-(3-tert-Butoxy-2-pyrazinylmethyl)-4-[2-(2-methylphenyl)ethyl]piperidin-4-ol

The title compound (138 mg, 71% yield) was obtained in the same manner as Example 1 from 119 mg of 3-tert-butoxypyrazine-2-carboxaldehyde and 130 mg of 4-hydroxy-4-[2-(2-methylphenyl)ethyl]piperidine hydrochloride.

1H-NMR (400 MHz, CDCl3); δ (ppm) 1.60 (9H, s), 1.60-1.72 (4H, m), 1.84 (2H, td, J=13.6, 4.4 Hz), 2.30 (3H, s), 2.51 (2H, td, J=11.4, 2.4 Hz), 2.66-2.71 (2H, m), 2.75-2.82 (2H, m), 3.68 (2H, s), 7.07-7.15 (4H, m), 7.92 (1H, d, J=2.8 Hz), 8.05 (1H, d, J=2.8 Hz).

Example 84

2-tert-Butoxy-3-[4-fluoro-4-(2-fluorophenoxymethyl)piperidino]methyl-pyrazine

4-Fluoro-4-(2-fluorophenoxymethyl)piperidine hydrochloride (119 mg, 100% yield) was obtained in the same manner as Example 71 from 150 mg of 1-(tert-butoxycarbonyl)-4-fluoro-4-(2-fluorophenoxymethyl)piperidine.

The title compound (18 mg, 20% yield) was then obtained from 53 mg of 3-tert-butoxypyrazine-2-carboxaldehyde and 60 mg of the 4-fluoro-4-(2-fluorophenoxymethyl)piperidine hydrochloride.

1H-NMR (400 MHz, CDCl3); δ (ppm) 1.61 (9H, s), 1.86-1.95 (2H, m), 1.98-2.06 (2H, m), 2.49-2.56 (2H, m), 2.85-2.91 (2H, m), 3.69 (2H, s), 4.02 (2H, d, J=18.8 Hz), 6.89-6.96 (1H, m), 6.98 (1H, dd, J=8.0, 1.6 Hz), 7.00-7.10 (2H, m), 7.93 (1H, d, J=2.6 Hz), 8.05 (1H, d, J=2.6 Hz).

Example 85

2-tert-Butoxy-3-[4-(2-fluorophenoxymethyl)-4-[2-(2-fluorophenyl)ethyl]piperidino]methyl-pyrazine The title compound (40 mg, 40% yield) was obtained in the same manner as Example 1 from 47 mg of 3-tert-butoxypyrazine-2-carboxaldehyde and 74 mg of 4-(2-fluorophenoxymethyl)-4-[2-(2-fluorophenyl)ethyl]piperidine hydrochloride.

1H-NMR (400 MHz, CDCl3); δ (ppm) 1.60 (9H, s), 1.69-1.87 (6H, m), 2.51-2.65 (6H, m), 3.66 (2H, s), 3.89 (2H, s), 6.84-7.26 (8H, m), 7.90-7.93 (1H, m), 8.03-8.05 (1H, m).

Example 86

2-tert-Butoxy-3-[4-[2-(2-fluorophenyl)ethyl]-4-(2-methylphenoxymethyl)piperidino]methyl-pyrazine The title compound (21 mg, 18% yield) was obtained in the same manner as Example 1 from 56 mg of 3-tert-butoxypyrazine-2-carboxaldehyde and 87 mg of 4-[2-(2-fluorophenyl)ethyl]-4-(2-methylphenoxymethyl)piperidine hydrochloride.

1H-NMR (400 MHz, CDCl3); δ (ppm) 1.60 (9H, s), 1.67-1.87 (6H, m), 2.25 (3H, s), 2.55-2.63 (6H, m), 3.66 (2H, s), 3.80 (2H, s), 6.74-6.91 (2H, m), 6.95-7.04 (2H, m), 7.05-7.22 (4H, m), 7.92 (1H, d, J=2.6 Hz), 8.04 (1H, d, J=2.6 Hz).

Example 87

7-(3-tert-Butoxy-2-pyrazinylmethyl)-2-(2-fluorophenoxy)-7-azaspiro[3.5]nonane 2-(2-Fluorophenoxy)-7-azaspiro[3.5]nonane hydrochloride (176 mg) was obtained in the same manner as Example 71 from 163 mg of 7-(tert-butoxycarbonyl)-2-(2-fluorophenoxy)-7-azaspiro[3.5]nonane.

The title compound (33 mg, 38% yield) was then obtained from 51 mg of 3-tert-butoxypyrazine-2-carboxaldehyde and 59 mg of 2-(2-fluorophenoxy)-7-azaspiro[3.5]nonane hydrochloride.

1H-NMR (400 MHz, CDCl3); δ (ppm) 1.57 (9H, s), 1.66-1.72 (4H, m), 1.94-2.01 (2H, m), 2.35-2.40 (2H, m), 2.45 (2H, brs), 2.51 (2H, brs), 3.60 (2H, s), 4.68 (1H, quintet, J=6.8 Hz), 6.79 (1H, td, J=8.2, 1.6 Hz), 6.86 (1H, tdd, J=7.8, 4.4, 1.6 Hz), 6.99-7.03 (1H, m), 7.06 (1H, ddd, J=11.4, 7.8, 1.6 Hz), 7.92 (1H, d, J=2.8 Hz), 8.04 (1H, d, J=2.8 Hz).

Example 88

2-tert-Butoxy-3-[4-[2-(2-methylphenyl)ethyl]azepan-1-yl]methyl-pyrazine

The title compound (109 mg, 72% yield) was obtained in the same manner as Example 21 from 105 mg of 3-tert-butoxypyrazine-2-carboxaldehyde and 84 mg of 4-[2-(2-methylphenyl)ethyl]azepane.

1H-NMR (400 MHz, CDCl3); δ (ppm) 1.34-1.52 (4H, m), 1.60 (9H, s), 1.61-1.67 (2H, m), 1.71-1.84 (3H, m), 2.29 (3H, s), 2.55-2.59 (2H, m), 2.68 (1H, ddd, J=13.0, 9.6, 3.0 Hz), 2.76-2.80 (2H, m), 2.88 (1H, ddd, J=13.0, 7.2, 3.0 Hz), 3.75-3.76 (2H, m), 7.06-7.14 (4H, m), 7.91 (1H, d, J=2.8 Hz), 8.02 (1H, d, J=2.8 Hz).

Example 89

4-tert-Butoxy-5-[4-(2-fluorophenoxymethyl)piperidino]methyl-pyrimidine

After dissolving 976 mg of ethyl 4-tert-butoxypyrimidine-5-carboxylate in 15 ml of toluene, the solution was cooled to −78° C. 3.2 ml of diisobutylaluminium hydride (1.5 M, toluene solution) was added dropwise while stirring, and then after 30 minutes, an aqueous solution of potassium sodium (+)-tartrate was added and the mixture was stirred at room temperature. Water was added to the reaction solution and extraction was performed with ethyl acetate. The organic layer was washed with water and saturated brine in that order and dried over anhydrous magnesium sulfate, and then the solvent was distilled off under reduced pressure to obtain 0.85 g of crude 4-tert-butoxypyrimidine-5-carboxaldehyde.

This was dissolved in 5 ml of dichloromethane, and then 200 mg of 4-(2-fluorophenoxymethyl)piperidine hydrochloride and 259 mg of sodium triacetoxyborohydride were added and the mixture was stirred overnight at room temperature. Aqueous sodium bicarbonate solution was added to the reaction mixture and extraction was performed with ethyl acetate. The organic layer was washed with water and saturated brine in that order and dried over anhydrous magnesium sulfate, and then the solvent was distilled off under reduced pressure. The residue was purified by silica gel column chromatography (solvent: n-hexane/ethyl acetate) to obtain the title compound (167 mg, 55% yield).

1H-NMR (400 MHz, CDCl3); δ (ppm) 1.34-1.49 (2H, m), 1.63 (9H, s), 1.75-1.92 (3H, m), 2.07-2.15 (2H, m), 2.89-2.96 (2H, m), 3.45 (2H, s), 3.86 (2H, d, J=6.0 Hz), 6.85-6.91 (1H, m), 6.95 (1H, dt, J=8.0, 1.6 Hz), 7.01-7.10 (2H, m), 8.41 (1H, s), 8.61 (1H, s).

Example 90

2-tert-Butoxy-3-[4-[2-(2-fluorophenoxy)ethyl]piperidino]methyl-pyrazine

The title compound (244 mg, 81% yield) was obtained in the same manner as Example 1 from 161 mg of 3-tert-butoxypyrazine-2-carboxaldehyde and 202 mg of 4-[2-(2-fluorophenoxy)ethyl]piperidine hydrochloride.

1H-NMR (400 MHz, CDCl3); δ(ppm) 1.34-1.47 (2H, m), 1.50-1.66 (1H, m), 1.60 (9H, s), 1.67-1.80 (4H, m), 2.08-2.17 (2H, m), 2.94-3.03 (2H, m), 3.63 (2H, s), 4.06 (2H, t, J=6.4 Hz), 6.84-6.91 (1H, m), 6.95 (1H, td, J=8.2, 1.6 Hz), 7.01-7.10 (2H, m), 7.92 (1H, d, J=2.8 Hz), 8.04 (1H, d, J=2.8 Hz).

Example 91

2-tert-Butoxy-3-[2-[4-(2-fluorophenoxymethyl)piperidino]ethyl]pyrazine

After adding 139 mg of (Z)-2-tert-butoxy-3-(2-methoxyvinyl)pyrazine and 196 mg of 4-(2-fluorophenoxymethyl)piperidine hydrochloride in 5 ml of dichloromethane, 213 mg of sodium triacetoxyborohydride was added and the mixture was stirred overnight at room temperature. Aqueous sodium carbonate solution was added to the reaction mixture and extraction was performed with ethyl acetate. The organic layer was washed with water and saturated brine in that order and dried over anhydrous magnesium sulfate, and then the solvent was distilled off under reduced pressure. The residue was purified by silica gel column chromatography (solvent: n-hexane/ethyl acetate) to obtain the title compound (26 mg, 10% yield).

1H-NMR (400 MHz, CDCl3); δ(ppm) 1.36-1.48 (2H, m), 1.60 (9H, s), 1.82-1.93 (3H, m), 2.09-2.17 (2H, m), 2.74-2.80 (2H, m), 2.96-3.01 (2H, m), 3.03-3.10 (2H, m), 3.87 (2H, d, J=6.4 Hz), 6.85-6.91 (1H, m), 6.95 (1H, dt, J=8.0, 1.6 Hz), 7.01-7.10 (2H, m) 7.89 (1H, d, J=2.8 Hz), 7.94 (1H, d, J=2.8 Hz).

Example 92

2-tert-Butoxy-3-[4-(2-fluorobenzyloxymethyl)piperidino]methyl-pyrazine

The title compound (259 mg, 95% yield) was obtained in the same manner as Example 1 from 152 mg of 3-tert-butoxypyrazine-2-carboxaldehyde and 183 mg of 4-(2-fluorobenzyloxymethyl)piperidine hydrochloride.

1H-NMR (400 MHz, CDCl3); δ(ppm) 1.30-1.42 (2H, m), 1.55-1.78 (3H, m), 1.60 (9H, s), 2.06-2.16 (2H, m), 2.97-3.04 (2H, m), 3.35 (2H, d, J=6.8 Hz), 3.64 (2H, s), 4.57 (2H, s), 7.03 (1H, ddd, J=9.6, 7.8, 1.2 Hz), 7.13 (1H, td, J=7.8, 1.2 Hz), 7.22-7.31 (1H, m), 7.42 (1H, td, J=7.8, 1.2 Hz), 7.92 (1H, d, J=2.8 Hz), 8.05 (1H, d, J=2.8 Hz).

Example 93

(E)-2-tert-Butoxy-3-[4-[2-(3-chloro-2-thienyl)vinyl]piperidino]methyl-pyrazine

The title compound (259 mg, 80% yield) was obtained in the same manner as Example 1 from 175 mg of 3-tert-butoxypyrazine-2-carboxaldehyde and 211 mg of (E)-4-[2-(3-chloro-2-thienyl)vinyl]piperidine hydrochloride.

1H-NMR (400 MHz, CDCl3); δ(ppm) 1.53-1.66 (2H, m), 1.61 (9H, s), 1.70-1.78 (2H, m), 2.08-2.22 (3H, m), 2.99-3.05 (2H, m), 3.65 (2H, s), 6.04 (1H, dd, J=16.0, 7.2 Hz), 6.56 (1H, ddd, J=16.0, 1.2, 0.8 Hz), 6.83 (1H, d, J=5.4 Hz), 7.05 (1H, dd, J=5.4, 0.8 Hz), 7.93 (1H, d, J=2.8 Hz), 8.05 (1H, d, J=2.8 Hz).

Example 94

2-tert-Butoxy-3-[4-[2-(3-fluoro-2-thienyl)ethyl]piperidino]methyl-pyrazine

The title compound (69 mg, 35% yield) was obtained in the same manner as Example 21 from 113 mg of 3-tert-butoxypyrazine-2-carboxaldehyde and 112 mg of 4-[2-(3-fluoro-2-thienyl)ethyl]piperidine.

1H-NMR (400 MHz, CDCl3); δ(ppm) 1.24-1.40 (3H, m), 1.52-1.73 (4H, m), 1.59 (9H, s), 2.03-2.12 (2H, m), 2.70-2.76 (2H, m), 2.94-3.01 (2H, m), 3.62 (2H, s), 6.72 (1H, dd, J=5.6, 0.8 Hz), 6.96 (1H, dd, J=5.6, 4.0 Hz), 7.91 (1H, d, J=2.8 Hz), 8.04 (1H, d, J=2.8 Hz).

Example 95

(E)-2-tert-Butoxy-3-[4-[2-(3-fluoro-2-thienyl)vinyl]piperidino]methyl-pyrazine

The title compound (242 mg, 94% yield) was obtained in the same manner as Example 1 from 147 mg of 3-tert-butoxypyrazine-2-carboxaldehyde and 169 mg of (E)-4-[2-(3-fluoro-2-thienyl)vinyl]piperidine hydrochloride.

1H-NMR (400 MHz, CDCl3); δ(ppm) 1.50-1.64 (2H, m), 1.60 (9H, s), 1.69-1.76 (2H, m), 2.04-2.21 (3H, m), 2.98-3.05 (2H, m), 3.64 (2H, s), 5.93 (1H, dd, J=16.0, 6.8 Hz), 6.44 (1H, dd, J=16.0, 0.8 Hz), 6.72 (1H, dd, J=5.6, 0.8 Hz), 6.94 (1H, dd, J=5.6, 4.0 Hz), 7.93 (1H, d, J=2.8 Hz), 8.05 (1H, d, J=2.8 Hz).

Example 96

2-tert-Butoxy-3-[4-[(1-(2-fluorophenoxy)ethyl]piperidino]methyl-pyrazine

The title compound (400 mg, 96% yield) was obtained in the same manner as Example 21 from 231 mg of 3-tert-butoxypyrazine-2-carboxaldehyde and 239 mg of 4-[1-(2-fluorophenoxy)ethyl]piperidine.

1H-NMR (400 MHz, CDCl3); δ(ppm) 1.26 (3H, d, J=6.4 Hz), 1.42-1.58 (2H, m), 1.60 (9H, s), 1.60-1.77 (2H, m), 1.88-1.96 (1H, m), 2.07-2.16 (2H, m), 3.01-3.09 (2H, m), 3.64 (2H, s), 4.09-4.16 (1H, m), 6.85-6.91 (1H, m), 6.95 (1H, td, J=8.4, 2.0 Hz), 7.00-7.09 (2H, m), 7.92 (1H, d, J=2.8 Hz), 8.04 (1H, d, J=2.8 Hz).

Example 97

2-tert-Butoxy-6-[2-[4-(2-fluorophenoxymethyl)piperidino]ethyl]pyrazine

After dissolving 262 mg of 2-tert-butoxy-6-vinylpyrazine and 401 mg of 4-(2-fluorophenoxymethyl)piperidine [CAS No. 63608-34-4] in 3 ml of ethanol, the mixture was stirred for 2 days at 80° C. The reaction solution was concentrated under reduced pressure, and the residue was purified by NH silica gel column chromatography (solvent: n-hexane/ethyl acetate) to obtain the title compound (67 mg, 12% yield).

1H-NMR (400 MHz, CDCl3); δ(ppm) 1.35-1.48 (2H, m), 1.59 (9H, s), 1.82-1.94 (3H, m), 2.04-2.13 (2H, m), 2.73-2.79 (2H, m), 2.85-2.91 (2H, m), 3.00-3.06 (2H, m), 3.87 (2H, d, J=6.4 Hz), 6.85-6.91 (1H, m), 6.95 (1H, dt, J=8.0, 1.6 Hz), 7.02-7.10 (2H, m), 7.91 (1H, s), 7.93 (1H, s).

Example 98

2-tert-Butoxy-6-[2-[4-(2-methoxyphenoxymethyl)piperidino]ethyl]pyrazine

The title compound (305 mg, 33% yield) was obtained in the same manner as Example 97 from 418 mg of 2-tert-butoxy-6-vinylpyrazine and 510 mg of 4-(2-methoxyphenoxymethyl)piperidine [CAS No. 63608-36-6].

1H-NMR (400 MHz, CDCl3); δ (ppm) 1.34-1.46 (2H, m), 1.59 (9H, s), 1.88-1.99 (3H, m), 2.04-2.12 (2H, m), 2.73-2.78 (2H, m), 2.85-2.91 (2H, m), 2.99-3.06 (2H, m), 3.86 (2H, d, J=6.0 Hz), 3.86 (3H, s), 6.87-9.65 (4H, m), 7.91 (1H, s), 7.93 (1H, s).

Example 99

2-tert-Butoxy-6-[2-[4-(2,3-difluorophenoxymethyl)piperidino]ethyl]pyrazine

The title compound (172 mg, 19% yield) was obtained in the same manner as Example 97 from 384 mg of 2-tert-butoxy-6-vinylpyrazine and 490 mg of 4-(2,3-difluorophenoxymethyl)piperidine.

1H-NMR (400 MHz, CDCl3); δ(ppm) 1.36-1.48 (2H, m), 1.60 (9H, s), 1.82-1.94 (3H, m), 2.05-2.13 (2H, m), 2.74-2.80 (2H, m), 2.85-2.91 (2H, m), 3.00-3.07 (2H, m), 3.87 (2H, d, J=6.4 Hz), 6.69-6.80 (2H, m), 6.93-7.00 (1H, m), 7.91 (1H, s), 7.94 (1H, s).

Example 100

2-tert-Butoxy-6-[2-[4-[2-(2-fluorophenyl)ethyl]piperidino]ethyl]pyrazine

The title compound (309 mg, 47% yield) was obtained in the same manner as Example 97 from 311 mg of 2-tert-butoxy-6-vinylpyrazine and 362 mg of 4-[2-(2-fluorophenyl)ethyl]piperidine.

1H-NMR (400 MHz, CDCl3); δ(ppm) 1.24-1.37 (3H, m), 1.53-1.62 (2H, m), 1.59 (9H, s), 1.74-1.82 (2H, m), 1.96-2.05 (2H, m), 2.63-2.69 (2H, m), 2.70-2.76 (2H, m), 2.84-2.90 (2H, m), 2.95-3.01 (2H, m), 6.97-7.03 (1H, m), 7.05 (1H, dt, J=7.2, 1.2 Hz), 7.13-7.21 (2H, m), 7.90 (1H, s), 7.93 (1H, s).

Example 101

2-tert-Butoxy-6-[2-[4-[(2-fluorophenyl)ethynyl]piperidino]ethyl]pyrazine

The title compound (59 mg, 10% yield) was obtained in the same manner as Example 97 from 286 mg of 2-tert-butoxy-6-vinylpyrazine and 326 mg of 4-[(2-fluorophenyl)ethynyl]piperidine.

1H-NMR (400 MHz, CDCl3); δ(ppm) 1.59 (9H, s), 1.74-1.85 (2H, m), 1.92-2.01 (2H, m), 2.28-2.40 (2H, m), 2.70 (1H, br s), 2.74-2.91 (6H, m), 7.02-7.09 (2H, m), 7.22-7.28 (1H, m), 7.39 (1H, dt, J=7.2, 1.6 Hz), 7.91 (1H, s), 7.94 (1H, s).

Example 102

2-tert-Butoxy-6-[2-[3-(2-fluorophenoxymethyl)piperidino]ethyl]pyrazine

The title compound (160 mg, 24% yield) was obtained in the same manner as Example 97 from 300 mg of 2-tert-butoxy-6-vinylpyrazine and 352 mg of 3-(2-fluorophenoxymethyl)piperidine.

1H-NMR (400 MHz, CDCl3); δ(ppm) 1.12-1.23 (1H, m), 1.59 (9H, s), 1.58-1.68 (1H, m), 1.69-1.85 (2H, m), 1.98-2.22 (3H, m), 2.70-2.84 (5H, m), 3.08 (1H, d, J=9.6 Hz), 3.88 (1H, dd, J=9.6, 7.2 Hz), 3.92 (1H, dd, J=5.6, 9.6 Hz), 6.85-6.92 (1H, m), 6.94 (1H, dt, J=8.0, 1.6 Hz), 7.01-7.10 (2H, m), 7.89 (1H, s), 7.92 (1H, s).

Example 103

2-tert-Butoxy-6-[2-[4-(2,6-difluorophenoxymethyl)piperidino]ethyl]pyrazine

The title compound (316 mg, 39% yield) was obtained in the same manner as Example 97 from 363 mg of 2-tert-butoxy-6-vinylpyrazine and 463 mg of 4-(2,6-difluorophenoxymethyl)piperidine.

1H-NMR (400 MHz, CDCl3); δ (ppm) 1.34-1.45 (2H, m), 1.59 (9H, s), 1.76-1.93 (3H, m), 2.04-2.12 (2H, m), 2.72-2.78 (2H, m), 2.85-2.91 (2H, m), 2.99-3.06 (2H, m), 3.97 (2H, d, J=6.0 Hz), 6.83-6.98 (3H, m), 7.91 (1H, s), 7.93 (1H, s).

Example 104

2-tert-Butoxy-6-[2-[4-(2,5-difluorophenoxymethyl)piperidino]ethyl]pyrazine

The title compound (236 mg, 26% yield) was obtained in the same manner as Example 97 from 402 mg of 2-tert-butoxy-6-vinylpyrazine and 504 mg of 4-(2,5-difluorophenoxymethyl)piperidine.

1H-NMR (400 MHz, CDCl3); δ (ppm) 1.35-1.49 (2H, m), 1.59 (9H, s), 1.83-1.94 (3H, m), 2.04-2.16 (2H, m), 2.72-2.81 (2H, m), 2.84-2.92 (2H, m), 3.00-3.08 (2H, m), 3.83 (2H, d, J=6.0 Hz), 6.52-6.59 (1H, m), 6.64-6.70 (1H, m), 6.96-7.04 (1H, m), 7.90 (1H, s), 7.93 (1H, s).

Example 105

2-[1-[2-(6-tert-Butoxypyrazin-2-yl)ethyl]piperidin-4-yl]-1-(2-fluorophenyl)ethanone The title compound (93 mg, 14% yield) was obtained in the same manner as Example 97 from 295 mg of 2-tert-butoxy-6-vinylpyrazine and 463 mg of 1-(2-fluorophenyl)-2-(piperidin-4-yl)ethanone.

1H-NMR (400 MHz, CDCl3); δ (ppm) 1.35-1.49 (2H, m), 1.58 (9H, s), 1.75-1.83 (2H, m), 1.94-2.18 (3H, m), 2.67-3.04 (8H, m), 7.24-7.28 (1H, m), 7.40-7.48 (1H, m), 7.59-7.64 (1H, m), 7.70-7.74 (1H, m), 7.90 (1H, s), 7.92 (1H, s).

Example 106

1-[2-(6-tert-Butoxypyrazin-2-yl)ethyl]-4-(2-fluorophenoxymethyl)piperidin-4-ol

The title compound (274 mg, 31% yield) was obtained in the same manner as Example 97 from 398 mg of 2-tert-butoxy-6-vinylpyrazine and 503 mg of 4-(2-fluorophenoxymethyl)-4-hydroxypiperidine.

1H-NMR (400 MHz, CDCl3); δ (ppm) 1.59 (9H, s), 1.71-1.87 (4H, m), 2.25 (1H, br s), 2.48-2.57 (2H, m), 2.74-2.84 (4H, m), 2.88-2.92 (2H, m), 3.87 (2H, s), 6.89-7.00 (2H, m), 7.03-7.12 (2H, m), 7.91 (1H, s), 7.94 (1H, s).

Example 107

7-[2-(6-tert-Butoxypyrazin-2-yl)ethyl]-2-(2-fluorophenoxy)-7-azaspiro[3.5]nonane The title compound (7 mg, 8% yield) was obtained in the same manner as Example 97 from 47 mg of 2-tert-butoxy-6-vinylpyrazine and 52 mg of 2-(2-fluorophenoxy)-7-azaspiro[3.5]nonane.

1H-NMR (400 MHz, CDCl3); δ(ppm) 1.59 (9H, s), 1.65-1.71 (4H, m), 1.99 (2H, dd, J=13.2, 6.4 Hz), 2.36-2.50 (6H, m), 2.71 (2H, dd, J=9.2, 6.8 Hz), 2.56 (2H, dd, J=9.2, 6.8 Hz), 4.69 (1H, quintet, J=6.8 Hz), 6.79 (1H, td, J=8.4, 7.0 Hz), 6.87 (1H, tdd, J=7.6, 4.4, 1.6 Hz), 7.01 (1H, t, J=7.8 Hz), 7.07 (1H, ddd, J=11.6, 8.0, 1.6 Hz), 7.90 (1H, s), 7.92 (1H, s).

Example 108

1-[2-(6-tert-Butoxypyrazin-2-yl)ethyl]-4-[(2-fluorophenyl)ethynyl]piperidin-4-ol The title compound (146 mg, 67% yield) was obtained in the same manner as Example 97 from 110 mg of 2-tert-butoxy-6-vinylpyrazine and 121 mg of 4-(2-fluorophenyl)ethynyl-4-hydroxypiperidine.

1H-NMR (400 MHz, CDCl3); δ (ppm) 1.58 (9H, s), 1.95 (2H, ddd, J=13.0, 5.6, 3.6 Hz), 2.04-2.12 (2H, m), 2.56 (2H, t, J=9.4 Hz), 2.79-2.91 (6H, m), 7.04-7.12 (2H, m), 7.26-7.33 (1H, m), 7.38-7.44 (1H, m), 7.91 (1H, s), 7.93 (1H, s).

Example 109

2-tert-Butoxy-4-[2-[4-(2-fluorophenoxymethyl)piperidino]ethyl]pyrimidine

After dissolving 221 mg of 2-tert-butoxy-4-vinylpyrimidine and 200 mg of 4-(2-fluorophenoxymethyl)piperidine hydrochloride in 5 ml of ethanol, 123 mg of anhydrous potassium carbonate was added and the mixture was heated to reflux for 50 minutes. Ethyl acetate was added to the reaction mixture, the insoluble portion was filtered off, and the filtrate was concentrated under reduced pressure. The residue was purified by NH silica gel column chromatography (solvent: n-hexane/ethyl acetate) to obtain the title compound (293 mg, 93% yield).

1H-NMR (400 MHz, CDCl3); δ(ppm) 1.33-1.48 (2H, m), 1.63 (9H, s), 1.81-1.93 (3H, m), 2.04-2.12 (2H, m), 2.74-2.80 (2H, m), 2.84-2.91 (2H, m), 2.98-3.04 (2H, m), 3.86 (2H, d, J=6.0 Hz), 6.75 (1H, d, J=4.8 Hz), 6.85-6.91 (1H, m), 6.94 (1H, dt, J=8.0, 1.6 Hz), 7.01-7.10 (2H, m), 8.32 (1H, d, J=4.8 Hz).

Example 110

4-tert-Butoxy-2-[2-[4-(2-fluorophenoxymethyl)piperidino]ethyl]pyrimidine

The title compound (282 mg, 89% yield) was obtained in the same manner as Example 109 from 221 mg of 4-tert-butoxy-2-vinylpyrimidine and 200 mg of 4-(2-fluorophenoxymethyl)piperidine hydrochloride.

1H-NMR (400 MHz, CDCl3); δ(ppm) 1.35-1.47 (2H, m), 1.61 (9H, s), 1.82-1.93 (3H, m), 2.06-2.14 (2H, m), 2.86-2.92 (2H, m), 3.01-3.08 (4H, m), 3.86 (2H, d, J=6.0 Hz), 6.42 (1H, d, J=6.0 Hz), 6.84-6.91 (1H, m), 6.95 (1H, dt, J=8.0, 1.6 Hz), 7.01-7.10 (2H, m), 8.27 (1H, d, J=6.0 Hz).

Example 111

1-[2-(6-tert-Butoxypyridin-2-yl)ethyl]-4-(2-fluorophenoxymethyl)piperidin-4-ol

After dissolving 400 mg of 2-tert-butoxy-6-vinylpyridine and 601 mg of 4-(2-fluorophenoxymethyl)-4-hydroxypiperidine hydrochloride in 5 ml of N,N-dimethylformamide, 0.44 ml of N,N-diisopropylethylamine was added and the mixture was stirred for 24 hours at 100° C. Water was added to the reaction solution and extraction was performed with ethyl acetate. The organic layer was washed with water and saturated brine in that order and dried over anhydrous magnesium sulfate, and then the solvent was distilled off under reduced pressure. The residue was purified by NH silica gel column chromatography (solvent: n-hexane/ethyl acetate) to obtain the title compound (18 mg, 2% yield).

1H-NMR (400 MHz, CDCl3); δ (ppm) 1.58 (9H, s), 1.73-1.88 (4H, m), 2.49-2.58 (2H, m), 2.76-2.93 (6H, m), 3.88 (2H, s), 6.46 (1H, d, J=8.0 Hz), 6.68 (1H, d, J=7.6 Hz), 6.89-7.00 (2H, m), 7.03-7.12 (2H, m), 7.41 (1H, dd, J=8.0, 7.6 Hz).

Example 112

2-tert-Butoxy-6-[2-[4-(2,4-difluorophenoxymethyl)piperidino]ethyl]pyrazine

The title compound (280 mg, 31% yield) was obtained in the same manner as Example 97 from 405 mg of 2-tert-butoxy-6-vinylpyrazine and 508 mg of 4-(2,4-difluorophenoxymethyl)piperidine.

1H-NMR (400 MHz, CDCl3); δ(ppm) 1.35-1.47 (2H, m), 1.59 (9H, s), 1.80-1.91 (3H, m), 2.04-2.12 (2H, m), 2.73-2.79 (2H, m), 2.85-2.91 (2H, m), 3.00-3.06 (2H, m), 3.83 (2H, d, J=6.0 Hz), 6.74-6.80 (1H, m), 6.82-6.93 (2H, m), 7.91 (1H, s), 7.93 (1H, s).

Example 113

(E)-2-tert-Butoxy-6-[2-[4-[2-(2-fluorophenyl)vinyl]piperidino]ethyl]pyrazine

The title compound (13 mg, 5% yield) was obtained in the same manner as Example 109 from 180 mg of 2-tert-butoxy-6-vinylpyrazine and 160 mg of (E)-4-[2-(2-fluorophenyl)vinyl]piperidine hydrochloride.

1H-NMR (400 MHz, CDCl3); δ (ppm) 1.51-1.64 (2H, m), 1.60 (9H, s), 1.77-1.85 (2H, m), 2.08-2.24 (3H, m), 2.74-2.80 (2H, m), 2.86-2.92 (2H, m), 3.00-3.07 (2H, m), 6.24 (1H, dd, J=16.0, 7.2 Hz), 6.55 (1H, d, J=16.0 Hz), 7.01 (1H, ddd, J=10.8, 8.4, 1.2 Hz), 7.06 (1H, dt, J=7.6, 1.2 Hz), 7.15-7.20 (1H, m), 7.44 (1H, dt, J=7.6, 1.6 Hz), 7.91 (1H, s), 7.94 (1H, s).

Example 114

2-tert-Butoxy-6-[2-[4-(2-chlorophenoxymethyl)piperidino]ethyl]pyrazine

After adding 1.16 g of 2-tert-butoxy-6-vinylpyrazine, 860 mg of 4-(2-chlorophenoxymethyl)piperidine hydrochloride and 0.43 g of anhydrous potassium carbonate to 10 ml of N,N-dimethylformamide, the mixture was stirred for 2 days at 100° C. Ice water was added to the reaction mixture and extraction was performed with ethyl acetate. The organic layer was washed with water and saturated brine in that order and dried over anhydrous magnesium sulfate, and then the solvent was distilled off under reduced pressure. The residue was purified by NH silica gel column chromatography (solvent: n-hexane/ethyl acetate) to obtain the title compound (145 mg, 11% yield).

1H-NMR (400 MHz, CDCl3); δ (ppm) 1.36-1.50 (2H, m), 1.59 (9H, s), 1.84-1.96 (3H, m), 2.06-2.14 (2H, m), 2.74-2.80 (2H, m), 2.86-2.91 (2H, m), 3.01-3.07 (2H, m), 3.86 (2H, d, J=6.0 Hz), 6.88 (1H, dt, J=7.6, 1.2 Hz), 6.90 (1H, dt, J=8.0, 1.2 Hz), 7.20 (1H, ddd, J=8.0, 7.6, 1.6 Hz), 7.35 (1H, dd, J=7.6, 1.6 Hz), 7.91 (1H, d, J=0.4 Hz), 7.93 (1H, d, J=0.4 Hz).

Example 115

2-tert-Butoxy-6-[2-[4-(2-methylphenoxymethyl)piperidino]ethyl]pyrazine

The title compound (152 mg, 21% yield) was obtained in the same manner as Example 114 from 516 mg of 2-tert-butoxy-6-vinylpyrazine and 450 mg of 4-(2-methylphenoxymethyl)piperidine hydrochloride.

1H-NMR (400 MHz, CDCl3); δ (ppm) 1.39-1.52 (2H, m), 1.59 (9H, s), 1.80-1.92 (3H, m), 2.06-2.14 (2H, m), 2.23 (3H, s), 2.74-2.80 (2H, m), 2.86-2.92 (2H, m), 3.01-3.07 (2H, m), 3.81 (2H, d, J=6.0 Hz), 6.80 (1H, d, J=8.0 Hz), 6.85 (1H, dt, J=7.6, 0.8 Hz), 7.11-7.17 (2H, m), 7.91 (1H, s), 7.94 (1H, s).

Example 116

2-tert-Butoxy-6-[2-[4-(3-fluorophenoxymethyl)piperidino]ethyl]pyrazine

The title compound (304 mg, 30% yield) was obtained in the same manner as Example 97 from 470 mg of 2-tert-butoxy-6-vinylpyrazine and 543 mg of 4-(3-fluorophenoxymethyl)piperidine.

1H-NMR (400 MHz, CDCl3); δ (ppm) 1.36-1.48 (2H, m), 1.59 (9H, s), 1.76-1.89 (3H, m), 2.04-2.12 (2H, m), 2.73-2.79 (2H, m), 2.85-2.92 (2H, m), 3.00-3.07 (2H, m), 3.79 (2H, d, J=6.0 Hz), 6.58-6.69 (3H, m), 7.21 (1H, dt, J=8.4, 6.8 Hz), 7.91 (1H, s), 7.93 (1H, s).

Example 117

6-[2-[3-(2-Fluorophenoxymethyl)piperidino]ethyl]-1H-pyrazin-2-one

After dissolving 160 mg of 2-tert-butoxy-6-[2-[3-(2-fluorophenoxymethyl)piperidino]ethyl]pyrazine in 2 ml of ethyl acetate, 2 ml of 4N hydrogen chloride/ethyl acetate was added, and the mixture was allowed to stand at room temperature for 30 minutes. Aqueous sodium bicarbonate solution was added to the reaction solution and extraction was performed with dichloromethane. After drying over anhydrous magnesium sulfate, the solvent was distilled off under reduced pressure. The residue was dissolved in ethyl acetate, active carbon was added, and the mixture was filtered. The filtrate was concentrated under reduced pressure to obtain the title compound (108 mg, 79% yield).

1H-NMR (400 MHz, CDCl3); δ(ppm) 1.27-1.40 (1H, m), 1.71-1.89 (3H, m), 2.15-2.36 (3H, m), 2.62-2.67 (2H, m), 2.74-2.79 (2H, m), 2.87-2.94 (1H, m), 3.08-3.15 (1H, m), 3.91 (1H, dd, J=9.6, 7.2 Hz), 4.01 (1H, dd, J=5.2, 9.6 Hz), 6.86-6.92 (1H, m), 6.97-7.08 (3H, m), 7.11 (1H, s), 7.99 (1H, s).

Example 118

6-[2-[4-Hydroxy-4-(2-fluorophenoxymethyl)piperidino]ethyl]-1H-pyrazin-2-one After dissolving 274 mg of 1-[2-(6-tert-butoxypyrazin-2-yl)ethyl]-4-(2-fluorophenoxymethyl)piperidin-4-ol in 3 ml of ethyl acetate, 3 ml of 4N hydrogen chloride/ethyl acetate was added and the mixture was allowed to stand at room temperature for 2 hours. Aqueous sodium bicarbonate solution was added to the reaction solution and extraction was performed with dichloromethane. After drying over anhydrous magnesium sulfate, the solvent was distilled off under reduced pressure. Diethyl ether was added to the residue and the mixture was filtered to obtain the title compound (186 mg, 79% yield).

1H-NMR (400 MHz, CDCl3); δ (ppm)1.77-1.87 (2H, m), 1.88-1.95 (2H, m), 2.54-2.68 (4H, m), 2.79-2.84 (2H, m), 2.85-2.92 (2H, m), 3.93 (2H, s), 6.91-7.01 (2H, m), 7.04-7.12 (2H, m), 7.16 (1H, s), 8.01 (1H, s).

Example 119

6-[2-[2-(2-Fluorophenoxy)-7-azaspiro[3.5]non-7-yl]ethyl]-1H-pyrazin-2-one

The title compound (6 mg, 99% yield) was obtained in the same manner as Example 118 from 7 mg of 7-[2-(6-tert-butoxypyrazin-2-yl)ethyl]-2-(2-fluorophenoxy)-7-azaspiro[3.5]nonane.

1H-NMR (400 MHz, CDCl3); δ (ppm) 1.75-1.78 (4H, m), 2.00-2.10 (2H, m), 2.39-2.65 (8H, m), 2.69-2.74 (2H, m), 4.71 (1H, quintet, J=6.8 Hz), 6.79 (1H, td, J=8.2, 1.6 Hz), 6.88 (1H, tdd, J=7.6, 4.4, 1.6 Hz), 7.03 (1H, tt, J=7.6, 1.4 Hz), 7.07 (1H, ddd, J=11.2, 8.0, 1.6 Hz), 7.13 (1H, s), 8.02 (1H, s).

Example 120

6-[2-[4-Hydroxy-4-[(2-fluorophenyl)ethynyl]piperidino]ethyl]-1H-pyrazin-2-one The title compound (96 mg, 77% yield) was obtained in the same manner as Example 118 from 146 mg of 1-[2-(6-tert-butoxypyrazin-2-yl)ethyl]-4-[(2-fluorophenyl)ethynyl]piperidin-4-ol.

1H-NMR (400 MHz, CDCl3); δ (ppm) 2.03-2.11 (2H, m), 2.14-2.22 (2H, m), 2.60-2.68 (4H, m), 2.80 (2H, dd, J=6.6, 4.6 Hz), 2.85-2.94 (2H, m), 7.08 (1H, ddd, J=9.2, 8.4, 0.8 Hz), 7.10 (1H, td, J=7.4, 1.0 Hz), 7.15 (1H, s), 7.28-7.35 (1H, m), 7.43 (1H, td, J=7.2, 1.6 Hz), 8.03 (1H, s).

Example 121

1-(3-Oxo-3,4-dihydro-2-pyrazinylmethyl)-4-(2-methylphenoxymethyl)piperidine-4-carbonitrile

The title compound (37 mg, 92% yield) was obtained in the same manner as Example 118 from 47 mg of 1-(3-tert-butoxy-2-pyrazinylmethyl)-4-(2-methylphenoxymethyl)piperidine-4-carbonitrile.

1H-NMR (400 MHz, CDCl3); δ (ppm) 1.89 (2H, td, J=13.6, 3.4 Hz), 2.17 (2H, d, J=13.2 Hz), 2.28 (3H, s), 2.65 (2H, t, J=11.6 Hz), 3.14 (2H, d, J=12 Hz), 3.86 (2H, s), 3.98 (2H, s), 6.76 (1H, d, J=8.4 Hz), 6.91 (1H, t, J=7.4 Hz), 7.13-7.18 (2H, m), 7.40-7.48 (1H, m), 7.62-7.67 (1H, m).

Example 122

1-(2-Oxo-1,2-dihydro-3-pyridylmethyl)-4-(2-methylphenoxymethyl)piperidine-4-carbonitrile

After adding 10 ml of 4N hydrogen chloride/ethyl acetate to 273 mg of 1-(tert-butoxycarbonyl)-4-cyano-4-(2-methylphenoxymethyl)piperidine, the mixture was stirred for 6 hours at room temperature. The solvent was distilled off under reduced pressure to obtain 336 mg of 4-cyano-4-(2-methylphenoxymethyl)piperidine hydrochloride.

After then adding 117 mg of the 4-cyano-4-(2-methylphenoxymethyl)piperidine hydrochloride and 70 mg of 2-oxo-1,2-dihydropyridine-3-carboxaldehyde [CAS No. 36404-89-4] to 10 ml of dichloromethane, the mixture was stirred for 20 minutes at room temperature. 139 mg of sodium triacetoxyborohydride was added and the mixture was stirred overnight at room temperature. Saturated aqueous sodium bicarbonate solution was added to the reaction mixture and extraction was performed with ethyl acetate and chloroform. After drying the organic layer over magnesium sulfate, the solvent was distilled off under reduced pressure. The obtained residue was purified by NH silica gel column chromatography (solvent: chloroform/methanol) to obtain the title compound (7 mg, 5% yield).

1H-NMR (400 MHz, CDCl3); δ (ppm) 1.82 (2H, td, J=13.0, 3.4 Hz), 2.12-2.16 (2H, m), 2.28 (s, 3H), 2.50-2.57 (2H, m), 3.00 (2H, d, J=9.6 Hz), 3.56 (2H, s), 3.98 (2H, s), 6.31 (1H, t, J=6.6 Hz), 6.76 (1H, d, J=8.4 Hz), 6.91 (1H, td, J=6.8, 0.8 Hz), 7.13-7.18 (2H, m), 7.33 (1H, dd, J=6.4, 2.0 Hz), 7.50-7.52 (1H, m).

Example 123

1-(2-Oxo-1,2-dihydro-3-pyridylmethyl)-4-(2-fluorophenoxymethyl)piperidine-4-carbonitrile

The title compound (8 mg, 6% yield) was obtained in the same manner as Example 122 from 103 mg of 4-cyano-4-(2-fluorophenoxymethyl)piperidine hydrochloride and 61 mg of 2-oxo-1,2-dihydropyridine-3-carboxaldehyde.

1H-NMR (400 MHz, CDCl3); δ (ppm) 1.85 (2H, td, J=13.2, 3.2 Hz), 2.11 (2H, d, J=13.2 Hz), 2.53 (2H, t, J=11.0 Hz), 2.96-3.03 (2H, m), 3.56 (2H, s), 4.05 (2H, s), 6.33 (1H, d, J=6.6 Hz), 6.94-7.02 (2H, m), 7.04-7.12 (2H, m), 7.34 (1H, dd, J=6.4, 1.6 Hz), 7.52-7.57 (1H, m).

Example 124

3-[4-Fluoro-4-(2-fluorophenoxymethyl)piperidino]methyl-1H-pyridin-2-one

The title compound (9 mg, 12% yield) was obtained in the same manner as Example 122 from 60 mg of 4-fluoro-4-(2-fluorophenoxymethyl)piperidine hydrochloride and 36 mg of 2-oxo-1,2-dihydropyridine-3-carboxaldehyde.

1H-NMR (400 MHz, CDCl3); δ (ppm) 1.78-2.08 (4H, m), 2.52 (2H, t, J=11.6 Hz), 2.78-2.83 (2H, m), 3.54 (2H, s), 4.05 (2H, d, J=18 Hz), 6.33 (1H, t, J=6.6 Hz), 6.89-7.11 (4H, m), 7.35 (1H, dd, J=6.4, 2.0 Hz), 7.57 (1H, d, J=6.8 Hz).

Example 125

3-[4-Hydroxy-4-[2-(2-methylphenyl)ethyl]piperidino]methyl-1H-pyridin-2-one

The title compound (10 mg, 8% yield) was obtained in the same manner as Example 122 from 102 mg of 4-hydroxy-4-[2-(2-methylphenyl)ethyl]piperidine hydrochloride and 64 mg of 2-oxo-1,2-dihydropyridine-3-carboxaldehyde.

1H-NMR (400 MHz, CDCl3); δ (ppm) 1.71-1.76 (4H, m), 1.89-1.98 (2H, m), 2.31 (3H, s), 2.67-2.79 (4H, m), 2.82-2.91 (2H, m), 3.69 (2H, s), 6.39 (1H, t, J=6.6 Hz), 7.07-7.14 (4H, m), 7.38 (1H, dd, J=6.2, 1.8 Hz), 7.74-7.82 (1H, m).

Example 126

3-[4-Hydroxy-4-[2-(2-fluorophenyl)ethyl]fluorophenyl)ethyl]piperidino]methyl-1H-pyridin-2-one

The title compound (4 mg, 5% yield) was obtained in the same manner as Example 122 from 51 mg of 4-hydroxy-4-[2-(2-fluorophenyl)ethyl]piperidine hydrochloride and 41 mg of 2-oxo-1,2-dihydropyridine-3-carboxaldehyde.

1H-NMR (400 MHz, CDCl3); δ (ppm) 1.60-1.84 (6H, m), 2.51-2.63 (2H, m), 2.73-2.77 (4H, m), 3.57 (2H, s), 6.34 (1H, t, J=6.6 Hz), 6.97-7.07 (2H, m), 7.13-7.22 (2H, m), 7.34 (1H, td, J=6.8, 2.0 Hz), 7.58-7.64 (1H, m).

Example 127

3-[4-(2-Fluorophenoxymethyl)-4-[2-(2-fluorophenyl)ethyl]piperidino]methyl-1H-pyridin-2-one

The title compound (6 mg, 7% yield) was obtained in the same manner as Example 122 from 74 mg of 4-(2-fluorophenoxymethyl)-4-[2-(2-fluorophenyl)ethyl]piperidine hydrochloride and 32 mg of 2-oxo-1,2-dihydropyridine-3-carboxaldehyde.

1H-NMR (400 MHz, CDCl3); δ (ppm) 1.69-1.88 (6H, m), 2.58-2.65 (6H, m), 3.53 (2H, s), 3.92 (2H, s), 6.35 (1H, t, J=6.6 Hz), 6.85-6.93 (1H, m), 6.95-7.09 (5H, m), 7.10-7.20 (2H, m), 7.31-7.35 (1H, m), 7.56-7.61 (1H, m).

Example 128

3-[4-[2-(2-Fluorophenyl)ethyl]-4-(2-methylphenoxymethyl)piperidino]methyl-1H-pyridin-2-one

The title compound (6 mg, 6% yield) was obtained in the same manner as Example 122 from 87 mg of 4-(2-methylphenoxymethyl)-4-[2-(2-fluorophenyl)ethyl]piperidine hydrochloride and 38 mg of 2-oxo-1,2-dihydropyridine-3-carboxaldehyde.

1H-NMR (400 MHz, CDCl3); δ(ppm) 1.57-1.88 (4H, m), 2.25 (3H, s), 2.52-2.64 (6H, m), 3.45-3.51 (2H, m), 3.57 (2H, s), 3.87 (2H, s), 6.35 (1H, t, J=6.6 Hz), 6.75-6.89 (2H, m), 6.96-7.09 (2H, m), 7.10-7.21 (4H, m), 7.35 (1H, d, J=6.2 Hz), 7.58-7.66 (1H, m).

Example 129 anti-(E)-3-[9-[2-(2-Fluorophenyl)vinyl]-3-azabicyclo[3.3.1]non-3-yl]methyl-1H-pyridin-2-one After suspending 200 mg of anti-(E)-9-[2-(2-fluorophenyl)vinyl]-3-azabicyclo[3.3.1]nonane hydrochloride in 5 ml of 1,2-dichloroethane, 105 mg of 2-oxo-1,2-dihydropyridine-3-carboxaldehyde and 241 mg of sodium triacetoxyborohydride were added and the mixture was stirred overnight at room temperature. Aqueous sodium carbonate solution was added to the reaction mixture and extraction was performed with ethyl acetate. The organic layer was washed with water and saturated brine in that order and dried over anhydrous magnesium sulfate, and then the solvent was distilled off under reduced pressure. The residue was purified by NH silica gel column chromatography (solvent: ethyl acetate/methanol) to obtain the title compound (207 mg, 83% yield).

1H-NMR (400 MHz, CDCl3); δ(ppm) 1.54-1.68 (3H, m), 1.86-1.91 (2H, m), 1.92-2.03 (2H, m), 2.43-2.51 (3H, m), 2.65-2.79 (1H, m), 3.05-3.11 (2H, m), 3.42 (2H, s), 6.35 (1H, t, J=6.8 Hz), 6.55-6.67 (2H, m), 7.02 (1H, ddd, J=10.8, 8.0, 1.2 Hz), 7.09 (1H, dt, J=8.0, 1.2 Hz), 7.14-7.21 (1H, m), 7.33 (1H, dd, J=6.8, 2.0 Hz), 7.49 (1H, dt, J=8.0, 1.2 Hz), 7.61 (1H, dd, J=6.8, 2.0 Hz), 12.62 (1H, br s).

Example 130 anti-(E)-5-Chloro-3-[9-[2-(2-fluorophenyl)vinyl]-3-azabicyclo[3.3.1]non-3-yl]methyl-1H-pyridin-2-one After dissolving 164 mg of anti-(E)-3-(5-chloro-2-methoxypyridin-3-yl)methyl-9-[2-(2-fluorophenyl)vinyl]-3-azabicyclo[3.3.1]nonane in 5 ml of ethanol, 15 ml of 4N hydrogen chloride/ethyl acetate was added and the mixture was heated to reflux for 6 hours. Aqueous sodium bicarbonate solution was added to the reaction solution and extraction was performed with ethyl acetate. The organic layer was washed with water and saturated brine in that order and dried over anhydrous magnesium sulfate, and then the solvent was distilled off under reduced pressure. The residue was purified by NH silica gel column chromatography (solvent: ethyl acetate/methanol) to obtain the title compound (141 mg, 89% yield).

1H-NMR (400 MHz, CDCl3); δ(ppm) 1.58-1.69 (3H, m), 1.88-2.05 (4H, m), 2.48-2.63 (4H, m), 3.04-3.10 (2H, m), 3.41 (2H, s), 6.57-6.66 (2H, m), 7.03 (1H, ddd, J=10.8, 8.0, 1.2 Hz), 7.09 (1H, dt, J=8.0, 1.2 Hz), 7.15-7.21 (1H, m), 7.46-7.54 (3H, m).

Example 131

3-[3-[2-(2-Fluorophenoxy)ethyl]azetidin-1-yl]methyl-1H-pyrazin-2-one

The title compound (23 mg, 51% yield) was obtained in the same manner as Example 118 from 54 mg of 2-tert-butoxy-3-[3-[2-(2-fluorophenoxy)ethyl]azetidin-1-yl]methyl-pyrazine.

1H-NMR (400 MHz, CDCl3); δ (ppm) 2.11 (2H, q, J=6.0 Hz), 2.81-2.90 (1H, m), 3.19 (2H, t, J=8.0 Hz), 3.74 (2H, t, J=8.0 Hz), 3.93 (2H, s), 4.02 (2H, t, J=6.0 Hz), 6.86-6.95 (2H, m), 7.01-7.09 (2H, m), 7.71 (1H, d, J=2.8 Hz), 7.75 (1H, d, J=2.8 Hz).

Example 132

3-[3-(2-Fluorophenoxymethyl)pyrrolidino]methyl-1H-pyrazin-2-one oxalate

After dissolving 245 mg of 3-[3-(2-fluorophenoxymethyl)pyrrolidino]methyl-2-methoxypyrazine in 5 ml of ethanol, 15 ml of 4N hydrogen chloride/ethyl acetate was added, and the mixture was heated to reflux for 8 hours and then stirred overnight at 60° C. Aqueous sodium bicarbonate solution was added to the reaction solution and extraction was performed with ethyl acetate. The organic layer was washed with water and saturated brine in that order and dried over anhydrous magnesium sulfate, and then the solvent was distilled off under reduced pressure. The residue was purified by NH silica gel column chromatography (solvent: ethyl acetate/methanol). This was dissolved in a small amount of ethanol, and then 47 mg of oxalic acid anhydrous and ethyl acetate were added and the precipitate was filtered out to obtain the title compound (171 mg, 56% yield).

1H-NMR (400 MHz, DMSO-d6); δ(ppm) 1.76-1.87 (1H, m), 2.12-2.22 (1H, m), 2.78-2.90 (1H, m), 3.16-3.25 (1H, m), 3.32-3.44 (2H, m), 3.50-3.60 (1H, m), 4.02-4.14 (2H, m), 4.40 (2H, s), 6.93-6.99 (1H, m), 7.05-7.25 (3H, m), 7.36 (1H, d, J=4.0 Hz), 7.50 (1H, d, J=4.0 Hz).

Example 133

3-[3-(2-Methoxyphenoxymethyl)pyrrolidino]methyl-1H-pyrazin-2-one oxalate

The title compound (167 mg, 38% yield) was obtained in the same manner as Example 132 from 352 mg of 2-methoxy-3-[3-(2-methoxyphenoxymethyl)pyrrolidino]methyl-pyrazine.

1H-NMR (400 MHz, DMSO-d6); δ(ppm) 1.77-1.87 (1H, m), 2.10-2.21 (1H, m), 2.77-2.86 (1H, m), 3.14-3.25 (1H, m), 3.32-3.44 (2H, m), 3.51-3.62 (1H, m), 3.93-4.02 (2H, m), 4.42 (2H, s), 6.85-7.00 (4H, m), 7.36 (1H, d, J=4.0 Hz), 7.51 (1H, d, J=4.0 Hz).

Example 134

3-[3-[2-(2-Fluorophenyl)ethyl]pyrrolidino]methyl-1H-pyrazin-2-one

The title compound (169 mg, 53% yield) was obtained in the same manner as Example 130 from 332 mg of 3-[3-[2-(2-fluorophenyl)ethyl]pyrrolidino]methyl-2-methoxypyrazine.

1H-NMR (400 MHz, CDCl3); δ(ppm) 1.53-1.63 (1H, m), 1.68-1.80 (2H, m), 2.09-2.19 (1H, m), 2.21-2.33 (1H, m), 2.37-2.44 (1H, m), 2.57-2.70 (2H, m), 2.71-2.80 (1H, m), 2.82-2.90 (1H, m), 2.96-3.02 (1H, m), 3.94 (1H, d, J=15.2 Hz), 3.99 (1H, d, J=15.2 Hz), 6.97-7.08 (2H, m), 7.13-7.21 (2H, m), 7.87 (1H, d, J=2.8 Hz), 7.90 (1H, d, J=2.8 Hz).

Example 135

3-[3-[2-(2-Methoxyphenyl)ethyl]pyrrolidino]methyl-1H-pyrazin-2-one oxalate

The title compound (235 mg, 61% yield) was obtained in the same manner as Example 132 from 314 mg of 2-methoxy-3-[3-[2-(2-methoxyphenyl)ethyl]pyrrolidino]methyl-pyrazine.

1H-NMR (400 MHz, DMSO-d6); δ(ppm) 1.57-1.72 (3H, m), 2.08-2.17 (1H, m), 2.20-2.32 (1H m), 2.48-2.61 (2H, m), 2.92-3.00 (1H, m), 3.32-3.42 (2H, m), 3.48-3.56 (1H, m), 3.77 (3H, s), 4.40 (2H, s), 6.87 (1H, dt, J=7.2, 1.2 Hz), 6.95 (1H, dd, J=8.0, 1.2 Hz), 7.12-7.21 (2H, m), 7.36 (1H, d, J=4.0 Hz), 7.51 (1H, d, J=4.0 Hz).

Example 136

3-[3-(2-Methylphenoxymethyl)pyrrolidino]methyl-1H-pyrazin-2-one oxalate

The title compound (205 mg, 62% yield) was obtained in the same manner as Example 132 from 262 mg of 2-methoxy-3-[3-(2-methylphenoxymethyl)pyrrolidino]methylpyrazine.

1H-NMR (400 MHz, DMSO-d6); δ(ppm) 1.81-1.91 (1H, m), 2.13-2.23 (4H, m), 2.78-2.90 (1H, m), 3.18-3.28 (1H, m), 3.36-3.44 (2H, m), 3.54-3.61 (1H, m), 3.94-4.05 (2H, m), 4.41 (2H, s), 6.85 (1H, dt, J=7.2, 0.8 Hz), 6.92 (1H, d, J=8.0 Hz), 7.13-7.18 (2H, m), 7.36 (1H, d, J=4.0 Hz), 7.51 (1H, d, J=4.0 Hz).

Example 137

2-[4-(2-Fluorophenoxymethyl)piperidino]methyl-3H-pyrimidin-4-one

After dissolving 282 mg of 4-tert-butoxy-2-[2-[4-(2-fluorophenoxymethyl)piperidino]ethyl]pyrimidine in 3 ml of ethyl acetate, 3 ml of 4N hydrogen chloride/ethyl acetate was added and the mixture was allowed to stand at room temperature for 50 minutes. Aqueous sodium bicarbonate solution was added to the reaction solution and extraction was performed with ethyl acetate. The organic layer was washed with water and brine in that order and dried over anhydrous magnesium sulfate, and then the solvent was distilled off under reduced pressure. Diethyl ether was added to the residue and the mixture was filtered to obtain the title compound (212 mg, 89% yield).

1H-NMR (400 MHz, CDCl3); δ(ppm) 1.45-1.57 (2H, m), 1.92-2.04 (3H, m), 2.13-2.21 (2H, m), 2.77-2.84 (4H, m), 3.10-3.18 (2H, m), 3.91 (2H, d, J=6.4 Hz), 6.29 (1H, d, J=6.8 Hz), 6.86-6.93 (1H, m), 6.96 (1H, dt, J=8.4, 1.6 Hz), 7.03-7.11 (2H, m), 7.81 (1H, d, J=6.4 Hz).

Example 138

(E)-3-[4-[2-(2-Fluorophenyl)vinyl]piperidino]methyl-1H-pyrazin-2-one

After dissolving 296 mg of (E)-3-[4-[2-(2-fluorophenyl)vinyl]piperidino]methyl-2-methoxypyrazine in 5 ml of ethanol, 1 ml of thionyl chloride was added and the mixture was heated to reflux for 9 hours. Aqueous sodium carbonate solution was added to the reaction solution and extraction was performed with ethyl acetate. The organic layer was washed with water and saturated brine in that order and dried over anhydrous magnesium sulfate, and then the solvent was distilled off under reduced pressure. Ethyl acetate was added to the residue and the mixture was filtered to obtain the title compound (180 mg, 63% yield).

1H-NMR (400 MHz, CDCl3); δ(ppm) 1.61-1.73 (2H, m), 1.86-1.94 (2H, m), 2.13-2.43 (3H, m), 3.02-3.10 (2H, m), 3.88 (2H, s), 6.22 (1H, dd, J=16.0, 6.8 Hz), 6.57 (1H, d, J=16.0 Hz), 7.02 (1H, ddd, J=10.8, 7.6, 1.2 Hz), 7.08 (1H, dt, J=7.6, 1.2 Hz), 7.15-7.22 (1H, m), 7.43 (1H, dt, J=7.6, 1.6 Hz), 7.92 (1H, d, J=2.8 Hz), 7.94-7.98 (1H, m).

Example 139

3-[4-[2-(2-Fluorophenyl)-2-oxoethyl]piperidino]methyl-1H-pyrazin-2-one

The title compound (249 mg, 83% yield) was obtained in the same manner as Example 130 from 313 mg of 2-[1-(3-methoxy-2-pyrazinylmethyl)piperidin-4-yl]-1-(2-fluorophenyl)ethanone.

1H-NMR (400 MHz, CDCl3); δ(ppm) 1.35-1.47 (2H, m), 1.78-1.85 (2H, m), 2.01-2.14 (1H, m), 2.16-2.24 (2H, m), 2.89-2.96 (4H, m), 3.53 (2H, s), 7.14 (1H, ddd, J=11.2, 8.4, 0.8 Hz), 7.23 (1H, ddd, J=8.4, 7.2, 0.8 Hz), 7.41 (1H, d, J=2.8 Hz), 7.49-7.56 (1H, m), 7.71 (1H, br s), 7.83 (1H, dt, J=7.2, 1.6 Hz).

Example 140

3-[4-[2-(2,3-Dihydrobenzofuran-7-yl)ethyl]piperidino]methyl-1H-pyrazin-2-one

The title compound (131 mg, 55% yield) was obtained in the same manner as Example 130 from 249 mg of 3-[4-[2-(2,3-dihydrobenzofuran-7-yl)ethyl]piperidino]methyl-2-methoxypyrazine.

1H-NMR (400 MHz, CDCl3); δ (ppm) 1.32-1.46 (3H, m), 1.55-1.63 (2H, m), 1.80-1.90 (2H, m), 2.22-2.31 (2H, m), 2.56-2.62 (2H, m), 2.96-3.03 (2H, m), 3.21 (2H, t, J=8.8 Hz), 3.84 (2H, s), 4.54 (2H, t, J=8.8 Hz), 6.78 (1H, t, J=7.4 Hz), 6.92 (1H, d, J=7.4 Hz), 7.05 (1H, dd, J=7.4, 1.2 Hz), 7.92 (1H, d, J=2.8 Hz), 7.99 (1H, d, J=2.8 Hz).

Example 141

3-[4-(2-Fluorobenzyloxy)piperidino]methyl-1H-pyrazin-2-one

The title compound (78 mg, 39% yield) was obtained in the same manner as Example 130 from 210 mg of 3-[4-(2-fluorobenzyloxy)piperidino]methyl-2-methoxypyrazine.

1H-NMR (400 MHz, CDCl3); δ (ppm) 1.80-1.92 (2H, m), 1.93-2.04 (2H, m), 2.45-2.59 (2H, m), 2.83-2.94 (2H, m), 3.56-3.65 (1H, m), 3.86 (2H, s), 4.61 (2H, s), 7.04 (1H, ddd, J=10.0, 8.0, 1.2 Hz), 7.15 (1H, td, J=8.0, 1.2 Hz), 7.25-7.32 (1H, m), 7.44 (1H, td, J=8.0, 2.0 Hz), 7.92 (1H, d, J=2.8 Hz), 7.95 (1H, br s).

Example 142

3-[4-(2-Fluorophenoxymethyl)piperidino]methyl-1H-pyrazin-2-one

The title compound (27 mg, 39% yield) was obtained in the same manner as Example 130 from 72 mg of 3-[4-(2-fluorophenoxymethyl)piperidino]methyl-2-methoxypyrazine.

1H-NMR (400 MHz, CDCl3); δ (ppm) 1.46-1.58 (2H, m), 1.92-2.03 (3H, m), 2.30-2.38 (2H, m), 3.04-3.10 (2H, m), 3.87 (2H, s), 3.89 (2H, d, J=6.0 Hz), 6.87-6.98 (2H, m), 7.02-7.11 (2H, m), 7.91 (1H, d, J=2.8 Hz), 7.94 (1H, br s).

Example 143

3-[4-(2-Methoxyphenoxymethyl)piperidino]methyl-1H-pyrazin-2-one

The title compound (83 mg, 58% yield) was obtained in the same manner as Example 130 from 148 mg of 2-methoxy-3-[4-(2-methoxyphenoxymethyl)piperidino]methylpyrazine.

1H-NMR (400 MHz, CDCl3); δ (ppm) 1.42-1.57 (2H, m), 1.95-2.05 (2H, m), 2.10-2.40 (3H, m), 3.02-3.08 (2H, m), 3.84-3.90 (7H, m), 6.86-6.96 (4H, m), 7.92 (1H, d, J=2.8 Hz), 7.97 (1H, br s).

Example 144

3-[4-[2-(2-Fluorophenyl)-2-hydroxyethyl]piperidino]methyl-1H-pyrazin-2-one

After dissolving 217 mg of 3-[4-[2-(2-fluorophenyl)-2-oxoethyl]piperidino]methyl-1H-pyrazin-2-one in 30 ml of methanol, 25 mg of sodium borohydride was added while stirring on ice, and the stirring was continued for 1 hour. Acetone was added to the reaction solution and the mixture was concentrated under reduced pressure. The residue was purified by NH silica gel column chromatography (solvent: ethyl acetate/methanol) to obtain the title compound (179 mg, 82% yield).

1H-NMR (400 MHz, CDCl3); δ(ppm) 1.36-1.50 (2H, m), 1.56-1.68 (2H, m), 1.76-1.95 (3H, m), 2.24-2.34 (2H, m), 2.95-3.04 (2H, m), 3.84 (2H, s), 5.12 (1H, dd, J=9.2, 4.4 Hz), 7.03 (1H, ddd, J=10.8, 8.4, 1.2 Hz), 7.16 (1H, dt, J=7.6, 1.2 Hz), 7.23-7.29 (1H, m), 7.46 (1H, dt, J=7.6, 1.6 Hz), 7.89 (1H, d, J=2.8 Hz), 7.94 (1H, d, J=2.8 Hz).

Example 145

3-[4-[2-(2-Methoxyphenyl)-2-oxoethyl]piperidino]methyl-1H-pyrazin-2-one

The title compound (115 mg, 57% yield) was obtained in the same manner as Example 130 from 211 mg of 1-(2-methoxyphenyl)-2-[1-(3-methoxy-2-pyrazinylmethyl)piperidin-4-yl]ethanone.

1H-NMR (400 MHz, CDCl3); δ (ppm) 1.37-1.48 (2H, m), 1.81-1.88 (2H, m), 2.04-2.16 (1H, m), 2.30-2.39 (2H, m), 2.93-3.02 (4H, m), 3.85 (2H, d, J=0.8 Hz), 3.91 (3H, s), 6.95-7.03 (2H, m), 7.46 (1H, ddd, J=8.4, 7.6, 2.0 Hz), 7.64 (1H, dd, J=7.6, 2.0 Hz), 7.93 (1H, d, J=2.8 Hz), 7.98 (1H, br s).

Example 146

3-[4-[2-(Benzofuran-7-yl)ethyl]piperidino]methyl-1H-pyrazin-2-one

After dissolving 218 mg of 3-[4-[2-(benzofuran-7-yl)ethyl]piperidino]methyl-2-methoxypyrazine in 20 ml of acetonitrile, 914 mg of sodium iodide and 0.39 ml of chlorotrimethylsilane were added while stirring on ice, and the stirring was continued for 30 minutes. After further stirring for 1 hour at room temperature, ice water and aqueous sodium carbonate solution were added to the reaction solution and extraction was performed with ethyl acetate. The organic layer was washed with water, aqueous sodium thiosulfate solution and saturated brine in that order and dried over anhydrous magnesium sulfate. The solvent was distilled off under reduced pressure, diethyl ether was added to the residue and the mixture was filtered to obtain the title compound (70 mg, 34% yield).

1H-NMR (400 MHz, CDCl3); δ (ppm) 1.36-1.50 (3H, m), 1.70-1.78 (2H, m), 1.82-1.94 (2H, m), 2.22-2.33 (2H, m), 2.90-2.97 (2H, m), 2.97-3.04 (2H, m), 3.85 (2H, s), 6.77 (1H, d, J=2.0 Hz), 7.08 (1H, dd, J=7.6, 1.2 Hz), 7.16 (1H, t, J=7.6 Hz), 7.45 (1H, dd, J=7.6, 1.2 Hz), 7.62 (1H, d, J=2.0 Hz), 7.91 (1H, d, J=2.8 Hz), 7.98 (1H, d, J=2.8 Hz).

Example 147

3-[4-(2-Methylphenoxymethyl)piperidino]methyl-1H-pyrazin-2-one

The title compound (155 mg, 69% yield) was obtained in the same manner as Example 130 from 236 mg of 2-methoxy-3-[4-(2-methylphenoxymethyl)piperidino]methyl-pyrazine.

1H-NMR (400 MHz, CDCl3); δ (ppm) 1.52-1.64 (2H, m), 1.90-2.00 (3H, m), 2.22 (3H, s), 2.32-2.40 (2H, m), 3.04-3.11 (2H, m), 3.84 (2H, d, J=6.0 Hz), 3.88 (2H, s), 6.79 (1H, d, J=7.6 Hz), 6.86 (1H, dt, J=7.6, 1.2 Hz), 7.12-7.18 (2H, m), 7.92 (1H, d, J=2.8 Hz), 7.96 (1H, br s).

Example 148

3-[4-[2-(2-Methoxyphenoxy)ethyl]piperidino]methyl-1H-pyrazin-2-one

The title compound (82 mg, 47% yield) was obtained in the same manner as Example 130 from 180 mg of 3-[4-[2-(2-methoxyphenoxy)ethyl]piperidino]methyl-2-methoxypyrazine.

1H-NMR (400 MHz, CDCl3); δ (ppm) 1.38-1.50 (2H, m), 1.64-1.78 (1H, m), 1.80-1.91 (4H, m), 2.27-2.36 (2H, m), 2.97-3.05 (2H, m), 3.85 (2H, d, J=0.8 Hz), 3.86 (3H, s), 4.07 (2H, t, J=6.4 Hz), 6.86-6.96 (4H, m), 7.92 (1H, d, J=2.8 Hz), 7.98 (1H, br s).

Example 149

3-[3-(2-Methoxyphenoxymethyl)piperidino]methyl-1H-pyrazin-2-one

The title compound (135 mg, 46% yield) was obtained in the same manner as Example 130 from 309 mg of 2-methoxy-3-[3-(2-methoxyphenoxymethyl)piperidino]methyl-pyrazine.

1H-NMR (400 MHz, CDCl3); δ (ppm) 1.18-1.30 (1H, m), 1.66-1.95 (3H, m), 2.18-2.37 (3H, m), 2.89-2.97 (1H, m), 3.20-3.27 (1H, m), 3.81-3.88 (5H, m), 3.90-3.96 (2H, m), 6.85-6.97 (4H, m), 7.93 (1H, d, J=2.8 Hz), 7.98 (1H, br s).

Example 150

3-[3-(2-Fluorophenoxymethyl)piperidino]methyl-1H-pyrazin-2-one

The title compound (72 mg, 44% yield) was obtained in the same manner as Example 130 from 170 mg of 3-[3-(2-fluorophenoxymethyl)piperidino]methyl-2-methoxypyrazine.

1H-NMR (400 MHz, CDCl3); δ (ppm) 1.24-1.37 (1H, m), 1.68-1.94 (3H, m), 2.22-2.34 (3H, m), 2.90-2.98 (1H, m), 3.12-3.22 (1H, m), 3.82-3.98 (4H, m), 6.87-6.96 (2H, m), 7.01-7.10 (2H, m), 7.92 (1H, d, J=2.8 Hz), 7.95 (1H, br s).

Example 151

3-[4-(2,5-Difluorophenoxymethyl)piperidino]methyl-1H-pyrazin-2-one

The title compound (221 mg, 74% yield) was obtained in the same manner as Example 130 from 309 mg of 3-[4-(2,5-difluorophenoxymethyl)piperidino]methyl-2-methoxypyrazine.

1H-NMR (400 MHz, CDCl3); δ(ppm) 1.47-1.59 (2H, m), 1.92-2.04 (3H, m), 2.29-2.38 (2H, m), 3.05-3.12 (2H, m), 3.86 (2H, d, J=5.6 Hz), 3.87 (2H, s), 6.55-6.61 (1H, m), 6.67 (1H, ddd, J=10.0, 6.8, 2.8 Hz), 7.01 (1H, ddd, J=10.8, 10.0, 5.6 Hz), 7.88 (2H, br s).

Example 152

3-[4-(2-Methylbenzyloxy)piperidino]methyl-1H-pyrazin-2-one

The title compound (151 mg, 55% yield) was obtained in the same manner as Example 130 from 286 mg of 2-methoxy-3-[4-(2-methylbenzyloxy)piperidino]methyl-pyrazine.

1H-NMR (400 MHz, CDCl3); δ(ppm) 1.79-1.90 (2H, m), 1.94-2.03 (2H, m), 2.34 (3H, s), 2.46-2.57 (2H, m), 2.85-2.94 (2H, m), 3.55-3.62 (1H, m), 3.85 (2H, d, J=0.8 Hz), 4.53 (2H, s), 7.15-7.24 (3H, m), 7.31-7.35 (1H, m), 7.89 (1H, d, J=2.8 Hz), 7.92 (1H, br s).

Example 153

3-[4-(3-Methylphenoxymethyl)piperidino]methyl-1H-pyrazin-2-one

The title compound (191 mg, 92% yield) was obtained in the same manner as Example 130 from 217 mg of 2-methoxy-3-[4-(3-methylphenoxymethyl)piperidino]methyl-pyrazine.

1H-NMR (400 MHz, CDCl3); δ (ppm) 1.46-1.59 (2H, m), 1.85-1.98 (3H, m), 2.28-2.38 (5H, m), 3.03-3.10 (2H, m), 3.82 (2H, d, J=6.0 Hz), 3.87 (2H, s), 6.67-6.74 (2H, m), 6.77 (1H, d, J=7.6 Hz), 7.16 (1H, t, J=7.6 Hz), 7.92 (1H, d, J=2.8 Hz), 7.95 (1H, br s).

Example 154

3-[3-(2-Methylphenoxymethyl)piperidino]methyl-1H-pyrazin-2-one

The title compound (50 mg, 37% yield) was obtained in the same manner as Example 130 from 140 mg of 2-methoxy-3-[3-(2-methylphenoxymethyl)piperidino]methyl-pyrazine.

1H-NMR (400 MHz, CDCl3); δ (ppm) 1.20-1.36 (1H, m) 1.70-1.94 (3H, m), 2.18 (3H, s), 2.20-2.32 (3H, m), 2.93-3.01 (1H, m), 3.14-3.20 (1H, m), 3.77-3.90 (4H, m), 6.76 (1H, d, J=7.6 Hz), 6.85 (1H, t, J=7.6 Hz), 7.10-7.16 (2H, m), 7.92 (1H, d, J=2.4 Hz), 7.96 (1H, br s).

Example 155

3-[3-[2-(2-Methoxyphenyl)ethyl]piperidino]methyl-1H-pyrazin-2-one

The title compound (133 mg, 52% yield) was obtained in the same manner as Example 130 from 269 mg of 3-[3-[2-(2-methoxyphenyl)ethyl]piperidino]methyl-2-methoxypyrazine.

1H-NMR (400 MHz, CDCl3); δ (ppm) 0.97-1.10 (1H, m), 1.44-1.58 (2H, m), 1.60-1.82 (3H, m), 1.88-2.06 (2H, m), 2.18-2.28 (1H, m), 2.53-2.69 (2H, m), 2.88-3.04 (2H, m), 3.80 (3H, s), 3.84 (2H, s), 6.83 (1H, d, J=7.6 Hz), 6.87 (1H, td, J=7.6, 1.2 Hz), 7.08 (1H, dd, J=7.6, 1.6 Hz), 7.17 (1H, td, J=7.6, 1.6 Hz), 7.93 (1H, d, J=2.8 Hz), 8.01 (1H, d, J=2.8 Hz).

Example 156

3-[3-[2-(2-Fluorophenyl)ethyl]piperidino]methyl-1H-pyrazin-2-one

The title compound (42 mg, 28% yield) was obtained in the same manner as Example 130 from 159 mg of 3-[3-[2-(2-fluorophenyl)ethyl]piperidino]methyl-2-methoxypyrazine.

1H-NMR (400 MHz, CDCl3); δ (ppm) 0.98-1.12 (1H, m), 1.48-1.58 (2H, m), 1.60-1.82 (3H, m), 1.88-2.06 (2H, m), 2.19-2.29 (1H, m), 2.56-2.72 (2H, m), 2.88-3.00 (2H, m), 3.84 (2H, s), 6.99 (1H, ddd, J=8.8, 8.0, 1.2 Hz), 7.04 (1H, td, J=7.6, 1.2 Hz), 7.11-7.19 (2H, m), 7.94 (1H, d, J=2.8 Hz), 8.00 (1H, br s).

Example 157

(E)-3-[4-[2-(3-Methyl-2-thienyl)vinyl]piperidino]methyl-1H-pyrazin-2-one

The title compound (18 mg, 16% yield) was obtained in the same manner as Example 130 from 120 mg of (E)-2-methoxy-3-[4-[2-(3-methyl-2-thienyl)vinyl]piperidino]methyl-pyrazine.

1H-NMR (400 MHz, CDCl3); δ (ppm) 1.58-1.70 (2H, m), 1.82-1.92 (2H, m), 2.10-2.40 (3H, m), 2.22 (3H, s), 3.00-3.08 (2H, m), 3.87 (2H, s), 5.93 (1H, dd, J=16.0, 6.8 Hz), 6.53 (1H, d, J=16.0 Hz), 6.77 (1H, d, J=5.0 Hz), 7.01 (1H, d, J=5.0 Hz), 7.93 (1H, d, J=2.4 Hz), 7.98 (1H, br s).

Example 158

3-[4-(2-Chlorophenoxymethyl)piperidino]methyl-1H-pyrazin-2-one

The title compound (153 mg, 78% yield) was obtained in the same manner as Example 137 from 229 mg of 2-tert-butoxy-3-[4-(2-chlorophenoxymethyl)piperidino]methyl-pyrazine.

1H-NMR (400 MHz, CDCl3); δ (ppm) 1.49-1.62 (2H, m), 1.95-2.06 (3H, m), 2.31-2.40 (2H, m), 3.05-3.11 (2H, m), 3.88 (2H, s), 3.89 (2H, d, J=7.6 Hz), 6.87-6.92 (2H, m), 7.20 (1H, ddd, J=8.4, 7.6, 1.6 Hz), 7.36 (1H, dd, J=8.4, 1.2 Hz), 7.91 (1H, d, J=2.8 Hz), 7.93 (1H, br s).

Example 159

3-[4-[2-(2-Fluorophenoxy)ethyl]piperidino]methyl-1H-pyrazin-2-one

The title compound (85 mg, 41% yield) was obtained in the same manner as Example 137 from 244 mg of 2-tert-butoxy-3-[4-[2-(2-fluorophenoxy)ethyl]piperidino]methyl-pyrazine.

1H-NMR (400 MHz, CDCl3); δ (ppm) 1.37-1.50 (2H, m), 1.66-1.90 (5H, m), 2.26-2.38 (2H, m), 2.97-3.05 (2H, m), 3.86 (2H, s), 4.08 (2H, t, J=6.0 Hz), 6.86-6.93 (1H, m), 6.96 (1H, td, J=8.4, 2.0 Hz), 7.02-7.11 (2H, m), 7.92 (1H, d, J=2.8 Hz), 7.98 (1H, br s).

Example 160

3-[4-(2-Fluorobenzyloxymethyl)piperidino]methyl-1H-pyrazin-2-one

The title compound (119 mg, 54% yield) was obtained in the same manner as Example 137 from 259 mg of 2-tert-butoxy-3-[4-(2-fluorobenzyloxymethyl)piperidino]methyl-pyrazine.

1H-NMR (400 MHz, CDCl3); δ (ppm) 1.34-1.47 (2H, m), 1.68-1.90 (3H, m), 2.24-2.35 (2H, m), 2.95-3.05 (2H, m), 3.37 (2H, d, J=6.4 Hz), 3.85 (2H, s), 4.57 (2H, s), 7.04 (1H, ddd, J=9.6, 7.8, 1.2 Hz), 7.14 (1H, td, J=7.8, 1.2 Hz), 7.25-7.31 (1H, m), 7.39 (1H, td, J=7.8, 1.6 Hz), 7.92 (1H, d, J=2.4 Hz), 7.97 (1H, br s).

Example 161

3-[4-(3-Methoxyphenoxymethyl)piperidino]methyl-1H-pyrazin-2-one

The title compound (129 mg, 48% yield) was obtained in the same manner as Example 130 from 278 mg of 2-methoxy-3-[4-(3-methoxyphenoxymethyl)piperidino]methyl-pyrazine.

1H-NMR (400 MHz, CDCl3); δ (ppm) 1.47-1.60 (2H, m), 1.85-1.98 (3H, m), 2.29-2.38 (2H, m), 3.03-3.10 (2H, m), 3.79 (3H, s), 3.82 (2H, d, J=6.0 Hz), 3.87 (2H, s), 6.44-6.53 (3H, m), 7.18 (1H, t, J=8.0 Hz), 7.91 (1H, d, J=2.8 Hz), 7.93 (1H, br s).

Example 162

3-[4-(3-Fluorophenoxymethyl)piperidino]methyl-1H-pyrazin-2-one

The title compound (138 mg, 72% yield) was obtained in the same manner as Example 137 from 223 mg of 2-tert-butoxy-3-[4-(3-fluorophenoxymethyl)piperidino]methyl-pyrazine.

1H-NMR (400 MHz, CDCl3); δ (ppm) 1.47-1.60 (2H, m), 1.86-1.97 (3H, m), 2.29-2.38 (2H, m), 3.04-3.10 (2H, m), 3.81 (2H, d, J=5.6 Hz), 3.87 (2H, s), 6.60 (1H, dt, J=11.2, 2.4 Hz), 6.63-6.69 (2H, m), 7.22 (1H, dt, J=8.4, 7.2 Hz), 7.91 (1H, d, J=2.8 Hz), 7.92 (1H, br s).

Example 163

3-[4-(2,4-Difluorophenoxymethyl)piperidino]methyl-1H-pyrazin-2-one

The title compound (98 mg, 62% yield) was obtained in the same manner as Example 137 from 183 mg of 2-tert-butoxy-3-[4-(2,4-difluorophenoxymethyl)piperidino]methyl-pyrazine.

1H-NMR (400 MHz, CDCl3); δ(ppm) 1.46-1.58 (2H, m), 1.89-2.00 (3H, m), 2.29-2.37 (2H, m), 3.04-3.10 (2H, m), 3.86 (2H, d, J=7.2 Hz), 3.87 (2H, s), 6.75-6.81 (1H, m), 6.82-6.93 (2H, m), 7.88-7.92 (2H, m).

Example 164

3-[4-[2-(Trifluoromethyl)phenoxymethyl]piperidino]methyl-1H-pyrazin-2-one

The title compound (159 mg, 62% yield) was obtained in the same manner as Example 130 from 255 mg of 2-methoxy-3-[4-[2-(trifluoromethyl)phenoxymethyl]piperidino]methyl-pyrazine.

1H-NMR (400 MHz, CDCl3); δ (ppm) 1.47-1.60 (2H, m), 1.94-2.05 (3H, m), 2.32-2.41 (2H, m), 3.04-3.11 (2H, m), 3.88 (2H, s), 3.90 (2H, d, J=6.0 Hz), 6.96 (1H, d, J=8.0 Hz), 7.01 (1H, t, J=8.0 Hz), 7.48 (1H, dt, J=8.0, 1.2 Hz), 7.57 (1H, dd, J=8.0, 1.2 Hz), 7.92 (1H, d, J=2.8 Hz), 7.96 (1H, br s).

Example 165

3-[4-(2-Ethoxyphenoxymethyl)piperidino]methyl-1H-pyrazin-2-one

The title compound (52 mg, 34% yield) was obtained in the same manner as Example 137 from 178 mg of 2-tert-butoxy-3-[4-(2-ethoxyphenoxymethyl)piperidino]methyl-pyrazine.

1H-NMR (400 MHz, CDCl3); δ (ppm) 1.43 (3H, t, J=6.8 Hz), 1.46-1.59 (2H, m), 1.94-2.04 (3H, m), 2.30-2.39 (2H, m), 3.03-3.10 (2H, m), 3.87 (2H, s), 3.88 (2H, d, J=4.4 Hz), 4.07 (2H, q, J=6.8 Hz), 6.87-6.94 (4H, m), 7.91 (1H, d, J=2.8 Hz), 7.94 (1H, br s).

Example 166

3-[4-(2-Cyanophenoxymethyl)piperidino]methyl-1H-pyrazin-2-one

The title compound (121 mg, 79% yield) was obtained in the same manner as Example 137 from 180 mg of 2-tert-butoxy-3-[4-(2-cyanophenoxymethyl)piperidino]methyl-pyrazine.

1H-NMR (400 MHz, CDCl3); δ (ppm) 1.44-1.57 (2H, m), 1.99-2.11 (3H, m), 2.31-2.40 (2H, m), 3.05-3.12 (2H, m), 3.88 (2H, s), 3.92 (2H, d, J=6.4 Hz), 6.95 (1H, d, J=8.4 Hz), 7.02 (1H, dt, J=7.2, 0.8 Hz), 7.53 (1H, ddd, J=8.4, 7.2, 1.2 Hz), 7.57 (1H, dd, J=7.2, 1.2 Hz), 7.91 (2H, br s).

Example 167

3-[4-[2-(Trifluoromethoxy)phenoxymethyl]piperidino]methyl-1H-pyrazin-2-one

The title compound (206 mg, 80% yield) was obtained in the same manner as Example 137 from 292 mg of 2-tert-butoxy-3-[4-[2-(trifluoromethoxy)phenoxymethyl]piperidino]methyl-pyrazine.

1H-NMR (400 MHz, CDCl3); δ (ppm) 1.46-1.58 (2H, m), 1.93-2.04 (3H, m), 2.31-2.40 (2H, m), 3.05-3.11 (2H, m), 3.87 (2H, d, J=6.0 Hz), 3.88 (2H, s), 6.92-6.99 (2H, m), 7.21-7.26 (2H, m), 7.90 (1H, d, J=2.4 Hz), 7.92 (1H, br s).

Example 168

(E)-3-[4-[2-(3-Chloro-2-thienyl)vinyl]piperidino]methyl-1H-pyrazin-2-one

The title compound (167 mg, 78% yield) was obtained in the same manner as Example 137 from 250 mg of (E)-2-tert-butoxy-3-[4-[2-(3-chloro-2-thienyl)vinyl]piperidino]methyl-pyrazine.

1H-NMR (400 MHz, CDCl3); δ (ppm) 1.58-1.71 (2H, m), 1.84-1.92 (2H, m), 2.20-2.42 (3H, m), 3.00-3.08 (2H, m), 3.88 (2H, s), 6.03 (1H, dd, J=16.0, 7.0 Hz), 6.61 (1H, dt, J=16.0, 1.0 Hz), 6.86 (1H, d, J=5.2 Hz), 7.08 (1H, d, J=5.2 Hz), 7.92 (1H, d, J=2.8 Hz), 7.96 (1H, br s).

Example 169

3-[4-[2-(3-Chloro-2-thienyl)-2-oxoethyl]piperidino]methyl-1H-pyrazin-2-one

The title compound (140 mg, 72% yield) was obtained in the same manner as Example 137 from 226 mg of 2-[1-(3-tert-butoxy-2-pyrazinylmethyl)-piperidin-4-yl]-1-(3-chloro-2-thienyl)ethanone.

1H-NMR (400 MHz, CDCl3); δ (ppm) 1.42-1.54 (2H, m), 1.85-1.93 (2H, m), 2.06-2.26 (1H, m), 2.30-2.40 (2H, m), 2.95-3.04 (2H, m), 2.99 (2H, d, J=6.4 Hz), 3.86 (2H, s), 7.04 (1H, d, J=5.4 Hz), 7.55 (1H, d, J=5.4 Hz), 7.92 (1H, d, J=2.8 Hz), 7.97 (1H, br s).

Example 170

3-[4-[(2-Fluorophenyl)ethynyl]piperidino]methyl-1H-pyrazin-2-one

The title compound (258 mg, 90% yield) was obtained in the same manner as Example 137 from 338 mg of 2-tert-butoxy-3-[4-[(2-fluorophenyl)ethynyl]piperidino]methylpyrazine.

1H-NMR (400 MHz, CDCl3); δ(ppm) 1.86-1.96 (2H, m), 1.99-2.09 (2H, m), 2.44-2.68 (2H, m), 2.78-3.00 (3H, m), 3.87 (2H, s), 7.03-7.10 (2H, m), 7.24-7.31 (1H, m), 7.39 (1H, dd, J=7.2, 2.0 Hz), 7.90 (2H, br s).

Example 171

(E)-3-[4-[2-(2-Methylphenyl)vinyl]piperidino]methyl-1H-pyrazin-2-one

The title compound (203 mg, 83% yield) was obtained in the same manner as Example 137 from 289 mg of (E)-2-tert-butoxy-3-[4-[2-(2-methylphenyl)vinyl]piperidino]methyl-pyrazine.

1H-NMR (400 MHz, CDCl3); δ (ppm) 1.61-1.73 (2H, m), 1.85-1.93 (2H, m), 2.22-2.42 (3H, m), 2.33 (3H, s), 3.03-3.10 (2H, m), 3.87 (2H, s), 6.03 (1H, dd, J=16.0, 7.2 Hz), 6.61 (1H, dd, J=16.0, 0.8 Hz), 7.12-7.19 (3H, m), 7.41 (1H, dd, J=8.0, 2.0 Hz), 7.90 (1H, d, J=2.8 Hz), 7.91 (1H, br s).

Example 172

3-[4-[2-(3-Fluoro-2-thienyl)ethyl]piperidino]methyl-1H-pyrazin-2-one

The title compound (37 mg, 63% yield) was obtained in the same manner as Example 137 from 69 mg of 2-tert-butoxy-3-[4-[2-(3-fluoro-2-thienyl)ethyl]piperidino]methyl-pyrazine.

1H-NMR (400 MHz, CDCl3); δ (ppm) 1.32-1.45 (3H, m), 1.58-1.66 (2H, m), 1.78-1.86 (2H, m), 2.22-2.32 (2H, m), 2.72-2.79 (2H, m), 2.96-3.04 (2H, m), 3.85 (2H, s), 6.73 (1H, dd, J=5.6, 0.8 Hz), 6.98 (1H, dd, J=5.6, 4.0 Hz), 7.92 (1H, d, J=2.8 Hz), 7.98 (1H, br s).

Example 173

(E)-3-[4-[2-(3-Fluoro-2-thienyl)vinyl]piperidino]methyl-1H-pyrazin-2-one

The title compound (54 mg, 26% yield) was obtained in the same manner as Example 137 from 242 mg of (E)-2-tert-butoxy-3-[4-[2-(3-fluoro-2-thienyl)vinyl]piperidino]methylpyrazine.

1H-NMR (400 MHz, CDCl3); δ (ppm) 1.57-1.69 (2H, m), 1.82-1.92 (2H, m), 2.16-2.30 (1H, m), 2.31-2.40 (2H, m), 3.00-3.08 (2H, m), 3.87 (2H, s), 5.93 (1H, dd, J=16.0, 6.8 Hz), 6.48 (1H, dd, J=16.0, 1.2 Hz), 6.74 (1H, d, J=5.6 Hz), 6.97 (1H, dd, J=5.6, 4.0 Hz), 7.93 (1H, d, J=2.8 Hz), 7.97 (1H, br s).

Example 174

3-[4-[2-(2-Chlorophenyl)-2-oxoethyl]piperidino]methyl-1H-pyrazin-2-one

The title compound (114 mg, 59% yield) was obtained in the same manner as Example 137 from 224 mg of 2-[1-(3-tert-butoxy-2-pyrazinylmethyl)-piperidin-4-yl]-1-(2-chlorophenyl)ethanone.

1H-NMR (400 MHz, CDCl3); δ(ppm) 1.40-1.52 (2H, m), 1.84-1.91 (2H, m), 2.06-2.18 (1H, m), 2.34 (2H, dt, J=12.0, 2.4 Hz), 2.92 (2H, d, J=6.4 Hz), 2.97-3.04 (2H, m), 3.85 (2H, d, J=0.4 Hz), 7.30-7.44 (4H, m), 7.90 (1H, d, J=2.8 Hz), 7.91-7.94 (1H, m).

Example 175

3-[4-[1-(2-Fluorophenoxy)ethyl]piperidino]methyl-1H-pyrazin-2-one

The title compound (189 mg, 55% yield) was obtained in the same manner as Example 137 from 400 mg of 2-tert-butoxy-3-[4-[1-(2-fluorophenoxy)ethyl]piperidino]methylpyrazine.

1H-NMR (400 MHz, CDCl3); δ (ppm) 1.29 (3H, d, J=6.0 Hz), 1.48-1.56 (2H, m), 1.69-1.88 (2H, m), 2.04-2.11 (1H, m), 2.25-2.35 (2H, m), 3.04-3.11 (2H, m), 3.86 (2H, s), 4.01-4.09 (1H, m), 6.88-6.94 (1H, m), 6.96 (1H, td, J=8.4, 1.6 Hz), 7.02-7.11 (2H, m), 7.92 (1H, d, J=2.4 Hz), 7.96 (1H, d, J=2.4 Hz).

Example 176

(E)-3-[4-[2-(3-Fluorophenyl)vinyl]piperidino]methyl-1H-pyrazin-2-one

The title compound (134 mg, 82% yield) was obtained in the same manner as Example 137 from 191 mg of (E)-2-tert-butoxy-3-[4-[2-(3-fluorophenyl)vinyl]piperidino]methyl-pyrazine.

1H-NMR (400 MHz, CDCl3); δ(ppm) 1.60-1.72 (2H, m), 1.84-1.92 (2H, m), 2.21-2.41 (3H, m), 3.02-3.10 (2H, m), 3.88 (2H, s), 6.17 (1H, dd, J=16.0, 7.2 Hz), 6.38 (1H, d, J=16.0 Hz), 6.91 (1H, dt, J=8.4, 2.0 Hz), 7.05 (1H, dt, J=10.4, 2.0 Hz), 7.10 (1H, d, J=7.6 Hz), 7.19-7.33 (1H, m), 7.92 (1H, d, J=2.8 Hz), 7.94 (1H, br s).

Example 177

3-[4-[2-(2-Fluorophenyl)ethyl]piperidino]methyl-1H-pyrazin-2-one

The title compound (103 mg, 44% yield) was obtained in the same manner as Example 137 from 275 mg of 2-tert-butoxy-3-[4-[2-(2-fluorophenyl)ethyl]piperidino]methylpyrazine.

1H-NMR (400 MHz, CDCl3); δ (ppm) 1.34-1.46 (3H, m), 1.56-1.63 (2H, m), 1.79-1.90 (2H, m), 2.22-2.33 (2H, m), 2.63-2.70 (2H, m), 2.96-3.04 (2H, m), 3.85 (2H, s), 6.97-7.08 (2H, m), 7.14-7.20 (2H, m), 7.92 (1H, d, J=2.8 Hz), 7.97 (1H, d, J=2.8 Hz).

Example 178

3-[4-[2-Fluoro-2-(2-fluorophenyl)ethyl]piperidino]methyl-1H-pyrazin-2-one

After dissolving 64 mg of 4-[2-fluoro-2-(2-fluorophenyl)ethyl]piperidine in 3 ml of tetrahydrofuran, 61 mg of 3-tert-butoxy-2-pyrazinecarboxaldehyde and 90 mg of sodium triacetoxyborohydride were added while stirring, and the stirring was continued overnight at room temperature. A 1N sodium hydroxide solution was added to the reaction mixture and extraction was performed with ethyl acetate. The organic layer was washed with saturated brine and dried over anhydrous magnesium sulfate, and then the solvent was distilled off under reduced pressure. The residue was purified by NH silica gel column chromatography (solvent: n-hexane/ethyl acetate). Two milliliters of a 4N hydrogen chloride/ethyl acetate solution was added to the obtained product while stirring, and the stirring was continued for 2.5 hours at room temperature. A 1N sodium hydroxide solution was added to the reaction solution and extraction was performed with dichloromethane. The organic layer was washed with saturated brine and dried over anhydrous magnesium sulfate, and then the solvent was distilled off under reduced pressure. Diethyl ether/n-hexane was added to the residue and the insoluble portion was filtered out to obtain the title compound (5 mg, 5% yield).

1H-NMR (400 MHz, CDCl3); δ (ppm) 1.35-2.40 (9H, m), 2.96-3.07 (2H, m), 3.86 (2H, s), 5.53 (1H, ddd, J=82.0, 9.2, 3.0 Hz), 6.97-7.43 (4H, m), 7.92 (1H, d, J=2.4 Hz), 7.97 (1H, s).

Example 179

3-[4-[2-(2-Fluorophenyl)acetyl]piperidino]methyl-1H-pyrazin-2-one

After adding 5 ml of 4N hydrogen chloride/ethyl acetate to 334 mg of 1-[1-(3-tert-butoxy-2-pyrazinylmethyl)-piperidin-4-yl]-2-(2-fluorophenyl)ethanone, the mixture was stirred for 2 hours at room temperature. A 1N sodium hydroxide solution and saturated aqueous sodium bicarbonate solution were added to the reaction solution for neutralization, and extraction was performed with dichloromethane. The extract was washed with saturated brine and dried over anhydrous magnesium sulfate, and then the solvent was distilled off under reduced pressure. Diethyl ether was added and the insoluble portion was filtered out to obtain the title compound (260 mg, 91% yield).

1H-NMR (400 MHz, CDCl3); δ(ppm) 1.80-1.92 (2H, m), 1.93-2.01 (2H, m), 2.29-2.39 (2H, m), 2.52-2.62 (1H, m), 3.00-3.08 (2H, m), 3.79 (2H, d, J=1.2 Hz), 3.84 (2H, s), 7.06 (1H, ddd, J=9.6, 7.8, 1.2 Hz), 7.11 (1H, td, J=7.8, 1.2 Hz), 7.17 (1H, td, J=7.8, 2.0 Hz), 7.24-7.30 (1H, m), 7.87 (2H, br s).

After dissolving 527 mg of 3-[4-[2-(2-fluorophenyl)acetyl]piperidino]methyl-1H-pyrazin-2-one in 100 ml of dichloromethane, 0.44 ml of 4N hydrogen chloride/ethyl acetate was added and the mixture was concentrated under reduced pressure. Ethyl acetate was added to the residue and the precipitate was filtered out (577 mg). A 400 mg portion thereof was recrystallized from 2.5 ml ethanol/0.5 ml water to obtain a hydrochloride (279 mg).

1H-NMR (400 MHz, DMSO-d6); δ(ppm) 1.78-1.95 (2H, m), 2.06-2.15 (2H, m), 2.78-2.90 (1H, m), 3.09-3.26 (2H, m), 3.54-3.68 (2H, m), 3.96 (2H, s), 4.36 (2H, s), 7.10-7.18 (2H, m), 7.21-7.34 (2H, m), 7.40 (1H, d, J=4.0 Hz), 7.53 (1H, d, J=4.0 Hz), 10.16 (1H, br s), 12.80 (1H, br s).

Example 180

3-[4-[1-Hydroxy-2-(2-fluorophenyl)ethyl]piperidino]methyl-1H-pyrazin-2-one

After suspending 200 mg of 3-[4-[2-(2-fluorophenyl)acetyl]piperidino]methyl-1H-pyrazin-2-one in 6 ml of methanol, an excess of sodium borohydride was added while stirring at room temperature until completion of the reaction. Water was added to the reaction solution and extraction was performed with dichloromethane. The organic layer was washed with saturated brine and dried over anhydrous magnesium sulfate, and then the solvent was distilled off under reduced pressure. Diethyl ether was added and the insoluble portion was filtered out to obtain the title compound (112 mg, 56% yield).

1H-NMR (400 MHz, CDCl3); δ (ppm) 1.46-1.70 (3H, m), 1.78-1.86 (1H, m), 1.98-2.05 (1H, m), 2.24-2.34 (2H, m), 2.64 (1H, dd, J=7.6, 4.8 Hz), 3.00 (1H, dd, J=7.6, 2.0 Hz), 3.04-3.12 (2H, m), 3.66-3.72 (1H, m), 3.86 (2H, s), 7.05 (1H, ddd, J=10.0, 8.0, 1.2 Hz), 7.12 (1H, td, J=8.0, 1.2 Hz), 7.20-7.28 (2H, m), 7.92 (1H, d, J=2.8 Hz), 7.96 (1H, d, J=2.8 Hz).

Example 181

4-[2-[4-(2-Fluorophenoxymethyl)piperidino]ethyl]-3H-pyrimidin-2-one

The title compound (190 mg, 76% yield) was obtained in the same manner as Example 137 from 293 mg of 2-tert-butoxy-4-[2-[4-(2-fluorophenoxymethyl)piperidino]ethyl]pyrimidine.

1H-NMR (400 MHz, CDCl3); δ (ppm) 1.38-1.51 (2H, m), 1.86-1.98 (3H, m), 2.08-2.16 (2H, m), 2.73-2.82 (4H, m), 3.03-3.10 (2H, m), 3.88 (2H, d, J=6.4 Hz), 6.18 (1H, d, J=4.8 Hz), 6.86-6.98 (2H, m), 7.02-7.11 (2H, m), 8.25 (1H, br s).

Example 182

3-[4-(2-Methyl-5-phenylpyrrol-1-yl)methyl-piperidino]methyl-1H-pyrazin-2-one

The title compound (81 mg, 84% yield) was obtained in the same manner as Example 137 from 112 mg of 2-tert-butoxy-3-[4-(2-methyl-5-phenylpyrrol-1-yl)methyl-piperidino]methyl-pyrazine.

1H-NMR (400 MHz, CDCl3); δ (ppm) 1.09 (2H, ddd, J=25.2, 12.6, 3.3 Hz), 1.34-1.42 (2H, m), 1.42-1.50 (1H, m), 2.01 (2H, d, J=11.6 Hz), 2.30 (3H, s), 2.85 (2H, d, J=11.2 Hz), 3.70 (2H, s), 3.87 (2H, d, J=7.2 Hz), 5.95 (1H, d, J=3.6 Hz), 6.08 (1H, d, J=3.6 Hz), 7.27-7.40 (5H, m), 7.75-7.81 (2H, m).

Example 183

3-[4-[2-(2-Chlorophenyl)acetyl]piperidino]methyl-1H-pyrazin-2-one

The title compound (38 mg, 39% yield) was obtained in the same manner as Example 118 from 112 mg of 1-[1-(3-tert-butoxy-2-pyrazinylmethyl)-piperidin-4-yl]-2-(2-chlorophenyl)ethanone.

1H-NMR (400 MHz, CDCl3); δ (ppm) 1.82-2.04 (4H, m), 2.30-2.40 (2H, m), 2.55-2.65 (1H, m), 3.00-3.08 (2H, m), 3.85 (2H, s), 3.91 (2H, s), 7.18-7.28 (3H, m), 7.36-7.41 (1H, m), 7.88-7.93 (2H, m).

Example 184

3-[4-[2-(2-Methylphenyl)acetyl]piperidino]methyl-1H-pyrazin-2-one

After adding 3 ml of 4N hydrogen chloride/ethyl acetate to 153 mg of 1-[1-(3-tert-butoxy-2-pyrazinylmethyl)-piperidin-4-yl]-2-(2-methylphenyl)ethanone, the mixture was stirred for 5 hours at room temperature. Aqueous 1N sodium hydroxide was added to the reaction solution and extraction was performed with dichloromethane. The organic layer was washed with saturated brine and dried over anhydrous magnesium sulfate, and then the solvent was distilled off under reduced pressure. Diethyl ether was added and the insoluble portion was filtered out to obtain the title compound (66 mg, 51% yield).

1H-NMR (400 MHz, CDCl3); δ (ppm) 1.79-1.95 (4H, m), 2.21 (3H, s), 2.25-2.35 (2H, m), 2.50-2.59 (1H, m), 2.98-3.06 (2H, m), 3.77 (2H, s), 3.84 (2H, s), 7.07-7.11 (1H, m), 7.14-7.22 (3H, m), 7.86-7.94 (2H, m).

Example 185

4-Fluoro-2-[1-(3-oxo-3,4-dihydro-2-pyrazinylmethyl)piperidin-4-yl]-2,3-dihydroisoindol-1-one The title compound (60 mg, 32% yield) was obtained in the same manner as Example 178 from 115 mg of 4-fluoro-1-(piperidin-4-yl)-2,3-dihydro-isoindol-1-one hydrochloride and 105 mg of 3-tert-butoxypyrazine-2-carboxaldehyde.

1H-NMR (400 MHz, CDCl3); δ (ppm) 1.90-1.98 (4H, m), 2.45-2.52 (2H, m), 3.13-3.18 (2H, m), 3.89 (2H, s), 4.38 (2H, s), 4.34-4.44 (1H, m), 7.09 (1H, t, J=8.4 Hz), 7.45-7.57 (2H, m), 7.76-7.82 (1H, m), 7.82-7.87 (1H, m).

Example 186

4-Fluoro-2-[1-(3-oxo-3,4-dihydro-2-pyrazinylmethyl)piperidin-4-yl]methyl-isoindole-1,3-dione The title compound (3 mg, 35% yield) was obtained in the same manner as Example 137 from 10 mg of 2-[1-(3-tert-butoxy-2-pyrazinylmethyl)-piperidin-4-yl]methyl-4-fluoro-isoindole-1,3-dione.

1H-NMR (400 MHz, CDCl3); δ (ppm) 1.50 (2H, ddd, J=24.6, 11.8, 3.6 Hz), 1.74-1.80 (2H, m), 1.85-1.95 (1H, m), 2.22-2.29 (2H, m), 2.98-3.03 (2H, m), 3.62 (2H, d, J=7.2 Hz), 3.83 (2H, s), 7.36-7.41 (1H, m), 7.66-7.76 (3H, m), 7.88-7.91 (1H, m).

Example 187

3-[4-[3-(2-Fluorophenyl)-1,2,4-oxadiazol-5-yl]piperidino]methyl-1H-pyrazin-2-one The title compound (47 mg, 89% yield) was obtained in the same manner as Example 137 from 61 mg of 2-tert-butoxy-3-[4-[3-(2-fluorophenyl)-1,2,4-oxadiazol-5-yl]piperidino]methyl-pyrazine.

1H-NMR (400 MHz, CDCl3); δ (ppm) 2.09-2.28 (4H, m), 2.49 (2H, t, J=10.4 Hz), 3.05-3.18 (3H, m), 3.88 (2H, s), 7.21-7.27 (1H, m), 7.29 (1H, dd, J=7.8, 1.0 Hz), 7.47-7.53 (1H, m), 7.78-7.82 (1H, m), 7.82-7.86 (1H, m), 8.06 (1H, td, J=7.2, 1.6 Hz).

Example 188

3-[4-[3-(3-Fluorophenyl)-1,2,4-oxadiazol-5-yl]piperidino]methyl-1H-pyrazin-2-one The title compound (11 mg, 100% yield) was obtained in the same manner as Example 137 from 12 mg of 2-tert-butoxy-3-[4-[3-(3-fluorophenyl)-1,2,4-oxadiazol-5-yl]piperidino]methyl-pyrazine.

1H-NMR (400 MHz, CDCl3); δ (ppm) 2.10-2.31 (4H, m), 2.49 (2H, d, J=11.0 Hz), 3.05-3.18 (3H, m), 3.88 (2H, s), 7.21 (1H, tdd, J=8.4, 2.6, 1.0 Hz), 7.46 (1H, td, J=8.0, 5.6 Hz), 7.78 (1H, ddd, J=9.2, 2.4, 1.2 Hz), 7.78-7.83 (1H, m), 7.83-7.88 (1H, m), 7.88 (1H, ddd, J=4.0, 1.6, 0.8 Hz).

Example 189

3-[4-[3-(4-Fluorophenyl)-1,2,4-oxadiazol-5-yl]piperidino]methyl-1H-pyrazin-2-one The title compound (12 mg, 87% yield) was obtained in the same manner as Example 137 from 16 mg of 2-tert-butoxy-3-[4-[3-(4-fluorophenyl)-1,2,4-oxadiazol-5-yl]piperidino]methyl-pyrazine.

1H-NMR (400 MHz, CDCl3); δ (ppm) 2.10-2.29 (4H, m), 2.50 (2H, t, J=10.2 Hz), 3.05-3.15 (3H, m), 3.89 (2H, s), 7.14-7.20 (2H, m), 7.80-7.88 (2H, m), 8.05-8.10 (2H, m).

Example 190

3-[4-[2-(2-Fluorophenyl)-1-methoxyethyl]piperidino]methyl-1H-pyrazin-2-one

The title compound (47 mg, 40% yield) was obtained in the same manner as Example 118 from 138 mg of 2-tert-butoxy-3-[4-[2-(2-fluorophenyl)-1-methoxyethyl]piperidino]methyl-pyrazine.

1H-NMR (400 MHz, CDCl3); δ (ppm) 1.44-1.78 (4H, m), 1.89-1.97 (1H, m), 2.20-2.28 (2H, m), 2.76 (1H, dd, J=14.4, 8.0 Hz), 2.88 (1H, dd, J=14.4, 6.4 Hz), 3.00-3.10 (2H, m), 3.19-3.27 (1H, m), 3.24 (3H, s), 3.82 (1H, d, J=14.4 Hz), 3.86 (1H, d, J=14.4 Hz), 7.02 (1H, ddd, J=9.8, 8.4, 1.2 Hz), 7.08 (1H, td, J=7.6, 1.2 Hz), 7.18-7.28 (2H, m), 7.92 (1H, d, J=2.8 Hz), 7.98 (1H, d, J=2.8 Hz).

Example 191

3-[4-[2-(3-Fluorophenyl)acetyl]piperidino]methyl-1H-pyrazin-2-one

The title compound (65 mg, 58% yield) was obtained in the same manner as Example 118 from 132 mg of 1-[1-(3-tert-butoxy-2-pyrazinylmethyl)-piperidin-4-yl]-2-(3-fluorophenyl)ethanone.

1H-NMR (400 MHz, CDCl3); δ (ppm) 1.76-1.96 (4H, m), 2.26-2.37 (2H, m), 2.50-2.58 (1H, m), 2.98-3.06 (2H, m), 3.75 (2H, s), 3.83 (2H, s), 6.88-6.93 (1H, m), 6.94-7.00 (2H, m), 7.26-7.33 (1H, m), 7.88 (2H, br s).

Example 192

3-[4-[2-(3-Methylphenyl)acetyl]piperidino]methyl-1H-pyrazin-2-one

The title compound (70 mg, 76% yield) was obtained in the same manner as Example 118 from 108 mg of 1-[1-(3-tert-butoxy-2-pyrazinylmethyl)-piperidin-4-yl]-2-(3-methylphenyl)ethanone.

1H-NMR (400 MHz, CDCl3); δ (ppm) 1.76-1.93 (4H, m), 2.26-2.35 (2H, m), 2.34 (3H, s), 2.50-2.59 (1H, m), 2.96-3.05 (2H, m), 3.71 (2H, s), 3.83 (2H, s), 6.96-7.01 (2H, m), 7.08 (1H, d, J=7.6 Hz), 7.22 (1H, t, J=7.6 Hz), 7.86-7.94 (2H, m).

Example 193

3-[4-[2-(2-Methoxyphenyl)acetyl]piperidino]methyl-1H-pyrazin-2-one

After dissolving 249 mg of 1-(1-benzylpiperidin-4-yl)-2-(2-methoxyphenyl)ethanone in 4 ml of 1,2-dichloroethane, 0.1 ml of 1-chloroethyl chloroformate was added while stirring on ice and the mixture was heated to reflux for 1 hour. The reaction solution was concentrated under reduced pressure, 4 ml of methanol was added to the residue, and heating to reflux was continued for 1 hour. The reaction solution was concentrated under reduced pressure, ethyl acetate was added to the residue and the precipitate was filtered out. It was then suspended in 3 ml of dichloromethane, 90 mg of 3-tert-butoxypyrazine-2-carboxaldehyde and 132 mg of sodium triacetoxyborohydride were added while stirring on ice, and the stirring was continued overnight at room temperature. Aqueous 1N sodium hydroxide was added to the reaction mixture and extraction was performed with ethyl acetate. The organic layer was washed with saturated brine and dried over anhydrous magnesium sulfate, and then the solvent was distilled off under reduced pressure. The residue was purified by silica gel column chromatography (solvent: n-hexane/ethyl acetate).

After adding 2 ml of 4N hydrogen chloride/ethyl acetate to the obtained 1-[1-(3-tert-butoxy-2-pyrazinylmethyl)piperidin-4-yl]-2-(2-methoxyphenyl)ethanone, the mixture was stirred overnight at room temperature. Aqueous 1N sodium hydroxide was added to the reaction solution for adjustment to pH 8, and extraction was performed with dichloromethane. The organic layer was washed with saturated brine and dried over anhydrous magnesium sulfate, and the solvent was distilled off under reduced pressure. Diethyl ether was added and the precipitate was filtered out to obtain the title compound (89 mg, 34% yield, 3 steps).

1H-NMR (400 MHz, CDCl3); δ(ppm) 1.80-1.98 (4H, m), 2.28-2.38 (2H, m), 2.50-2.60 (1H, m), 2.97-3.06 (2H, m), 3.73 (2H, s), 3.79 (3H, s), 3.84 (2H, s), 6.87 (1H, d, J=8.0 Hz), 6.93 (1H, td, J=7.6, 1.2 Hz), 7.11 (1H, dd, J=7.6, 1.6 Hz), 7.24-7.29 (1H, m), 7.91 (1H, br s), 7.93 (1H, br s).

Example 194

3-[4-[2-(2,5-Difluorophenyl)acetyl]piperidino]methyl-1H-pyrazin-2-one

The title compound (92 mg, 66% yield) was obtained in the same manner as Example 118 from 162 mg of 1-[1-(3-tert-butoxy-2-pyrazinylmethyl)-piperidin-4-yl]-2-(2,5-difluorophenyl)ethanone.

1H-NMR (400 MHz, CDCl3); δ (ppm) 1.80-1.92 (2H, m), 1.94-2.02 (2H, m), 2.30-2.40 (2H, m), 2.52-2.62 (1H, m), 3.00-3.09 (2H, m), 3.77 (2H, d, J=1.2 Hz), 3.85 (2H, s), 6.86-7.05 (3H, m), 7.88 (2H, br s).

Example 195

3-[4-[2-(2,6-Difluorophenyl)acetyl]piperidino]methyl-1H-pyrazin-2-one

The title compound (32 mg, 86% yield) was obtained in the same manner as Example 118 from 43 mg of 1-[1-(3-tert-butoxy-2-pyrazinylmethyl)-piperidin-4-yl]-2-(2,6-difluorophenyl)ethanone.

1H-NMR (400 MHz, CDCl3); δ (ppm) 1.84-1.97 (2H, m), 1.98-2.06 (2H, m), 2.32-2.43 (2H, m), 2.56-2.66 (1H, m), 3.01-3.10 (2H, m), 3.83 (2H, s), 3.86 (2H, s), 6.86-6.94 (2H, m), 7.20-7.28 (1H, m), 7.89 (2H, br s).

Example 196

3-[4-(2-Phenylacetyl)piperidino]methyl-1H-pyrazin-2-one

The title compound (24 mg, 53% yield) was obtained in the same manner as Example 118 from 54 mg of 1-[1-(3-tert-butoxy-2-pyrazinylmethyl)-piperidin-4-yl]-2-phenylethanone.

1H-NMR (400 MHz, CDCl3); δ (ppm) 1.77-1.92 (4H, m), 2.27-2.34 (2H, m), 2.51-2.58 (1H, m), 2.98-3.04 (2H, m), 3.76 (2H, s), 3.83 (2H, s), 7.17-7.20 (2H, m), 7.26-7.36 (3H, m), 7.88 (2H, br s).

Example 197

3-[4-[2-(2,4-Difluorophenyl)acetyl]piperidino)methyl-1H-pyrazin-2-one

The title compound (16 mg, 63% yield) was obtained in the same manner as Example 118 from 33 mg of 1-[1-(3-tert-butoxy-2-pyrazinylmethyl)-piperidin-4-yl]-2-(2,4-difluorophenyl)ethanone.

1H-NMR (400 MHz, CDCl3); δ (ppm) 1.88-1.96 (2H, m), 1.98-2.06 (2H, m), 2.40-2.64 (3H, m), 3.06-3.14 (2H, m), 3.76 (2H, s), 3.90 (2H, s), 6.80-6.88 (2H, m), 7.13 (1H, dd, J=8.2, 6.4 Hz), 7.81 (2H, br s).

Example 198

3-[4-(Phenoxymethyl)piperidino]methyl-1H-pyrazin-2-one

The title compound (150 mg, 82% yield) was obtained in the same manner as Example 137 from 217 mg of 2-tert-butoxy-3-(4-phenoxymethylpiperidino)methyl-pyrazine.

1H-NMR (400 MHz, CDCl3); δ(ppm) 1.48-1.61 (2H, m), 1.86-1.98 (3H, m), 2.29-2.38 (2H, m), 3.04-3.11 (2H, m), 3.83 (2H, d, J=6.0 Hz), 3.87 (2H, s), 6.87-6.91 (2H, m), 6.93-6.97 (1H, m), 7.26-7.32 (2H, m), 7.90 (1H, d, J=2.8 Hz), 7.93 (1H, br s).

Example 199

3-[4-(4-Fluorophenoxymethyl)piperidino]methyl-1H-pyrazin-2-one

The title compound (105 mg, 60% yield) was obtained in the same manner as Example 137 from 204 mg of 2-tert-butoxy-3-[4-(4-fluorophenoxymethyl)piperidino]methyl-pyrazine.

1H-NMR (400 MHz, CDCl3); δ (ppm) 1.47-1.60 (2H, m), 1.84-1.97 (3H, m), 2.29-2.38 (2H, m), 3.04-3.11 (2H, m), 3.79 (2H, d, J=6.0 Hz), 3.87 (2H, s), 6.79-6.85 (2H, m), 6.93-7.01 (2H, m), 7.91 (1H, d, J=2.8 Hz), 7.93 (1H, br s).

Example 200

3-[4-[2-(2,3-Difluorophenyl)acetyl]piperidino]methyl-1H-pyrazin-2-one

The title compound (12 mg, 27% yield) was obtained in the same manner as Example 118 from 44 mg of 1-[1-(3-tert-butoxy-2-pyrazinylmethyl)-piperidin-4-yl]-2-(2,3-difluorophenyl)ethanone.

1H-NMR (400 MHz, CDCl3); δ (ppm) 1.87-2.06 (4H, m), 2.42-2.52 (2H, m), 2.58-2.66 (1H, m), 3.06-3.16 (2H, m), 3.83 (2H, s), 3.89 (2H, s), 6.90-6.94 (1H, m), 7.02-7.14 (2H, m), 7.83 (2H, br s).

Example 201

3-[4-(2,6-Difluorophenoxymethyl)piperidino]methyl-1H-pyrazin-2-one

The title compound (141 mg, 78% yield) was obtained in the same manner as Example 137 from 213 mg of 2-tert-butoxy-3-[4-(2,6-difluorophenoxymethyl)piperidino]methyl-pyrazine.

1H-NMR (400 MHz, CDCl3); δ (ppm) 1.46-1.58 (2H, m), 1.86-2.02 (3H, m), 2.30-2.39 (2H, m), 3.03-3.10 (2H, m), 3.88 (2H, s), 3.98 (2H, d, J=6.4 Hz), 6.85-6.99 (3H, m), 7.92 (1H, d, J=2.8 Hz), 7.96 (1H, br s).

Example 202

3-[4-[1-Hydroxyimino-2-(2-fluorophenyl)ethyl]piperidino]methyl-1H-pyrazin-2-one

After suspending 150 mg of 3-[4-[2-(2-fluorophenyl)acetyl]piperidino]methyl-1H-pyrazin-2-one in 3 ml of ethanol, 47 mg of hydroxylamine hydrochloride and 193 mg of sodium carbonate were added while stirring and the mixture was heated to reflux for 1 hour. Water and saturated aqueous ammonium chloride solution were added to the reaction solution for adjustment to pH 7, and extraction was performed with dichloromethane. The organic layer was washed with brine and dried over anhydrous magnesium sulfate, and then the solvent was distilled off under reduced pressure. Diethyl ether was added and the insoluble portion was filtered out to obtain the title compound (109 mg, 70% yield).

1H-NMR (400 MHz, CDCl3); δ(ppm) 1.68-1.88 (4H, m), 1.97-2.36 (3H, m), 2.98-3.08 (2H, m), 3.53-3.8-4 (4H, m), 7.01-7.12 (2H, m), 7.18-7.28 (2H, m), 7.86-7.93 (2H, m).

Example 203

3-[4-[2-(2-Fluorophenyl)-1-(methoxyimino)ethyl]piperidino]methyl-1H-pyrazin-2-one

The title compound (80 mg, 49% yield) was obtained in the same manner as Example 202 from 150 mg of 3-[4-[2-(2-fluorophenyl)acetyl]piperidino]methyl-1H-pyrazin-2-one and 57 mg of O-methylhydroxylamine hydrochloride.

1H-NMR (400 MHz, CDCl3); δ(ppm) 1.68-1.86 (4H, m), 2.15-2.50 (3H, m), 2.94-3.04 (2H, m), 3.52-3.88 (7H, m), 7.00-7.30 (4H, m), 7.90 (1H, d, J=2.8 Hz), 7.95 (1H, br s).

Example 204

3-[4-(2-Fluorophenoxymethyl)piperidino]methyl-1H-quinoxalin-2-one

The title compound (116 mg, 77% yield) was obtained in the same manner as Example 118 from 174 mg of 2-tert-butoxy-3-[4-(2-fluorophenoxymethyl)piperidino]methyl-quinoxaline.

1H-NMR (400 MHz, CDCl3); δ(ppm) 1.50-1.62 (2H, m), 1.86-1.99 (3H, m), 2.23-2.32 (2H, m), 3.22-3.29 (2H, m), 3.88 (2H, d, J=6.4 Hz), 3.90 (2H, s), 6.85-6.91 (1H, m), 6.95 (1H, dt, J=8.0, 1.6 Hz), 7.01-7.10 (2H, m), 7.31-7.38 (2H, m), 7.52 (1H, dt, J=8.0, 1.6 Hz), 7.92 (1H, dd, J=8.0, 0.8 Hz).

Example 205

3-[4-(2-Methoxyphenoxymethyl)piperidino]methyl-1H-quinoxalin-2-one

2-tert-Butoxy-3-[4-(2-methoxyphenoxymethyl)piperidino]methylquinoxaline (181 mg, 64% yield) was obtained in the same manner as Example 1 from 150 mg of 3-tert-butoxyquinoxaline-2-carboxaldehyde and 185 mg of 4-(2-methoxyphenoxymethyl)piperidine hydrochloride.

This was subjected to the same process as in Example 118 to obtain the title compound (126 mg, 79% yield).

1H-NMR (400 MHz, CDCl3); δ(ppm) 1.49-1.62 (2H, m), 1.88-2.04 (3H, m), 2.22-2.32 (2H, m), 3.20-3.27 (2H, m), 3.85 (3H, s), 3.87 (2H, d, J=7.2 Hz), 3.88 (2H, s), 6.87-6.94 (4H, m), 7.26-7.32 (1H, m), 7.35 (1H, dt, J=8.4, 1.6 Hz), 7.51 (1H, dt, J=8.4, 1.6 Hz), 7.92 (1H, dd, J=8.4, 1.6 Hz).

Example 206

3-[4-[2-(2-Fluorophenyl)acetyl]piperidino]methyl-1H-quinoxalin-2-one

The title compound (109 mg, 84% yield) was obtained in the same manner as Example 118 from 150 mg of 1-[1-(3-tert-butoxy-2-quinoxalinylmethyl)piperidin-4-yl]-2-(2-fluorophenyl)ethanone.

1H-NMR (400 MHz, CDCl3); δ(ppm) 1.83-1.95 (4H, m), 2.24-2.33 (2H, m), 2.46-2.55 (1H, m), 3.19-3.26 (2H, m), 3.79 (2H, s), 3.86 (2H, s), 7.02-7.07 (1H, m), 7.10 (1H, dt, J=7.6, 1.2 Hz), 7.16 (1H, dt, J=8.0, 2.0 Hz), 7.20-7.28 (2H, m), 7.35 (1H, dt, J=8.0, 1.2 Hz), 7.51 (1H, dt, J=8.0, 1.2 Hz), 7.92 (1H, dd, J=8.0, 1.2 Hz)

Example 207

3-[4-[2-(2-Methylphenyl)acetyl]piperidino]methyl-1H-quinoxalin-2-one

After suspending 183 mg of 2-(2-methylphenyl)-1-(piperidin-4-yl)ethanone hydrochloride in 3 ml of dichloromethane, 150 mg of 2-tert-butoxyquinoxaline-3-carboxaldehyde and 180 mg of sodium triacetoxyborohydride were added while stirring, and the stirring was continued overnight at room temperature. Aqueous sodium bicarbonate solution was added to the reaction mixture and extraction was performed with ethyl acetate. The organic layer was washed with water and saturated brine in that order and dried over anhydrous magnesium sulfate, and then the solvent was distilled off under reduced pressure. The residue was purified by silica gel column chromatography (solvent: n-hexane/ethyl acetate) to obtain 1-[1-(3-tert-butoxy-2-quinoxalinylmethyl)piperidin-4-yl]-2-(2-methylphenyl)ethanone (177 mg, 63% yield).

This was dissolved in 3 ml of ethyl acetate, and then 3 ml of 4N hydrogen chloride/ethyl acetate was added and the mixture was allowed to stand at room temperature for 30 minutes. Aqueous sodium bicarbonate solution was added to the reaction solution and extraction was performed with dichloromethane. The extract was dried over anhydrous magnesium sulfate and the solvent was distilled off under reduced pressure. The residue was purified by NH silica gel column chromatography (solvent: ethyl acetate/methanol), diethyl ether was added and the insoluble portion was filtered out to obtain the title compound (177 mg, 79% yield).

1H-NMR (400 MHz, CDCl3); δ(ppm) 1.83-1.96 (4H, m), 2.21 (3H, s), 2.22-2.30 (2H, m), 2.44-2.53 (1H, m), 3.19-3.26 (2H, m), 3.77 (2H, s), 3.86 (2H, s), 7.06-7.11 (1H, m), 7.13-7.19 (3H, m), 7.24-7.28 (1H, m), 7.35 (1H, dt, J=8.0, 0.8 Hz), 7.51 (1H, dt, J=8.0, 1.2 Hz), 7.92 (1H, dd, J=8.0, 1.2 Hz).

Example 208

3-[3-[2-(2-Fluorophenyl)acetyl]piperidino]methyl-1H-pyrazin-2-one

The title compound (143 mg, 87% yield) was obtained in the same manner as Example 118 from 193 mg of 1-[1-(3-tert-butoxy-2-pyrazinylmethyl)-piperidin-3-yl]-2-(2-fluorophenyl)ethanone.

1H-NMR (400 MHz, CDCl3); δ (ppm) 1.42-1.54 (1H, m), 1.66-1.79 (1H, m), 1.80-1.88 (1H, m), 2.02-2.11 (1H, m), 2.20-2.29 (1H, m), 2.39-2.48 (1H, m), 2.84-2.96 (2H, m), 3.03-3.10 (1H, m), 3.74-3.88 (4H, m), 7.05 (1H, ddd, J=9.6, 7.8, 1.2 Hz), 7.09 (1H, td, J=7.8, 1.2 Hz), 7.15 (1H, td, J=7.8, 2.0 Hz), 7.22-7.30 (1H, m), 7.79 (1H, br s), 7.83 (1H, d, J=2.8 Hz).

Example 209

3-[2-[2-(2-Fluorophenoxy)ethyl]piperidino]methyl-1H-pyrazin-2-one

The title compound (10 mg, 78% yield) was obtained in the same manner as Example 137 from 15 mg of 2-tert-butoxy-3-[2-[2-(2-fluorophenoxy)ethyl]piperidino]methyl-pyrazine.

1H-NMR (400 MHz, CDCl3); δ (ppm) 1.51-1.56 (1H, m), 1.62-1.80 (4H, m), 1.89-1.95 (1H, m), 1.97-2.06 (1H, m), 2.23-2.31 (1H, m), 2.49-2.55 (1H, m), 2.88-2.92 (1H, m), 2.92-3.00 (1H, m), 3.84 (1H, d, J=15.6 Hz), 4.01-4.16 (2H, m), 4.22 (1H, d, J=15.6 Hz), 6.86-6.89 (2H, m), 7.02-7.09 (2H, m), 7.88 (1H, d, J=2.8 Hz), 7.91 (1H, br s).

Example 210

3-[4-Hydroxy-4-(2-methylphenoxymethyl)piperidino]methyl-1H-pyrazin-2-one

The title compound (23 mg, 100% yield) was obtained in the same manner as Example 137 from 27 mg of 1-(3-tert-butoxy-2-pyrazinylmethyl)-4-(2-methylphenoxymethyl)piperidin-4-ol.

1H-NMR (400 MHz, CDCl3); δ (ppm) 1.86-1.92 (4H, m), 2.25 (3H, s), 2.78 (2H, td, J=10.6, 5.2 Hz), 2.85-2.91 (2H, m), 3.85 (2H, s), 3.92 (2H, s), 6.81 (1H, d, J=7.6 Hz), 6.88-6.93 (1H, m), 7.15-7.19 (2H, m), 7.84-7.88 (2H, m).

Example 211

3-[4-Hydroxy-4-(2-fluorophenoxymethyl)piperidino]methyl-1H-pyrazin-2-one

The title compound (23 mg, 100% yield) was obtained in the same manner as Example 137 from 27 mg of 1-(3-tert-butoxy-2-pyrazinylmethyl)-4-(2-fluorophenoxymethyl)piperidin-4-ol.

1H-NMR (400 MHz, CDCl3); δ (ppm) 1.79-1.93 (4H, m), 2.77 (2H, td, J=11.6, 3.2 Hz), 2.84-2.90 (2H, m), 3.90 (2H, s), 3.92 (2H, s), 6.91-6.99 (2H, m), 7.04-7.12 (2H, m), 7.88 (2H, s).

Example 212

3-[4-Hydroxy-4-(2-methyl-5-phenylpyrrol-1-yl)methyl-piperidino]methyl-1H-pyrazin-2-one The title compound (32 mg, 88% yield) was obtained in the same manner as Example 137 from 42 mg of 1-(3-tert-butoxy-2-pyrazinylmethyl)-4-(2-methyl-5-phenylpyrrol-1-yl)methyl-piperidin-4-ol.

1H-NMR (400 MHz, CDCl3); δ (ppm) 1.19-1.43 (6H, m), 2.37 (3H, s), 2.40-2.50 (2H, m), 2.52-2.66 (2H, m), 3.74 (2H, s), 6.00 (1H, dd, J=3.2, 2.4 Hz), 6.13 (1H, d, J=3.2 Hz), 7.26-7.34 (3H, m), 7.36-7.42 (2H, m), 7.84 (2H, br s).

Example 213

2-Fluoro-N-[4-hydroxy-1-(3-oxo-3,4-dihydro-2-pyrazinylmethyl)piperidin-4-yl]benzamide The title compound (8 mg, 51% yield) was obtained in the same manner as Example 137 from 18 mg of N-[1-(3-tert-butoxy-2-pyrazinylmethyl)-4-hydroxypiperidin-4-yl]methyl-2-fluorobenzamide.

1H-NMR (400 MHz, CDCl3); δ (ppm) 1.72-1.82 (2H, m), 2.04-2.31 (4H, m), 2.73-2.85 (2H, m), 3.55 (2H, d, J=6.0 Hz), 3.91 (2H, s), 6.76-6.83 (1H, m), 7.43-7.48 (2H, m), 7.51-7.56 (1H, m), 7.79-7.82 (2H, m), 7.89 (1H, s).

Example 214

2-Fluoro-N-(2-fluorobenzoyl)-N-[4-hydroxy-1-(3-oxo-3,4-dihydro-2-pyrazinylmethyl)piperidin-4-yl]benzamide The title compound (8 mg, 51% yield) was obtained in the same manner as Example 137 from 18 mg of N-[1-(3-tert-butoxy-2-pyrazinylmethyl)-4-hydroxypiperidin-4-yl]methyl-2-fluoro-N-(2-fluorobenzoyl)benzamide.

1H-NMR (400 MHz, CDCl3); δ (ppm) 1.96-2.05 (2H, m), 2.44-2.52 (2H, m), 2.60-2.70 (2H, m), 2.88-2.91 (2H, m), 3.87 (2H, s), 4.12 (2H, dd, J=6.4, 1.2 Hz), 7.07-7.20 (2H, m), 7.23-7.29 (1H, m), 7.42-7.65 (3H, m), 7.72-7.78 (1H, m), 7.79-7.84 (1H, m), 7.94 (1H, td, J=7.8, 1.8 Hz), 8.04-8.09 (1H, m).

Example 215

3-[4-(3-Phenyl-1,2,4-oxadiazol-5-yl)piperidino]methyl-1H-pyrazin-2-one

The title compound (48 mg, 93% yield) was obtained in the same manner as Example 137 from 60 mg of 2-tert-butoxy-3-[4-(3-phenyl-1,2,4-oxadiazol-5-yl)piperidino]methyl-pyrazine.

1H-NMR (400 MHz, CDCl3); δ (ppm) 2.09-2.27 (4H, m), 2.48 (2H, t, J=10.2 Hz), 3.05-3.16 (3H, m), 3.87 (2H, s), 7.45-7.53 (3H, m), 7.73 (1H, br s), 7.79-7.82 (1H, m), 8.06-8.09 (2H, m).

Example 216

3-[4-(Ethoxycarbonyl)-4-(2-phenylethyl)piperidino]methyl-1H-pyrazin-2-one

The title compound (24 mg, 100% yield) was obtained in the same manner as Example 137 from 20 mg of ethyl 1-(3-tert-butoxy-2-pyrazinylmethyl)-4-(2-phenylethyl)piperidine-4-carboxylate.

1H-NMR (400 MHz, CDCl3); δ (ppm) 1.30 (3H, t, J=7.2 Hz), 1.60-1.68 (2H, m), 1.83-1.88 (2H, m), 2.30 (2H, d, J=12.8 Hz), 2.41 (2H, t, J=11.6 Hz), 2.49-2.54 (2H, m), 2.85-2.92 (2H, m), 3.82 (2H, s), 4.19 (2H, q, J=7.2 Hz), 7.13 (2H, d, J=6.8 Hz), 7.19 (1H, t, J=7.4 Hz), 7.28 (2H, d, J=7.2 Hz), 7.80-7.86 (2H, m).

Example 217

3-[4-(2-Fluorophenyl)ethynyl-4-hydroxypiperidino]methyl-1H-pyrazin-2-one

The title compound (79 mg, 91% yield) was obtained in the same manner as Example 137 from 102 mg of 1-(3-tert-butoxy-2-pyrazinylmethyl)-4-[(2-fluorophenyl)ethynyl]piperidin-4-ol.

1H-NMR (400 MHz, CDCl3); δ (ppm) 2.05-2.11 (2H, m), 2.12-2.20 (2H, m), 2.75 (2H, t, J=9.0 Hz), 2.90-2.97 (2H, m), 3.89 (2H, s), 7.06-7.13 (2H, m), 7.29-7.36 (1H, m), 7.39-7.44 (1H, m), 7.79 (1H, br s), 7.82-7.85 (1H, m).

Example 218

3-[4-(2-Methylphenyl)ethynyl-4-hydroxypiperidino]methyl-1H-pyrazin-2-one

The title compound (65 mg, 74% yield) was obtained in the same manner as Example 137 from 103 mg of 1-(3-tert-butoxy-2-pyrazinylmethyl)-4-[(2-methylphenyl)ethynyl]piperidin-4-ol.

1H-NMR (400 MHz, CDCl3); δ (ppm) 2.05-2.10 (2H, m), 2.12-2.18 (2H, m), 2.43 (3H, s), 2.74 (2H, d, J=10.2 Hz), 2.90-2.99 (2H, m), 3.87 (2H, d, J=3.2 Hz), 7.11-7.17 (1H, m), 7.18-7.27 (2H, m), 7.39 (1H, d, J=7.6 Hz), 7.68-7.76 (1H, m), 7.76-7.82 (1H, m).

Example 219

3-[4-Hydroxymethyl-4-(2-phenylethyl)piperidino]methyl-1H-pyrazin-2-one

The title compound (50 mg, 94% yield) was obtained in the same manner as Example 137 from 62 mg of 1-(3-tert-butoxy-2-pyrazinylmethyl)-4-(2-phenylethyl)piperidine-4-methanol.

1H-NMR (400 MHz, CDCl3); δ (ppm) 1.60-1.77 (6H, m), 2.53-2.74 (6H, m), 3.59 (2H, s), 3.86 (2H, s), 7.12-7.21 (3H, m), 7.26-7.31 (2H, m), 7.86-7.94 (2H, m).

Example 220

3-[4-[2-(2-Fluorophenyl)ethyl]-4-hydroxypiperidino]methyl-1H-pyrazin-2-one

The title compound (5 mg, 31% yield) was obtained in the same manner as Example 137 from 19 mg of 1-(3-tert-butoxy-2-pyrazinylmethyl)-4-[2-(2-fluorophenyl)ethyl]piperidin-4-ol.

1H-NMR (400 MHz, CDCl3); δ (ppm) 1.72-1.86 (6H, m), 2.68-2.83 (6H, m), 3.90 (2H, s), 6.98-7.09 (2H, m), 7.14-7.22 (2H, m), 7.89-7.93 (2H, m).

Example 221

3-[4-Cyano-4-(2-fluorophenoxymethyl)piperidino]methyl-1H-pyrazin-2-one

The title compound (46 mg, 97% yield) was obtained in the same manner as Example 137 from 55 mg of 1-(3-tert-butoxy-2-pyrazinylmethyl)-4-(2-fluorophenoxymethyl)piperidine-4-carbonitrile.

1H-NMR (400 MHz, CDCl3); δ (ppm) 1.91 (2H, td, J=13.6, 3.4 Hz), 2.09-2.20 (2H, m), 2.58-2.68 (2H, m), 3.10-3.17 (2H, m), 3.84 (2H, s), 4.06 (2H, s), 6.95-7.02 (2H, m), 7.04-7.13 (2H, m), 7.40-7.49 (1H, m), 7.62-7.68 (1H, m).

Example 222

3-[4-Hydroxy-4-[2-(2-methylphenyl)ethyl]piperidino]methyl-1H-pyrazin-2-one

The title compound (100 mg, 85% yield) was obtained in the same manner as Example 137 from 138 mg of 1-(3-tert-butoxy-2-pyrazinylmethyl)-4-[2-(2-methylphenyl)ethyl]piperidin-4-ol.

1H-NMR (400 MHz, CDCl3); δ (ppm) 1.73-1.77 (4H, m), 1.84 (2H, td, J=13.0, 4.4 Hz), 2.32 (3H, s), 2.68-2.75 (4H, m), 2.79-2.87 (2H, m), 3.90 (2H, s), 7.09-7.17 (4H, m), 7.87 (2H, br s).

Example 223

3-[4-Fluoro-4-(2-fluorophenoxymethyl)piperidino]methyl-1H-pyrazin-2-one

The title compound (11 mg, 71% yield) was obtained in the same manner as Example 137 from 18 mg of 2-tert-butoxy-3-[4-fluoro-4-(2-fluorophenoxymethyl)piperidino]methyl-pyrazine.

1H-NMR (400 MHz, CDCl3); δ (ppm) 1.90-2.14 (4H, m), 2.64 (2H, td, J=12.0, 2.6 Hz), 2.93-2.98 (2H, m), 3.87 (2H, s), 4.06 (2H, d, J=30.0 Hz), 6.91-7.01 (2H, m), 7.03-7.11 (2H, m), 7.63 (1H, br s), 7.75 (1H, d, J=3.2 Hz).

Example 224

3-[4-(2-Fluorophenoxymethyl)-4-[2-(2-fluorophenyl)ethyl]piperidino]methyl-1H-pyrazin-2-one The title compound (26 mg, 81% yield) was obtained in the same manner as Example 137 from 36 mg of 2-tert-butoxy-3-[4-(2-fluorophenoxymethyl)-4-[2-(2-fluorophenyl)ethyl]piperidino]methyl-pyrazine.

1H-NMR (400 MHz, CDCl3); δ (ppm) 1.75-1.90 (6H, m), 2.61-2.66 (2H, m), 2.68-2.76 (4H, m), 3.88 (2H, s), 3.93 (2H, s), 6.90-7.20 (8H, m), 7.82-7.86 (2H, m).

Example 225

3-[4-[2-(2-Fluorophenyl)ethyl]-4-(2-methylphenoxymethyl)piperidino]methyl-1H-pyrazin-2-one The title compound (14 mg, 75% yield) was obtained in the same manner as Example 137 from 21 mg of 2-tert-butoxy-3-[4-[2-(2-fluorophenyl)ethyl]-4-(2-methylphenoxymethyl)piperidino]methyl-pyrazine.

1H-NMR (400 MHz, CDCl3); δ (ppm) 1.60-1.91 (4H, m), 2.26 (3H, s), 2.60-2.65 (2H, m), 2.72-2.77 (4H, m), 3.79-3.86 (2H, m), 3.88 (4H, s), 6.76-6.91 (2H, m), 6.97-7.07 (2H, m), 7.09-7.20 (4H, m), 7.88 (2H, br s).

Example 226

3-[2-(2-Fluorophenoxy)-7-azaspiro[3.5]non-7-yl]methyl-1H-pyrazin-2-one

The title compound (25 mg, 88% yield) was obtained in the same manner as Example 137 from 33 mg of 7-(3-tert-butoxy-2-pyrazinylmethyl)-2-(2-fluorophenoxy)-7-azaspiro[3.5]nonane.

1H-NMR (400 MHz, CDCl3); δ(ppm) 1.78 (4H, dt, J=15.2, 5.4 Hz), 2.02-2.07 (2H, m), 2.40-2.70 (6H, m), 3.83 (2H, s), 4.71 (1H, quintet, J=6.8 Hz), 6.78 (1H, td, J=8.2, 1.6 Hz), 6.88 (1H, tdd, J=7.8, 4.4, 1.6 Hz), 7.02 (1H, tt, J=8.0, 1.2 Hz), 7.07 (1H, ddd, J=11.6, 8.0, 1.6 Hz), 7.91 (1H, d, J=2.8 Hz), 7.94 (1H, br s).

Example 227

3-[4-[2-(2-Methylphenyl)ethyl]azepan-1-yl]methyl-1H-pyrazin-2-one oxalate

3-[4-[2-(2-Methylphenyl)ethyl]azepan-1-yl]methyl-1H-pyrazin-2-one (67 mg) was obtained in the same manner as Example 118 from 109 mg of 1-(3-tert-butoxy-2-pyrazinylmethyl)-4-[2-(2-methylphenyl)ethyl]azepane, and was then converted to an oxalate by a ordinary method to obtain the title compound (71 mg, 61% yield, 2 steps).

1H-NMR (400 MHz, DMSO-d6); δ(ppm) 1.27-1.35 (1H, m), 1.39-1.45 (2H, m), 1.56-1.64 (2H, m), 1.70-1.90 (4H, m), 2.23 (3H, br s), 2.51-2.55 (2H, m), 3.07-3.29 (4H, m), 4.17 (2H, s), 7.04-7.11 (4H, m), 7.35 (1H, d, J=4 Hz), 7.48 (1H, d, J=4 Hz).

Example 228

(E)-5-[4-[2-(2-Fluorophenyl)vinyl]piperidino]methyl-1H,3H-pyrimidine-2,4-dione

After dissolving 100 mg of (E)-4-[2-(2-fluorophenyl)vinyl]piperidine in 3 ml of tetrahydrofuran, 116 mg of 2,4-dioxo-1,2,3,4-tetrahydropyrimidine-5-carboxaldehyde, 0.05 ml of acetic acid and 198 mg of sodium triacetoxyborohydride were added while stirring, and the stirring was continued for 20 hours at room temperature. An additional 200 mg of sodium triacetoxyborohydride was then added and the mixture was stirred overnight at room temperature. Aqueous sodium carbonate solution was added to the reaction mixture and extraction was performed with ethyl acetate. The organic layer was washed with brine and dried over anhydrous magnesium sulfate, and then the solvent was distilled off under reduced pressure. The residue was purified by NH silica gel column chromatography (solvent: tetrahydrofuran/methanol). Ethyl acetate was added and the mixture was filtered to obtain the title compound (90 mg, 38% yield).

1H-NMR (400 MHz, DMSO-d6); δ (ppm) 1.32-1.44 (2H, m), 1.66-1.73 (2H, m), 1.94-2.02 (2H, m), 2.07-2.18 (1H, m), 2.79-2.85 (2H, m), 3.11 (2H, s), 6.35 (1H, dd, J=16.0, 6.4 Hz), 6.47 (1H, d, J=16.0 Hz), 7.12-7.19 (2H, m), 7.22-7.29 (2H, m), 7.57 (1H, dt, J=7.2, 1.6 Hz), 10.76 (1H, br s), 11.04 (1H, br s).

Example 229

4-[4-(2-Fluorophenoxymethyl)piperidino]methyl-2H-pyridazin-3-one

After dissolving 1.82 g of methyl 3-methoxypyridazine-4-carboxylate in 50 ml of tetrahydrofuran, 11 ml of diisobutylaluminium hydride (1.01 M, toluene solution) was added dropwise while stirring at below −70° C. and the stirring was continued for 1 hour. The temperature was raised to −45° C. and saturated aqueous ammonium chloride solution was added. After adding 1N hydrochloric acid to the reaction solution, extraction was performed with ethyl acetate. The organic layer was washed with saturated brine and dried over anhydrous magnesium sulfate, and then the solvent was distilled off under reduced pressure. The residue was purified by silica gel column chromatography (solvent: n-hexane/ethyl acetate). The obtained product was dissolved in 3 ml of dichloromethane, and then 220 mg of 4-(2-fluorophenoxymethyl)piperidine hydrochloride and 288 mg of sodium triacetoxyborohydride were added while stirring on ice and the stirring was continued overnight at room temperature. A 1N sodium hydroxide solution was added to the reaction mixture and extraction was performed with ethyl acetate. The organic layer was washed with brine and dried over anhydrous magnesium sulfate, and then the solvent was distilled off under reduced pressure. The residue was purified by silica gel column chromatography (solvent: n-hexane/ethyl acetate). The obtained product was dissolved in 4 ml of ethanol, 1 ml of 4N hydrogen chloride/ethyl acetate was added while stirring, and the mixture was heated to reflux for 3 hours. The reaction solution was allowed to cool, and then 1 ml of concentrated hydrochloric acid was added and the mixture was heated to reflux for 3 hours and then stirred at room temperature for 7 days. A 5N sodium hydroxide solution was added to the reaction solution and extraction was performed with ethyl acetate. The organic layer was washed with saturated brine and dried over anhydrous magnesium sulfate, and then the solvent was distilled off under reduced pressure. Diethyl ether was added and the insoluble portion was filtered out to obtain the title compound (13 mg, 0.4% yield).

1H-NMR (400 MHz, CDCl3); δ(ppm) 1.41-1.56 (2H, m), 1.84-1.97 (3H, m), 2.16-2.24 (2H, m), 2.88-2.94 (2H, m), 3.51 (2H, d, J=1.2 Hz), 3.89 (2H, d, J=6.0 Hz), 6.86-6.92

(1H, m), 6.96 (1H, td, J=8.0, 1.6 HZ), 7.02-7.11 (2H, m), 7.39 (1H, dt, J=4.0, 1.6 Hz), 7.80 (1H, d, J=4.0 Hz).

Example 230

5-[4-(2-Fluorophenoxymethyl)piperidino]methyl-3H-pyrimidin-4-one

The title compound (116 mg, 81% yield) was obtained in the same manner as Example 137 from 167 mg of 4-tert-butoxy-5-[4-(2-fluorophenoxymethyl)piperidino]methyl-pyrimidine.

1H-NMR (400 MHz, CDCl3); δ(ppm) 1.39-1.52 (2H, m), 1.84-1.96 (3H, m), 2.11-2.20 (2H, m), 2.96-3.03 (2H, m), 3.47 (2H, s), 3.88 (2H, d, J=6.4 Hz), 6.85-6.92 (1H, m), 6.95 (1H, dt, J=8.0, 1.6 Hz), 7.02-7.10 (2H, m), 8.10 (1H, s), 8.19 (1H, s).

Example 231

6-[2-[4-Hydroxy-4-(2-fluorophenoxymethyl)piperidino]ethyl]-1H-pyridin-2-one

The title compound (12 mg, 77% yield) was obtained in the same manner as Example 118 from 18 mg of 1-[2-(6-tert-butoxypyridin-2-yl)ethyl]-4-(2-fluorophenoxymethyl)piperidin-4-ol.

1H-NMR (400 MHz, CDCl3); δ (ppm) 1.81-1.94 (4H, m), 2.35 (1H, br s), 2.31-2.59 (2H, m), 2.63-2.69 (2H, m), 2.74-2.80 (2H, m), 2.86-2.92 (2H, m), 3.93 (2H, s), 5.92 (1H, dd, J=6.8, 0.8 Hz), 6.38 (1H, dd, J=9.2, 0.8 Hz), 6.90-7.01 (2H, m), 7.04-7.12 (2H, m), 7.27 (1H, dd, J=9.2, 6.8 Hz).

Example 232

3-[2-[4-(2-Fluorophenoxymethyl)piperidino]ethyl]-1H-pyrazin-2-one

The title compound (23 mg, 77% yield) was obtained in the same manner as Example 137 from 36 mg of 2-tert-butoxy-3-[2-[4-(2-fluorophenoxymethyl)piperidino]ethyl]pyrazine.

1H-NMR (400 MHz, CDCl3); δ(ppm) 1.52-1.64 (2H, m), 1.93-2.06 (3H, m), 2.26-2.36 (2H, m), 2.83-2.88 (2H, m), 3.07-3.13 (2H, m), 3.20-3.28 (2H, m), 3.90 (2H, d, J=6.4 Hz), 6.87-6.98 (2H, m), 7.03-7.11 (2H, m), 7.74 (1H, brs), 7.78 (1H, br s).

Example 233

6-[2-[4-(2-Fluorophenoxymethyl)piperidino]ethyl]-1H-pyrazin-2-one

After dissolving 167 mg of 2-tert-butoxy 6-[2-[4-(2-fluorophenoxymethyl)piperidino]ethyl]pyrazine in 3 ml of ethyl acetate, 3 ml of 4N hydrogen chloride/ethyl acetate was added and the mixture was allowed to stand at room temperature for 30 minutes. Aqueous sodium carbonate solution was added to the reaction solution and extraction was performed with dichloromethane. The organic layer was washed with saturated brine and dried over anhydrous magnesium sulfate, and then the solvent was distilled off under reduced pressure. Diethyl ether was added to the residue and the mixture was filtered to obtain the title compound (113 mg, 79% yield).

1H-NMR (400 MHz, CDCl3); δ(ppm) 1.44-1.56 (2H, m), 1.91-2.04 (3H, m), 2.11-2.19 (2H, m), 2.61-2.66 (2H, m), 2.73-2.78 (2H, m), 3.08-3.15 (2H, m), 3.91 (2H, d, J=6.4 Hz), 6.86-6.93 (1H, m), 6.96 (1H, dt, J=8.4, 1.6 Hz), 7.03-7.11 (2H, m), 7.12 (1H, s), 8.02 (1H, s).

Example 234

(E)-6-[2-[4-(2-(2-Fluorophenyl)vinyl]piperidino]ethyl]-1H-pyrazin-2-one

The title compound (3 mg, 30% yield) was obtained in the same manner as Example 118 from 13 mg of (E)-2-tert-butoxy-6-[2-[4-[2-(2-fluorophenyl)vinyl]piperidino]ethyl]pyrazine.

1H-NMR (400 MHz, CDCl3); δ(ppm) 1.62-1.75 (2H, m), 1.85-1.93 (2H, m), 2.14-2.32 (3H, m), 2.61-2.66 (2H, m), 2.74-2.79 (2H, m), 3.07-3.14 (2H, m), 6.25 (1H, dd, J=16.0, 7.2 Hz), 6.58 (1H, d, J=16.0 Hz), 7.02 (1H, ddd, J=10.8, 8.0, 1.2 Hz), 7.09 (1H, dt, J=7.6, 1.2 Hz), 7.12 (1H, s), 7.15-7.22 (1H, m), 7.45 (1H, dt, J=7.6, 1.6 Hz), 8.03 (1H, s).

Example 235

6-[2-[4-(2-Chlorophenoxymethyl)piperidino]ethyl]-1H-pyrazin-2-one

The title compound (55 mg, 44% yield) was obtained in the same manner as Example 137 from 145 mg of 2-tert-butoxy-6-[2-[4-(2-chlorophenoxymethyl)piperidino]ethyl]pyrazine.

1H-NMR (400 MHz, CDCl3); δ (ppm) 1.46-1.59 (2H, m), 1.93-2.06 (3H, m), 2.12-2.21 (2H, m), 2.61-2.66 (2H, m), 2.74-2.79 (2H, m), 3.09-3.16 (2H, m), 3.90 (2H, d, J=6.4 Hz), 6.87-6.94 (2H, m), 7.12 (1H, s), 7.22 (1H, dt, J=7.6, 1.6 Hz), 7.36 (1H, dd, J=7.6, 1.6 Hz), 8.02 (1H, s).

Example 236

6-[2-[4-(2-Methylphenoxymethyl)piperidino]ethyl]-1H-pyrazin-2-one

The title compound (86 mg, 66% yield) was obtained in the same manner as Example 137 from 152 mg of 2-tert-butoxy-6-[2-[4-(2-methylphenoxymethyl)piperidino]ethyl]pyrazine.

1H-NMR (400 MHz, CDCl3); δ (ppm) 1.49-1.62 (2H, m), 1.88-2.01 (3H, m), 2.12-2.20 (2H, m), 2.24 (3H, s), 2.61-2.66 (2H, m), 2.74-2.79 (2H, m), 3.09-3.16 (2H, m), 3.86 (2H, d, J=6.0 Hz), 6.80 (1H, d, J=8.4 Hz), 6.86 (1H, dt, J=7.6, 1.2 Hz), 7.12-7.18 (3H, m), 8.02 (1H, s).

Example 237

6-[2-[4-[2-(2-Fluorophenyl)acetyl]piperidino]ethyl]-1H-pyrazin-2-one

After dissolving 1.00 g of 2-(2-fluorophenyl)-1-(piperidin-4-yl)ethanone hydrochloride in 8 ml of N,N-dimethylformamide, 643 mg of potassium carbonate and 899 mg of 2-tert-butoxy-6-vinylpyrazine were added while stirring, and the stirring was continued for 64 hours at 100° C. Water was added to the reaction mixture and extraction was performed with ethyl acetate. The organic layer was washed with saturated brine and dried over anhydrous magnesium sulfate, and then the solvent was distilled off under reduced pressure. The residue was purified by NH silica gel column chromatography (solvent: n-hexane/ethyl acetate). Three milliliters of 4N hydrogen chloride/ethyl acetate was added to the obtained product and the mixture was stirred for 2.5 hours at room temperature. A 1N sodium hydroxide solution was added to the reaction solution and extraction was performed with dichloromethane. The organic layer was washed with saturated brine and dried over anhydrous magnesium sulfate, and then the solvent was distilled off under reduced pressure. The residue was purified by silica gel column chromatography (solvent: chloroform/methanol/ammonia water) to obtain the title compound (27 mg, 2% yield).

1H-NMR (400 MHz, CDCl3); δ (ppm) 1.83-1.94 (2H, m), 1.96-2.04 (2H, m), 2.19-2.28 (2H, m), 2.50-2.62 (3H, m), 2.71-2.76 (2H, m), 2.99-3.06 (2H, m), 3.80 (2H, s), 7.06 (1H, ddd, J=9.8, 8.0, 1.2 Hz), 7.09-7.14 (2H, m), 7.18 (1H, td, J=8.0, 2.0 Hz), 7.24-7.30 (1H, m), 8.02 (1H, s).

Example 238

6-[2-[4-(3-Fluorophenoxymethyl)piperidino]ethyl]-1H-pyrazin-2-one

The title compound (219 mg, 84% yield) was obtained in the same manner as Example 118 from 304 mg of 2-tert-butoxy-6-[2-[4-(3-fluorophenoxymethyl)piperidino]ethyl]pyrazine.

1H-NMR (400 MHz, CDCl3); δ (ppm) 1.45-1.57 (2H, m), 1.84-1.99 (3H, m), 2.10-2.18 (2H, m), 2.61-2.66 (2H, m), 2.74-2.79 (2H, m), 3.08-3.15 (2H, m), 3.83 (2H, d, J=6.4 Hz), 6.58-6.70 (3H, m), 7.12 (1H, s), 7.22 (1H, dt, J=8.0, 6.8 Hz), 8.02 (1H, s).

Example 239

6-[2-[4-(2,4-Difluorophenoxymethyl)piperidino]ethyl]-1H-pyrazin-2-one

The title compound (201 mg, 83% yield) was obtained in the same manner as Example 118 from 280 mg of 2-tert-butoxy-6-[2-[4-(2,4-difluorophenoxymethyl)piperidino]ethyl]pyrazine.

H-NMR (400 MHz, CDCl3); δ (ppm) 1.43-1.56 (2H, m), 1.88-2.02 (3H, m), 2.10-2.19 (2H, m), 2.61-2.66 (2H, m), 2.73-2.79 (2H, m), 3.08-3.16 (2H, m), 3.87 (2H, d, J=6.4 Hz), 6.76-6.94 (3H, m), 7.12 (1H, s) 8.02 (1H, s).

Example 240

6-[2-[4-(2-Methoxyphenoxymethyl)piperidino]ethyl]-1H-pyrazin-2-one

The title compound (192 mg, 56% yield) was obtained in the same manner as Example 118 from 305 mg of 2-tert-butoxy-6-[2-[4-(2-methoxyphenoxymethyl)piperidino]ethyl]pyrazine.

1H-NMR (400 MHz, CDCl3); δ (ppm) 1.44-1.56 (2H, m), 1.94-2.06 (3H, m), 2.10-2.18 (2H, m), 2.61-2.66 (2H, m), 2.73-2.78 (2H, m), 3.07-3.14 (2H, m), 3.87 (3H, s), 3.89 (2H, d, J=6.4 Hz), 6.87-6.96 (4H, m), 7.13 (1H, s), 8.01 (1H, s).

Example 241

6-[2-[4-(2,5-Difluorophenoxymethyl)piperidino]ethyl]-1H-pyrazin-2-one

The title compound (178 mg, 88% yield) was obtained in the same manner as Example 118 from 236 mg of 2-tert-butoxy-6-[2-[4-(2,5-difluorophenoxymethyl)piperidino]ethyl]pyrazine.

1H-NMR (400 MHz, CDCl3); δ (ppm) 1.44-1.57 (2H, m), 1.90-2.03 (3H, m), 2.11-2.21 (2H, m), 2.61-2.67 (2H, m), 2.73-2.81 (2H, m), 3.08-3.17 (2H, m), 3.87 (2H, d, J=6.4 Hz), 6.54-6.61 (1H, m), 6.65-6.72 (1H, m), 6.96-7.04 (1H, m), 7.12 (1H, s), 8.01 (1H, s).

Example 242

6-[2-[4-(2,3-Difluorophenoxymethyl)piperidino]ethyl]-1H-pyrazin-2-one

The title compound (124 mg, 85% yield) was obtained in the same manner as Example 118 from 172 mg of 2-tert-butoxy-6-[2-[4-(2,3-difluorophenoxymethyl)piperidino]ethyl]pyrazine.

1H-NMR (400 MHz, CDCl3); δ (ppm) 1.44-1.56 (2H, m), 1.91-2.03 (3H, m), 2.12-2.20 (2H, m), 2.61-2.67 (2H, m), 2.74-2.80 (2H, m), 3.09-3.16 (2H, m), 3.91 (2H, d, J=6.4 Hz), 6.70-6.81 (2H, m), 6.98 (1H, ddt, J=8.4, 6.0, 2.4 Hz), 7.13 (1H, s), 8.02 (1H, s).

Example 243

6-[2-[4-[2-(2-Fluorophenyl)ethyl]piperidino]ethyl]-1H-pyrazin-2-one

The title compound (240 mg, 91% yield) was obtained in the same manner as Example 118 from 309 mg of 2-tert-butoxy-6-[2-[4-[2-(2-fluorophenyl)ethyl]piperidino]ethyl]pyrazine.

1H-NMR (400 MHz, CDCl3); δ(ppm) 1.28-1.47 (3H, m), 1.57-1.64 (2H, m), 1.80-1.88 (2H, m), 2.02-2.11 (2H, m), 2.59-2.75 (6H, m), 3.02-3.09 (2H, m), 6.97-7.03 (1H, m), 7.06 (1H, dt, J=7.2, 1.2 Hz), 7.12 (1H, s), 7.13-7.21 (2H, m), 8.01 (1H, s).

Example 244

6-[2-[4-[(2-Fluorophenyl)ethynyl]piperidino]ethyl]-1H-pyrazin-2-one

The title compound (36 mg, 74% yield) was obtained in the same manner as Example 118 from 59 mg of 2-tert-butoxy-6-[2-[4-[(2-fluorophenyl)ethynyl]piperidino]ethyl]pyrazine.

1H-NMR (400 MHz, CDCl3); δ(ppm) 1.88-1.97 (2H, m), 2.01-2.10 (2H, m), 2.52 (1H, br s), 2.61-2.67 (2H, m), 2.75-2.80 (2H, m), 2.86 (4H, br s), 7.03-7.11 (2H, m), 7.13 (1H, s), 7.24-7.30 (1H, m), 7.41 (1H, dt, J=7.2, 1.6 Hz), 8.03 (1H, s).

Example 245

6-[2-[4-(Phenoxymethyl)piperidino]ethyl]-1H-pyrazin-2-one

After dissolving 471 mg of 2-tert-butoxy-6-vinylpyrazine and 505 mg of 4-(phenoxymethyl)piperidine in 10 ml of ethanol, the mixture was stirred for 4 days at 80° C. The reaction solution was concentrated under reduced pressure and the residue was purified by NH silica gel column chromatography (solvent: n-hexane/ethyl acetate) to obtain 2-tert-butoxy-6-[2-(4-phenoxymethylpiperidino)ethyl]pyrazine.

This was dissolved in 3 ml of ethyl acetate, 3 ml of 4N hydrogen chloride/ethyl acetate was added, and the mixture was allowed to stand at room temperature for 1.5 hours. Aqueous sodium bicarbonate solution was added to the reaction solution and extraction was performed with ethyl acetate. The organic layer was washed with water and saturated brine in that order and dried over anhydrous magnesium sulfate, and then the solvent was distilled off under reduced pressure. Diethyl ether was added to the residue and the mixture was filtered to obtain the title compound (273 mg, 94% yield, 2 steps).

1H-NMR (400 MHz, CDCl3); δ(ppm) 1.46-1.58 (2H, m), 1.85-2.00 (3H, m), 2.11-2.19 (2H, m), 2.61-2.66 (2H, m), 2.74-2.78 (2H, m), 3.08-3.15 (2H, m), 3.85 (2H, d, J=6.4 Hz), 6.88-6.97 (3H, m), 7.12 (1H, s), 7.26-7.32 (2H, m), 8.02 (1H, s).

Example 246

6-[2-[4-(4-Fluorophenoxymethyl)piperidino]ethyl]-1H-pyrazin-2-one

The title compound (242 mg, 30% yield) was obtained in the same manner as Example 245 from 436 mg of 2-tert-butoxy-6-vinylpyrazine and 512 mg of 4-(4-fluorophenoxymethyl)piperidine.

1H-NMR (400 MHz, CDCl3); δ (ppm) 1.45-1.57 (2H, m), 1.83-1.98 (3H, m), 2.10-2.18 (2H, m), 2.61-2.66 (2H, m), 2.73-2.78 (2H, m), 3.08-3.15 (2H, m), 3.81 (2H, d, J=6.4 Hz), 6.80-6.86 (2H, m), 6.94-7.01 (2H, m), 7.12 (1H, s), 8.02 (1H, s).

Example 247

6-[2-[4-(2,6-Difluorophenoxymethyl)piperidino]ethyl]-1H-pyrazin-2-one

The title compound (242 mg, 89% yield) was obtained in the same manner as Example 118 from 316 mg of 2-tert-butoxy-6-[2-[4-(2,6-difluorophenoxymethyl)piperidino]ethyl]pyrazine.

1H-NMR (400 MHz, CDCl3); δ (ppm) 1.43-1.55 (2H, m), 1.85-2.03 (3H, m), 2.10-2.18 (2H, m), 2.61-2.66 (2H, m), 2.73-2.78 (2H, m), 3.07-3.14 (2H, m), 4.00 (2H, d, J=6.4 Hz), 6.85-6.99 (3H, m), 7.12 (1H, s), 8.01 (1H, s).

Example 248

6-[2-[4-[2-(2-Fluorophenyl)-2-oxoethyl]piperidino]ethyl]-1H-pyrazin-2-one

The title compound (36 mg, 45% yield) was obtained in the same manner as Example 118 from 89 mg of 2-[1-[2-(6-tert-butoxy-2-pyrazinyl)ethyl]-piperidin-4-yl]-1-(2-fluorophenyl)ethanone.

1H-NMR (400 MHz, CDCl3); δ (ppm) 1.44-1.54 (2H, m), 1.84-1.93 (2H, m), 2.10-2.22 (3H, m), 2.60-2.66 (2H, m), 2.73-2.78 (2H, m), 2.93-2.98 (2H, m), 3.04-3.53 (2H, m), 7.13 (1H, s), 7.28-7.32 (1H, m), 7.45-7.51 (1H, m), 7.63-7.68 (1H, m), 7.74-7.78 (1H, m), 8.03 (1H, s).

Example 249

6-[2-[4-(2-Fluorophenoxymethyl)piperidino]ethyl]-1-methyl-1H-pyrazin-2-one

After dissolving 330 mg of 6-[2-[4-(2-fluorophenoxymethyl)piperidino]ethyl]-1H-pyrazin-2-one in 3 ml of N,N-dimethylformamide, 44 mg of sodium hydride (70% suspension in oil) was added while stirring, and the stirring was continued for 1 hour at room temperature. Next, 0.068 ml of methyl iodide was added and the mixture was stirred overnight at room temperature. Water was added to the reaction solution and extraction was performed with ethyl acetate. The organic layer was washed with water and saturated brine in that order and dried over anhydrous magnesium sulfate, and then the solvent was distilled off under reduced pressure. The residue was purified by NH silica gel column chromatography (solvent: ethyl acetate). Diethyl ether was added and the mixture was filtered to obtain the title compound (116 mg, 34% yield).

1H-NMR (400 MHz, CDCl3); δ(ppm) 1.35-1.48 (2H, m), 1.83-1.94 (3H, m), 2.07-2.16 (2H, m), 2.63-2.68 (2H, m), 2.78-2.84 (2H, m), 2.96-3.03 (2H, m), 3.52 (3H, s), 3.87 (2H, d, J=6.4 Hz), 6.86-6.92 (1H, m), 6.96 (1H, dt, J=8.8, 1.6 Hz), 7.02-7.10 (2H, m), 7.23 (1H, s), 8.03 (1H, s).

Example 250

3-(2-Fluorobenzyl)-8-(2-oxo-1,2-dihydro-3-pyridylmethyl)-1-oxa-3,8-diazaspiro[4.5]decan-2-one The title compound (6 mg, 48% yield) was obtained in the same manner as Example 130 from 13 mg of 3-(2-fluorobenzyl)-8-(2-methoxypyridin-3-yl)methyl-1-oxa-3,8-diazaspiro[4.5]decan-2-one.

1H-NMR (400 MHz, CDCl3); δ (ppm) 1.73-1.80 (2H, m), 1.90-1.95 (2H, m), 2.55-2.68 (4H, m), 3.20 (2H, s), 3.49 (2H, s), 4.50 (2H, s), 6.29 (1H, t, J=2.6 Hz), 7.07 (1H, t, J=9.2 Hz), 7.15 (1H, t, J=7.4 Hz), 7.28-7.36 (3H, m), 7.50 (1H, d, J=6.4 Hz).

Example 251

3-[4-Hydroxy-4-(2-methyl-5-phenylpyrrol-1-yl)methyl-piperidino]methyl-1H-pyridin-2-one After dissolving 35 mg of 4-hydroxy-4-(2-phenyl-5-methylpyrrol-1-yl)methyl-piperidine in 5 ml of dichloromethane, 16 mg of 2-oxo-1,2-dihydropyridine-3-carboxaldehyde and 0.02 ml of acetic acid were added and the mixture was stirred for 20 minutes at room temperature. Next, 41 mg of sodium triacetoxyborohydride was added and the mixture was stirred overnight at room temperature. Saturated aqueous sodium bicarbonate solution was added to the reaction mixture and extraction was performed with ethyl acetate and chloroform. After drying the organic layer over magnesium sulfate, the solvent was distilled off under reduced pressure. The obtained residue was purified by NH silica gel column chromatography to obtain the title compound (19 mg, 39% yield).

1H-NMR (400 MHz, CDCl3); δ (ppm) 1.25-1.51 (6H, m), 2.18-2.30 (2H, m), 2.39 (3H, s), 2.45-2.55 (2H, m), 3.38 (2H, s), 6.00 (1H, d, J=3.6 Hz), 6.12 (1H, d, J=3.6 Hz), 6.25-6.33 (1H, m), 7.26-7.44 (7H, m).

3-[4-Hydroxy-4-(2-methylphenoxymethyl)piperidino]methyl-1H-pyridin-2-one

The title compound (16 mg, 31% yield) was obtained in the same manner as Example 122 from 40 mg of 4-hydroxy-4-(2-methylphenoxymethyl)piperidine hydrochloride and 19 mg of 2-oxo-1,2-dihydropyridine-3-carboxaldehyde.

1H-NMR (400 MHz, CDCl3); δ (ppm) 1.80-1.85 (4H, m), 2.25 (3H, s), 2.55-2.63 (2H, m), 2.71-2.77 (2H, m), 3.55 (2H, s), 3.84 (2H, s), 6.33 (1H, t, J=6.6 Hz), 6.81 (1H, d, J=8.0 Hz), 6.89-6.91 (1H, m), 7.14-7.18 (2H, m), 7.36 (1H, dd, J=6.4, 2.0 Hz), 7.55-7.58 (1H, m).

Example 253

3-[4-Hydroxy-4-(2-fluorophenoxymethyl)piperidino]methyl-1H-pyridin-2-one

The title compound (3 mg, 16% yield) was obtained in the same manner as Example 122 from 40 mg of 4-(2-fluorophenoxymethyl)-4-hydroxypiperidine hydrochloride and 19 mg of 2-oxo-1,2-dihydropyridine-3-carboxaldehyde.

1H-NMR (400 MHz, CDCl3); δ (ppm) 1.80-1.85 (4H, m), 2.55-2.63 (2H, m), 2.71-2.77 (2H, m), 3.55 (2H, s), 3.89 (2H, s), 6.33 (1H, t, J=6.8 Hz), 6.89-6.95 (1H, m), 6.97 (1H, td, J=8.4, 1.6 Hz), 7.03-7.11 (2H, m), 7.34-7.38 (1H, m), 7.54-7.57 (1H, m).

Example 254

5-Chloro-3-[4-hydroxy-4-(2-fluorophenoxymethyl)piperidino]methyl-1H-pyridin-2-one The title compound (18 mg, 32% yield) was obtained in the same manner as Example 122 from 40 mg of 4-(2-fluorophenoxymethyl)-4-hydroxypiperidine hydrochloride and 29 mg of 5-chloro-2-oxo-1,2-dihydropyridine-3-carboxaldehyde.

1H-NMR (400 MHz, CDCl3); δ (ppm) 1.75-1.90 (4H, m), 2.63 (2H, td, J=11.4, 3.0 Hz), 2.73-2.80 (2H, m), 3.59 (2H, s), 3.89 (2H, s), 6.90-6.97 (1H, m), 6.98 (1H, dd, J=12.2, 1.8 Hz), 7.04-7.07 (1H, m), 7.08-7.12 (1H, m), 7.44 (1H, d, J=2.4 Hz), 7.69 (1H, br s).

Example 255

3-[4-(Ethoxycarbonyl)-4-(2-phenylethyl)piperidino]methyl-1H-pyridin-2-one

The title compound (17 mg, 88% yield) was obtained in the same manner as Example 130 from 20 mg of ethyl 1-(2-methoxy-3-pyridinylmethyl)-4-(2-phenylethyl)piperidine-4-carboxylate.

1H-NMR (400 MHz, CDCl3); δ (ppm) 1.29 (3H, t, J=7.2 Hz), 1.43-1.63 (2H, m), 1.81-1.86 (2H, m), 2.20-2.28 (4H, m), 2.49-2.54 (2H, m), 2.75-2.82 (2H, m), 3.46 (2H, s), 4.19 (2H, q, J=7.2 Hz), 6.32 (1H, t, J=6.6 Hz), 7.14 (1H, d, J=6.8 Hz), 7.15-7.20 (1H, m), 7.25-7.29 (3H, m), 7.32-7.36 (1H, m), 7.52-7.58 (1H, m).

Example 256

3-[4-Hydroxymethyl-4-(2-phenylethyl)piperidino]methyl-1H-pyridin-2-one

The title compound (4 mg, 32% yield) was obtained in the same manner as Example 130 from 23 mg of 1-(2-methoxypyridin-3-yl)methyl-4-(2-phenylethyl)piperidine-4-methanol.

1H-NMR (400 MHz, CDCl3); δ (ppm) 1.56-1.61 (4H, m), 1.69-1.74 (2H, m), 2.50-2.60 (6H, m), 3.50 (2H, s), 3.56 (2H, s), 6.30-6.38 (1H, m), 7.17-7.21 (3H, m), 7.26-7.31 (3H, m), 7.48-7.53 (1H, m).

Example 257

3-[4-(2-Fluorophenoxymethyl)-4-(2-phenylethyl)piperidino]methyl-1H-pyridin-2-one The title compound (2 mg, 41% yield) was obtained in the same manner as Example 130 from 5 mg of 3-[4-(2-fluorophenoxymethyl)-4-(2-phenylethyl)piperidino]methyl-2-methoxypyridine.

1H-NMR (400 MHz, CDCl3); δ (ppm) 1.53-1.94 (6H, m), 2.32-2.45 (2H, m), 2.59-2.63 (2H, m), 3.15-3.40 (2H, m), 4.16 (2H, s), 4.39 (2H, s), 6.45-6.55 (1H, m), 7.11-7.55 (11H, m).

Example 258

3-[4-Hydroxy-4-[(2-fluorophenyl)ethynyl]piperidino]methyl-1H-pyridin-2-one

After dissolving 1.4 g of 1-(tert-butoxycarbonyl)-4-hydroxy-4-[(2-fluorophenyl)ethynyl]piperidine in 20 ml of ethyl acetate, 10 ml of 4N hydrogen chloride/ethyl acetate was added and the mixture was stirred overnight at room temperature. The solvent was distilled off under reduced pressure to obtain 1.28 g of 4-hydroxy-4-[(2-fluorophenyl)ethynyl]piperidine hydrochloride.

After then adding 253 mg of the 4-hydroxy-4-[(2-fluorophenyl)ethynyl]piperidine hydrochloride to 10 ml of dichloromethane, 158 mg of 2-oxo-1,2-dihydropyridine-3-carboxaldehyde was added and the mixture was stirred for 10 minutes at room temperature. Next, 315 mg of sodium triacetoxyborohydride was added and the mixture was stirred overnight at room temperature. Saturated aqueous sodium bicarbonate solution was added to the reaction mixture and extraction was performed with ethyl acetate. After drying the organic layer over magnesium sulfate, the solvent was distilled off under reduced pressure. The residue was purified by NH silica gel column chromatography to obtain the title compound (32 mg, 10% yield).

1H-NMR (400 MHz, CDCl3); δ (ppm) 1.99 (2H, ddd, J=12.8, 9.2, 3.6 Hz), 2.04-2.13 (2H, m), 2.56-2.62 (2H, m), 2.80-2.84 (2H, m), 3.54 (2H, s), 6.32 (1H, t, J=6.6 Hz), 7.04-7.11 (2H, m), 7.26-7.33 (1H, m), 7.35 (1H, dd, J=6.4, 2.0 Hz), 7.38-7.43 (1H, m), 7.57-7.60 (1H, m).

Example 259

3-[4-Hydroxy-4-[(2-methylphenyl)ethynyl]piperidino]methyl-1H-pyridin-2-one

The title compound (18 mg, 21% yield) was obtained in the same manner as Example 122 from 66 mg of 4-hydroxy-4-[(2-methylphenyl)ethynyl]piperidine hydrochloride and 42 mg of 2-oxo-1,2-dihydropyridine-3-carboxaldehyde.

1H-NMR (400 MHz, CDCl3); δ (ppm) 1.95-2.02 (2H, m), 2.04-2.11 (2H, m), 2.42 (3H, s), 2.53-2.62 (2H, m), 2.79-2.85 (2H, m), 3.54 (2H, s), 6.31 (1H, t, J=6.6 Hz), 7.10-7.14

U(1H, m), 7.18-7.24 (2H, m), 7.34 (1H, d, J=6.4 Hz), 7.38 (1H, d, J=8.0 Hz), 7.58 (1H, d, J=6.8 Hz).

Example 260

2-Amino-3-[4-(2-fluorophenoxymethyl)piperidino]methyl-pyrazine

After adding 4 ml of n-butyllithium (2.46 M, n-hexane solution) to a solution of 1.384 g of 2,2,6,6-tetramethylpiperidine in tetrahydrofuran (15 ml) at −20° C. under a nitrogen atmosphere, the mixture was stirred for 30 minutes while cooling on ice. The reaction mixture was cooled to −70° C., and then a solution of 800 mg of 2-(tert-butoxycarbonylamino)pyrazine in tetrahydrofuran (3 ml) was added dropwise, the mixture was stirred for 1 hour, 3 ml of N,N-dimethylformaldehyde was added, and stirring was continued for 30 minutes. After removing the cooling bath and stirring for 30 minutes, water was added and extraction was performed with ethyl acetate. The extract was dried and concentrated and then purified by silica gel column chromatography (solvent: ethyl acetate/n-hexane) to obtain 72 mg of crude 2-(tert-butoxycarbonylamino)pyrazine-3-carboxaldehyde.

This was dissolved in 3 ml of dichloromethane, and then 79 mg of 4-(2-fluorophenoxymethyl)piperidine hydrochloride and 102 mg of sodium triacetoxyborohydride were added and the mixture was stirred overnight at room temperature. A 2N sodium hydroxide solution was added to the reaction mixture, extraction was performed with ethyl acetate and the extract was concentrated under reduced pressure.

The residue was dissolved in 1 ml of dichloromethane, 1 ml of trifluoroacetic acid was added while cooling on ice and the mixture was stirred for 1 hour. The reaction solution was concentrated and distributed in ethyl acetate/water, and the organic layer was washed with water and dried. After concentration under reduced pressure, the residue was purified by NH-silica gel column chromatography (solvent: ethyl acetate/n-hexane) to obtain the title compound (8 mg, 8% yield, 3 steps).

1H-NMR (400 MHz, CDCl3); δ(ppm) 1.34-1.45 (2H, m), 1.86-1.96 (3H, m), 2.11-2.17 (2H, m), 2.87 (2H, d, J=11.6 Hz), 3.69 (2H, s), 3.88 (2H, d, J=6.0 Hz), 5.91 (2H, br s), 6.86-6.97 (2H, m), 7.03-7.10 (2H, m), 7.79 (1H, d, J=3.0 Hz), 7.90 (1H, d, J=3.0 Hz).

Example 261

2-tert-Butylthio-3-[4-(2-fluorophenoxymethyl)piperidino]methyl-pyrazine

The title compound (205 mg, 57% yield) was obtained in the same manner as Example 1 from 180 mg of 2-(tert-butylthio)pyrazine-3-carboxaldehyde and 248 mg of 4-(2-fluorophenoxymethyl)piperidine hydrochloride.

1H-NMR (400 MHz, CDCl3); δ(ppm) 1.41-1.52 (2H, m), 1.59 (9H, s), 1.79-1.94 (3H, m), 2.12-2.20 (2H, m), 2.95-3.02 (2H, m), 3.64 (2H, s), 3.85 (2H, d, J=6.4 Hz), 6.84-6.90 (1H, m), 6.94 (1H, dt, J=8.8, 1.6 Hz), 7.01-7.09 (2H, m), 8.21 (1H, d, J=2.8 Hz), 8.23 (1H, d, J=2.8 Hz).

Example 262

3-[4-(2-Fluorophenoxymethyl)piperidino]methyl-1H-pyrazine-2-thione

The title compound (54 mg, 31% yield) was obtained in the same manner as Example 130 from 205 mg of 2-tert-butylthio-3-[4-(2-fluorophenoxymethyl)piperidino]methyl-pyrazine.

1H-NMR (400 MHz, CDCl3); δ(ppm) 1.73-1.86 (2H, m), 2.11-2.24 (3H, m), 2.80-2.90 (2H, m), 3.43-3.50 (2H, m), 3.94 (2H, d, J=6.0 Hz), 4.17 (2H, s), 6.91-6.97 (2H, m), 7.03-7.12 (2H, m), 7.85 (1H, d, J=2.8 Hz), 8.23 (1H, br s).

Example 263

2-tert-Butoxy-3-[4-(2-fluorobenzylthio)piperidino]methyl-pyrazine

The title compound (224 mg, 66% yield) was obtained in the same manner as Example 1 from 187 mg of 3-tert-butoxypyrazine-2-carboxaldehyde and 227 mg of 4-(2-fluorobenzylthio)piperidine hydrochloride.

1H-NMR (400 MHz, CDCl3); δ (ppm) 1.58 (9H, s), 1.63-1.75 (2H, m), 1.90-1.98 (2H, m), 2.16-2.25 (2H, m), 2.55-2.64 (1H, m), 2.89-2.97 (2H, m), 3.61 (2H, s), 3.76 (2H, s), 7.01 (1H, ddd, J=9.8, 8.0, 1.2 Hz), 7.08 (1H, td, J=8.0, 1.2 Hz), 7.17-7.24 (1H, m), 7.34 (1H, td, J=8.0, 2.0 Hz), 7.90 (1H, d, J=2.8 Hz), 8.01 (1H, d, J=2.8 Hz).

Example 264

2-tert-Butoxy-3-[4-(2-fluorobenzylsulfonyl)piperidino]methyl-pyrazine

The title compound (168 mg, 59% yield) was obtained in the same manner as Example 1 from 147 mg of 3-tert-butoxypyrazine-2-carboxaldehyde and 200 mg of 4-(2-fluorobenzylsulfonyl)piperidine hydrochloride.

1H-NMR (400 MHz, CDCl3); δ (ppm) 1.58 (9H, s), 1.90-2.18 (6H, m), 2.72-2.81 (1H, m), 3.10-3.18 (2H, m), 3.63 (2H, s), 4.28 (2H, s), 7.11 (1H, ddd, J=9.8, 8.0, 1.2 Hz), 7.19 (1H, td, J=8.0, 1.2 Hz), 7.34-7.40 (1H, m), 7.50 (1H, td, J=8.0, 2.0 Hz), 7.93 (1H, d, J=2.8 Hz), 8.01 (1H, d, J=2.8 Hz).

Example 265

2-tert-Butoxy-3-[4-[(2-fluorophenylthio)methyl]piperidino]methyl-pyrazine

The title compound (70 mg, 90% yield) was obtained in the same manner as Example 1 from 43 mg of 3-tert-butoxypyrazine-2-carboxaldehyde and 52 mg of 4-[(2-fluorophenylthio)methyl]piperidine hydrochloride.

1H-NMR (400 MHz, CDCl3); δ (ppm) 1.34-1.62 (3H, m), 1.58 (9H, s), 1.80-1.88 (2H, m), 2.03-2.12 (2H, m), 2.82 (1H, d, J=6.8 Hz), 2.94-3.01 (2H, m), 3.61 (2H, s), 6.99-7.09 (2H, m), 7.14-7.20 (1H, m), 7.32 (1H, td, J=8.0, 2.0 Hz), 7.90 (1H, d, J=2.8 Hz), 8.02 (1H, d, J=2.8 Hz).

Example 266

2-tert-Butoxy-3-[4-[(2-fluorophenylsulfinyl)methyl]piperidino]methyl-pyrazine

4-[(2-Fluorophenylsulfinyl)methyl]piperidine (49 mg) was obtained in the same manner as Production Example 116 from 68 mg of 1-(tert-butoxycarbonyl)-4-[(2-fluorophenylsulfinyl)methyl]piperidine.

After then dissolving 44 mg of 3-tert-butoxypyrazine-2-carboxaldehyde and 49 mg of the 4-[(2-fluorophenylsulfi- 3nyl)methyl]piperidine in 2 ml of dichloromethane, 65 mg of sodium triacetoxyborohydride was added and the mixture was stirred overnight at room temperature. A 1N sodium hydroxide solution was added to the reaction mixture and extraction was performed with ethyl acetate. The organic layer was washed with saturated brine and dried over anhydrous magnesium sulfate, and then the solvent was distilled off under reduced pressure. The residue was purified by silica gel column chromatography (solvent: ethyl acetate/methanol) to obtain the title compound (43 mg, 52% yield).

1H-NMR (400 MHz, CDCl3); δ (ppm) 1.43-1.76 (3H, m), 1.60 (9H, s), 1.98-2.24 (4H, m), 2.75-2.84 (2H, m) 2.94-3.06 (2H, m), 3.63 (2H, s), 7.09 (1H, ddd, J=9.6, 8.0, 1.2 Hz), 7.37 (1H, td, J=8.0, 1.2 Hz), 7.43-7.50 (1H, m), 7.83 (1H, td, J=8.0, 2.0 Hz), 7.91 (1H, d, J=2.8 Hz), 8.02 (1H, d, J=2.8 Hz).

Example 267

2-tert-Butoxy-3-[4-[(2-fluorophenylsulfonyl)methyl]piperidino]methyl-pyrazine

The title compound (48 mg, 93% yield) was obtained in the same manner as Example 1 from 26 mg of 3-tert-butoxypyrazine-2-carboxaldehyde and 36 mg of 4-[(2-fluorophenylsulfonyl)methyl]piperidine hydrochloride.

1H-NMR (400 MHz, CDCl3); δ (ppm) 1.42-1.62 (2H, m), 1.57 (9H, s), 1.81-1.89 (2H, m), 1.98-2.18 (3H, m), 2.89-2.97 (2H, m), 3.22 (2H, d, J=6.4 Hz), 3.59 (2H, s), 7.19-7.26 (1H, m), 7.33 (1H, td, J=8.0, 1.2 Hz), 7.60-7.66 (1H, m), 7.89-7.96 (2H, m), 8.01 (1H, d, J=2.8 Hz).

Example 268

5-tert-Butoxy-3-chloro-2-[4-(2-fluorobenzyloxy)piperidino]methyl-pyrazine

The title compound (137 mg, 49% yield) was obtained in the same manner as Example 1 from 146 mg of 5-tert-butoxy-3-chloropyrazine-2-carboxaldehyde and 201 mg of 4-(2-fluorobenzyloxy)piperidine hydrochloride.

1H-NMR (400 MHz, CDCl3); δ (ppm) 1.39-1.51 (2H, m), 1.60 (9H, s), 1.81-1.94 (3H, m), 2.14-2.22 (2H, m), 2.97-3.03 (2H, m), 3.70 (2H, s), 3.84 (2H, d, J=6.0 Hz), 6.83-6.88 (1H, m), 6.89-6.95 (1H, m), 6.99-7.08 (2H, m), 8.01 (1H, s).

Example 269

2-tert-Butoxy-3-[3-[2-(2-fluorophenyl)ethyl]morpholin-1-yl]methyl-pyrazine

After dissolving 180 mg of 3-tert-butoxypyrazine-2-carboxaldehyde and 251 mg of 3-[2-(2-fluorophenyl)ethyl]morpholine in 5 ml of tetrahydrofuran, 0.07 ml of acetic acid and 318 mg of sodium triacetoxyborohydride were added and the mixture was stirred overnight at room temperature. Aqueous sodium carbonate solution was added to the reaction mixture and extraction was performed with ethyl acetate. The organic layer was washed with saturated brine and dried over anhydrous magnesium sulfate, and then the solvent was distilled off under reduced pressure. The residue was purified by silica gel column chromatography (solvent: n-hexane/ethyl acetate) to obtain the title compound (329 mg, 88% yield).

1H-NMR (400 MHz, CDCl3); δ (ppm) 1.59 (9H, s), 1.62-1.71 (1H, m), 1.72-1.82 (1H, m), 2.04 (1H, t, J=11.2 Hz), 2.33 (1H, dt, J=11.2, 3.6 Hz), 2.63-2.72 (1H, m), 2.76-2.86 (3H, m), 3.50-3.58 (1H, m), 3.61 (1H, d, J=14.0 Hz), 3.65 (1H, d, J=14.0 Hz), 3.71 (1H, dt, J=11.2, 2.4 Hz), 3.84-3.89 (1H, m), 6.94-7.04 (2H, m), 7.10-7.19 (2H, m), 7.92 (1H, d, J=2.8 Hz), 8.02 (1H, d, J=2.8 Hz).

Example 270

(E)-2-tert-Butoxy-3-[3-[2-(2-fluorophenyl)vinyl]morpholin-1-yl]methyl-pyrazine

The title compound (178 mg, 69% yield) was obtained in the same manner as Example 1 from 126 mg of 3-tert-butoxypyrazine-2-carboxaldehyde and 170 mg of (E)-3-[2-(2-fluorophenyl)vinyl]morpholine hydrochloride.

1H-NMR (400 MHz, CDCl3); δ (ppm) 1.60 (9H, s), 2.19 (1H, dt, J=11.2, 10.4 Hz), 2.39 (1H, dt, J=11.2, 3.2 Hz), 2.80-2.85 (1H, m), 2.95-3.00 (1H, m), 3.67 (2H, s), 3.83 (1H, dt, J=11.2, 2.4 Hz), 3.94 (1H, ddd, J=11.2, 3.2, 1.2 Hz), 4.24-4.30 (1H, m), 6.23 (1H, dd, J=16.0, 5.6 Hz), 6.77 (1H, dd, J=16.0, 1.2 Hz), 7.00 (1H, ddd, J=10.8, 8.4, 1.2 Hz), 7.06 (1H, dt, J=7.6, 1.2 Hz), 7.15-7.21 (1H, m), 7.40 (1H, dt, J=7.6, 2.0 Hz), 7.93 (1H, d, J=2.8 Hz), 8.04 (1H, d, J=2.8 Hz).

Example 271

2-tert-Butoxy-3-[3-(2-fluorophenoxymethyl)morpholin-1-yl]methyl-pyrazine

The title compound (258 mg, 83% yield) was obtained in the same manner as Example 1 from 150 mg of 3-tert-butoxypyrazine-2-carboxaldehyde and 248 mg of 3-(2-fluorophenoxymethyl)morpholine hydrochloride.

1H-NMR (400 MHz, CDCl3); δ (ppm) 1.59 (9H, s), 2.27 (1H, dt, J=11.2, 5.6 Hz), 2.39 (1H, dt, J=11.2, 3.6 Hz), 2.78-2.84 (1H, m), 3.01-3.06 (1H, m), 3.69 (2H, s), 3.79 (1H, dt, J=11.2, 2.4 Hz), 3.88-3.93 (1H, m), 3.98-4.10 (3H, m), 6.85-6.91 (1H, m), 6.93-7.07 (3H, m), 7.93 (1H, d, J=2.8 Hz), 8.02 (1H, d, J=2.8 Hz).

Example 272

1-[1-(3-tert-Butoxy-2-pyrazinylmethyl)piperidin-4-yl]-2-[2-(methylthio)phenyl]ethanone The title compound (196 mg, 83% yield) was obtained in the same manner as Example 1 from 115 mg of 3-tert-butoxypyrazine-2-carboxaldehyde and 169 mg of 2-[2-(methylthio)phenyl]-1-(piperidin-4-yl)ethanone hydrochloride.

1H-NMR (400 MHz, CDCl3); δ (ppm) 1.59 (9H, s), 1.74-1.92 (4H, m), 2.12-2.22 (2H, m), 2.40-2.50 (1H, m), 2.41 (3H, s), 2.98-3.05 (2H, m), 3.63 (2H, s), 3.88 (2H, s), 7.06-7.15 (2H, m), 7.21-7.28 (2H, m), 7.91 (1H, d, J=2.8 Hz), 8.02 (1H, d, J=2.8 Hz).

Example 273

1-[1-(3-tert-Butoxy-2-pyrazinylmethyl)piperidin-4-yl]-2-[2-(trifluoromethyl)phenyl]ethanone After suspending 200 mg of 1-(piperidin-4-yl)-2-[2-(trifluoromethyl)phenyl]ethanone hydrochloride in 2 ml of dichloromethane, a solution of 140 mg of 3-tert-butoxypyrazine-2-carboxaldehyde in dichloromethane (2 ml) and 207 mg of sodium triacetoxyborohydride were added while stirring, and the stirring was continued overnight at room temperature. A 1N sodium hydroxide solution was added to the reaction mixture and extraction was performed with ethyl acetate. The organic layer was washed with saturated brine and dried over anhydrous magnesium sulfate, and then the solvent was distilled off under reduced pressure. The residue was purified by silica gel column chromatography (solvent: n-hexane/ethyl acetate) to obtain the title compound (249 mg, 88% yield).

1H-NMR (400 MHz, CDCl3); δ (ppm) 1.60 (9H, s), 1.74-1.91 (4H, m), 2.14-2.22 (2H, m), 2.39-2.48 (1H, m), 3.00-3.07 (2H, m), 3.64 (2H, s), 3.95 (2H, d, J=1.2 Hz), 7.21 (1H, d, J=7.6 Hz), 7.35 (1H, t, J=7.6 Hz), 7.49 (1H, t, J=7.6 Hz), 7.63 (1H, d, J=7.6 Hz), 7.92 (1H, d, J=2.8 Hz), 8.03 (1H, d, J=2.8 Hz).

Example 274

1-[1-(3-tert-Butoxy-2-pyrazinylmethyl)piperidin-4-yl]-2-[2-(trifluoromethoxy)phenyl]ethanone The title compound (266 mg, 95% yield) was obtained in the same manner as Example 1 from 133 mg of 3-tert-butoxypyrazine-2-carboxaldehyde and 200 mg of 1-(piperidin-4-yl)-2-[2-(trifluoromethoxy)phenyl]ethanone hydrochloride.

1H-NMR (400 MHz, CDCl3); δ (ppm) 1.59 (9H, s), 1.74-1.90 (4H, m), 2.14-2.22 (2H, m), 2.38-2.47 (1H, m), 2.99-3.06 (2H, m), 3.63 (2H, s), 3.80 (2H, s), 7.18-7.32 (4H, m), 7.91 (1H, d, J=2.8 Hz), 8.02 (1H, d, J=2.8 Hz).

Example 275

3-[1-(3-tert-Butoxy-2-pyrazinylmethyl)piperidin-4-yl]-6-methyl-3,4-dihydropyrido[2,3-e][1,3]oxazin-2-one The title compound (37 mg, 56% yield) was obtained in the same manner as Example 1 from 37 mg of 3-tert-butoxypyrazine-2-carboxaldehyde and 48 mg of 6-methyl-3-(piperidin-4-yl)-3,4-dihydropyrido[2,3-e][1,3]oxazin-2-one hydrochloride.

1H-NMR (400 MHz, CDCl3); δ (ppm) 1.61 (9H, s), 1.74-1.80 (2H, m), 1.90-2.02 (2H, m), 2.27-2.35 (2H, m), 2.51 (3H, s), 2.97-3.14 (2H, m), 3.67 (2H, s), 4.23-4.32 (1H, m), 4.44 (2H, s), 7.05 (1H, d, J=8.0 Hz), 7.20 (1H, d, J=8.0 Hz), 7.93 (1H, d, J=2.8 Hz), 8.04 (1H, d, J=2.8 Hz).

Example 276

2-[1-[4-(2-Fluorophenoxymethyl)piperidino]ethyl]-3-methoxypyrazine

After dissolving 1.09 g of 4-(2-fluorophenoxymethyl)piperidine in 15 ml of methanol, 1.53 ml of titanium (IV) tetraisopropoxide and 400 mg of 2-acetyl-3-methoxypyrazine [CAS No. 56343-40-9] were added and the mixture was stirred overnight at room temperature. The reaction solution was cooled on ice, 148 mg of sodium borohydride was added and the mixture was stirred for 5 hours at room temperature. Water and ethyl acetate were added to the reaction solution and the mixture was filtered with celite. The filtrate was extracted with ethyl acetate and the extract was washed with saturated brine and then dried over anhydrous magnesium sulfate. The solvent was distilled off under reduced pressure, and the residue was purified by NH silica gel column chromatography (solvent: n-hexane/ethyl acetate) to obtain the title compound (100 mg, 11% yield).

1H-NMR (400 MHz, CDCl3); δ (ppm) 1.30-1.51 (2H, m), 1.40 (3H, d, J=6.8 Hz), 1.70-1.88 (3H, m), 2.03-2.12 (2H, m), 2.87-2.94 (1H, m), 3.16-3.23 (1H, m), 3.82 (2H, d, J=6.4 Hz), 3.96 (3H, s), 4.15 (1H, q, J=6.8 Hz), 6.82-6.94 (2H, m), 6.98-7.07 (2H, m), 7.95 (1H, d, J=2.8 Hz), 8.13 (1H, d, J=2.8 Hz).

Example 277

1-[1-(3-tert-Butoxy-2-pyrazinylmethyl)piperidin-4-yl]-2-(2-ethoxyphenyl)ethanone The title compound (264 mg, 91% yield) was obtained in the same manner as Example 1 from 152 mg of 3-tert-butoxypyrazine-2-carboxaldehyde and 200 mg of 2-(2-ethoxyphenyl)-1-(piperidin-4-yl)ethanone hydrochloride.

1H-NMR (400 MHz, CDCl3); δ (ppm) 1.35 (3H, t, J=7.0 Hz), 1.59 (9H, s), 1.72-1.88 (4H, m), 2.11-2.19 (2H, m), 2.38-2.47 (1H, m), 2.97-3.04 (2H, m), 3.62 (2H, s), 3.70 (2H, s), 3.99 (2H, t, J=7.0 Hz), 6.82 (1H, dd, J=7.6, 1.2 Hz), 6.87 (1H, td, J=7.6, 1.2 Hz), 7.08 (1H, dd, J=7.6, 1.6 Hz), 7.20 (1H, td, J=7.6, 1.6 Hz), 7.91 (1H, d, J=2.8 Hz), 8.02 (1H, d, J=2.8 Hz).

Example 278

1-[1-(3-tert-Butoxy-2-pyrazinylmethyl)piperidin-4-yl]-2-(2-n-propoxyphenyl)ethanone The title compound (276 mg, 97% yield) was obtained in the same manner as Example 1 from 145 mg of 3-tert-butoxypyrazine-2-carboxaldehyde and 200 mg of 1-(piperidin-4-yl)-2-(2-n-propoxyphenyl)ethanone hydrochloride.

1H-NMR (400 MHz, CDCl3); δ (ppm) 1.00 (3H, t, J=7.4 Hz), 1.59 (9H, s), 1.70-1.87 (6H, m), 2.10-2.18 (2H, m), 2.37-2.47 (1H, m), 2.96-3.04 (2H, m), 3.62 (2H, s), 3.71 (2H, s), 3.88 (2H, t, J=6.6 Hz), 6.82 (1H, dd, J=7.6, 1.2 Hz), 6.87 (1H, td, J=7.6, 1.2 Hz), 7.08 (1H, dd, J=7.6, 1.6 Hz), 7.20 (1H, td, J=7.6, 1.6 Hz), 7.91 (1H, d, J=2.8 Hz), 8.02 (1H, d, J=2.8 Hz).

Example 279

1-[1-(3-tert-Butoxy-2-pyrazinylmethyl)piperidin-4-yl]-2-(2-fluorophenyl)propanone The title compound (300 mg, 86% yield) was obtained in the same manner as Example 21 from 189 mg of 3-tert-butoxypyrazine-2-carboxaldehyde and 206 mg of 2-(2-fluorophenyl)-1-(piperidin-4-yl)propanone.

1H-NMR (400 MHz, CDCl3); δ (ppm) 1.35 (3H, d, J=7.0 Hz), 1.47-1.86 (4H, m), 1.57 (9H, s), 1.98-2.14 (2H, m), 2.30-2.40 (1H, m), 2.88-3.01 (2H, m), 3.58 (2H, s), 4.26 (1H, q, J=7.0 Hz), 7.04 (1H, ddd, J=9.6, 7.6, 1.2 Hz), 7.09 (1H, dd, J=7.6, 1.2 Hz), 7.15 (1H, td, J=7.6, 2.0 Hz), 7.18-7.26 (1H, m), 7.89 (1H, d, J=2.8 Hz), 8.00 (1H, d, J=2.8 Hz).

Example 280

1-[1-[1-(3-Methoxy-2-pyrazinyl)ethyl]piperidin-4-yl]-2-(2-fluorophenyl)ethanone

After dissolving 1.012 g of triethylamine in 10 ml of ethanol, 2.575 g of 2-(2-fluorophenyl)-1-(piperidin-4-yl)ethanone hydrochloride, 10 ml of ethanol, 2.951 ml of titanium (IV) tetraisopropoxide and 760 mg of 2-acetyl-3- methoxypyrazine were added in that order and the mixture was stirred for 5 hours and 20 minutes at room temperature. Next, 1.59 g of sodium triacetoxyborohydride was added to the reaction mixture and the mixture was stirred overnight at room temperature. A sodium carbonate solution and ethyl acetate were added to the reaction mixture and the mixture was filtered with celite. The filtrate was extracted with ethyl acetate, and the extract was washed with water and saturated brine and then dried over anhydrous magnesium sulfate. The solvent was distilled off under reduced pressure, and then the residue was dissolved in ethyl acetate and filtered with silica gel. The solvent was distilled off under reduced pressure, and the residue was purified by silica gel column chromatography (solvent: n-hexane/ethyl acetate) to obtain the title compound (169 mg, 9% yield).

1H-NMR (400 MHz, CDCl3); δ (ppm) 1.38 (3H, d, J=6.8 Hz), 1.63-1.88 (4H, m), 2.04-2.18 (2H, m), 2.32-2.41 (1H, m), 2.90-2.97 (1H, m), 3.10-3.16 (1H, m), 3.74 (2H, d, J=0.8 Hz), 3.95 (3H, s), 4.16 (1H, q, J=6.8 Hz), 6.98-7.15 (3H, m), 7.19-7.26 (1H, m), 7.95 (1H, d, J=2.8 Hz), 8.11 (1H, d, J=2.8 Hz).

Example 281 cis-1-(3-tert-Butoxy-2-pyrazinylmethyl)-3-(2-fluorophenoxymethyl)piperidin-4-ol

The title compound (198 mg, 75% yield) was obtained in the same manner as Example 269 from 122 mg of 3-tert-butoxypyrazine-2-carboxaldehyde and 153 mg of cis-3-(2-fluorophenoxymethyl)-4-hydroxypiperidine.

1H-NMR (400 MHz, CDCl3); δ (ppm) 1.58 (9H, s), 1.73-1.82 (1H, m), 1.85-1.94 (1H, m), 2.31-2.39 (1H, m), 2.57-2.76 (4H, m), 3.65 (1H, d, J=14.0 Hz), 3.70 (1H, d, J=14.0 Hz), 4.05-4.22 (3H, m), 6.85-6.92 (1H, m), 6.95 (1H, dt, J=8.4, 1.6 Hz), 7.00-7.08 (2H, m), 7.91 (1H, d, J=2.8 Hz), 8.00 (1H, d, J=2.8 Hz).

Example 282 trans-1-(3-tert-Butoxy-2-pyrazinylmethyl)-3-(2-fluorophenoxymethyl)piperidin-4-ol The title compound (149 mg, 78% yield) was obtained in the same manner as Example 269 from 88 mg of 3-tert-butoxypyrazine-2-carboxaldehyde and 110 mg of trans-3-(2-fluorophenoxymethyl)-4-hydroxypiperidine.

1H-NMR (400 MHz, CDCl3); δ (ppm) 1.58 (9H, s), 1.68-1.79 (1H, m), 1.94-2.00 (1H, m), 2.08-2.26 (3H, m), 2.96-3.03 (1H, m), 3.07-3.13 (1H, m), 3.58-3.71 (3H, m), 4.04-4.14 (2H, m), 6.85-6.91 (1H, m), 6.95 (1H, dt, J=8.4, 1.6 Hz), 7.00-7.08 (2H, m), 7.92 (1H, d, J=2.8 Hz), 8.02 (1H, d, J=2.8 Hz).

Example 283

1-[1-(3-tert-Butoxy-2-pyrazinylmethyl)piperidin-4-yl]-2-(1-naphthyl)ethanone

The title compound (126 mg, 78% yield) was obtained in the same manner as Example 1 from 149 mg of 3-tert-butoxypyrazine-2-carboxaldehyde and 200 mg of 2-(1-naphthyl)-1-(piperidin-4-yl)ethanone hydrochloride.

1H-NMR (400 MHz, CDCl3); δ (ppm) 1.58 (9H, s), 1.76-1.87 (4H, m), 2.06-2.15 (2H, m), 2.42-2.51 (1H, m), 2.95-3.02 (2H, m), 3.60 (2H, s), 4.16 (2H, s), 7.32 (1H, d, J=6.8 Hz), 7.39-7.51 (3H, m), 7.75-7.87 (3H, m), 7.90 (1H, d, J=2.8 Hz), 8.01 (1H, d, J=2.8 Hz).

Example 284

3-[4-(2-Fluorophenoxymethyl)piperidino]methyl-2-methoxy-5-methylpyrazine

The title compound (126 mg, 78% yield) was obtained in the same manner as Example 1 from 149 mg of 3-methoxy-6-methylpyrazine-2-carboxaldehyde and 200 mg of 4-(2-fluorophenoxymethyl)piperidine hydrochloride.

1H-NMR (400 MHz, CDCl3); δ (ppm) 1.40-1.52 (2H, m), 1.80-1.92 (3H, m), 2.15 (2H, dt, J=11.6, 2.4 Hz), 2.46 (3H, d, J=0.4 Hz), 3.03-3.09 (2H, m), 3.67 (2H, s), 3.84 (2H, d, J=6.0 Hz), 3.93 (3H, s), 6.82-6.89 (1H, m), 6.92 (1H, dt, J=8.8, 1.6 Hz), 6.98-7.08 (2H, m), 7.82 (1H, d, J=0.4 Hz).

Example 285

2-(2-Fluorophenyl)-1-[1-(3-methoxy-6-methyl-2-pyrazinylmethyl)piperidin-4-yl]ethanone The title compound (130 mg, 48% yield) was obtained in the same manner as Example 1 from 118 mg of 3-methoxy-6-methylpyrazine-2-carboxaldehyde and 229 mg of 2-(2-fluorophenyl)-1-(piperidin-4-yl)ethanone hydrochloride.

1H-NMR (400 MHz, CDCl3); δ (ppm) 1.74-1.89 (4H, m), 2.16 (2H, dt, J=11.6, 3.2 Hz), 2.39-2.48 (1H, m), 2.46 (3H, s), 3.01-3.08 (2H, m), 3.65 (2H, s), 3.76 (2H, s), 3.93 (3H, s), 7.00-7.10 (2H, m), 7.14 (1H, dt, J=7.6, 1.6 Hz), 7.20-7.26 (1H, m), 7.82 (1H, s).

Example 286

2-tert-Butoxy-3-[4-(2-chlorophenoxymethyl)-4-methylpiperidino]methyl-pyrazine

The title compound (237 mg, 88% yield) was obtained in the same manner as Example 269 from 120 mg of 3-tert-butoxypyrazine-2-carboxaldehyde and 192 mg of 4-(2-chlorophenoxymethyl)-4-methylpiperidine.

1H-NMR (400 MHz, CDCl3); δ (ppm) 1.13 (3H, s), 1.54-1.61 (2H, m), 1.60 (9H, s), 1.70-1.78 (2H, m), 2.46-2.54 (2H, m), 2.63-2.70 (2H, m), 3.66 (2H, s), 3.72 (2H, s), 6.82-6.90 (2H, m), 7.18 (1H, ddd, J=8.4, 7.6, 1.6 Hz), 7.33 (1H, dd, J=7.6 1.6 Hz), 7.91 (1H, d, J=2.8 Hz), 8.03 (1H, d, J=2.8 Hz).

Example 287

2-tert-Butoxy-3-[4-methyl-4-(2-methylphenoxymethyl)piperidino]methyl-pyrazine

The title compound (244 mg, 95% yield) was obtained in the same manner as Example 269 from 120 mg of 3-tert-butoxypyrazine-2-carboxaldehyde and 175 mg of 4-methyl-4-(2-methylphenoxymethyl)piperidine.

1H-NMR (400 MHz, CDCl3); δ (ppm) 1.10 (3H, s), 1.50-1.58 (2H, m), 1.60 (9H, s), 1.70-1.78 (2H, m), 2.23 (3H, s), 2.46-2.54 (2H, m), 2.62-2.70 (2H, m), 3.65 (2H, s), 3.67 (2H, s), 6.78 (1H, d, J=8.0 Hz), 6.82 (1H, t, J=7.2 Hz), 7.09-7.15 (2H, m), 7.90 (1H, d, J=2.4 Hz), 8.03 (1H, d, J=2.4 Hz).

Example 288

2-tert-butoxy-3-[4-(2-methoxyphenoxymethyl)-4-methylpiperidino]methyl-pyrazine

The title compound (202 mg, 76% yield) was obtained in the same manner as Example 269 from 120 mg of 3-tert-butoxypyrazine-2-carboxaldehyde and 188 mg of 4-(2-methoxyphenoxymethyl)-4-methylpiperidine.

1H-NMR (400 MHz, CDCl3); δ (ppm) 1.11 (3H, s), 1.49-1.57 (2H, m), 1.60 (9H, s), 1.71-1.79 (2H, m), 2.45-2.53 (2H, m), 2.63-2.70 (2H, m), 3.65 (2H, s), 3.71 (2H, s), 3.83 (3H, s), 6.82-6.92 (4H, m), 7.90 (1H, d, J=2.8 Hz), 8.03 (1H, d, J=2.8 Hz).

Example 289

1-[1-(3-tert-Butoxy-2-pyrazinylmethyl)piperidin-4-yl]-2-[2-(methylsulfonyl)phenyl]ethanone The title compound (196 mg, 83% yield) was obtained in the same manner as Example 1 from 115 mg of 3-tert-butoxypyrazine-2-carboxaldehyde and 169 mg of 2-[2-(methylsulfonyl)phenyl]-1-(piperidin-4-yl)ethanone hydrochloride.

1H-NMR (400 MHz, CDCl3); δ (ppm) 1.60 (9H, s), 1.76-1.88 (2H, m), 1.91-1.98 (2H, m), 2.07-2.26 (2H, m), 2.49-2.58 (1H, m), 3.00 (3H, s), 3.03-3.10 (2H, m), 3.66 (2H, s), 4.36 (2H, s), 7.18 (1H, dd, J=7.6, 1.2 Hz), 7.47 (1H, td, J=7.6, 1.2 Hz), 7.56 (1H, td, J=7.6, 1.4 Hz), 7.93 (1H, d, J=2.8 Hz), 8.01 (1H, dd, J=7.6, 1.4 Hz), 8.04 (1H, d, J=2.8 Hz).

Example 290

1-[1-(4-tert-Butoxy-5-pyrimidinylmethyl)piperidin-4-yl]-2-(2-fluorophenyl)ethanone The title compound (205 mg, 17% yield) was obtained in the same manner as Example 89 from 0.72 g of ethyl 4-tert-butoxypyrimidine-5-carboxylate and 258 mg of 2-(2-fluorophenyl)-1-(piperidin-4-yl)ethanone hydrochloride.

1H-NMR (400 MHz, CDCl3); δ (ppm) 1.61 (9H, s), 1.71-1.79 (2H, m), 1.83-1.90 (2H, m), 2.08-2.14 (2H, m), 2.44 (1H, dt, J=11.6, 4.0 Hz), 2.87-2.94 (2H, m), 3.42 (2H, s), 3.77 (2H, s), 7.00-7.11 (2H, m), 7.15 (1H, dt, J=7.6, 2.0 Hz), 7.20-7.27 (1H, m), 8.36 (1H, s), 8.59 (1H, s)

Example 291

1-[1-(3-tert-Butoxy-2-pyrazinylmethyl)piperidin-4-yl]-2-(2-biphenyl)ethanone

The title compound (210 mg, 75% yield) was obtained in the same manner as Example 1 from 137 mg of 3-tert-butoxypyrazine-2-carboxaldehyde and 200 mg of 2-(2-biphenyl)-1-(piperidin-4-yl)ethanone hydrochloride.

1H-NMR (400 MHz, CDCl3); δ (ppm) 1.53-1.64 (4H, m), 1.58 (9H, s), 1.99-2.08 (2H, m), 2.09-2.18 (1H, m), 2.87-2.94 (2H, m), 3.57 (2H, s), 3.71 (2H, s), 7.14-7.38 (9H, m), 7.90 (1H, d, J=2.8 Hz), 8.01 (1H, d, J=2.8 Hz).

Example 292

2-(2-Fluorophenyl)-1-[1-(3-methoxy-2-pyrazinylmethyl)piperidin-4-yl]ethanone

The title compound (105 mg, 42% yield) was obtained in the same manner as Example 1 from 100 mg of 3-methoxy pyrazine-2-carboxaldehyde and 224 mg of 2-(2-fluorophenyl)-1-(piperidin-4-yl)ethanone hydrochloride.

1H-NMR (400 MHz, CDCl3); δ (ppm) 1.76-1.90 (4H, m), 2.17 (2H, dt, J=11.2, 3.2 Hz), 2.41-2.49 (1H, m), 3.01-3.07 (2H, m), 3.68 (2H, s), 3.76 (2H, s), 3.96 (3H, s), 6.99-7.10 (2H, m), 7.14 (1H, dt, J=7.6, 1.6 Hz), 7.19-7.27 (1H, m), 7.98 (1H, d, J=2.8 Hz), 8.10 (1H, d, J=2.8 Hz).

Example 293

1-[1-(3-tert-Butoxy-2-pyrazinylmethyl)piperidin-4-yl]-2-(4-fluorophenyl)ethanone The title compound (254 mg, 85% yield) was obtained in the same manner as Example 1 from 168 mg of 3-tert-butoxypyrazine-2-carboxaldehyde and 200 mg of 2-(4-fluorophenyl)-1-(piperidin-4The title compound (105 mg, 42% yield) was obtained in the same manner as Example 1 from 100 mg of 3-methoxy-yl)ethanone hydrochloride.

1H-NMR (400 MHz, CDCl3); δ (ppm) 1.59 (9H, s), 1.70-1.84 (4H, m), 2.11-2.18 (2H, m), 2.35-2.44 (1H, m), 2.97-3.03 (2H, m), 3.62 (2H, s), 3.70 (2H, s), 6.95-7.02 (2H, m), 7.09-7.14 (2H, m), 7.91 (1H, d, J=2.8 Hz), 8.01 (1H, d, J=2.8 Hz).

Example 294

5-Fluoro-3-[4-(2-fluorophenoxymethyl)piperidino]methyl-2-methoxypyrazine

The title compound (93 mg, 35% yield) was obtained in the same manner as Example 1 from 120 mg of 6-fluoro-3-methoxypyrazine-2-carboxaldehyde and 209 mg of 4-(2-fluorophenoxymethyl)piperidine hydrochloride.

1H-NMR (400 MHz, CDCl3); δ (ppm) 1.41-1.53 (2H, m), 1.81-1.92 (3H, m), 2.14-2.22 (2H, m), 3.05-3.09 (2H, m), 3.65 (2H, s), 3.85 (2H, d, J=6.0 Hz), 3.97 (3H, s), 6.83-6.89 (1H, m), 6.93 (1H, dt, J=8.8, 1.6 Hz), 6.98-7.08 (2H, m), 7.81 (1H, d, J=8.4 Hz).

Example 295

1-[1-(6-Fluoro-3-methoxy-2-pyrazinylmethyl)piperidin-4-yl]-2-(2-fluorophenyl)ethanone The title compound (95 mg, 34% yield) was obtained in the same manner as Example 1 from 120 mg of 6-fluoro-3-methoxypyrazine-2-carboxaldehyde and 219 mg of 2-(2-fluorophenyl)-1-(piperidin-4-yl)ethanone hydrochloride.

1H-NMR (400 MHz, CDCl3); δ (ppm) 1.74-1.90 (4H, m), 2.20 (2H, dt, J=11.2, 2.8 Hz), 2.40-2.49 (1H, m), 3.01-3.07 (2H, m), 3.63 (2H, s), 3.76 (2H, s), 3.96 (3H, s), 7.00-7.10 (2H, m), 7.14 (1H, dt, J=7.6, 1.6 Hz), 7.20-7.26 (1H, m), 7.81 (1H, d, J=8.4 Hz).

Example 296

2-[1-(3-tert-Butoxy-2-pyrazinylmethyl)piperidin-4-yl]-3-(2-fluorophenyl)propionitrile The title compound (188 mg, 64% yield) was obtained in the same manner as Example 1 from 161 mg of 3-tert-butoxypyrazine-2-carboxaldehyde and 200 mg of 3-(2-fluorophenyl)-2-(piperidin-4-yl)propionitrile hydrochloride.

1H-NMR (400 MHz, CDCl3); δ (ppm) 1.50-1.70 (3H, m), 1.60 (9H, s), 1.74-1.81 (1H, m), 1.87-1.94 (1H, m), 2.08-2.17 (2H, m), 2.70-2.84 (2H, m), 3.01-3.11 (3H, m), 3.64

Example 297

2-[1-(3-tert-Butoxy-2-pyrazinylmethyl)piperidin-4-yl]-2-(2-fluorobenzyl)-3-(2-fluorophenyl)propionitrile The title compound (206 mg, 77% yield) was obtained in the same manner as Example 1 from 115 mg of 3-tert-butoxypyrazine-2-carboxaldehyde and 200 mg of 2-(2-fluorobenzyl)-3-(2-fluorophenyl)-2-(piperidin-4-yl)propionitrile hydrochloride.

1H-NMR (400 MHz, CDCl3); δ (ppm) 1.56-1.63 (1H, m), 1.57 (9H, s), 1.67-1.80 (2H, m), 1.94-2.09 (4H, m), 2.82 (2H, d, J=14.0 Hz), 3.04 (2H, d, J=14.0 Hz), 3.10-3.18 (2H, m), 3.62 (2H, s), 7.05 (2H, ddd, J=9.6, 7.6, 1.2 Hz), 7.11 (2H, td, J=7.6, 1.2 Hz), 7.23-7.30 (2H, m), 7.35 (2H, td, J=7.6, 1.6 Hz), 7.84 (2H, br s).

Example 298

2-(2-Bromophenyl)-1-[1-(3-tert-butoxy-2-pyrazinylmethyl)piperidin-4-yl]ethanone

The title compound (461 mg, 82% yield) was obtained in the same manner as Example 1 from 271 mg of 3-tert-butoxypyrazine-2-carboxaldehyde and 400 mg of 2-(2-bromophenyl)-1-(piperidin-4-yl)ethanone hydrochloride.

1H-NMR (400 MHz, CDCl3); δ (ppm) 1.59 (9H, s), 1.77-1.93 (4H, m), 2.14-2.22 (2H, m), 2.42-2.51 (1H, m), 2.99-3.06 (2H, m), 3.63 (2H, s), 3.90 (2H, s), 7.11 (1H, td, J=7.6, 2.0 Hz), 7.16 (1H, dd, J=7.6, 2.0 Hz), 7.22-7.28 (1H, m), 7.54 (1H, dd, J=7.6, 1.2 Hz), 7.91 (1H, d, J=2.8 Hz), 8.02 (1H, d, J=2.8 Hz).

Example 299

1-(3-tert-Butoxy-2-pyrazinylmethyl)-3-[2-(2-fluorophenyl)ethyl]piperidin-4-one

The title compound (207 mg, 65% yield) was obtained in the same manner as Example 269 from 150 mg of 3-tert-butoxypyrazine-2-carboxaldehyde and 203 mg of 3-[2-(2-fluorophenyl)ethyl]-4-oxopiperidine.

1H-NMR (400 MHz, CDCl3); δ (ppm) 1.43-1.53 (1H, m), 1.60 (9H, s), 2.07-2.17 (1H, m), 2.31-2.40 (2H, m), 2.56-2.70 (5H, m), 3.15-3.21 (1H, m), 3.23-3.39 (1H, m), 3.76 (2H, s), 6.93-6.98 (1H, m), 7.01 (1H, dt, J=7.2, 1.6 Hz), 7.11-7.17 (2H, m), 7.95 (1H, d, J=2.8 Hz), 8.05 (1H, d, J=2.8 Hz).

Example 300

2-(2-Fluorophenyl)-1-[1-(3-methoxy-4-pyridazinylmethyl)piperidin-4-yl]ethanone

After dissolving 527 mg of methyl 3-methoxypyridazine-4-carboxylate in 10 ml of toluene, 2 ml of diisobutylaluminium hydride (1.5 M, toluene solution) was added dropwise while stirring at below −70° C., and the stirring was continued for 40 minutes. Next, 1N hydrochloric acid was added and the temperature was raised to room temperature. Diluted ammonia water was added to the reaction solution and extraction was performed with dichloromethane. The extract was washed with saturated aqueous sodium bicarbonate solution and saturated brine in that order and dried over anhydrous magnesium sulfate. The solvent was distilled off under reduced pressure. The residue was dissolved in 3 ml of dichloromethane, and then 150 mg of 2-(2-fluorophenyl)-1-(piperidin-4-yl)ethanone hydrochloride and 123 mg of sodium triacetoxyborohydride were added and the mixture was stirred for 2 days at room temperature. A 1N sodium hydroxide solution was added to the reaction mixture and extraction was performed with ethyl acetate. The organic layer was washed with saturated brine and dried over anhydrous magnesium sulfate, and then the solvent was distilled off under reduced pressure. The residue was purified by silica gel column chromatography (solvent: n-hexane/ethyl acetate) to obtain the title compound (74 mg, 37% yield).

1H-NMR (400 MHz, CDCl3); δ (ppm) 1.73-1.84 (2H, m), 1.85-1.93 (2H, m), 2.13-2.21 (2H, m), 2.46-2.55 (1H, m), 2.85-2.92 (2H, m), 3.47 (2H, d, J=1.2 Hz), 3.79 (2H, d, J=1.2 Hz), 4.13 (3H, s), 7.05 (1H, ddd, J=9.6, 7.6, 1.2 Hz), 7.09 (1H, td, J=7.6, 1.2 Hz), 7.16 (1H, td, J=7.6, 1.6 Hz), 7.22-7.28 (1H, m), 7.48 (1H, dt, J=4.8, 1.2 Hz), 8.77 (1H, d, J=4.8 Hz).

Example 301

1-[1-(3-tert-Butoxy-2-pyrazinylmethyl)-4-methylpiperidin-4-yl]-2-(2-fluorophenyl)ethanone After suspending 126 mg of 2-(2-fluorophenyl)-1-(4-methylpiperidin-4-yl)ethanone hydrochloride in 3 ml of dichloromethane, 100 mg of 3-tert-butoxypyrazine-2-carboxaldehyde and 146 mg of sodium triacetoxyborohydride were added and the mixture was stirred overnight at room temperature. The reaction mixture was diluted with ethyl acetate, saturated aqueous sodium bicarbonate solution was added and extraction was performed with ethyl acetate. The organic layer was washed with saturated brine and dried over anhydrous magnesium sulfate, and then the solvent was distilled off under reduced pressure. The residue was purified by silica gel column chromatography (solvent: n-hexane/ethyl acetate) to obtain the title compound (135 mg, 69% yield).

1H-NMR (400 MHz, CDCl3); δ (ppm) 1.22 (3H, s), 1.58-1.70 (2H, m), 1.59 (9H, s), 2.14-2.22 (2H, m), 2.32-2.41 (2H, m), 2.67-2.74 (2H, m), 3.60 (2H, s), 3.80 (2H, d, J=0.8 Hz), 6.99-7.05 (1H, m), 7.08 (1H, dt, J=7.2, 1.2 Hz), 7.14 (1H, dt, J=7.2, 1.6 Hz), 7.20-7.26 (1H, m), 7.90 (1H, d, J=2.8 Hz), 8.02 (1H, d, J=2.8 Hz).

Example 302 trans-1-[1-(3-tert-Butoxy-2-pyrazinylmethyl)-3-methylpiperidin-4-yl]-2-(2-fluorophenyl)ethanone The title compound (112 mg, 47% yield) was obtained in the same manner as Example 1 from 100 mg of 3-tert-butoxypyrazine-2-carboxaldehyde and 181 mg of trans-2-(2-fluorophenyl)-1-(3-methylpiperidin-4-yl)ethanone hydrochloride.

1H-NMR (400 MHz, CDCl3); δ (ppm) 0.78 (3H, d, J=6.4 Hz), 1.59 (9H, s), 1.66-1.82 (3H, m), 2.03-2.21 (3H, m), 2.93-2.99 (1H, m), 3.03-3.09 (1H, m), 3.61 (1H, d, J=14.0 Hz), 3.65 (1H, d, J=14.0 Hz), 3.73 (1H, d, J=18.0 Hz), 3.77 (1H, d, J=18.0 Hz), 7.00-7.11 (2H, m), 7.14 (1H, dt, J=7.6, 1.6 Hz), 7.20-7.26 (1H, m), 7.92 (1H, d, J=2.8 Hz), 8.03 (1H, d, J=2.8 Hz).

Example 303

2-tert-Butoxy-6-[4-(2-fluorophenoxymethyl)piperidino]methyl-pyrazine

The title compound (202 mg, 65% yield) was obtained in the same manner as Example 1 from 150 mg of 6-tert-butoxypyrazine-2-carboxaldehyde and 246 mg of 4-(2-fluorophenoxymethyl)piperidine hydrochloride.

1H-NMR (400 MHz, CDCl3); δ (ppm) 1.36-1.49 (2H, m), 1.59 (9H, s), 1.80-1.92 (3H, m), 2.16 (2H, dt, J=11.6, 2.0 Hz), 2.96-3.02 (2H, m), 3.60 (2H, s), 3.86 (2H, d, J=6.4 Hz), 6.83-6.90 (1H, m), 6.93 (1H, dt, J=8.0, 1.6 Hz), 7.00-7.08 (2H, m), 7.95 (1H, s), 8.13 (1H, s).

Example 304

1-[1-(6-tert-Butoxy-2-pyrazinylmethyl)piperidin-4-yl]-2-(2-fluorophenyl)ethanone The title compound (172 mg, 56% yield) was obtained in the same manner as Example 1 from 150 mg of 6-tert-butoxypyrazine-2-carboxaldehyde and 258 mg of 2-(2-fluorophenyl)-1-(piperidin-4-yl)ethanone hydrochloride.

1H-NMR (400 MHz, CDCl3); δ (ppm) 1.58 (9H, s), 1.71-1.82 (2H, m), 1.84-1.91 (2H, m), 2.16 (2H, dt, J=11.6, 2.8 Hz), 2.40-2.49 (1H, m), 2.94-3.00 (2H, m), 3.58 (2H, s), 3.77 (2H, d, J=1.2 Hz), 7.00-7.11 (2H, m), 7.15 (1H, dt, J=7.2, 2.0 Hz), 7.21-7.27 (1H, m), 7.95 (1H, s), 8.11 (1H, s).

Example 305

1-[1-(3-tert-Butoxy-2-pyrazinylmethyl)piperidin-4-yl]-2-(3-pyridyl)ethanone

After dissolving 399 mg of 1-(1-benzylpiperidin-4-yl)-2-(3-pyridyl)ethanone in 5 ml of methanol, 206 mg of 10% palladium-carbon and 504 mg of ammonium formate were added and the mixture was heated to reflux for 2.5 hours. The reaction mixture was filtered and the solvent of the filtrate was distilled off under reduced pressure. The residue was dissolved in 5 ml of dichloromethane, 346 mg of 3-tert-butoxypyrazine-2-carboxaldehyde and 407 mg of sodium triacetoxyborohydride were added and the mixture was stirred overnight at room temperature. Water and a 1N sodium hydroxide solution were added to the reaction mixture to render it alkaline, and then extraction was performed with ethyl acetate. The organic layer was washed with saturated brine and dried over anhydrous magnesium sulfate, and then the solvent was distilled off under reduced pressure. The residue was purified by NH silica gel column chromatography (solvent: n-hexane/ethyl acetate) to obtain the title compound (173 mg, 29% yield).

1H-NMR (400 MHz, CDCl3); δ (ppm) 1.59 (9H, s), 1.70-1.90 (4H, m), 2.14-2.27 (2H, m), 2.38-2.48 (1H, m), 3.00-3.08 (2H, m), 3.66 (2H, s), 3.74 (2H, s), 7.22-7.27 (1H, m), 7.51 (1H, ddd, J=7.8, 2.4, 1.8 Hz), 7.92 (1H, d, J=2.8 Hz), 8.02 (1H, d, J=2.8 Hz), 8.40 (1H, d, J=2.4 Hz), 8.49 (1H, dd, J=4.8, 1.8 Hz).

Example 306

1-[1-(3-tert-Butoxy-2-pyrazinylmethyl)-4-fluoropiperidin-4-yl]-2-(2-fluorophenyl)ethanone The title compound (210 mg, 63% yield) was obtained in the same manner as Example 1 from 150 mg of 3-tert-butoxypyrazine-2-carboxaldehyde and 276 mg of 2-(2-fluorophenyl)-1-(4-fluoropiperidin-4-yl)ethanone hydrochloride.

1H-NMR (400 MHz, CDCl3); δ (ppm) 1.60 (9H, s), 1.80-1.89 (2H, m), 2.04-2.24 (2H, m), 2.49 (2H, dt, J=12.0, 1.6 Hz), 2.87-2.94 (2H, m), 3.68 (2H, s), 3.99 (2H, dd, J=2.4, 1.2 Hz), 7.00-7.17 (3H, m), 7.21-7.27 (1H, m), 7.92 (1H, d, J=2.8 Hz), 8.03 (1H, d, J=2.8 Hz).

Example 307

2-tert-Butoxy-3-[4-[2-(2-fluorophenyl)ethyl]-3,3-dimethoxypiperidino]methyl-pyrazine The title compound (165 mg, 69% yield) was obtained in the same manner as Example 1 from 130 mg of 3-tert-butoxypyrazine-2-carboxaldehyde and 169 mg of 3,3-dimethoxy-4-[2-(2-fluorophenyl)ethyl]piperidine hydrochloride.

1H-NMR (400 MHz, CDCl3); δ (ppm) 1.54-1.62 (3H, m), 1.59 (9H, s), 1.80-1.87 (1H, m), 1.98-2.12 (2H, m), 2.44-2.57 (2H, m), 2.69-2.83 (3H, m), 3.04 (3H, s), 3.15 (3H, s), 3.66 (2H, s), 6.98 (1H, ddd, J=9.6, 7.6, 1.2 Hz), 7.03 (1H, td, J=7.6, 1.2 Hz), 7.11-7.20 (2H, m), 7.90 (1H, d, J=2.8 Hz), 7.98 (1H, d, J=2.8 Hz).

Example 308

1-[1-(3-tert-Butoxy-2-pyrazinylmethyl)-4-fluoropiperidin-4-yl]-2-[2-(trifluoromethyl)phenyl]ethanone The title compound (211 mg, 56% yield) was obtained in the same manner as Example 1 from 150 mg of 3-tert-butoxypyrazine-2-carboxaldehyde and 326 mg of 1-(4-fluoropiperidin-4-yl)-2-[2-(trifluoromethyl)phenyl]ethanone hydrochloride.

1H-NMR (400 MHz, CDCl3); δ (ppm) 1.60 (9H, s), 1.82-1.92 (2H, m), 2.04-2.24 (2H, m), 2.45-2.54 (2H, m), 2.87-2.95 (2H, m), 3.68 (2H, s), 4.18 (2H, d, J=1.2 Hz), 7.18 (1H, d, J=7.6 Hz), 7.37 (1H, t, J=7.6 Hz), 7.50 (1H, t, J=7.6 Hz), 7.64 (1H, d, J=7.6 Hz), 7.92 (1H, d, J=2.8 Hz), 8.03 (1H, d, J=2.8 Hz).

Example 309

1-[1-(3-tert-Butoxy-2-pyrazinylmethyl)-4-methylpiperidin-4-yl]-2-[2-(trifluoromethyl)phenyl]ethanone The title compound (53 mg, 84% yield) was obtained in the same manner as Example 1 from 33 mg of 3-tert-butoxypyrazine-2-carboxaldehyde and 45 mg of 1-(4-methylpiperidin-4-yl)-2-[2-(trifluoromethyl)phenyl]ethanone hydrochloride.

1H-NMR (400 MHz, CDCl3); δ (ppm) 1.23 (3H, s), 1.60 (9H, s), 1.60-1.70 (2H, m), 2.13-2.21 (2H, m), 2.36-2.46 (2H, m), 2.66-2.74 (2H, m), 3.63 (2H, s), 4.02 (2H, s), 7.15 (1H, d, J=7.6 Hz), 7.35 (1H, t, J=7.6 Hz), 7.49 (1H, t, J=7.6 Hz), 7.64 (1H, d, J=7.6 Hz), 7.91 (1H, d, J=2.8 Hz), 8.03 (1H, d, J=2.8 Hz).

Example 310

1-[1-(3-tert-Butoxy-2-pyrazinylmethyl)piperidin-4-yl]-3-(2-fluorophenyl)propan-2-one The title compound (145 mg, 50% yield) was obtained in the same manner as Example 1 from 150 mg of 3-tertbutoxypyrazine-2-carboxaldehyde and 272 mg of 4-[3-(2-fluorophenyl)-2-oxopropyl]piperidine hydrochloride.

1H-NMR (400 MHz, CDCl3); δ (ppm) 1.23-1.35 (2H, m), 1.56-1.66 (2H, m), 1.58 (9H, s), 1.78-1.91 (1H, m), 2.07-2.15 (2H, m), 2.39 (2H, d, J=6.4 Hz), 2.89-2.96 (2H, m), 3.60 (2H, s), 3.69 (2H, s), 7.01-7.11 (2H, m), 7.14 (1H, dt, J=7.2, 2.0 Hz), 7.20-7.27 (1H, m), 7.89 (1H, d, J=2.8 Hz), 8.02 (1H, d, J=2.8 Hz).

Example 311

1-[1-(3-tert-Butoxy-2-pyrazinylmethyl)piperidin-4-yl]-3-(2-fluorophenyl)propanone The title compound (124 mg, 42% yield) was obtained in the same manner as Example 1 from 110 mg of 3-tert-butoxypyrazine-2-carboxaldehyde and 272 mg of 1-(piperidin-4-yl)-3-(2-fluorophenyl)propanone hydrochloride.

1H-NMR (400 MHz, CDCl3); δ (ppm) 1.58 (9H, s), 1.63-1.82 (4H, m), 2.09-2.18 (2H, m), 2.21-2.30 (1H, m), 2.75 (2H, t, J=7.2 Hz), 2.89 (2H, t, J=7.2 Hz), 2.95-3.02 (2H, m), 3.61 (2H, s), 6.94-7.05 (2H, m), 7.12-7.19 (2H, m), 7.91 (1H, d, J=2.4 Hz), 8.01 (1H, d, J=2.4 Hz).

Example 312

1-[1-[1-(3-Methoxy-2-pyrazinyl)ethyl]piperidin-4-yl]-2-[2-(trifluoromethyl)phenyl]ethanone The title compound (117 mg, 6% yield) was obtained in the same manner as Example 280 from 702 mg of 2-acetyl-3-methoxypyrazine and 2.83 g of 1-(piperidin-4-yl)-2-[2-(trifluoromethyl)phenyl]ethanone hydrochloride.

1H-NMR (400 MHz, CDCl3); δ (ppm) 1.39 (3H, d, J=6.8 Hz), 1.66-1.89 (4H, m), 2.06-2.19 (2H, m), 2.32-2.41 (1H, m), 2.92-2.98 (1H, m), 3.10-3.19 (1H, m), 3.92 (2H, d, J=1.2 Hz), 3.96 (3H, s), 4.17 (1H, q, J=6.8 Hz), 7.19 (1H, d, J=7.6 Hz), 7.34 (1H, t, J=7.6 Hz), 7.48 (1H, t, J=7.6 Hz), 7.62 (1H, d, J=7.6 Hz), 7.96 (1H, d, J=2.8 Hz), 8.12 (1H, d, J=2.8 Hz).

Example 313

1-[1-(3-Methoxy-5-methyl-2-pyrazinylmethyl)piperidin-4-yl]-2-(2-fluorophenyl)ethanone The title compound (352 mg, 75% yield) was obtained in the same manner as Example 1 from 200 mg of 3-methoxy-5-methylpyrazine-2-carboxaldehyde and 407 mg of 2-(2-fluorophenyl)-1-(piperidin-4-yl)ethanone hydrochloride.

1H-NMR (400 MHz, CDCl3); δ (ppm) 1.74-1.88 (4H, m), 2.15 (2H, dt, J=11.2, 3.2 Hz), 2.39-2.48 (1H, m), 2.42 (3H, s), 2.98-3.04 (2H, m), 3.64 (2H, s), 3.76 (2H, s), 3.94 (3H, s), 6.99-7.10 (2H, m), 7.13 (1H, dt, J=7.2, 1.6 Hz), 7.19-7.26 (1H, m), 7.96 (1H, s).

Example 314

1-[1-(3-tert-Butoxy-5-fluoro-2-pyrazinylmethyl)piperidin-4-yl]-2-(2-fluorophenyl)ethanone The title compound (122 mg, 43% yield) was obtained in the same manner as Example 1 from 138 mg of 3-tert-butoxy-5-fluoropyrazine-2-carboxaldehyde and 216 mg of 2-(2-fluorophenyl)-1-(piperidin-4-yl)ethanone hydrochloride.

1H-NMR (400 MHz, CDCl3); δ (ppm) 1.60 (9H, s), 1.70-1.90 (4H, m), 2.11-2.21 (2H, m), 2.49-2.58 (1H, m), 2.94-3.02 (2H, m), 3.62 (2H, s), 3.76 (2H, s), 6.99-7.17 (3H, m), 7.19-7.27 (1H, m), 7.86 (1H, d, J=8.4 Hz).

Example 315

1-[1-(3-tert-Butoxy-2-pyrazinylmethyl)piperidin-4-yl]-2-[2-fluoro-6-(trifluoromethyl)phenyl]ethanone The title compound (62 mg, 86% yield) was obtained in the same manner as Example 269 from 43 mg of 3-tert-butoxypyrazine-2-carboxaldehyde and 45 mg of 2-[2-fluoro-6-(trifluoromethyl)phenyl]-1-(piperidin-4-yl)ethanone.

1H-NMR (400 MHz, CDCl3); δ (ppm) 1.60 (9H, s), 1.78-1.95 (4H, m), 2.21 (2H, dt, J=10.4, 3.2 Hz), 2.43-2.52 (1H, m), 3.01-3.08 (2H, m), 3.65 (2H, s), 3.98 (2H, s), 7.24 (1H, t, J=8.8 Hz), 7.32-7.38 (1H, m), 7.44 (1H, d, J=8.0 Hz), 7.92 (1H, d, J=2.8 Hz), 8.03 (1H, d, J=2.8 Hz).

Example 316

1-[1-(3-tert-Butoxy-2-pyrazinylmethyl)piperidin-4-yl]-2-(3-methyl-2-thienyl)ethanone The title compound (132 mg, 59% yield) was obtained in the same manner as Example 1 from 136 mg of 3-tert-butoxypyrazine-2-carboxaldehyde and 150 mg of 2-(3-methyl-2-thienyl)-1-(piperidin-4-yl)ethanone hydrochloride.

1H-NMR (400 MHz, CDCl3); δ (ppm) 1.59 (9H, s), 1.72-1.84 (4H, m), 2.12 (3H, s), 2.11-2.21 (2H, m), 2.40-2.48 (1H, m), 2.97-3.04 (2H, m), 3.62 (2H, s), 3.82 (2H, s), 6.81 (1H, d, J=5.2 Hz), 7.09 (1H, d, J=5.2 Hz), 7.91 (1H, d, J=2.8 Hz), 8.02 (1H, d, J=2.8 Hz).

Example 317

1-[1-(3-tert-Butoxy-2-pyrazinylmethyl)piperidin-4-yl]-2-[2-(3-pyridyl)phenyl]ethanone The title compound (315 mg, 100% yield) was obtained in the same manner as Example 21 from 120 mg of 3-tert-butoxypyrazine-2-carboxaldehyde and 205 mg of 1-(piperidin-4-yl)-2-[2-(3-pyridyl)phenyl]ethanone.

1H-NMR (400 MHz, CDCl3); δ (ppm) 1.53-1.64 (4H, m), 1.59 (9H, s), 2.03-2.11 (2H, m), 2.14-2.24 (1H, m), 2.91-2.98 (2H, m), 3.60 (2H, s), 3.72 (2H, s), 7.18-7.41 (5H, m), 7.54-7.58 (1H, m), 7.93 (1H, d, J=2.8 Hz), 8.03 (1H, d, J=2.8 Hz), 8.50 (1H, dd, J=2.4, 0.8 Hz), 8.59 (1H, dd, J=4.8, 1.6 Hz).

Example 318

Methyl 2-[1-(3-tert-butoxy-2-pyrazinylmethyl)piperidin-4-yl]methoxy-benzoate

The title compound (230 mg, 86% yield) was obtained in the same manner as Example 1 from 190 mg of 3-tert-butoxypyrazine-2-carboxaldehyde and 190 mg of 4-[2-(methoxycarbonyl)phenoxymethyl]piperidine hydrochloride.

1H-NMR (400 MHz, CDCl3); δ (ppm) 1.41-1.53 (2H, m), 1.60 (9H, s), 1.83-1.95 (3H, m), 2.14-2.21 (2H, m), 3.01-3.08 (2H, m), 3.66 (2H, s), 3.85 (2H, d, J=6.4 Hz), 3.87 (3H, s), 6.94-6.98 (2H, m), 7.40-7.46 (1H, m), 7.78 (1H, dd, J=8.0, 1.6 Hz), 7.92 (1H, d, J=2.8 Hz), 8.05 (1H, d, J=2.8 Hz).

Example 319

1-[2-[1-(3-tert-Butoxy-2-pyrazinylmethyl)piperidin-4-yl]methoxy-phenyl]ethanone

The title compound (134 mg, 51% yield) was obtained in the same manner as Example 1 from 155 mg of 3-tert-butoxypyrazine-2-carboxaldehyde and 177 mg of 4-(2-acetylphenoxymethyl)piperidine hydrochloride.

1H-NMR (400 MHz, CDCl3); δ (ppm) 1.44-1.56 (2H, m), 1.61 (9H, s), 1.80-1.94 (3H, m), 2.13-2.22 (2H, m), 2.63 (3H, s), 3.02-3.08 (2H, m), 3.66 (2H, s), 3.90 (2H, d, J=6.4 Hz), 6.91-7.00 (2H, m), 7.41-7.46 (1H, m), 7.72 (1H, dd, J=8.0, 2.0 Hz), 7.93 (1H, d, J=2.8 Hz), 8.05 (1H, d, J=2.8 Hz).

Example 320

2-[1-(3-tert-Butoxy-2-pyrazinylmethyl)piperidin-4-yl]methoxy-benzamide

After dissolving 106 mg of 3-tert-butoxypyrazine-2-carboxaldehyde and 105 mg of 4-(2-carbamoylphenoxymethyl)piperidine in 5 ml of dichloromethane, 153 mg of sodium triacetoxyborohydride was added and the mixture was stirred overnight at room temperature. Aqueous sodium bicarbonate solution was added to the reaction mixture and extraction was performed with ethyl acetate. The organic layer was washed with saturated brine and dried over anhydrous magnesium sulfate, and then the solvent was distilled off under reduced pressure. The residue was purified by NH silica gel column chromatography (solvent: n-hexane/ethyl acetate) to obtain the title compound (171 mg, 95% yield).

1H-NMR (400 MHz, CDCl3); δ (ppm) 1.46-1.59 (2H, m), 1.61 (9H, s), 1.77-1.95 (3H, m), 2.14-2.22 (2H, m), 3.03-3.09 (2H, m), 3.66 (2H, s), 3.98 (2H, d, J=6.4 Hz), 5.77 (1H, br s), 6.96 (1H, d, J=7.6 Hz), 7.04-7.10 (1H, m), 7.42-7.48 (1H, m), 7.76 (1H, br s), 7.93 (1H, d, J=2.8 Hz), 8.05 (1H, d, J=2.8 Hz), 8.20 (1H, dd, J=8.0, 1.6 Hz).

Example 321

2-tert-Butoxy-3-[4-(2-nitrophenoxymethyl)piperidino]methyl-pyrazine

The title compound (183 mg, 95% yield) was obtained in the same manner as Example 1 from 114 mg of 3-tert-butoxypyrazine-2-carboxaldehyde and 132 mg of 4-(2-nitrophenoxymethyl)piperidine hydrochloride.

1H-NMR (400 MHz, CDCl3); δ (ppm) 1.39-1.52 (2H, m), 1.61 (9H, s), 1.82-1.94 (3H, m), 2.12-2.21 (2H, m), 3.00-3.07 (2H, m), 3.66 (2H, s), 3.90 (2H, d, J=6.4 Hz), 6.97-7.07 (2H, m), 7.47-7.52 (1H, m), 7.81 (1H, dd, J=8.0, 1.6 Hz), 7.92 (1H, d, J=2.4 Hz), 8.05 (1H, d, J=2.4 Hz).

Example 322

N-[2-[1-(3-tert-Butoxy-2-pyrazinylmethyl)piperidin-4-yl]methoxy-phenyl]acetamide

The title compound (130 mg, 60% yield) was obtained in the same manner as Example 1 from 115 mg of 3-tert-butoxypyrazine-2-carboxaldehyde and 150 mg of 4-[2-(acetylamino)phenoxymethyl]piperidine hydrochloride.

1H-NMR (400 MHz, CDCl3); δ (ppm) 1.44-1.57 (2H, m), 1.61 (9H, s), 1.76-1.93 (3H, m), 2.14-2.22 (5H, m), 3.02-3.09 (2H, m), 3.67 (2H, s), 3.88 (2H, d, J=6.4 Hz), 6.85 (1H, dd, J=8.0, 1.2 Hz), 6.92-7.04 (2H, m), 7.73 (1H, br s), 7.93 (1H, d, J=2.8 Hz), 8.05 (1H, d, J=2.8 Hz), 8.34 (1H, dd, J=8.0, 1.6 Hz).

Example 323

N-[2-[1-(3-tert-Butoxy-2-pyrazinylmethyl)piperidin-4-yl]methoxy-phenyl]methanesulfonamide

The title compound (140 mg, 33% yield) was obtained in the same manner as Example 320 from 190 mg of 3-tert-butoxypyrazine-2-carboxaldehyde and 271 mg of 4-[2-(methanesulfonylamino)phenoxymethyl]piperidine.

1H-NMR (400 MHz, CDCl3); δ (ppm) 1.42-1.54 (2H, m), 1.61 (9H, s), 1.75-1.91 (3H, m), 2.13-2.22 (2H, m), 2.94 (3H, s), 3.01-3.08 (2H, m), 3.66 (2H, s), 3.86 (2H, d, J=6.4 Hz), 6.77 (1H, br s), 6.89 (1H, dd, J=8.4, 1.2 Hz), 6.93-6.99 (1H, m), 7.09-7.14 (1H, m), 7.54 (1H, dd, J=8.0, 1.6 Hz), 7.93 (1H, d, J=2.8 Hz), 8.05 (1H, d, J=2.8 Hz).

Example 324

2-tert-Butoxy-3-[4-[2-(dimethylamino)phenoxymethyl]piperidino]methyl-pyrazine

The title compound (205 mg, 62% yield) was obtained in the same manner as Example 320 from 150 mg of 3-tert-butoxypyrazine-2-carboxaldehyde and 233 mg of 4-[2-(dimethylamino)phenoxymethyl]piperidine.

1H-NMR (400 MHz, CDCl3); δ (ppm) 1.43-1.55 (2H, m), 1.60 (9H, s), 1.84-2.01 (3H, m), 2.13-2.21 (2H, m), 2.79 (6H, s), 3.01-3.08 (2H, m), 3.65 (2H, s), 3.84 (2H, d, J=6.8 Hz), 6.82-6.96 (4H, m), 7.92 (1H, d, J=2.8 Hz), 8.05 (1H, d, J=2.8 Hz).

Example 325

3-[2-[1-(3-tert-Butoxy-2-pyrazinylmethyl)piperidin-4-yl]methoxy-phenyl]-1-methylthiourea

The title compound (76 mg, 27% yield) was obtained in the same manner as Example 1 from 150 mg of 3-tert-butoxypyrazine-2-carboxaldehyde and 200 mg of 4-[2-(3-methylthioureido)phenoxymethyl]piperidine hydrochloride.

1H-NMR (400 MHz, CDCl3); δ (ppm) 1.40-1.52 (2H, m), 1.61 (9H, s), 1.77-1.98 (3H, m), 2.12-2.20 (2H, m), 3.00-3.07 (2H, m), 3.13 (3H, d, J=4.4 Hz), 3.65 (2H, s), 3.81 (2H, d, J=6.4 Hz), 6.22-6.31 (1H, m), 6.92-7.00 (2H, m), 7.20 (1H, dt, J=8.0, 1.6 Hz), 7.28-7.42 (1H, m), 7.52 (1H, br s), 7.93 (1H, d, J=2.8 Hz), 8.05 (1H, d, J=2.8 Hz).

Example 326

3-[2-[1-(3-tert-Butoxy-2-pyrazinylmethyl)piperidin-4-yl]methoxy-phenyl]-1-methylurea

The title compound (337 mg, 95% yield) was obtained in the same manner as Example 320 from 150 mg of 3-tert-butoxypyrazine-2-carboxaldehyde and 260 mg of 4-[2-(3-methylureido)phenoxymethyl]piperidine.

1H-NMR (400 MHz, CDCl3); δ (ppm) 1.61 (9H, s), 1.64-1.88 (5H, m), 2.12-2.20 (2H, m), 2.84 (3H, d, J=4.8 Hz), 3.02-3.09 (2H, m), 3.65 (2H, s), 3.87 (2H, d, J=4.8 Hz), 5.34 (1H, br s), 6.78-6.83 (1H, m), 6.85 (1H, br s), 6.89-6.96 (2H, m), 7.95 (1H, d, J=2.8 Hz), 8.00-8.06 (2H, m).

Example 327

1-[1-(3-tert-Butoxy-2-pyrazinylmethyl)piperidin-4-yl]-2-(4-fluoro-3-thienyl)ethanone The title compound (262 mg, 88% yield) was obtained in the same manner as Example 1 from 178 mg of 3-tert-butoxypyrazine-2-carboxaldehyde and 200 mg of 2-(4-fluoro-3-thienyl)-1-(piperidin-4-yl)ethanone hydrochloride.

1H-NMR (400 MHz, CDCl3); δ (ppm) 1.59 (9H, s), 1.71-1.88 (4H, m), 2.13-2.21 (2H, m), 2.37-2.46 (1H, m), 2.98-3.05 (2H, m), 3.63 (2H, s), 3.66 (2H, d, J=0.8 Hz), 6.69 (1H, dd, J=3.6, 0.8 Hz), 7.02 (1H, tt, J=3.6, 0.8 Hz), 7.91 (1H, d, J=2.8 Hz), 8.02 (1H, d, J=2.8 Hz).

Example 328

2-tert-Butoxy-3-[4-(2-fluorophenoxymethyl)azepan-1-yl]methyl-pyrazine

The title compound (109 mg, 65% yield) was obtained in the same manner as Example 269 from 93 mg of 3-tert-butoxypyrazine-2-carboxaldehyde and 100 mg of 4-(2-fluorophenoxymethyl)azepane.

1H-NMR (400 MHz, CDCl3); δ (ppm) 1.50-2.20 (16H, m), 2.79-2.96 (4H, m), 3.77 (2H, d, J=2.4 Hz), 3.82 (2H, d, J=6.8 Hz), 6.84-7.08 (4H, m), 7.92 (1H, d, J=2.8 Hz), 8.02 (1H, d, J=2.8 Hz).

Example 329

1-[1-(3-tert-Butoxy-2-pyrazinylmethyl)piperidin-4-yl]-2-(2-cyanophenyl)ethanone

After dissolving 298 mg of 2-(2-bromophenyl)-1-[1-(3-tert-butoxy-2-pyrazinylmethyl)piperidin-4-yl]ethanone in 2 ml of N,N-dimethylformamide, 235 mg of zinc cyanide and 77 mg of tetrakis(triphenylphosphine)palladium(0) were added and the mixture was stirred overnight at 100° C. A 1N sodium hydroxide solution was added to the reaction mixture and extraction was performed with ethyl acetate. The organic layer was washed with saturated brine and dried over anhydrous magnesium sulfate, and then the solvent was distilled off under reduced pressure. The residue was purified by silica gel column chromatography (solvent: n-hexane/ethyl acetate) to obtain the title compound (90 mg, 34% yield).

1H-NMR (400 MHz, CDCl3); δ (ppm) 1.56 (9H, s), 1.77-1.88 (2H, m), 1.88-1.96 (2H, m), 2.16-2.25 (2H, m), 2.45-2.55 (1H, m), 3.01-3.08 (2H, m), 3.64 (2H, m), 4.00 (2H, s), 7.28 (1H, d, J=7.6 Hz), 7.35 (1H, td, J=7.6, 1.2 Hz), 7.53 (1H, td, J=7.6, 1.2 Hz), 7.63 (1H, dd, J=7.6, 1.2 Hz), 7.92 (1H, d, J=2.8 Hz), 8.02 (1H, d, J=2.8 Hz).

Example 330

1-[1-(3-tert-Butoxy-2-pyrazinylmethyl)piperidin-4-yl]-2-(2,3-dihydrobenzofuran-7-yl)ethanone The title compound (107 mg, 86% yield) was obtained in the same manner as Example 1 from 66 mg of 3-tert-butoxypyrazine-2-carboxaldehyde and 86 mg of 2-(2,3-dihydrobenzofuran-7-yl)-1-(piperidin-4-yl)ethanone hydrochloride.

1H-NMR (400 MHz, CDCl3); δ (ppm) 1.59 (9H, s), 1.70-1.88 (4H, m), 2.12-2.19 (2H, m), 2.38-2.47 (1H, m), 2.97-3.03 (2H, m), 3.21 (2H, t, J=8.8 Hz), 3.62 (2H, s), 3.68 (2H, s), 4.53 (2H, t, J=8.8 Hz), 6.79 (1H, t, J=7.4 Hz), 6.90 (1H, d, J=7.4 Hz), 7.09 (1H, dd, J=7.4, 1.2 Hz), 7.92 (1H, d, J=2.8 Hz), 8.03 (1H, d, J=2.8 Hz).

Example 331

2-tert-Butoxy-3-[4-(2-fluorophenoxymethyl)-4-methylpiperidino]methyl-pyrazine 4-(2-Fluorophenoxymethyl)-4-methylpiperidine hydrochloride (203 mg) was obtained in the same manner as Production Example 113 from 203 mg of 1-(tert-butoxycarbonyl)-4-(2-fluorophenoxymethyl)-4-methylpiperidine. The title compound (95 mg, 67% yield) was then obtained in the same manner as Example 1 from 86 mg of 3-tert-butoxypyrazine-2-carboxaldehyde and 95 mg of the 4-(2-fluorophenoxymethyl)-4-methylpiperidine hydrochloride.

1H-NMR (400 MHz, CDCl3); δ (ppm) 1.11 (3H, s), 1.49-1.58 (2H, m), 1.60 (9H, s), 1.74 (2H, ddd, J=13.6, 9.6, 4.0 Hz), 2.47-2.53 (2H, m), 2.65-2.71 (2H, m), 3.67 (2H, s), 3.73 (2H, s), 6.83-6.91 (1H, m), 6.95 (1H, td, J=8.4, 2.0 Hz), 6.99-7.08 (2H, m), 7.92 (1H, d, J=2.6 Hz), 8.05 (1H, d, J=2.6 Hz).

Example 332

1-[1-(3-tert-Butoxy-2-pyrazinylmethyl)piperidin-4-yl]-2-(2-fluoro-3-thienyl)ethanone The title compound (114 mg, 63% yield) was obtained in the same manner as Example 1 from 107 mg of 3-tert-butoxypyrazine-2-carboxaldehyde and 120 mg of 1-(2-fluoro-3-thienyl)-1-(piperidin-4-yl)ethanone hydrochloride.

1H-NMR (400 MHz, CDCl3); δ(ppm) 1.59 (9H, s), 1.70-1.87 (4H, m), 2.13-2.21 (2H, m), 2.36-2.45 (1H, m), 2.98-3.05 (2H, m), 3.63 (2H, s), 3.64 (2H, d, J=1.2 Hz), 6.59-6.63 (2H, m), 7.93 (1H, d, J=2.8 Hz), 8.03 (1H, d, J=2.8 Hz).

Example 333

(E)-3-[4-[2-[2-(Cyclohexylmethyloxy)phenyl]vinyl]piperidino]methyl-2-methoxypyrazine After dissolving 131 mg of 3-methoxypyrazine-2-carboxaldehyde and 236 mg of (E)-4-[2-[2-(cyclohexylmethyloxy)phenyl]vinyl]piperidine in 3 ml of 1,2-dichloroethane, 0.07 ml of acetic acid and 276 mg of sodium triacetoxyborohydride were added and the mixture was stirred overnight at room temperature. Aqueous sodium carbonate solution was added to the reaction mixture and extraction was performed with ethyl acetate. The extract was washed with water and saturated brine and dried over anhydrous magnesium sulfate, and then the solvent was distilled off under reduced pressure. The residue was purified by silica gel column chromatography (solvent: n-hexane/ethyl acetate) to obtain the title compound (255 mg, 77% yield).

1H-NMR (400 MHz, CDCl3); δ(ppm) 1.01-1.38 (5H, m), 1.58-1.92 (10H, m), 2.08-2.24 (3H, m), 3.02-3.08 (2H, m), 3.71 (2H, s), 3.76 (2H, d, J=6.0 Hz), 3.98 (3H, s), 6.18 (1H, dd, J=16.0, 7.2 Hz), 6.70 (1H, d, J=16.0 Hz), 6.82 (1H, dd, J=8.0, 0.8 Hz), 6.87 (1H, dt, J=7.6, 0.8 Hz), 7.14 (1H, ddd, J=8.0, 7.6, 1.6 Hz), 7.40 (1H, dd, J=7.6, 1.6 Hz), 7.99 (1H, d, J=2.4 Hz), 8.13 (1H, d, J=2.4 Hz).

Example 334 trans-1-[1-(3-tert-Butoxy-2-pyrazinylmethyl)-2-methylpiperidin-4-yl]-2-(2-fluorophenyl)ethanone The title compound (228 mg, 64% yield) was obtained in the same manner as Example 269 from 150 mg of 3-tert-butoxypyrazine-2-carboxaldehyde and 216 mg of trans-2-(2-fluorophenyl)-1-(2-methylpiperidin-4-yl)ethanone.

1H-NMR (400 MHz, CDCl3); δ(ppm) 1.10 (3H, d, J=6.4 Hz), 1.59 (9H, s), 1.64-1.71 (1H, m), 1.74-1.85 (2H, m), 1.93-2.01 (1H, m), 2.53-2.60 (1H, m), 2.64-2.79 (2H, m), 3.02-3.10 (1H, m), 3.63 (1H, d, J=14.0 Hz), 3.67 (1H, d, J=14.0 Hz), 3.76 (2H, s), 7.00-7.10 (2H, m), 7.15 (1H, dt, J=7.6, 2.0 Hz), 7.20-7.26 (1H, m), 7.89 (1H, d, J=2.8 Hz), 7.99 (1H, d, J=2.8 Hz).

Example 335 cis-1-[1-(3-tert-Butoxy-2-pyrazinylmethyl)-2-methylpiperidin-4-yl]-2-(2-fluorophenyl)ethanone The title compound (46 mg, 19% yield) was obtained in the same manner as Example 1 from 100 mg of 3-tert-butoxypyrazine-2-carboxaldehyde and 182 mg of cis-2-(2-fluorophenyl)-1-(2-methylpiperidin-4-yl)ethanone hydrochloride.

1H-NMR (400 MHz, CDCl3); δ(ppm) 1.27 (3H, d, J=6.4 Hz), 1.47-1.57 (1H, m), 1.60 (9H, s), 1.64-1.72 (1H, m), 1.76-1.86 (2H, m), 2.18-2.26 (1H, m), 2.37-2.45 (1H, m), 2.47-2.56 (1H, m), 3.04-3.10 (1H, m), 3.48 (1H, d, J=13.6 Hz), 3.75 (2H, d, J=0.8 Hz), 4.08 (1H, d, J=13.6 Hz), 7.00-7.10 (2H, m), 7.13 (1H, dt, J=7.2, 2.0 Hz), 7.19-7.26 (1H, m), 7.90 (1H, d, J=2.8 Hz), 8.01 (1H, d, J=2.8 Hz).

Example 336

3-[4-[(2-Fluorophenylthio)methyl]piperidino]methyl-1H-pyrazin-2-one

The title compound (46 mg, 77% yield) was obtained in the same manner as Example 118 from 70 mg of 2-tert-butoxy-3-[4-[(2-fluorophenylthio)methyl]piperidino]methyl-pyrazine.

1H-NMR (400 MHz, CDCl3); δ (ppm) 1.37-1.65 (3H, m), 1.94-2.01 (2H, m), 2.22-2.30 (2H, m), 2.86 (2H, d, J=6.8 Hz), 2.97-3.04 (2H, m), 3.84 (2H, s), 7.03-7.12 (2H, m), 7.20-7.27 (1H, m), 7.37 (1H, td, J=8.0, 2.0 Hz), 7.91 (1H, d, J=2.4 Hz), 7.95 (1H, br s).

Example 337

3-[4-[(2-Fluorophenylsulfinyl)methyl]piperidino]methyl-1H-pyrazin-2-one

The title compound (16 mg, 43% yield) was obtained in the same manner as Example 118 from 43 mg of 2-tert-butoxy-3-[4-[(2-fluorophenylsulfinyl)methyl]piperidino]methyl-pyrazine.

1H-NMR (400 MHz, CDCl3); δ (ppm) 1.48-1.66 (2H, m), 1.76-1.84 (1H, m), 2.10-2.42 (4H, m), 2.80-2.89 (2H, m), 2.97-3.10 (2H, m), 3.86 (2H, s), 7.13 (1H, ddd, J=9.6, 8.0, 1.2 Hz), 7.40 (1H, td, J=8.0, 1.2 Hz), 7.47-7.54 (1H, m), 7.82-7.93 (3H, m).

Example 338

3-[4-[(2-Fluorophenylsulfonyl)methyl]piperidino]methyl-1H-pyrazin-2-one

The title compound (32 mg, 77% yield) was obtained in the same manner as Example 118 from 48 mg of 2-tert-butoxy-3-[4-[(2-fluorophenylsulfonyl)methyl]piperidino]methyl-pyrazine.

1H-NMR (400 MHz, CDCl3); δ (ppm) 1.42-1.61 (2H, m), 1.96-2.05 (2H, m), 2.14-2.36 (3H, m), 2.95-3.02 (2H, m), 3.26 (2H, d, J=6.4 Hz), 3.83 (2H, s), 7.23-7.30 (1H, m), 7.36 (1H, td, J=8.0, 1.2 Hz), 7.64-7.70 (1H, m), 7.86-7.98 (3H, m).

Example 339

6-Chloro-5-[4-(2-fluorobenzyloxy)piperidino]methyl-1H-pyrazin-2-one

The title compound (29 mg, 24% yield) was obtained in the same manner as Example 118 from 137 mg of 5-tert-butoxy-3-chloro-2-[4-(2-fluorobenzyloxy)piperidino]methyl-pyrazine.

1H-NMR (400 MHz, DMSO-d6); δ (ppm) 1.28-1.42 (2H, m), 1.72-1.87 (3H, m), 2.25-2.36 (2H, m), 2.95-3.04 (2H, m), 3.71 (2H, s), 3.88 (2H, d, J=6.0 Hz), 6.87-6.94 (1H, m), 7.06-7.21 (3H, m), 7.87 (1H, s).

Example 340

3-[3-[2-(2-Fluorophenyl)ethyl]morpholin-1-yl]methyl-1H-pyrazin-2-one

The title compound (223 mg, 80% yield) was obtained in the same manner as Example 137 from 329 mg of 2-tert-butoxy-3-[3-[2-(2-fluorophenyl)ethyl]morpholin-1-yl]methyl-pyrazine.

1H-NMR (400 MHz, CDCl3); δ (ppm) 1.64-1.84 (2H, m), 2.12 (1H, dd, J=11.2, 10.0 Hz), 2.41 (1H, dt, J=11.2, 3.2 Hz), 2.64-2.73 (1H, m), 2.78-2.88 (3H, m), 3.53-3.62 (1H, m), 3.73 (1H, dt, J=11.6, 2.4 Hz), 3.76 (1H, d, J=15.2 Hz), 3.80 (1H, d, J=15.2 Hz), 3.91-3.97 (1H, m), 6.95-7.05 (2H, m), 7.12-7.18 (2H, m), 7.62 (1H, br s), 7.73 (1H, d, J=3.2 Hz).

Example 341

(E)-3-[3-[2-(2-Fluorophenyl)vinyl]morpholin-1-yl]methyl-1H-pyrazin-2-one

The title compound (120 mg, 79% yield) was obtained in the same manner as Example 137 from 178 mg of (E)-2-tert-butoxy-3-[3-[2-(2-fluorophenyl)vinyl]morpholin-1-yl]methyl-pyrazine.

1H-NMR (400 MHz, CDCl3); δ (ppm) 2.26 (1H, dt, J=11.2, 10.8 Hz), 2.47 (1H, dt, J=11.2, 3.2 Hz), 2.86-2.92 (1H, m), 3.00-3.05 (1H, m), 3.78-3.90 (3H, m), 3.98-4.04 (1H, m), 4.28-4.34 (1H, m), 6.23 (1H, dd, J=16.4, 6.0 Hz), 6.80 (1H, dd, J=16.4, 1.2 Hz), 6.88-7.09 (2H, m), 7.16-7.23 (1H, m), 7.40 (1H, dt, J=7.6, 1.6 Hz), 7.56 (1H, br s), 7.70 (1H, d, J=3.6 Hz).

Example 342

3-[3-(2-Fluorophenoxymethyl)morpholin-1-yl]methyl-1H-pyrazin-2-one

The title compound (175 mg, 79% yield) was obtained in the same manner as Example 137 from 258 mg of 2-tert-butoxy-3-[3-(2-fluorophenoxymethyl)morpholin-1-yl]methyl-pyrazine.

1H-NMR (400 MHz, CDCl3); δ (ppm) 2.35 (1H, dt, J=11.2, 5.6 Hz), 2.45 (1H, dt, J=11.2, 3.6 Hz), 2.86-2.92 (1H, m), 3.08-3.14 (1H, m), 3.79 (1H, d, J=15.6 Hz), 3.79-3.87 (2H, m), 3.94-4.13 (4H, m), 6.87-7.08 (4H, m), 7.45-7.51 (1H, m), 7.65 (1H, d, J=3.6 Hz).

Example 343

3-[4-[2-[2-(Methylthio)phenyl]acetyl]piperidino]methyl-1H-pyrazin-2-one

After adding 3 ml of 4N hydrogen chloride/ethyl acetate to 200 mg of 1-[1-(3-tert-butoxy-2-pyrazinylmethyl)piperidin-4-yl]-2-[2-(methylthio)phenyl]ethanone while cooling on ice, the mixture was stirred for 30 minutes. A 2N sodium hydroxide solution was added to the reaction solution for neutralization, and extraction was performed with dichloromethane. The organic layer was washed with saturated brine and dried over anhydrous magnesium sulfate, and then the solvent was distilled off under reduced pressure. Diethyl ether was added to the residue and the mixture was filtered to obtain the title compound (146 mg, 84% yield).

1H-NMR (400 MHz, CDCl3); δ (ppm) 1.82-1.94 (2H, m), 1.94-2.02 (2H, m), 2.28-2.38 (2H, m), 2.43 (3H, s), 2.54-2.64 (1H, m), 2.98-3.06 (2H, m), 3.83 (2H, s), 3.89 (2H, s), 7.08-7.16 (2H, m), 7.23-7.29 (2H, m), 7.88 (2H, br s).

Example 344

3-[4-[2-[2-(Trifluoromethyl)phenyl]acetyl]piperidino]methyl-1H-pyrazin-2-one After adding 3 ml of 4N hydrogen chloride/ethyl acetate to 249 mg of 1-[1-(3-tert-butoxy-2-pyrazinylmethyl)piperidin-4-yl]-2-[2-(trifluoromethyl)phenyl]ethanone while cooling on ice, the mixture was stirred for 30 minutes. A 2N sodium hydroxide solution was added to the reaction solution for neutralization, and extraction was performed with dichloromethane. The organic layer was washed with saturated brine and dried over anhydrous magnesium sulfate, and the solvent was distilled off under reduced pressure. Diethyl ether was added to the residue and the mixture was filtered to obtain the title compound (155 mg, 71% yield).

1H-NMR (400 MHz, CDCl3); δ (ppm) 1.81-2.02 (4H, m), 2.30-2.40 (2H, m), 2.52-2.62 (1H, m), 3.01-3.09 (2H, m), 3.84 (2H, s), 3.97 (2H, s), 7.22 (1H, d, J=7.6 Hz), 7.38 (1H, t, J=7.6 Hz), 7.51 (1H, t, J=7.6 Hz), 7.65 (1H, d, J=7.6 Hz), 7.86 (2H, br s).

Example 345

3-[4-[2-[2-(Trifluoromethoxy)phenyl]acetyl]piperidino]methyl-1H-pyrazin-2-one The title compound (153 mg, 66% yield) was obtained in the same manner as Example 344 from 266 mg of 1-[1-(3-tert-butoxy-2-pyrazinylmethyl)piperidin-4-yl]-2-[2-(trifluoromethoxy)phenyl]ethanone.

1H-NMR (400 MHz, CDCl3); δ (ppm) 1.80-2.01 (4H, m), 2.29-2.39 (2H, m), 2.51-2.60 (1H, m), 2.99-3.08 (2H, m), 3.82 (2H, s), 3.84 (2H, s), 7.18-7.34 (4H, m), 7.87 (2H, br s).

Example 346

6-Methyl-3-[1-(3-oxo-3,4-dihydro-2-pyrazinylmethyl)piperidin-4-yl]-3,4-dihydropyrido[2,3-e][1,3]oxazin-2-one The title compound (20 mg, 63% yield) was obtained in the same manner as Example 365 from 37 mg of 3-[1-(3-tert-butoxy-2-pyrazinylmethyl)piperidin-4-yl]-6-methyl-3,4-dihydropyrido[2,3-e][1,3]oxazin-2-one.

1H-NMR (400 MHz, CDCl3); δ (ppm) 1.84-1.91 (2H, m), 1.96-2.08 (2H, m), 2.39-2.48 (2H, m), 2.52 (3H, s), 3.12-3.20 (2H, m), 3.85 (2H, s), 4.32-4.42 (1H, m), 4.46 (2H, s), 7.06 (1H, d, J=8.0 Hz), 7.21 (1H, d, J=8.0 Hz), 7.70 (1H, br s), 7.76-7.80 (1H, m).

Example 347

3-[4-[2-(2-Ethoxyphenyl)acetyl]piperidino]methyl-1H-pyrazin-2-one

The title compound (166 mg, 73% yield) was obtained in the same manner as Example 344 from 264 mg of 1-[1-(3-tert-butoxy-2-pyrazinylmethyl)piperidin-4-yl]-2-(2-ethoxyphenyl)ethanone.

1H-NMR (400 MHz, CDCl3); δ (ppm) 1.36 (3H, t, J=7.0 Hz), 1.78-1.98 (4H, m), 2.25-2.35 (2H, m), 2.51-2.61 (1H, m), 2.96-3.05 (2H, m), 3.72 (2H, s), 3.82 (2H, s), 4.01 (2H, t, J=7.0 Hz), 6.83 (1H, d, J=7.6 Hz), 6.89 (1H, t, J=7.6 Hz), 7.10 (1H, dd, J=7.6, 1.6 Hz), 7.19-7.26 (1H, m), 7.85-7.93 (2H, m).

Example 348

3-[4-[2-(2-n-Propoxyphenyl)acetyl]piperidino]methyl-1H-pyrazin-2-one

The title compound (165 mg, 69% yield) was obtained in the same manner as Example 344 from 276 mg of 1-[1-(3-tert-butoxy-2-pyrazinylmethyl)piperidin-4-yl]-2-(2-n-propoxyphenyl)ethanone.

1H-NMR (400 MHz, CDCl3); δ (ppm) 1.01 (3H, t, J=7.4 Hz), 1.71-1.96 (6H, m), 2.24-2.35 (2H, m), 2.50-2.60 (1H, m), 2.95-3.04 (2H, m), 3.73 (2H, s), 3.82 (2H, s), 3.90 (2H, t, J=6.6 Hz), 6.84 (1H, d, J=7.6 Hz), 6.89 (1H, t, J=7.6 Hz), 7.10 (1H, dd, J=7.6, 1.6 Hz), 7.19-7.26 (1H, m), 7.86-7.94 (2H, m).

Example 349

3-[4-[2-(2-Fluorophenyl)propionyl]piperidino]methyl-1H-pyrazin-2-one

The title compound (227 mg, 88% yield) was obtained in the same manner as Example 344 from 300 mg of 1-[1-(3-tert-butoxy-2-pyrazinylmethyl)piperidin-4-yl]-2-(2-fluorophenyl)propanone.

1H-NMR (400 MHz, CDCl3); δ (ppm) 1.38 (3H, d, J=6.8 Hz), 1.58-1.65 (1H, m), 1.70-1.85 (2H, m), 1.91-1.98 (1H, m), 2.14-2.32 (2H, m), 2.43-2.52 (1H, m), 2.88-3.03 (2H, m), 3.79 (2H, s), 4.25 (1H, q, J=6.8 Hz), 7.06 (1H, ddd, J=9.6, 7.6, 1.2 Hz), 7.11 (1H, dd, J=7.6, 1.2 Hz), 7.15 (1H, td, J=7.6, 2.0 Hz), 7.21-7.27 (1H, m), 7.84-7.92 (2H, m).

Example 350

3-[1-[4-[2-(2-Fluorophenyl)acetyl]piperidino]ethyl]-1H-pyrazin-2-one

After dissolving 118 mg of 1-[1-[1-(3-methoxy-2-pyrazinyl)ethyl]piperidin-4-yl]-2-(2-fluorophenyl)ethanone in 2 ml of ethanol, 6 ml of 4N hydrogen chloride/ethyl acetate was added and the mixture was heated to reflux for 9 hours. Saturated aqueous sodium bicarbonate solution was added to the reaction solution and extraction was performed with ethyl acetate. The organic layer was washed with water and saturated brine in that order and dried over anhydrous magnesium sulfate, and then the solvent was distilled off under reduced pressure. The residue was purified by NH silica gel column chromatography (solvent: ethyl acetate/methanol), diethyl ether was added and the precipitate was filtered out to obtain the title compound (61 mg, 38% yield).

1H-NMR (400 MHz, CDCl3); δ (ppm) 1.44 (3H, d, J=6.8 Hz), 1.77-1.93 (2H, m), 1.95-2.04 (2H, m), 2.29-2.39 (1H, m), 2.47-2.61 (2H, m), 2.91-3.01 (2H, m), 3.78 (2H, s), 3.96 (1H, q, J=6.8 Hz), 7.01-7.18 (3H, m), 7.22-7.29 (1H, m), 7.93 (1H, d, J=2.4 Hz), 7.96 (1H, br s).

Example 351 cis-3-[3-(2-Fluorophenoxymethyl)-4-hydroxypiperidino]methyl-1H-pyrazin-2-one

After dissolving 198 mg of cis-1-(3-tert-butoxy-2-pyrazinylmethyl)-3-(2-fluorophenoxymethyl)piperidin-4-ol in 3 ml of ethyl acetate, 3 ml of 4N hydrogen chloride/ethyl acetate was added while stirring on ice. After 1 hour, aqueous sodium bicarbonate solution was added to the reaction solution and extraction was performed with dichloromethane. The extract was dried over anhydrous magnesium sulfate, and then the solvent was distilled off under reduced pressure. Diethyl ether was added to the residue and the mixture was filtered to obtain the title compound (68 mg, 40% yield).

1H-NMR (400 MHz, CDCl3); δ (ppm) 1.86-2.00 (2H, m), 2.33-2.42 (1H, m), 2.72-2.84 (4H, m), 3.90 (2H, s), 4.06-4.18 (2H, m), 4.26-4.30 (1H, m), 6.88-6.98 (2H, m), 7.01-7.09 (2H, m), 7.84 (2H, br s).

Example 352 trans-3-[3-(2-Fluorophenoxymethyl)-4-hydroxypiperidino]methyl-1H-pyrazin-2-one

The title compound (63 mg, 50% yield) was obtained in the same manner as Example 351 from 149 mg of trans-1-(3-tert-butoxy-2-pyrazinylmethyl)-3-(2-fluorophenoxymethyl)piperidin-4-ol.

1H-NMR (400 MHz, CDCl3); δ (ppm) 1.77-1.89 (1H, m), 2.03-2.11 (1H, m), 2.21-2.40 (3H, m), 3.00-3.08 (1H, m), 3.12-3.18 (1H, m), 3.70-3.78 (1H, m), 3.83 (1H, d, J=16.0 Hz), 3.87 (1H, d, J=16.0 Hz), 4.09 (1H, dd, J=9.6, 4.8 Hz), 4.16 (1H, dd, J=9.6, 4.8 Hz), 6.86-7.09 (4H, m), 7.71 (1H, br s), 7.78 (1H, d, J=2.8 Hz).

Example 353

3-[4-[2-(1-Naphthyl)acetyl]piperidino]methyl-1H-pyrazin-2-one

The title compound (126 mg, 65% yield) was obtained in the same manner as Example 344 from 224 mg of 1-[1-(3-tert-butoxy-2-pyrazinylmethyl)piperidin-4-yl]-2-(1-naphthyl)ethanone.

1H-NMR (400 MHz, CDCl3); δ (ppm) 1.80-1.88 (4H, m), 2.18-2.28 (2H, m), 2.52-2.62 (1H, m), 2.95-3.02 (2H, m), 3.79 (2H, s), 4.18 (2H, s), 7.34 (1H, d, J=6.8 Hz), 7.41-7.53 (3H, m), 7.78-7.91 (5H, m).

Example 354

3-[4-(2-Chlorophenoxymethyl)-4-methylpiperidino]methyl-1H-pyrazin-2-one

After dissolving 237 mg of 2-tert-butoxy-3-[4-(2-chlorophenoxymethyl)-4-methylpiperidino]methyl-pyrazine in 3 ml of ethyl acetate, 3 ml of 4N hydrogen chloride/ethyl acetate was added while stirring on ice. After 1 hour, aqueous sodium carbonate solution was added to the reaction solution and extraction was performed with ethyl acetate. The organic layer was washed with water and saturated brine and dried over anhydrous magnesium sulfate, and then the solvent was distilled off under reduced pressure. Diethyl ether was added to the residue and the precipitate was filtered out to obtain the title compound (104 mg, 51% yield).

1H-NMR (400 MHz, CDCl3); δ (ppm) 1.18 (3H, s), 1.62-1.69 (2H, m), 1.82-1.91 (2H, m), 2.58-2.68 (2H, m), 2.75-2.84 (2H, m), 3.76 (2H, s), 3.89 (2H, s), 6.86-6.92 (2H, m), 7.19 (1H, dd, J=8.0, 1.6 Hz), 7.34 (1H, dd, J=8.4, 1.6 Hz), 7.90 (1H, d, J=2.8 Hz), 7.93 (1H, br s).

Example 355

3-[4-Methyl-4-(2-methylphenoxymethyl)piperidino]methyl-1H-pyrazin-2-one

The title compound (135 mg, 64% yield) was obtained in the same manner as Example 354 from 244 mg of 2-tert-butoxy-3-[4-methyl-4-(2-methylphenoxymethyl)piperidino]methyl-pyrazine.

1H-NMR (400 MHz, CDCl3); δ (ppm) 1.16 (3H, s), 1.57-1.65 (2H, m), 1.83-1.92 (2H, m), 2.24 (3H, s), 2.57-2.67 (2H, m), 2.72-2.82 (2H, m), 3.71 (2H, s), 3.89 (2H, s), 6.78 (1H, d, J=8.0 Hz), 6.85 (1H, t, J=7.6 Hz), 7.10-7.17 (2H, m), 7.91 (1H, d, J=2.8 Hz), 7.94 (1H, br s).

Example 356

3-[4-(2-Methoxyphenoxymethyl)-4-methylpiperidino]methyl-1H-pyrazin-2-one

The title compound (153 mg, 87% yield) was obtained in the same manner as Example 354 from 202 mg of 2-tert-butoxy-3-[4-(2-methoxyphenoxymethyl)-4-methylpiperidino]methyl-pyrazine.

1H-NMR (400 MHz, CDCl3); δ (ppm) 1.15 (3H, s), 1.58-1.66 (2H, m), 1.81-1.90 (2H, m), 2.58-2.66 (2H, m), 2.76-2.84 (2H, m), 3.75 (2H, s), 3.84 (3H, s), 3.88 (2H, s), 6.86-6.94 (4H, m), 7.87 (1H, d, J=2.8 Hz), 7.91 (1H, d, J=2.8 Hz).

Example 357

3-[4-[2-[2-(Methylsulfonyl)phenyl]acetyl]piperidino]methyl-1H-pyrazin-2-one

The title compound (70 mg, 41% yield) was obtained in the same manner as Example 344 from 196 mg of 1-[1-(3-tert-butoxy-2-pyrazinylmethyl)piperidin-4-yl]-2-[2-(methylsulfonyl)phenyl]ethanone.

1H-NMR (400 MHz, CDCl3); δ (ppm) 1.84-1.96 (2H, m), 2.04-2.12 (2H, m), 2.37-2.46 (2H, m), 2.62-2.72 (1H, m), 3.01 (3H, s), 3.05-3.13 (2H, m), 3.88 (2H, s), 4.34 (2H, s), 7.19 (1H, dd, J=7.6, 1.2 Hz), 7.49 (1H, td, J=7.6, 1.2 Hz), 7.57 (1H, td, J=7.6, 1.6 Hz), 7.85 (2H, br s), 8.00 (1H, dd, J=7.6, 1.6 Hz).

Example 358

5-[4-[2-(2-Fluorophenyl)acetyl]piperidino]methyl-3H-pyrimidin-4-one

The title compound (133 mg, 76% yield) was obtained in the same manner as Example 365 from 205 mg of 1-[1-(4-tert-butoxy-5-pyrimidinylmethyl)piperidin-4-yl]-2-(2-fluorophenyl)ethanone.

1H-NMR (400 MHz, CDCl3); δ (ppm) 1.72-1.83 (2H, m), 1.85-1.93 (2H, m), 2.11-2.20 (2H, m), 2.48 (1H, dt, J=11.2, 4.0 Hz), 2.92-2.99 (2H, m), 3.44 (2H, s), 3.78 (2H, s), 7.01-7.11 (2H, m), 7.15 (1H, dt, J=7.2, 2.0 Hz), 7.21-7.27 (1H, m), 8.06 (1H, s), 8.13 (1H, s)

Example 359

3-[4-[2-(2-Biphenyl)acetyl]piperidino]methyl-1H-pyrazin-2-one

The title compound (155 mg, 85% yield) was obtained in the same manner as Example 344 from 210 mg of 1-[1-(3-tert-butoxy-2-pyrazinylmethyl)piperidin-4-yl]-2-(2-biphenyl)ethanone.

1H-NMR (400 MHz, CDCl3); δ (ppm) 1.55-1.68 (4H, m), 2.14-2.28 (3H, m), 2.84-2.93 (2H, m), 3.74 (2H, s), 3.78 (2H, s), 7.16-7.27 (4H, m), 7.30-7.40 (5H, m), 7.85-7.92 (2H, m).

Example 360

3-(2-Fluorophenyl)-2-[1-(3-oxo-3,4-dihydro-2-pyrazinylmethyl)piperidin-4-yl]propionitrile After adding 3 ml of 4N hydrogen chloride/ethyl acetate to 188 mg of 2-[1-(3-tert-butoxy-2-pyrazinylmethyl)piperidin-4-yl]-3-(2-fluorophenyl)propionitrile while cooling on ice, the mixture was stirred 1 hour. A 2N sodium hydroxide solution was added to the reaction solution for neutralization, and extraction was performed with ethyl acetate. The organic layer was washed with saturated brine and dried over anhydrous magnesium sulfate, and then the solvent was distilled off under reduced pressure. Diethyl ether was added to the residue and the mixture was filtered to obtain the title compound (129 mg, 80% yield).

1H-NMR (400 MHz, CDCl3); δ (ppm) 1.62-1.75 (3H, m), 1.85-1.94 (1H, m), 2.00-2.08 (1H, m), 2.22-2.33 (2H, m), 2.76 (2H, m), 3.02-3.15 (3H, m), 3.84 (2H, s), 7.06 (1H, ddd, J=9.6, 7.6, 1.2 Hz), 7.12 (1H, td, J=7.6, 1.2 Hz), 7.24-7.31 (2H, m), 7.86 (2H, br s).

Example 361

2-(2-Fluorobenzyl)-3-(2-fluorophenyl)-2-[1-(3-oxo-3,4-dihydro-2-pyrazinylmethyl)piperidin-4-yl]propionitrile The title compound (122 mg, 67% yield) was obtained in the same manner as Example 360 from 206 mg of 2-[1-(3-tert-butoxy-2-pyrazinylmethyl)piperidin-4-yl]-2-(2-fluorobenzyl)-3-(2-fluorophenyl)propionitrile.

1H-NMR (400 MHz, CDCl3); δ (ppm) 1.55-1.65 (1H, m), 1.72-1.84 (2H, m), 2.06-2.13 (2H, m), 2.19-2.28 (2H, m), 2.84 (2H, d, J=14.0 Hz), 3.06 (2H, d, J=14.0 Hz), 3.14-3.22 (2H, m), 3.85 (2H, s), 7.07 (2H, ddd, J=9.2, 7.6, 1.2 Hz), 7.14 (2H, td, J=7.6, 1.2 Hz), 7.24-7.32 (2H, m), 7.36 (2H, td, J=7.6, 2.0 Hz), 7.84 (2H, br s).

Example 362

3-[4-[2-(2-Bromophenyl)acetyl]piperidino]methyl-1H-pyrazin-2-one

The title compound (39 mg, 84% yield) was obtained in the same manner as Example 344 from 53 mg of 2-(2-bromophenyl)-1-[1-(3-tert-butoxy-2-pyrazinylmethyl)piperidin-4-yl]ethanone.

1H-NMR (400 MHz, CDCl3); δ (ppm) 1.83-1.95 (2H, m), 1.96-2.05 (2H, m), 2.30-2.40 (2H, m), 2.55-2.65 (1H, m), 3.00-3.07 (2H, m), 3.84 (2H, s), 3.92 (2H, s), 7.14 (1H, td, J=7.6, 1.6 Hz), 7.18 (1H, dd, J=7.6, 1.6 Hz), 7.23-7.30 (1H, m), 7.56 (1H, dd, J=7.6, 1.2 Hz), 7.88 (2H, br s).

Example 363

3-[4-[2-(2-Cyanophenyl)acetyl]piperidino]methyl-1H-pyrazin-2-one

The title compound (60 mg, 78% yield) was obtained in the same manner as Example 344 from 90 mg of 1-[1-(3-tert-butoxy-2-pyrazinylmethyl)piperidin-4-yl]-2-(2-cyanophenyl)ethanone.

1H-NMR (400 MHz, CDCl3); δ (ppm) 1.83-1.95 (2H, m), 2.00-2.08 (2H, m), 2.32-2.42 (2H, m), 2.58-2.68 (1H, m), 3.02-3.10 (2H, m), 3.85 (2H, s), 4.02 (2H, s), 7.28-7.32 (1H, m), 7.38 (1H, td, J=7.6, 1.2 Hz), 7.56 (1H, td, J=7.6, 1.6 Hz), 7.63-7.67 (1H, m) 7.86 (2H, br s).

Example 364

4-[4-[2-(2-Fluorophenyl)acetyl]piperidino]methyl-2H-pyridazin-3-one

After dissolving 74 mg of 2-(2-fluorophenyl)-1-[1-(3-methoxy-4-pyridazinylmethyl)piperidin-4-yl]ethanone in 2 ml of 5N hydrochloric acid, the mixture was heated to reflux for 4.5 hours. A 5N sodium hydroxide solution was added to the reaction solution for neutralization, and extraction was performed with dichloromethane. The organic layer was washed with saturated aqueous sodium bicarbonate solution and saturated brine and dried over anhydrous magnesium sulfate. The solvent was distilled off under reduced pressure, diethyl ether was added to the residue and the mixture was filtered to obtain the title compound (27 mg, 38% yield).

1H-NMR (400 MHz, CDCl3); δ (ppm) 1.72-1.84 (2H, m), 1.85-1.93 (2H, m), 2.16-2.24 (2H, m), 2.46-2.56 (1H, m), 2.85-2.94 (2H, m), 3.49 (2H, d, J=1.6 Hz), 3.79 (2H, s), 7.05 (1H, ddd, J=9.6, 7.6, 1.2 Hz), 7.09 (1H, td, J=7.6, 1.2 Hz), 7.16 (1H, td, J=7.6, 1.6 Hz), 7.22-7.28 (1H, m), 7.34-7.38 (1H, m), 7.78 (1H, d, J=4.4 Hz).

Example 365

3-[4-[2-(2-Fluorophenyl)acetyl]-4-methylpiperidino]methyl-1H-pyrazin-2-one

After dissolving 135 mg of 1-[1-(3-tert-butoxy-2-pyrazinylmethyl)-4-methylpiperidin-4-yl]-2-(2-fluorophenyl)ethanone in 2 ml of ethyl acetate, 2 ml of 4N hydrogen chloride/ethyl acetate was added while stirring on ice. After 1 hour, saturated aqueous sodium bicarbonate solution was added to the reaction solution and extraction was performed with dichloromethane. The extract was dried over anhydrous magnesium sulfate, and then the solvent was distilled off under reduced pressure. Diethyl ether was added to the residue and the mixture was filtered to obtain the title compound (94 mg, 86% yield).

1H-NMR (400 MHz, CDCl3); δ (ppm) 1.29 (3H, s), 1.66-1.74 (2H, m), 2.22-2.30 (2H, m), 2.39-2.51 (2H, m), 2.75-2.84 (2H, m), 3.80 (2H, s), 3.81 (2H, s), 7.00-7.18 (3H, m), 7.22-7.28 (1H, m), 7.78-7.85 (2H, m).

Example 366 trans-3-[4-[2-(2-Fluorophenyl)acetyl]-3-methylpiperidino]methyl-1H-pyrazin-2-one The title compound (92 mg, 100% yield) was obtained in the same manner as Example 365 from 112 mg of trans-1-[1-(3-tert-butoxy-2-pyrazinylmethyl)-3-methylpiperidin-4-yl]-2-(2-fluorophenyl)ethanone.

1H-NMR (400 MHz, CDCl3); δ (ppm) 0.82 (3H, d, J=6.4 Hz), 1.73-1.84 (1H, m), 1.87-1.98 (2H, m), 2.11-2.33 (3H, m), 2.93-2.99 (1H, m), 3.04-3.10 (1H, m), 3.77 (2H, s), 3.82 (2H, s), 7.03-7.13 (2H, m), 7.16 (1H, dt, J=7.2, 1.6 Hz), 7.23-7.29 (1H, m), 7.86 (2H, br s).

Example 367

6-[4-(2-Fluorophenoxymethyl)piperidino]methyl-1H-pyrazin-2-one

The title compound (153 mg, 89% yield) was obtained in the same manner as Example 365 from 202 mg of 2-tert-butoxy-6-[4-(2-fluorophenoxymethyl)piperidino]methyl-pyrazine.

1H-NMR (400 MHz, CDCl3); δ (ppm) 1.36-1.48 (2H, m), 1.84-1.96 (3H, m), 2.21 (2H, dt, J=11.6, 2.4 Hz), 2.82-2.88 (2H, m), 3.40 (2H, s), 3.87 (2H, d, J=6.4 Hz), 6.85-6.98 (2H, m), 7.02-7.10 (2H, m), 7.22 (1H, s), 8.05 (1H, s).

Example 368

6-[4-[2-(2-Fluorophenyl)acetyl]piperidino]methyl-1H-pyrazin-2-one

The title compound (135 mg, 91% yield) was obtained in the same manner as Example 365 from 172 mg of 1-[1-(6-tert-butoxy-2-pyrazinylmethyl)piperidin-4-yl]-2-(2-fluorophenyl)ethanone.

1H-NMR (400 MHz, CDCl3); δ (ppm) 1.71-1.82 (2H, m), 1.86-1.94 (2H, m), 2.22 (2H, dt, J=11.6, 2.8 Hz), 2.47-2.55 (1H, m), 2.81-2.87 (2H, m), 3.39 (2H, s), 3.78 (2H, d, J=0.4 Hz), 7.02-7.07 (1H, m), 7.10 (1H, dt, J=7.2, 1.2 Hz), 7.16 (1H, dt, J=7.6, 2.0 Hz), 7.21-7.28 (2H, m), 8.05 (1H, s).

Example 369

3-[4-[2-(3-Pyridyl)acetyl]piperidino]methyl-1H-pyrazin-2-one

The title compound (56 mg, 38% yield) was obtained in the same manner as Example 344 from 173 mg of 1-[1-(3-tert-butoxy-2-pyrazinylmethyl)piperidin-4-yl]-2-(3-pyridyl)ethanone.

1H-NMR (400 MHz, CDCl3); δ (ppm) 1.79-1.91 (2H, m), 1.92-2.00 (2H, m), 2.28-2.38 (2H, m), 2.51-2.60 (1H, m), 3.01-3.09 (2H, m), 3.78 (2H, s), 3.84 (2H, s), 7.25-7.30 (1H, m), 7.54 (1H, ddd, J=7.8, 2.4, 1.6 Hz), 7.82 (1H, br s), 7.84 (1H, br s), 8.44 (1H, d, J=2.4 Hz), 8.53 (1H, dd, J=4.8, 1.6 Hz).

Example 370

3-[4-Fluoro-4-[2-(2-fluorophenyl)acetyl]piperidino]methyl-1H-pyrazin-2-one

The title compound (157 mg, 91% yield) was obtained in the same manner as Example 365 from 200 mg of 1-[1-(3-tert-butoxy-2-pyrazinylmethyl)-4-fluoropiperidin-4-yl]-2-(2-fluorophenyl)ethanone.

1H-NMR (400 MHz, CDCl3); δ (ppm) 1.88-1.97 (2H, m), 2.09-2.28 (2H, m), 2.60 (2H, dt, J=12.0, 2.0 Hz), 2.93-3.00 (2H, m), 3.85 (2H, s), 4.00 (2H, dd, J=2.4, 1.2 Hz), 7.02-7.17 (3H, m), 7.23-7.29 (1H, m), 7.66 (1H, br s), 7.75 (1H, d, J=3.2 Hz).

Example 371

3-[4-[2-(2-Fluorophenyl)ethyl]-3-oxopiperidino]methyl-1H-pyrazin-2-one

The title compound (88 mg, 70% yield) was obtained in the same manner as Example 365 from 165 mg of 2-tert-butoxy-3-[4-[2-(2-fluorophenyl)ethyl]-3,3-dimethoxypiperidino]methyl-pyrazine.

1H-NMR (400 MHz, CDCl3); δ (ppm) 1.50-1.86 (2H, m), 2.15-2.34 (3H, m), 2.64-2.74 (3H, m), 3.02 (1H, d, J=13.6 Hz), 3.08-3.17 (1H, m), 3.41 (1H, dd, J=13.4, 1.6 Hz), 3.79 (1H, d, J=15.0 Hz), 3.85 (1H, d, J=15.0 Hz), 6.98 (1H, ddd, J=9.6, 7.6, 1.2 Hz), 7.04 (1H, td, J=7.6, 1.2 Hz), 7.12-7.21 (2H, m), 7.37-7.42 (1H, m), 7.59 (1H, d, J=3.6 Hz).

Example 372

3-[4-Fluoro-4-[2-[2-(trifluoromethyl)phenyl]acetyl]piperidino]methyl-1H-pyrazin-2-one The title compound (178 mg, 95% yield) was obtained in the same manner as Example 365 from 211 mg of 1-[1-(3-tert-butoxy-2-pyrazinylmethyl)-4-fluoropiperidin-4-yl]-2-[2-(trifluoromethyl)phenyl]ethanone.

1H-NMR (400 MHz, CDCl3); δ (ppm) 1.90-1.99 (2H, m), 2.08-2.28 (2H, m), 2.61 (2H, t, J=12.0 Hz), 2.94-3.01 (2H, m), 3.85 (2H, s), 4.19 (2H, s), 7.20 (1H, d, J=7.6 Hz), 7.39 (1H, t, J=7.6 Hz), 7.51 (1H, t, J=7.6 Hz), 7.61-7.68 (2H, m), 7.73-7.77 (1H, m).

Example 373

3-[4-Methyl-4-[2-[2-(trifluoromethyl)phenyl]acetyl]piperidino]methyl-1H-pyrazin-2-one The title compound (37 mg, 78% yield) was obtained in the same manner as Example 365 from 53 mg of 1-[1-(3-tert-butoxy-2-pyrazinylmethyl)-4-methylpiperidin-4-yl]-2-[2-(trifluoromethyl)phenyl]ethanone.

1H-NMR (400 MHz, CDCl3); δ (ppm) 1.31 (3H, s), 1.66-1.76 (2H, m), 2.19-2.29 (2H, m), 2.42-2.56 (2H, m), 2.74-2.84 (2H, m), 3.83 (2H, s), 4.02 (2H, s), 7.17 (1H, d, J=7.6 Hz), 7.38 (1H, t, J=7.6 Hz), 7.51 (1H, t, J=7.6 Hz), 7.66 (1H, d, J=7.6 Hz), 7.86 (2H, br s).

Example 374

3-[4-[3-(2-Fluorophenyl)-2-oxopropyl]piperidino]methyl-1H-pyrazin-2-one

The title compound (118 mg, 95% yield) was obtained in the same manner as Example 365 from 145 mg of 1-[1-(3-tert-butoxy-2-pyrazinylmethyl)piperidin-4-yl]-3-(2-fluorophenyl)propan-2-one.

1H-NMR (400 MHz, CDCl3); δ (ppm) 1.26-1.38 (2H, m), 1.72-1.80 (2H, m), 1.91-2.04 (1H, m), 2.26-2.74 (2H, m), 2.44 (2H, d, J=6.8 Hz), 2.92-2.98 (2H, m), 3.70 (2H, s), 3.82 (2H, s), 7.03-7.12 (2H, m), 7.16 (1H, dt, J=7.2, 2.0 Hz), 7.23-7.29 (1H, m), 7.89 (1H, d, J=2.8 Hz), 7.94 (1H, br s).

Example 375

3-[4-[3-(2-Fluorophenyl)propionyl]piperidino]methyl-1H-pyrazin-2-one

The title compound (88 mg, 83% yield) was obtained in the same manner as Example 365 from 124 mg of 1-[1-(3-tert-butoxy-2-pyrazinylmethyl)piperidin-4-yl]-3-(2-fluorophenyl)propan-1-one.

1H-NMR (400 MHz, CDCl3); δ (ppm) 1.70-1.82 (2H, m), 1.85-1.93 (2H, m), 2.24-2.42 (3H, m), 2.75-2.80 (2H, m), 2.92 (2H, t, J=7.6 Hz), 2.96-3.03 (2H, m), 3.81 (2H, s), 6.96-7.06 (2H, m), 7.14-7.20 (2H, m) 7.86 (2H, br s).

Example 376

3-[4-[2-[2-Fluoro-6-(trifluoromethyl)phenyl]acetyl]piperidino]methyl-1H-pyrazin-2-one The title compound (52 mg, 93% yield) was obtained in the same manner as Example 365 from 62 mg of 1-[1-(3-tert-butoxy-2-pyrazinylmethyl)piperidin-4-yl]-2-[2-fluoro-6-(trifluoromethyl)phenyl]ethanone.

1H-NMR (400 MHz, CDCl3); δ (ppm) 1.86-1.96 (2H, m), 1.98-2.08 (2H, m), 2.33-2.42 (2H, m), 2.56-2.65 (1H, m), 3.02-3.09 (2H, m), 3.85 (2H, s), 4.00 (2H, s), 7.23-7.29 (1H, m), 7.34-7.41 (1H, m), 7.46 (1H, d, J=8.0 Hz), 7.86 (2H, br s).

Example 377

3-[4-[2-(3-Methyl-2-thienyl)acetyl]piperidino]methyl-1H-pyrazin-2-one

The title compound (111 mg, 99% yield) was obtained in the same manner as Example 365 from 132 mg of 1-[1-(3-tert-butoxy-2-pyrazinylmethyl)piperidin-4-yl]-2-(3-methyl-2-thienyl)ethanone.

1H-NMR (400 MHz, CDCl3); δ (ppm) 1.78-1.94 (4H, m), 2.13 (3H, s), 2.28-2.35 (2H, m), 2.53-2.62 (1H, m), 2.98-3.06 (2H, m), 3.82 (2H, s), 3.83 (2H, s), 6.82 (1H, d, J=5.2 Hz), 7.11 (1H, d, J=5.2 Hz), 7.85 (2H, br s).

Example 378

3-[4-[2-[2-(3-Pyridyl)phenyl]acetyl]piperidino]methyl-1H-pyrazin-2-one

The title compound (150 mg, 58% yield) was obtained in the same manner as Example 365 from 315 mg of 1-[1-(3-tert-butoxy-2-pyrazinylmethyl)piperidin-4-yl]-2-[2-(3-pyridyl)phenyl]ethanone.

1H-NMR (400 MHz, CDCl3); δ(ppm) 1.58-1.74 (4H, m), 2.16-2.34 (3H, m), 2.88-2.98 (2H, m), 3.74 (2H, s), 3.79 (2H, s), 7.18-7.28 (2H, m), 7.32-7.42 (3H, m), 7.57 (1H, dt, J=8.0, 1.6 Hz), 7.85 (2H, br s), 8.50 (1H, d, J=2.0 Hz), 8.61 (1H, dd, J=4.8, 1.6 Hz).

Example 379

Methyl 2-[1-(3-oxo-3,4-dihydro-2-pyrazinylmethyl)piperidin-4-yl]methoxy-benzoate The title compound (172 mg, 86% yield) was obtained in the same manner as Example 365 from 230 mg of methyl 2-[1-(3-tert-butoxy-2-pyrazinylmethyl)piperidin-4-yl]methoxy-benzoate.

1H-NMR (400 MHz, CDCl3); δ (ppm) 1.52-1.65 (2H, m), 1.93-2.05 (3H, m), 2.31-2.40 (2H, m), 3.06-3.12 (2H, m), 3.88 (2H, s), 3.90 (3H, s), 3.92 (2H, d, J=6.0 Hz), 6.92-7.01 (2H, m), 7.42-7.48 (1H, m), 7.80 (1H, dd, J=7.6, 1.6 Hz), 7.87-7.94 (2H, m).

Example 380

3-[4-(2-Acetylphenoxymethyl)piperidino]methyl-1H-pyrazin-2-one

The title compound (99 mg, 85% yield) was obtained in the same manner as Example 365 from 134 mg of 1-[2-[1-(3-tert-butoxy-2-pyrazinylmethyl)piperidin-4-yl]methoxyphenyl]ethanone.

1H-NMR (400 MHz, CDCl3); δ (ppm) 1.52-1.64 (2H, m), 1.93-2.06 (3H, m), 2.31-2.40 (2H, m), 2.63 (3H, s), 3.06-3.15 (2H, m), 3.88 (2H, s), 3.94 (2H, d, J=6.0 Hz), 6.94 (1H, d, J=7.6 Hz), 6.98-7.03 (1H, m), 7.42-7.48 (1H, m), 7.72 (1H, dd, J=7.6, 1.6 Hz), 7.88 (2H, br s).

Example 381

2-[1-(3-Oxo-3,4-dihydro-2-pyrazinylmethyl)piperidin-4-yl]methoxy-benzamide

The title compound (80 mg, 54% yield) was obtained in the same manner as Example 365 from 171 mg of 2-[1-(3-tert-butoxy-2-pyrazinylmethyl)piperidin-4-yl]methoxy-benzamide.

1H-NMR (400 MHz, CDCl3); δ (ppm) 1.52-1.65 (2H, m), 1.88-2.06 (3H, m), 2.28-2.37 (2H, m), 3.08-3.15 (2H, m), 3.85 (2H, s), 4.02 (2H, d, J=6.4 Hz), 6.43 (1H, br s), 6.98 (1H, d, J=7.6 Hz), 7.06-7.12 (1H, m), 7.44-7.50 (1H, m), 7.70 (1H, br s), 7.73 (1H, br s), 7.77-7.82 (1H, m), 8.20 (1H, dd, J=8.0, 1.6 Hz).

Example 382

3-[4-(2-Nitrophenoxymethyl)piperidino]methyl-1H-pyrazin-2-one

The title compound (140 mg, 88% yield) was obtained in the same manner as Example 365 from 183 mg of 2-tert-butoxy-3-[4-(2-nitrophenoxymethyl)piperidino]methyl-pyrazine.

1H-NMR (400 MHz, CDCl3); δ (ppm) 1.45-1.57 (2H, m), 1.96-2.06 (3H, m), 2.29-2.38 (2H, m), 3.05-3.12 (2H, m), 3.87 (2H, s), 3.95 (2H, d, J=6.4 Hz), 7.01-7.08 (2H, m), 7.50-7.55 (1H, m), 7.84 (1H, dd, J=8.0, 1.6 Hz), 7.88 (2H, br s).

Example 383

N-[2-[1-(3-Oxo-3,4-dihydro-2-pyrazinylmethyl) piperidin-4-yl]methoxy-phenyl]methanesulfonamide The title compound (77 mg, 63% yield) was obtained in the same manner as Example 365 from 140 mg of N-[2-[1-(3-tert-butoxy-2-pyrazinylmethyl)piperidin-4-yl]methoxy-phenyl]methanesulfonamide.

1H-NMR (400 MHz, CDCl3); δ (ppm) 1.45-1.58 (2H, m), 1.89-2.04 (3H, m), 2.29-2.39 (2H, m), 2.96 (3H, s), 3.05-3.13 (2H, m), 3.88 (2-H, s), 3.90 (2H, d, J=6.4 Hz), 6.76 (1H, br s), 6.90 (1H, d, J=8.4 Hz), 6.96-7.01 (1H, m), 7.10-7.16 (1H, m), 7.54 (1H, dd, J=8.0, 1.6 Hz), 7.80-7.93 (2H, m).

Example 384

3-[4-[2-(Dimethylamino)phenoxymethyl]piperidino] methyl-1H-pyrazin-2-one

The title compound (172 mg, 97% yield) was obtained in the same manner as Example 365 from 205 mg of 2-tert-butoxy-3-[4-[2-(dimethylamino)phenoxymethyl]piperidino] methyl-pyrazine.

1H-NMR (400 MHz, CDCl3); δ (ppm) 1.51-1.65 (2H, m), 1.95-2.10 (3H, m), 2.30-2.39 (2H, m), 2.79 (6H, s), 3.04-3.10 (2H, m), 3.87 (2H, s), 3.88 (2H, d, J=6.0 Hz), 6.81-6.96 (4H, m), 7.88-7.96 (2H, m).

Example 385

3-[2-[1-(3-Oxo-3,4-dihydro-2-pyrazinylmethyl)piperidin-4-yl]methoxy-phenyl]-1-methylthiourea The title compound (47 mg, 71% yield) was obtained in the same manner as Example 365 from 76 mg of 3-[2-[1-(3-tert-butoxy-2-pyrazinylmethyl)piperidin-4-yl]methoxy-phenyl]-1-methylthiourea.

1H-NMR (400 MHz, CDCl3); δ (ppm) 1.41-1.54 (2H, m), 1.92-2.02 (3H, m), 2.30-2.38 (2H, m), 3.03-3.10 (2H, m), 3.14 (3H, d, J=4.0 Hz), 3.84 (2H, d, J=6.4 Hz), 3.87 (2H, s), 6.10-6.28 (1H, m), 6.92-7.01 (2H, m), 7.19-7.38 (2H, m), 7.46 (1H, br s), 7.89 (2H, br s).

Example 386

3-[2-[1-(3-Oxo-3,4-dihydro-2-pyrazinylmethyl)piperidin-4-yl]methoxy-phenyl]-1-methylurea The title compound (181 mg, 62% yield) was obtained in the same manner as Example 365 from 337 mg of 3-[2-[1-(3-tert-butoxy-2-pyrazinylmethyl)piperidin-4-yl]methoxy-phenyl]-1-methylurea.

1H-NMR (400 MHz, CDCl3); δ (ppm) 1.71-1.99 (5H, m), 2.30-2.40 (2H, m), 2.86 (3H, d, J=4.8 Hz), 3.07-3.14 (2H, m), 3.86 (2H, s), 3.91 (2H, d, J=4.2 Hz), 5.57 (1H, br s), 6.78-6.84 (1H, m), 6.86-6.98 (3H, m), 7.64-7.82 (2H, m), 8.00-8.06 (1H, m).

Example 387

3-[4-[2-(4-Fluoro-3-thienyl)acetyl]piperidino]methyl-1H-pyrazin-2-one

The title compound (219 mg, 97% yield) was obtained in the same manner as Example 365 from 262 mg of 1-[1-(3-tert-butoxy-2-pyrazinylmethyl)piperidin-4-yl]-2-(4-fluoro-3-thienyl)ethanone.

1H-NMR (400 MHz, CDCl3); δ (ppm) 1.78-1.90 (2H, m), 1.91-1.99 (2H, m), 2.28-2.37 (2H, m), 2.50-2.58 (1H, m), 2.98-3.08 (2H, m), 3.68 (2H, d, J=0.4 Hz), 3.83 (2H, s), 6.71 (1H, d, J=3.2 Hz), 7.02-7.06 (1H, m), 7.78-7.86 (2H, m).

Example 388

3-[4-(2-Fluorophenoxymethyl)azepan-1-yl]methyl-1H-pyrazin-2-one

The title compound (63 mg, 68% yield) was obtained in the same manner as Example 118 from 109 mg of 2-tert-butoxy-3-[4-(2-fluorophenoxymethyl)azepan-1-yl]methyl-pyrazine.

1H-NMR (400 MHz, CDCl3); δ(ppm) 1.47-2.24 (7H, m), 2.79-3.00 (4H, m), 3.81-3.89 (2H, m), 3.97 (2H, s), 6.87-7.10 (4H, m), 7.89 (1H, d, J=2.8 Hz), 7.95 (1H, d, J=2.8 Hz).

Example 389

3-[4-[2-(4-Fluorophenyl)acetyl]piperidino]methyl-1H-pyrazin-2-one

The title compound (131 mg, 76% yield) was obtained in the same manner as Example 344 from 201 mg of 1-[1-(3-tert-butoxy-2-pyrazinylmethyl)piperidin-4-yl]-2-(4-fluorophenyl)ethanone.

1H-NMR (400 MHz, CDCl3); δ (ppm) 1.76-1.95 (4H, m), 2.26-2.36 (2H, m), 2.48-2.57 (1H, m), 2.97-3.05 (2H, m), 3.72 (2H, s), 3.82 (2H, s), 6.98-7.04 (2H, m), 7.10-7.16 (2H, m), 7.86 (2H, br s).

Example 390

3-[4-(2-Fluorophenoxymethyl)piperidino]methyl-5-methyl-1H-pyrazin-2-one

The title compound (70 mg, 56% yield) was obtained in the same manner as Example 364 from 130 mg of 3-[4-(2-fluorophenoxymethyl)piperidino]methyl-2-methoxy-5-methylpyrazine.

1H-NMR (400 MHz, CDCl3); δ (ppm) 1.44-1.58 (2H, m), 1.91-2.03 (3H, m), 2.28-2.37 (2H, m), 2.41 (3H, s), 3.01-3.08 (2H, m), 3.84 (2H, s), 3.88 (2H, d, J=6.0 Hz), 6.85-6.97 (2H, m), 7.00-7.10 (2H, m), 7.86 (1H, s).

Example 391

3-[4-[2-(2-Fluorophenyl)acetyl]piperidino]methyl-5-methyl-1H-pyrazin-2-one

The title compound (81 mg, 55% yield) was obtained in the same manner as Example 364 from 152 mg of 2-(2-fluorophenyl)-1-[1-(3-methoxy-6-methyl-2-pyrazinylmethyl)piperidin-4-yl]ethanone.

1H-NMR (400 MHz, CDCl3); δ (ppm) 1.78-1.90 (2H, m), 1.93-2.00 (2H, m), 2.28-2.38 (2H, m), 2.40 (3H, s), 2.52-2.61 (1H, m), 2.97-3.04 (2H, m), 3.78 (2H, s), 3.81 (2H, s), 6.92-7.12 (2H, m), 7.16 (1H, dt, J=7.6, 2.0 Hz), 7.22-7.28 (1H, m), 7.84 (1H, s).

Example 392

5-Fluoro-3-[4-(2-fluorophenoxymethyl)piperidino]methyl-1H-pyrazin-2-one

The title compound (52 mg, 58% yield) was obtained in the same manner as Example 364 from 93 mg of 5-fluoro-3-[4-(2-fluorophenoxymethyl)piperidino]methyl-2-methoxypyrazine.

1H-NMR (400 MHz, CDCl3); δ (ppm) 1.46-1.59 (2H, m), 1.92-2.04 (3H, m), 2.32-2.41 (2H, m), 3.01-3.08 (2H, m), 3.82 (2H, s), 3.89 (2H, d, J=6.0 Hz), 6.86-6.97 (2H, m), 7.01-7.10 (2H, m), 7.88 (1H, d, J=8.0 Hz).

Example 393

5-Fluoro-3-[4-[2-(2-fluorophenyl)acetyl]piperidino]methyl-1H-pyrazin-2-one

The title compound (76 mg, 83% yield) was obtained in the same manner as Example 364 from 95 mg of 1-[1-(6-fluoro-3-methoxy-2-pyrazinyl)methylpiperidin-4-yl]-2-(2-fluorophenyl)ethanone.

1H-NMR (400 MHz, CDCl3); δ (ppm) 1.79-1.92 (2H, m), 1.94-2.03 (2H, m), 2.32-2.42 (2H, m), 2.54-2.64 (1H, m), 2.96-3.04 (2H, m), 3.79 (2H, s), 3.80 (2H, s), 7.02-7.13 (2H, m), 7.16 (1H, dt, J=7.6, 1.6 Hz), 7.22-7.30 (1H, m), 7.89 (1H, d, J=8.0 Hz).

Example 394

3-[1-[4-[2-[2-(Trifluoromethyl)phenyl]acetyl]piperidino]ethyl]-1H-pyrazin-2-one oxalate After dissolving 117 mg of 1-[1-[1-(3-methoxy-2-pyrazinyl)ethyl]piperidin-4-yl]-2-[2-(trifluoromethyl)phenyl]ethanone in 3 ml of 5N hydrochloric acid, the mixture was heated to reflux for 3 hours. Aqueous sodium carbonate solution was added to the reaction solution to render it alkaline, and extraction was performed with dichloromethane. The extract was dried over anhydrous magnesium sulfate and the solvent was distilled off under reduced pressure. The residue was purified by NH silica gel column chromatography (solvent: ethyl acetate/methanol).

The obtained product was dissolved in ethanol, and then 26 mg of oxalic acid anhydrous was added. Diethyl ether was added and the precipitate was filtered out to obtain the title compound (100 mg, 71% yield).

1H-NMR (400 MHz, DMSO-d6); δ (ppm) 1.43 (3H, d, J=6.8 Hz), 1.62-1.82 (2H, m), 1.95-2.06 (2H, m), 2.70-2.80 (1H, m), 2.82-2.94 (2H, m), 3.25-3.34 (1H, m), 3.36-3.48 (1H, m), 4.10 (2H, s), 4.70 (1H, q, J=6.8 Hz), 7.35 (1H, d, J=7.6 Hz), 7.41 (1H, d, J=4.0 Hz), 7.46 (1H, t, J=7.6 Hz), 7.52 (1H, d, J=4.0 Hz) 7.61 (1H, t, J=7.6 Hz), 7.68 (1H, d, J=7.6 Hz).

Example 395

3-[1-[4-(2-Fluorophenoxymethyl)piperidino]ethyl]-1H-pyrazin-2-one oxalate

3-[1-[4-(2-Fluorophenoxymethyl)piperidino]ethyl]-1H-pyrazin-2-one was obtained in the same manner as Example 364 from 100 mg of 2-[1-[4-(2-fluorophenoxymethyl)piperidino]ethyl]-3-methoxypyrazine, and was then converted to an oxalate by an ordinary method to obtain the title compound (20 mg, 63% yield).

1H-NMR (400 MHz, CDCl3); δ (ppm) 1.48 (3H, d, J=6.8 Hz), 1.50-1.76 (3H, m), 1.88-2.10 (3H, m), 2.95-3.09 (2H, m), 3.46-3.66 (1H, m), 3.94 (2H, d, J=5.2 Hz), 4.71-4.80 (1H, m), 6.89-6.96 (1H, m), 7.08-7.23 (3H, m), 7.43 (1H, d, J=4.0 Hz), 7.56 (1H, d, J=4.0 Hz)

Example 396

3-[3-[2-(2-Fluorophenyl)ethyl]-4-oxopiperidino]methyl-1H-pyrazin-2-one oxalate 3-[3-[2-(2-fluorophenyl)ethyl]-4-oxopiperidino]methyl-1H-pyrazin-2-one was obtained in the same manner as Example 365 from 207 mg of 1-(3-tert-butoxy-2-pyrazinylmethyl)-3-[2-(2-fluorophenyl)ethyl]piperidin-4-one, and was then converted to an oxalate by an ordinary method to obtain the title compound (130 mg, 57% yield).

1H-NMR (400 MHz, CDCl3); δ (ppm) 1.34-1.46 (1H, m), 1.90-2.02 (1H, m), 2.24-2.32 (1H, m), 2.54-2.60 (5H, m), 2.80-2.89 (1H, m), 3.24-3.32 (1H, m), 3.34-3.42 (1H, m), 3.85 (1H, d, J=14.8 Hz), 3.90 (1H, d, J=14.8 Hz), 7.07-7.15 (2H, m), 7.19-7.29 (2H, m), 7.31 (1H, d, J=4.0 Hz), 7.40 (1H, d, J=4.0 Hz).

Example 397

N-[2-[1-(3-Oxo-3,4-dihydro-2-pyrazinylmethyl)piperidin-4-yl]methoxy-phenyl]acetamide oxalate N-[2-[1-(3-Oxo-3,4-dihydro-2-pyrazinylmethyl)piperidin-4-yl]methoxy-phenyl]acetamide was obtained in the same manner as Example 365 from 130 mg of N-[2-[1-(3-tert-butoxy-2-pyrazinylmethyl)piperidin-4-yl]methoxy-phenyl]acetamide, and was then converted to an oxalate by an ordinary method to obtain the title compound (112 mg, 78% yield).

1H-NMR (400 MHz, DMSO-d6); δ (ppm) 1.54-1.66 (2H, m), 1.94-2.12 (6H, m), 2.92-3.04 (2H, m), 3.40-3.52 (2H, m), 3.90 (2H, d, J=6.0 Hz), 4.23 (2H, s), 6.88-6.94 (1H, m), 7.00-7.10 (2H, m), 7.39 (1H, d, J=4.0 Hz), 7.52 (1H, d, J=4.0 Hz), 7.81 (1H, d, J=7.6 Hz), 8.92 (1H, s).

Example 398

3-[4-(2-Fluorobenzylsulfinyl)piperidino]methyl-1H-pyrazin-2-one

After dissolving 57 mg of 3-[4-(2-fluorobenzylthio)piperidino]methyl-1H-pyrazin-2-one in 3 ml of dichloromethane, 31 mg of 3-chloroperbenzoic acid was added at below −70° C., the mixture was stirred for 30 minutes, and then an additional 5 mg of 3-chloroperbenzoic acid was added and the stirring was continued for 20 minutes. Aqueous sodium thiosulfate solution was added to the reaction solution and extraction was performed with dichloromethane. The organic layer was washed with saturated brine and dried over anhydrous magnesium sulfate, and then the solvent was distilled off under reduced pressure. The residue was purified by silica gel column chromatography (solvent: chloroform/methanol/ammonia water) to obtain the title compound (16 mg, 27% yield).

1H-NMR (400 MHz, CDCl3); δ (ppm) 1.95-2.04 (2H, m), 2.32-2.45 (2H, m), 2.63-2.73 (1H, m), 3.14-3.22 (2H, m), 3.45-3.52 (2H, m), 3.81 (2H, s), 4.63 (2H, s), 7.04 (1H, ddd, J=9.8, 8.0, 1.2 Hz), 7.13 (1H, td, J=8.0, 1.2 Hz), 7.22-7.29 (1H, m), 7.36 (1H, td, J=8.0, 2.0 Hz), 7.81 (1H, d, J=2.4 Hz), 8.16 (1H, d, J=2.4 Hz).

Example 399

2-(2-Fluorophenyl)-1-[1-[(4-hydroxy-[1,2,5]thiadiazol-3-yl)methyl]piperidin-4-yl]ethanone After dissolving 682 mg of 3-hydroxy-4-hydroxymethyl-[1,2,5]thiadiazole in 40 ml of tetrahydrofuran, 6.8 g of manganese dioxide was added and the mixture was stirred overnight at room temperature. The reaction mixture was filtered and the filtrate was distilled off under reduced pressure. The residue was dissolved in tetrahydrofuran and the solution was filtered with celite. The filtrate was then distilled off under reduced pressure. The residue was suspended in 10 ml of tetrahydrofuran, 486 mg of 2-(2-fluorophenyl)-1-(piperidin-4-yl)ethanone and 513 mg of sodium triacetoxyborohydride were added and the mixture was stirred for 2 hours. The reaction mixture was concentrated under reduced pressure, water and diluted hydrochloric acid were added to the residue for adjustment to pH 4, and extraction was performed with chloroform. The extract was dried over anhydrous magnesium sulfate, and then the solvent was distilled off under reduced pressure. The residue was purified by silica gel column chromatography (solvent: chloroform/methanol). Diethyl ether was added and the mixture was filtered to obtain the title compound (179 mg, 10% yield).

1H-NMR (400 MHz, CDCl3); δ (ppm) 1.80-1.92 (2H, m), 1.96-2.04 (2H, m), 2.31-2.41 (2H, m), 2.55-2.64 (1H, m), 2.94-3.02 (2H, m), 3.79 (2H, d, J=1.2 Hz), 3.88 (2H, s), 7.02-7.13 (2H, m), 7.16 (1H, dt, J=7.2, 2.0 Hz), 7.23-7.24 (1H, m).

Example 400

6-Fluoro-3-[4-[2-(2-fluorophenyl)acetyl]piperidino]methyl-1H-pyrazin-2-one

After dissolving 122 mg of 1-[1-[(3-tert-butoxy-5-fluoro-2-pyrazinylmethyl)piperidin-4-yl]-2-(2-fluorophenyl)ethanone in 3 ml of trifluoroacetic acid, the mixture was stirred for 1.5 hours at room temperature. The reaction solution was cooled on ice, the pH was adjusted to 7 with a 5% sodium hydroxide solution, and extraction was performed with dichloromethane. The extract was dried over anhydrous magnesium sulfate, and then the solvent was distilled off under reduced pressure. Diethyl ether was added to the residue and the mixture was filtered to obtain the title compound (97 mg, 93% yield).

1H-NMR (400 MHz, CDCl3); δ (ppm) 1.85-1.97 (2H, m), 1.99-2.07 (2H, m), 2.42-2.54 (2H, m), 2.59-2.68 (1H, m), 2.94-3.12 (2H, m), 3.79 (2H, s), 3.89 (2H, d, J=1.2 Hz), 7.02-7.13 (2H, m), 7.16 (1H, dt, J=7.6, 1.6 Hz), 7.23-7.30 (1H, m), 7.72 (1H, d, J=8.4 Hz).

Example 401

3-[4-[2-(2-Fluorophenyl)acetyl]piperidino]methyl-6-methyl-1H-pyrazin-2-one

After dissolving 352 mg of 1-[(1-(3-methoxy-5-methyl-2-pyrazinylmethyl)piperidin-4-yl]-2-(2-fluorophenyl)ethanone in 3 ml of dichloromethane, 0.5 ml of iodotrimethylsilane was added and the mixture was stirred for 45 minutes at room temperature. Next, 2 ml of iodotrimethylsilane was added and the mixture was further stirred for 2 hours at room temperature. Water was added to the reaction solution, the mixture was rendered alkaline with sodium carbonate, and extraction was performed with dichloromethane. The extract was dried over anhydrous magnesium sulfate and then the solvent was distilled off under reduced pressure. The residue was purified by NH silica gel column chromatography (solvent: ethyl acetate/methanol). Diethyl ether was added and the mixture was filtered to obtain the title compound (92 mg, 27% yield).

1H-NMR (400 MHz, CDCl3); δ (ppm) 1.78-1.90 (2H, m), 1.91-1.98 (2H, m), 2.25-2.34 (2H, m), 2.38 (3H, s), 2.50-2.59 (1H, m), 2.98-3.06 (2H, m), 3.78 (4H, s), 7.01-7.12 (2H, m), 7.15 (1H, dt, J=7.6, 2.0 Hz), 7.22-7.28 (1H, m), 7.69 (1H, br s).

Example 402

3-[4-(2-Fluorophenoxymethyl)piperidino]methyl-1-methyl-1H-pyrazin-2-one

The title compound (28 mg, 42% yield) was obtained in the same manner as Production Example 63 from 62 mg of 3-[4-(2-fluorophenoxymethyl)piperidino]methyl-1H-pyrazin-2-one.

1H-NMR (400 MHz, CDCl3); δ (ppm) 1.46-1.59 (2H, m), 1.81-1.95 (3H, m), 2.12-2.21 (2H, m), 3.08-3.15 (2H, m), 3.52 (3H, s), 3.71 (2H, s), 3.85 (2H, d, J=6.4 Hz), 6.82-6.89 (1H, m), 6.90-6.96 (1H, m), 6.99-7.08 (3H, m), 7.30 (1H, d, J=4.4 Hz).

Example 403

3-[4-[2-(2-Fluorophenyl)acetyl]piperidino]methyl-1-methyl-1H-pyrazin-2-one

After dissolving 300 mg of 3-[4-[2-(2-fluorophenyl)acetyl]piperidino]methyl-1-1H-pyrazin-2-one in 5 ml of N,N-dimethylformamide, 113 mg of potassium tert-butoxide was added, the mixture was stirred for 30 minutes while cooling on ice, 0.063 ml of methyl iodide was added and the stirring was continued for 1 hour. Ice water was added to the reaction solution and extraction was performed with ethyl acetate. The organic layer was washed with water and saturated brine in that order and dried over anhydrous magnesium sulfate, and then the solvent was distilled off under reduced pressure. The residue was purified by silica gel column chromatography (solvent: ethyl acetate/methanol). Diisopropyl ether was added and the mixture was filtered to obtain the title compound (61 mg, 20% yield).

1H-NMR (400 MHz, CDCl3); δ (ppm) 1.79-1.92 (4H, m), 2.13-2.24 (2H, m), 2.42-2.51 (1H, m), 3.08-3.14 (2H, m), 3.52 (3H, s), 3.70 (2H, s), 3.77 (2H, s), 7.00-7.10 (3H, m), 7.14 (1H, dt, J=7.6, 1.6 Hz), 7.20-7.27 (1H, m), 7.29 (1H, d, J=4.4 Hz).

Example 404

3-[4-(1,3-Dihydroisobenzofuran-1-carbonyl)piperidino]methyl-1H-pyrazin-2-one

After dissolving 517 mg of (1-benzylpiperidin-4-yl)-(1,3-dihydroisobenzofuran-1-yl)methanone in 5 ml of 1,2-dichloroethane, 0.49 ml of 1-chloroethyl chloroformate was added and the mixture was heated to reflux for 1 hour. The reaction solution was distilled off under reduced pressure, 5 ml of methanol was added to the residue and heating to reflux was continued for 1 hour. The reaction solution was distilled off under reduced pressure, saturated aqueous sodium bicarbonate solution was added and extraction was performed with ethyl acetate. The extract was dried over anhydrous magnesium sulfate and then the solvent was distilled off under reduced pressure to obtain 104 mg of (1,3-dihydroisobenzofuran-1-yl)-(piperidin-4-yl)methanone hydrochloride.

After then dissolving 93 mg of the (1,3-dihydroisobenzofuran-1-yl)-(piperidin-4-yl)methanone hydrochloride in 3 ml of tetrahydrofuran, 89 mg of 3-tert-butoxypyrazine-2-carboxaldehyde, 130 mg of sodium triacetoxyborohydride and 0.03 ml of acetic acid were added while stirring, and the stirring was continued overnight at room temperature. A 2N sodium hydroxide solution was added to the reaction mixture and extraction was performed with ethyl acetate. The extract was dried over anhydrous magnesium sulfate and then the solvent was distilled off under reduced pressure. The residue was purified by silica gel column chromatography (solvent: n-hexane/ethyl acetate).

After dissolving the product in 1 ml of ethanol, 1 ml of 4N hydrogen chloride/ethyl acetate was added and the mixture was stirred for 30 minutes at room temperature. The reaction solution was concentrated under reduced pressure, a 2N sodium hydroxide solution was added and extraction was performed with ethyl acetate. The extract was dried over anhydrous magnesium sulfate and then the solvent was distilled off under reduced pressure. Diethyl ether was added to the residue and the insoluble portion was filtered out to obtain the title compound (8 mg, 1% yield).

1H-NMR (400 MHz, CDCl3); δ(ppm) 1.47-2.40 (6H, m), 2.89-3.07 (3H, m), 3.81 (2H, s), 5.24-5.34 (2H, m), 5.54-5.57 (1H, m), 7.19-7.36 (4H, m), 7.86 (2H, s).

Example 405

5-[4-(2-Fluorophenoxymethyl)piperidino]methyl-2,4-dihydro-[1,2,4]triazol-3-one

After adding 150 mg of 5-chloromethyl-2,4-dihydro-[1,2,4]triazol-3-one, 331 mg of 4-(2-fluorophenoxymethyl)piperidine hydrochloride and 180 mg of anhydrous potassium carbonate to acetonitrile, the mixture was stirred overnight at room temperature. Water and ethyl acetate were added to the reaction mixture and the insoluble portion was filtered out to obtain the title compound (70 mg, 21% yield).

1H-NMR (400 MHz, DMSO-d6); δ (ppm) 1.26-1.38 (2H, m), 1.67-1.80 (3H, m), 1.95-2.04 (2H, m), 2.77-2.84 (2H, m), 3.24 (2H, s), 3.88 (2H, d, J=5.6 Hz), 6.87-6.94 (1H, m), 7.06-7.21 (3H, m), 11.19 (1H, s), 11.27 (1H, br s).

Example 406

3-[4-(2-Fluorophenoxymethyl)-4-methylpiperidino]methyl-1H-pyrazin-2-one

The title compound (66 mg, 81% yield) was obtained in the same manner as Example 118 from 96 mg of 2-tert-butoxy-3-[4-(2-fluorophenoxymethyl)-4-methylpiperidino]methyl-pyrazine.

1H-NMR (400 MHz, CDCl3); δ(ppm) 1.17 (3H, s), 1.64 (2H, dt, J=14.4, 4.2 Hz), 1.83 (2H, ddd, J=13.6, 9.6, 4.0 Hz), 2.59-2.68 (2H, m), 2.74-2.82 (2H, m), 3.78 (2H, s), 3.89 (2H, s), 6.87-6.95 (1H, m), 6.96 (1H, td, J=8.4, 1.6 Hz), 7.01-7.10 (2H, m), 7.87-7.96 (2H, m).

Example 407

3-[8-(2-Fluorophenyl)-7-oxo-3-azabicyclo[4.3.0]non-3-yl]methyl-1H-pyrazin-2-one

After adding 191 mg of 3-benzyloxycarbonyl-7-oxo-3-azabicyclo[4.3.0]nonane, 16 mg of palladium acetate and 104 mg of BINAP (2,2'-bis(diphenylphosphino)-1,1'-binaphthyl) to 3 ml of toluene under a nitrogen atmosphere, the mixture was stirred for 15 minutes, and then 245 mg of o-bromofluorobenzene, 134 mg of sodium tert-butoxide and 6 ml of toluene were added and the mixture was stirred overnight at 100° C. Saturated aqueous ammonium chloride solution was added to the reaction solution and extraction was performed with ethyl acetate. The extract was dried over anhydrous magnesium sulfate and the solvent was distilled off under reduced pressure. The residue was purified by NH silica gel column chromatography (solvent: n-hexane/ethyl acetate) to obtain 133 mg of 3-benzyloxycarbonyl-8-(2-fluorophenyl)-7-oxo-3-azabicyclo[4.3.0]nonane.

After then dissolving 50 mg of the 3-benzyloxycarbonyl-8-(2-fluorophenyl)-7-oxo-3-azabicyclo[4.3.0]nonane in 30 ml of methanol, 100 mg of 10% palladium-carbon was added and the mixture was stirred for 4 days at room temperature under a hydrogen atmosphere (1 atm). The reaction mixture was filtered and the filtrate was distilled off under reduced pressure to obtain 62 mg of 8-(2-fluorophenyl)-7-oxo-3-azabicyclo[4.3.0]nonane.

3-(3-tert-Butoxy-2-pyrazinylmethyl)-8-(2-fluorophenyl)-7-oxo-3-azabicyclo[4.3.0]nonane was obtained in the same manner as Example 320 from 60 mg of 3-tert-butoxypyrazine-2-carboxaldehyde and 60 mg of 8-(2-fluorophenyl)-7-oxo-3-azabicyclo[4.3.0]nonane.

This was subjected to the same process as in Example 118 to obtain the title compound (43 mg, 49% yield).

1H-NMR (400 MHz, CDCl3); δ(ppm) 1.90-2.11 (2H, m), 2.13-2.60 (3H, m), 2.64-2.74 (1H, m), 2.80-2.94 (2H, m), 3.09 (1H, q, J=5.6 Hz), 3.57 (1H, t, J=10.2 Hz), 3.72-3.85 (3H, m), 7.00-7.15 (3H, m), 7.20-7.29 (1H, m), 7.61-7.71 (1H, m), 7.71-7.81 (1H, m).

Example 408

5-[4-[2-(2-Fluorophenyl)acetyl]piperidino]methyl-2,4-dihydro-[1,2,4]triazol-3-one

After adding 150 mg of 5-chloromethyl-2,4-dihydro-[1,2,4]triazol-3-one, 335 mg of 2-(2-fluorophenyl)-1-(piperidin-4-yl)ethanone hydrochloride and 180 mg of anhydrous potassium carbonate to acetonitrile, the mixture was stirred overnight at room temperature. Water was added to the reaction mixture and extraction was performed with ethyl acetate. The organic layer was washed with water and saturated brine and dried over anhydrous magnesium sulfate, and then the solvent was distilled off under reduced pressure. Diethyl ether was added to the residue and the mixture was filtered to obtain the title compound (23 mg, 7% yield).

1H-NMR (400 MHz, DMSO-d6); δ (ppm) 1.42-1.56 (2H, m), 1.79-1.87 (2H, m), 1.98-2.07 (2H, m), 2.45-2.55 (1H, m), 2.75-2.82 (2H, m), 3.25 (2H, s), 3.89 (2H, s), 7.09-7.16 (2H, m), 7.19-7.32 (2H, m), 11.20 (1H, s), 11.26 (1H, br s).

Example 409

3-[4-[2-(2-Fluoro-3-thienyl)acetyl]piperidino]methyl-1H-pyrazin-2-one

The title compound (103 mg, 100% yield) was obtained in the same manner as Example 365 from 114 mg of 1-[1-(3-tert-butoxy-2-pyrazinylmethyl)piperidin-4-yl]-2-(2-fluoro-3-thienyl)ethanone.

1H-NMR (400 MHz, CDCl3); δ (ppm) 1.77-1.88 (2H, m), 1.90-1.98 (2H, m), 2.28-2.37 (2H, m), 2.49-2.58 (1H, m), 2.99-3.07 (2H, m), 3.66 (2H, s), 3.83 (2H, s), 6.60-6.66 (2H, m), 7.87 (2H, br s).

Example 410

3-[4-[2-(2,3-Dihydrobenzofuran-7-yl)acetyl]piperidino]methyl-1H-pyrazin-2-one

The title compound (69 mg, 75% yield) was obtained in the same manner as Example 118 from 107 mg of 1-[1-(3-tert-butoxy-2-pyrazinylmethyl)piperidin-4-yl]-2-(2,3-dihydrobenzofuran-7-yl)ethanone.

1H-NMR (400 MHz, CDCl3); δ (ppm) 1.77-1.99 (4H, m), 2.27-2.37 (2H, m), 2.52-2.61 (1H, m), 2.95-3.05 (2H, m), 3.23 (2H, t, J=8.8 Hz), 3.70 (2H, s), 3.83 (2H, s), 4.54 (2H, t, J=8.8 Hz), 6.81 (1H, t, J=7.4 Hz), 6.92 (1H, d, J=7.4 Hz), 7.10 (1H, dd, J=7.4, 1.2 Hz), 7.90 (1H, br s), 7.92 (1H, br s).

Example 411

3-[4-(2-Fluorobenzylthio)piperidino]methyl-1H-pyrazin-2-one

The title compound (180 mg, 94% yield) was obtained in the same manner as Example 118 from 224 mg of 2-tert-butoxy-3-[4-(2-fluorobenzylthio)piperidino]methyl-pyrazine.

1H-NMR (400 MHz, CDCl3); δ (ppm) 1.69-1.80 (2H, m), 1.99-2.08 (2H, m), 2.31-2.43 (2H, m), 2.65-2.76 (1H, m), 2.91-3.00 (2H, m), 3.78 (2H, s), 3.82 (2H, s), 7.03 (1H, ddd, J=9.8, 8.0, 1.2 Hz), 7.10 (1H, td, J=8.0, 1.2 Hz), 7.18-7.26 (1H, m), 7.34 (1H, td, J=8.0, 2.0 Hz), 7.88 (1H, br s), 7.90 (1H, br s).

Example 412

(E)-3-[4-[2-[2-(Cyclohexylmethyloxy)phenyl]vinyl]piperidino]methyl-1H-pyrazin-2-one oxalate The title compound (207 mg, 68% yield) was obtained in the same manner as Example 132 from 255 mg of (E)-3-[4-[2-[2-(cyclohexylmethyloxy)phenyl]vinyl]piperidino]methyl-2-methoxypyrazine.

1H-NMR (400 MHz, CDCl3); δ(ppm) 1.03-1.61 (5H, m), 1.62-2.04 (10H, m), 2.34-2.46 (1H, m), 2.96-3.10 (2H, m), 3.42-3.52 (2H, m), 3.80 (2H, d, J=6.0 Hz), 4.25 (2H, br s), 6.26 (1H, dd, J=16.0, 6.8 Hz), 6.66 (1H, d, J=16.0 Hz), 6.89 (1H, t, J=7.2 Hz), 6.96 (1H, d, J=7.2 Hz), 7.19 (1H, dt, J=7.2, 1.6 Hz), 7.40 (1H, d, J=4.0 Hz), 7.44 (1H, dd, J=7.2, 1.6 Hz), 7.53 (1H, d, J=4.0 Hz).

Example 413

3-[4-(2-Fluorobenzylsulfonyl)piperidino]methyl-1H-pyrazin-2-one

The title compound (125 mg, 86% yield) was obtained in the same manner as Example 118 from 168 mg of 2-tert-butoxy-3-[4-(2-fluorobenzylsulfonyl)piperidino]methyl-pyrazine.

1H-NMR (400 MHz, CDCl3); δ (ppm) 1.98-2.30 (6H, m), 2.79-2.88 (1H, m), 3.15-3.23 (2H, m), 3.81 (2H, s), 4.30 (2H, s), 7.14 (1H, ddd, J=9.8, 8.0, 1.2 Hz), 7.22 (1H, td, J=8.0, 1.2 Hz), 7.37-7.44 (1H, m), 7.53 (1H, td, J=8.0, 2.0 Hz), 7.68 (1H, br s), 7.76 (1H, br s).

Example 414 trans-3-[4-[2-(2-Fluorophenyl)acetyl]-2-methylpiperidino]methyl-1H-pyrazin-2-one The title compound (126 mg, 68% yield) was obtained in the same manner as Example 365 from 228 mg of trans-1-[1-(3-tert-butoxy-2-pyrazinylmethyl)-2-methylpiperidin-4-yl]-2-(2-fluorophenyl)ethanone.

1H-NMR (400 MHz, CDCl3); δ(ppm) 1.15 (3H, d, J=6.8 Hz), 1.74-1.82 (1H, m), 1.87-1.98 (2H, m), 2.00-2.09 (1H, m), 2.62-2.69 (1H, m), 2.70-2.88 (2H, m), 3.08-3.20 (1H, m), 3.78 (2H, s), 3.83 (1H, d, J=14.2 Hz), 4.00 (1H, d, J=14.2 Hz), 7.02-7.13 (2H, m), 7.16 (1H, dt, J=7.6, 2.0 Hz), 7.22-7.29 (1H, m), 7.89 (1H, d, J=2.4 Hz), 7.93 (1H, br s).

Example 415 cis-3-[4-[2-(2-Fluorophenyl)acetyl]-2-methylpiperidino]methyl-1H-pyrazin-2-one

The title compound (36 mg, 95% yield) was obtained in the same manner as Example 365 from 46 mg of cis-1-[1-(3-tert-butoxy-2-pyrazinylmethyl)-2-methylpiperidin-4-yl]-2-(2-fluorophenyl)ethanone.

1H-NMR (400 MHz, CDCl3); δ(ppm) 1.25 (3H, d, J=6.0 Hz), 1.55-1.66 (1H, m), 1.72-1.84 (1H, m), 1.89-1.98 (2H, m), 2.31-2.40 (1H, m), 2.48-2.57 (1H, m), 2.59-2.68 (1H, m), 3.03-3.10 (1H, m), 3.59 (1H, d, J=16.0 Hz), 3.78 (2H, s), 4.32 (1H, d, J=16.0 Hz), 7.02-7.13 (2H, m), 7.15 (1H, dt, J=7.2, 2.0 Hz), 7.22-7.29 (1H, m), 7.85-7.95 (2H, m).

The structural formulas for the compounds obtained in the above Production Examples and Examples are shown below.

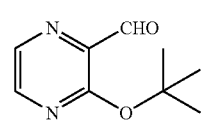

Production Example 1

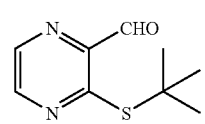

Production Example 2

-continued

Production Example 3

Production Example 4

Production Example 5

Production Example 6

Production Example 7

Production Example 8

Production Example 9

Production Example 10

Production Example 11

Production Example 12

Production Example 13

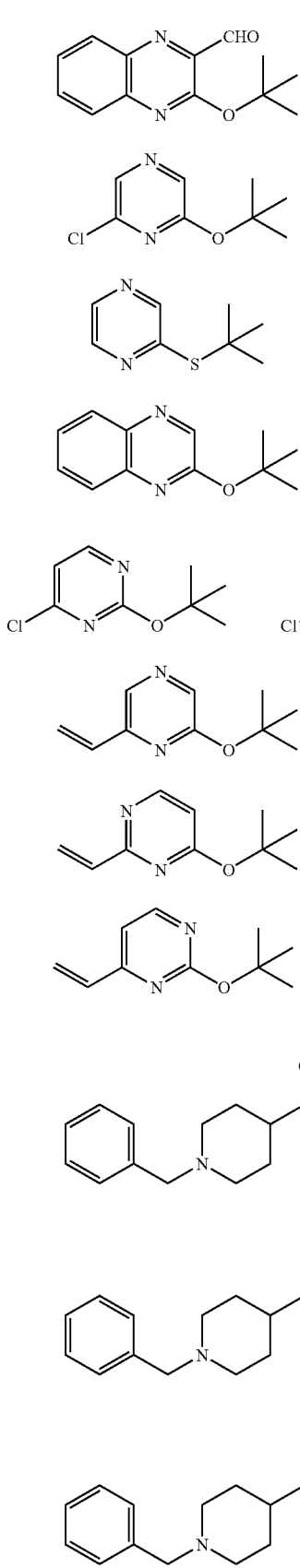

-continued

Production Example 14

Production Example 15

Production Example 16

Production Example 17

Production Example 18

Production Example 19

Production Example 20

Production Example 21

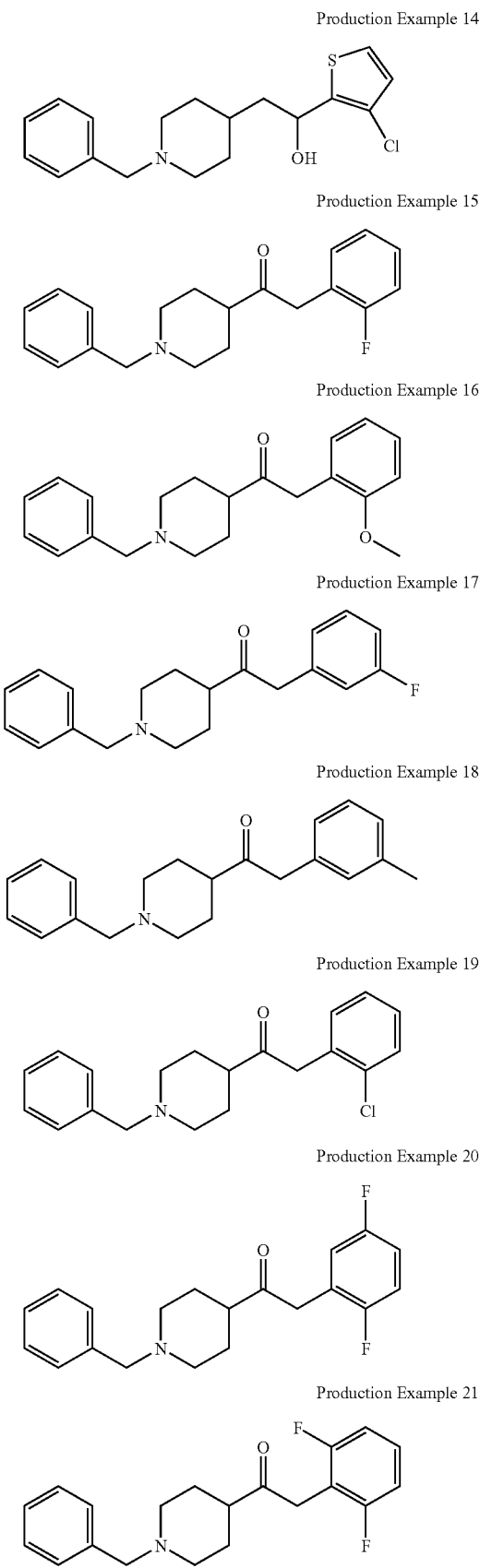

Production Example 22
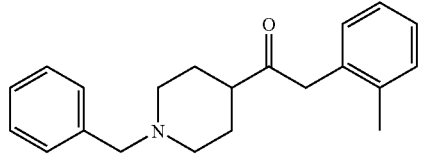
Production Example 23
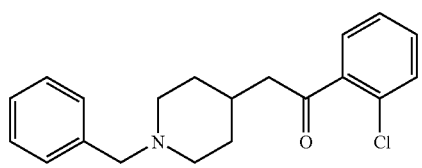
Production Example 24
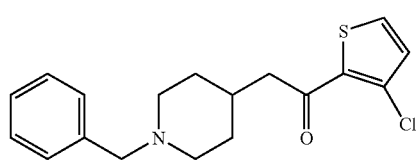
Production Example 25
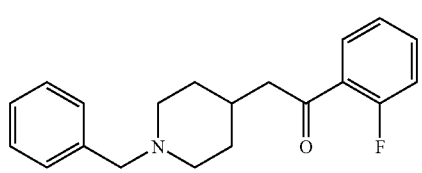
Production Example 26
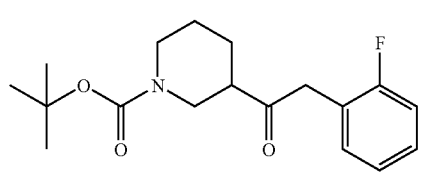
Production Example 27
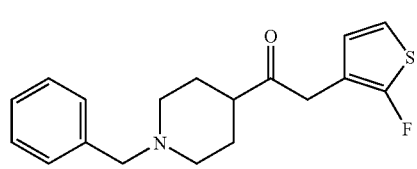
Production Example 28
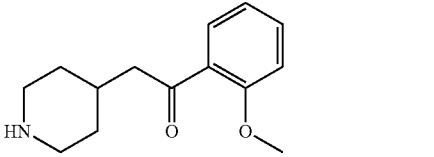
Production Example 29
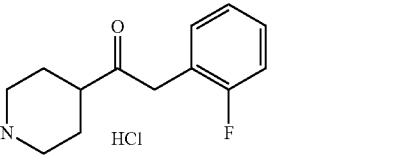
Production Example 30
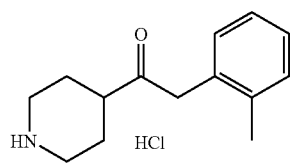
Production Example 31
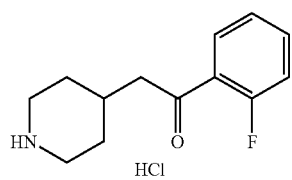
Production Example 32
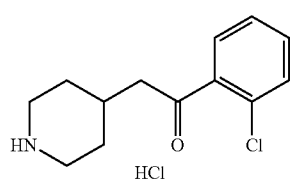
Production Example 33
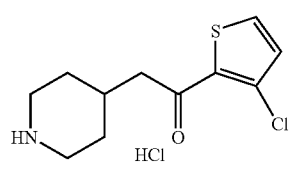
Production Example 34
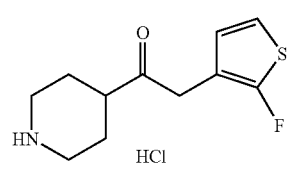
Production Example 35
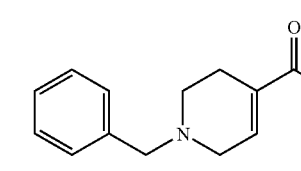
Production Example 36
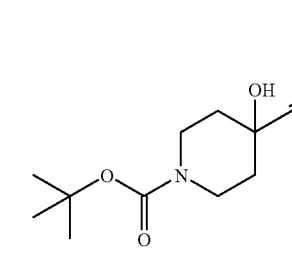

-continued
Production Example 37
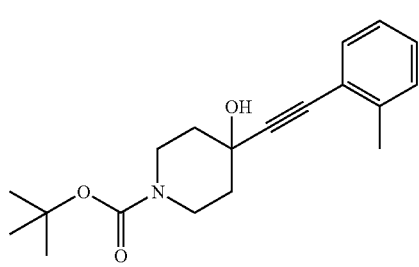
Production Example 38
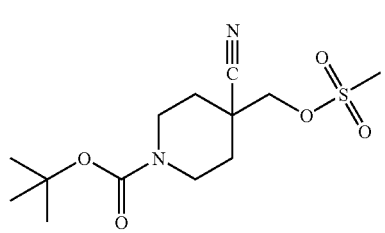
Production Example 39
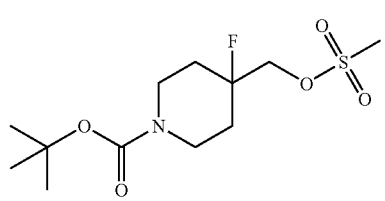
Production Example 40
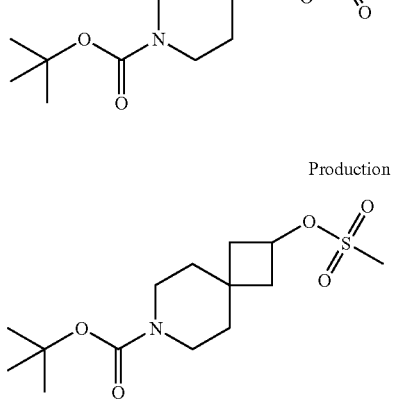
Production Example 41
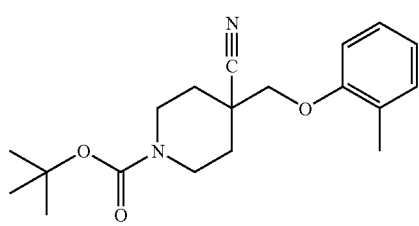
Production Example 42
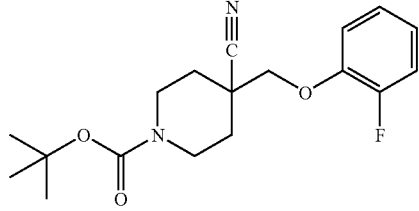
-continued
Production Example 43
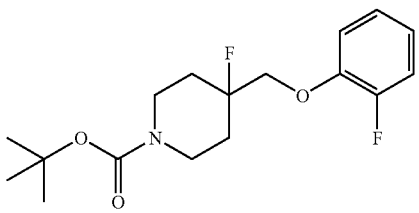
Production Example 44
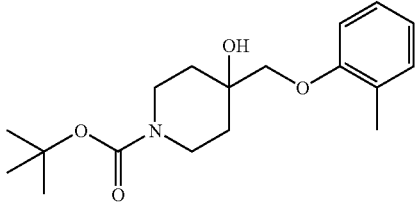
Production Example 45
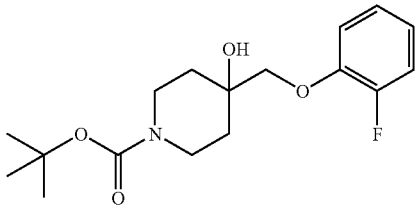
Production Example 46
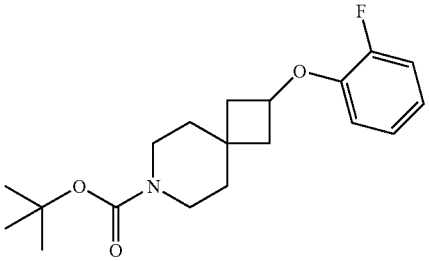
Production Example 47
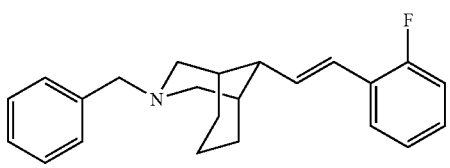
Production Example 48
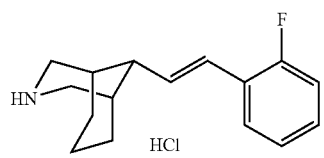
Production Example 49
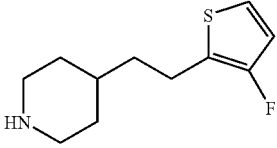

-continued

Production Example 50

Production Example 51

Production Example 52

Production Example 53

Production Example 54

Production Example 55

Production Example 56

Production Example 57

Production Example 58

-continued

Production Example 59

Production Example 60

Production Example 61

Production Example 62

Production Example 63

Production Example 64

Production Example 65

Production Example 66

-continued
Production Example 67
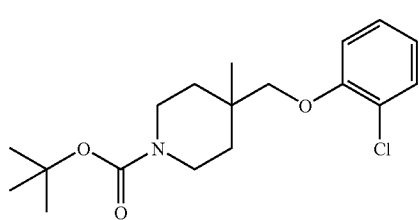
Production Example 68
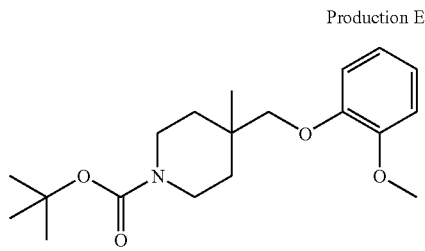
Production Example 69
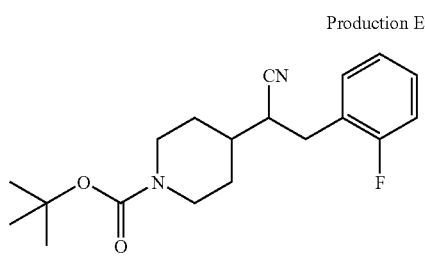
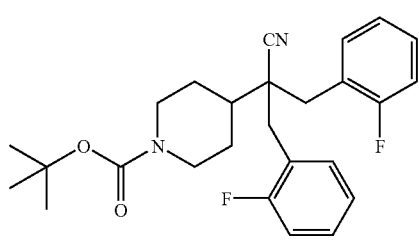
Production Example 70
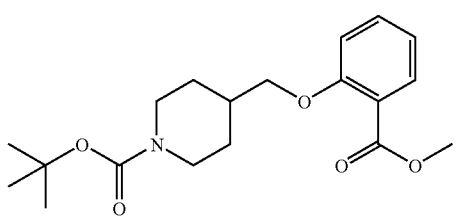
Production Example 71
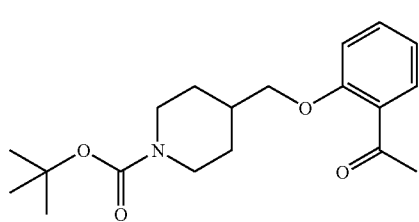
-continued
Production Example 72
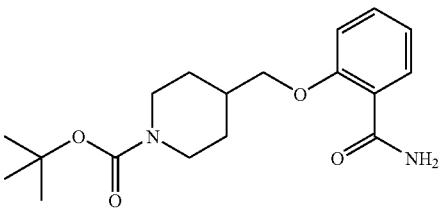
Production Example 73
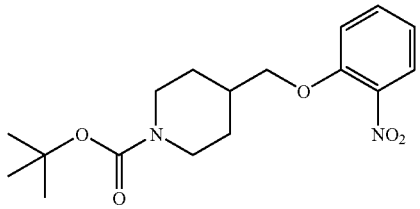
Production Example 74
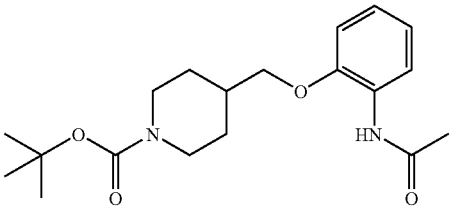
Production Example 75
Production Example 76
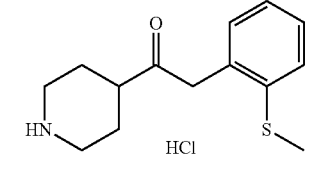
Production Example 77
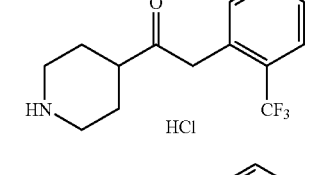
Production Example 78
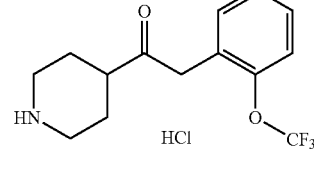
Production Example 79
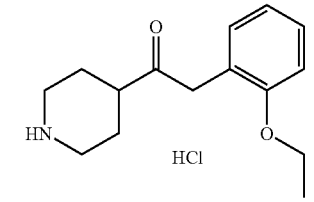

-continued
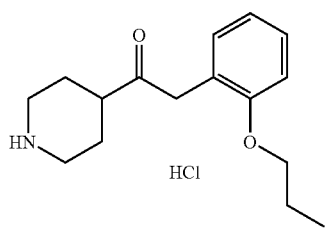
Production Example 80
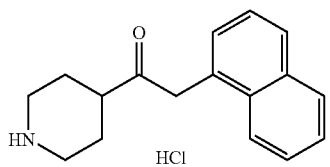
Production Example 81
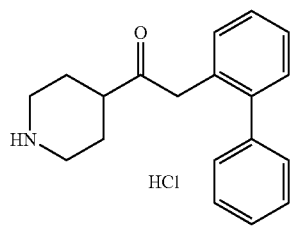
Production Example 82
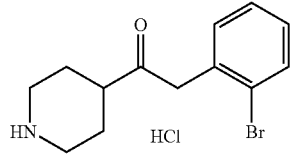
Production Example 83
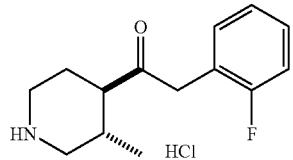
Production Example 84
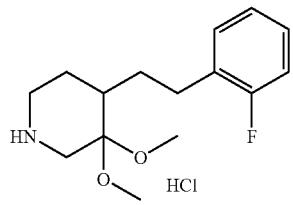
Production Example 85
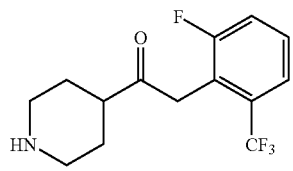
Production Example 86
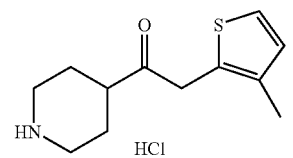
Production Example 87
-continued
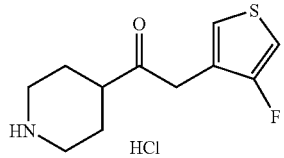
Production Example 88
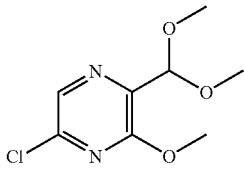
Production Example 89
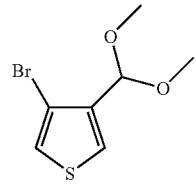
Production Example 90
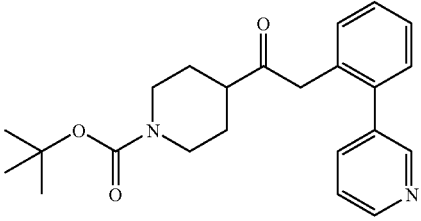
Production Example 91
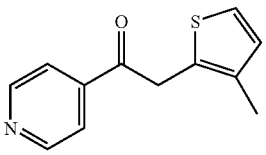
Production Example 92
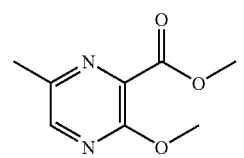
Production Example 93
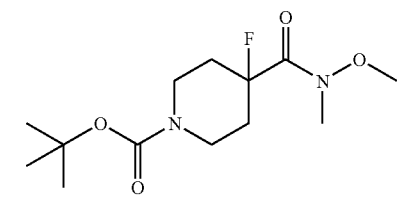
Production Example 94
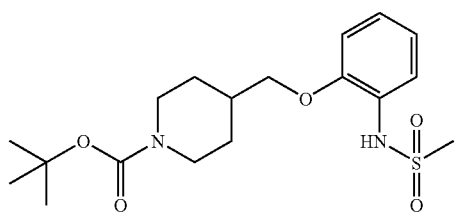
Production Example 95

-continued

Production Example 96
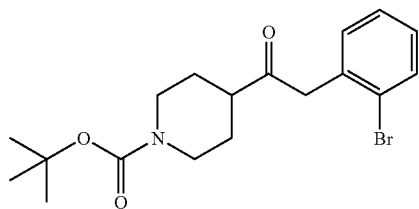

Production Example 97
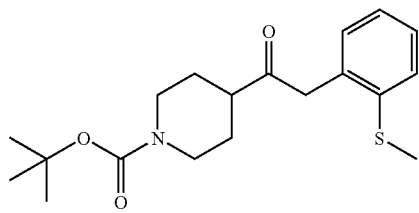

Production Example 98
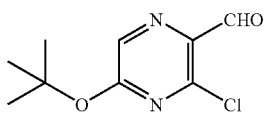

Production Example 99
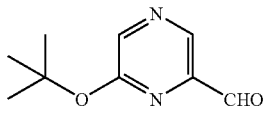

Production Example 100
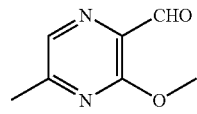

Production Example 101
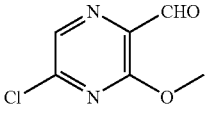

Production Example 102
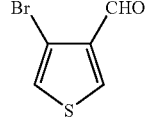

Production Example 103
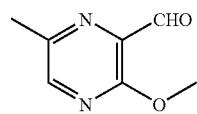

Production Example 104
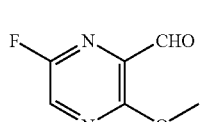

Production Example 105
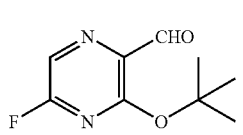

-continued

Production Example 106
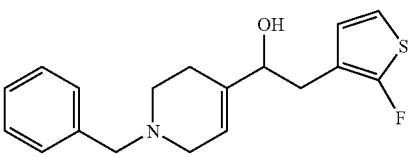

Production Example 107
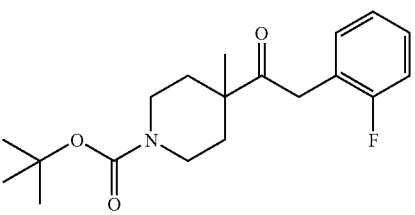

Production Example 108
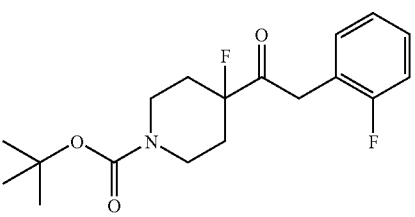

Production Example 109
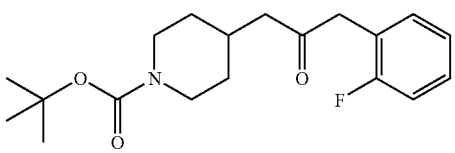

Production Example 110
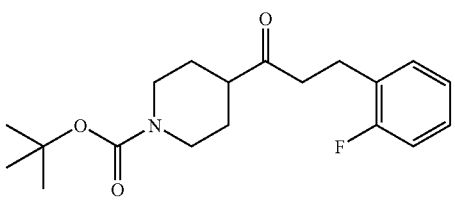

Production Example 111
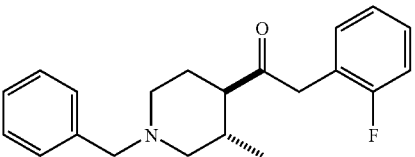

Production Example 112
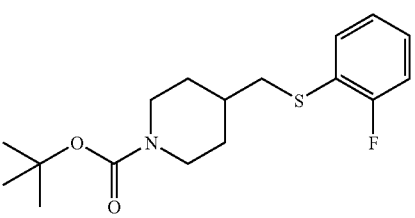

-continued

Production Example 113

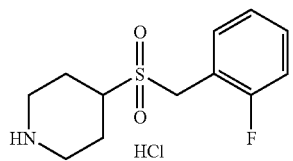

Production Example 114

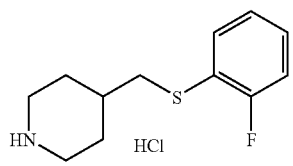

Production Example 115

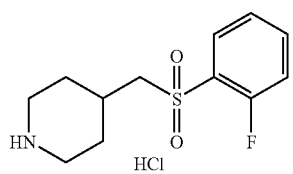

Production Example 116

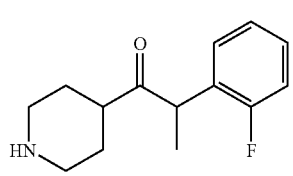

Production Example 117

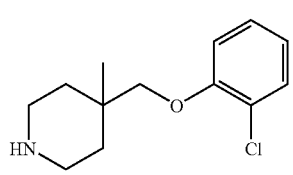

Production Example 118

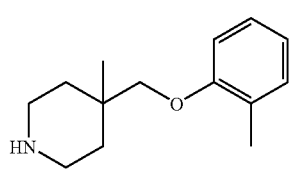

Production Example 119

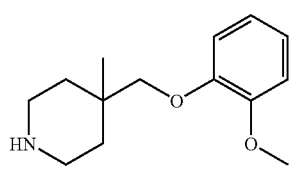

Production Example 120

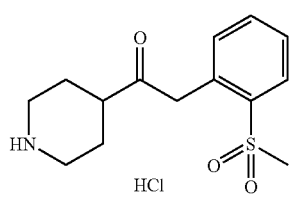

Production Example 121

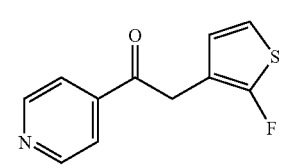

-continued

Production Example 122

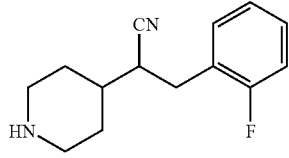

Production Example 123

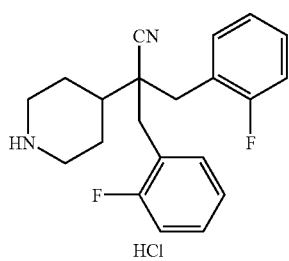

Production Example 124

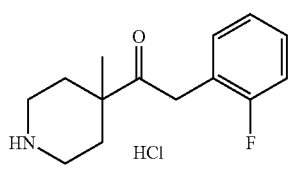

Production Example 125

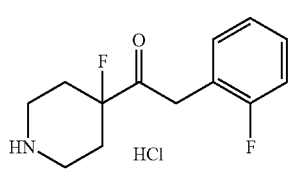

Production Example 126

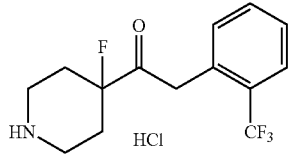

Production Example 127

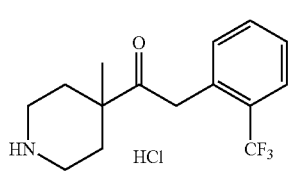

Production Example 128

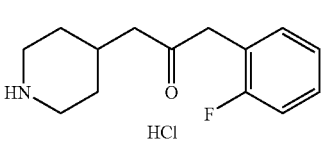

Production Example 129

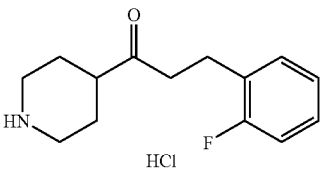

Production Example 130

Production Example 131

Production Example 132

Production Example 133

Production Example 134

Production Example 135

Production Example 136

Production Example 137

Production Example 138

Production Example 139

Production Example 140

Production Example 141

Production Example 142

Production Example 143

Production Example 144

Production Example 145
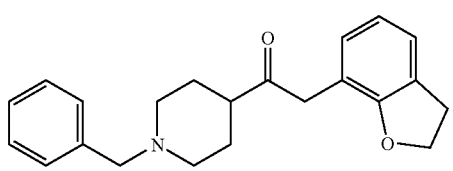
Production Example 146
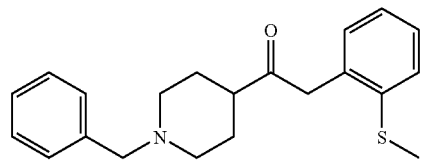
Production Example 147
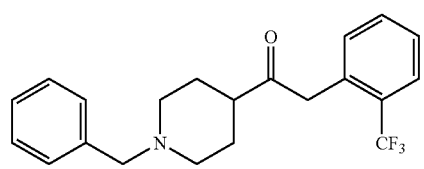
Production Example 148
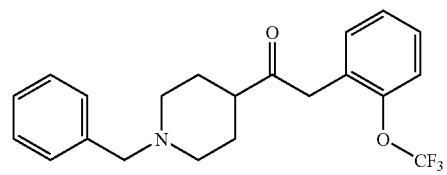
Production Example 149
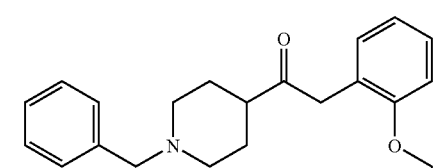
Production Example 150
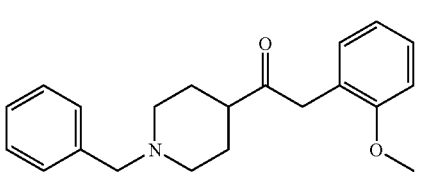
Production Example 151
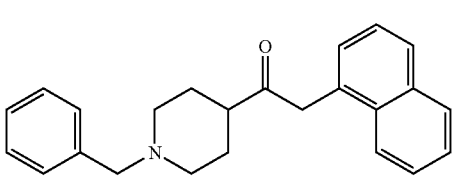
Production Example 152
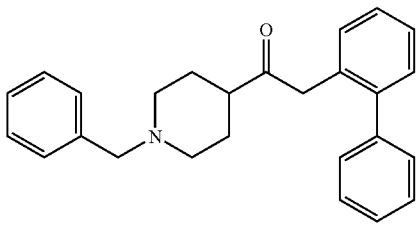
Production Example 153
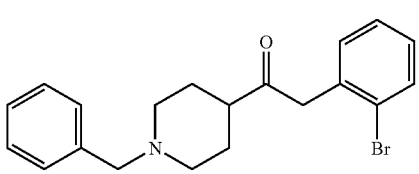
Production Example 154
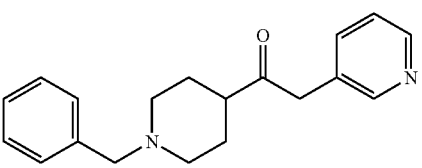
Production Example 155
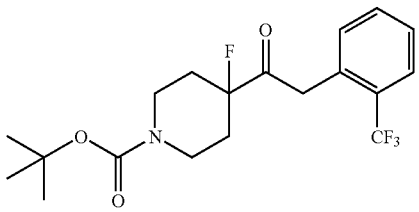
Production Example 156
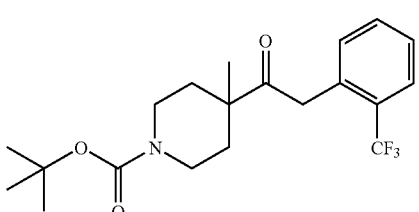
Production Example 157
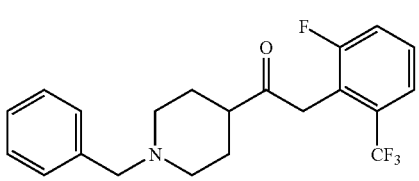
Production Example 158
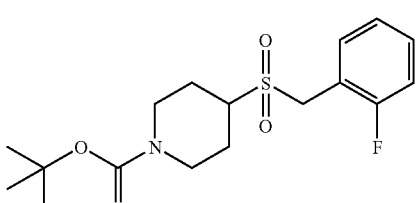

-continued
Production Example 159
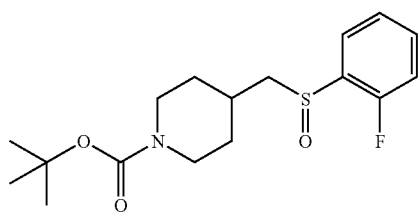
Production Example 160
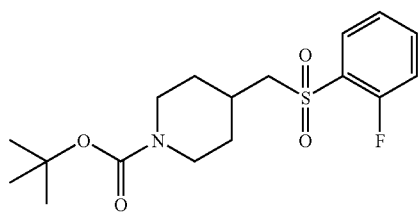
Production Example 161
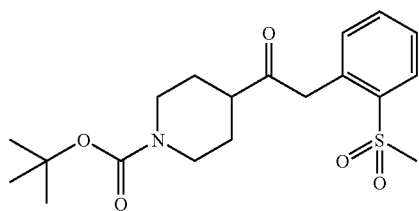
Production Example 162
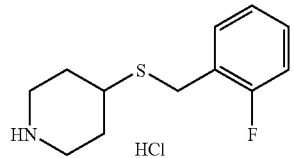
Production Example 163
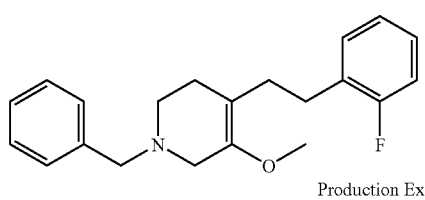
Production Example 164
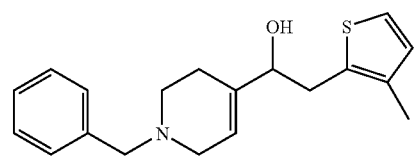
Production Example 165
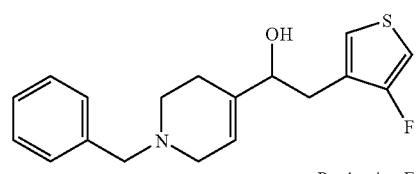
Production Example 166
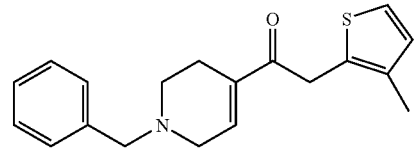
-continued
Production Example 167
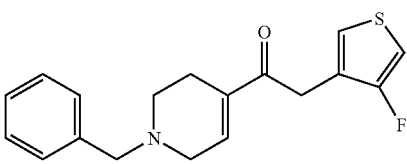
Production Example 168
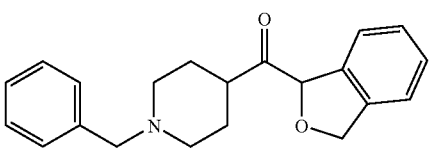
Production Example 169
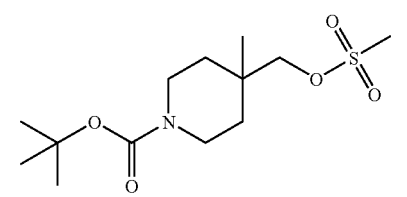
Production Example 170
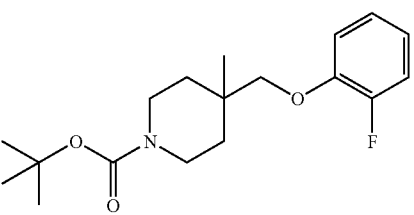
Production Example 171
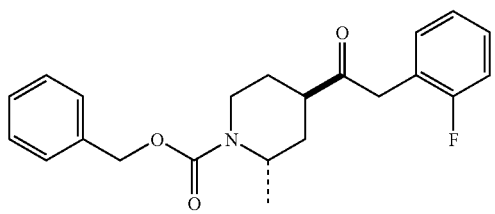
Production Example 172
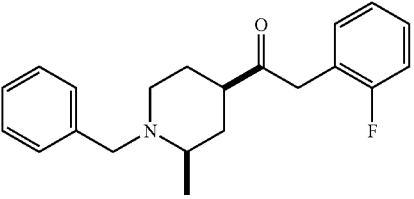
Production Example 173
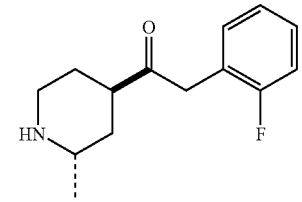

-continued

Production Example 174

Example 1

Example 2

Example 3

Example 4

Example 5

-continued

Example 6

Example 7

Example 8

Example 9

Example 10

Example 11

Example 12

Example 13
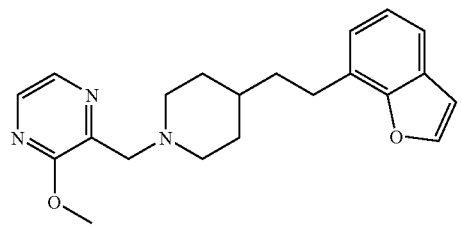
Example 14
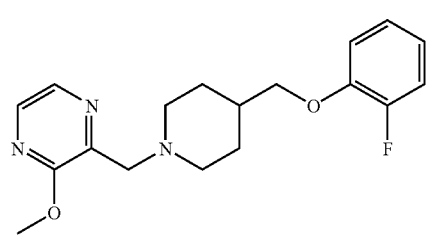
Example 15
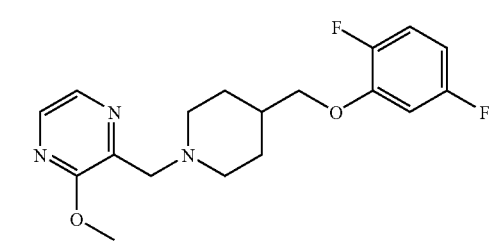
Example 16
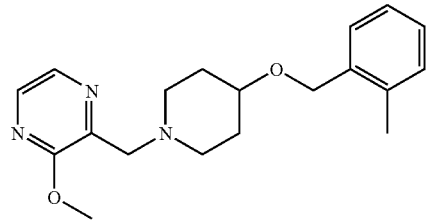
Example 17
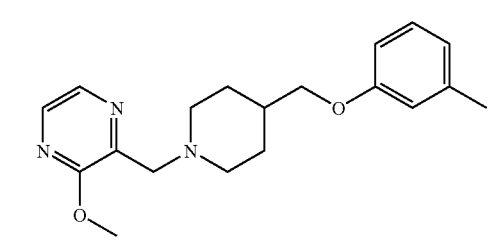
Example 18
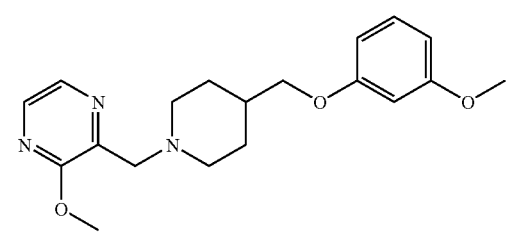
Example 19
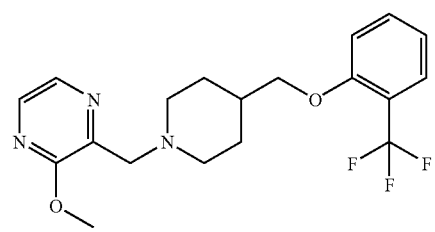
Example 20
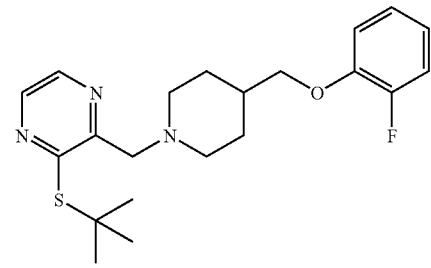
Example 21
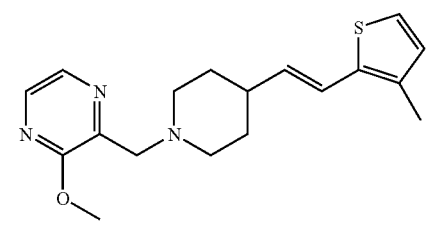
Example 22
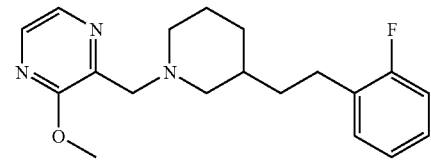
Example 23
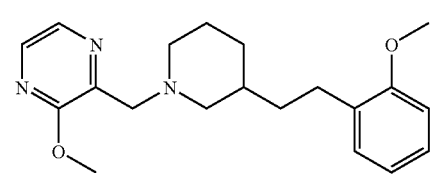
Example 24
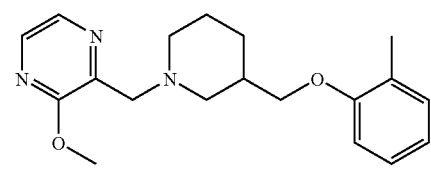
Example 25
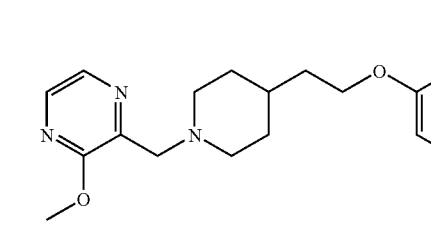

237
-continued
Example 26
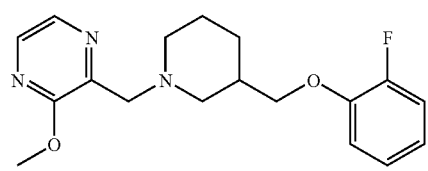
Example 27
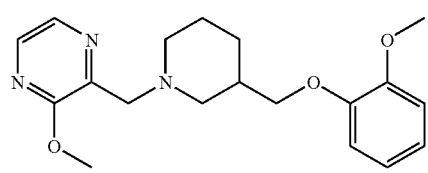
Example 28
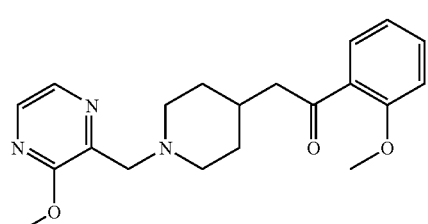
Example 29
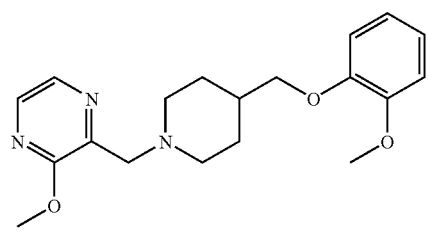
Example 30
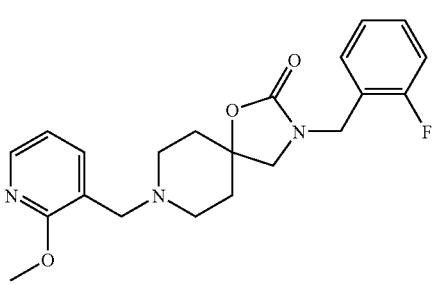
Example 31
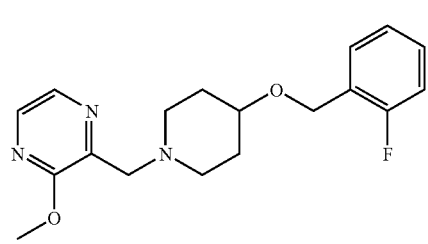
Example 32
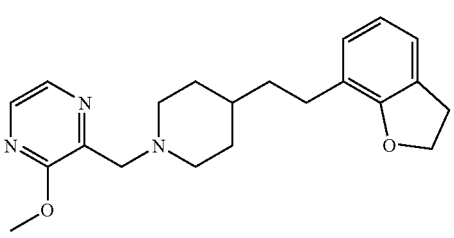
238
-continued
Example 33
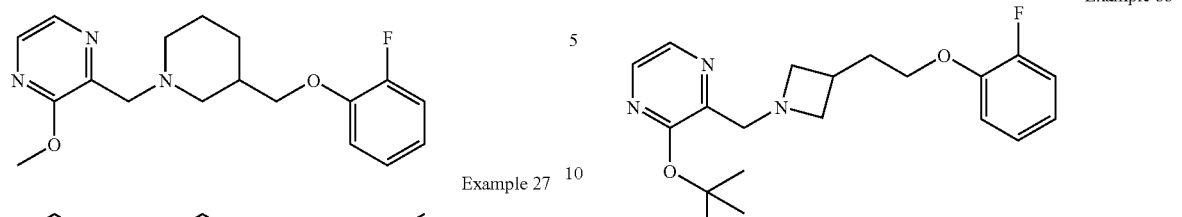
Example 34
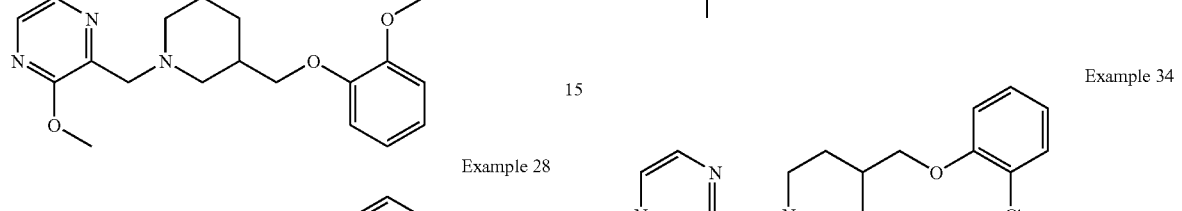
Example 35
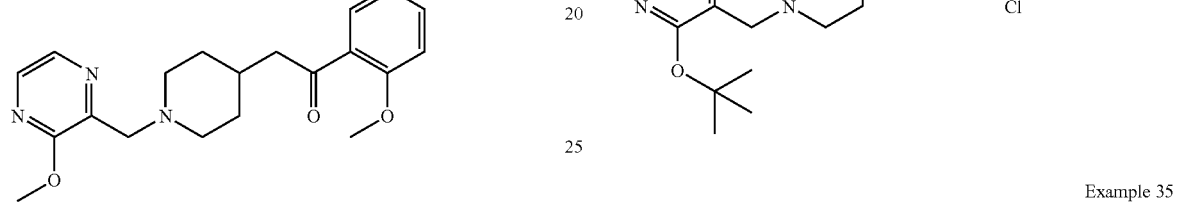
Example 36
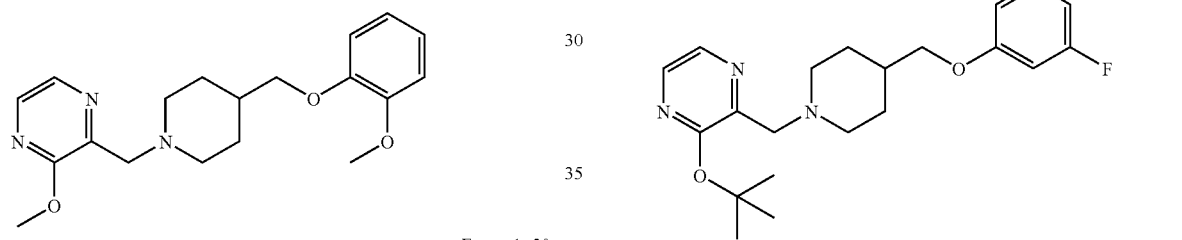
Example 37
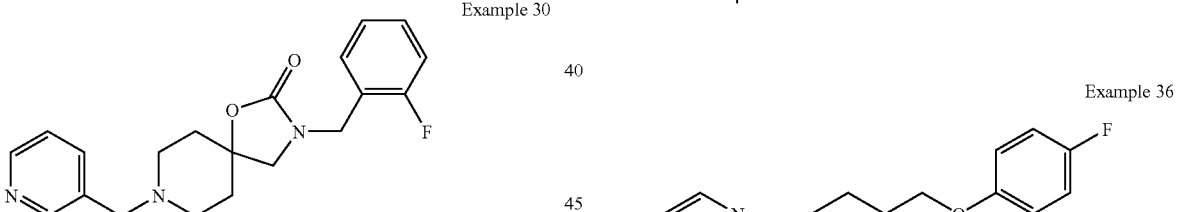

-continued
Example 38
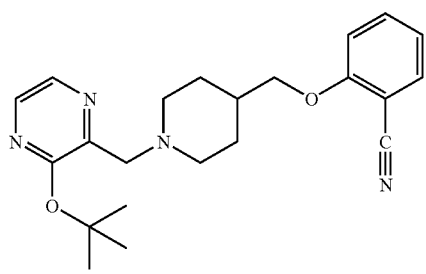
Example 39
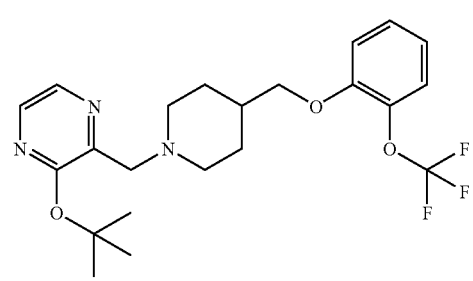
Example 40
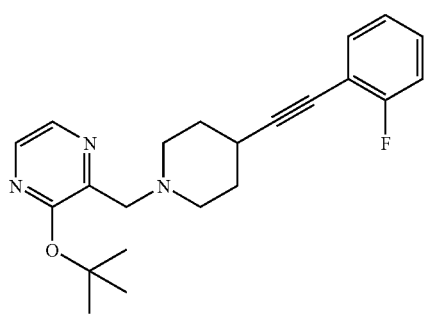
Example 41
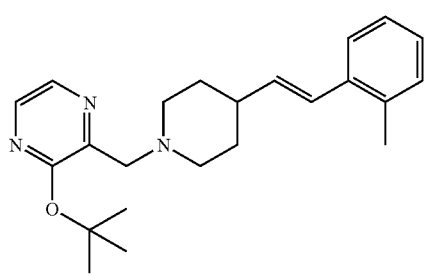
Example 42
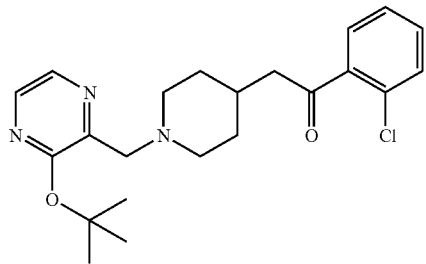
-continued
Example 43
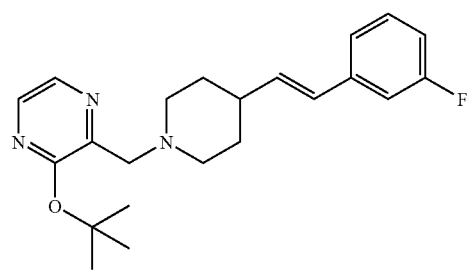
Example 44
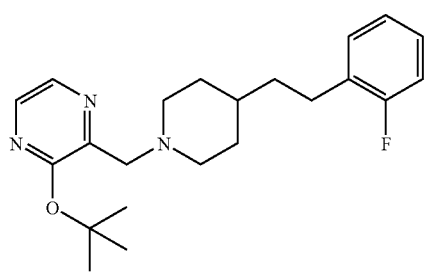
Example 45
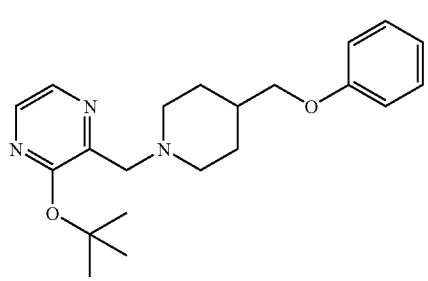
Example 46
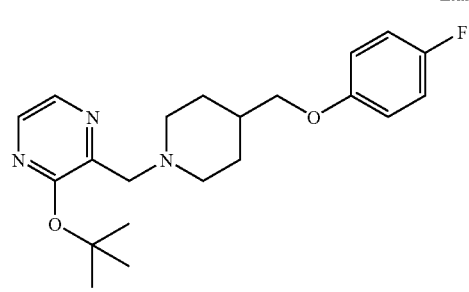
Example 47
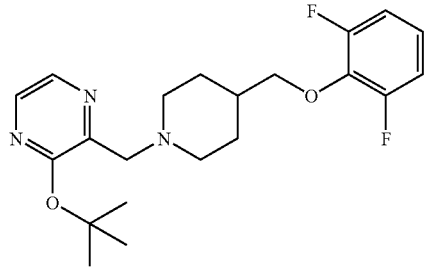

Example 48
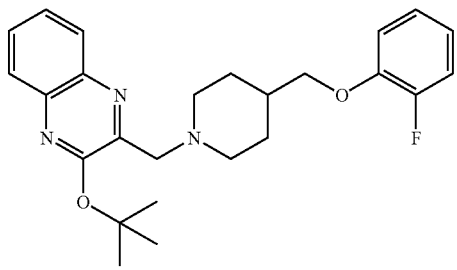
Example 49
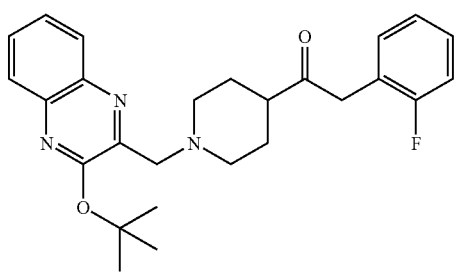
Example 50
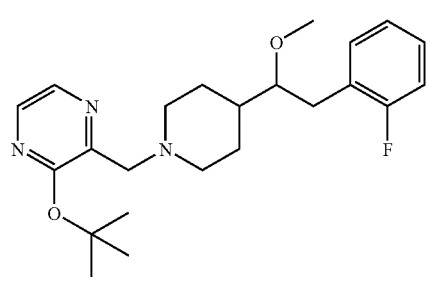
Example 51
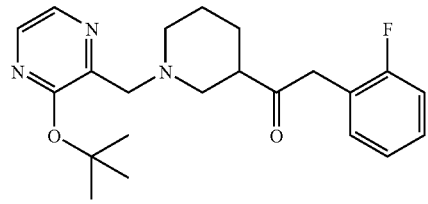
Example 52
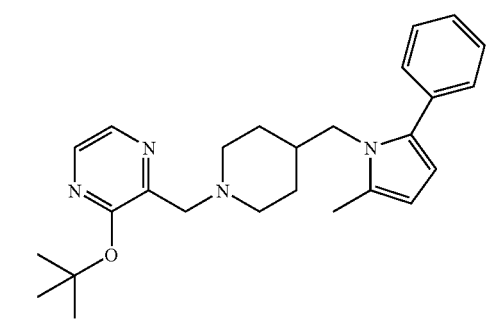
Example 53
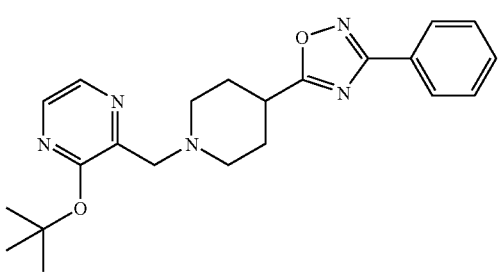
Example 54
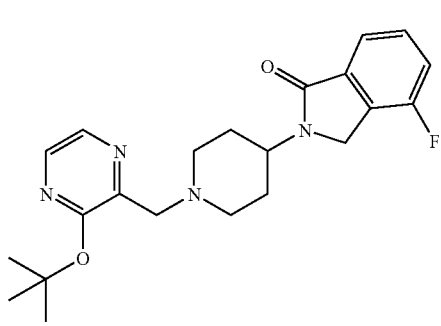
Example 55
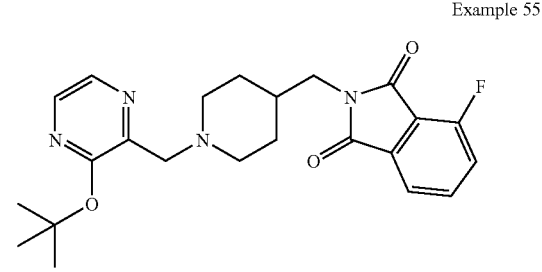
Example 56
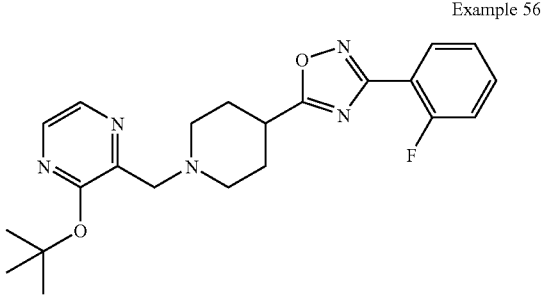
Example 57
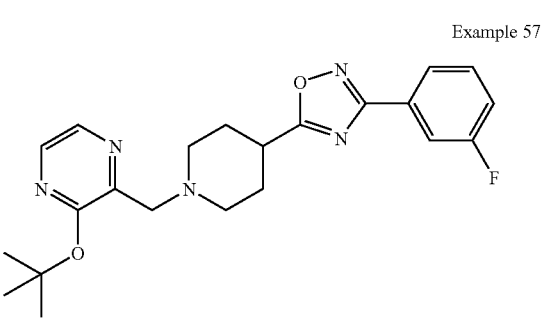

-continued
Example 58
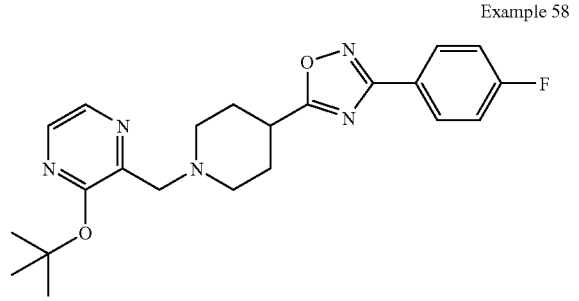
Example 59
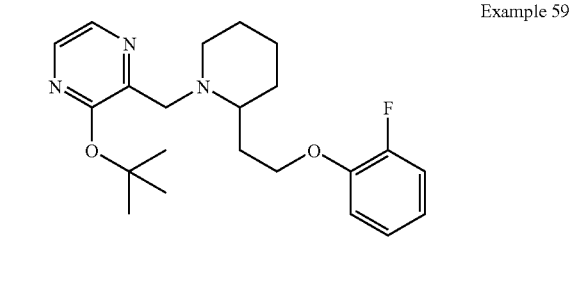
Example 60
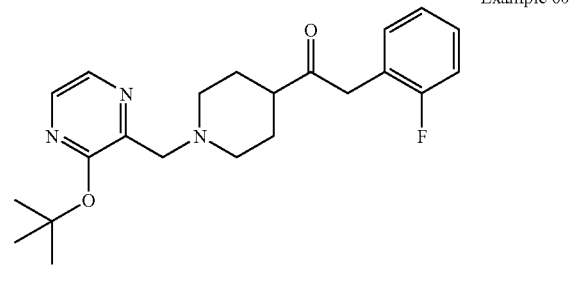
Example 61
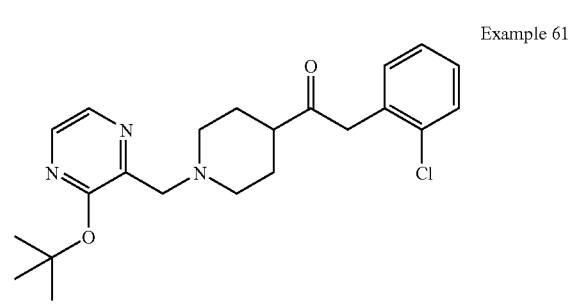
Example 62
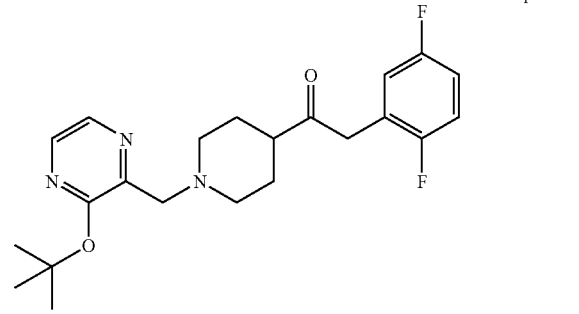
-continued
Example 63
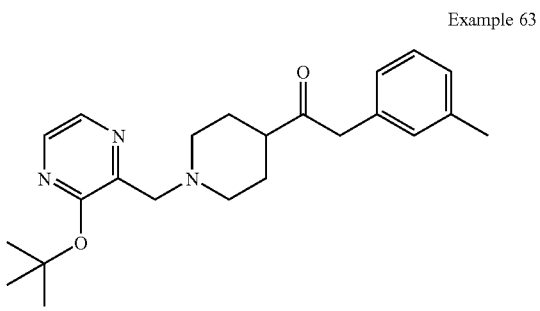
Example 64
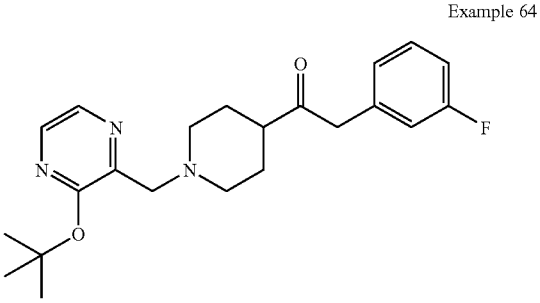
Example 65
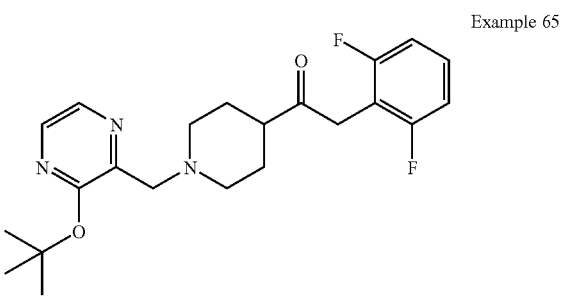
Example 66
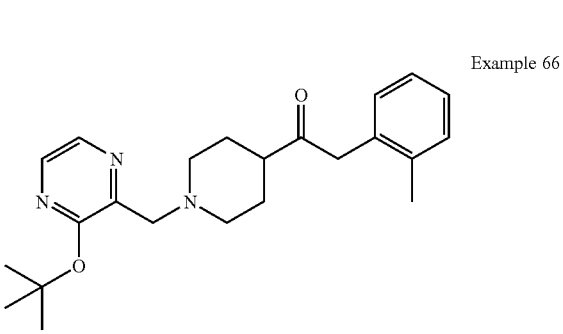
Example 67
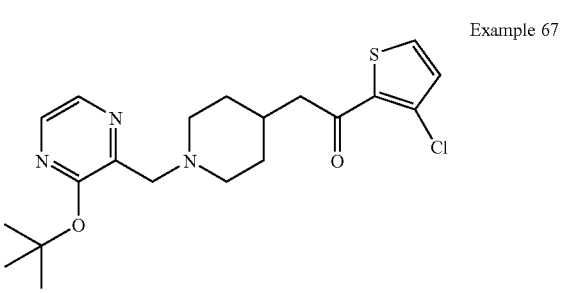

-continued
Example 68
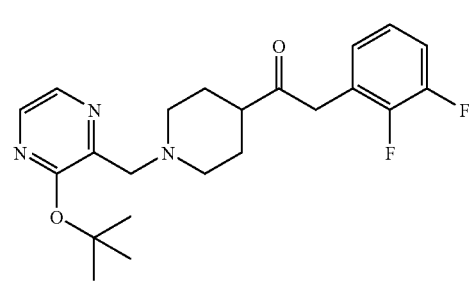
Example 69
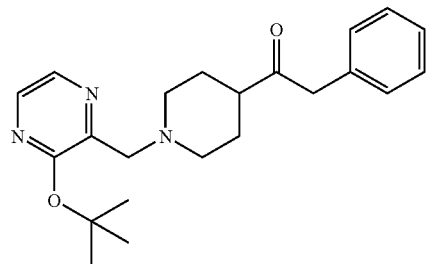
Example 70
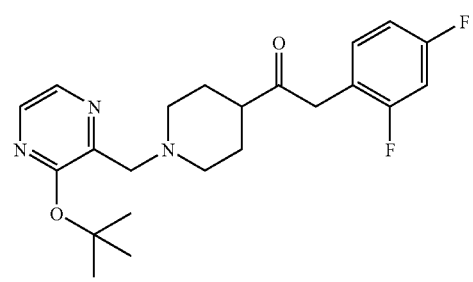
Example 71
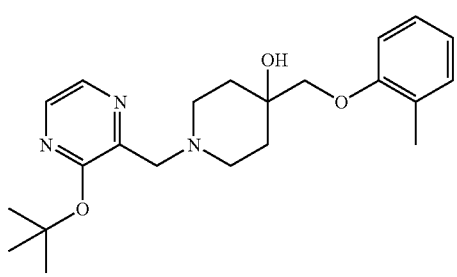
Example 72
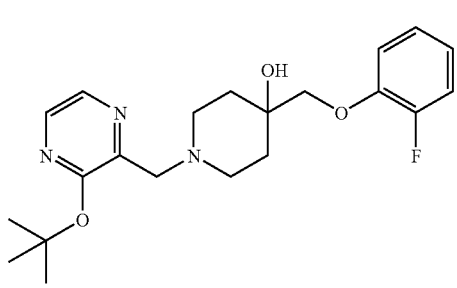
-continued
Example 73
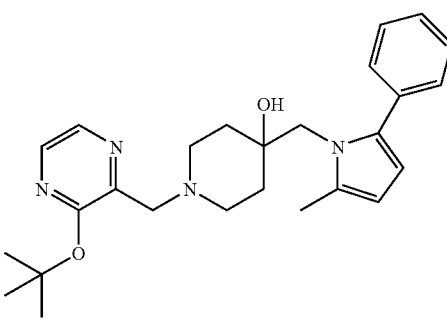
Example 74
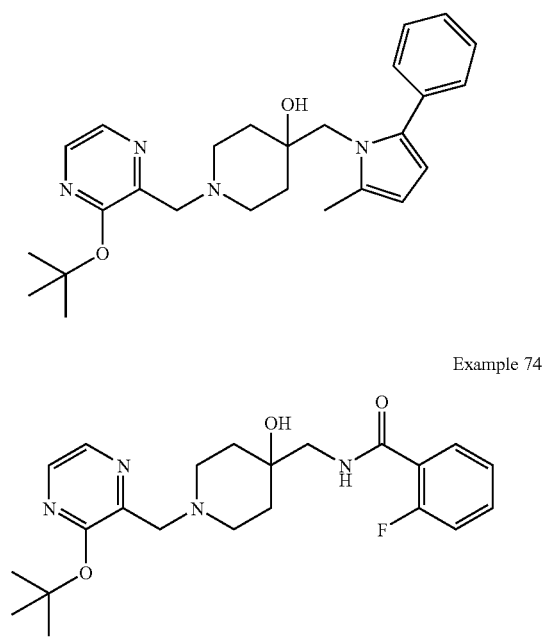
Example 75
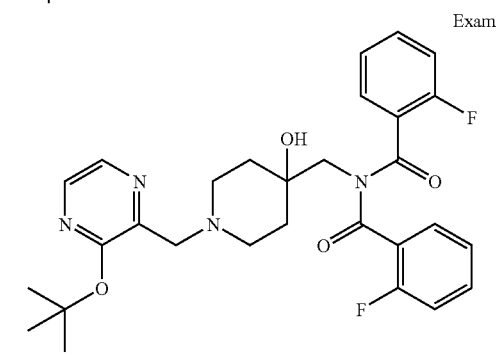
Example 76
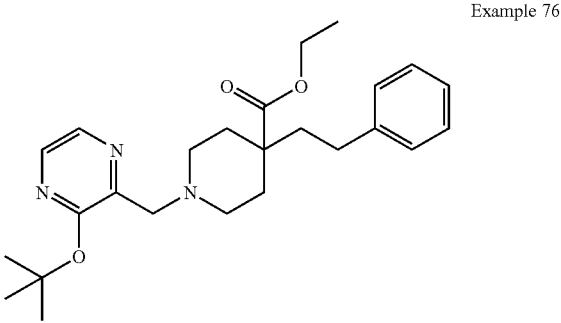
Example 77
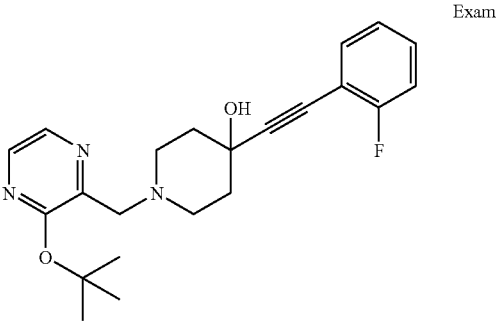

Example 78
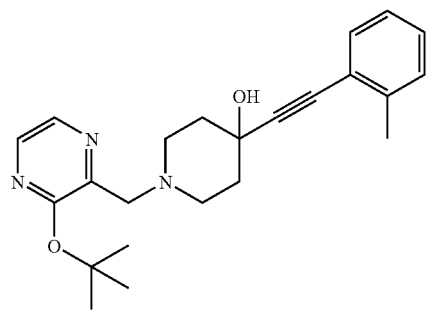
Example 79
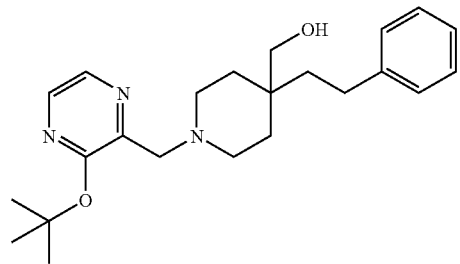
Example 80
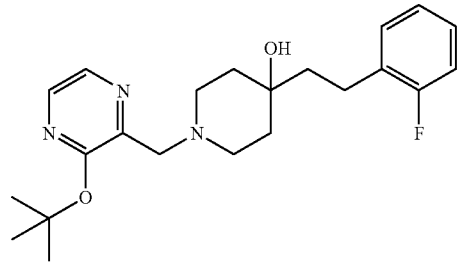
Example 81
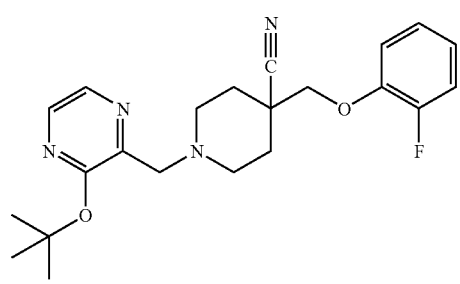
Example 82
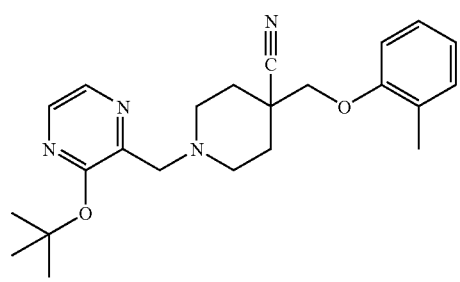
Example 83
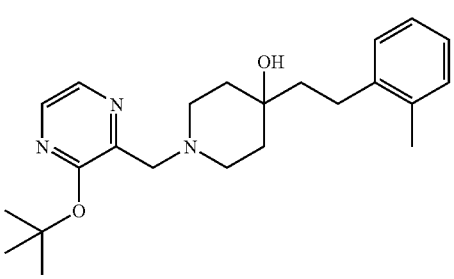
Example 84
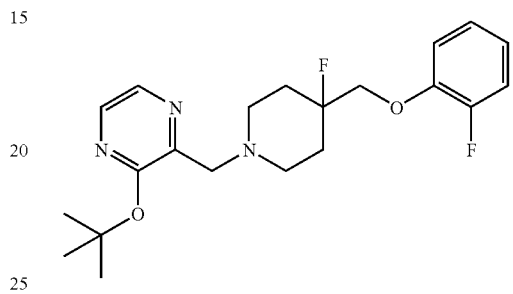
Example 85
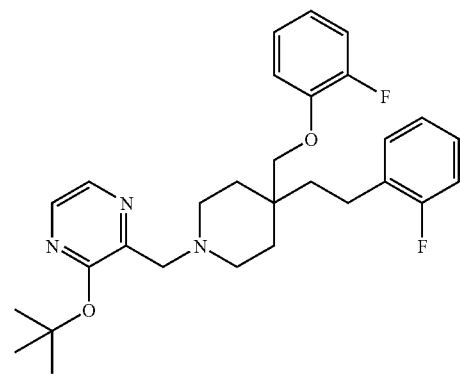
Example 86
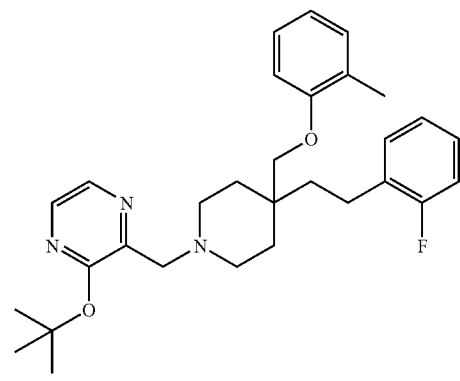
Example 87
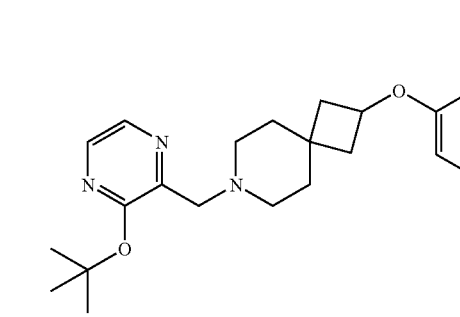

-continued
Example 88
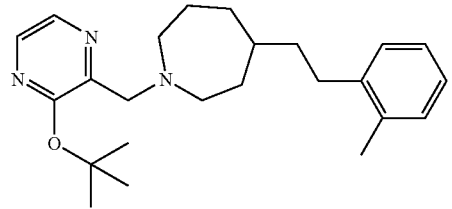
Example 89
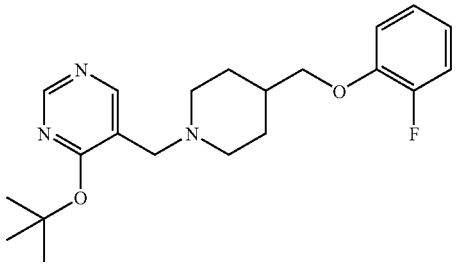
Example 90
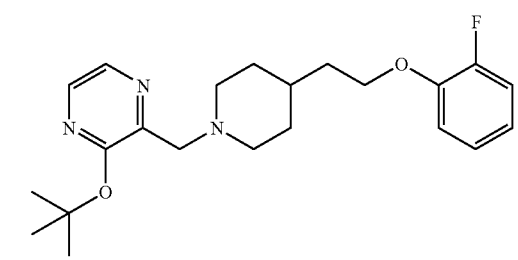
Example 91
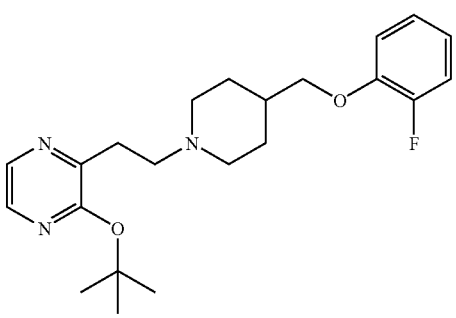
Example 92
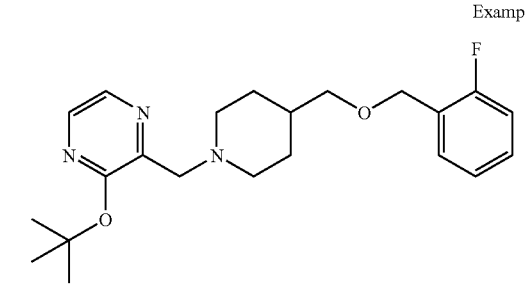
Example 93
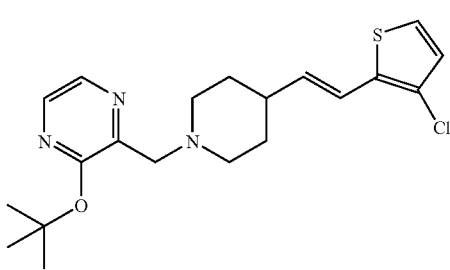
-continued
Example 94
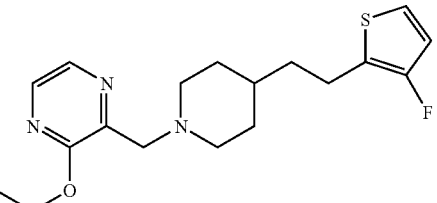
Example 95
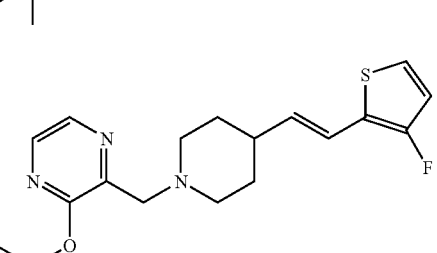
Example 96
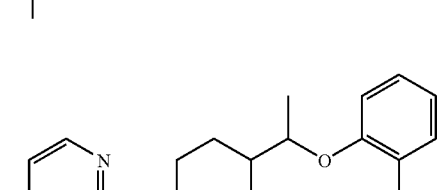
Example 97
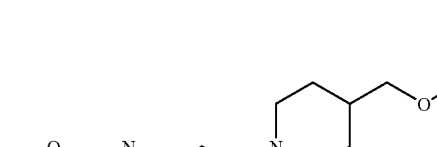
Example 98
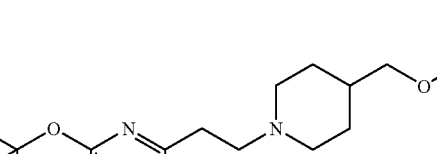
Example 99
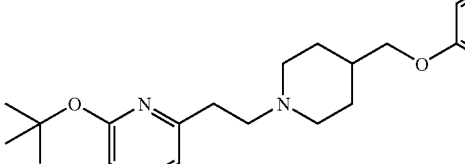

Example 100
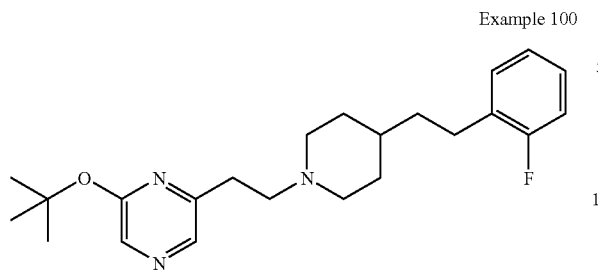
Example 101
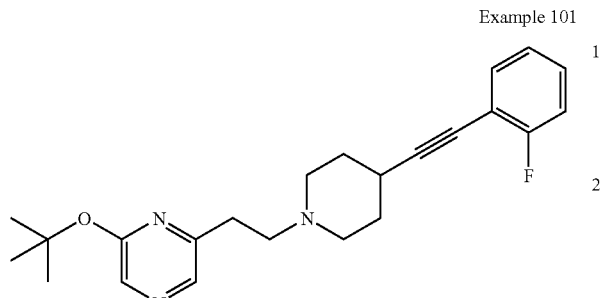
Example 102
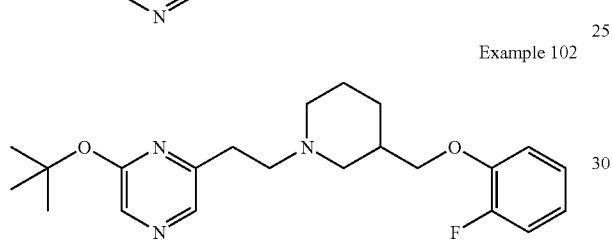
Example 103
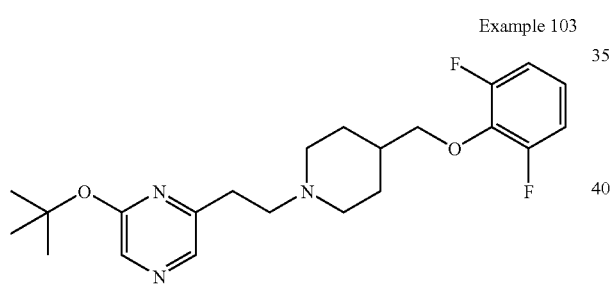
Example 104
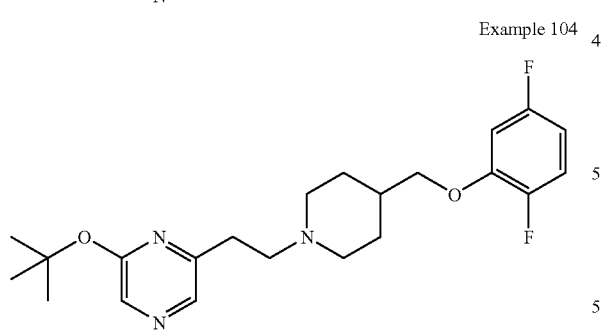
Example 105
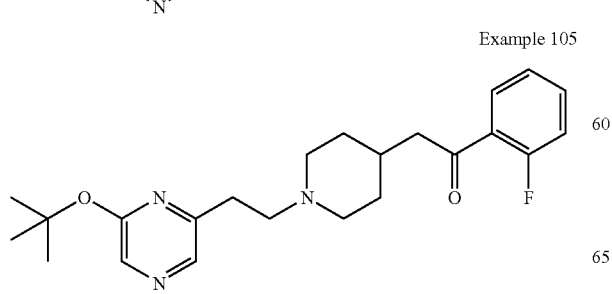
Example 106
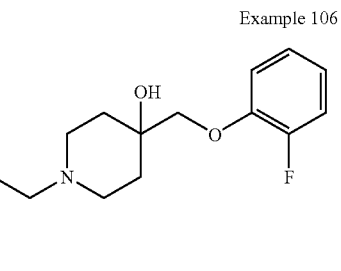
Example 107
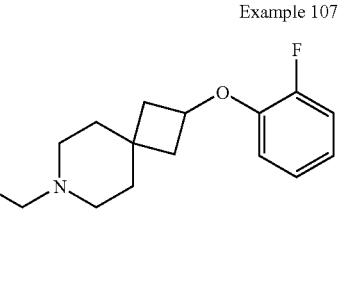
Example 108
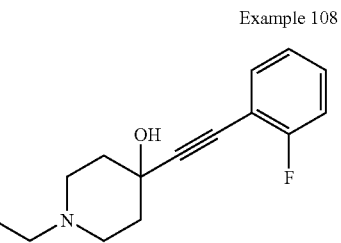
Example 109
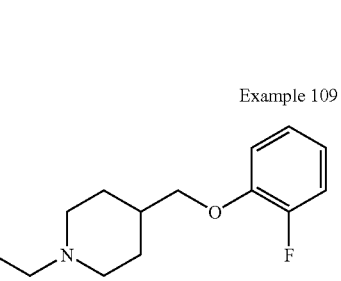
Example 110
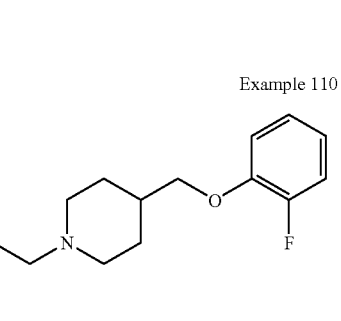
Example 111
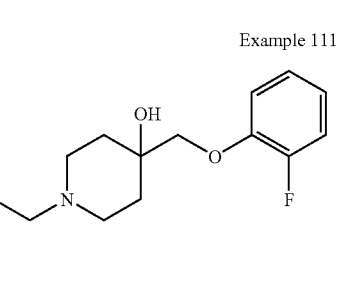

Example 112
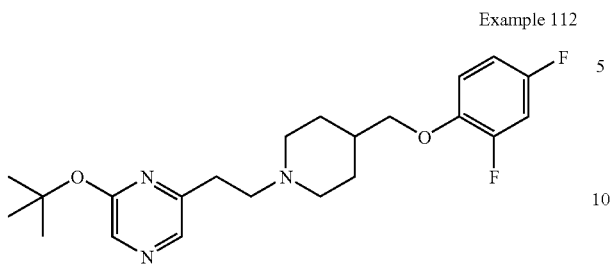
Example 113
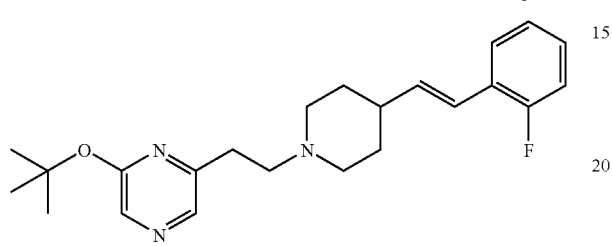
Example 114
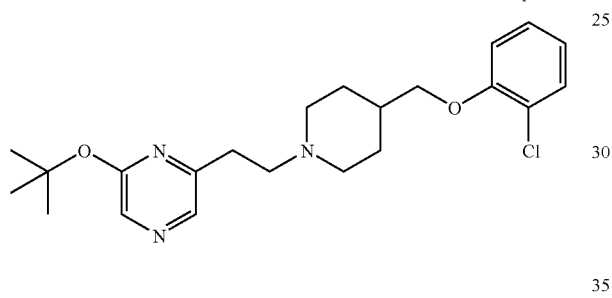
Example 115
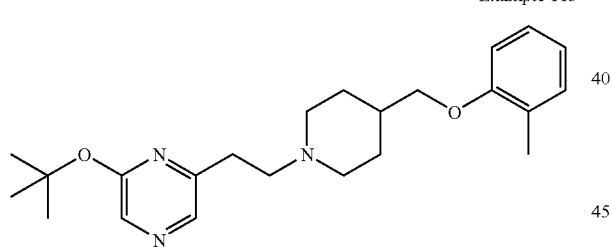
Example 116
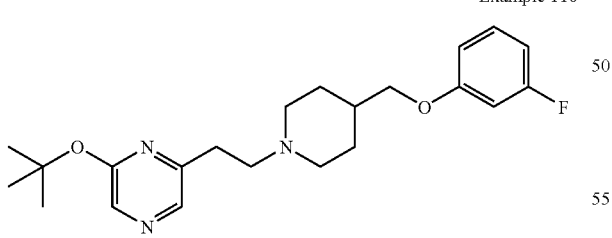
Example 117
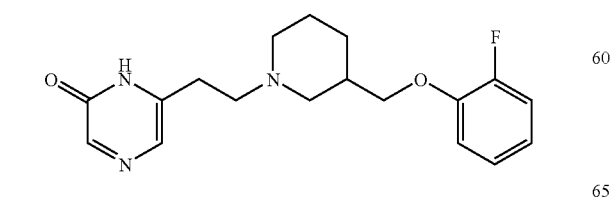
Example 118
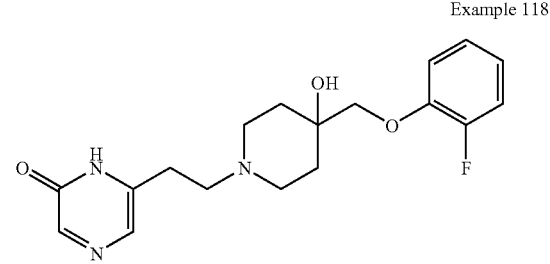
Example 119
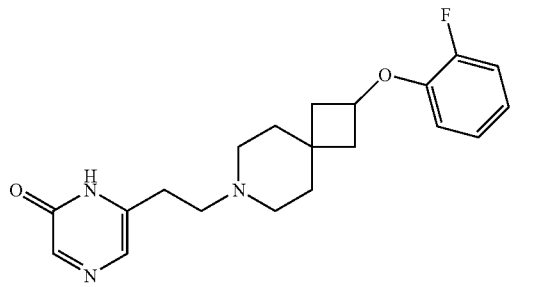
Example 120
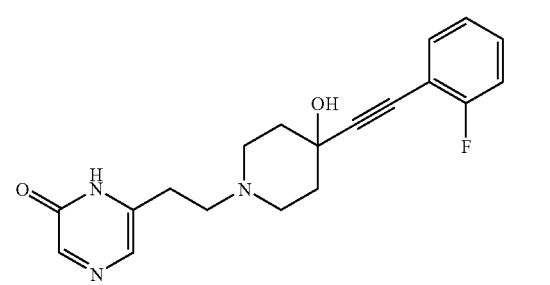
Example 121
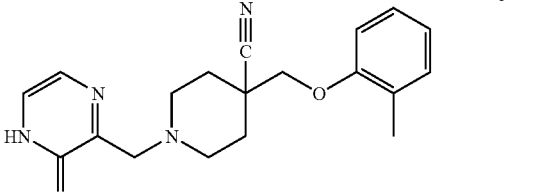
Example 122
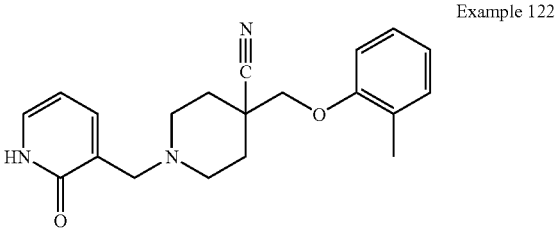
Example 123
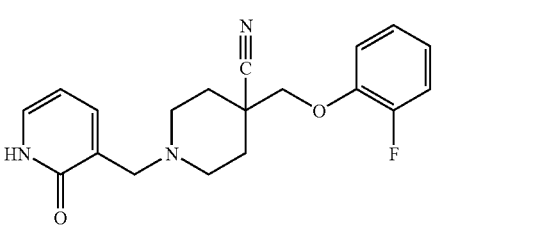

Example 124
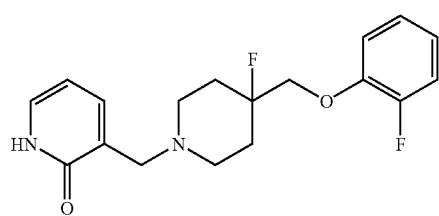
Example 125
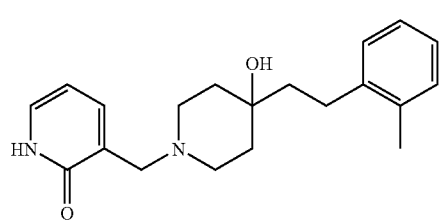
Example 126
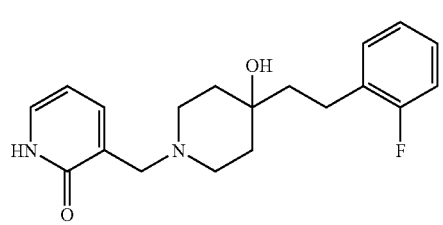
Example 127
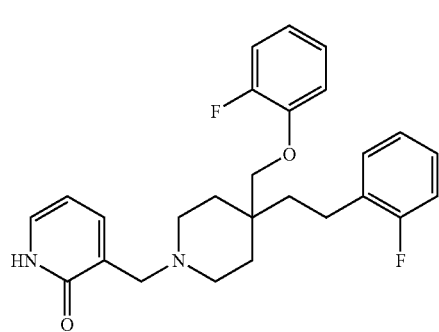
Example 128
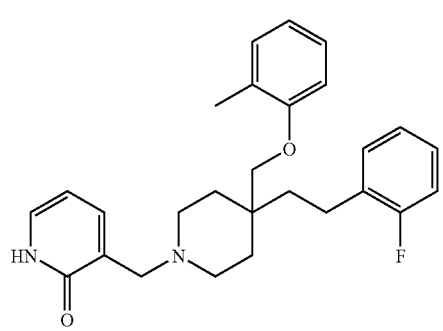
Example 129
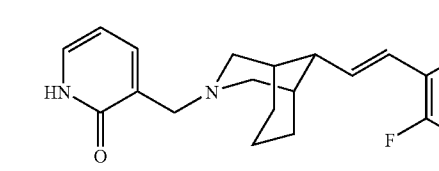
Example 130
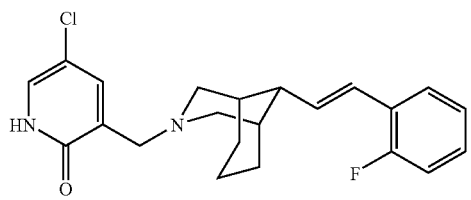
Example 131
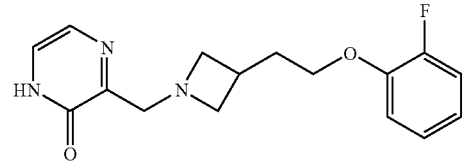
Example 132
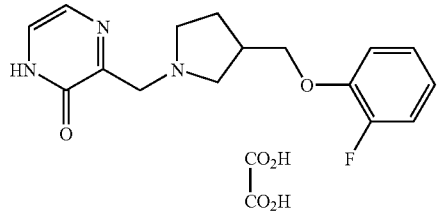
Example 133
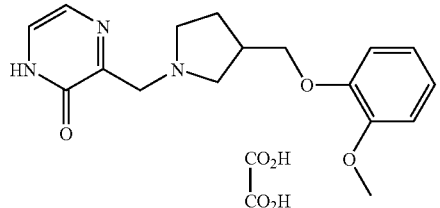
Example 134
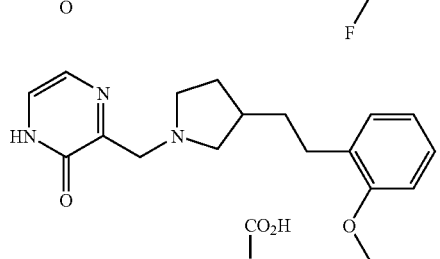
Example 135
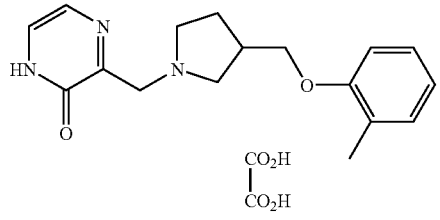
Example 136

Example 137
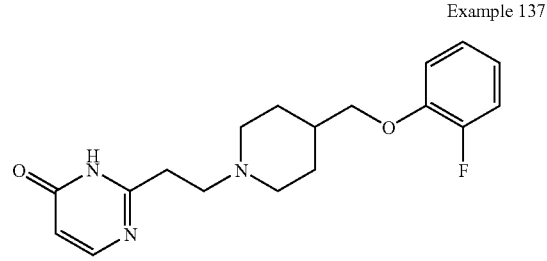
Example 138
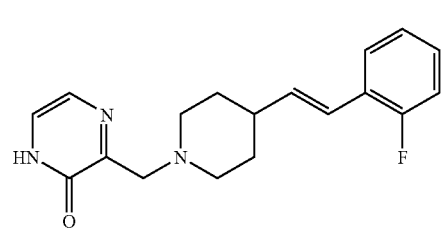
Example 139
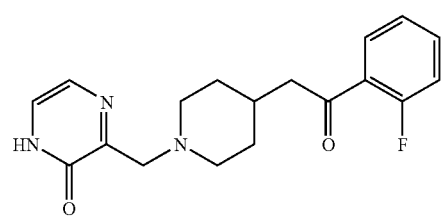
Example 140
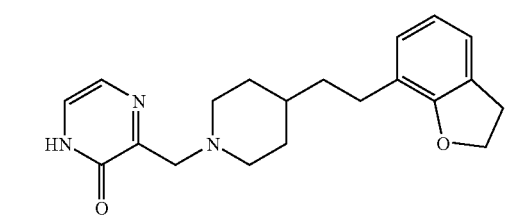
Example 141
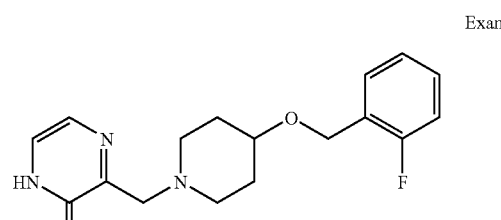
Example 142
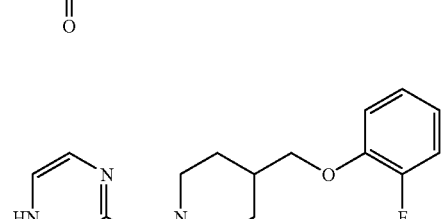
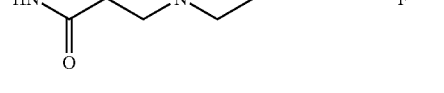
Example 143
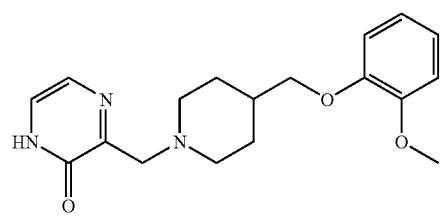
Example 144
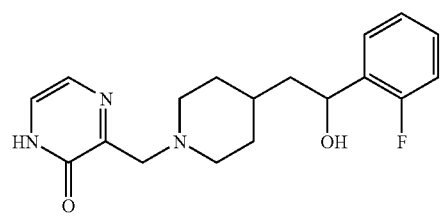
Example 145
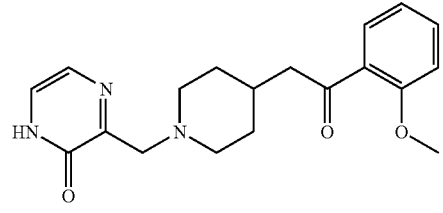
Example 146
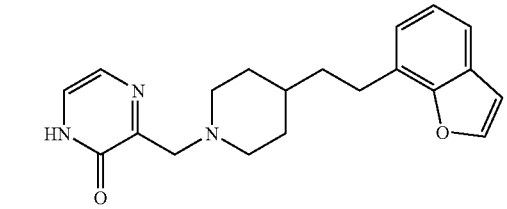
Example 147
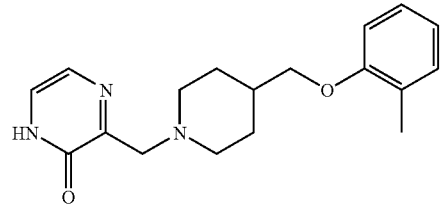
Example 148
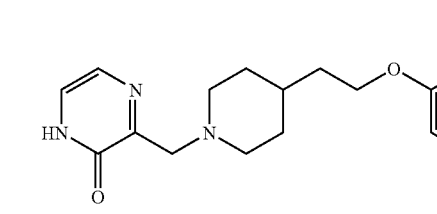
Example 149
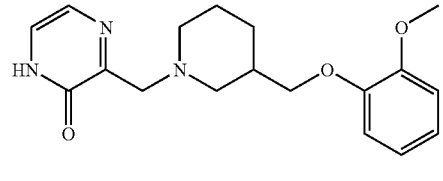

Example 150
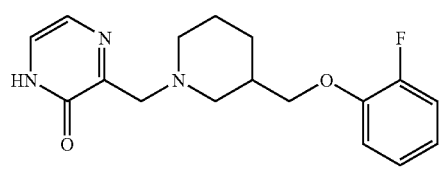
Example 151
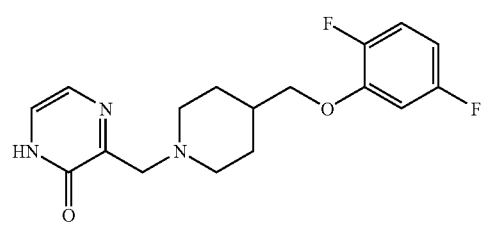
Example 152
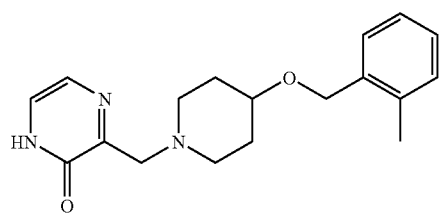
Example 153
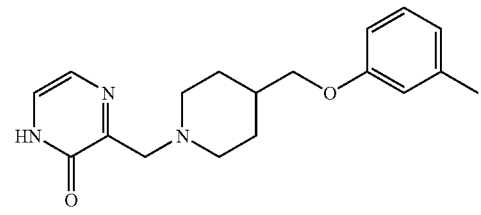
Example 154
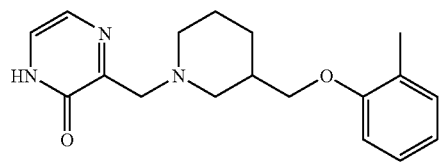
Example 155
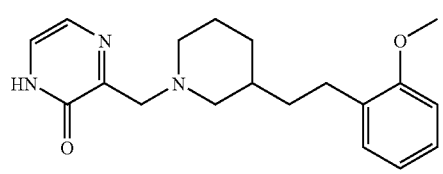
Example 156
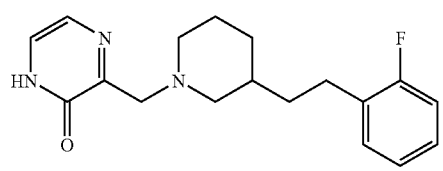
Example 157
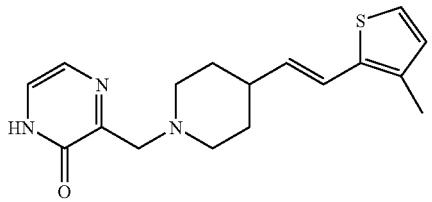
Example 158
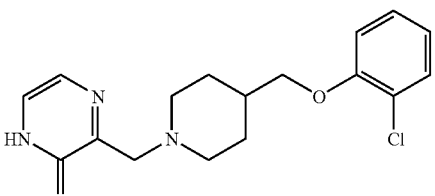
Example 159
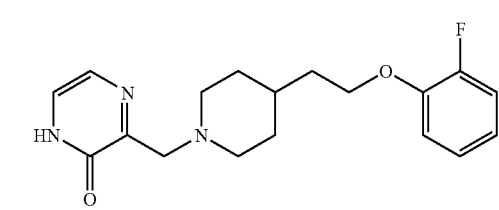
Example 160
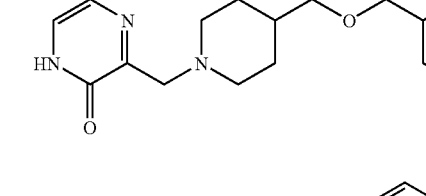
Example 161
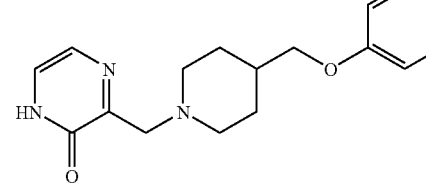
Example 162
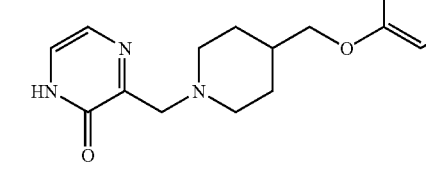
Example 163

Example 164
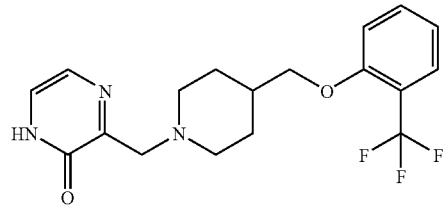
Example 165
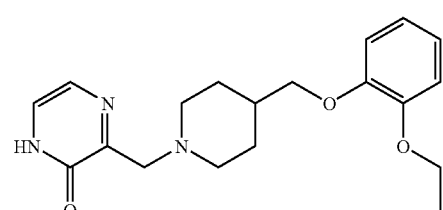
Example 166
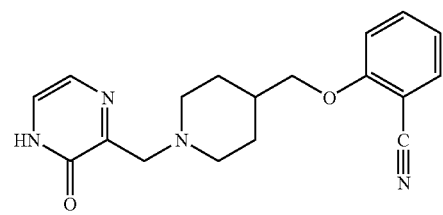
Example 167
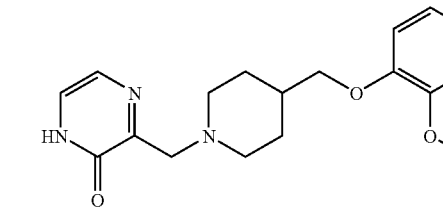
Example 168
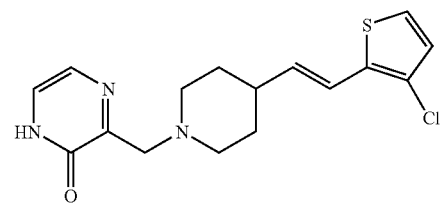
Example 169
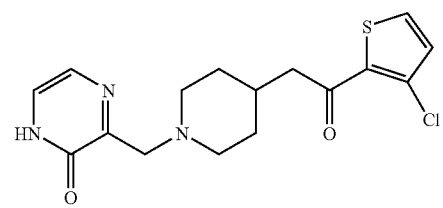
Example 170
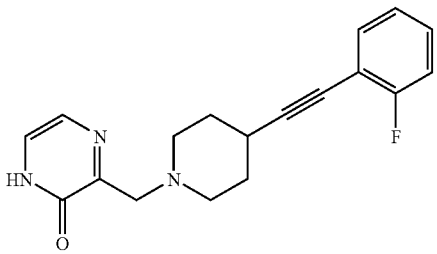
Example 171
Example 172
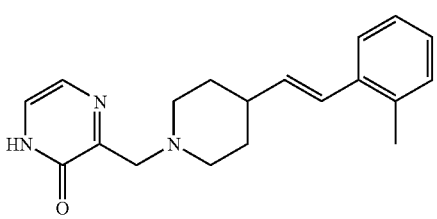
Example 173
Example 174
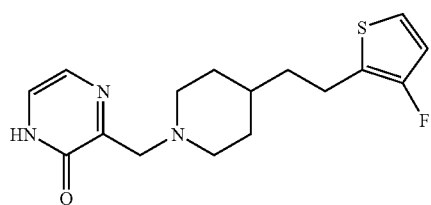
Example 175
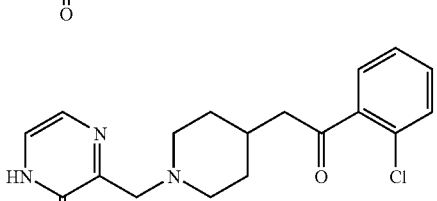
Example 176
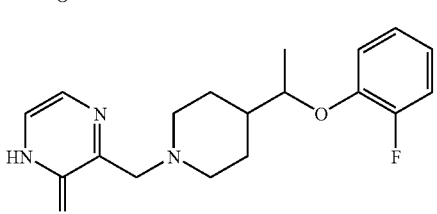
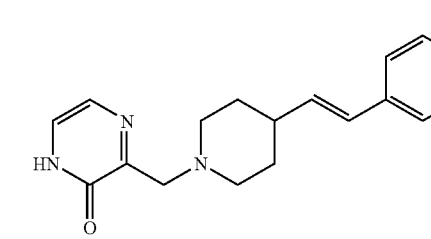

Example 177
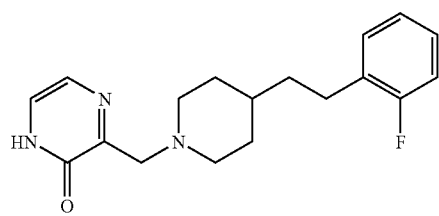
Example 178
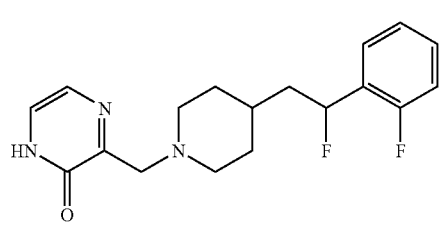
Example 179
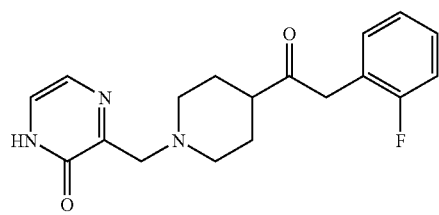
Example 180
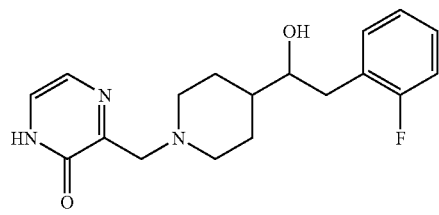
Example 181
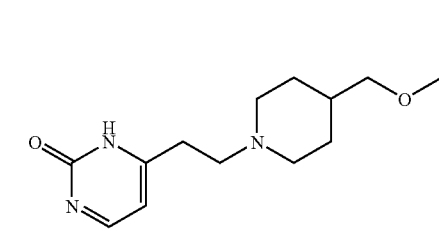
Example 182
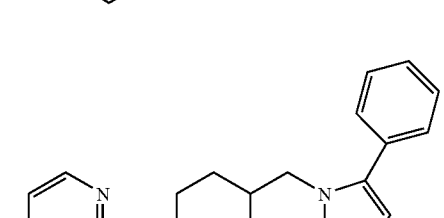
Example 183
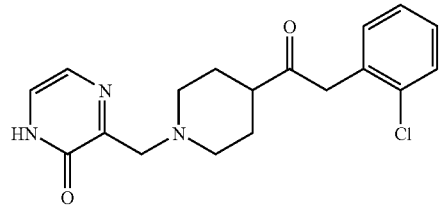
Example 184
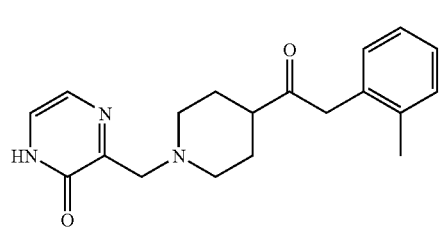
Example 185
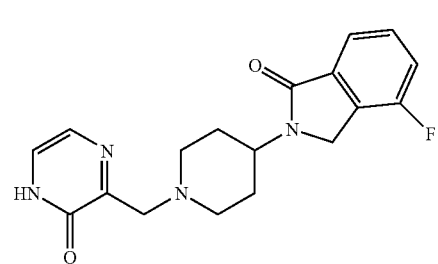
Example 186
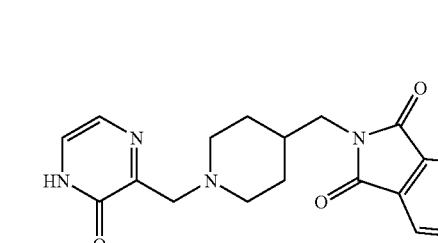
Example 187
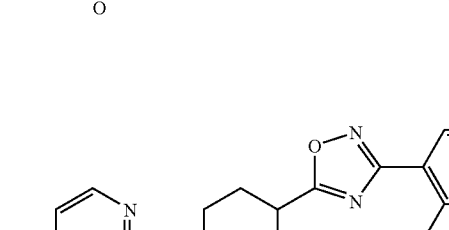
Example 188
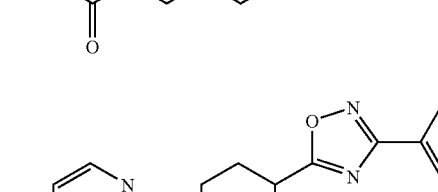

-continued

Example 189

Example 190

Example 191

Example 192

Example 193

Example 194

-continued

Example 195

Example 196

Example 197

Example 198

Example 199

Example 200

Example 201
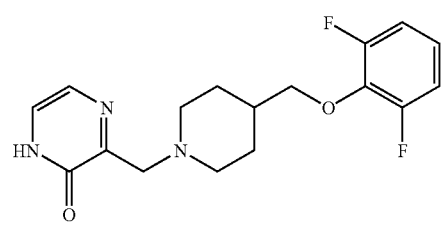
Example 202
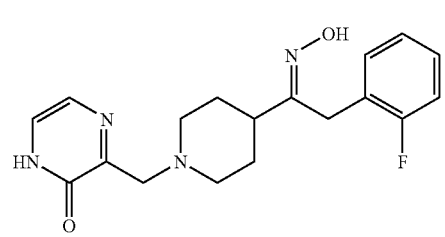
Example 203
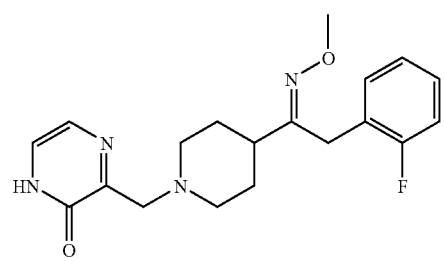
Example 204
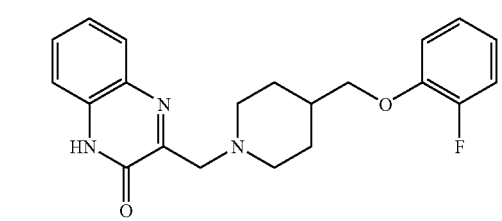
Example 205
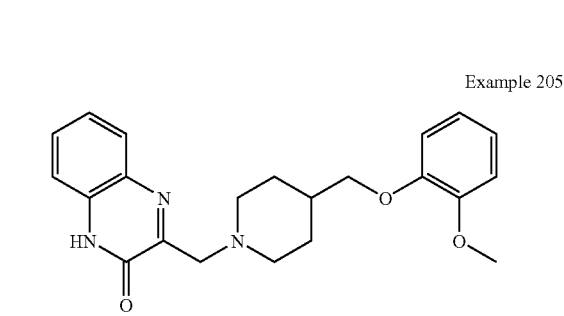
Example 206
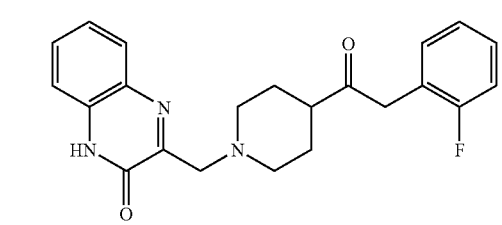
Example 207
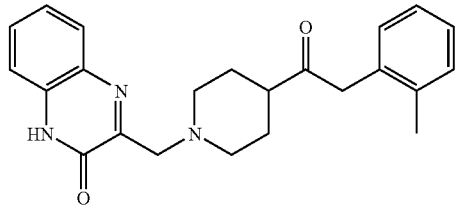
Example 208
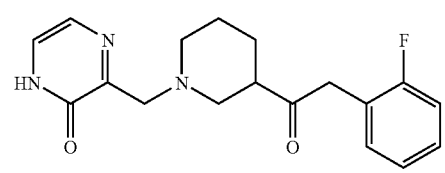
Example 209
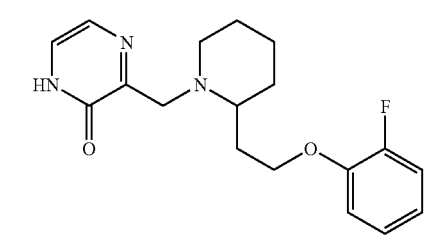
Example 210
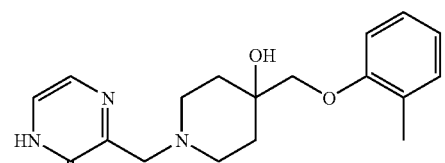
Example 211
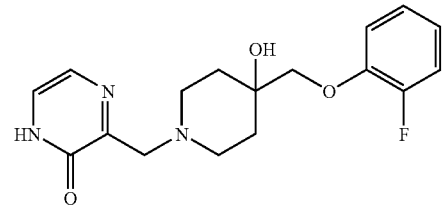
Example 212
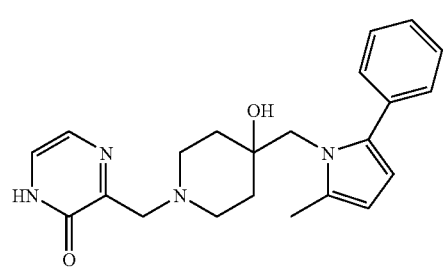
Example 213
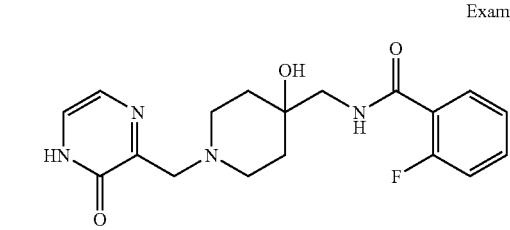

-continued
Example 214
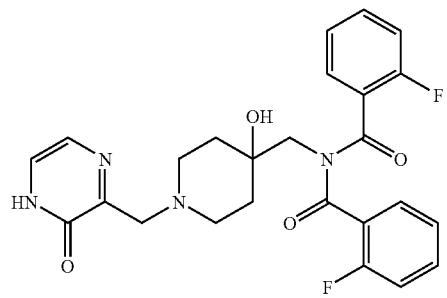
Example 215
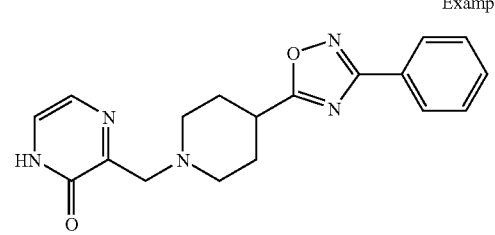
Example 216
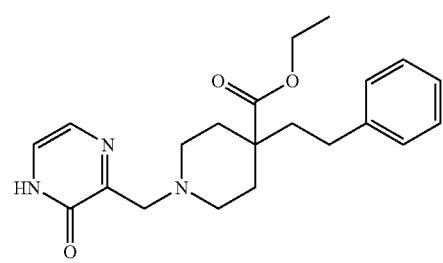
Example 217
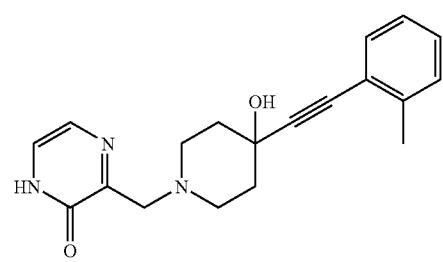
Example 218
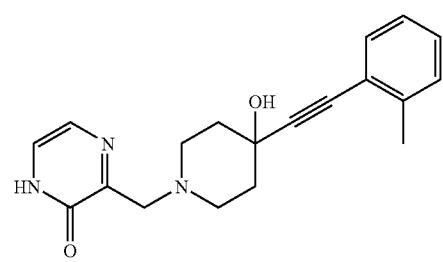
Example 219
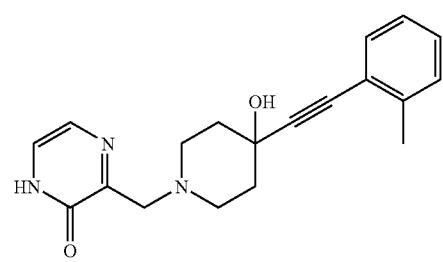
-continued
Example 220
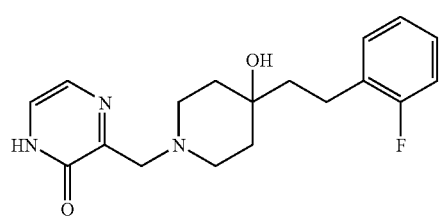
Example 221
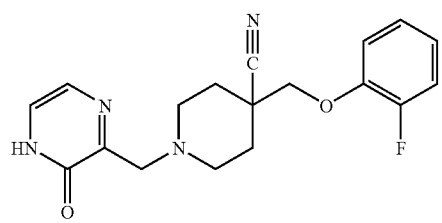
Example 222
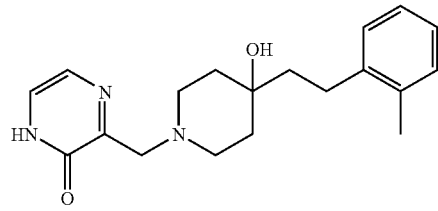
Example 223
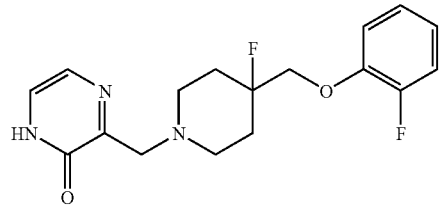
Example 224
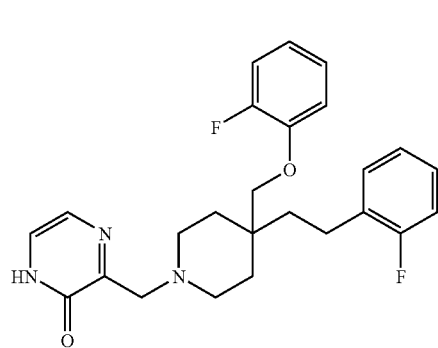
Example 225
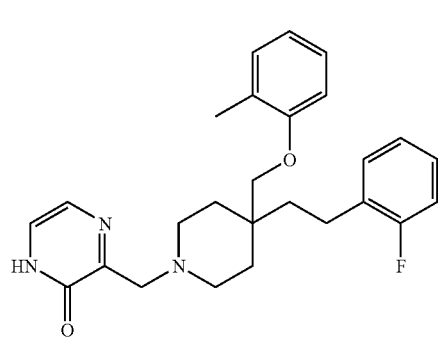

Example 226
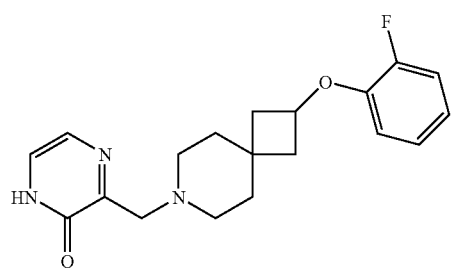
Example 227
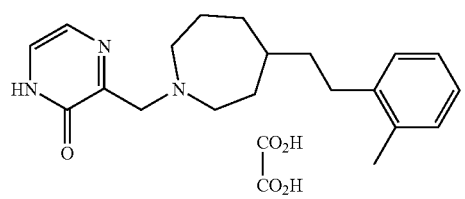
Example 228
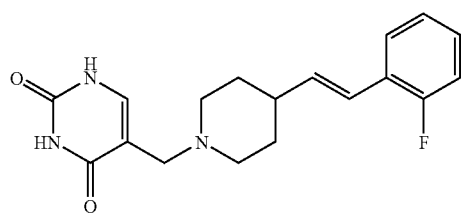
Example 229
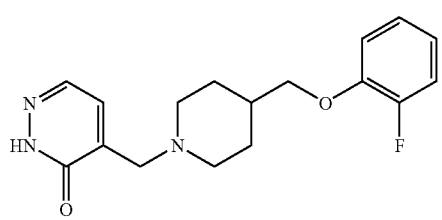
Example 230
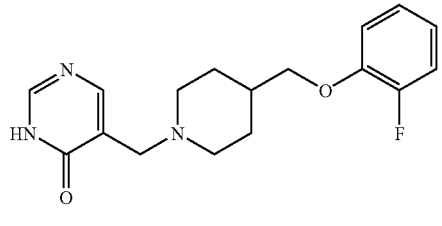
Example 231
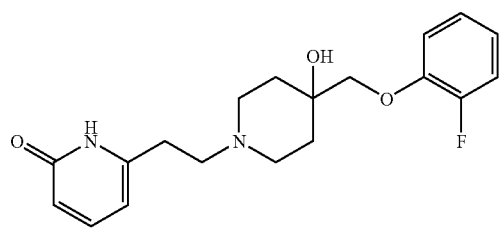
Example 232
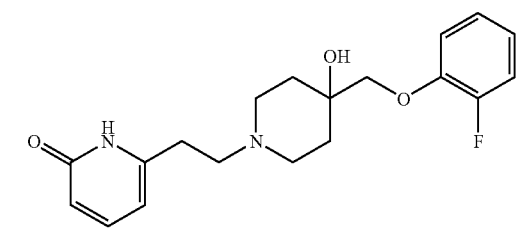
Example 233
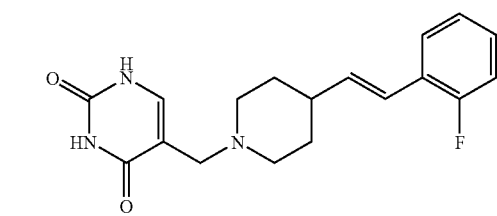
Example 234
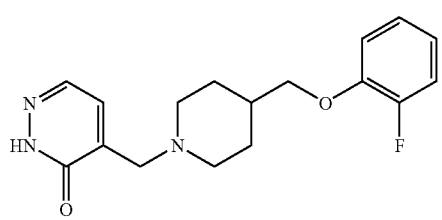
Example 235
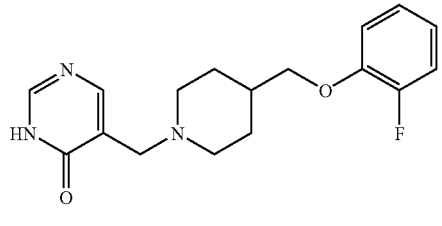
Example 236
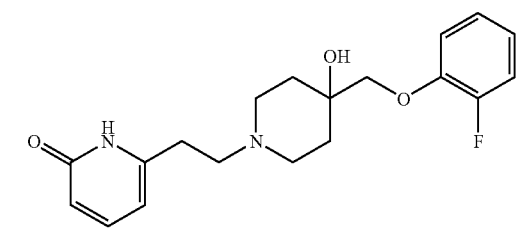
Example 237
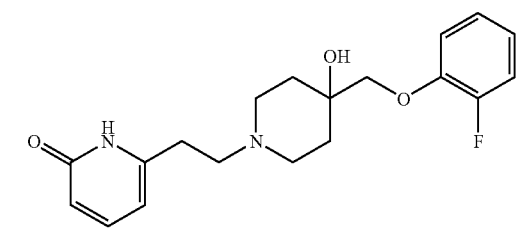

-continued
Example 238
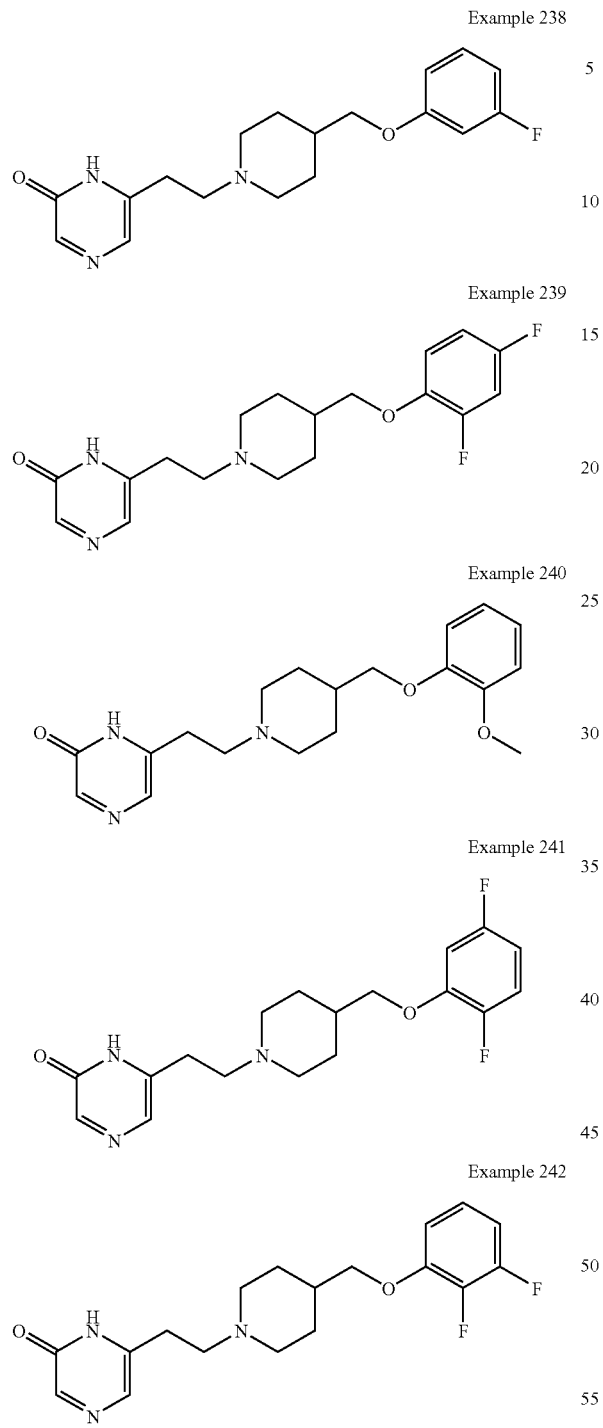
Example 239
Example 240
Example 241
Example 242
Example 243
-continued
Example 244
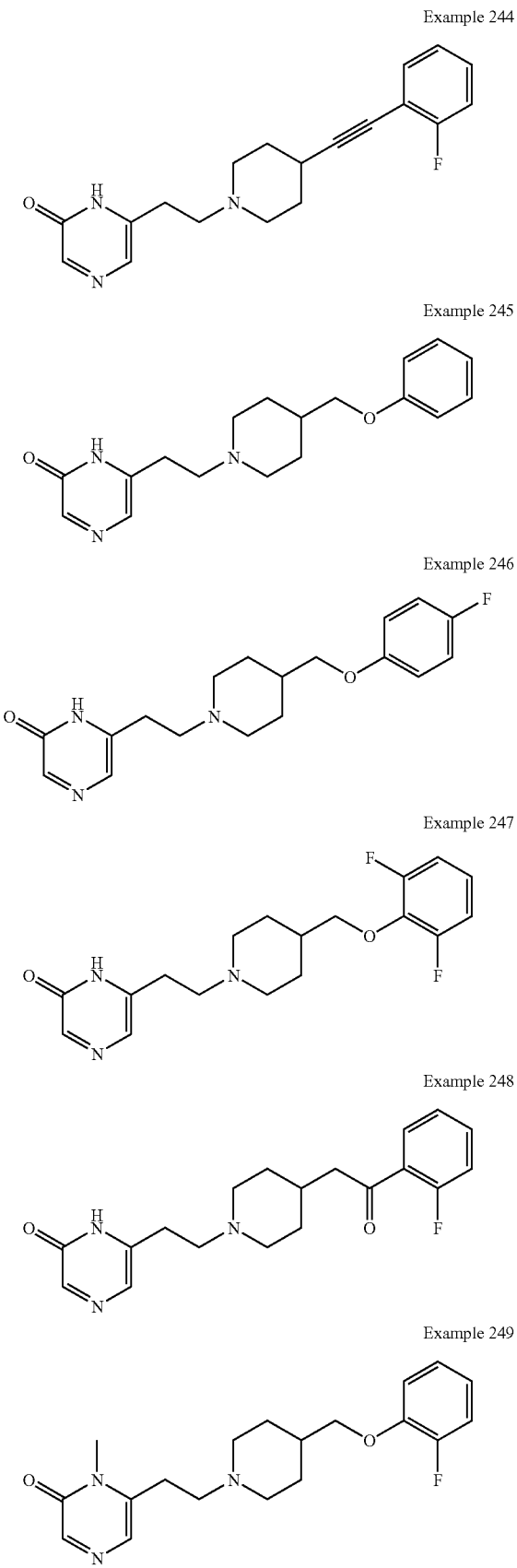
Example 245
Example 246
Example 247
Example 248
Example 249

-continued
Example 250
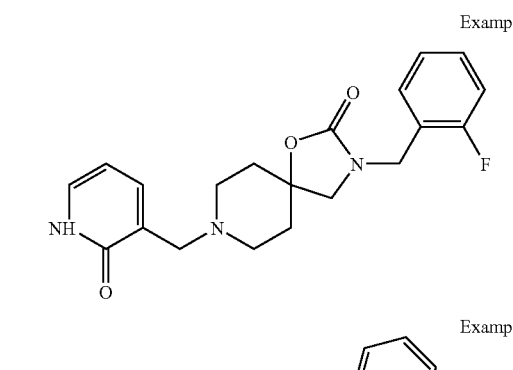
Example 251
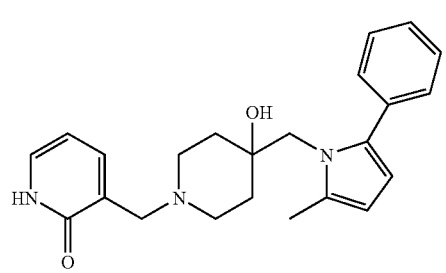
Example 252
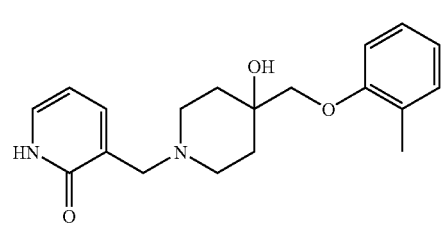
Example 253
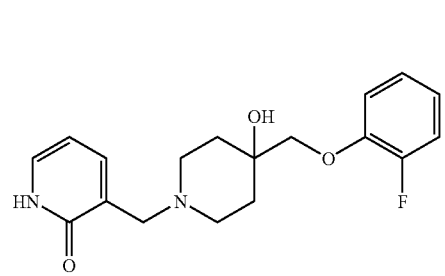
Example 254
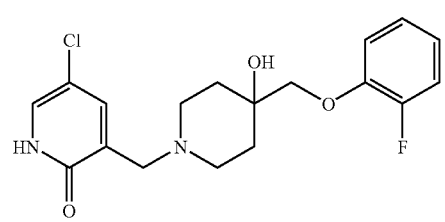
Example 255
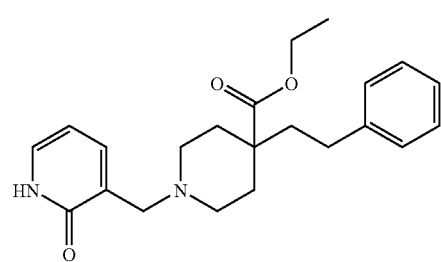
-continued
Example 256
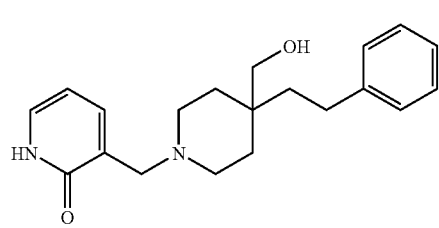
Example 257
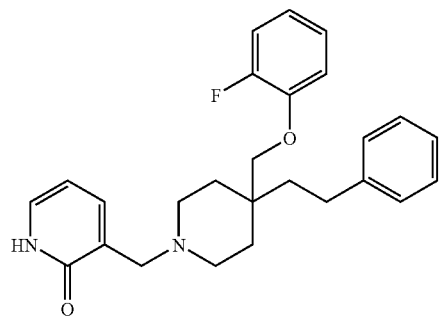
Example 258
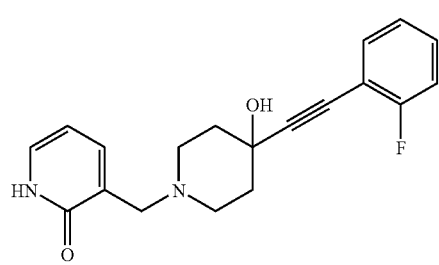
Example 259
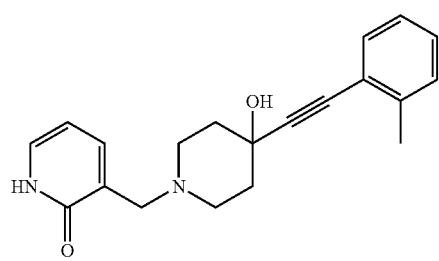
Example 260
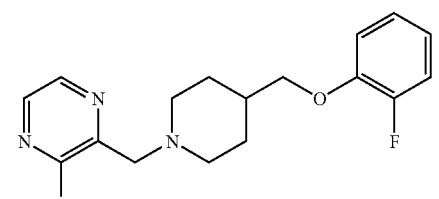
Example 261
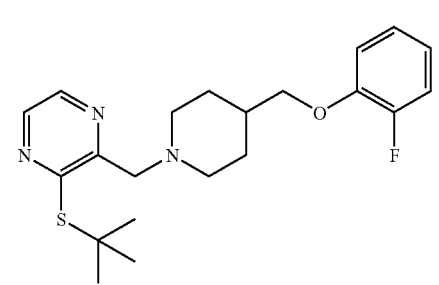

-continued

Example 262

Example 263

Example 264

Example 265

Example 266

-continued

Example 267

Example 268

Example 269

Example 270

Example 271

Example 272

Example 273
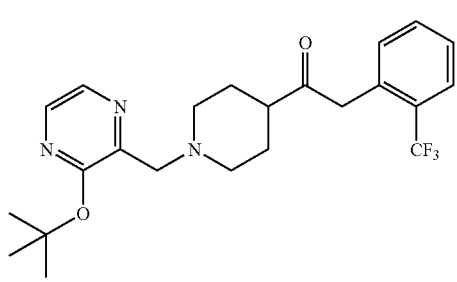
Example 274
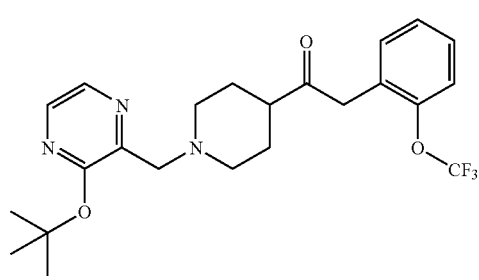
Example 275
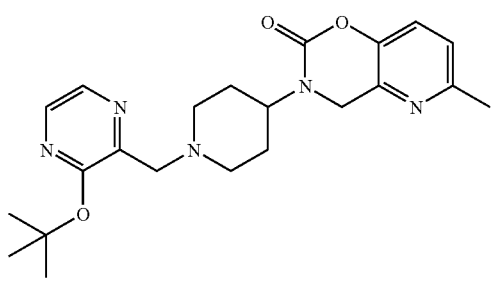
Example 276
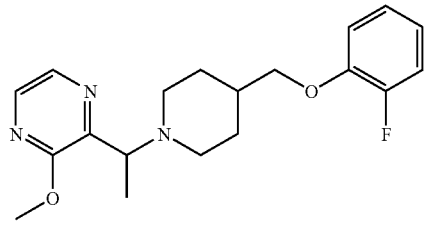
Example 277
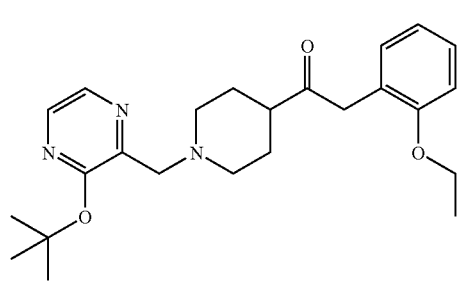
Example 278
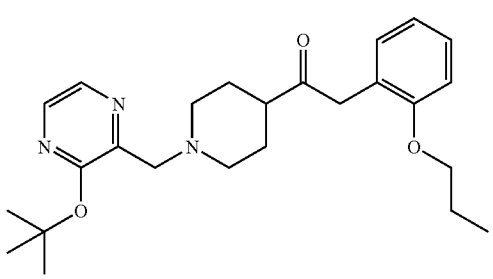
Example 279
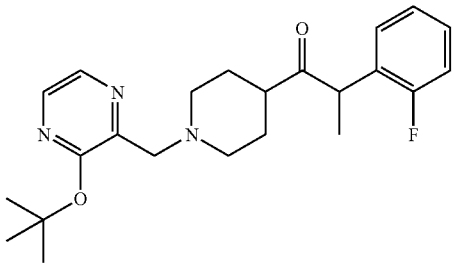
Example 280
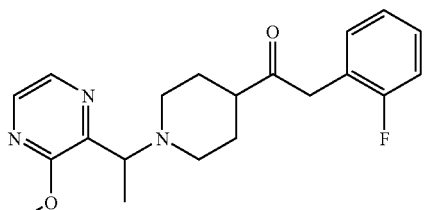
Example 281
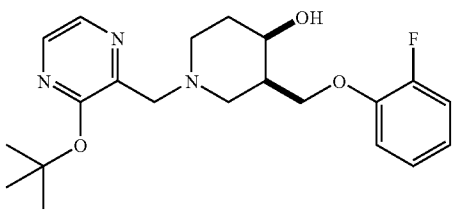
Example 282
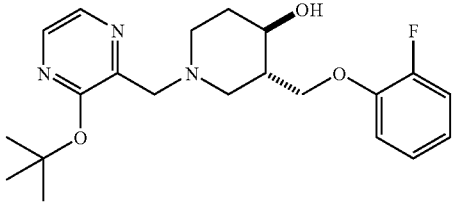
Example 283
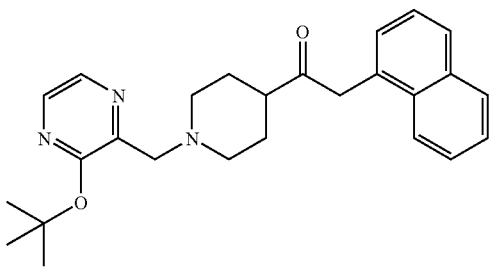

Example 284
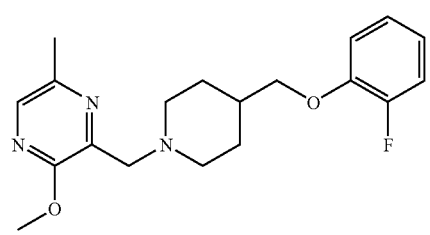
Example 285
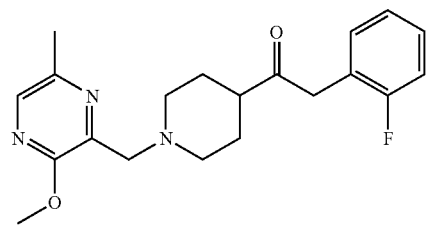
Example 286
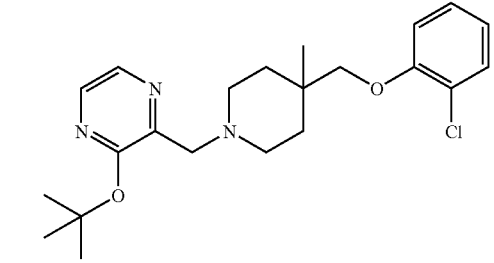
Example 287
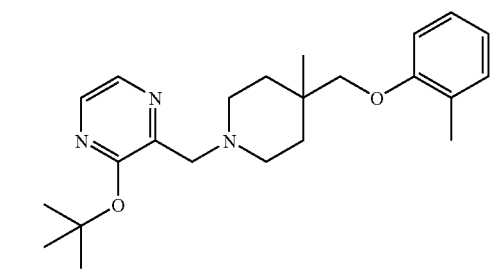
Example 288
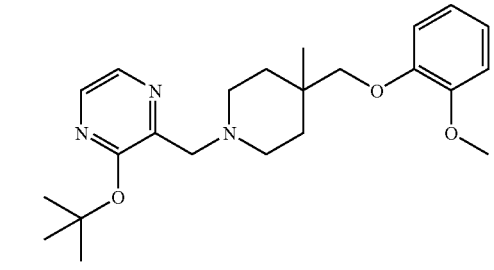
Example 289
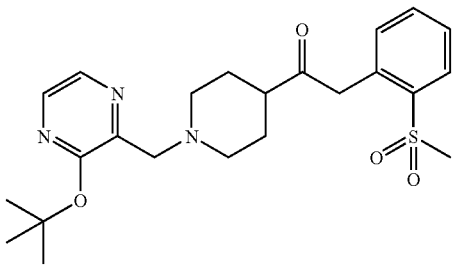
Example 290
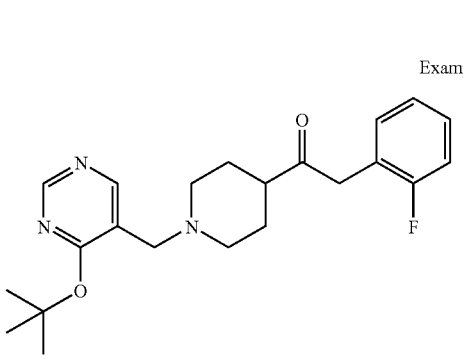
Example 291
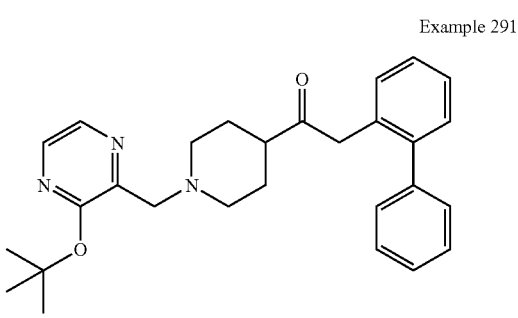
Example 292
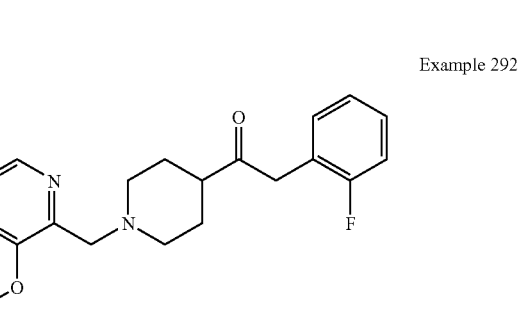
Example 293
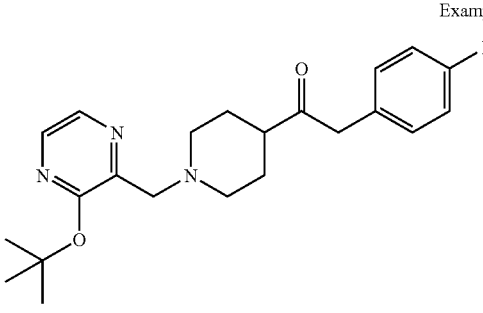

Example 294
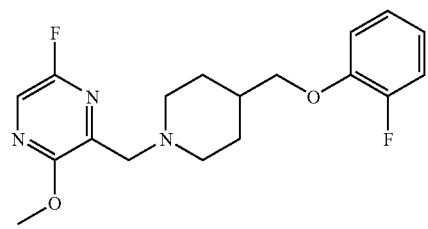
Example 295
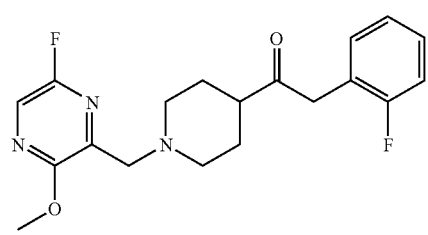
Example 296
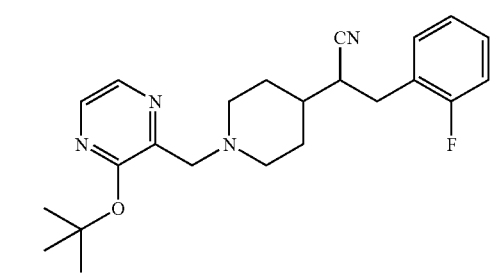
Example 297
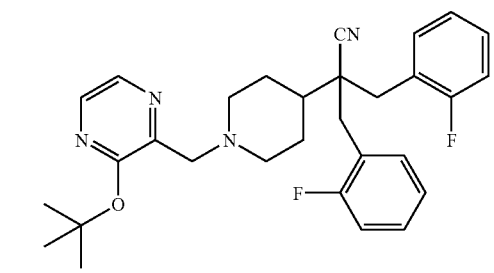
Example 298
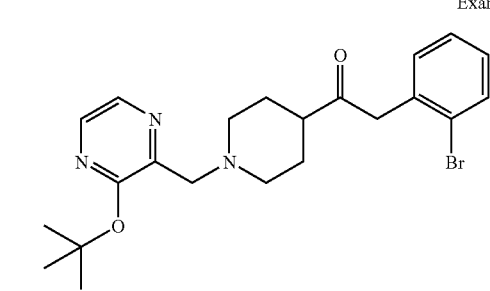
Example 299
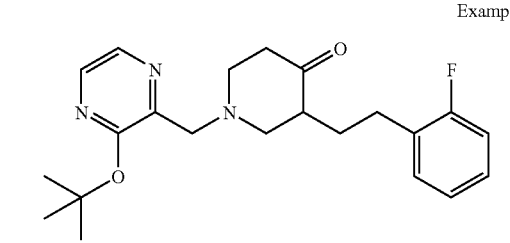
Example 300
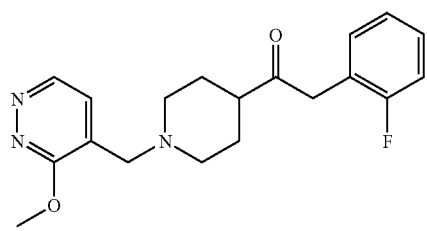
Example 301
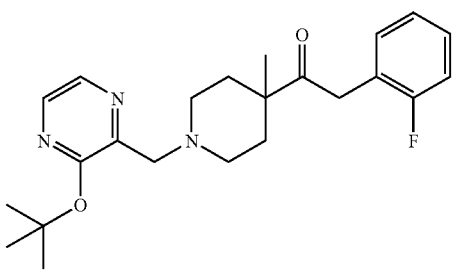
Example 302
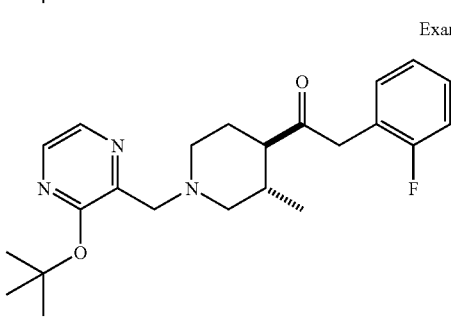
Example 303
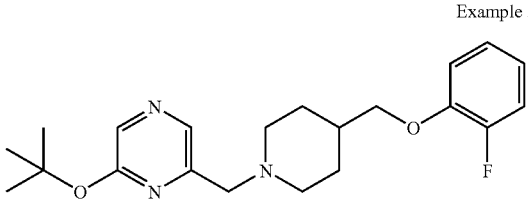
Example 304
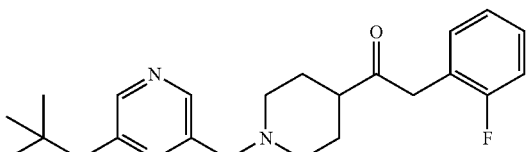
Example 305
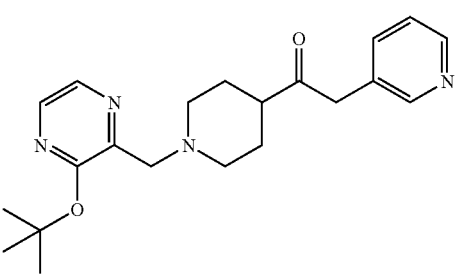

Example 306
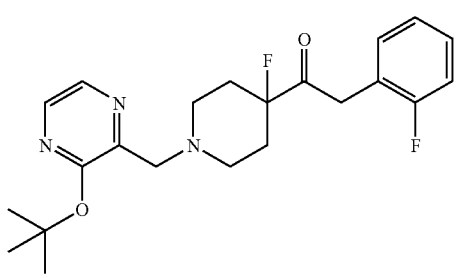
Example 307
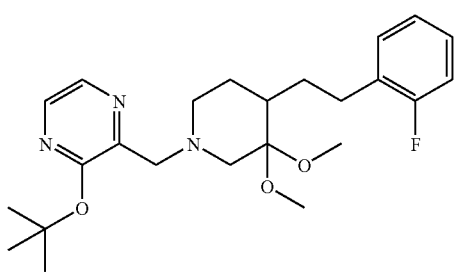
Example 308
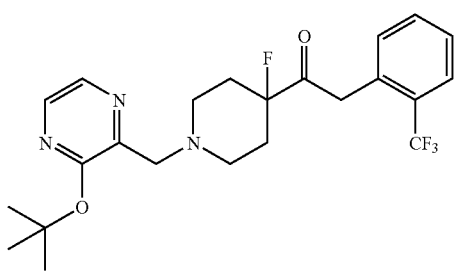
Example 309
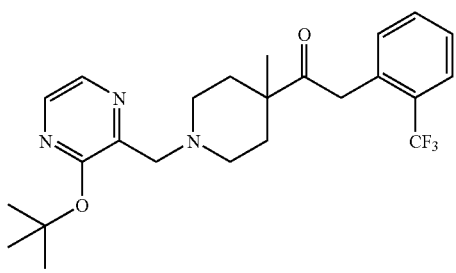
Example 310
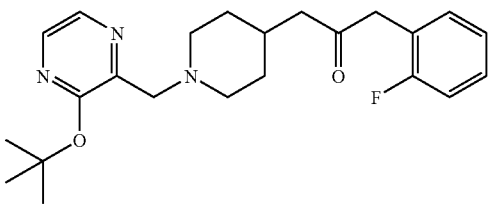
Example 311
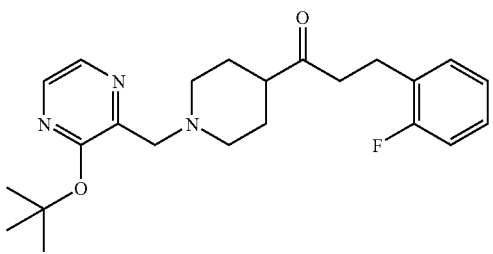
Example 312
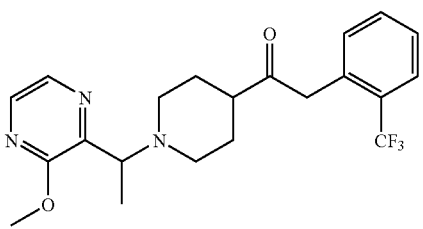
Example 313
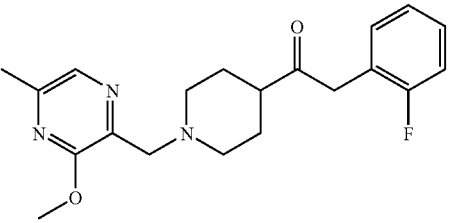
Example 314
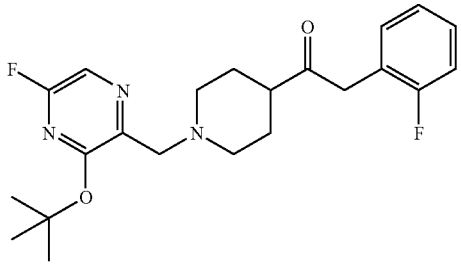
Example 315
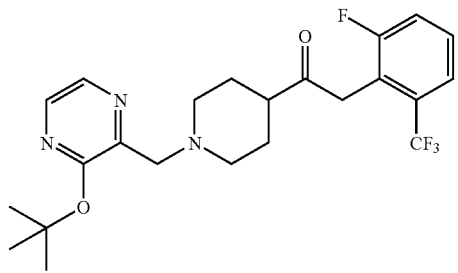

Example 316
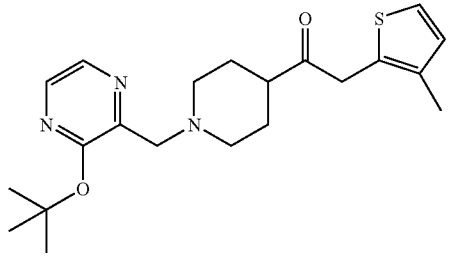
Example 317
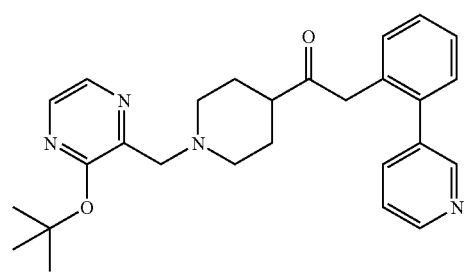
Example 318
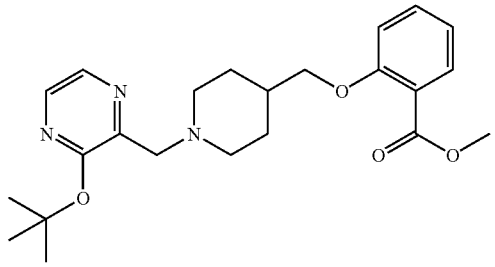
Example 319
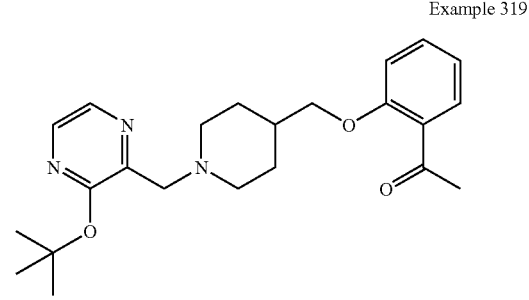
Example 320
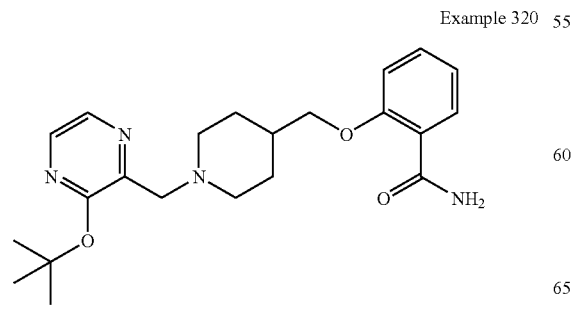
Example 321
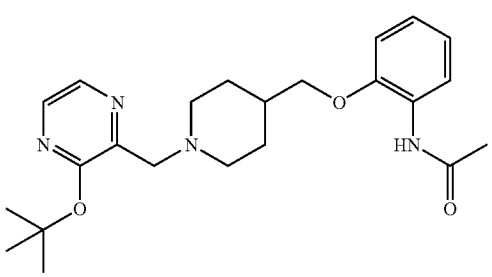
Example 322
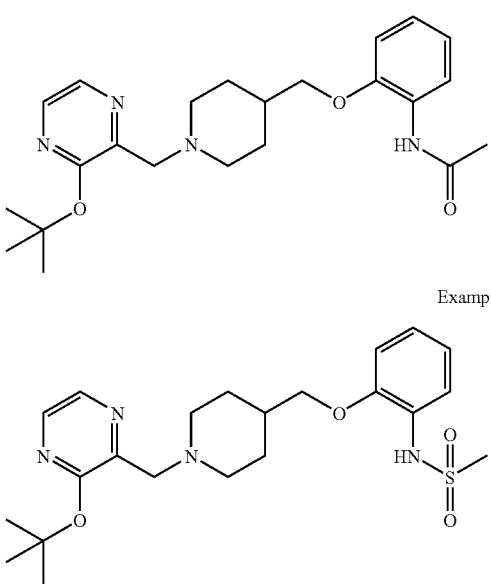
Example 323
Example 324
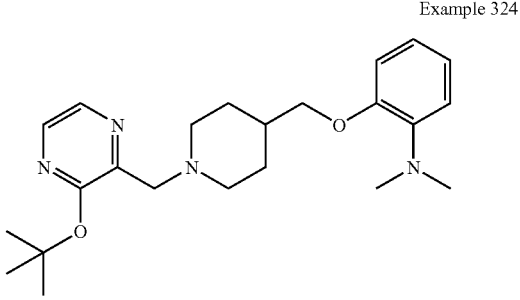
Example 325
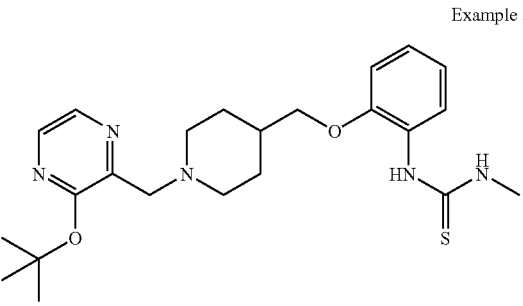

Example 326
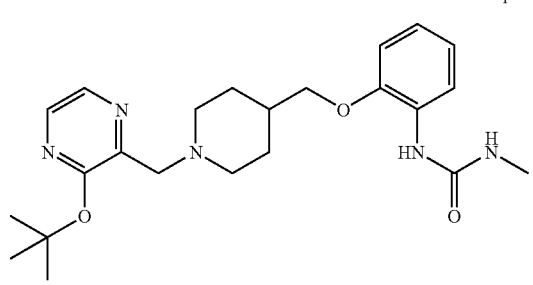
Example 327
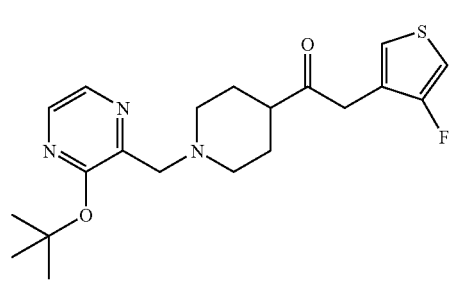
Example 328
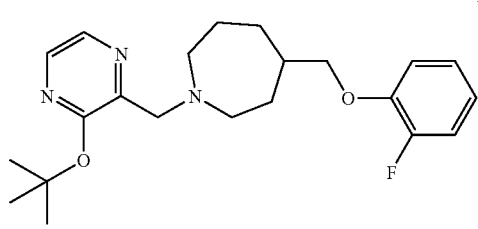
Example 329
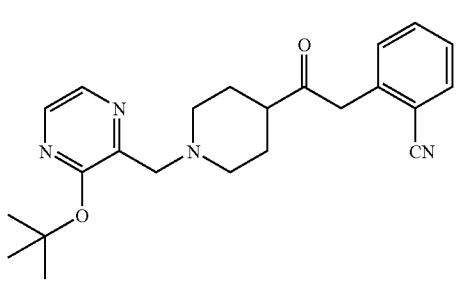
Example 330
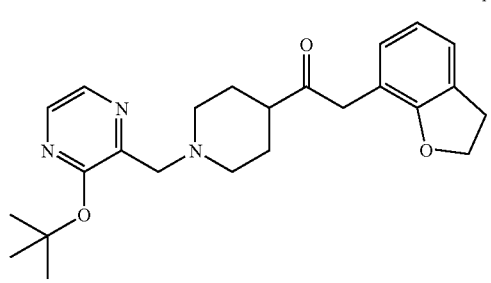
Example 331
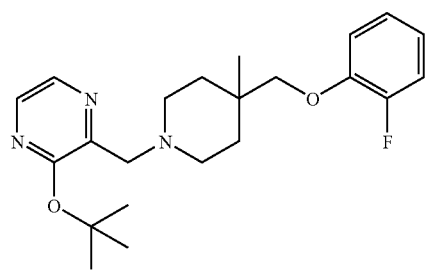
Example 332
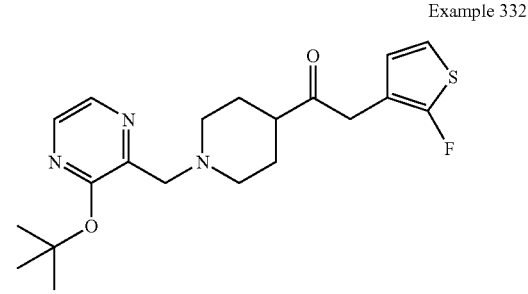
Example 333
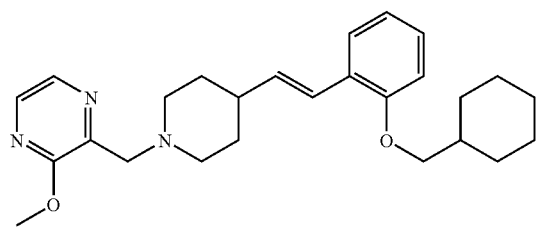
Example 334
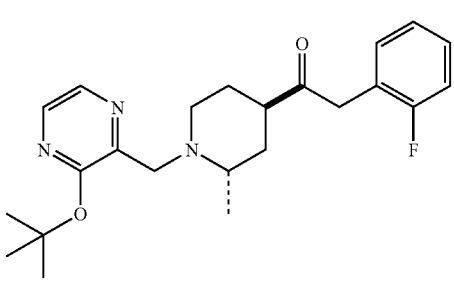
Example 335
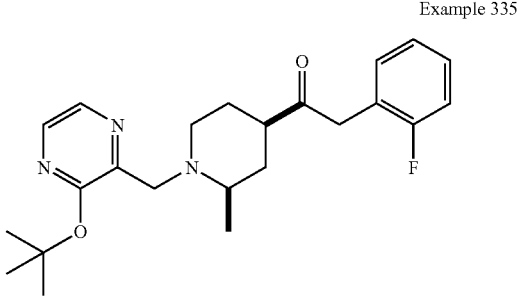

-continued
Example 336
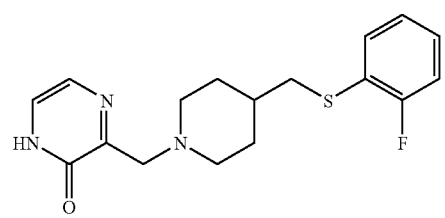
Example 337
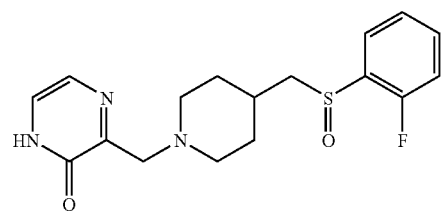
Example 338
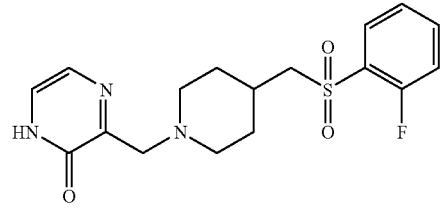
Example 339
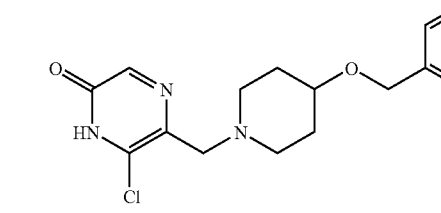
Example 340
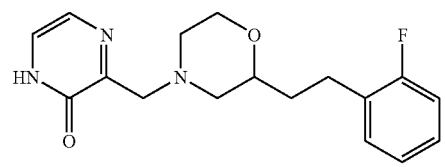
Example 341
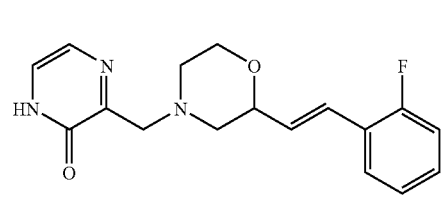
Example 342
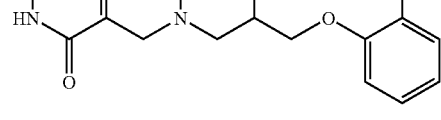
-continued
Example 343
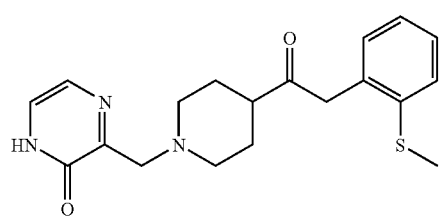
Example 344
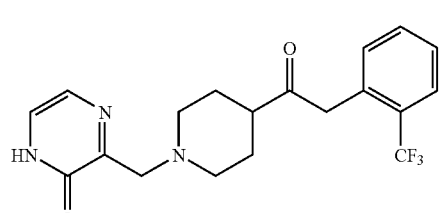
Example 345
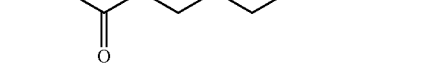
Example 346
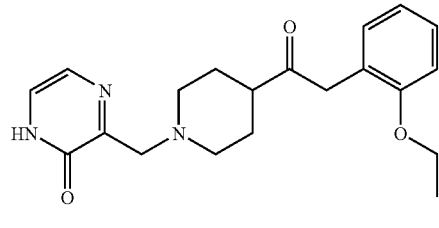
Example 347
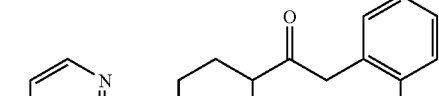
Example 348
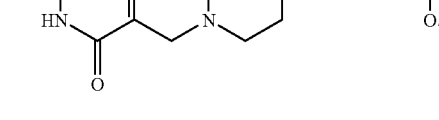

-continued
Example 349
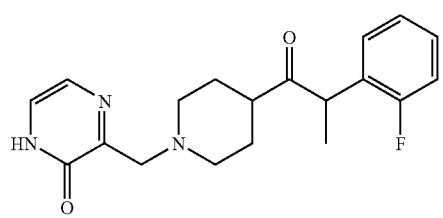
Example 350
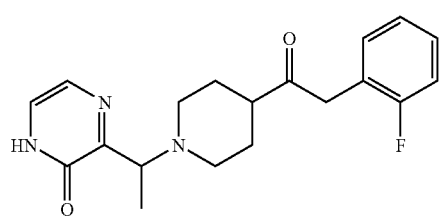
Example 351
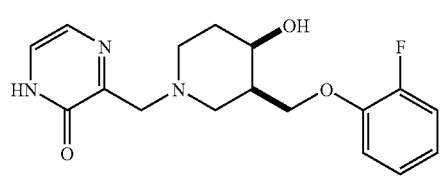
Example 352
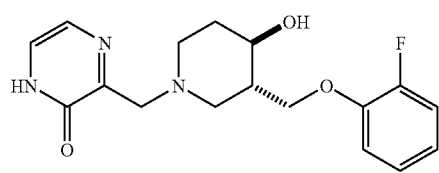
Example 353
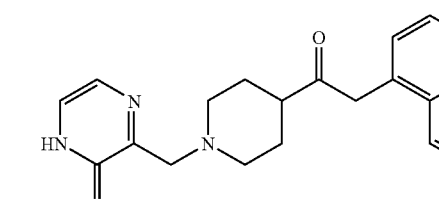
Example 354
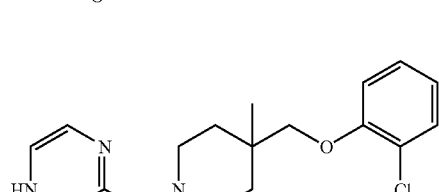
Example 355
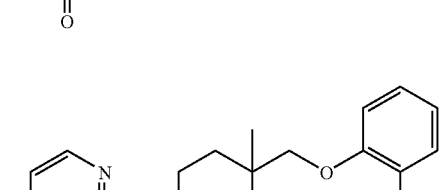
-continued
Example 356
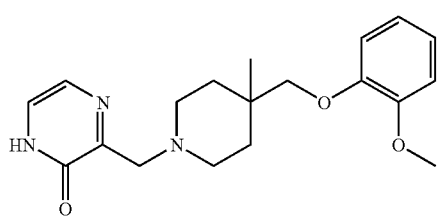
Example 357
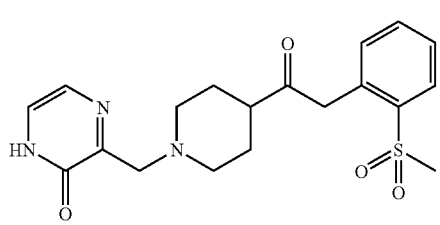
Example 358
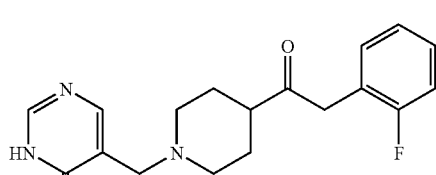
Example 359
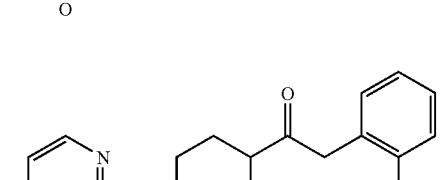
Example 360
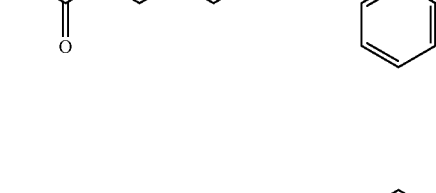
Example 361
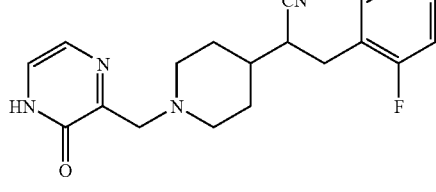

-continued
Example 362
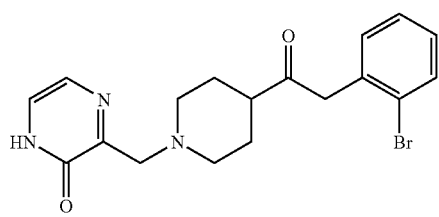
Example 363
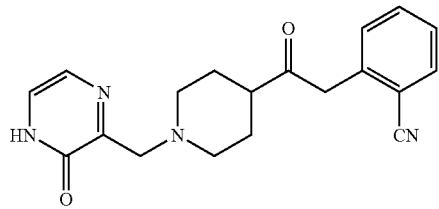
Example 364
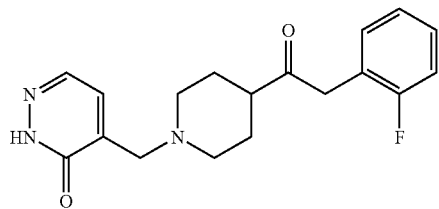
Example 365
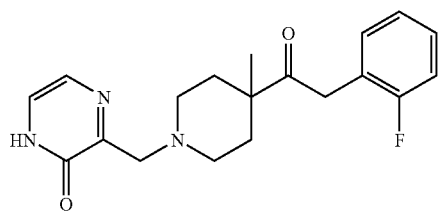
Example 366
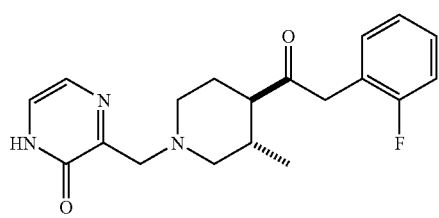
Example 367
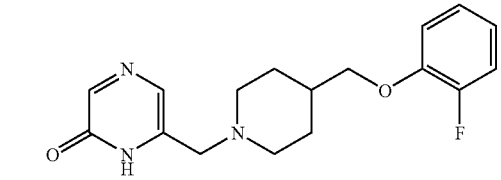
Example 368
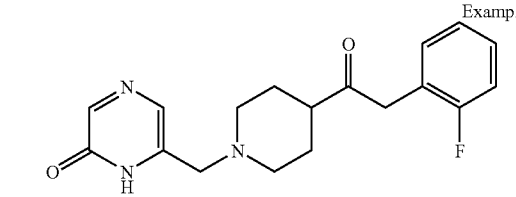
-continued
Example 369
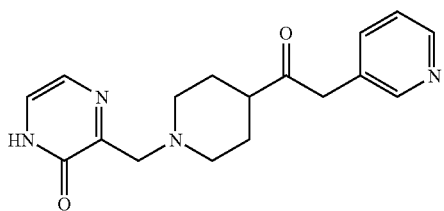
Example 370
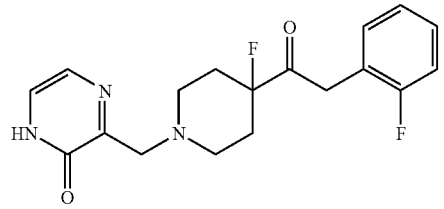
Example 371
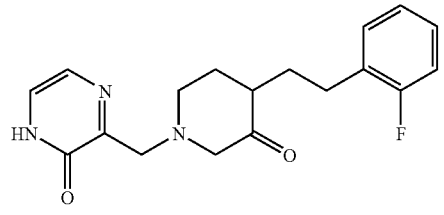
Example 372
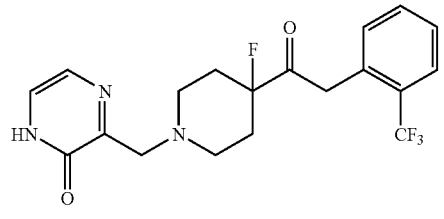
Example 373
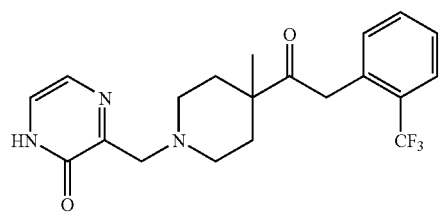
Example 374
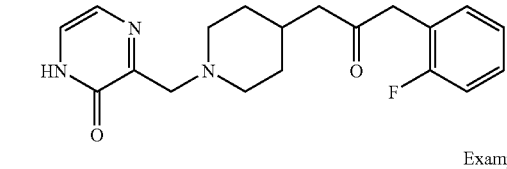
Example 375
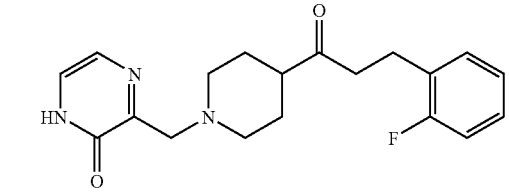

Example 376
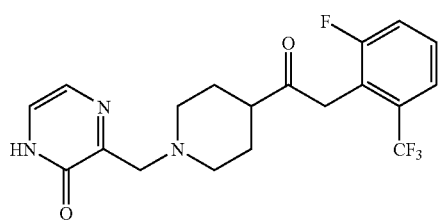
Example 382
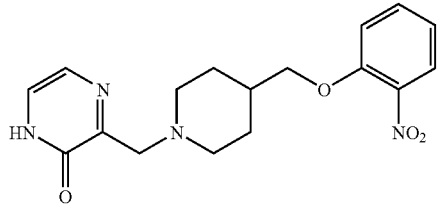
Example 377
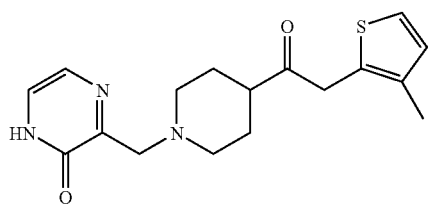
Example 383
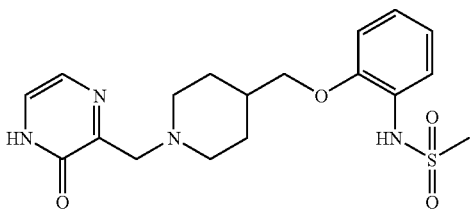
Example 378
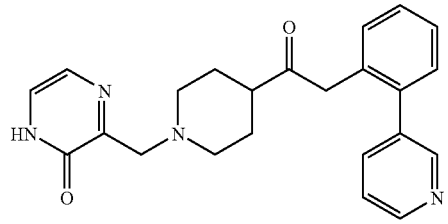
Example 384
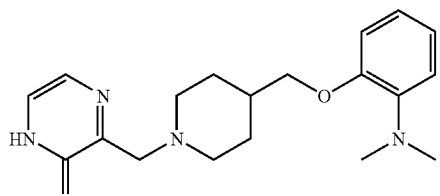
Example 385
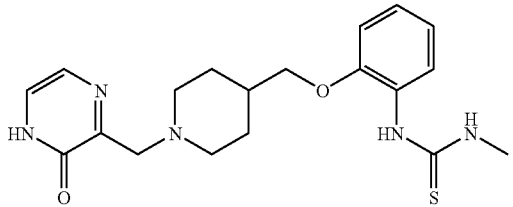
Example 379
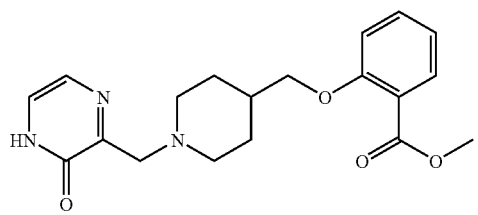
Example 386
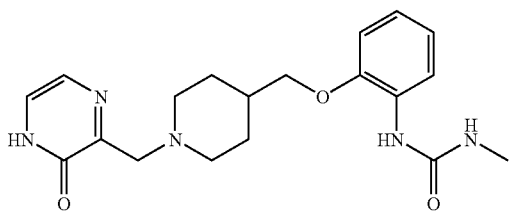
Example 380
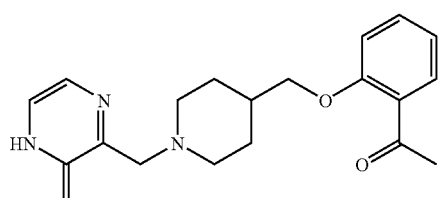
Example 387
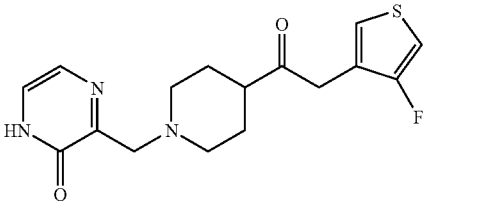
Example 381
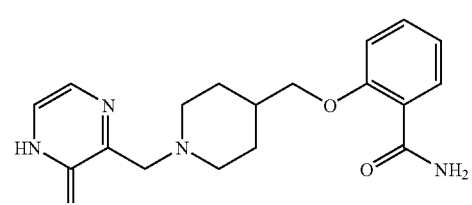
Example 388

-continued
Example 389
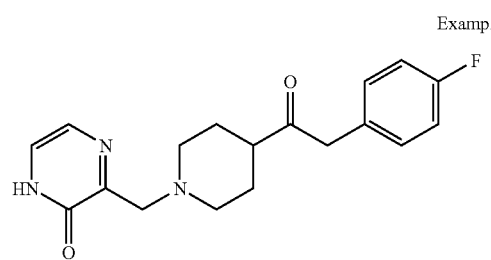
Example 390
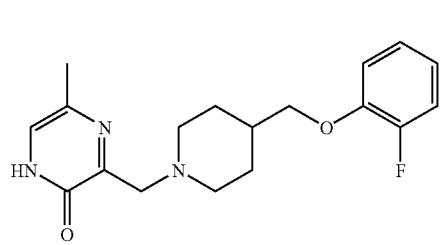
Example 391
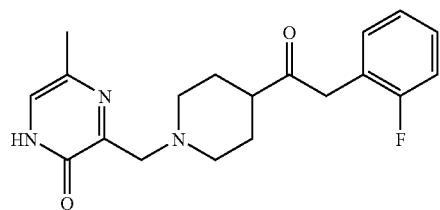
Example 392
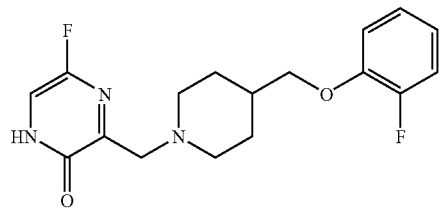
Example 393
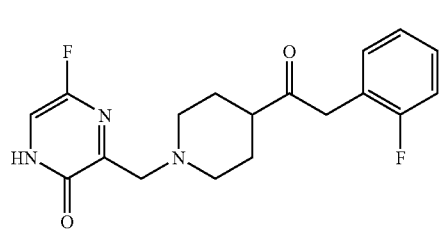
Example 394
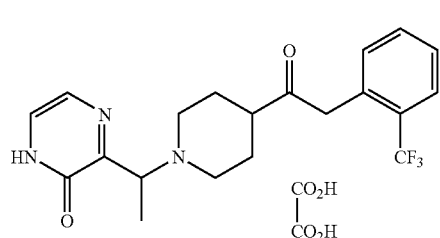
-continued
Example 395
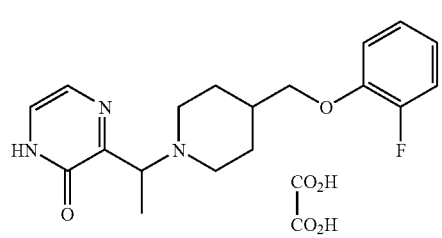
Example 396
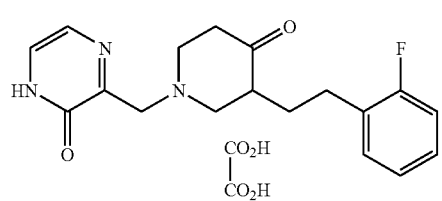
Example 397
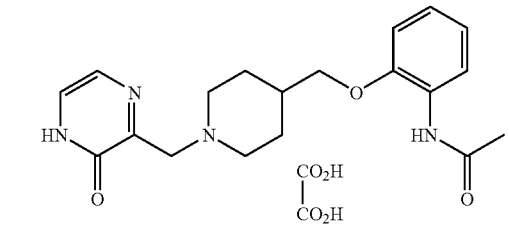
Example 398
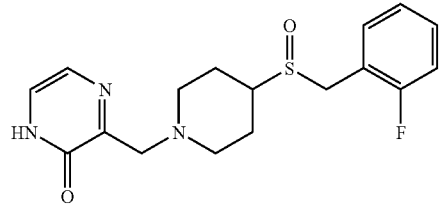
Example 399
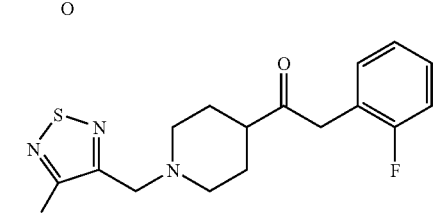
Example 400
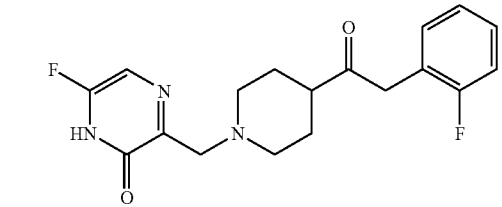
Example 401

-continued
Example 402
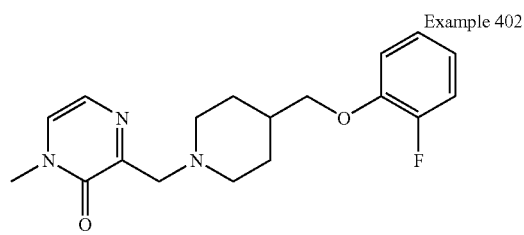
Example 403
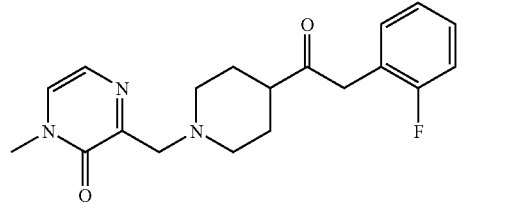
Example 404
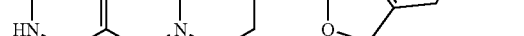
Example 405
Example 406
Example 407
Example 408
-continued
Example 409
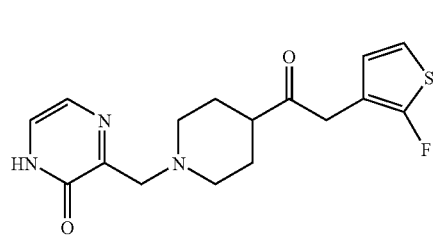
Example 410
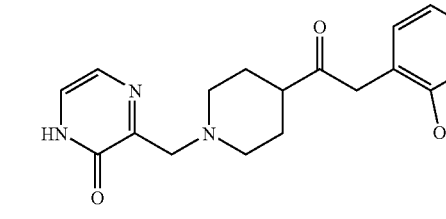
Example 411
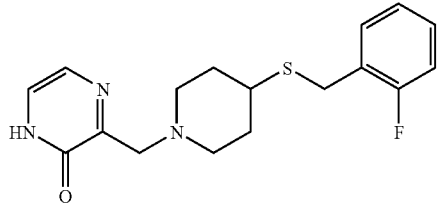
Example 412
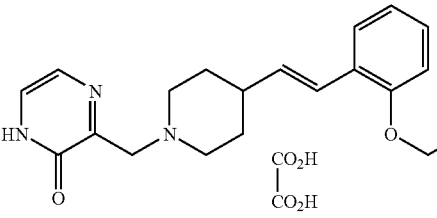
Example 413
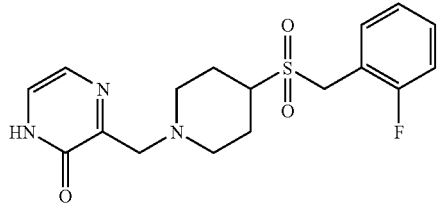
Example 414
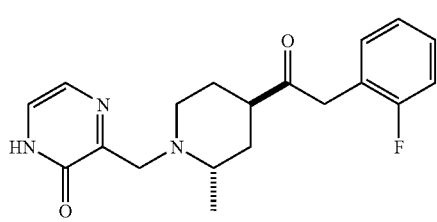
Example 415

Test Examples

Test Example 1

<Inhibition of Ectopic Firing>

(1) The inhibitory effect on ectopic firing was evaluated by the following method, with reference to Burchiel, K J., Exp. Neurol., 102, 249-253(1988).

(2) The left saphenous nerve of rats, in which ectopic firing was observed, was cut near the knee joint, and approximately 3 mm was cut off to avoid reattachment of the cut nerve. After more than a week, the left saphenous nerve was exposed under urethane (1 g/kg body weight) anesthesia, and the proximal part up to approximately 1 cm from the cut site was detached from the surrounding tissue. A catheter was inserted in the right cervical vein beforehand for administration of the compound.

(3) The detached nerve was placed on a platinum hook electrode and wetted with liquid paraffin to avoid drying of the nerve. The electrode was connected to a microelectrode amplifier, and the change in potential was recorded from an oscilloscope through an A/D converter onto a computer. The recorded nerve firing was evaluated based on the number of firings in 10 seconds, using analyzing software (AcqKnowledge).

<Test Results>

Table 1 shows the inhibition of different compounds of the examples against ectopic firing, for Test Example 1. An $ID_{50}$ of greater than 1 mg/kg and up to 3 mg/kg is indicated by +, an $ID_{50}$ of greater than 0.5 mg/kg and up to 1 mg/kg is indicated by ++, and an $ID_{50}$ of up to 0.5 mg/kg is indicated by +++. As the results in Table 1 clearly show, the compounds of the invention exhibited excellent inhibition of ectopic firing.

TABLE 1

| Example | Inhibition of ectopic firing |
|---------|------------------------------|
| 122 | +++ |
| 124 | +++ |
| 127 | ++ |
| 128 | ++ |
| 129 | ++ |
| 132 | ++ |
| 134 | ++ |
| 135 | +++ |
| 136 | ++ |
| 137 | ++ |
| 139 | ++ |
| 140 | +++ |
| 141 | +++ |
| 142 | +++ |
| 143 | +++ |
| 145 | ++ |
| 146 | +++ |
| 147 | +++ |
| 151 | ++ |
| 152 | ++ |
| 153 | ++ |
| 154 | ++ |
| 156 | ++ |
| 157 | +++ |
| 158 | +++ |
| 160 | ++ |
| 162 | ++ |
| 163 | +++ |
| 164 | +++ |
| 167 | +++ |
| 168 | ++ |
| 169 | ++ |
| 170 | +++ |
| 171 | +++ |
| 172 | ++ |
| 174 | +++ |
| 176 | ++ |
| 177 | +++ |
| 178 | +++ |
| 179 | +++ |
| 181 | +++ |
| 183 | +++ |
| 184 | +++ |
| 187 | ++ |
| 188 | ++ |
| 192 | ++ |
| 193 | +++ |
| 195 | ++ |
| 198 | +++ |
| 200 | ++ |
| 201 | ++ |
| 204 | ++ |
| 205 | ++ |
| 208 | ++ |
| 210 | ++ |
| 212 | ++ |
| 214 | ++ |
| 222 | ++ |
| 223 | ++ |
| 224 | ++ |
| 225 | ++ |
| 230 | +++ |
| 232 | +++ |
| 233 | +++ |
| 234 | ++ |
| 235 | +++ |
| 236 | +++ |
| 237 | ++ |
| 239 | ++ |
| 241 | ++ |
| 243 | +++ |
| 246 | ++ |
| 251 | ++ |
| 252 | ++ |
| 253 | +++ |
| 254 | ++ |
| 256 | ++ |
| 257 | +++ |
| 258 | +++ |
| 259 | +++ |
| 343 | +++ |
| 344 | +++ |
| 347 | +++ |
| 350 | +++ |
| 365 | +++ |
| 373 | +++ |
| 376 | +++ |
| 394 | +++ |
| 415 | +++ |
| Mexiletine | + |

Test Example 2

<Evaluation of Sodium Channels Using Rat Cultured Hippocampal Neurons>

(1) This experiment was conducted using rat fetal (E17-E19) cultured hippocampal neurons. The hippocampal neurons were cultured for 3-4 weeks until spontaneous firing occurred.

(2) The sodium-sensitive dye SBFI-AM [CAS No. 129423-53-6] (Sigma) was added to the hippocampal culture supernatant and incorporated therein for several hours at 37° C.

(3) The sodium ion concentration in the hippocampal neurons was measured in the presence of 4-aminopyridine as an index of the SBFI fluorescent intensity. The measurement was conducted at room temperature using an FDSS2000 (Hamamatsu Photonics K.K.). In order to detect the change in intracellular sodium concentration upon addition of the test substance, the fluorescent intensity was measured immediately prior to addition of the test substance and 5 minutes afterwards (excitation wavelengths: 340 nm and 380 nm, fluorescent wavelength: 500 nm).

(4) The sodium channel-inhibiting activity of the test substance was calculated from the change in fluorescent intensity before and after addition of the test substance (fluorescent intensity at excitation wavelength of 340 nm/fluorescent intensity at excitation wavelength of 380 nm). The change in fluorescent intensity using 1 μM tetrodotoxin (TTX) as a positive control was defined as 100% and the change in fluorescent intensity with the solution alone as a negative control was defined as 0%. The relative value of the change in fluorescent intensity for the test substance was calculated as the sodium channel-inhibiting activity ($IC_{50}$ (μM)).

<Test Results>

Tables 2 and 3 show the sodium channel-inhibiting activities ($IC_{50}$ (μM)) of different compounds of the examples, for Test Example 2. As clearly shown by the results in Tables 2 and 3, the compounds of the invention exhibited excellent sodium channel-inhibiting activity.

TABLE 2

| Example | $IC_{50}$ (μM) | Example | $IC_{50}$ (μM) | Example | $IC_{50}$ (μM) | Example | $IC_{50}$ (μM) |
|---|---|---|---|---|---|---|---|
| 117 | 4.4 | 168 | 2.1 | 210 | 6.0 | 340 | 7.1 |
| 118 | 3.1 | 169 | 3.5 | 211 | 8.2 | 341 | 7.1 |
| 119 | 8.4 | 170 | 0.4 | 212 | 6.1 | 342 | 3.0 |
| 120 | 8.5 | 171 | 0.6 | 214 | 8.7 | 343 | 3.5 |
| 121 | 5.7 | 172 | 5.0 | 215 | 4.1 | 344 | 4.4 |
| 124 | 7.8 | 173 | 4.3 | 216 | 3.2 | 345 | 2.1 |
| 125 | 5.0 | 174 | 3.6 | 217 | 1.8 | 347 | 3.0 |
| 129 | 2.1 | 175 | 2.6 | 218 | 3.6 | 348 | 2.6 |
| 132 | 6.2 | 176 | 5.4 | 219 | 1.6 | 349 | 8.9 |
| 134 | 3.1 | 177 | 4.5 | 221 | 4.9 | 350 | 6.0 |
| 135 | 4.0 | 179 | 4.6 | 222 | 2.5 | 353 | 1.7 |
| 136 | 4.7 | 182 | 7.8 | 223 | 6.0 | 354 | 2.8 |
| 140 | 5.6 | 183 | 2.6 | 224 | 1.6 | 355 | 2.5 |
| 142 | 4.2 | 184 | 2.9 | 225 | 1.6 | 356 | 2.9 |
| 143 | 3.1 | 187 | 3.5 | 226 | 4.5 | 359 | 1.4 |
| 144 | 5.8 | 188 | 5.0 | 235 | 5.0 | 362 | 4.5 |
| 145 | 9.5 | 189 | 7.2 | 236 | 7.0 | 364 | 9.3 |
| 146 | 2.0 | 190 | 1.2 | 238 | 5.6 | 365 | 3.4 |
| 147 | 2.5 | 191 | 7.1 | 239 | 9.1 | 366 | 4.2 |
| 151 | 2.9 | 192 | 3.8 | 240 | 6.4 | 370 | 9.6 |
| 152 | 5.3 | 193 | 2.9 | 241 | 5.0 | 371 | 9.0 |
| 153 | 4.1 | 194 | 6.6 | 242 | 6.2 | 372 | 3.3 |
| 154 | 3.1 | 195 | 2.0 | 243 | 5.7 | 373 | 1.6 |
| 155 | 3.5 | 196 | 6.2 | 244 | 3.1 | 376 | 1.1 |
| 156 | 4.5 | 198 | 1.6 | 245 | 4.4 | 388 | 4.7 |

TABLE 3

| Example | $IC_{50}$ (μM) | Example | $IC_{50}$ (μM) | Example | $IC_{50}$ (μM) | Example | $IC_{50}$ (μM) |
|---|---|---|---|---|---|---|---|
| 157 | 3.6 | 199 | 6.2 | 249 | 3.2 | 394 | 2.8 |
| 158 | 3.7 | 200 | 1.6 | 251 | 8.4 | 395 | 6.7 |
| 159 | 9.4 | 201 | 6.7 | 253 | 9.2 | 398 | 3.4 |
| 160 | 3.5 | 202 | 4.9 | 254 | 8.9 | 406 | 3.0 |
| 161 | 3.5 | 203 | 2.3 | 255 | 3.1 | 410 | 5.7 |
| 162 | 4.6 | 204 | 8.1 | 256 | 5.8 | 411 | 4.8 |
| 164 | 3.3 | 205 | 2.6 | 258 | 4.2 | 412 | 1.2 |
| 165 | 8.4 | 206 | 5.2 | 336 | 4.7 | 414 | 7.9 |
| 166 | 8.7 | 208 | 5.5 | 337 | 6.5 | 415 | 4.6 |
| 167 | 2.3 | 209 | 2.1 | 338 | 9.8 | | |

Test Example 3

<Evaluation of Cardiovascular Dynamics and Electrocardiogram in Anesthetized Dogs>

Method

Anesthetized dogs were used for the experiment. After isolating the left and right femoral veins, a microchip pressure transducer catheter was inserted therein, and the tip was situated near the aortic orifice and in the left ventricle, for measurement of the arterial pressure (AP) and left ventricular pressure (LVP). The LVP was differentiated using a differentiation unit, and the maximum value of the first derivative of the left ventricular pressure (LVdP/dt) (LVdP/dtmax) was used as the index of the cariac contractility. The heart rate (HR) was measured using an instantaneous heart rate counter, with the LVP waveforms as the trigger. A needle electrode was fixed to the right anterior limb and left and right posterior limbs, and a standard II-lead electrocardiogram was taken. The parameters were recorded on a recording sheet.

The test substance was administered through the venous catheter inserted in the femoral vein.

Administration of Test Substance and Recording

Single Administration:

The test substance was administered through the catheter for 1 minute. The electrocardiogram was recorded at 2 minutes after administration, and the change in the cardiovascular dynamic was recorded continuously for 10 minutes after the administration. After 10 minutes, the dose was increased and the recording was repeated.

Continuous Intravenous Infusion:

The test substance was administered through the catheter for a period of one minute, and then a sustained dose was administered by continuous intravenous infusion. The electrocardiogram was recorded at the 5 and 10 minute points, and the change in cardiovascular dynamic was recorded continuously for 10 minutes from the start of administration. After 10 minutes, the dose was increased and the recording was repeated.

Analysis

The HR, mean arterial pressure (mAP), LVdP/dtmax and electrocardiogram parameters (RR interval, PQ interval, QRS interval, QT interval) were read from the recording sheet. The QT interval was heart rate-corrected and represented as the QTc interval.

<Test Results>

Tables 4 to 8 show the changes in the electrocardiogram parameters upon single administration of known sodium channel inhibitors for Test Example 3. The numbers in the tables indicate the percent changes with respect to the measured values prior to administration of each sodium channel inhibitor. As clearly shown by the results in Tables 4 to 8, the known sodium channel-inhibiting compounds such as Mexiletine, Pilsicainide, Flecainide, Aprindine and Amitriptyline exhibited effects on the cardiovascular system.

TABLE 4

Mexiletine

| Dose (mg/kg weight) | HR | mAP | LVdP/dt | PQ interval | QRS interval | QTc interval |
|---|---|---|---|---|---|---|
| 2.2 | −2.8 | −6.2 | −20.8 | 0.7 | 1.8 | −3.0 |
| 6.6 | −10.6 | −44.2 | −47.8 | 3.4 | 6.3 | −4.6 |

TABLE 5

Pilsicainide

| Dose (mg/kg weight) | HR | mAP | LVdP/dt | PQ interval | QRS interval | QTc interval |
|---|---|---|---|---|---|---|
| 1 | −1.0 | −3.2 | −20.6 | 17.4 | | 4.6 |
| 3 | −5.0 | −8.2 | −31.7 | 55.1 | | 5.3 |

TABLE 6

Flecainide

| Dose (mg/kg weight) | HR | mAP | LVdP/dt | PQ interval | QRS interval | QTc interval |
|---|---|---|---|---|---|---|
| 1 | −8.6 | −14.2 | −18.2 | 8.8 | 6.4 | 2.3 |
| 3 | −24.8 | −42.9 | −56.9 | 36.1 | 37.1 | 9.3 |

TABLE 7

Aprindine

| Dose (mg/kg weight) | HR | mAP | LVdP/dt | PQ interval | QRS interval | QTc interval |
|---|---|---|---|---|---|---|
| 2 | −12.8 | −34.7 | −29 | 14.2 | | 4.5 |
| 4 | −19.2 | −47.7 | −47.5 | 36.8 | | −0.4 |

TABLE 8

Amitriptyline

| Dose (mg/kg weight) | HR | mAP | LVdP/dt | PQ interval | QRS interval | QTc interval |
|---|---|---|---|---|---|---|
| 0.3 | −2.9 | −0.9 | −5.9 | −1.5 | 0.4 | 1.9 |
| 1 | −4.0 | −25.4 | −21.7 | 8.7 | 15.4 | 13.1 |

In Test Example 3, the effects of the representative compounds of the invention on the cardiovascular system were also evaluated, and it was confirmed that single administration at 1 mg/kg body weight and greater produced virtually no effect on the HR, mean arterial pressure (mAP), LVdP/dtmax and electrocardiogram parameters (RR interval, PQ interval, QRS interval, QT interval).

Test Example 4

<Evaluation of Drug Metabolizing Enzyme (Cytochrome P450)>

This experiment was conducted using an activity measuring kit (GENTES) employing a P450 recombinant expression system and a fluorescent substrate, following the included instruction manual, and the inhibiting activity $IC_{50}$ was calculated. The evaluated P450 molecular species were the following five: CYP1A2, CYP2C9, CYP2C19, CYP2D6, CYP3A4 and the like. The experiment conditions were as shown below. A plate reader (CYTO FLUOR Multi-Well Plate Reader Series 4000, by PerSeptive Biosystems) was used for measurement of the fluorescent intensity. The inhibition strength was measured 9 times each second and the average value was calculated, based on the intensity of fluorescence emitted by the fluorescent substrate metabolite.

The substrates, metabolites, inhibitors, excitation wavelengths and fluorescent wavelengths used for the measurement are shown in Table 9.

TABLE 9

| P450 speices | substrate | metabolite | inhibitor | excitation wavelength (nm) | emission wavelength (nm) |
|---|---|---|---|---|---|
| CYP1A2 | CEC | CHC | Furafyline | 409 | 460 |
| CYP2C9 | MFC | HFC | Sulfaphenazole | 409 | 530 |
| CYP2C19 | CEC | CHC | Tranylcypromine | 409 | 460 |
| CYP2D6 | AMMC | AHMC | Quinidine | 390 | 460 |
| CYP3A4 | BFC | HFC | Ketoconazole | 409 | 530 |

The abbreviations used to represent the substrates and metabolites are shown below in Table 10.

TABLE 10

| | |
|---|---|
| CEC | 3-Cyano-7-ethoxycoumarin |
| CHC | 3-Cyano-7-hydroxycoumarin |
| MFC | 7-Methoxy-4-trifluoromethylcoumarin |
| HFC | 7-Hydroxy-4-trifluoromethylcoumarin |
| CEC | 7-Ethoxy-3-cyanocoumarin |
| CHC | 7-Hydroxy-3-cyanocoumarin |
| AMMC | 3-[2-(N,N-diethyl-N-methylamino)ethyl]-7-methoxy-4-methylcoumarin |
| AHMC | 3-[2-(N,N-diethylamino)ethyl]-7-hydroxy-4-methylcoumarin |
| BFC | 7-Benzyloxy-4-(trifluoromethyl)-coumarin |
| HFC | 7-hydroxy-4-(trifluoromethyl)-coumarin |

<Test Results>

As a result of evaluating the metabolic inhibition of the compounds of the invention against P450 for Test Example 4, it was confirmed that the representative compounds of the invention exhibit an $IC_{50}$ of 10 μM or greater for the following five P450 molecular species: CYP1A2, CYP2C9, CYP2C19, CYP2D6, CYP3A4.

Test Example 5

<Inhibition of hERG Channel Current>

(1) The inhibiting effect on hERG channel current was evaluated with reference to Zhou, Z. et al., Biophysical Journal, 74, 230-241 (1998).

(2) The experiment was conducted using HEK-293 cells introduced the hERG channel gene (subtype 1) (cell line established by this company).

(3) From one to several days prior to the experiment, the cells were seeded onto a polylysine-coated glass plate and cultured up to the day of the experiment. At the start of the experiment, the cell-seeded glass plate was transferred to a current measuring bath. The hERG channel current was observed by the voltage-clamp method using a patch clamp. The measurement was conducted using a current amplifier (Axon Instruments), and the current was recorded and analyzed using pCLAMP software (Axon Instruments).

(4) The hERG channel current was induced by applying to the cells a depolarizing pulse from a holding potential of −80 mV to +20 mV for 5 seconds and to −50 mV for 4 seconds, at 20 second intervals. Upon stabilization of the current in normal solution, perfusion was carried out with solutions containing the test compound at different concentrations.

(5) The amplitude of the hERG channel current was defined as the peak value of the tail current observed upon restoring the potential to −50 mV. The inhibiting effect ($IC_{50}$) of the test compound on the hERG channel current was calculated based on the change in the peak value of the tail current recorded with addition of the test compound at each concentration, with respect to the peak value of the tail current recorded in normal solution as 100%.

<Test Results>

As a result of evaluating the inhibiting effects of the representative compounds of the invention against hERG channel current for Test Example 5, they were found to exhibit $IC_{50}$ values of 10 μM or greater.

INDUSTRIAL APPLICABILITY

As explained above, the present invention provides novel nitrogen containing heterocyclic-compounds which have excellent sodium channel-inhibiting activity and are highly useful as medicines in general consideration of their pharmacological activity and safety (in terms of effects on the cardiovascular system, inhibiting action on drug metabolizing enzymes, enzyme induction, etc.), as well as salts thereof and novel pharmaceutical compositions comprising them. The compounds of the invention and pharmaceutical compositions comprising them exhibit excellent therapeutic or prophylactic effects against diseases wherein sodium channel inhibition is effective as treatment and prevention, such as various types of neuralgia (for example, diabetic neuralgia, HIV neuralgia, postherpetic neuralgia, trigeminal neuralgia, stump pain, post spinal injury pain, thalamic pain, post-stroke pain, etc.), neuropathy, epilepsy, insomnia, premature ejaculation, and the like, and are therefore useful as therapeutic or prophylactic agents and analgesics.

What is claimed is:

1. A compound represented by the following formula:

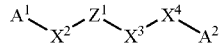

a salt or hydrate thereof, wherein:

$X^2$ represents methylene, 1,2-ethylene or 1,1-ethylene;
—$X^3$—$X^4$— represents methylene, oxygen, a single bond or a group represented by the formula:

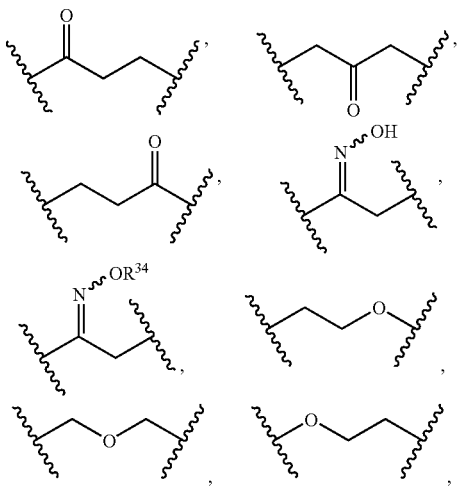

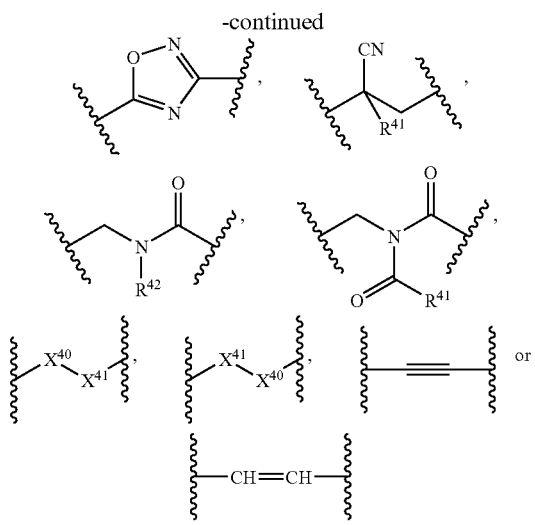

wherein $X^{40}$ is (1) methylene having between 0 and 2 substituents selected from the group consisting of halogen, hydroxyl, $C_{1-6}$ alkyl, $C_{1-6}$ alkoxy, and cyano, (2) oxygen, (3) —CO—, (4) —S—, (5) —S(O)— or (6) —S(O)$_2$—;

$X^{41}$ is methylene having 0, 1, or 2 substituents selected from the group consisting of halogen, hydroxyl, $C_{1-6}$ alkyl, $C_{1-6}$ alkoxy, and cyano;

$R^{34}$ represents $C_{1-6}$ alkyl;

$R^{41}$ represents (1) phenyl having between 0 and 2 substituents selected from the group consisting of halogen, hydroxyl, $C_{1-6}$ alkyl, $C_{1-6}$ alkoxy, and cyano, (2) phenyl-$C_{1-6}$ alkyl having 0-3 substituents selected from the group consisting of halogen, hydroxyl, $C_{1-6}$ alkyl, $C_{1-6}$ alkoxy, and cyano or (3) $C_{1-6}$ alkyl having 0-3 substituents selected from the group consisting of halogen, hydroxyl, $C_{1-6}$ alkoxy, and cyano; and $R^{42}$ represents (1) $C_{1-6}$ alkyl having 0-3 substituents selected from the group consisting of halogen, hydroxyl, $C_{1-6}$ alkoxy, and cyano or (2) hydrogen;

$Z^1$ represents azetidine-diyl, pyrrolidine-diyl, azepane-diyl, piperazine-diyl, or a group represented by the formula:

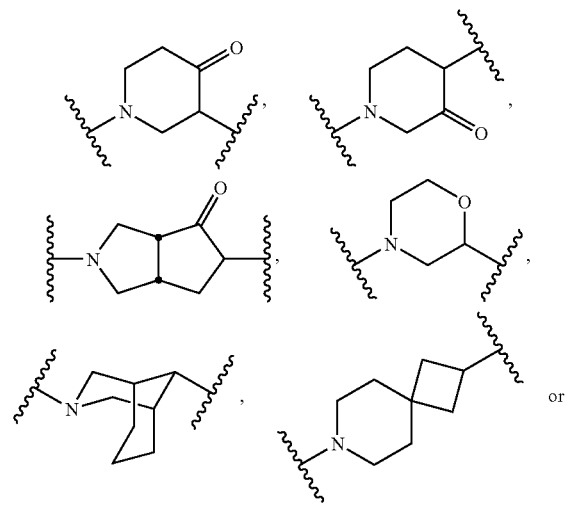

-continued

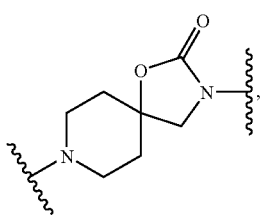

wherein $Z^1$ is substituted with 0-3 groups selected from the group consisting of (1) hydrogen, (2) halogen, (3) cyano, (4) hydroxyl, (5) $C_{2-7}$ alkoxycarbonyl, (6) $C_{1-6}$ alkyl having 0-4 substituents selected from the group consisting of hydroxyl, $C_{1-6}$ alkoxy and halogen, (7) $C_{1-6}$ alkoxy having 0-4 substituents selected from the group consisting of hydroxyl, $C_{1-6}$ alkoxy and halogen, (8) 2-methylphenyloxymethyl and (9) 2-fluorophenyloxymethyl;

$A^2$ represents phenyl, 1-naphthyl, 2-naphthyl, an aromatic ring having 5 to 10 atoms in the ring and containing one or more heteroatoms among the atoms of the ring, or a 9- to 11-membered benzene fused ring group, wherein $A^2$ is substituted with 0-3 groups selected from the group consisting of (1) $C_{1-6}$ alkyl having 0-3 substituents selected from the group consisting of halogen, $C_{1-6}$ alkoxy, cyano, hydroxyl and $C_{3-8}$ cycloalkyl, (2) $C_{1-6}$ alkoxy having 0-3 substituents selected from the group consisting of halogen, $C_{1-6}$ alkoxy, cyano, hydroxyl and $C_{3-8}$ cycloalkyl, (3) halogen, (4) $C_{3-8}$ cycloalkyl, (5) $C_{2-7}$ alkoxycarbonyl, (6) $C_{2-7}$ acyl, (7) $C_{1-6}$ alkylthio, (8) $C_{1-6}$ alkylsulfinyl, (9) $C_{1-6}$ alkylsulfonyl, (10) cyano, (11) nitro, (12) phenyl, (13) pyridyl, (14) ethylenedioxy, (15) methylenedioxy, (16) a group represented by the formula:

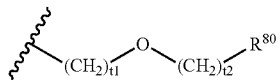

wherein t1 and t2 each independently represents zero or an integer from 1 to 3, and $R^{80}$ represents hydrogen, $C_{1-6}$ alkyl or $C_{3-8}$ cycloalkyl, and (17) a group represented by the formula:

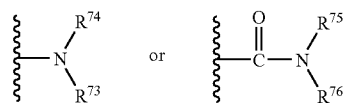

wherein $R^{73}$ and $R^{74}$ each independently represents hydrogen, $C_{1-6}$ alkyl, $C_{2-7}$ acyl, $C_{1-6}$ alkylsulfonyl, —CO—NR$^{75}$R$^{76}$ or —CS—NR$^{75}$R$^{76}$, and $R^{75}$ and $R^{76}$ each independently represents hydrogen or $C_{1-6}$ alkyl; and wherein $A^1$ represents a group represented by the formula:

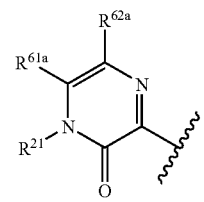

wherein $R^{21}$ represents hydrogen or $C_{1-6}$ alkyl, and $R^{61a}$ and $R^{62a}$ each independently represents hydrogen, halogen, $C_{1-6}$ alkoxy, $C_{1-6}$ alkyl or cyano.

2. A compound represented by the following formula:

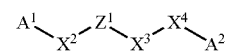

a salt or hydrate thereof, wherein:

$X^2$ represents methylene, 1,2-ethylene or 1,1-ethylene;

—$X^3$—$X^4$— represents methylene, oxygen, a single bond or a group represented by the formula:

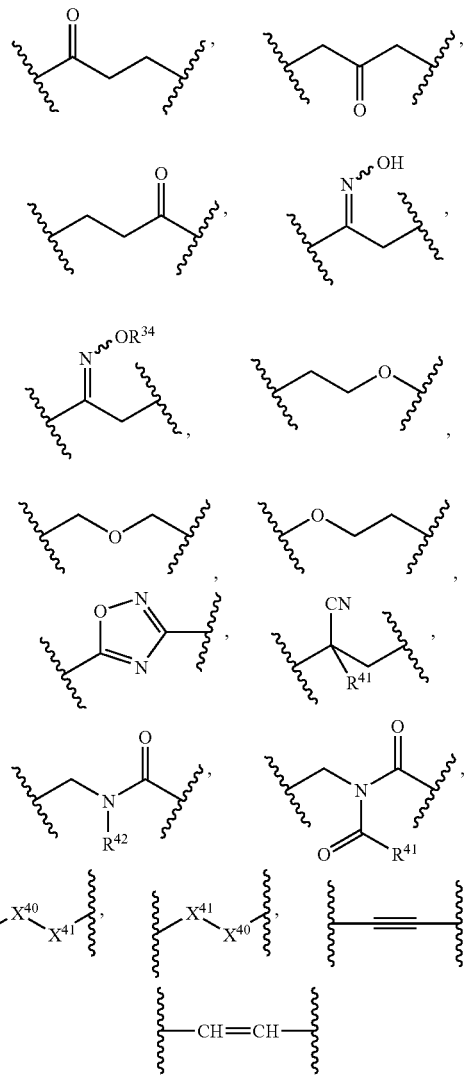

wherein $X^{40}$ is (1) methylene having between 0 and 2 substituents selected from the group consisting of halogen, hydroxyl, $C_{1-6}$ alkyl, $C_{1-6}$ alkoxy, and cyano, (2) oxygen, (3) —CO—, (4) —S—, (5) —S(O)— or (6) —S(O)$_2$—;

$X^{41}$ is methylene having 0, 1, or 2 substituents selected from the group consisting of halogen, hydroxyl, $C_{1-6}$ alkyl, $C_{1-6}$ alkoxy, and cyano;

$R^{34}$ represents $C_{1-6}$ alkyl;

$R^{41}$ represents (1) phenyl having between 0 and 2 substituents selected from the group consisting of halogen, hydroxyl, $C_{1-6}$ alkyl, $C_{1-6}$ alkoxy, and cyano, (2) phenyl-$C_{1-6}$ alkyl having 0-3 substituents selected from the group consisting of halogen, hydroxyl, $C_{1-6}$ alkyl, $C_{1-6}$ alkoxy, and cyano or (3) $C_{1-6}$ alkyl having 0-3 substituents selected from the group consisting of halogen, hydroxyl, $C_{1-6}$ alkoxy, and cyano; and $R^{42}$ represents (1) $C_{1-6}$ alkyl having 0-3 substituents selected from the group consisting of halogen, hydroxyl, $C_{1-6}$ alkoxy, and cyano or (2) hydrogen;

$Z^1$ represents azetidine-diyl, pyrrolidine-diyl, azepane-diyl, piperazine-diyl, or a group represented by the formula:

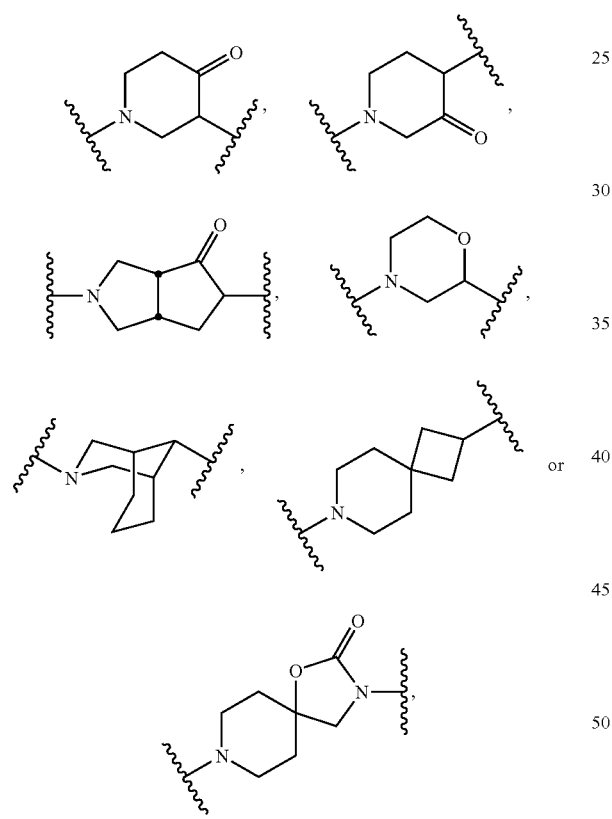

wherein $Z^1$ is substituted with 0-3 groups selected from the group consisting of (1) hydrogen, (2) halogen, (3) cyano, (4) hydroxyl, (5) $C_{2-7}$ alkoxycarbonyl, (6) $C_{1-6}$ alkyl having 0-4 substituents selected from the group consisting of hydroxyl, $C_{1-6}$ alkoxy and halogen, (7) $C_{1-6}$ alkoxy having 0-4 substituents selected from the group consisting of hydroxyl, $C_{1-6}$ alkoxy and halogen, (8) 2-methylphenyloxymethyl and (9) 2-fluorophenyloxymethyl;

$A^2$ represents a monovalent group derived by removing a hydrogen atom from a compound represented by the formula:

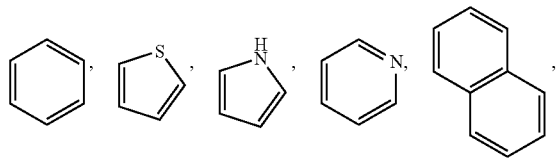

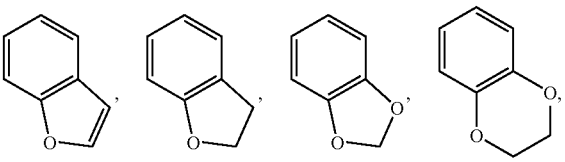

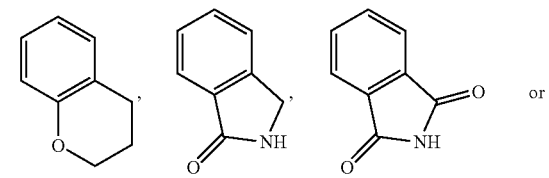

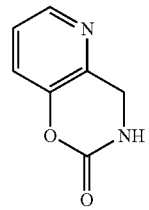

wherein $A^2$ is substituted with 0-3 groups selected from the group consisting of (1) $C_{1-6}$ alkyl having 0-3 substituents selected from the group consisting of halogen, $C_{1-6}$ alkoxy, cyano, hydroxyl and $C_{3-8}$ cycloalkyl, (2) $C_{1-6}$ alkoxy having 0-3 substituents selected from the group consisting of halogen, $C_{1-6}$ alkoxy, cyano, hydroxyl and $C_{3-8}$ cycloalkyl, (3) halogen, (4) $C_{3-8}$ cycloalkyl, (5) $C_{2-7}$ alkoxycarbonyl, (6) $C_{2-7}$ acyl, (7) $C_{1-6}$ alkylthio, (8) $C_{1-6}$ alkylsulfinyl, (9) $C_{1-6}$ alkylsulfonyl, (10) cyano, (11) nitro, (12) phenyl, (13) pyridyl, (14) ethylenedioxy, (15) methylenedioxy, (16) a group represented by the formula:

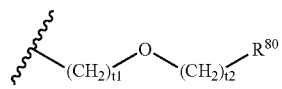

wherein t1 and t2 each independently represents zero or an integer from 1 to 3, and $R^{80}$ represents hydrogen, $C_{1-6}$ alkyl or $C_{3-8}$ cycloalkyl, and (17) a group represented by the formula:

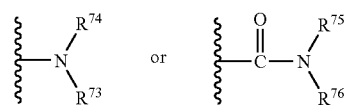

wherein $R^{73}$ and $R^{74}$ each independently represents hydrogen, $C_{1-6}$ alkyl, $C_{2-7}$ acyl, $C_{1-6}$ alkylsulfonyl, —CO—NR$^{75}$R$^{76}$ or —CS—NR$^{75}$R$^{76}$, and $R^{75}$ and $R^{76}$ each independently represents hydrogen or $C_{1-6}$ alkyl; and $A^1$ represents a group represented by the formula:

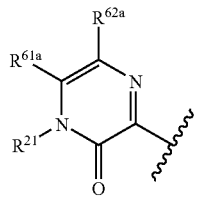

wherein $R^{21}$ represents hydrogen or $C_{1-6}$ alkyl, and $R^{61a}$ and $R^{62a}$ each independently represents hydrogen, halogen, $C_{1-6}$ alkoxy, $C_{1-6}$ alkyl or cyano.

3. The compound according to claim 1, wherein —$X^3$—$X^4$— is a group represented by the formula:

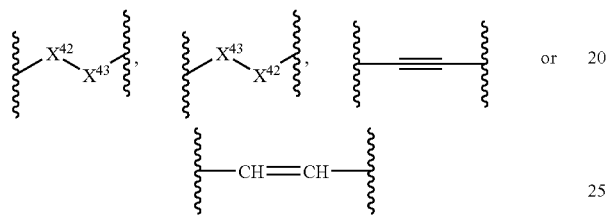

wherein $X^{42}$ represents (1) methylene having 0 or 1 substituent selected from the group consisting of halogen, hydroxyl, $C_{1-6}$ alkyl, $C_{1-6}$ alkoxy, and cyano, (2) oxygen, (3) —CO—, (4) —S—, (5) —S(O)—, (6) —S(O)$_2$— or (7) —CF$_2$—; and $X^{43}$ represents either methylene having 0 or 1 substituent selected from the group consisting of halogen, hydroxyl, $C_{1-6}$ alkyl, $C_{1-6}$ alkoxy, and cyano, or —CF$_2$—.

4. The compound according to claim 1, wherein —$X^3$—$X^4$— is a group represented by the formula:

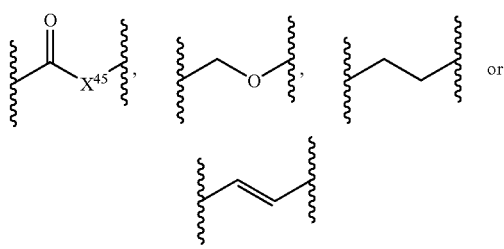

wherein $X^{45}$ represents either methylene having 0 or 1 substituent selected from the group consisting of fluorine, hydroxyl, $C_{1-6}$ alkyl, $C_{1-6}$ alkoxy, and cyano, or —CF$_2$—.

5. The compound according to claim 1, wherein —$X^3$—$X^4$— is

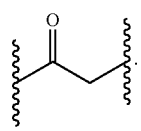

6. The compound according to claim 1, wherein $A^2$ is a monovalent group derived by removing a hydrogen atom from a compound represented by the formula:

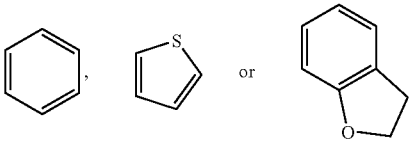

and wherein $A^2$ is substituted with 0-3 groups selected from (1) $C_{1-6}$ alkyl having 0-3 substituents selected from the group consisting of halogen, $C_{1-6}$ alkoxy, cyano, hydroxyl and $C_{3-8}$ cycloalkyl, (2) $C_{1-6}$ alkoxy having 0-3 substituents selected from the group consisting of halogen, $C_{1-6}$ alkoxy, cyano, hydroxyl and $C_{3-8}$ cycloalkyl, (3) halogen, (4) $C_{3-8}$ cycloalkyl, (5) $C_{2-7}$ alkoxycarbonyl, (6) $C_{2-7}$ acyl, (7) $C_{1-6}$ alkylthio, (8) $C_{1-6}$ alkylsulfinyl, (9) $C_{1-6}$ alkylsulfonyl, (10) cyano, (11) nitro, (12) phenyl, (13) pyridyl, (14) ethylenedioxy, (15) methylenedioxy, (16) a group represented by the formula:

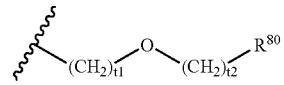

wherein t1 and t2 each independently represents zero or an integer from 1 to 3, and $R^{80}$ represents hydrogen, $C_{1-6}$ alkyl or $C_{3-8}$ cycloalkyl, and (17) a group represented by the formula:

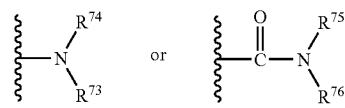

wherein $R^{73}$ and $R^{74}$ each independently represents hydrogen, $C_{1-6}$ alkyl, $C_{2-7}$ acyl, $C_{1-6}$ alkylsulfonyl, —CO—NR$^{75}$R$^{76}$ or —CS—NR$^{75}$R$^{76}$, and $R^{75}$ and $R^{76}$ each independently represents hydrogen or $C_{1-6}$ alkyl.

7. A compound according to claim 1, wherein $A^2$ is substituted with 0-3 groups selected from the group consisting of halogen, $C_{1-6}$ alkyl having 0-3 substituents selected from halogen, $C_{1-6}$ alkoxy, cyano, hydroxyl and $C_{3-8}$ cycloalkyl, $C_{1-6}$ alkoxy having 0-3 substituents selected from halogen, $C_{1-6}$ alkoxy, cyano, hydroxyl and $C_{3-8}$ cycloalkyl, $C_{3-8}$ cycloalkyl, $C_{1-6}$ alkylthio and a group represented by the formula:

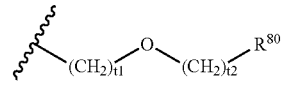

wherein t1 and t2 each independently represents zero or an integer from 1 to 3, and $R^{80}$ represents hydrogen, $C_{1-6}$ alkyl or $C_{3-8}$ cycloalkyl.

8. The compound according to claim 1, wherein A is a group represented by the formula

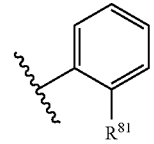

wherein R[81] represents (1) $C_{1-6}$ alkyl having 1-3 substituents selected from the group consisting of halogen, $C_{3-8}$ cycloalkyl and $C_{1-6}$ alkoxy, (2) $C_{1-6}$ alkoxy having 0-3 substituents selected from the group consisting of halogen, $C_{3-8}$ cycloalkyl and $C_{1-6}$ alkoxy, (3) hydrogen, (4) $C_{1-6}$ alkylthio having 0-3 substituents selected from the group consisting of halogen, $C_{3-8}$ cycloalkyl and $C_{1-6}$ alkoxy or (5) halogen.

9. The compound according to claim 1, wherein $A^2$ is a group represented by the formula:

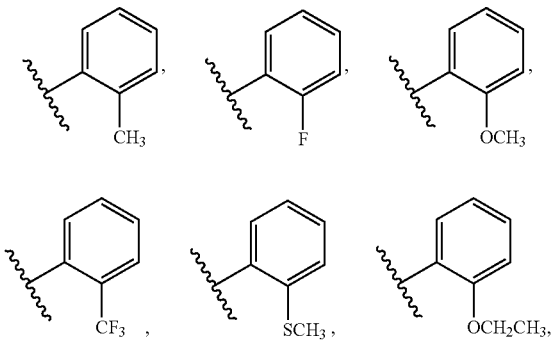

-continued

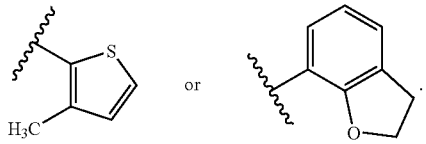

10. The compound according to claim 1, wherein $R^{21}$ is hydrogen.

11. The compound according to claim 1, wherein $R^{61a}$ and $R^{62a}$ are both hydrogen.

12. A method for treating neuralgia, comprising administering to a patient a pharmacologically effective dose of a compound according to claim 1.

13. A method for treating diabetic neuralgia, HIV neuralgia, postherpetic neuralgia, trigeminal neuralgia, stump pain, post spinal injury pain, thalamic pain or post-stroke pain, comprising administering to a patient a pharmacologically effective dose of a compound according to claim 1.

14. A method for treating low back pain, inflammatory pain, arthralgia, postoperative pain or cancer pain comprising administering to a patient a pharmacologically effective dose of a compound according to claim 1.

15. A pharmaceutical composition comprising a compound of claim 1, and a pharmaceutically acceptable carrier.

\* \* \* \* \*